(12) United States Patent
Shibouta et al.

(10) Patent No.: US 6,235,731 B1
(45) Date of Patent: May 22, 2001

(54) FUSED IMIDAZOPYRIDINE DERIVATIVES AS ANTIHYPERLIPIDEMIC AGENTS

(75) Inventors: Yumiko Shibouta, Osaka; Yasuo Sugiyama, Hyogo; Tetsuji Kawamoto, Osaka; Muneo Takatani, Kyoto, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/155,889

(22) PCT Filed: Apr. 23, 1997

(86) PCT No.: PCT/JP97/01395

§ 371 Date: Oct. 8, 1998

§ 102(e) Date: Oct. 8, 1998

(87) PCT Pub. No.: WO97/40051

PCT Pub. Date: Oct. 30, 1997

(30) Foreign Application Priority Data

Apr. 24, 1996 (JP) .................................. 8-102303
Dec. 11, 1996 (JP) .................................. 8-330801

(51) Int. Cl.⁷ ...................... A61K 31/549; C07D 513/18
(52) U.S. Cl. ............................. 514/224.5; 544/34
(58) Field of Search .............................. 544/34; 514/63, 514/224.5

(56) References Cited

FOREIGN PATENT DOCUMENTS

| 0 261 439 | 3/1988 | (EP) . |
| 0 372 445 | 6/1990 | (EP) . |
| 0 471 236 | 2/1992 | (EP) . |
| 0 520 552 | 12/1992 | (EP) . |

*Primary Examiner*—Richard L. Raymond
(74) *Attorney, Agent, or Firm*—Wenderoth, Lind & Ponack, L.L.P.

(57) ABSTRACT

A novel compound of the formula:

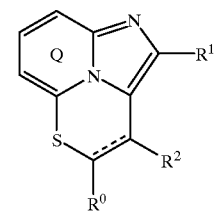

(I)

wherein ring Q is an optionally substituted pyridine ring;

One of $R^0$, $R^1$ and $R^2$ is —$Y^0$—$Z^0$, and the other tow groups are a hydrogen, a halogen, an optionally substituted hydroxy group, a hydrocarbon group that may be an optionally substituted hydrocarbon group or an acyl group;

$Y^0$ is a bond or an optionally substituted bivalent hydrocarbon group;

$Z^0$ is a basic group which may be bonded via oxygen, nitrogen, —CO—, —CS—, —$SO_2N(R^3)$— (where $R^3$ is hydrogen or an optionally substituted hydrocarbon group), or $S(O)_n$ (wherein n is to 0, 1 or 2);

┄┄┄┄ is a single bond or a double bond, or a salt thereof, which has an excellent LDL receptor up-regulating, blood-lipids lowering, blood-sugar lowering and diabetic complication-ameliorating activity.

48 Claims, No Drawings

FUSED IMIDAZOPYRIDINE DERIVATIVES AS ANTIHYPERLIPIDEMIC AGENTS

This application is a 371 of PCT/JP97/01395, filed Apr. 23, 1997.

TECHNICAL FIELD

The present invention relates to novel fused imidazopyridine derivatives which are useful for prophylaxis and/or therapy of hyperlipemia, their production and use.

BACKGROUND ART

It has been shown by many epidemiological surveys that, alongside of hypertension and smoking, hypercholesterolemia is one of the three major risk factors for atherosclerotic diseases such as myocardial infarction, angina pectoris, and cerebral infarction. Therefore, adequate control of blood cholesterol concentration is of paramount importance for the prevention and treatment of atherosclerotic diseases such as ischemic heart diseases. As drugs for lowering cholesterol in blood, drugs which inhibit bile acid absorption by binding with bile acid, such as colestyramin and colestipol (disclosed in e.g. U.S. Pat. No. 4,027,009), drugs which inhibit acyl-CoA cholesterol O-acyltransferase (ACAT) to suppress the intestinal absorption of cholesterol, such as melinamide (disclosed in French Patent 1476569), and drugs which inhibit cholesterol biosynthesis, such as lovastatin (U.S. Pat. No. 4,231,938), simvastatin (U.S. Pat. No. 4,231,938), (U.S. Pat. No. 4,444,784), and pravastatin (U.S. Pat. No. 4,346,227), all of which are inhibitors of 3-hydroxy-3-methylglutaryl-coenzyme A reductase (HMG-CoA reductase), are attracting many attentions. However, inhibition of HMG-CoA reductase results in inhibition of not only cholesterol biosynthesis but also biosynthesis of other vital physiological substances such as ubiquinones, dolichols, and heme A. Accordingly, these drugs are not fully satisfactory for use as medicines in view of the consequent adverse effects.

Meanwhile, liver low-density lipoprotein (LDL) receptors are playing a principal role in cholesterol homeostasis. Cholesterol circulating in the form of LDL is eliminated from plasma by specific LDL receptors, and taken up in the cells by the mechanism of receptor-mediated intracellular uptake. Taken up in the cells, LDL particles are decomposed by the lysosomes, whereupon cholesterol is released to increase the intracellular concentration of free cholesterol. The increased free cholesterol concentration transmits a signal to liver cells to lower the transcription rate of the gene of the key enzyme in the cholesterol biosynthetic pathway, and decrease biosynthesis of cholesterol. Furthermore, the LDL receptor mRNA and protein are down-regulated by increased intracellular cholesterol so that the capacity of liver to eliminate the excess LDL cholesterol from plasma is compromised. Therefore, the mechanism for independent up-regulation of LDL receptors is expected to lower the plasma cholesterol level still more remarkably and it is possible that any drug as up-regulating LDL receptors could be a novel hypolipemic agent.

Incidentally, there is not a single known compound structurally analogous to the compound of the present invention.

In the above state of the art, development of a new type of antihyperlipemic drug having low-density lipoprotein (LDL) receptor up-regulating activity has been awaited.

DISCLOSURE OF INVENTION

The novel fused imidazopyridine derivatives represented by the following formula (I) have been found to possess an excellent LDL receptor up-regulating, blood-lipids lowering, blood-sugar lowering and diabetic complication-ameliorating action. And, the inventors have completed the present invention.

The compound (I) of the present invention is directed to:

(1) a compound of the formula:

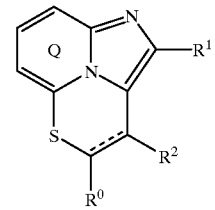

wherein ring Q is an optionally substituted pyridine ring;

one of $R^0$, $R^1$ and $R^2$ is $-Y^0-Z^0$, and the other two groups are a hydrogen, a halogen, an optionally substituted hydroxy group, an optionally substituted hydrocarbon group or an acyl group;

$Y^0$ is a bond or an optionally substituted divalent hydrocarbon group;

$Z^0$ is a basic group which may be bonded via oxygen, nitrogen, —CO—, —CS—, —$SO_2N(R^3)$— (wherein $R^3$ is a hydrogen or an optionally substituted hydrocarbon group), or —S(O)n— (wherein n is 0, 1 or 2); and ═══ is a single bond or a double bond, or a salt thereof, (2) a compound of above (1), wherein $R^0$ is —$Y^0-Z^0$, wherein $Y^0$ and $Z^0$ are of the same meanings as defined in above (1), (3) a compound of above (1), wherein $Z^0$ is a group with a molecular weight of not greater than 1000, (4) a compound of above (1) which is a compound of the formula:

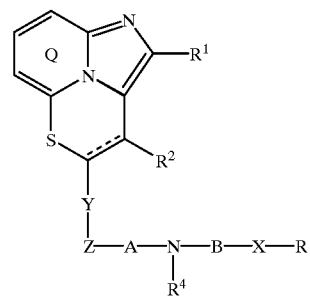

wherein ring Q is an optionally substituted pyridine ring;

A and B independently are an optionally substituted divalent hydrocarbon group which may be bonded via —$CON(R^{4a})$—, —CO— or —$N(R^{4a})$—;

X is a bond, oxygen, sulfur, —$N(R^5)CO$—, —$CO(R^5)$—, —CO— or —$N(R^5)$—,

Y is a bond, —CH=CH— or

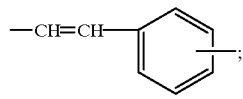

Z is —CO—, —COO—, —CON(R³)—, —SO₂N(R³)— or —S(O)m— (wherein m is 0, 1 or 2);

$R^1$ and $R^2$ independently are a hydrogen, a halogen, an optionally substituted hydroxy group, an optionally substituted hydrocarbon group or an acyl group;

$R^3$, $R^4$, $R^{4a}$ and $R^5$ independently are a hydrogen or an optionally substituted hydrocarbon group; or $R^3$ and A, $R^4$ and A, $R^4$ and B, $R^4$ and $R^5$, or $R^4$ and R may independently be bonded to each other to form a ring;

R is an optionally substituted hydrocarbon group or an optionally substituted heterocyclic group; and ----- is a single bond or a double bond, or a salt thereof, (5) a compound of above (1) which is a compound of the formula:

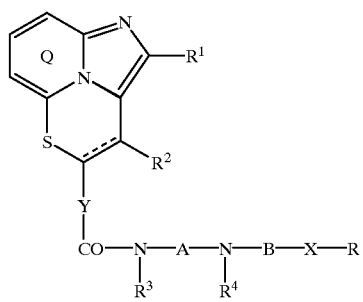

wherein ring Q is an optionally substituted pyridine ring;

A and B independently are an optionally substituted divalent hydrocarbon group which may be bonded via —CON(R$^{4a}$)—, —CO— or —N(R$^{4a}$)—;

X is a bond, oxygen, sulfur, —N(R⁵)CO—, —CO(R⁵)—, —CO— or —N(R⁵)—;

Y is a bond, —CH=CH— or

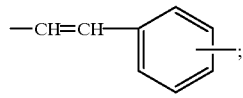

Z is —CO—, —COO—, —CON(R³)—, —SO₂N(R³)— or —S(O)m— (wherein m is 0, 1 or 2);

$R^1$ and $R^2$ independently are a hydrogen, a halogen, an optionally substituted hydroxy group, an optionally substituted hydrocarbon group or an acyl group;

$R^3$, $R^4$, $R^{4a}$ and $R^5$ independently are a hydrogen or an optionally substituted hydrocarbon group; or $R^3$ and A, $R^4$ and A, $R^4$ and B, $R^4$ and $R^5$, or $R^4$ and R independently may be bonded to each other to form a ring;

R is an optionally substituted hydrocarbon group or an optionally substituted heterocyclic group; and ----- is a single bond or a double bond, or a salt thereof, (6) a compound of above (5), wherein A and B independently are an alkylene group; X is a bond; and $R^3$ and $R^4$ independently are a hydrogen or an optionally substituted alkyl, cycloalkyl, alkenyl, aralkyl or aryl group, (7) a compound of above (5), wherein ring Q is an unsubstituted pyridine ring; X is a bond; Y is a bond,

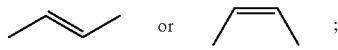

A and B independently are a $C_{1-15}$ alkylene group; $R^1$ and $R^2$ independently are a hydrogen;

$R^3$ and $R^4$ independently are a hydrogen or a $C_{1-15}$ alkyl, $C_{3-8}$ cycloalkyl, $C_{2-18}$ alkenyl, $C_{7-16}$ aralkyl or $C_{6-14}$ aryl group; and R is a $C_{6-14}$ aryl group, (8) a compound of above (1) which is a compound of the formula:

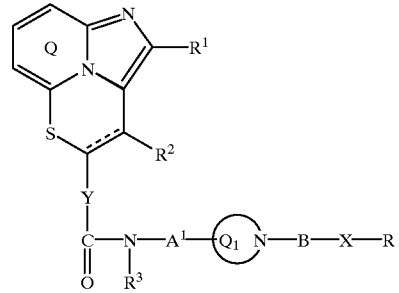

wherein ring Q is an optionally substituted pyridine ring;

ring $Q_1$ is an optionally substituted nitrogen-containing heterocyclic ring;

$A^1$ is a bond or an optionally substituted divalent hydrocarbon group which may be bonded via —CON(R$^{4a}$)—, —CO— or —N(R$^{4a}$)—;

B is an optionally substituted divalent hydrocarbon group;

X is a bond, oxygen, sulfur, —N(R⁵)CO—, —CO(R⁵)—, —CO— or —N(R⁵)—;

Y is a bond, —CH=CH— or —CH=CH

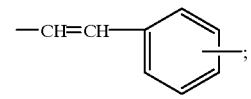

$R^1$ and $R^2$ independently are a hydrogen, a halogen, an optionally substituted hydroxy group, an optionally substituted hydrocarbon group or an acyl group;

$R^3$, $R^{4a}$ and $R^5$ independently are a hydrogen or an optionally substituted hydrocarbon group; or $R^3$ and $A^1$ may be bonded to each other to form a ring;

R is an optionally substituted hydrocarbon group or an optionally substituted heterocyclic group; and ----- is a single bond or a double bond, or a salt thereof, (9) a compound of above (8), wherein ring Q is an unsubstituted pyridine ring; $R^1$ and $R^2$ are a hydrogen;

$R^3$ is a hydrogen or a $C_{1-15}$ alkyl, $C_{3-8}$ cycloalkyl, $C_{2-18}$ alkenyl, $C_{7-16}$ arlkyl or $C_{6-14}$ aryl group; $A^1$ is (i) a bond, (ii) a $C_{1-15}$ alkylene group which may be substituted by 1 to 3 substituents selected from the group consisting of hydroxy, oxo and phenyl, (iii) a $C_{2-16}$ alkenylene group or (iv) a phenylene group; B is (i) a $C_{1-15}$ alkylene group which may be substituted by 1 to 3 substituents selected from the group consisting of hydroxy, oxo and phenyl, (ii) a $C_{2-16}$ alkenylene group or (iii) a phenylene group; ring $Q_1$ is a group of the formula:

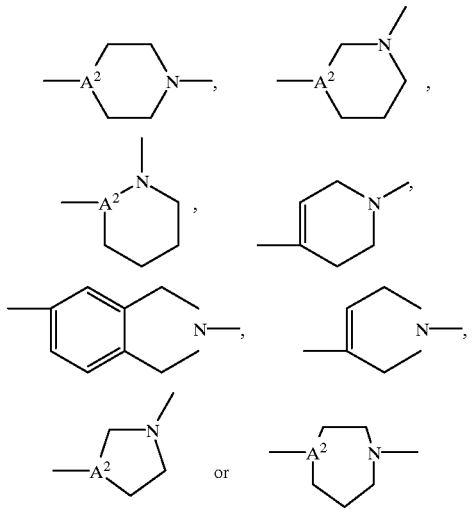

wherein $A^2$ is =C or CH; X is a bond, oxygen, sulfur or —CON($R^5$)—; $R^5$ is a hydrogen or a $C_{1-15}$ alkyl group,

(10) a compound of above (1) which is a compound of the formula:

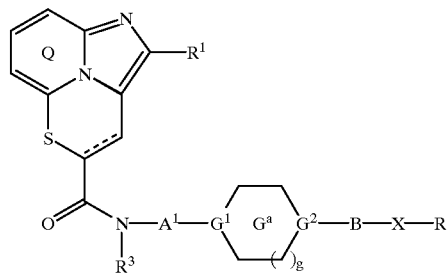

wherein ring Q is an optionally substituted pyridine ring;
$A^1$ is a bond or an optionally substituted divalent hydrocarbon group which may be bonded via —CON($R^{4a}$)—, —CO— or —N($R^{4a}$)—;
B is an optionally substituted divalent hydrocarbon group;
X is a bond, oxygen, sulfur, —N($R^5$)CO—, —CON($R^5$)—, —CO— or —N($R^5$)—;
$R^1$ is a hydrogen, a halogen, an optionally substituted hydroxy group, an optionally substituted hydrocarbon group or an acyl group;
$R^3$, $R^{4a}$ and $R^5$ independently are a hydrogen or an optionally substituted hydrocarbon group;
R is an optionally substituted hydrocarbon group or an optionally substituted heterocyclic group;
one of $G^1$ and $G^2$ is N, and the other is CH or N;
ring $G^a$ is an optionally substituted ring;
g is 0, 1 or 2; and
----- is a single bond or a double bond, or a salt thereof,

(11) A compound of above (10), wherein ring Q is a pyridine ring which may be substituted by 1 to 3 substituents selected from the group consisting of nitro, hydroxy, cyano, carbamoyl, mono- or di-$C_{1-4}$ alkyl-carbamoyl, carboxy, $C_{1-4}$ alkoxy-carbonyl, sulfo, halogen, $C_{1-4}$ alkoxy, phenoxy, naphthoxy, benzyloxy, halophenoxy, $C_{1-4}$ alkylthio, mercapto, phenylthio, pyridylthio, $C_{1-4}$ alkylsulfinyl, phenylsulfinyl, $C_{1-4}$ alkylsulfonyl, phenylsulfonyl, amino, $C_{1-3}$ acylamino, mono- or di-$C_{1-4}$ alkylamino, $C_{1-4}$ alkyl and $C_{1-4}$ haloalkyl,

(12) a compound of above (10), $A^1$ is a bond or a $C_{1-15}$ alkylene, $C_{2-16}$ alkenylene group which may be bonded via —CON($R^{4a}$)—, —CO— or —N($R^{4a}$)—, wherein $R^{4a}$ is of the same meaning as defined in above (10),

(13) a compound of above (10), B is a $C_{1-15}$ alkylene or $C_{2-16}$ alkenylene group,

(14) a compound of above (10), X is a bond, oxygen, sulfur, —CONH— or —CO—,

(15) a compound of above (10), $R^1$ is (i) a hydrogen, (ii) a halogen, (iii) a hydroxy group which may be substituted by a $C_{1-6}$ alkyl, phenyl, $C_{7-10}$ aralkyl, formyl, $C_{1-6}$ alkyl-carbonyl, phenyloxycarbonyl, $C_{7-10}$ aralkyloxy-carbonyl, pyranyl, furanyl or silyl group, (iv) a $C_{1-15}$ alkyl, $C_{3-8}$ cycloalkyl, $C_{2-18}$ alkenyl, $C_{7-16}$ aralkyl or $C_{6-14}$ aryl group or (v) a $C_{1-6}$ alkoxy-carbonyl, mono-$C_{1-6}$ alkyl-carbamoyl, di-$C_{1-6}$ alkyl-carbamoyl or $C_{1-10}$ alkanoyl group,

(16) a compound of above (10), $R^3$ is a hydrogen or a $C_{1-15}$ alkyl, $C_{3-8}$ cycloalkyl, $C_{2-18}$ alkenyl, $C_{7-16}$ aralkyl or $C_{6-14}$ aryl group,

(17) a compound of above (10), R is (I) a $C_{1-15}$ alkyl, $C_{3-8}$ cycloalkyl or $C_{2-18}$ alkenyl group which may be substituted by 1 to 5 substituents selected from the group consisting of (i) nitro, (ii) hydroxy, (iii) cyano, (iv) carbamoyl, (v) mono- or di-$C_{1-4}$ alkyl-carbamoyl, (vi) carboxy, (vii) $C_{1-4}$ alkoxy-carbonyl, (viii) sulfo, (ix) halogen, (x) $C_{1-4}$ alkoxy, (xi) phenoxy, (xii) halophenoxy, (xiii) $C_{1-4}$ alkylthio, (xiv) mercapto, (xv) phenylthio, (xvi) pyridylthio, (xvii) $C_{1-4}$ alkylsulfinyl, (xviii) $C_{1-4}$ alkylsulfonyl, (xix) amino, (xx) $C_{1-3}$ alkanoylamino, (xxi) mono- or di-$C_{1-4}$ alkylamino, (xxii) 4- to 6-membered cyclic amino, (xxiii) $C_{1-3}$ alkanoyl, (xxiv) benzoyl and (xxv) 5- to 10-membered heterocyclic group;

(II) a $C_{7-16}$ aralkyl group which may be substituted by 1 to 4 substituents selected from the group consisting of (i) halogen, (ii) $C_{1-4}$ alkyl, (iii) $C_{2-6}$ alkenyl, (iv) $C_{1-3}$ alkanoyl, (v) $C_{1-4}$ alkoxy, (vi) nitro, (vii) cyano, (viii) hydroxy, (ix) $C_{1-4}$ alkoxy-carbonyl, (x) carbamoyl, (xi) mono- or di-$C_{1-4}$ alkyl-carbamoyl and (xii) mono- or di-$C_{2-4}$ alkenyl-carbamoyl;

(III) a $C_{6-14}$ aryl group which may be substituted by 1 to 4 substituents selected from the group consisting of (i) halogen, (ii) $C_{1-4}$ alkyl, (iii) $C_{1-4}$ haloalkyl, (iv) $C_{1-4}$ haloalkoxy, (v) $C_{1-4}$ alkoxy, (vi) $C_{1-4}$ alkylthio, (vii) hydroxy, (viii) carboxy, (ix) cyano, (x) nitro, (xi) amino, (xii) mono- or di-$C_{1-4}$ alkylamino, (xiii) formyl, (xiv) mercapto, (xv) $C_{1-4}$ alkyl-carbonyl, (xvi) $C_{1-4}$ alkoxy-carbonyl, (xvii) sulfo, (xviii) $C_{1-4}$ alkylsulfonyl, (xix) carbamoyl, (xx) mono- or di-$C_{1-4}$ alkyl-carbamoyl, (xxi) oxo and (xxii) thioxo; or (IV) a 5- or 6-membered monocyclic heterocyclic group containing 1 to 4 hetero-atoms selected from oxygen, sulfur and nitrogen or a fused bicyclic heterocyclic group containing 1 to 6 hetero-atoms selected from oxygen, sulfur and nitrogen, each of which may be substituted by 1 to 4 substituents selected from the group consisting of (i) halogen, (ii) $C_{1-4}$ alkyl, (iii) $C_{1-4}$ haloalkyl, (iv) $C_{1-4}$ haloalkoxy, (v) $C_{1-4}$ alkoxy, (vi) $C_{1-4}$ alkylthio, (vii) hydroxy, (viii) carboxy, (ix) cyano, (x) nitro, (xi) amino, (xii) mono- or di-$C_{1-4}$ alkylamino, (xiii) formyl, (xiv) mercapto, (xv) $C_{1-4}$ alkyl-carbonyl, (xvi) $C_{1-4}$ alkoxy-carbonyl, (xvii) sulfo, (xviii) $C_{1-4}$ alkylsulfonyl, (xix) carbamoyl, (xx) mono- or di-$C_{1-4}$ alkyl-carbamoyl, (xxi) oxo and (xxii) thioxo,

(18) a compound of above (10), wherein ring $G^a$ is a ring which may be substituted by 1 or 2 substituents selected from the group consisting of oxo and $C_{1-6}$ alkyl,

(19) a compound of above (10), wherein ring Q is an unsubstituted pyridine ring; $R^1$ and $R^3$ are a hydrogen; $G^1$ is CH; $G^2$ is N; g is 1; and R is an optionally substituted hydrocarbon group or an optionally substituted heterocyclic group,

(20) a compound of above (19), wherein ring $G^a$ is unsubstituted ring,

(21) a compound of above (19), wherein $A^1$ is a bond or a $C_{1-6}$ alkylene group,

(22) A compound of above (19), wherein $A^1$ is a bond,

(23) A compound of above (19), wherein B is a $C_{1-6}$ alkylene group,

(24) a compound of above (19), X is a bond,

(25) A compound of above (10), ring Q is an unsubstituted pyridine ring; $R^1$ and $R^3$ are a hydrogen; $A^1$ is a bond; $G^1$ is CH; $G^2$ is N; ring $G^a$ is a ring which may be substituted by 1 or 2 substituents selected from the group consisting of oxo and $C_{1-6}$ alkyl; g is 1; B is a $C_{1-6}$ alkylene group; X is a bond; and R is an optionally substituted phenyl group,

(26) a compound of above (25), ring $G^a$ is unsubstituted ring,

(27) a compound of above (25), wherein R is a phenyl group which may be substituted by 1 to 3 substituents selected from the group consisting of halogen, hydroxy, $C_{1-4}$ alkyl, $C_{1-4}$ haloalkyl, $C_{1-4}$ alkoxy and $C_{1-4}$ haloalkoxy,

(28) a compound of above (1) which is a compound of the formula:

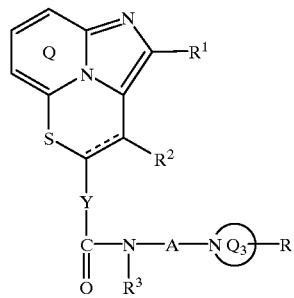

wherein ring Q is an optionally substituted pyridine ring;

ring $Q_2$ is an optionally substituted nitrogen-containing heterocyclic ring;

A is an optionally substituted divalent hydrocarbon group which may be bounded via —CON($R^{4a}$)—, —CO— or —N($R^{4a}$)—;

Y is a bond, —CH=CH— or

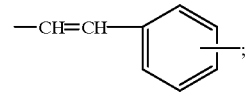

$R^1$ and $R^2$ independently are a hydrogen, a halogen, an optionally substituted hydroxy group, an optionally substituted hydrocarbon group or an acyl group;

$R^3$ and $R^{4a}$ independently are a hydrogen or an optionally substituted hydrocarbon group; or $R^3$ and A may be bonded to each other to form a ring;

R is an optionally substituted hydrocarbon group or an optionally substituted heterocyclic group; and ----- is a single bond or a double bond, or a salt thereof,

(29) a compound of above (28), wherein ring Q is an unsubstituted pyridine ring; $R^1$ and $R^2$ are a hydrogen; $R^3$ is a hydrogen or a $C_{1-15}$ alkyl, $C_{3-8}$ cycloalkyl, $C_{2-18}$ alkenyl, $C_{7-16}$ aralkyl or $C_{6-14}$ aryl group; A is (i) a $C_{1-15}$ alkylene group which may be substituted by 1 to 3 substituents selected from the group consisting of hydroxy, oxo and phenyl, (ii) a $C_{2-16}$ alkenylene group or (iii) a phenylene group; ring $Q_2$ is a group of the formula:

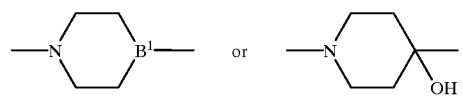

wherein $B^1$ is =C, CH or N,

(30) a compound of above (1) which is a compound of the formula:

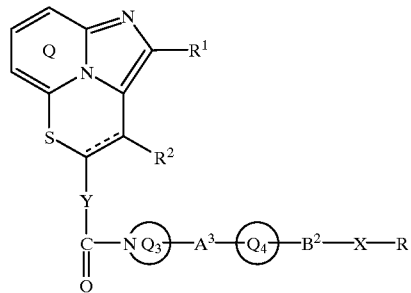

wherein ring Q is an optionally substituted pyridine ring;

ring $Q_3$ and $Q_4$ independently are an optionally substituted nitrogen-containing heterocyclic ring;

$A^3$ and $B^2$ independently are a bond or an optionally substituted divalent hydrocarbon group;

X is a bond, oxygen, sulfur, —N($R^5$)CO—, —CON($R^5$)—, —CO— or —N($R^5$)—;

Y is a bond, —CH=CH— or

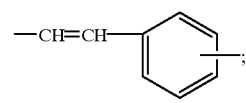

$R^1$ and $R^2$ independently are a hydrogen, a halogen, an optionally substituted hydroxy group, an optionally substituted hydrocarbon group or an acyl group;

$R^5$ is a hydrogen or an optionally substituted hydrocarbon group;

R is an optionally substituted hydrocarbon group or an optionally substituted heterocyclic group; and ----- is a single bond or a double bond, or a salt thereof,

(31) a compound of above (30), wherein ring Q is an unsubstituted pyridine ring; $R^1$ and $R^2$ are a hydrogen; $A^3$ and $B^2$ independently are a bond or a $C_{1-15}$ alkylene, $C_{2-16}$ alkenylene or phenylene group; ring $Q_3$ is a group of the formula:

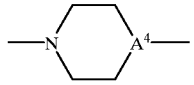

wherein $A^4$ is =C or CH; ring $Q_4$ is a group of the formula:

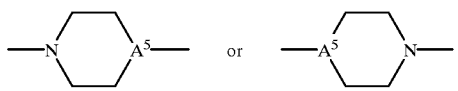

wherein $A^5$ is =C or CH,

(32) a compound of above (1) which is a compound of the formula:

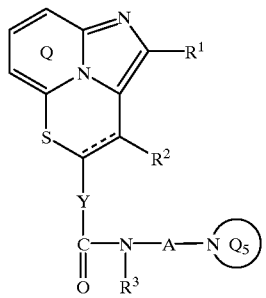

wherein ring Q is an optionally substituted pyridine ring;

ring $Q_5$ is an optionally substituted nitrogen-containing heterocyclic ring;

A is an optionally substituted divalent hydrocarbon group which may be bonded via —CON($R^{4a}$)—, —CO— or —N($R^{4a}$)—;

Y is a bond, —CH=CH— or —CH=CH

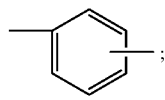

$R^1$ and $R^2$ independently are a hydrogen, a halogen, an optionally substituted hydroxy group, an optionally substituted hydrocarbon group or an acyl group;

$R^3$ and $R^{4a}$ independently are a hydrogen or an optionally substituted hydrocarbon group; and ----- is a single bond or a double bond, or a salt thereof,

(33) a compound of above (32), wherein ring Q is an unsubstituted pyridine ring; $R^1$ and $R^2$ are a hydrogen; $R^3$ is a hydrogen or a $C_{1-15}$ alkyl, $C_{3-8}$ cycloalkyl, $C_{2-18}$ alkenyl, $C_{7-16}$ aralkyl or $C_{6-14}$ aryl group; A is a $C_{1-15}$ alkylene, $C_{2-16}$ alkenylene or phenylene group; ring $Q_5$ is a group of the formula:

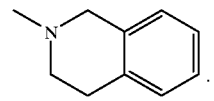

(34) a compound of above (1) which is (R)-N-[1-(1,4-benzodioxan-2-ylmethyl)piperidin-4-ylmethyl]-5-thia-1,8b-diazaacenaphthylene-4-carboxamide, or a pharmaceutically acceptable salt thereof,

(35) a compound of above (1) which is N-[1-(3-phenylpropyl)piperidin-4-ylmethyl]-3-(5-thia-1,8b-diaza acenaphthylene-4-yl)acrylamide, or a pharmaceutically acceptable salt thereof,

(36) a compound of above (1) which is N-[4-(4-phenylpiperidin-1-yl)butan-1-yl]-5-thia-1,8b-diazaacena phthylene-4-carboxamide, or a pharmaceutically acceptable salt thereof,

(37) a compound of above (1) which is N-[1-(3-phenylpropan-1-yl)piperidin-4-yl]-5-thia-1,8b-diazaacen aphthylene-4-carboxamide, or a pharmaceutically acceptable salt thereof, The "halogen" in this specification means fluorine, chlorine, bromine, iodine, etc.

The "hydrocarbon group" in the term "optionally substituted hydrocarbon group" in this specification means alkyl, alkenyl, aralkyl, aryl, etc.

The "alkyl" includes "straight-chain or branched $C_{1-15}$ alkyl" such as methyl, ethyl, propyl, isopropyl, butyl, isobutyl, sec-butyl, tert-butyl, pentyl, hexyl, heptyl, octyl, nonyl, decyl, undecyl, tridecyl, tetradecyl, pentadecyl, etc. and "$C_{3-8}$ cycloalkyl" such as cyclopropyl, cyclobutyl, cyclopentyl, cyclohexyl, cycloheptyl, cyclooctyl, etc.

The substituent groups which may be substituted on said "straight-chain or branched $C_{1-15}$ alkyl and $C_{3-8}$ cycloalkyl" include (i) nitro, (ii) hydroxy, (iii) cyano, (iv) carbamoyl, (v) mono- or di-$C_{1-4}$ alkylcarbamoyl (e.g. N-methylcarbamoyl, N-ethylcarbamoyl, N,N-dimethylcarbamoyl, N,N-diethylcarbamoyl, etc.), (vi) carboxy, (vii) $C_{1-4}$ alkoxycarbonyl (e.g. methoxycarbonyl, ethoxycarbonyl, propoxycarbonyl, isopropoxycarbonyl, etc.), (viii) sulfo, (ix) halogen (e.g. fluorine, chlorine, bromine, iodine, etc.), (x) $C_{1-4}$ alkoxy (e.g. methoxy, ethoxy, propoxy, isopropoxy, etc.), (xi) phenoxy, (xii) halophenoxy (e.g. o-, m- or p-chlorophenoxy, o-, m- or p-bromophenoxy, etc.), (xiii) $C_{1-4}$ alkylthio (e.g. methylthio, ethylthio, propylthio, isopropylthio, butylthio, etc), (xiv) mercapto, (xv) phenylthio, (xvi) pyridylthio, (xvii) $C_{1-4}$ alkylsulfinyl (e.g. methylsulfinyl, ethylsulfinyl, etc.), (xviii) $C_{1-4}$ alkylsulfonyl (e.g. methylsulfonyl, ethylsulfonyl, etc.), (xix) amino, (xx) $C_{1-3}$ alkanoylamino (e.g. acetylamino, propionylamino, etc.), (xxi) mono- or di-$C_{1-4}$ alkylamino (e.g. methylamino, ethylamino, dimethylamino, diethylamino, etc.), (xxii) 4- to 6-membered cyclic amino (e.g. 1-azetidinyl, 1-pyrrolidinyl, piperidino, morpholino, thiomorpholino, 1-piperazinyl, etc.), (xxiii) $C_{1-3}$ alkanoyl (e.g. formyl, acetyl, etc.), (xxiv) benzoyl and (xxv) 5- to 10-membered heterocyclic group (e.g. 2- or 3-thienyl; 2- or 3-furyl; 3-, 4- or 5-pyrazolyl; 2-, 4- or 5-thiazolyl; 3-, 4- or 5-isothiazolyl; 2-, 4- or 5-oxazolyl; 1,2,3- or 1,2,4-triazolyl; 1H- or 2H-tetrazolyl; 2-, 3- or 4-pyridyl; 2-, 4- or 5-pyrimidinyl; 3- or 4-pyridazinyl; quinolyl; isoquinolyl; indolyl; etc.). The "alkyl" may have 1 to 5 (preferably 1 to 3) substituents in the substitutable positions on the alkyl.

Preferred examples of the "alkyl" are straight-chain or branched $C_{1-6}$ alkyl groups such as methyl, ethyl, propyl, isopropyl, butyl, isobutyl, sec-butyl, tert-butyl, pentyl, hexyl, etc. The substituent group which may be substituted on the "$C_{1-6}$ alkyl" includes said halogen, $C_{1-4}$ alkoxy, hydroxy, $C_{1-4}$ alkoxy-carbonyl, carboxy, carbamoyl, mono- or di-$C_{1-4}$ alkyl-carbamoyl, pyridylthio, etc. The number of substituents may range from 1 to 3.

The "alkenyl" includes "$C_{2-18}$ alkenyl" such as vinyl, allyl, isopropenyl, 3-butenyl, 3-octenyl, 9-octadecenyl, etc. The substituent groups which may be substituted on the "alkenyl" are of the same groups as the substituent groups of said "alkyl". The number of substituent groups may range from 1 to 3. Preferred examples of the "alkenyl" are $C_{2-6}$ alkenyl groups such as vinyl, allyl, 2-butenyl, 3-butenyl, etc. The substituent groups which may be substituted on said "$C_{2-6}$ alkenyl" are of the same groups as the substituent groups of said "$C_{1-6}$ alkyl". The number of substituent groups may range from 1 to 3.

The "aralkyl" includes $C_{7-16}$ aralkyl, typically, phenyl-$C_{1-6}$ alkyl such as benzyl, phenethyl, 3-phenylpropyl, 4-phenylbutyl, etc. and naphthyl-$C_{1-6}$ alkyl such as (1-naphthyl)methyl, 2-(1-naphthyl)ethyl, etc.

The substituent groups which may be substituted on said "aralkyl", include (i) halogen (e.g. fluorine, chlorine, bromine, iodine, etc.), (ii) $C_{1-4}$ alkyl (e.g. methyl, ethyl, propyl, isopropyl, butyl, etc.), (iii) $C_{2-6}$ alkenyl (e.g. vinyl, allyl, 2-butenyl, 3-butenyl, etc.), (iv) $C_{1-3}$ alkanoyl (e.g. formyl, acetyl, etc.), (v) $C_{1-4}$ alkoxy (e.g. methoxy, ethoxy, propoxy, isopropoxy, etc.), (vi) nitro, (vii) cyano, (viii) hydroxy, (ix) $C_{1-4}$ alkoxy-carbonyl (e.g. methoxycarbonyl, ethoxycarbonyl, propoxycarbonyl, isopropoxycarbonyl, etc.), (x) carbamoyl, (xi) mono- or di-$C_{1-4}$ alkyl-carbamoyl (e.g. N-methylcarbamoyl, N-ethylcarbamoyl, N,N-dimethylcarbamoyl, N,N-diethylcarbamoyl, etc.) and (xii) mono- or di-$C_{2-4}$ alkenyl-carbamoyl (e.g. N-vinylcarbamoyl etc.). The "aralkyl" may have 1 to 4 (preferably 1 to 3) substituent groups such as those mentioned above in substitutable positions on the aralkyl.

The "aryl" includes aromatic monocyclic, dicyclic or tricyclic $C_{6-14}$ aryl such as phenyl, 1-naphthyl, 2-naphthyl, phenanthryl, anthryl, etc. Preferred is phenyl.

The substituent groups which may be substituted on said "aryl" include (i) halogen (e.g. fluorine, chlorine, bromine, iodine, etc.), (ii) $C_{1-4}$ alkyl (e.g. methyl, ethyl, propyl, isopropyl, butyl, etc.), (iii) $C_{1-4}$ haloalkyl (e.g. trifluoromethyl, 2,2,2-trifluoroethyl, trichloromethyl, etc.), (iv) $C_{1-4}$ halo-alkoxy (e.g. trifluoromethoxy, trichloromethoxy, 2,2,2-trifluoroethoxy), (v) $C_{1-4}$ alkoxy (e.g. methoxy, ethoxy, propoxy, isopropoxy, etc.), (vi) $C_{1-4}$ alkylthio (e.g. methylthio, ethylthio, propylthio, isopropylthio, butylthio, etc.), (vii) hydroxy, (viii) carboxy, (ix) cyano, (x) nitro, (xi) amino, (xii) mono- or di-$C_{1-4}$ alkylamino (e.g. methylamino, ethylamino, dimethylamino, diethylamino, etc.), (xiii) formyl, (xiv) mercapto, (xv) $C_{1-6}$ alkyl-carbonyl (e.g. acetyl, propionyl, butyryl, hexanoyl, etc.), (xvi) $C_{1-4}$ alkoxy-carbonyl (e.g. methoxycarbonyl, ethoxycarbonyl, propoxycarbonyl, isopropoxycarbonyl, etc.), (xvii) sulfo, (xviii) $C_{1-4}$ alkylsulfonyl (e.g. methylsulfonyl, ethylsulfonyl, etc.), (xix) carbamoyl, (xx) mono- or di-$C_{1-4}$ alkyl-carbamoyl (e.g. N-methylcarbamoyl, N-ethylcarbamoyl, N,N-dimethylcarbamoyl, N,N-diethylcarbamoyl, etc.), (xxi) oxo and (xxii) thioxo. The "aryl" may have 1 to 4 (preferably 1 or 2) substituent groups such as those mentioned above in substitutable positions on the aryl. The aryl having oxo group(s) includes benzoquinonyl, naphthoquinolyl, anthraquinonyl, etc.

The term "acyl" in this specification includes acyl derived from carboxylic acid, such as alkoxy-carbonyl, alkyl-carbamoyl and alkanoyl.

The "alkoxy-carbonyl" includes $C_{1-6}$ alkoxy-carbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neo-pentyloxycarbonyl, tert-pentyloxycarbonyl, etc.

The "alkyl-carbamoyl" includes N-mono-$C_{1-6}$ alkyl-carbamoyl such as N-methylcarbamoyl, N-ethylcarbamoyl, N-propylcarbamoyl, N-butylcarbamoyl, etc.; N,N-di-$C_{1-6}$ alkyl-carbamoyl such as N,N-dimethylcarbamoyl, N,N-diethylcarbamoyl, N,N-dipropylcarbamoyl, N,N-dibutylcarbamoyl, N-ethyl-N-methylcarbamoyl, etc.; and 4- to 6-membered cyclic carbamoyl formed jointly by two alkyl moieties, such as 1-azetidinylcarbonyl, morpholinocarbonyl, 1-pyrrolidinylcarbonyl, 1-piperidinocarbonyl, 1-piperazinylcarbonyl, (1-piperazinylcarbonyl), etc.

The "alkanoyl" includes $C_{1-10}$ alkanoyl such as formyl and $C_{1-9}$ alkyl-carbonyl (e.g. acetyl, propionyl, butyryl, isobutyryl, valeryl, isovaleryl, pivaloyl, hexanoyl, etc.).

The "acyl group" further may be substituted by 1 to 3 substituents such as the substituent groups on the above-mentioned alkyl group.

The "divalent hydrocarbon group" in the term "optionally substituted divalent hydrocarbon group" in this specification includes divalent acyclic hydrocarbon groups such as $C_{1-15}$ alkylene (e.g. methylene, ethylene, propylene, butylene, pentamethylene, hexamethylene, heptamethylene, octamethylene, etc.), $C_{2-16}$ alkenylene (e.g. vinylene, propenylene, 1-butenylene, 2-butenylene, 1-pentenylene, 2-pentenylene, 3-pentenylene, etc.) and $C_{2-16}$ alkinylene (e.g. ethinylene, propinylene, 1-butinylene, 2-butinylene, 1-pentinylene, 2-pentinylene, 3-pentinylene, etc.), phenylene and various combinations of these groups. Preferable examples of the divalent hydrocarbon groups are $C_{1-15}$ alkylene (e.g. methylene, ethylene, propylene, butylene, pentamethylene, hexamethylene, heptamethylene, octamethylene, etc.) and $C_{2-16}$ alkenylene (e.g. vinylene, propenylene, 1-butenylene, 2-butenylene, 1-pentenylene, 2-pentenylene, 3-pentenylene, etc.). The "divalent hydrocarbon group" may contain —CO—, —CON($R^{4a}$)— or —N($R^{4a}$)— (wherein $R^{4a}$ represents a hydrogen or an optionally substituted hydrocarbon group) as a terminal or interrupting group.

The substituent groups which may be substituted on said "divalent acyclic hydrocarbon group" include an optionally substituted alkyl group, an optionally substituted aralkyl group, an optionally substituted aryl group, a hydroxy, an oxo, an amino and a halogen, and preferable examples of them are an optionally substituted alkyl group.

The "alkyl" of said "optionally substituted alkyl group substituted", the "aralkyl" of said "an optionally substituted aralkyl group", and the "aryl" of said "an optionally substituted aryl group" may be respectively the same groups as mentioned hereinbefore.

The substituent group which may be substituted on the "alkyl", "aralkyl" and "aryl" mentioned as substituents on said "divalent acyclic hydrocarbon group" may be the same groups as those mentioned as examples of the substituent group on the "optionally substituted hydrocarbon group". The number of substituents may range from 1 to 4.

The "phenylene" may be substituted. The substituent group which may be substituted on the phenylene includes (i) halogen (e.g. fluorine, chlorine, bromine, iodine, etc.), (ii) $C_{1-4}$ alkyl (e.g. methyl, ethyl, propyl, isopropyl, butyl, etc.), (iii) $C_{1-4}$ alkoxy (e.g. methoxy, ethoxy, propoxy, isopropoxy, etc.), (iv) $C_{1-4}$ alkylthio (e.g. methylthio, ethylthio, propylthio, iso-propylthio, etc), (v) hydroxy, (vi) carboxy, (vii) cyano, (viii) nitro, (ix) amino, (x) mono- or di-$C_{1-4}$ alkylamino (e.g. methylamino, ethylamino, dimethylamino, diethylamino, etc.), (xi) formyl, (xii) mercapto, (xiii) $C_{1-4}$ alkyl-carbonyl (e.g. acetyl, propionyl, butyryl, etc.), (xiv) $C_{1-4}$ alkoxy-carbonyl (e.g. methoxycarbonyl, ethoxycarbonyl, propoxycarbonyl, etc.), (xv) sulfo, (xvi) $C_{1-4}$ alkylsulfonyl (e.g. methylsulfonyl, ethylsulfonyl, propylsulfonyl, etc.), (xvii) carbamoyl and (xviii) mono- or di-$C_{1-4}$ alkyl-carbamoyl (e.g. N-methylcarbamoyl, N-ethylcarbamoyl, N,N-dimethylcarbamoyl, N,N-diethylcarbamoyl, etc.). The number of substituents may range from 1 to 4.

The "heterocyclic group" in the term "optionally substituted heterocyclic group" in this specification includes 5- or 6-membered monocyclic heterocyclic groups which contain 1 to 4 hetero-atoms selected from, for example, oxygen, sulfur and nitrogen, and bicyclic fused heterocyclic groups which contain 1 to 6 hetero-atoms selected from, for example, oxygen, sulfur and nitrogen.

In the above-mentioned "heterocyclic groups", the monocyclic heterocyclic group may be 5- or 6-membered monocyclic aromatic heterocyclic groups which contain 1 to 4 hetero-atoms selected from oxygen, sulfur and nitrogen and saturated or unsaturated monocyclic nonaromatic heterocyclic groups. The examples of them are thienyl (e.g. 2-thienyl, 3-thienyl, etc.), furyl (e.g. 2-furyl, 3-furyl, etc.), pyranyl, 2H-pyrrolyl, pyrrolyl (e.g. 2-pyrrolyl, 3-pyrrolyl, etc.), imidazolyl (e.g. 2-imidazolyl, 4-imidazolyl, etc.), pyrazolyl (e.g. 3-pyrazolyl, 4-pyrazolyl, etc.), isothiazolyl (e.g. 3-isothiazolyl, 4-isothiazolyl, etc.), isoxazolyl (e.g. 3-isoxazolyl, 4-isoxazolyl, etc.), pyridyl (e.g. 2-pyridyl, 3-pyridyl, 4-pyridyl, etc.), pyrazinyl, pyrimidinyl (e.g. 2-pyrimidinyl, 4-pyrimidinyl, etc.) and pyridazinyl (e.g. 3-pyridazinyl, 4-pyridazinyl, etc.). These monocyclic heterocyclic groups may be saturated or partially saturated, and such saturated or partially saturated monocyclic heterocyclic groups may, for example, be pyrrolidinyl (e.g. 2-pyrrolidinyl, 3-pyrrolidinyl, etc.), pyrrolinyl (e.g. 2-pyrrolin-3-yl, etc.), imidazolinyl (e.g. 2-imidazolin-4-yl, etc.), piperidyl (e.g. 2-piperidyl, 3-piperidyl, etc.), piperazinyl (e.g. 2-piperazinyl, etc.) and morpholinyl (e.g. 3-morpholinyl, etc.).

In the above-mentioned "heterocyclic group", the bicyclic fused heterocyclic group may be bicyclic fused aromatic heterocyclic groups which contain 1 to 6 hetero-atoms selected from oxygen, sulfur and nitrogen, or saturated or unsaturated bicyclic fused nonaromatic heterocycle groups. These typical examples are benzodioxanyl (e.g. 1,4-benzodioxan-2-yl, etc.), isobenzofuranyl (e.g. 1-benzofuranyl, etc.), chromenyl (e.g. 2H-chromen-3-yl, etc.), benzothienyl (e.g. 2-benzothienyl, etc.), indolizinyl (e.g. 2-indolizinyl, 3-indolizinyl, etc.), isoindolyl (e.g. 1-isoindolyl, etc.), 3H-indolyl (e.g. 3H-indol-2-yl, etc.), indolyl (e.g. 2-indolyl, etc.), 1H-indazolyl (e.g. 1H-indazol-3-yl, etc.), purinyl (e.g. 8-purinyl, etc.), isoquinolyl (e.g. 1-isoquinolyl, 3-isoquinolyl, etc.), quinolyl (e.g. 2-quinolyl, 3-quinolyl, etc.), phthalazinyl (e.g. 1-phthalazinyl, etc.), naphthyridinyl (e.g. 1,8-naphthyridin-2-yl, etc.), quinoxalinyl (e.g. 2-quinoxalinyl, etc.), quinazolinyl (e.g. 2-quinazolinyl, etc.) and cinnolinyl (e.g. 3-cinnolinyl, etc.). The bicyclic fused heterocyclic group may be partially saturated, and such partially saturated bicyclic fused heterocyclic group includes isochromanyl (e.g. 3-isochromanyl, etc.), indolinyl (e.g. 2-indolinyl, etc.), isoindolinyl (e.g. 1-isoindolinyl, etc.), 1,2,3,4-tetrahydro-2-quinolyl, 1,2,3,4-tetrahydro-3-isoquinolyl, etc.

The substituent group which may be substituted on said "heterocyclic group" includes the same groups as those mentioned as the substituent group which may be substituted on the "aryl" in said "optionally substituted hydrocarbon group", and the number of the substituents may range from 1 to 4 (preferably 1 to 3).

The substituent group on the "optionally substituted hydroxy group" in this specification includes (i) $C_{1-6}$ alkyl (e.g. methyl, ethyl, propyl, isopropyl, butyl, tert-butyl, etc.), (ii) phenyl, (iii) $C_{7-10}$ aralkyl (e.g. benzyl, etc.), (iv) formyl, (v) $C_{1-6}$ alkyl-carbonyl (e.g. methylcarbonyl, ethylcarbonyl, etc.), (vi) phenyloxycarbonyl, (vii) $C_{7-10}$ aralkyloxycarbonyl (e.g. benzyloxycarbonyl, etc.), (viii) pyranyl, (ix) furanyl and (x) silyl, each of which may be substituted. The substituent group which may be substituted on these groups includes halogen (e.g. fluorine, chlorine, bromine, iodine, etc.), $C_{1-4}$ alkyl (e.g. methyl, ethyl, propyl, isopropyl, etc.), phenyl, $C_{7-10}$ aralkyl (e.g. benzyl etc.), nitro, etc. and the number of substituents may range from 1 to 4.

The "substituent" on ring Q includes (i) nitro, (ii) hydroxy, (iii) cyano, (iv) carbamoyl, (v) mono- or di-$C_{1-4}$ alkyl-carbamoyl (e.g. N-methylcarbamoyl, N-ethylcarbamoyl, N,N-dimethylcarbamoyl, N,N-diethylcarbamoyl, etc.), (vi) carboxy, (vii) $C_{1-4}$ alkoxy-carbonyl (e.g. methoxycarbonyl, ethoxycarbonyl, propoxycarbonyl, isopropoxycarbonyl, etc.), (viii) sulfo, (ix) halogen (e.g. fluorine, chlorine, bromine, iodine, etc.), (x) $C_{1-4}$ alkoxy (e.g. methoxy, ethoxy, propoxy, isopropoxy, etc.), (xi) phenoxy, naphthoxy, benzyloxy, (xii) halophenoxy (e.g. o-, m- or p-chlorophenoxy, o-, m- or p-bromophenoxy, etc.), (xiii) $C_{1-4}$ alkylthio (e.g. methylthio, ethylthio, propylthio, isopropylthio, butylthio, etc), (xiv) mercapto, (xv) phenylthio, (xvi) pyridylthio, (xvii) $C_{1-4}$ alkylsulfinyl (e.g. methylsulfinyl, ethylsulfinyl, etc.), phenylsulfinyl, (xviii) $C_{1-4}$ alkylsulfonyl (e.g. methylsulfonyl, ethylsulfonyl, etc.), phenylsulfonyl, (xix) amino, (xx) $C_{1-3}$ acylamino (e.g. acetylamino, propionylamino, etc.), (xxi) mono- or di-$C_{1-4}$ alkylamino (e.g. methylamino, ethylamino, dimethylamino, diethylamino, etc.), (xxii) $C_{1-4}$ alkyl (e.g. methyl, ethyl, propyl, isopropyl, etc.) and (xxiii) $C_{1-4}$ haloalkyl (e.g. trifluoromethyl, trichloromethyl, 2,2,2-trifluoroethyl, etc.).

Ring Q may have 1 to 3 such substituents in substitutable positions on the ring Q, but is preferably unsubstituted.

The term "basic group" in this specification are, for example, (1) (i) an optionally substituted amino group and/or (ii) a group with a molecular weight of not greater than 1000 (preferably not greater than 300), such as a hydrocarbon group which has 1 to 10 (preferably 1 to 5) heterocyclic group(s) containing 1 to 4 hetero-atoms selected from nitrogen, oxygen and sulfur, as terminal and/or interrupting groups and (2) a group of the formula:

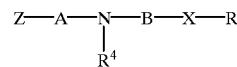

wherein all symbols are of the same meanings as defined hereinbefore.

The above-mentioned "optionally substituted amino group" includes N-mono-substituted amino and N,N-di-substituted amino.

The "N-mono-substituted amino" means an amino group having one substituent group, where the substituent group may, for example, be alkyl (particularly $C_{1-15}$ alkyl and $C_{3-8}$ cycloalkyl), aryl (particularly $C_{6-14}$ aryl), heterocyclic (particularly 5- or 6-membered monocyclic aromatic heterocyclic), and aralkyl (particularly $C_{7-16}$ aralkyl) groups as mentioned above.

The "N,N-di-substituted amino" means an amino group having two substituent groups. One of these two substituent groups are of the same substituent groups as mentioned for "N-mono-substituted amino". The other substituent group are the above-mentioned alkyl (particularly $C_{1-15}$ alkyl and $C_{3-8}$ cycloalkyl), aryl (particularly $C_{6-14}$ aryl) and aralkyl (particularly $C_{7-16}$ aralkyl) groups. The two substituents on the amino group may form a cyclic amino group taken together with the adjacent nitrogen atom. Examples of the cyclic amino group are 1-azetizinyl, 1-pyrrolidinyl, piperidino, morpholino, thiomorpholino, 1-piperazinyl and 1-piperazinyl having the above-mentioned alkyl (particularly $C_{1-15}$ alkyl or $C_{3-8}$ cycloalkyl), aryl (e.g. $C_{6-14}$ aryl) or aralkyl group (e.g. $C_{7-16}$ aralkyl) in the 4-position.

The "heterocyclic group which contains 1 to 4 hetero-atoms selected from nitrogen, oxygen and sulfur" includes (i) 5- or 6-membered heterocyclic groups such as imidazolyl, 2H-pyrrolyl, pyrrolyl, pyrazolyl, isoxazolyl, furazanyl, pyrrolidinyl, imidazolidinyl, imidazolinyl, pyrazolidinyl, pyrazolinyl, pyridyl, pyrazinyl, pyrimidinyl, pyridazinyl, piperidinyl, thiomorpholinyl, morpholinyl, etc. and (ii) bicyclic or tricyclic fused heterocyclic groups such as indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, phenanthrolinyl, phenazinyl, phenothiazinyl, phenoxazinyl, indolinyl, isoindolinyl, etc.

The hydrocarbon group in the term "hydrocarbon group having 1 to 10 (preferably 1 to 5) heterocyclic group(s) containing 1 to 4 hetero-atoms selected from nitrogen, oxygen and sulfur, as terminal and/or interrupting groups" may, for example, be the same group as the "optionally substituted hydrocarbon group" as mentioned above.

The "basic group" may be bonded to $Y^0$ either directly or via oxygen (—O—), nitrogen [—N($R^3$)—], carbonyl (—CO—), thiocarbonyl (—CS—), —S(O)$_n$— (wherein n is 0, 1 or 2), or a combination thereof: —CO—N—($R^3$)—, —CS—N($R^3$)—, —S(O)$_n$—N($R^3$)—, —COO—, —CS—O— (wherein $R^3$ is a hydrogen or an optionally substituted hydrocarbon group).

The "hydrocarbon group" and "substituent" on the hydrocarbon group of the "optionally substituted hydrocarbon group" as mentioned for $R^3$ include the same groups for the "optionally substituted hydrocarbon group" as mentioned hereinbefore.

The term "alkyl", "cycloalkyl", "alkenyl", "aralkyl", "aryl", and "substituent" on these group of the "optionally substituted alkyl, cycloalkyl, alkenyl, aralkyl or aryl group" may, for example, be the same groups as those respectively mentioned for said "optionally substituted hydrocarbon group".

The ring formed jointly by $R^4$ and A may, for example, be an optionally substituted heterocyclic group $Q_1$ which contains 1 to 4 nitrogen atoms.

The ring formed jointly by $R^4$ and B may, for example, be an optionally substituted heterocyclic group $Q_2$ which contains 1 to 4 nitrogen atoms.

The ring formed jointly by $R^3$ and A may for example, be an optionally substituted heterocyclic group $Q_3$ which contains 1 to 4 nitrogen atoms.

The ring formed jointly by $R^4$ and $R^5$ may, for example, be an optionally substituted heterocyclic group $Q_4$ which contains 1 to 4 nitrogen atoms.

The ring formed jointly by $R^4$ and R may, for example, be an optionally substituted heterocyclic group $Q_5$ which contains 1 to 4 nitrogen atoms.

Ring $Q_1$ includes a group of the formula:

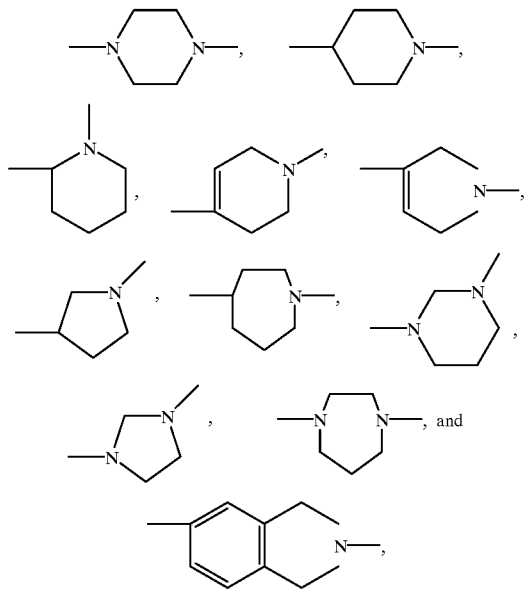

Ring $Q_2$ includes a group of the formula:

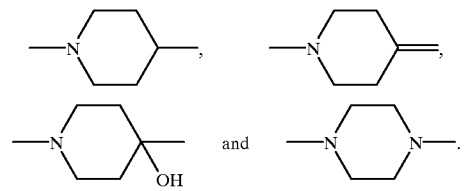

Ring $Q_3$ includes a group of the formula:

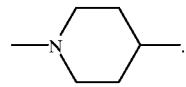

Ring $Q_4$ includes a group of the formula:

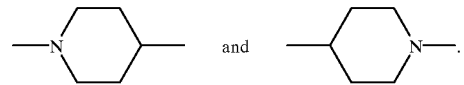

Ring $Q_5$ includes a group of the formula:

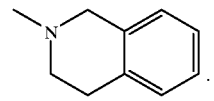

The substituent which may be substituted on the ring $Q_1$, ring $Q_2$, ring $Q_3$, ring $Q_4$ and ring $Q_5$ includes the same groups as mentioned for the substituent on said "optionally substituted heterocyclic group". The number of substituents is 1 to 4.

The protective group of the "optionally protected COOH group" in this specification includes an optionally substituted $C_{1-6}$ alkyl (e.g. methyl, ethyl, propyl, isopropyl, butyl, tert-butyl, etc.), phenyl, trityl and silyl group, etc., each of which may be substituted by 1 to 3 substituents selected from the group consisting of halogen (e.g. fluorine, chlorine, bromine, iodine, etc.), formyl, $C_{1-6}$ alkyl-carbonyl (e.g. acetyl, propionyl, butyryl, etc.) and nitro, etc.

The protective group of the "optionally protected $CH_2OH$ group" in this specification includes an optionally substituted $C_{1-6}$ alkyl (e.g. methyl, ethyl, propyl, isopropyl, butyl, tert-butyl, etc.), phenyl, $C_{7-10}$ aralkyl (e.g. benzyl), formyl, $C_{1-6}$ alkyl-carbonyl (e.g. acetyl, propionyl, butyryl, etc.), phenyloxycarbonyl (e.g. benzyloxycarbonyl, etc.), $C_{7-10}$ aralkyloxy-carbonyl (e.g. benzyloxycarbonyl, etc.), pyranyl, furanyl, silyl, etc., each of which may be substituted by 1 to 4 substituents selected from the group consisting of halogen (e.g. fluorine, chlorine, bromine, iodine, etc.), $C_{1-6}$ alkyl (e.g. methyl, ethyl, propyl, isopropyl, etc.), phenyl, $C_{7-10}$ aralkyl (e.g. benzyl, etc.) and nitro, etc.

The "optionally protected CHO group" in this specification includes CHO, acetals such as di-$C_{1-6}$ alkyl acetal (e.g. dimethyl, acetal, diethyl acetal, etc.) and 1,3-dioxolane.

Ring Q is preferably unsubstituted ring.

R is preferably an optionally substituted $C_{6-14}$ aryl group, an optionally substituted $C_{7-16}$ aralkyl group or an optionally substituted bicyclic aromatic heterocyclic or a saturated or unsaturated bicyclic nonaromatic heterocyclic group which contains 1 to 6 hetero-atoms selected from oxygen, sulfur and nitrogen.

The substituent group which may be substituted on said "$C_{6-14}$ aryl", "bicyclic aromatic heterocyclic group" or "saturated or unsaturated bicyclic non aromatic heterocyclic group" includes the same groups mentioned as the "substituent" on the aryl as an example of the "hydrocarbon group" of said "optionally substituted hydrocarbon group" as mentioned hereinbefore. These groups may be substituted by 1 to 5 substituents as mentioned above in the substitutable positions.

The substituent group which may be substituted on said "$C_{7-16}$ aralkyl" includes the same groups mentioned for the "substituent" which may be substituted on the aralkyl as an example of the "hydrocarbon group" of said "optionally substituted hydrocarbon group", and 1 to 4 of such substituents may be substituted in the substitutable positions.

X is preferably a bond, oxygen or sulfur.

Y is preferably a bond or a group of the formula:

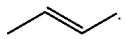

$R^1$ is preferably hydrogen, $C_{1-6}$ alkyl (e.g. methyl, ethyl, propyl, isopropyl, etc.) or phenyl. $R^2$ and $R^3$ each is preferably hydrogen.

$R^4$ is preferably $C_{1-10}$ alkyl (e.g. methyl, ethyl, propyl, isopropyl, etc.), or $R^4$ and A, $R^4$ and B, or $R^3$ and $R^4$ respectively, jointly and taken together with the adjacent nitrogen atom, form a ring. The preferred ring includes pyrrolidine, piperidine, piperazine, etc.

Preferable examples of A and B respectively are $C_{1-10}$ alkylene (e.g. methylene, ethylene, propylene, butylene, pentamethylene, hexamethylene, heptamethylene, octamethylene, etc.) or $C_{2-8}$ alkenylene (e.g. vinylene, propenylene, etc.). The bond between the 3- and 4-positions of the 5-thia-1,8b-diazaacenaphthylene nucleus is preferably a double bond.

The preferred compound of the present invention includes a compound of the formula (I'c):

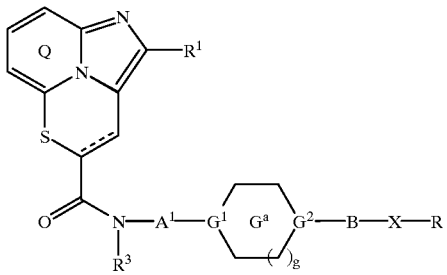

wherein ring Q is an optionally substituted pyridine ring;
$A^1$ is a bond or an optionally substituted divalent hydrocarbon group which may be bonded via —CON($R^{4a}$)—, —CO— or —N($R^{4a}$)—;
B is an optionally substituted divalent hydrocarbon group;
X is a bond, oxygen, sulfur, —N($R^5$)CO—, —CON($R^5$)—, —CO— or —N($R^5$)—;
$R^1$ is a hydrogen, a halogen, an optionally substituted hydroxy group, an optionally substituted hydrocarbon group or an acyl group;
$R^3$, $R^{4a}$ and $R^5$ independently are a hydrogen or an optionally substituted hydrocarbon group;
R is an optionally substituted hydrocarbon group or an optionally substituted heterocyclic group;
one of $G^1$ and $G^2$ is N, and the other is CH or N;
ring $G^a$ is an optionally substituted ring;
g is 0, 1 or 2; and
......... is a single bond or a double bond, or a salt thereof.

In the formula (I'c) as mentioned hereinbefore, preferred are compounds, wherein ring Q represents an unsubstituted pyridine ring; $R^1$ and $R^3$ both represent a hydrogen; $G^1$ represents CH; $G^2$ represents N; g represents 1; R represents an optionally substituted hydrocarbon group or an optionally substituted hetero-cyclic group (both as defined hereinbefore); and the other symbols are of the same meanings as defined hereinbefore. Particularly preferred are compounds, wherein ring $G^a$ is unsubstituted ring; $A^1$ represents a bond or a $C_{1-6}$ alkylene (e.g. methylene, ethylene, propylene, butylene, pentamethylene, etc.); $A^1$ is more preferably a bond; B represents a $C_{1-6}$ alkylene (e.g. methylene, ethylene, propylene, butylene, pentamethylene, etc.); and X represents a bond.

In the formula (I'c) as mentioned hereinbefore, preferred are compounds, wherein ring Q represents an unsubstituted pyridine ring; $R^1$ and $R^3$ both represent a hydrogen; $A^1$ represents a bond; $G^1$ represents CH; $G^2$ represents N; B represents a $C_{1-6}$ alkylene (e.g. methylene, ethylene, propylene, butylene, pentamethylene, etc.); X represents a bond; and R represents an optionally substituted phenyl group (the substituent group(s) of the phenyl may be similar to those which may be substituted on the aryl for said hydrocarbon group). Particularly preferred are compounds, wherein ring $G^a$ is unsubstituted ring; R represents a phenyl group which is substituted by 1 to 3 substituents selected from the group consisting of halogen (e.g. fluorine, chlorine, bromine, iodine, etc.), hydroxy, $C_{1-4}$ alkyl (methyl, ethyl, propyl, isopropyl, butyl, etc.), $C_{1-4}$ haloalkyl (e.g. trifluoromethyl, trichloromethyl, 2,2,2-trifluoroethyl, etc.), $C_{1-4}$ alkoxy (e.g. methoxy, ethoxy, propoxy, isopropoxy, etc.) and $C_{1-4}$ haloalkoxy (e.g. trifluoromethoxy, trichloromethoxy, 2,2,2-trifluoroethoxy, etc.), etc.

The salt of the compound (I) according to the present invention is preferably a physiologically acceptable acid additional salt. Among such salts are salts with inorganic acids (e.g. hydrochloric acid, phosphoric acid, hydrobromic acid, sulfuric acid, etc.) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.). Furthermore, in cases where the compound (I) of the present invention contains an acidic group such as carboxyl, the compound (I) may form physiologically acceptable salts with inorganic bases (e.g. alkali metal or alkaline earth metal elements such as sodium, potassium, calcium, magnesium, etc., or ammonia) or organic bases (e.g. tri-$C_{1-3}$ alkylamines such as triethylamine).

The starting compounds for the synthesis of the compound (I) may also be used in the salt form such as the above salt, but the kind of salt is not limited unless it is detrimental to the reaction.

The compound (I) may contain a double bond within the molecule. Two kinds (Z and E) of stereoisomers in the compound (I) and the mixtures thereof fall within the scope of the present invention.

While the compound (I) may also assume enol- and keto-forms with respect to the oxo group, the respective forms as well as mixtures thereof fall within the scope of the invention.

Some species of the compound (I) have asymmetric carbon within the molecule. And two kinds (R and S) of stereoisomers in the compound (I) and the mixtures thereof fall within the scope of the invention.

The typical compounds of the compound (I) are as follows.

N-[1-(3-Phenylpropan-1-yl)piperidin-4-ylmethyl]-5-thia-1,8b-diazaacenaphthylene-4-carboxamide and its acid additional salt.

N-[1-(3-(2-Fluorophenyl)propan-1-yl)piperidin-4-ylmethyl]-5-thia-1,8b-diazaacenaphthylene-4-carboxamide and its acid additional salt.

N-[1-(2-Fluorophenethyl)piperidin-4-ylmethyl]-5-thia-1,8b-diazaacenaphthylene-4-carboxamide and its acid additional salt.

N-[1-(4-Fluorophenethyl)piperidin-4-ylmethyl]-5-thia-1,8b-diazaacenaphthylene-4-carboxamide and its acid additional salt.

N-[1-(3-Fluorophenethyl)piperidin-4-ylmethyl]-5-thia-1,8b-diazaacenaphthylene-4-carboxamide and its acid additional salt.

N-[1-(3-(2-Chlorophenyl)propan-1-yl)piperidin-4-ylmethyl]-5-thia-1,8b-diazaacenaphthylene-4-carboxamide and its acid additional salt.

N-[1-(3-(2-Chlorophenyl)propan-1-yl)piperidin-4-yl]-5-thia-1,8b-diazaacenaphthylene-4-carboxamide and its acid additional salt.

N-[1-(2-Chlorophenethyl)piperidin-4-ylmethyl]-5-thia-1,8b-diazaacenaphthylene-4-carboxamide and its acid additional salt.

N-[1-(3-Chlorophenethyl)piperidin-4-ylmethyl]-5-thia-1,8b-diazaacenaphthylene-4-carboxamide and its acid additional salt.

N-[1-(4-Chlorophenethyl)piperidin-4-ylmethyl]-5-thia-1,8b-diazaacenaphthylene-4-carboxamide and its acid additional salt.

N-[2-(1-(2-Chlorophenethyl)piperidin-4-yl)ethan-1-yl]-5-thia-1,8b-diazaacenaphthylene-4-carboxamide and its acid additional salt.

N-(1-Phenethylpiperidin-4-ylmethyl)-5-thia-1,8b-diazaacenaphthylene-4-carboxamide and its acid additional salt.

N-[1-(3-Phenylpropan-1-yl)piperidin-4-yl]-5-thia-1,8b-diazaacenaphthylene-4-carboxamide and its acid additional salt.

N-(1-Phenethylpiperidin-4-yl)-5-thia-1,8b-diazaacenaphthylene-4-carboxamide and its acid additional salt.

N-[4-(4-Benzylpiperidin-1-yl)butan-1-yl]-5-thia-1,8b-diazaacenaphthylene-4-carboxamide and its acid additional salt.

N-[4-(4-Phenylpiperidin-1-yl)butan-1-yl]-5-thia-1,8b-diazaacenaphthylene-4-carboxamide and its acid additional salt.

N-[1-(1,4-Benzodioxan-2-ylmethyl)piperidin-4-ylmethyl]-5-thia-1,8b-diazaacenaphthylene-4-carboxamide and its acid additional salt.

(S)-N-[1-(1,4-Benzodioxan-2-ylmethyl)piperidin-4-ylmethyl]-5-thia-1,8b-diazaacenaphthylene-4-carboxamide and its acid additional salt.

(R)-N-[1-(1,4-Benzodioxan-2-ylmethyl)piperidin-4-ylmethyl]-5-thia-1,8b-diazaacenaphthylene-4-carboxamide and its acid additional salt.

N-[1-(3-Phenylpropan-1-yl)piperidin-4-ylmethyl]-3-(5-thia-1,8b-diazaacenaphthylen-4-yl)acrylamide and its acid additional salt.

N-(1-Phenethylpiperidin-4-yl)-3-(5-thia-1,8b-diazaacenaphthylen-4-yl)acrylamide and its acid additional salt.

N-(1-Phenethylpiperidin-4-ylmethyl)-3-(5-thia-1,8b-diazaacenaphthylen-4-yl)acrylamide and its acid additional salt.

The compound (I) of the present invention can be synthesized by, for example, the following process.

wherein $E^1$ represents halogen (e.g. chlorine) or $R_2CO$—O— (wherein $R^2$ is of the same meaning as defined hereinbefore); and the other symbols are of the same meanings as defined hereinbefore.

The compound (I') of the present invention can be synthesized by, for example, the following processes.

Process (A):

wherein E represents a leaving group such as, for example, halogen (e.g. chlorine, bromine, or iodine), methanesulfonyloxy or p-toluenesulfonyloxy; and the other symbols are of the same meanings as defined hereinbefore.

Process (B): Z=CON(R³)

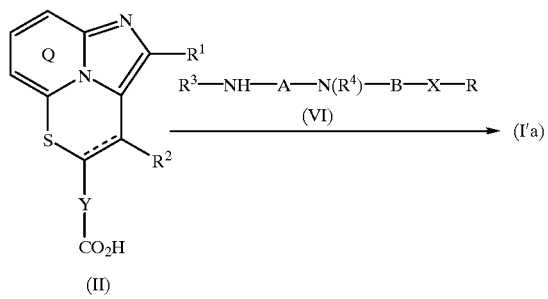

wherein all symbols are of the same meanings as defined hereinbefore.

Process (C): Z=CON(R³)

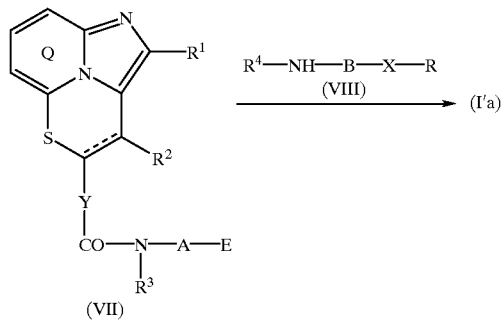

wherein all symbols are of the same meanings as defined hereinbefore.

Process D: Z=CON(R³)

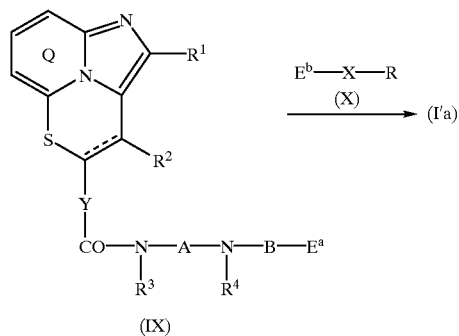

wherein $E^a$ and $E^b$ independently represent a leaving group which leaves on reaction of $E^a$ and $E^b$; thus, for example, when one represents hydrogen, the other represents halogen (e.g. chlorine, bromine, iodine), methanesulfonyloxy or p-toluenesulfonyloxy; and the other symbols are of the same meanings as defined hereinbefore.

Process (E): Z=CON(R³)

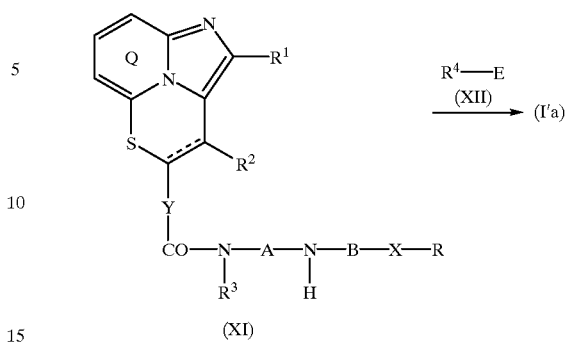

wherein all symbols are of the same meanings as defined hereinbefore.

Process (F): Z=COO

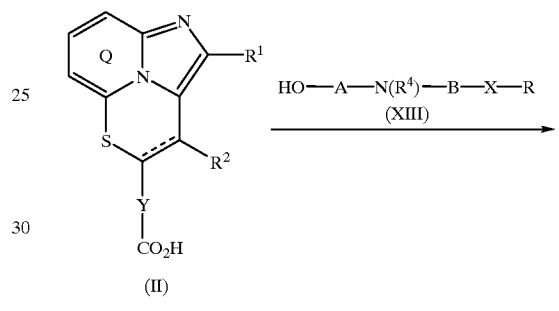

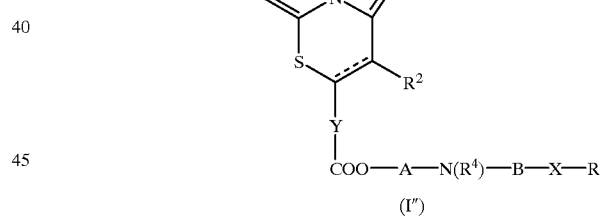

In the synthesis of the compound (I), the reaction between the compound (II') and compound: $R^2$—CO—$E^1$ is carried out using one equivalent to a large excess, preferably 1 to 10 equivalents, of compound $R^2$—CO—$E^1$ to one equivalent of the compound (II'). This reaction may be conducted in the presence of 1 to 10 equivalents of an inorganic base (e.g. potassium carbonate, sodium hydrogen carbonate, etc.) or an organic base (e.g. triethylamine, pyridine, dimethylaniline, 1,4-diazabicyclo[2.2.2]octane (DABCO), etc.). The reaction temperature may range from −30 to +100° C., preferably +25 to 80° C. The solvent which can be used in this reaction includes halogenated hydrocarbons (e.g. methylene chloride, chloroform, dichloroethane, etc.), ethers (e.g. diethyl ether, tetrahydrofuran, etc.), esters (e.g. methyl acetate, ethyl acetate, etc.) and aprotic polar solvents (e.g. N,N-dimethylformamide, dimethyl sulfoxide, acetonitrile, etc.). The reaction time may range from generally 10 minutes to 24 hours, and preferably 1 to 6 hours.

The cyclization reaction proceeds when the acyl compound is heated in the absence of a solvent at 100 to 150° C. This reaction can be carried out by using 1–10 equivalents of an inorganic salt (e.g. sodium hydride, lithium diisopropylamide, potassium carbonate, sodium hydrogen carbonate, etc.) or an organic base (e.g. 4-N,N-dimethylaminopyridine, triethylamine, pyridine, dimethylaniline, 1,4-diazabicyclo-[2.2.2]octane, etc.). The reaction temperature may range from 0 to 150° C. The solvent which can be used in this reaction includes halogenated hydrocarbons (e.g. methylene chloride, chloroform, dichloroethane, etc.), ethers (e.g. diethyl ether, tetrahydrofuran, etc.), esters. (e.g. methyl acetate, ethyl acetate, etc.) and aprotic polar solvents (e.g. N,N-dimethylformamide, dimethyl sulfoxide, acetonitrile, etc.). The reaction time may range from generally 10 minutes to 24 hours, and preferably 1 to 6 hours.

In the reduction of the double bond, one equivalent to a large excess, preferably 2 to 10 equivalents of a reducing agent are used. The reducing agent which can be used in this reaction includes metal hydride complex compounds (e.g. diisobutylaluminum hydride, sodium borohydride, sodium cyanoborohydride, lithium aluminum hydride, etc.) and diborane. The solvent which can be used in this reaction can be selected according to the type of reducing agent and includes alcohols (e.g. methanol, ethanol, etc.), ethers (e.g. tetrahydrofuran, dioxane, diethyl ether, etc.), halogenated hydrocarbons (e.g. methylene chloride, chloroform, etc.) and aprotic polar solvents (e.g. N,N-dimethylformamide, dimethyl sulfoxide, etc.). The reaction time may range from 0.5 to 72 hours, preferably 1 to 24 hours. This reaction can be conducted at −80° to +100° C., preferably −80° to +30° C.

In the synthesis of the compound (I'), the reaction between the compound (V) and the compound (IV) according to Process (A) is carried out by using one equivalent to a large excess (1 to 10 equivalents) of the compound (IV) with respect to the compound (V). This reaction may be conducted in the presence of 1 to 10 equivalents of a basic compound such as sodium hydroxide, potassium hydroxide, sodium hydride, potassium carbonate, triethylamine, diisopropylethylamine, 1,8-diazabicyclo[5.4.0]-7-undecene, or the like. This reaction can be carried out at −20 to +200° C. The solvent which can be used in this reaction includes lower alcohols (e.g. methanol, ethanol, propanol, etc.), ketones (e.g. acetone, methyl ethyl ketone, etc.), ethers (e.g. tetrahydrofuran etc.) and aprotic polar solvents (e.g. N,N-dimethylformamide, dimethyl sulfoxide, etc.). Furthermore, this reaction can be conducted by using one equivalent to a large excess (1 to 10 equivalents) of sodium iodide as a reaction promoter. The reaction time may range from generally 10 minutes to 24 hours, and preferably 0.5 to 6 hours.

The dehydrative condensation reaction between compound (II) and the compound (VI) according to Process (B) can be conducted with advantage by the conventional amide-forming reaction procedure. This amide-forming reaction can be advantageously carried out by using an amide-forming reagent alone. The amide-forming reagent which can be used in this reaction includes 1-ethoxycarbonyl-2-ethoxy-1,2-dihydroquinoline, dicyclohexylcarbodiimide, 1-cyclohexyl-3-(2-morpholinoethyl)carbodiimide, meso-p-toluenesulfonate, N,N'-carbonyldiimidazole, diphenylphosphoramide, diethyl cyanophosphate and 1-ethyl-3-(3-diethylaminopropyl) carbodiimide hydrochloride. The amide-forming reagent is used generally in a proportion of 1 to 3 equivalents to each equivalent of the compound (II). This condensation can be carried out advantageously by adding either a phenol compound (e.g. 2,4,5-trichlorophenol, pentachlorophenol, pentafluorophenol, 2-nitrophenol, 4-nitrophenol, etc.) or an N-hydroxy compound (e.g. N-hydroxysuccinimide, 1-hydroxybenzotriazole, N-hydroxypiperidine, N-hydroxy-5-norbornene-2,3-dicarbodiimide, etc.) and dicyclohexylcarbodiimide, to the compound (II) so as to prepare an active ester and, then, reacting the compound (VI) with this active ester. The proportion of said phenol or N-hydroxy compound is generally 1 to 3 equivalents to each equivalent of the compound (II). The proportion of dicyclohexylcarbodiimide is generally 1 to 3 equivalents to each equivalent of the compound (II). And, this amide-forming reaction can be carried out advantageously by reacting the compound (II) with an acid chloride (e.g. ethyl chlorocarbonate, isobutyl chlorocarbonate, benzyl chlorocarbonate, etc.) so as to convert a mixed acid anhydride and, then, reacting it with the compound (VI). The reaction can also be carried out with advantage by reacting the compound (II) with an acyl chloride (e.g. oxalyl chloride or thionyl chloride) so as to convert the acid chloride and, then, reacting it with the compound (VI). The proportion of the acyl chloride is generally 1 to 3 equivalents per equivalent of the compound (II). These amide- and ester-forming reactions can be carried out using generally 1 to 3 equivalents of the compound (VI) per equivalent of the compound (II). Moreover, if necessary, the reaction can be accelerated by adding an organic base such as a tertiary amine (e.g. triethylamine, pyridine, dimethylpyridine, N-methylpiperidine, etc.). The proportion of such a reaction promotor is generally one equivalent to a large excess (preferably 1 to 10 equivalents) per equivalent of the compound (II). The reaction is generally conducted in the temperature range of −30° C. to +50° C. This reaction may be conducted in the absence of a solvent or in a solvent. The solvent which can be used in this reaction is not limited according to kinds of the reactions and includes ether, toluene, benzene, chloroform, methylene chloride, dioxane and tetrahydrofuran, etc. The reaction time may range from generally 10 minutes to 48 hours, and preferably 1 to 24 hours.

The reaction between the compound (VII) and compound (VIII) according to Process (C) can be conducted typically under the same conditions as the reaction between the compound (V) and the compound (IV) according to Process (A).

The reaction between the compound (IX) and the compound (X) according to Process (D) can be conducted typically under the same conditions as the reaction between the compound (V) and the compound (IV) according to Process (A).

The reaction between the compound (XI) and the compound (XII) according to Process (E) can be conducted typically under the same conditions as the reaction between the compound (V) and the compound (IV) according to Process (A).

The dehydrative condensation reaction between the compound (II) and the compound (XIII) according to Process (F) can be carried out typically under the same conditions as the reaction between the compound (II) and the compound (VI) according to Process (B).

The compound (II') can be synthesized by, for example, the following process.

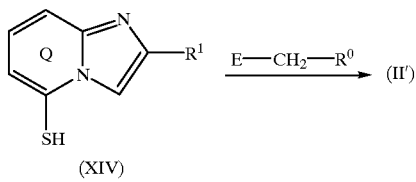

wherein all symbols are of the same meanings as defined hereinbefore.

The reaction between the compound (XIV) and compound: E—CH$_2$—R$^0$ can be conducted typically under the same conditions as the reaction between the compound (V) and the compound (IV) according to Process (A).

The compound (V) can be synthesized by, for example, the following process.

i) Z=CON(R$^3$):

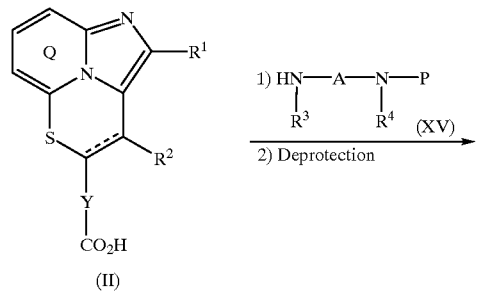

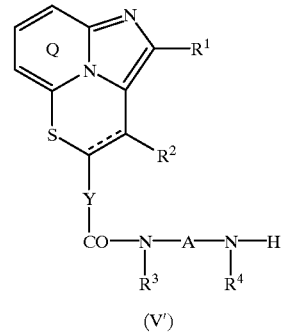

wherein P represents a hydrogen or an amino-protecting group; the other symbols are of the same meanings as defined hereinbefore.

The reaction between the compound (II) and the compound (XV) can be conducted typically under the same conditions as the reaction between the compound (II) and the compound (VI) according to Process (B). When P represents an amino-protecting group, the compound (V') can be obtained by removing the protective group following the condensation reaction. Amino deprotection reactions are per se known reactions and the relevant procedure can be selectively employed.

ii) Z represents CO, —S(O)$_n$— (n=0, 1, 2) or —SO$_2$N(R$^3$)— and Y represents

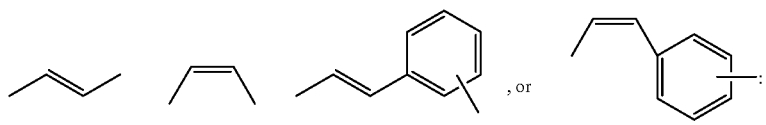

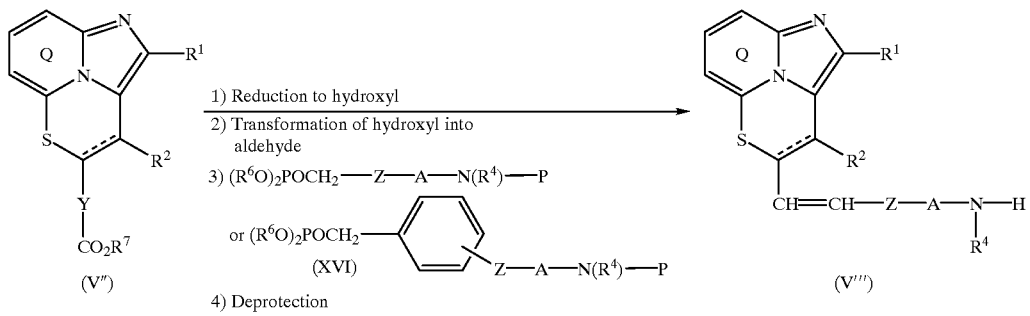

wherein R⁶ represents $C_{1-6}$ alkyl (e.g. methyl, ethyl, propyl, isopropyl, etc.), $C_{6-14}$ aryl (e.g. phenyl etc.) or $C_{7-16}$ aralkyl (e.g. benzyl etc.); R⁷ is of the same meaning as said protective group for the "optionally protected COOH group"; and the other symbols are of the same meanings as defined hereinbefore.

In the reduction of the compound (V"), a reducing agent is used in a proportion of one equivalent to a large excess, preferably 2 to 10 equivalents, relative to the compound (V"). The reducing agent which can be used in this reaction includes metal hydride complex compounds (e.g. diisobutylaluminum hydride, sodium borohydride, sodium cyanoborohydride, lithium aluminum hydride, etc.) and diborane. The solvent can be selected according to the kind of reducing agent used. Examples of the solvent are alcohols (e.g. methanol, ethanol, etc.), ethers (e.g. tetrahydrofuran, dioxane, diethyl ether, etc.), halogenated hydrocarbons (e.g. methylene chloride, chloroform, etc.) and aprotic polar solvents (e.g. N,N-dimethylformamide, dimethyl sulfoxide, etc.). The reaction time may range from 0.5 to 72 hours, preferably 1 to 24 hours. This reaction can be conducted at −80 to +100° C., preferably −80 to +30° C. The oxidation of the resultant alcohol compound to the corresponding aldehyde compound can be carried out by, for example, using 1 to 20 equivalents of an oxidizing agent per equivalent of the alcohol compound. The oxidizing agent which can be used in the reaction includes active manganese dioxide, pyridinium chlorochromate (PCC), pyridinium dichromate (PDC), dimethyl sulfoxide-acid anhydride (e.g. acetic anhydride, trifluoroacetic anhydride, etc.), dimethyl sulfoxide-thionyl chloride, dimethyl sulfoxide-sulfuryl chloride, dimethyl sulfoxide-oxalyl chloride, dimethyl sulfoxide-chlorine and dimethyl sulfoxide-dicyclohexylcarbodiimide (DCC) in the presence of an acid (e.g. phosphoric acid, trifluoroacetic acid, dichloroacetic acid, etc.). The solvent can be selected according to the oxidizing agent used, and includes ethers (e.g. tetrahydrofuran, dioxane, diethyl ether, etc.), halogenated hydrocarbons (e.g. methylene chloride, chloroform, etc.), ketones (e.g. acetone, methyl ethyl ketone, etc.), aprotic polar solvents (e.g. N,N-dimethylformamide, dimethyl sulfoxide, etc.), and so on. The reaction time may range from 0.5 to 48 hours, preferably 1 to 24 hours. The reaction temperature is selected according to the kind of oxidizing agent and may range from −80 to +100° C., preferably from −70 to +30° C.

The reaction between the aldehyde compound and the compound (XVI) can be generally conducted in a solvent with advantage. The solvent which can be used in this reaction includes halogenated hydrocarbons such as methylene chloride, chloroform, etc., ethers such as tetrahydrofuran, dimethoxyethane, dioxane, etc., aromatic hydrocarbons such as benzene, toluene, etc., alcohols such as methanol, ethanol, propanol, etc., amides such as N,N-dimethylforamide etc., aprotic polar solvents such as sulfoxides (e.g. dimethyl sulfoxide), mixtures of such solvents, and other solvents not adversely affecting this reaction. Generally, the compound (XVI) is preferably used in a proportion of 1 to 3 equivalents per equivalent of the aldehyde compound. A basic compound such as sodium hydride is used in a proportion of 1 to 10 equivalents, preferably 1 to 2 equivalents to the compound (XVI). The reaction temperature may range from 0° C. to the boiling point of the solvent, preferably 0 to +80° C. The reaction time may range from about 0.5 to 24 hours, and preferably 0.5 to 10 hours.

The compound (II) can be synthesized by, for example, the following process.

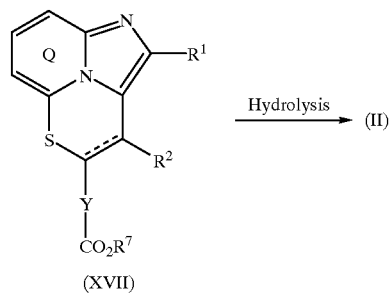

wherein R⁷ represents a carboxy-protecting group; and the other symbols are of the same meanings as defined hereinbefore.

The compound (III) can be produced in the same manner as the compound (II). Referring to the formulas (III) and (III-a), the compounds in which R' represents an optionally protected $CH_2OH$ group or an optionally protected CHO group can be produced by subjecting the compounds in which R' represents carboxy to the per se known reduction reaction.

Hydrolysis of the compound (XVII) can be carried out by treating the compound (XVII) with an acid or a base. Thus, the compound (XVII) is treated in a solution of an acid (e.g. hydrochloric acid, nitric acid, sulfuric acid, hydrobromic acid, iodic acid, etc.) or a base (e.g. sodium hydroxide, potassium hydroxide, barium hydroxide, lithium hydroxide, etc.) in either water or a lower alcohol (e.g. methanol, ethanol, propanol, etc.) at 0 to +100° C., preferably +10 to 50° C., for 0.5 to 50 hours, preferably 1 to 5 hours. The normality of the acid or base is preferably 1 to 10 N and more preferably 2 to 5 N.

The compound (VII) can be synthesized by, for example, the following process.

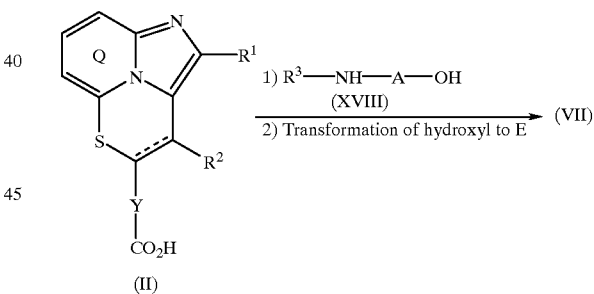

wherein all symbols are of the same meanings as defined hereinbefore.

The reaction between the compound (II) and the compound (XVIII) can be carried out typically under the same conditions as the reaction between the compound (II) and the compound (VI) according to Process (B). Transformation of hydroxyl to E, taking the case in which E represents halogen, is carried out using 1 to 10 equivalents, preferably 2 to 5 equivalents, of a halogenating agent such as a phosphorus halide (e.g. phosphorus trichloride, phosphorus oxychloride, phosphorus pentoxide, phosphorus trichloride, etc.), a red phosphorus-halogen or a thionyl chloride per equivalent of the alcohol compound. When E is toluenesulfonyloxy or methanesulfonyloxy, 1 to 10 equivalents, preferably 2 to 5 equivalents, of toluene-sulfonyl chloride or methanesulfonyl chloride is reacted with one equivalent of the alcohol compound. This reaction can be conducted in the presence of 1 to 10 equivalents of an inorganic base (e.g. potassium carbonate, sodium hydrogen carbonate, etc.) or an organic base (e.g. 4-N,N-dimethylaminopyridine, triethylamine, pyridine, dimethylaniline, 1,4-diazabicyclo [2.2.2]octane (DABCO), etc.). The solvent which can be used in this reaction includes halogenated hydrocarbons (e.g. methylene chloride, chloroform, dichloroethane, etc.), ethers (e.g. diethyl ether, tetrahydrofuran, etc.), esters (e.g. methyl acetate, ethyl acetate, etc.) and aprotic polar solvents (e.g. N,N-dimethylforamide, dimethyl sulfoxide, acetonitrile, etc.). This reaction temperature may range from 0 to +100° C., preferably 0 to +50° C. The reaction time may range from 10 minutes to 100 hours and preferably 3 to 24 hours.

The compound (IX) can be synthesized by, for example, the following process.

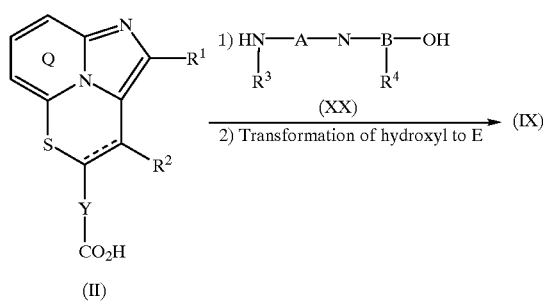

wherein all symbols are of the same meanings as defined hereinbefore.

The reaction for transformation of the compound (II) into the compound (IX) can be carried out typically under the same conditions as the reaction for transformation of the compound (II) into the compound (VII).

The compound (XI) can be synthesized by, for example, the following process.

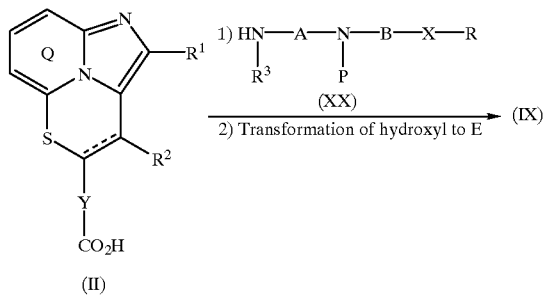

wherein all symbols are of the same meanings as defined hereinbefore.

The reaction for transformation of the compound (II) into the compound (XI) can be carried out typically under the same conditions as the reaction for the transformation of the compound (II) into the compound (V').

The compound (XVII) can be synthesized by, for example, the following process.

i) Where Y represents a bond and $R^2$ represents hydrogen:

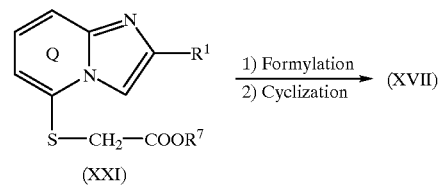

wherein all symbols are of the same meanings as defined hereinbefore.

For the transformation of the compound (XXI) into the compound (XVII), a formylating agent is used in a proportion of 1 to 50 equivalents, preferably 1 to 10 equivalents, per equivalent of the compound (XXI). The formylating agent which can be used in this reaction may, for example, be N,N-dimethylformamide-phosphorus oxychloride (Vilsmier reagent). In this process, the cyclization reaction can be caused to proceed under the formylating conditions. The solvent that can be used includes ethers (e.g. tetrahydrofuran, dioxane, diethyl ether, etc.), halogenated hydrocarbons (e.g. methylene chloride, chloroform, etc.), hydrocarbons (e.g. hexane, pentane, benzene, toluene, etc.), aprotic polar solvents (e.g. N,N-dimethylformamide, dimethyl sulfoxide, etc.), etc. The reaction time may range from 0.5 to 48 hours, preferably 1 to 24 hours. The reaction can be carried out at −20 to +150° C., preferably +80 to 120° C. The formylation of the compound (XXI) can also be carried out by reacting the compound (XXI) with 1 to 3 equivalents of a base such as sodium hydride, potassium hydride, lithium diisopropylamide, and then reacting 1 to 10 equivalents, preferably 2 to 5 equivalents, of a formamide (e.g. N,N-dimethylformamide or N-methylformanilide) or a formic acid ester (e.g. methyl formate or ethyl formate). The solvent which can be used in this formylation reaction includes ethers (e.g. tetrahydrofuran, dioxane, diethyl ether, etc.), hydrocarbons (e.g. hexane, pentane, benzene, toluene, etc.) and aprotic polar solvents (e.g. N,N-dimethylformamide, dimethyl sulfoxide, etc.). The reaction time may range from 0.5 to 48 hours, preferably 1 to 24 hours. This reaction can be carried out at −100 to +50° C. (preferably −80 to +30° C.). The compound (XVII) can be obtained by subjecting to ring closure reaction treating the formylation product with one equivalent to a large excess, preferably 1 to 50 equivalents, of an acid (e.g. acetic acid) at 0 to +150+ C., preferably +80 to 130° C., for 1 to 24 hours, preferably 10 to 20 hours. The solvent which can be used in this reaction includes carboxylic acids (e.g. acetic acid, formic acid, etc.), ethers (e.g. tetrahydrofuran, dioxane, diethyl ether, etc.), hydrocarbons (e.g. hexane, pentane, benzene, toluene, etc.) and aprotic polar solvents (e.g. N,N-dimethylformamide, dimethyl sulfoxide, etc.).

ii) Where Y represents a bond and $R^2$ represents an optionally substituted hydrocarbon group:

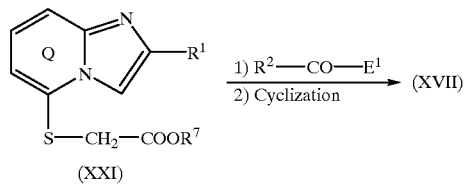

wherein all symbols are of the same meanings as defined hereinbefore.

The reaction between the compound (XXI) and the compound: $R^2CO—E^1$ is carried out using one equivalent to a large excess, preferably 1 to 10 equivalents, of the compound: $R^2CO—E^1$ per equivalent of the compound (XXI). This reaction may be conducted in the presence of 1 to 10 equivalents of an inorganic base (e.g. potassium carbonate, sodium hydrogen carbonate, etc.) or an organic base (e.g. triethylamine, pyridine, dimethylaniline, 1,4-diazabicyclo[2.2.2]octane (DABCO), etc.). The reaction can be carried out at −30 to +100° C., preferably +25 to 80° C. The solvent which can be used in this reaction includes halogenated hydrocarbons (e.g. methylene chloride, chloroform, dichloroethane, etc.), ethers (e.g. diethyl ether, tetrahydrofuran, etc.), esters (e.g. methyl acetate, ethyl acetate, etc.) and aprotic polar solvents (e.g. N,N-dimethylformamide, dimethyl sulfoxide, aceto-nitrile, etc.). The reaction time may range from 10 minutes to 24 hours, and preferably 1 to 6 hours. The ring closure reaction can be accelerated by heating the acyl compound in the absence of a solvent at +100 to 150° C. This reaction can be carried out using 1 to 10 equivalents of an inorganic salt (e.g. sodium hydride, lithium diisopropylamide, potassium carbonate, sodium hydrogen carbonate, etc.) or an organic base (e.g. 4-N,N-dimethylaminopyridine, triethylamine, pyridine, dimethylaniline, 1,4-diazabicyclo[2.2.2]octane, etc.). This reaction can be conducted at 0 to +150° C. The solvent which can be used in this reaction can be selected from halogenated hydrocarbons (e.g. methylene chloride, chloroform, dichloroethane, etc.), ethers (e.g. diethyl ether, tetrahydrofuran, etc.), esters (e.g. methyl acetate, ethyl acetate, etc.) and aprotic polar solvents (e.g. N,N-dimethylformamide, dimethyl sulfoxide, acetonitrile, etc.). The reaction time may range from 10 minutes to 24 hours, and preferably 1 to 6 hours.

iii) Where Y represents

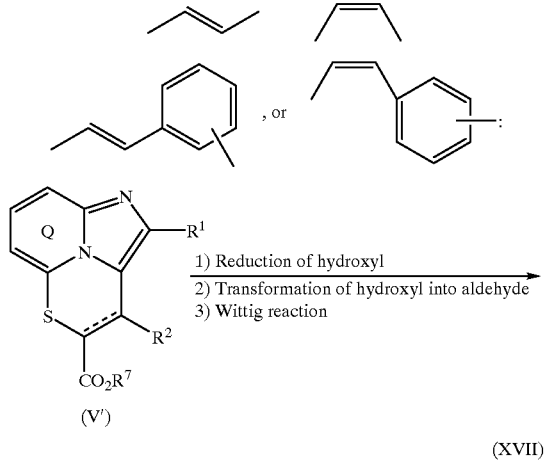

wherein all symbols are of the same meanings as defined hereinbefore.

In the reduction of the compound (V″), a reducing agent is used in a proportion of one equivalent to a large excess, preferably 2 to 10 equivalents, relative to the compound (V′). The reducing agent which can be used in this reaction includes metal hydride complex compounds (e.g. diisobutylaluminum hydride, sodium borohydride, sodium cyanoborohydride, lithium aluminum hydride, etc.) and diborane. The solvent which can be used in this reaction can be selected, according to the kind of reducing agent used, from among, for example, alcohols (e.g. methanol, ethanol, etc.), ethers (e.g. tetrahydrofuran, dioxane, diethyl ether, etc.), halogenated hydrocarbons (e.g. methylene chloride, chloroform, etc.) and aprotic polar solvents (e.g. N,N-dimethylformamide, dimethyl sulfoxide, etc.), etc. The reaction time may range from 0.5 to 72 hours, preferably 1 to 24 hours. This reaction can be carried out at −80 to +100° C., preferably −80 to +30° C. The oxidation of the resultant alcohol compound to the aldehyde compound can be carried out typically using 1 to 20 equivalents of an oxidizing agent per equivalent of the alcohol compound. The oxidizing agent which can be used in this reaction includes active manganese dioxide, pyridinium chlorochromate (PCC), pyridinium dichromate (PDC), dimethyl sulfoxide-acid anhydride (e.g. acetic anhydride, trifluoroacetic anhydride, etc.), dimethyl sulfoxide-thionyl chloride, dimethyl sulfoxide-sulfuryl chloride, dimethyl sulfoxide-oxalyl chloride, dimethyl sulfoxide-chlorine and dimethyl sulfoxide-dicyclohexylcarbodiimide (DCC) in the presence of an acid (e.g. phosphoric acid, trifluoroacetic acid, dichloroacetic acid, etc.). The solvent can be selected according to the oxidizing agent used, and includes ethers (e.g. tetrahydrofuran, dioxane, diethyl ether, etc.), halogenated hydrocarbons (e.g. methylene chloride, chloroform, etc.), ketones (e.g. acetone, methyl ethyl ketone, etc.), aprotic polar solvents (e.g. N,N-dimethylformamide, dimethyl sulfoxide, etc.), etc. The reaction time may range from 0.5 to 48 hours, preferably 1 to 24 hours. The reaction temperature is selected according to the kind of oxidizing agent and may range from −80 to +100° C., preferably −70 to +30° C.

The reaction of the aldehyde obtained as above with a Wittig reagent such as a phosphonium ylide or alkylidenephosphorane is advantageously carried out in a solvent. The solvent which can be used in this reaction includes halogenated hydrocarbons methylene chloride, chloroform, etc.), ethers (e.g. tetrahydrofuran, dimethoxyethane, dioxane, etc.), aromatic hydrocarbons (e.g. benzene, toluene, etc., alcohols (e.g. methanol, ethanol, propanol, etc.), aprotic polar solvents (e.g. amides such as N,N-dimethylforamide, etc.), sulfoxides (e.g. dimethyl sulfoxide etc.), mixtures of said solvents, and other solvents not adversely affecting the reaction. The Wittig reagent is used generally in a proportion of 1 to 3 equivalents per equivalent of the aldehyde compound. This reaction is carried out in the temperature range of 0° C. to the boiling point of the solvent, preferably 0 to 80° C. The reaction time may range from generally 1 to 24 hours, and preferably 0.5 to 10 hours.

The compound (XXI) can be synthesized by, for example, the following process.

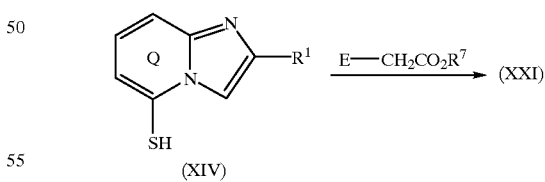

wherein the respective symbols are of the same meanings as defined hereinbefore.

The reaction between the compound (XIV) and the compound: $E—CH_2COOR^7$ can be carried out typically under the same conditions as the reaction between the compound (V) and the compound (IV) according to Process (A).

The objective the compound (III-a) or a salt thereof, which is a useful production intermediate of the objective compound (I) or a salt thereof can be produced by, for example, the following process.

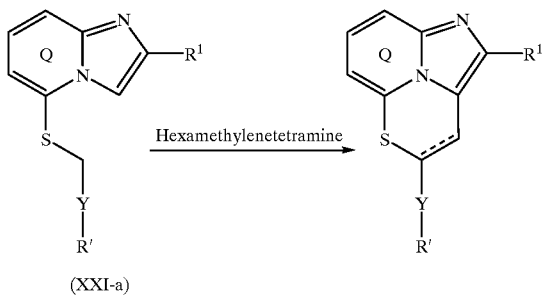

(XXI-a)

wherein all symbols are of the same meanings as defined hereinbefore.

In the above reaction, hexamethylenetetramine is used in a proportion of one equivalent to a large excess, preferably 1 to 10 equivalents, relative to the compound (XXI-a) or a salt thereof. The acid which can be used in this reaction includes an inorganic acid (e.g. hydrochloric acid, sulfuric acid, boric acid, etc.) or an organic acid (e.g. acetic acid, trifluoroacetic acid, formic acid, methanesulfonic acid, etc.). The preferable acid is acetic acid or boric acid. The acid is used in a proportion of one equivalent to a large excess, preferably 1 to 50 equivalents. The reaction temperature may range from about 0° C.–200° C., preferably about 50° C. to 150° C. The solvent which can be used in the reaction includes halogenated hydrocarbons (e.g. methylene chloride, chloroform, dichloroethane, etc.), ethers (e.g. diethyl ether, tetrahydrofuran, etc.), esters (e.g. methyl acetate, ethyl acetate, etc.), protic solvents (e.g. methanol, ethanol, etc.) and aprotic polar solvents (e.g. acetonitrile etc.). The solvent may contain water. Preferably, acetic acid which doubles as an acid and a solvent is used. The reaction time may range from generally 10 minutes to 24 hours, and preferably 1 to 15 hours.

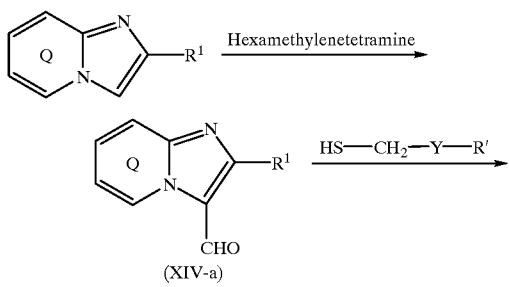

(XIV-a)

In particular, the compound having halogen or a leaving group (such as defined hereinbefore) in position

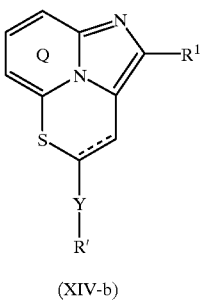

(XIV-b)

wherein all symbols are of the same meanings as defined hereinbefore.

In the above reaction, hexamethylenetetramine is used in a proportion of one equivalent to a large excess, preferably 1 to 10 equivalents, relative to the compound (XIV-a) or a salt thereof. As the acid, an inorganic acid (e.g. hydrochloric acid, sulfuric acid, boric acid, etc.) or an organic acid (e.g. acetic acid, trifluoroacetic acid, formic acid, methanesulfonic acid, etc.) is used. Preferred is acetic acid or boric acid. The proportion of the acid may range from one equivalent to a large excess, preferably 1 to 50 equivalents. The reaction temperature may range from about 0° C. to 200° C., preferably about 50° C. to 150° C. The solvent which can be used in this reaction includes halogenated hydrocarbons (e.g. methylene chloride, chloroform, dichloroethane, etc.), ethers (e.g. diethyl ether, tetrahydrofuran, etc.), esters (e.g. methyl acetate, ethyl acetate, etc.), protic solvents (e.g. methanol, ethanol, etc.), and aprotic polar solvents (e.g. acetonitrile etc.). The solvent may contain water. Preferably, acetic acid which doubles as an acid and a solvent is used. The reaction time may range from 10 minutes to 24 hours, and preferably 1 to 15 hours.

Then, with respect to the compound (XIV-b) or a salt thereof, a compound of the formula: HS—CH$_2$—Y—R' or a salt thereof (wherein all symbols of the same meanings as defined hereinbefore; preferably ethyl thioglycolate or the like) is reacted in a proportion of one equivalent to a large excess, preferably 1 to 10 equivalents. The base which can be used in this reaction may, for example, be an inorganic base (e.g. potassium carbonate, sodium carbonate, etc.), an organic base (e.g. triethylamine, pyridine, dimethylamine, 1,8-diazabicyclo[5.4.0]-7-undecene, etc.), an alcoholate (e.g. sodium methoxide, sodium ethoxide, potassium t-butoxide, etc.), an organometallic reagent (e.g. n-butyllithium etc.), sodium hydride, or sodium amide. The proportion of the base may range from one equivalent to a large excess, preferably 1 to 5 equivalents. The reaction temperature may range from about 0° C. to 200° C., preferably about 25° C. to 100° C. The solvent which can be used in this reaction includes halogenated hydrocarbons (e.g. methylene chloride, chloroform, dichloroethane, etc.), ethers (e.g. diethyl ether, tetrahydrofuran, etc.), esters (e.g. methyl acetate, ethyl acetate, etc.), protic solvents (e.g. acetic acid, methanol, ethanol, etc.), aprotic polar solvents (e.g. N,N-dimethylformamide, dimethyl sulfoxide, acetonitrile, etc.). The reaction time may range from 10 minutes to 24 hours, and preferably 1 to 10 hours.

The compound (XXI-a) or a salt thereof can be produced in the same manner as the compound (XXI) or a salt thereof.

The compound (XIV-a) or a salt thereof can be produced by the per se known technology or in the same manner as the compound (XIV) or a salt thereof.

The compound represented by the formula (A), which is a useful intermediate for producing the compound (II) of this invention, or a salt thereof can be produced by, for example, the methods described below.

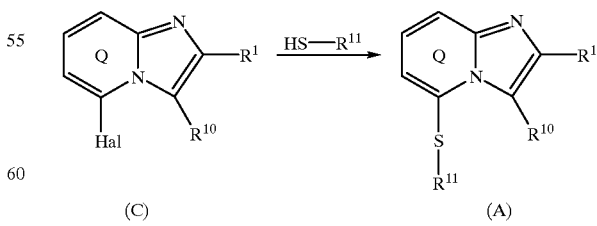

(C)　　　　　　　　　(A)

wherein $R^{10}$ is a hydrogen, an optionally substituted hydroxy group, an optionally substituted hydrocarbon group or an acyl group; Hal is a halogen atom; $R^{11}$ is an optionally substituted alkyl group; and the other symbols are of the same meanings as defined above. $R^{10}$ is of the same meaning as the groups defined in $R^1$. $R^{11}$ is preferably a $C_{1-6}$ alkyl (e.g., methyl, ethyl, propyl, etc.) which may be substituted by $COOR^{15}$ ($R^{15}$ is a lower alkyl group).

In the above-mentioned reaction for synthesizing the compound (A) or a salt thereof, the compound represented by the formula: $HS-R^{11}$ ($R^{11}$ is of the same meaning as defined above), preferably, for example, thioglycolic acid ethyl ester, is employed in an amount of 1 to excess, preferably 1 to 5 equivalents, relative to the compound (C) or a salt thereof. The reaction is conducted in the presence or absence of a base, preferably in the presence of a base. Examples of the base include inorganic bases (e.g., potassium carbonate and sodium carbonate), organic bases (e.g., triethylamine, pyridine, dimethylamine and 1,8-diazabicyclo[5.4.0]-7-undecene), alcoholates (e.g., sodium methylate, sodium ethylate and tert-butoxy potassium), organometallic reagents (e.g., n-butyl lithium), sodium hydride and sodium amide. The amount of the base in this reaction ranges from 1 to excess, preferably from 1 to 5 equivalents. The reaction temperature ranges form 0 to 100° C., preferably from 0 to 50° C. Examples of the solvent in this reaction include halogenated hydrocarbon (e.g., methylene chloride, chloroform and dichloroethane), ethers (e.g., diethyl ether and tetrahydrofuran), esters (e.g., methyl acetate and ethyl acetate), aprotic solvents (e.g., N,N-dimethylformamide, dimethyl sulfoxide, acetonitrile, acetone and toluene). The reaction time ranges usually from 10 minutes to 24 hours, preferably from 1 to 10 hours.

The compound (C) or a salt thereof can be produced by reacting a compound (E) or a salt thereof with a compound (H) or a salt thereof, such as below.

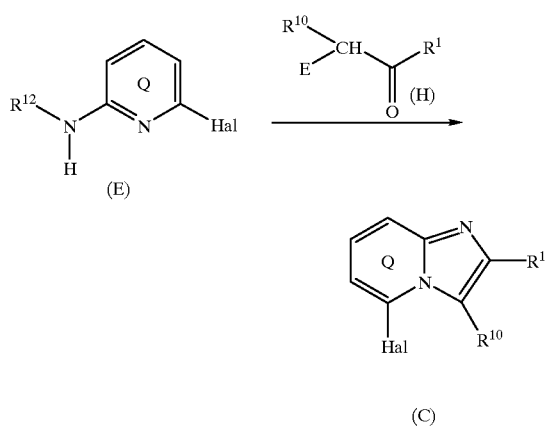

(E)

(C)

wherein $R^{12}$ is a hydrogen or a protective group of amino; and the other symbols are of the same meanings as defined above.

In the above-mentioned reaction for synthesizing the compound (C) or a salt thereof, an α-keto derivative represented by the formula:

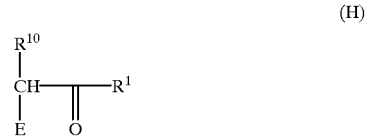

(H)

(wherein all symbols are of the same meaning as defined above), preferably chloroacetaldehyde, is employed in an amount of 1 to a large excess amount, preferably 1 to 5 equivalents, relative to the compound (E) or a salt thereof. The reaction temperature ranges from 0 to 150° C., preferably from 25 to 80° C. Examples of the solvent in this reaction include protonic solvents (e.g., water, methanol, ethanol and n-butanol) and aprotic solvents (e.g., N,N-dimethylformamide, dimethyl sulfoxide, acetonitrile and acetone). The reaction time ranges usually from 10 minutes to 10 hours, preferably from 1 to 4 hours.

The compound (A) or a salt thereof can be produced by reacting a compound (D) or a salt thereof with a compound (H) or a salt thereof, such as below.

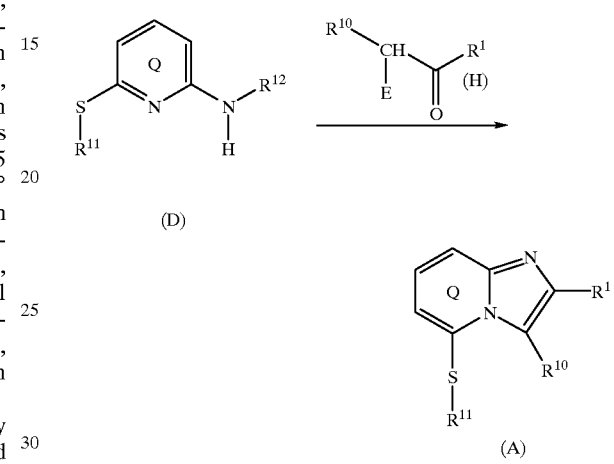

(D)

(A)

wherein all symbols are of the same meanings as defined above.

In the above-mentioned reaction, an α-keto derivative represented by the formula:

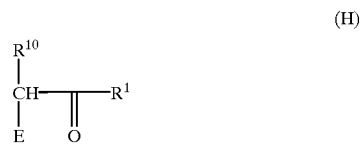

(H)

wherein all symbols are of the same meanings as defined above, is used in an amount of 1 to large excess, preferably from 1 to 5 equivalents, relative to the compound (D) or a salt thereof. The reaction temperature ranges from 0 to 150° C., preferably from 25 to 80° C. Examples of the solvent include protonic solvents (e.g., methanol, ethanol and n-butanol) and aprotic solvents (e.g., N,N-dimethylformamide, dimethyl sulfoxide, acetonitrile and acetone). The reaction time ranges from 10 minutes to 10 hours, preferably from 1 to 4 hours.

The compound (D) or a salt thereof can be produced by reacting the compound (F) or a salt thereof with $R^{12}NH_2$, such as the following reaction.

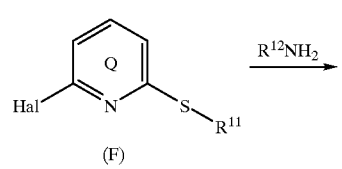

(F)

-continued

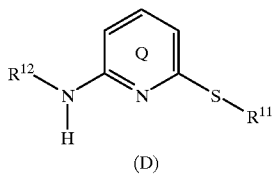

(D)

wherein all symbols are of the same meanings as defined above.

In this reaction, 1 to a large excess amount of the compound represented by the formula: $R^{12}NH_2$ (wherein $R^2$ is of the same meaning as defined above), in an amount of 1 to a large excess, preferably from 1 to 10 equivalents, relative to the compound (F) of a salt thereof. Preferable examples of a compound: $R^{12}NH_2$ include ammonia and formamide. The reaction can be conducted in the absence or the presence of the solvent. Examples of the solvent in this reaction include protonic solvents (e.g., water, methanol, ethanol and n-butanol) and aprotic solvents (e.g., N,N-dimethylformamide, dimethyl sulfoxide, acetonitrile and acetone). The reaction temperature ranges from 1 to 250° C., preferably from 100 to 180° C. The pressure inside the reaction vessel ranges from normal to 40 kgcm$^{-2}$, preferably from normal to 20 kgcm$^{-2}$. The reaction time ranges from 10 minutes to 24 hours, preferably from 1 to 8 hours.

And, the compound (D) or a salt thereof can be produced by reacting a compound (E) or a salt thereof with a compound: $R^{11}$—SH, such as below.

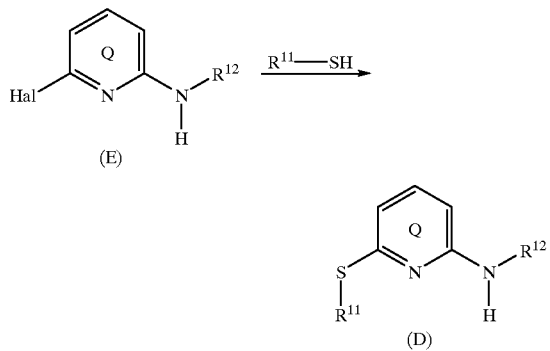

wherein all symbols are of the same meanings as defined above.

In this reaction, the compound represented by the formula: $R^{11}$—SH (wherein $R^{11}$ is of the same meaning as defined above, preferably, thioglycolic acid ethyl ester) is employed in an amount of 1 to excess, preferably from 1 to 5 equivalents, relative to the compound (E) or a salt thereof. The reaction is conducted in the presence or absence of a base. Examples of the base to be employed include inorganic bases (e.g., potassium carbonate and sodium carbonate), organic bases (e.g., triethylamine, pyridine, dimethylamine and 1,8-diazabicyclo[5.4.0]-7-undecene), alcoholates (e.g., sodium methylate, sodium ethylate and tert-butoxy potassium), organometallic reagents (e.g., n-butyl lithium), sodium hydride and sodium amide. The amount of the base in this reaction ranges from 1 to excess, preferably from 1 to 5 equivalents. The reaction temperature ranges from 0 to 100° C., preferably from 30 to 80° C. Examples of the solvent in this reaction include halogenated hydrocarbons (e.g., methylene chloride, chloroform and dichloroethane), ethers (e.g., diethyl ether and tetrahydrofuran), esters (e.g., methyl acetate and ethyl acetate), aprotic solvents (e.g., N,N-dimethylformamide, dimethyl sulfoxide, acetonitrile, acetone and toluene). The reaction time ranges usually from 10 minutes to 24 hours, preferably from 1 to 10 hours.

The compounds (E) and (F), or their salts can be produced from the compound (G) by the following reactions.

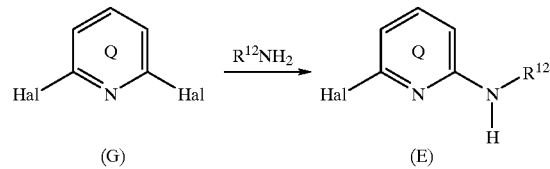

wherein all symbols are of the same meanings as defined above.

In this reaction, the compound: $R^{12}NH_2$ ($R^{12}$ is of the same meanings as defined above, preferably ammonia and formamide) is employed in an amount ranging from 1 to a large excess, preferably from 1 to 10 equivalents, relative to the compound (G) or a salt thereof. The reaction is conducted in the absence or presence of a solvent. Examples of the solvent to be employed include protonic solvents (e.g., water, methanol, ethanol and n-butanol), aprotic solvents (e.g., N,N-dimethylformamide, dimethyl sulfoxide, acetonitrile and acetone). The reaction temperature ranges from 1 to 250° C., preferably from 100 to 150° C. The pressure inside the reaction vessel ranges from normal to 50 kgcm$^{-2}$, preferably from normal to 20 kgcm$^{-2}$. The reaction time ranges from 10 minutes to 24 hours, preferably from 1 to 8 hours.

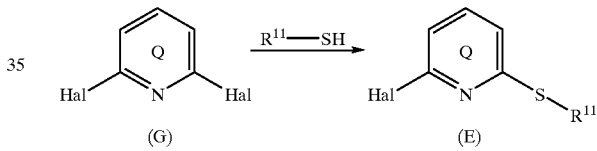

wherein all symbols are of the same meanings as defined above.

In this reaction, the compound: $R^{11}$—SH (wherein $R^4$ is of the same meaning as defined above, preferably, e.g., thioglycolic acid ethyl ester) is employed in an amount of 1 to excess, preferably from 1 to 2 equivalents, relative to the compound (G) or a salt thereof. The reaction is conducted in the presence or absence of a base. Examples of the base to be employed include inorganic bases (e.g., potassium carbonate and sodium carbonate), organic bases (e.g., triethylamine, pyridine, dimethylamine and 1,8-diazabicyclo[5.4.0]-7-undecene), alcoholates (e.g., sodium methylate, sodium ethylate and tert-butoxy potassium), organometallic reagents (e.g., n-butyl lithium), sodium hydride and sodium amide. The amount of the base in this reaction ranges from 1 to excess, preferably from 1 to 2 equivalents. The reaction temperature ranges from 0 to 100° C., preferably from 0 to 50° C. Examples of the solvent in this reaction include halogenated hydrocarbons (e.g., methylene chloride, chloroform and dichloroethane), ethers (e.g., diethyl ether and tetrahydrofuran), esters (e.g., methyl acetate and ethyl acetate), aprotic solvents (e.g., N,N-dimethylformamide, dimethyl sulfoxide, acetonitrile, acetone and toluene). The reaction time ranges usually from 10 minutes to 24 hours, preferably from 1 to 10 hours.

The compound (B) can be derived from a compound (A-2) or a salt thereof which is the compound (A) in which $R^{11}$ is $R^{14}$ ($R^{14}$ is alkyl group), by dealkylation.

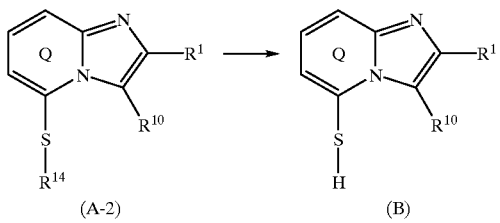

(A-2) → (B)

wherein $R^{14}$ is alkyl.

The "alkyl" of $R^{14}$ includes $C_{1-6}$ alkyl such as methyl, ethyl, propyl.

In this reaction, a base is employed in an amount of 1 to large excess relative to the compound (A-2) or a salt thereof. Examples of the base to be employed include inorganic bases (e.g., potassium carbonate and sodium carbonate), organic bases (e.g., triethylamine, pyridine, dimethylamine and 1,8-diazabicyclo[5.4.0]-7-undecene), alcoholates (e.g., sodium methylate, sodium ethylate and tert-butoxy potassium), organometallic reagents (e.g., n-butyl lithium), sodium hydride and sodium amide, preferably sodium hydride, n-butyl lithium, tert-butoxy potassium and sodium amide. The reaction temperature ranges from 50 to 200° C., preferably from 100 to 180° C. Examples of the solvent in this reaction include halogenated hydrocarbons (e.g., chloroform and dichloroethane), ethers (e.g., tetrahydrofuran), esters (e.g., ethyl acetate), aprotic solvents (e.g., N,N-dimethylformamide, dimethyl sulfoxide, acetonitrile, toluene and xylene). The reaction time ranges usually from 10 minutes to 10 hours, preferably from 1 to 3 hours.

Additionally stating, the compound (II) can be converted, by for example the method shown below, to the compound (I-1) included in the compound (I).

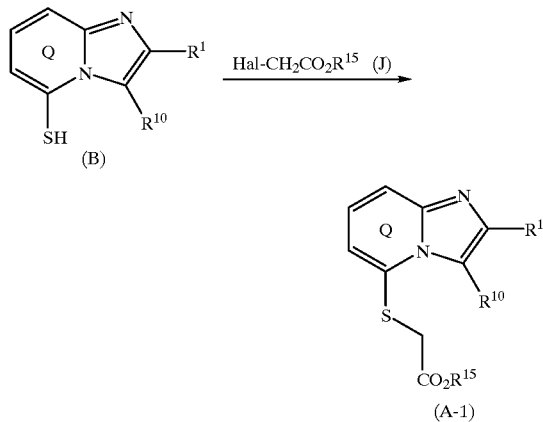

wherein $R^{15}$ is a lower alkyl group such as methyl, ethyl; and other symbols are of the same meanings as defined above.

One equivalent to a large excess (1 to 10 equivalents) of the compound: Hal—$CH_2COOR^{15}$ is employed relative to the compound (B), or a salt thereof. And, 1 to 10 equivalents of a basic compound such as sodium hydroxide, potassium hydroxide, sodium hydride, potassium carbonate, triethylamine, diisopropyl ethylamine and 1,8-diazabicyclo[5.4.0]-7-undecene may optionally be employed. The reaction can be conducted at temperatures ranging from −20 to +200° C. Examples of the solvent in this reaction include water, lower alcohols (e.g., methanol, ethanol and propanol), ketones (e.g., acetone and methyl ethyl ketone), ethers (e.g., tetrahydrofuran) and aprotic solvents (e.g., N,N-dimethylformamide and dimethyl sulfoxide). For this reaction, one equivalent to a large excess amount (1 to 10 equivalents) of sodium iodide can be optionally added as an accelerating agent of this reaction. The reaction time ranges usually from 10 minutes to 24 hours, preferably from 0.5 to 6 hours.

In the above reactions according to the present invention and the reactions for synthesizing the starting compounds used there, where any starting material compound has an amino group, a carboxyl group and/or a hydroxyl group as a substituent, such functional group or groups may be previously blocked or masked using protective groups which are conventionally used in peptide chemistry and the objective compound can then be obtained by eliminating the protective group or groups after the intended reaction.

The protective group that can be used for the amino function includes $C_{1-6}$ alkyl-carbonyl (e.g. formyl, methylcarbonyl, ethylcarbonyl, etc.), phenylcarbonyl, $C_{1-6}$ alkyl oxycarbonyl (e.g. methoxycarbonyl, ethoxycarbonyl, etc.), phenyloxycarbonyl (e.g. benzoxycarbonyl etc.), $C_{7-10}$ aralkyl(oxy)carbonyl (e.g. benzyloxycarbonyl etc.), trityl, phthaloyl, etc., each of which may be substituted. The substituent group includes halogen (e.g. fluorine, chlorine, bromine, iodine, etc.), $C_{1-6}$ alkyl-carbonyl (e.g. methylcarbonyl, ethylcarbonyl, butylcarbonyl, etc.), nitro, etc. The number of substituents may range from 1 to about 3.

The protective group that can be used for the carboxyl function includes $C_{1-6}$ alkyl (e.g. methyl, ethyl, propyl, isopropyl, butyl, tert-butyl, etc.), phenyl, trityl, silyl, etc., each of which may be substituted. The substituent group includes halogen (e.g. fluorine, chlorine, bromine, iodine, etc.), $C_{1-6}$ alkyl-carbonyl (e.g. formyl, methylcarbonyl, ethyl-carbonyl, butylcarbonyl, etc.), nitro, etc. The number of substituents may range from 1 to about 3.

The protective group that can be used for the hydroxyl function includes $C_{1-6}$ alkyl (e.g. methyl, ethyl, propyl, isopropyl, butyl, tert-butyl, etc.), phenyl, $C_{7-10}$ aralkyl (e.g. benzyl etc.), $C_{1-6}$ alkyl-carbonyl (e.g. formyl, methylcarbonyl, ethylcarbonyl, etc.), phenyloxycarbonyl, $C_{7-10}$-aralkyloxy-carbonyl (e.g. benzyloxycarbonyl etc.), pyranyl, furanyl, silyl, etc., each of which may be substituted. The substituent group present includes halogen (e.g. fluorine, chlorine, bromine, iodine, etc.), $C_{1-6}$ alkyl, phenyl, $C_{7-10}$ aralkyl, nitro, etc. The number of substituents may range from 1 to about 4.

Removal of such protective groups can be carried out by techniques either known per se or analogous to known techniques. By way of illustration, a method using an acid or a base, reductive deprotection, and a technique using any of ultraviolet light, hydrazine, phenylhydrazine, sodium N-methyldithiocarbamate, tetrabutylammonium fluoride, palladium acetate, etc. can be mentioned.

The compound (I) obtained by any of the above processes can be isolated and purified by the conventional procedures such as recrystallization, distillation, chromatography, etc. When the thus-obtained compound (I) is the free compound, it can be converted to a salt by a per se known procedure or an analogous procedure (e.g. neutralization). Conversely when the product compound is a salt, it can be converted to either the free compound or a different salt by the per se known procedure or an analogous procedure.

Furthermore, when the compound (I) is an optically active compound, it can be fractionated into the S- and R-compounds by the conventional optical resolution technology.

The starting compounds for the compound (I) or salt of the present invention may be salts and the kind of salt is not critical only if the reaction involved proceeds successfully. For example, the kinds of salts mentioned for the compound (I) can be used.

The compound (I) and its salt of the present invention have an excellent LDL receptor up-regulating lipids-lowering and blood sugar-lowering activity, and are low toxicity. Therefore, the compound (I) or a salt thereof can be safely used in mammals (e.g. mouse, rat, hamster, rabbit, cat, dog, bovine, horse, sheep, monkey, man, etc.) as a prophylactic and therapeutic agent for atherosclerotic diseases, hyperlipemia (hyperlipidemia), diabeties and diabetic complications.

The compound (I) or its salt can be administered either in the bulc form or in the form of a pharmaceutical composition. The pharmaceutical composition can be provided by the established pharmaceutical procedure using conventional carriers and additives selected from among, for example, an excipient (e.g. calcium carbonate, kaolin, sodium hydrogen carbonate, lactose, starch, crystalline cellulose, talc, granulated sugar, porous substances, etc.), a binder (e.g. dextrin, gum, starch alcohol, gelatin, hydroxypropylcellulose, hydroxypropylmethyl-cellulose, pullulan, etc.), a disintegrator (e.g. carboxymethylcellulose calcium, croscarmellose sodium, crospovidone, low-substitution-degree hydroxypropyl-cellulose, partially dextrinized starch, etc.), a lubricant (e.g. magnesium stearate, calcium stearate, talc, starch, sodium benzoate, etc.), a coloring agent (e.g. tar color, caramels, iron sesquioxide, titanium oxide, riboflavins, etc.), a corrigent (e.g. sweeteners, perfumes, etc.), a stabilizer (e.g. sodium sulfite etc.), a preservative (e.g. parabens, sorbic acid, etc.), in suitable proportions. The prophylactic and therapeutic agent or composition of the present invention should contain a therapeutically or prophylactically effective amount of the compound (I) or a salt thereof. The proportion of the compound (I) or salt in the total composition is generally 0.1 to 100 weight %. The pharmaceutical composition of the invention may contain one or more other medicinally active substances in addition to the compound (I) or salt thereof and there is no limitation on the kinds of active substances which can be used only if the object of the invention can be accomplished. Thus, such active substances can be formulated in suitable amounts. The specific dosage form which can be used includes tablets (inclusive of sugar-coated tablets and film-coated tablets), pills, capsules, granules, fine granules, powders, syrups, emulsions, suspensions, injections, inhalants, ointments. Such dosage forms can be respectively manufactured by the known pharmaceutical procedures (such as the procedures directed in the Japanese Pharmacopoeia).

Specifically, tablets can be prepared by granulating the compound (I) or a salt thereof as it is, or granulating a homogeneous mixture of it with an excipient, binder, disintegrator or other appropriate additives according to a suitable method, then adding a lubricant, etc., and compressing the mixture for shaping. Alternatively, tablets can directly be prepared by compressing the compound (I) or a salt thereof as it is or a homogeneous mixture of it with an excipient, binder, disintegrator or other appropriate additives. Furthermore, tablets can also be prepared by compressing granules per se prepared in advance or a homogeneous mixture of it with an appropriate additive. If necessary, the composition may contain a colorant, corrigent, etc. Further, the composition may be coated with an appropriate coating agent. Injections can be prepared by charging a suitable amount of the compound (I) or a salt thereof into water for injection, physiological saline, Ringer's solution in the case of using an aqueous solvent, or into vegetable oils in the case of using a nonaqueous solvent to make a suitable amount of the suspension or emulsion of it, and also by sealing a suitable amount of the compound (I) or a salt thereof into vials for injection.

Examples of the carriers for oral composition include materials conventionally used in pharmaceutics such as starch, mannit, crystalline cellulose, carboxymethylcellulose, etc. Examples of the carriers for injections include distilled water, physiological saline, glucose solution, transfusion solution, etc. In addition, additives generally used in pharmaceutics can appropriately be added.

The pharmaceutical composition of the present invention is of value as a drug because of its low toxicological potential and excellent LDL receptor up-regulating, lipids-lowering and blood sugar-lowering actions. Thus, the composition of the invention is useful for the prophylaxis and therapy of diseases caused by said pharmacological properties. Specifically, the composition can be used in the treatment or prevention of atherosclerosis, hyperlipemia, diabetes, diabetic complications, diabetic nephropathy, diabetic neuropathy, diabetic retinopathy, arrhythmia, peripheral vascular disease, thrombosis, disorders of pancreas, sequelae of myocardial infarction, valvular disease of the heart, and other diseases.

The compound (I) and its salt have cholesterol and triglyceride lowering activities. These biological properties suggest that the compound (I) and its salt are particularly suited for the therapy and prophylaxis of hyperlipemia (particularly hypertriglyceridemia, hyperlipoproteinemia, hypercholesterolemia) and the associated atherosclerotic vascular lesions and secondary diseases (e.g. coronary artery disease, ischemic diseases of the brain, aneurysm, cerebral arteriosclerosis, peripheral arteriosclerosis, intermittent claudication, gangrene).

In the treatment of these diseases, the compound (I) or salt of the invention can be used prophylactically and/or therapeutically, either independently or in combination with other lipids-lowering or cholesterol lowering agents. In such cases, the active substances are preferably administered in an oral dosage form, and, if necessary, they can be administered rectally in the suppository form. The active substances which can be used in multiple-drug regimens include (1) fibrates (e.g. clofibrate, bezafibrate, gemfibrozil, etc.), nicotinic acid and its derivatives and analogs (e.g. acipimox, probucol, etc.), (2) bile salt binding resins (e.g. colestyramin, colestipol, etc.), cholesterol absorption inhibitors (e.g. sitosterol, neomycin, etc.), (3) cholesterol biosynthesis inhibitors (e.g. HMG-CoA reductase inhibitors such as lovastatin, simvastatin, pravastatin, etc.), and squalene epoxidase inhibitors (e.g. NB-598 and its analogs, etc.).

Among other active substances which can be used in combination with the compound (I) or salt are squalene-lanosterol cyclases (e.g. decalin derivatives, azadecalin derivatives, indan derivatives, etc.).

Furthermore, because the compound (I) and its salt have lipids-lowering activity and blood sugar-lowering activity in diabetic fatty rats, they are expected to ameliorate insulin resistance. In consideration of these biological properties, the compound (I) and its salt are particularly suited for the treatment or prevention of hyperglycemia and its secondary diseases such as diabetic nephropathy, diabetic neuropathy, diabetic retinopathy, diabetic vascular diseases, etc. or insulin resistance and its associated diseases such as hypertension and impaired glucose tolerance, and even such secondary diseases as diseases of the heart, ischemic diseases of the brain, intermittent claudication, gangrene, etc.

In the prophylaxis and treatment of those diseases, the compound (I) or a salt thereof can be independently used or in combination with other hypoglycemic agents or antihypertensive agents. In such applications, these compounds are preferably administered in oral dosage forms and, in certain cases, may be administered rectally in the suppository form. The active substances that can be used in combination include (1) insulin preparations (e.g. human insulin etc.), (2) sulfonylureas (e.g. glibenclamide, glyclazide, etc.), (3) α-glucosidase inhibitors (e.g. vogribose, acarbose, etc.), (4) insulin sensitizers (e.g pioglitazone, troglitazone, etc.), (5) aldose reductase inhibitors (e.g. epalrestat, tolrestat, etc.), and glycosylation inhibitors (e.g. aminoguanidine etc.).

It is also possible to use the compound (I) or salt of the invention in combination with known antihypertensive agents such as (1) diuretics (e.g. furosemide, spironolactone, etc.), (2) sympatholytics (e.g. atenolol etc.), (3) angiotensin II receptor antagonists (e.g. losartan, candesartan, etc.), (4) angiotensin I converting enzyme inhibitors (e.g. enalapril maleate, delapril hydrochloride, etc.), and (5) calcium channel blockers (e.g. nifedipine, manidipine hydrochloride, etc.).

The compound (I) or salt of the invention is suitable for the prophylaxis and therapy of diseases associated with hyperchylomicronemia such as acute pancreatitis. As the mechanism of onset of pancreatitis, it has been suggested that microthrombus are formed in pancreatic capillaries due to chylomicrons, or because of hyperchylomicronemia, the triglycerides decomposed by pancreatic lipase increase free fatty acids which stimulate the locus strongly. Therefore, as lowering as the compound (I) or salt of the invention has triglyceride lowering activity, it can be independently used alone or in combination with known therapies in the prevention and treatment of pancreatitis. For the prophylaxis and therapy of this disease, the compound (I) or a salt thereof can be administered orally or topically, either independently or in combination with known active compounds such as aprotinin, gabaxate methanesulfonate, nafamstat methanesulfonate, citicoline, urinastatin, etc.

Another noteworthy indication for the compound (I) or a salt thereof is secondary hyperlipidemia. It includes diabetes, insulin resistance (syndrome X), hypopituitarism, nephrotic syndrome and chronic renal failure. While hyperlipidemia results from these diseases, it is generally acknowledged that in many cases hyperlipidemia exacerbate these diseases, thus forming a vicious cycle. In view of its lipid lowering activity, the compound (I) and its salt are suitable for the treatment and prevention of progression of such diseases. In this indication, the compound (I) or a salt thereof can be independently administered or in combination with known active compounds (e.g. dried thyroid, levothyroxine sodium, liothyronine sodium, etc.), or in combination with prednisolone, methylprednisolone succinate sodium, furosemide, bumetanide, azosemide, etc. in combination therapies with therapeutic drugs for kidney diseases. These medications are preferably made by the oral route.

A further possible application of the compound (I) or salt of the present invention is suppression of thrombus formation. Blood triglyceride and coagulation factor VII levels are positively correlated with each other and blood coagulation is suppressed when the triglyceride level is low due to the diet rich in ω-3 fatty acids, suggesting that hypertriglyceridemia encourages thrombus formation. Moreover, since VLDL in patients with hyperlipemia is known to increase secretion of plasminogen activator inhibitor from the vascular endothelial cells more prominently than does VLDL in patients with normolipidemia, it is thought that triglycerides may decrease fibrinogenolysis. Therefore, in view of its triglyceride-lowering activity, the compound (I) or a salt thereof is considered suitable for the prevention and treatment of thrombosis. In this application, the compound (I) or salt can be independently administered or in combination with known therapeutic drugs such as dipyridamole, dilazep hydrochloride, thrombolytics (e.g. heparin sodium, urokinase, etc.) and, or anti-thrombins (e.g. aspirin, sulfinpyrazone, ticlopidine hydrochloride, cilostazol, etc.), preferably by the oral route.

The dosage of the pharmaceutical composition of the present invention is dependent on the route of administration, patient's clinical status, age and body weight, and other factors but when it is to be administered orally to an adult patient, for example as a therapeutic agent for arteriosclerosis, a hypoglycemic agent, or a therapeutic agent for diabetic complications, the recommended daily dosage in terms of the compound (I) or a salt thereof is 0.2 to 50 mg/kg, preferably 0.5 to 30 mg/kg, which dosage is to be administered in one to a few divided doses. The route of administration may be whichever of the oral route and a non-oral route.

BEST MODE FOR CARRYING OUT THE INVENTION

The experimental data demonstrating the pharmacologic effects of the compound (I) and its salt are as follows.

Experimental Example 1

Increase in LDL-binding to HepG2 cells

LDL-binding was measured according to the method of J. L. Goldstein. HepG2 cells were purchased from ATCC (American type culture collection) and seeded in 6-well plate with collagen coating (Sumitomo Bakelite), and cultured in Eagle's minimum essential medium (MEM) containing 10%-fetal bovine serum at 37° C. for 4 days. After washing cells were cultured with MEM containing 10%-LPDS in the presence of test compound at a concentration of 10 $\mu$M for 20 hours. 25-Hydroxycholesterol was used as a negative control at a concentration of 2.3 $\mu$M. After washing with phosphate buffered saline cells were incubated with MEM containing 25 mM-HEPES and 1%-bovine serum albumin (fatty acid free) in the presence of human [$^{125}$I]LDL (4 $\mu$g/ml) at 6° C. for 2 hours. After washing cells bound [$^{125}$I]LDL was dissociated with dextran sulfate and the radioactivity was measured (total binding). [$^{125}$I]LDL binding to cells was also measured in the presence of LDL (300 $\mu$g/ml) as a non-specific binding (NSB). Specific [$^{125}$I]LDL-binding was calculated by subtracting NSB from total binding and was normalized by protein content measured by the method of lowry. Data was expressed as percentage of the control.

The result was shown in Table 1.

TABLE 1

| Example No. | LDL binding (% of control) |
| --- | --- |
| 1 | 202.6 |
| 2 | 172.5 |
| 3 | 194.2 |
| 9 | 247.4 |
| 10 | 169.3 |

TABLE 1-continued

| Example No. | LDL binding (% of control) |
|---|---|
| 22 | 125.5 |
| 26 | 189.1 |
| 27 | 167.6 |
| 28 | 193.7 |
| 36 | 218.5 |
| 46 | 165.8 |
| 52 | 183.1 |
| 67 | 162.0 |
| 76 | 281.5 |
| 77 | 168.3 |
| 80 | 248.3 |
| 113 | 140.4 |
| 117 | 136.8 |

Experimental Example 2

Cholesterol lowering activity in Golden hamster

Male Golden Syrian hamsters (110–130 g) were maintained freely on water and a laboratory diet (CE-2, Clea Japan Inc., Tokyo). Test compound was given orally at a dose of 20 mg/kg/d once daily for 4 days. Blood was taken from orbital sinus and plasma total cholesterol and triglyceride were measured an automatic analyzer (Hitachi 7070, Hitachi Ltd., Tokyo) using commercial kits (Wako Pure Chemical Industries, Osaka), and plasma HDL-cholesterol using a commercial kit (Kyowa Medex Co., Ltd., Tokyo) before and after the treatment of compound. Non-HDL cholesterol was calculated by subtracting HDL-cholesterol from total cholesterol.

The results are shown in Table 2.

TABLE 2

| Example No. | Non-HDL-C (% of control) | TG (% of control) |
|---|---|---|
| 1 | 68.6 | 78.4 |
| 2 | 65.1 | 102.2 |
| 3 | 69.5 | 91.3 |
| 9 | 62.3 | 67.0 |
| 10 | 61.0 | 70.8 |
| 22 | 58.8 | 62.3 |
| 26 | 66.4 | 82.0 |
| 27 | 73.9 | 83.9 |
| 28 | 62.9 | 61.3 |
| 29 | 68.1 | 73.9 |
| 32 | 76.6 | 76.5 |
| 33 | 77.1 | 85.6 |
| 34 | 72.2 | 74.7 |
| 36 | 61.9 | 74.7 |
| 39 | 62.7 | 62.6 |
| 46 | 69.6 | 72.4 |
| 58 | 74.0 | 71.2 |
| 67 | 62.0 | 67.9 |
| 68 | 58.5 | 74.3 |
| 70 | 47.9 | 71.2 |
| 74 | 73.5 | 67.9 |
| 76 | 74.0 | 58.1 |

Non-HDL-C (non-HDL-cholesterol): [total cholesterol]-[HDL-cholesterol]
TG: triglyceride It is apparent from Table 2 that whereas blood total cholesterol (TC) was elevated gradually in the control group, the elevation of blood cholesterol was suppressed by about 15–30% in the test groups. Thus, in the groups treated with compound (I) or salt of the invention, the non-HDL-cholesterol level was suppressed as compared with the control group. Because the compound (I) and its salt lower both the blood LDL- and VLDL-cholesterol levels, they are of value for the treatment of cardiovascular diseases such as atherosclerosis and hyperlipemia.

Experimental Example 3

Lipid-lowering effect in Wistar fatty rats

Male Waistar fatty rats were maintained on free access to normal diet (CE-2, Clea Japan) and water. Body weights were measured at 10 weeks of age and the blood was taken from the orbital sinus and determined for plasma total cholesterol (TC), triglyceride (TG), glucose, and HDL-cholesterol (HDL-C) with Wako Pure Chemical and Kyowa Medex kits using an automatic analyzer (Hitachi 7070). Non-HDL-cholesterol (non-HDL-C) was calculated by subtracting HDL-cholesterol from total cholesterol.

The rats were divided into 2 groups (n=6) and 30 mg/kg/day of the test compound (Example 22) in 0.5% methylcellulose solution was administered by a stomach tube to one of the groups once daily for 2 weeks (test group). 0.5% Methylcellulose solution only was similarly administered to the other group (control group). On day 14, body weights were measured again and the blood was taken from the orbital sinus and determined for plasma total cholesterol, HDL-cholesterol, triglyceride, and glucose in the same manner as before.

The results are presented in Table 3.

TABLE 3

| | Non-HDL-C (mg/dl) | Glucose (mg/dl) | TG (mg/dl) |
|---|---|---|---|
| Control group | 39.9 ± 3.7 | 366.8 ± 72.0 | 324.7 ± 74.2 |
| Test group (Example 22) | 30.0 ± 5.2** | 268.2 ± 81.9* | 258.3 ± 38.4* |

Mean ± SD (n = 6)
*Significant at $P < 0.05$ as compared with the control group of Wistar fatty rats
**Significant at $P < 0.01$ as compared with the control group of Wistar fatty rats It is apparent from Table 3 that the compound of the invention lowered not only glucose but also lowered non-HDL-cholesterol and triglyceride in the plasma significantly. Therefore, the compound of the invention is useful for the prevention and treatment of, for example, hyperglycemia or atherosclerosis. Since the compound of the invention lowers glucose significantly, it is of use as a therapeutic drug for diabetes or diabetic complications.

The following examples and reference examples are intended to describe the present invention merely in further detail and should by no means be construed as defining the scope of the invention. In these reference examples and examples, the term "room temperature" means 0 to +30° C., the ratio of solvents indicated in the description of the purification procedure by silica gel column chromatography is by volume (v/v), and the symbols used in the description of NMR data have the following meanings.

| | |
|---|---|
| s | singlet |
| d | doublet |
| t | triplet |
| quint | quintet |
| m | multiplet |
| br | broad |
| Hz | Hertz |

| CDCl₃ | deuteriated chloroform |
| CD₃OD | deuteriated methanol |
| DMSO-D₆ | deuteriated dimethyl sulfoxide |

Reference Example 1

Synthesis of N-[2-[1-(tert-butoxycarbonyl)piperidin-4-ylidene]ethyl]phthalimide

1) Synthesis of tert butyl 4-(2-hydroxyethylidene)-piperidine-1-carboxylate

To a solution of 19.901 g (73.888 mM) of tert-butyl 4-(ethoxycarbonylmethylene)piperidine-1-carboxylate in 100 ml of toluene was added 123 ml (185 mM) of 1.5 M diisobutylaluminum hydride-toluene at −78° C. and the mixture was stirred at −78° C. for 1 hour. Then, methanol was added at −78° C. and the mixture was stirred for 0.5 hour to decompose the excess diisobutylaluminum hydride. Then, water was added under ice-cooling and the mixture was stirred for 2 hours. The resulting precipitate was filtered off with the aid of celite and the celite was washed with ethyl acetate. The filtrate and washes were pooled and the solvent was distilled off under reduced pressure. The residue was purified by silica gel column chromatography (hexane/ethyl acetate=3/1 to 1/1) to provide the title compound.

Colorless liquid. Yield 15.292 g (91%)

$^1$H-NMR (CDCl₃, 200 MHz) δ:1.469 (9 H, s), 1.735 (H, br s), 2.174 (2 H, s, 5.9 Hz), 2.260 (2 H, t, 5.9 Hz), 3.383–3.462 (4 H, m), 4.172 (2 H, d, 7.0 Hz), 5.493 (1 H, t, 7.0 Hz).

2) Synthesis of tert-butyl 4-(2-bromoethylidene)-piperidine-1-carboxylate

To a solution of 15.292 g (67.277 mM) of tert-butyl 4-(2-hydroxyethylidene)piperidine-1-carboxylate and 24.5 g (74.0 mM) of carbon tetrabromide in 150 ml of acetonitrile was added 19.4 g (74.0 mM) of triphenylphosphine at −78° C. Then, at room temperature, the mixture was stirred for 2 hours. This reaction mixture was distilled under reduced pressure to remove the solvent. To the residue was added diethyl ether, followed by stirring, and the resulting precipitate was filtered off and washed with diethyl ether. The filtrate and washes were pooled and the solvent was distilled under reduced pressure. The residue was purified by silica gel column chromatography (hexane/ethyl acetate=30/1 to 9/1) to provide the title compound.

Colorless liquid. Yield 11.283 g (58%)

$^1$H-NMR (CDCl₃, 200 MHz) δ:1.471 (9 H, s), 2.203 (2 H, t, 6.0 Hz), 2.297 (2 H, t, 5.7 Hz), 3.405–3.478 (4 H, m), 4.007 (2 H, d, 8.4 Hz), 5.621 (1 H, t, 8.4 Hz).

3) Synthesis of N-[2-[1-(tert-butoxycarbonyl)piperidin-4-ylidene]ethyl]phthalimide A solution of 5.775 g (19.900 mM) of tert-butyl 4-(2-bromoethylidene)piperidine-1-carboxylate and 4.05 g (21.9 mM) of potassium phthalimide in 100 ml of N,N-dimethylformamide was stirred at 100° C. for 1 hour. This reaction mixture was poured in water and extracted with 3 portions of ethyl acetate. The pooled organic layer was dried over anhydrous magnesium sulfate (MgSO₄) and the solvent was distilled off under reduced pressure. The residue was purified by silica gel column chromatography (hexane/ethyl acetate=6/1 to 3/1) to provide the title compound.

Light-yellow solid. Yield 5.473 g (77%)

$^1$H-NMR (CDCl₃, 200 MHz), δ:1.469 (9 H, s), 2.143 (2 H, t, 5.2 Hz), 2.458 (2 H, t, 5.6 Hz), 3.401 (2 H, t, 5.9 Hz), 3.480 (2 H, t, 5.7 Hz), 4.294 (2 H, d, 7.4 Hz), 5.367 (1 H, t, 7.3 Hz), 7.693–7.759 (2 H, m), 7.801–7.885 (2 H, m).

Reference Example 2

Synthesis of N-[2-[1-(tert-butoxycarbonyl)-1,2,3,6-tetrahydropyridin-4-yl]ethyl]phthalimide 1) Synthesis of tert-butyl 4-(2-hydroxyethyl)-3,6-dihydro-2H-pyridine-1-carboxylate To a suspension of 0.66 g (17.5 mM) of lithium aluminum hydride in 100 ml of diethyl ether was added a solution of 4.719 g (17.521 mM) of tert-butyl 4-(ethoxycarbonylmethyl)-3,6-dihydro-2H-pyridine-1-carboxylate in 50 ml of tetrahydrofuran dropwise under ice-cooling and the mixture was stirred at room temperature for 1 hour. To this reaction mixture was added ethyl acetate with ice-cooling to decompose the excess lithium aluminum hydride. Then, water was added until a white precipitate had formed. The precipitate was filtered off with the aid of celite and the celite was washed with ethyl acetate. The filtrate and washes were pooled and the solvent was distilled off under reduced pressure. The residue was purified by silica gel column chromatography (hexane/ethyl acetate=3/1 to 1/1) to provide the title compound.

Colorless liquid. Yield 3.259 g (82%)

$^1$H-NMR (CDCl₃, 200 MHz) δ:1.467 (9 H, s), 1.663 (1 H, br s), 2.086 (2 H, br s), 2.282 (2 H, t, 6.0 Hz), 3.502 (2 H, t, 5.7 Hz), 3.709 (2 H, t, 6.4 Hz), 3.879 (2 H, br s), 5.480 (1 H, br s).

2) Synthesis of tert-butyl 4-(2-bromoethyl)-3,6-dihydro-2H-pyridine-1-carboxylate The procedure of Reference Example 1–2) was generally followed to provide the title compound as light-yellow liquid.

$^1$H-NMR (CDCl₃, 200 MHz) δ:1.469 (9 H, s), 2.071 (2 H, br s), 2.573 (2 H, t, 7.3 Hz), 3.443 (2 H, t, 7.3 Hz), 3.500 (2 H, t, 5.8 Hz), 3.884 (2 H, br s), 5.476 (1 H, br s).

3) Synthesis of N-[2-[1-(tert-butoxycarbonyl)-1,2,3,6-tetrahydropyridin-4-yl]ethyl]phthalimide The procedure of Reference Example 1–3) was generally followed to provide the title compound as light-yellow liquid.

$^1$H-NMR (CDCl₃, 200 MHz) δ:1.456 (9 H, s), 2.152 (2 H, br s), 2.376 (2 H, t, 6.8 Hz), 3.475 (2 H, t, 5.7 Hz), 3.757 (2 H, s), 3.793 (2 H, t, 7.0 Hz), 5.347 (1 H, br s), 7.689–7.755 (2 H, m), 7.796–7.895 (2 H, m).

Reference Example 3

Synthesis of tert-butyl 4-amino-1-piperidinecarboxylate

1) Synthesis of N-(1-benzylpiperidin-4-yl)trifluoroacetamide

To a solution of 25.94 g (136.3 mM) of 4-amino-1-benzylpiperidine and 22.1 ml (27.3 mM) of pyridine in 250 ml of tetrahydrofuran was added a solution of 21.2 ml (43.9 mM) of trifluoroacetic anhydride in 100 ml of tetrahydrofuran dropwise under ice-cooling and the mixture was stirred at room temperature overnight. The solvent was then distilled off under reduced pressure and the residue was diluted with water and extracted with 3 portions of ethyl acetate. The pooled organic layer was dried over MgSO₄ and the solvent was distilled off under reduced pressure. The residue was purified by silica gel column chromatography (hexane/ethyl acetate=3/1) and the purified solid was rinsed with diethyl ether to provide the title compound.

White solid. Yield 39.23 g (100%)

$^1$H-NMR (CDCl$_3$, 200 MHz) δ:2.045–2.330 (4 H, m), 2.675–2.804 (2 H, m), 3.515–3.573 (2 H, m), 3.987–4.074 (1 H, m), 4.150 (2 H, s), 7.371–7.479 (5 H, m), 7.957-7.806 (1 H, m).

2) Synthesis of tert-butyl 4-trifluoroacetamide-1-piperidinecarboxylate

Using 4 g of 10% palladium-on-carbon (50% hydrous) as a catalyst, 11.431 g (39.927 mM) of N-(1-benzyl-piperidin-4-yl)trifluoroacetamide was hydrogenated in 100 ml of methanol at room temperature and atmospheric pressure until the starting compound had disappeared (i.e. for 2 hours). The catalyst in the reaction mixture was filtered off with the aid of celite and washed with methanol. The filtrate and washes were pooled and the solvent was distilled off under reduced pressure to provide crude N-(piperidin-4-yl)trifluoroacetamide. This crude product was not purified but used as it was in the next reaction. To a solution of the crude N-(piperidin-4-yl)trifluoroacetamide and 6.68 ml (47.9 mM) of triethylamine in tetrahydrofuran (50 ml)-methanol (20 ml) was added 9.59 g (43.9 mM) of di-tert-butyl dicarbonate dropwise at room temperature and the mixture was stirred at the prevailing temperature overnight. The solvent was then distilled off under reduced pressure and the residue was purified by silica gel column chromatography (hexane/ethyl acetate=3/1) to provide the title compound.

White solid. Yield 8.505 g (72%)

$^1$H-NMR (CDCl$_3$, 200 MHz) δ:1.321–1.555 (2 H, m), 1.456 (9 H, s), 1.921–1.995 (2 H, m), 2.786–2.923 (2 H, m), 3.890–4.140 (3 H, m), 6.528 (1 H, br d, 7.0 Hz).

3) Synthesis of tert-butyl 4-amino-1-piperidinecarboxylate

A solution of 7.35 g (24.8 mM) of tert-butyl 4-trifluoroacetamido-1-piperidinecarboxylate and 5.71 g (41.3 mM) of potassium carbonate in 50 ml of methanol was stirred at 60° C. for 8 hours. This reaction mixture was poured in aqueous solution of sodium hydrogen carbonate and the mixture was saturated with sodium chloride and extracted with 10 portions of ethyl acetate. The pooled organic layer was dried over MgSO$_4$ and the solvent was distilled off under reduced pressure to recover the title compound as light-yellow liquid. This crude product was not purified but used as it was in the next reaction.

$^1$H-NMR (CDCl$_3$, 200 MHz), δ:1.076–1.358 (4 H, m), 1.456 (9 H, s), 1.725–1.822 (2 H, m), 2.703–2.855 (3 H, m), 3.993–4.077 (2 H, m).

Reference Example 4

Synthesis of N-[2-[1-(tert-butoxycarbonyl)-2,5-dihydro-1H-pyrrol-3-yl]ethyl]phthalimide 1) Synthesis of tert-butyl 3-oxopyrrolidine-1-carboxylate To a solution of 25.63 g (0.2942 M) of 3-pyrrolidinol in tetrahydrofuran (150 ml)-ethanol (50 ml) was added 70.6 g (0.324 M) of di-tert-butyl dicarbonate dropwise at room temperature and the mixture was stirred at room temperature for 1 hour. The solvent was then distilled off under reduced pressure to provide crude t-butyl 3-hydroxypyrrolidine-1-carboxylate. To a solution of 56.0 g (0.441 M) of oxalyl chloride in 400 ml of tetrahydrofuran was added 62.6 ml (0.883 M) of dimethyl sulfoxide dropwise at −78° C. and the mixture was stirred for 5 minutes. Then, a solution of the above crude tert-butyl 3-hydroxypyrrolidine-1-carboxylate in 150 ml of tetrahydrofuran was added dropwise and the mixture was stirred at −78° C. for 15 minutes. To this reaction mixture was added 246 ml (1.77 M) of triethylamine, and after room temperature was reestablished, the mixture was poured in water and extracted with 3 portions of ethyl acetate. The pooled organic layer was dried over MgSO$_4$ and the solvent was distilled off under reduced pressure. This crude product was purified by silica gel column chromatography (hexane/ethyl acetate=6/1 to 3/1) to provide the title compound.

Yellow liquid. Yield 50.44 g (93%)

$^1$H-NMR (CDCl$_3$, 200 MHz) δ:1.487 (9 H, s), 2.588 (2 H, t, 7.9 Hz), 3.756 (2 H, s), 3.777 (2 H, t, 7.8 Hz).

2) Synthesis of tert-butyl 3-(ethoxycarbonylmethyl)-2,5-dihydropyrrole-1-carboxylate A suspension of 60% sodium hydride in liquid paraffin, 3.41 g (85.2 mM), was washed with 3 portions of hexane and suspended in 50 ml of toluene. To this suspension was added a solution of 33.8 g (151 mM) of ethyl diethylphosphonoacetate in 50 ml of toluene dropwise under ice-cooling and the mixture was stirred at room temperature for 30 minutes. This mixture was added to a solution of 25.42 g (137.2 mM) of 1-(tert-butoxycarbonyl)pyrrolidin-3-one in 200 ml of toluene dropwise at room temperature and the mixture was stirred at room temperature for 1.5 hours. This reaction mixture was diluted with diethyl ether and washed with water and the aqueous layer was extracted with 2 portions of diethyl ether. The pooled organic layer was dried over MgSO$_4$ and the solvent was distilled off under reduced pressure. The resulting crude product was purified by silica gel column chromatography (hexane/ethyl acetate=6/1 to 3/1) to provide the title compound.

Yellow liquid. Yield 8.201 g (23%)

$^1$H-NMR (CDCl$_3$, 200 MHz) δ:1.280 (3 H, t, 7.1 Hz), 1.472 (9 H, s), 3.146 (2 H, s), 4.119–4.226 (6 H, m), 5.613–5.651 (1 H, m).

3) Synthesis of tert-butyl 3-(2-hydroxyethyl)-2,5-dihydropyrrole-1-carboxylate

To a suspension of 1.22 g (32.1 mM) of lithium aluminum hydride in 150 ml of tetrahydrofuran was added a solution of 8.201 g (32.122 mM) of tert-butyl 3-(ethoxycarbonylmethyl)-2,5-dihydropyrrole-1-carboxylate in 50 ml of tetrahydrofuran dropwise under ice-cooling and the mixture was stirred at room temperature for 1 hour. To this reaction mixture was added ethyl acetate with ice-cooling to decompose the excess lithium aluminum hydride, and water was added until a white precipitate had formed. The precipitate was filtered off with the aid of celite and the celite was washed with ethyl acetate. The filtrate and washes were pooled and the solvent was distilled off under reduced pressure. The residue was purified by silica gel column chromatography (hexane/ethyl acetate=3/1 to 1/1) to provide the title compound.

Colorless liquid. Yield 4.826 g (70%)

$^1$H-NMR (CDCl$_3$, 200 MHz) δ:1.473 (9 H, s), 1.767 (1 H, br s), 2.387 (2 H, br t, 6.2 Hz), 3.769 (2 H, t, 6.3 Hz), 4.083–4.139 (4 H, m), 5.499–5.537 (1 H, m).

4) Synthesis of N-[2-[1-(tert-butoxycarbonyl)-2,5-dihydro-1H-pyrrol-3-yl]ethyl]phthalimide To a solution of 4.818 g (22.590 mM) of tert-butyl 3-(2-hydroxyethyl)-2,5-dihydropyrrole-1-carboxylate and 4.72 ml (33.9 mM) of triethylamine in 100 ml of diethyl ether was added 2.10 ml (27.1 mM) of methanesulfonyl chloride dropwise under ice-cooling and the mixture was stirred at 0° C. for 0.5 hour. This reaction mixture was poured in aqueous solution of sodium hydrogen carbonate and extracted with 3 portions of diethyl ether. The pooled organic layer was dried over $MgSO_4$ and the solvent was distilled off under reduced pressure. The residue was dissolved in 100 ml of N,N-dimethylformamide, followed by addition of 4.60 g (24.8 mM) of potassium phthalimide, and the mixture was stirred at 100° C. for 5 hours. This reaction mixture was poured in water and stirred and the precipitate that formed was recovered by filtration, rinsed with water, and dried to provide the title compound.

Light-brown solid. Yield 5.522 g (71%)

$^1$H-NMR ($CDCl_3$, 200 MHz) δ: 1.482 (9 H, s), 2.498 (2 H, t, 6.9 Hz), 3.848 (2 H, t, 7.1 Hz), 4.075 (4 H, s), 5.504 (1 H, s), 7.702–7.744 (2 H, m), 7.832–7.874 (2 H, m).

Reference Example 5

Synthesis of 1-(3-phenylpropan-1-yl)piperidin-3-ylmethylamine dihydrochloride

1) Synthesis of N-[1-(3-phenylpropan-1-yl)piperidin-3-ylmethyl]phthalimide

To a solution of 10.07 g (87.43 mM) of 3-piperidinemethanol and 19.1 g (96.2 mM) of 1-bromo-3-phenylpropane in 150 ml of acetonitrile was added 18.1 g (131 mM) of potassium carbonate and the mixture was stirred at room temperature for one day. This reaction mixture was poured in water and extracted with 3 portions of ethyl acetate. The pooled organic layer was dried over $MgSO_4$ and the solvent was distilled off under reduced pressure to provide crude 1-(3-phenylpropan-1-yl)piperidine-3-methanol. This crude product was not purified but used as it was in the next reaction. To a solution of this crude 1-(3-phenylpropan-1-yl)piperidine-3-methanol and 14.6 ml (105 mM) of triethylamine in 150 ml of tetrahydrofuran was added a solution of 11.0 g (96.2 mM) of methanesulfonyl chloride in 50 ml of tetrahydrofuran dropwise under ice-cooling and the mixture was further stirred at the prevailing temperature for 0.5 hour. This reaction mixture was poured in water and extracted with 3 portions of ethyl acetate. The pooled organic layer was dried over $MgSO_4$ and the solvent was distilled off under reduced pressure. The residue was dissolved in 500 ml of N,N-dimethylformamide, followed by addition of 17.8 g (96.2 mM) of potassium phthalimide, and the mixture was stirred at 100° C. overnight. This reaction mixture was poured in water and extracted with 3 portions of ethyl acetate. The pooled organic layer was dried over $MgSO_4$ and the solvent was distilled off under reduced pressure. The residue was purified by silica gel column chromatography (hexane/ethyl acetate=1/1 to ethyl acetate) to provide the title compound.

Yellow liquid. Yield 25.905 g (82%)

$^1$H-NMR ($CDCl_3$, 200 MHz) δ: 0.954–1.123 (1 H, m), 1.437–2.153 (8 H, m), 2.336 (2 H, t, 7.9 Hz), 2.595 (2 H, t, 7.7 Hz), 2.752–2.807 (2 H, m), 3.542 (1 H, dd, 7.0 Hz, 13.6 Hz), 3.624 (1 H, dd, 6.9 Hz, 13.7 Hz), 7.105–7.295 (5 H, m), 7.666–7.769 (2 H, m), 7.804–7.871 (2 H, m).

2) Synthesis of N-tert-butoxycarbonyl-[1-(3-phenylpropan-1-yl)piperidin-3-ylmethyl]amine To a solution of 10.770 g (29.713 mM) of N-[1-(3-phenylpropan-1-yl)piperidin-3-ylmethyl]phthalimide in 50 ml of ethanol was added 1.44 ml (29.7 mM) of hydrazine monohydrate and the mixture was refluxed for 2 hours. After this reaction mixture was cooled to room temperature, 7.78 g (35.7 mM) of di-tert-butyl dicarbonate was added and the mixture was stirred at room temperature for 1 hour. This reaction mixture was poured in aqueous solution of sodium hydroxide and extracted with 3 portions of ethyl acetate. The pooled organic layer was dried over $MgSO_4$ and the solvent was distilled off under reduced pressure. The residue was purified by silica gel column chromatography (hexane/ethyl acetate=1/1 to ethyl acetate) to provide the title compound.

Light-yellow liquid. Yield 8.914 g (90%)

$^1$H-NMR ($CDCl_3$, 200 MHz) δ:0.846–1.117 (1 H, m), 1.434 (9 H, s), 1.568–1.960 (8 H, m), 2.339 (2 H, t, 7.5 Hz), 2.616 (2 H, t, 7.9 Hz), 2.757–2.835 (2 H, m), 3.009 (2 H, br s), 4.607 (1 H, br s), 7.133–7.318 (5 H, m).

3) Synthesis of 1-(3-phenylpropan-1-yl)piperidin-3-ylmethylamine dihydrochloride In 50 ml of methanol was dissolved 8.902 g of N-tert-butoxycarbonyl-[1-(3-phenylpropan-1-yl)piperidin-3-ylmethyl]amine, followed by addition of 10 ml of concentrated hydrochloric acid, and the mixture was stirred at room temperature for 3 hours. This reaction mixture was concentrated to provide the title compound.

Light-yellow foam. Yield 8.200 g (100%)

$^1$H-NMR ($CD_3OD$, 200 MHz) δ:1.212–1.434 (1 H, m), 1.785–2.438 (6 H, m), 2.728 (2 H, t, 7.6 Hz), 2.776–3.032 (4 H, m), 3.153 (2 H, t, 8.6 Hz), 3.538–3.690 (2 H, m), 7.161–7.347 (5 H, m).

Reference Example 6

Synthesis of 1-(3-phenylpropan-1-yl)-4,4'-bipiperidine dihydrochloride

1) Synthesis of 1-tert-butoxycarbonyl-1'-(3-phenylpropan-1-yl)-4,4'-bipiperidine To a solution of 10.98 g (45.52 mM) of 4,4'-bi-piperidine and 9.06 g (45.5 mM) of 1-bromo-3-phenylpropane in 150 ml of ethanol was added 18.9 g (137 mM) of potassium carbonate and the mixture was stirred at room temperature for one day. This reaction mixture was filtered and the solvent was removed from the filtrate under reduced pressure. The residue was dissolved in 100 ml of tetrahydrofuran, and after 11.9 g (54.6 mM) of di-tert-butyl dicarbonate was added, the mixture was stirred at room temperature for 6 hours. This reaction mixture was poured in aqueous solution of sodium hydroxide and extracted with 3 portions of ethyl acetate. The pooled organic layer was dried over $MgSO_4$ and the solvent was distilled off under reduced pressure. The residue was purified by silica gel column chromatography (hexane/ethyl acetate=3/1 to 1/1 ethyl acetate) to provide the title compound.

Yellow solid. Yield 3.597 g (20%)

$^1$H-NMR ($CDCl_3$, 200 MHz) δ: 1.009–1.381 (6 H, m), 1.451 (9 H, s), 1.628–1.683 (4 H, m), 1.744–1.896 (4 H, m), 2.333 (2 H, t, 7.7 Hz), 2.575–2.689 (4 H, m), 2.946 (2 H, br d, 11.8 Hz), 4.064–4.169 (2 H, m), 7.127–7.305 (5 H, m).

2) Synthesis of 1-(3-phenylpropan-1-yl)-4,4'-bipiperidine dihydrochloride

In 20 ml of methanol was dissolved 3.425 g (8.860 mM) of 1-tert-butoxycarbonyl-1'-(3-phenylpropan-1-yl)-4,4'-bipiperidine, followed by addition of 5 ml of concentrated hydrochloric acid, and the mixture was stirred at room temperature for 6 hours. This reaction mixture was concentrated and crystallized from methanol-diethyl ether to provide the title compound.

Light-yellow solid. Yield 2.965 g (93%)

$^1$H-NMR ($CD_3OD$, 200 MHz) δ: 1.413–1.659 (6 H, m), 1.945–2.170 (6 H, m), 2.715 (2 H, t, 7.5 Hz), 2.860–3.131

(6H ,m), 3.413 (2 H, br d, 12.6 Hz), 3.595 (2 H, br d, 12.4 Hz), 7.157–7.335 (5 H, m).

Reference Example 7

Synthesis of N-[2-(3-phenylpropan-1-yl)-2,3-dihydro-1H-isoindol-5-ylmethyl]phthalimide 1) Synthesis of (7,7-dimethyl-5,9-dihydro-6,8-dioxabenzocyclohepten-2-yl)methanol To a suspension of 25.1 g (661 mM) of lithium aluminum hydride in 1300 ml of tetrahydrofuran was added 50.77 g (264.2 mM) of 1,3-dioxo-1,3-dihydroisobenzofuran-5-carboxylic acid (trimellitic anhydride) in small portions under ice-cooling and the mixture was stirred at room temperature for one day. To this reaction mixture was added ethyl acetate with ice-cooling to decompose the excess lithium aluminum hydride and water was added until a white precipitate had formed. The precipitate was filtered off with the aid of celite and the celite was washed with ethyl acetate and ethanol. The filtrate and washes were pooled and the solvent was distilled off under reduced pressure. The crude [2,4-bis(hydroxymethyl)-phenyl]methanol thus obtained was dissolved in 100 ml of N,N-dimethylformamide. Then, 100 ml of acetone, 70 ml of 2,2-dimethoxypropane, and 5 g of DL-10-camphorsulfonic acid were added and the mixture was stirred at room temperature overnight. This reaction mixture was diluted with aqueous solution of sodium hydroxide and extracted with 6 portions of ethyl acetate. The pooled organic solution was dried over MgSO$_4$ and the solvent was distilled off under reduced pressure. The residue was purified by silica gel column chromatography (hexane/ethyl acetate=3/1 to 1/1) to provide the title compound.

White solid. Yield 20.20 g (37%)

$^1$H-NMR (CDCl$_3$, 200 MHz) δ:1.502 (6 H, s), 1.654 (1 H, br s), 4.630 (2 H, s), 4.839 (4 H, s), 7.044 (1 H, d, 7.8 Hz), 7.063 (1 H, s), 7.152 (1 H, d, 7.8 Hz).

2) Synthesis of tert-butyl-(7,7-dimethyl-5,9-dihydro-6,8-dioxabenzocyclohepten-2-yl)methoxydiphenylsilane To a solution of 3.227 g (15.495 mM) of (7,7-dimethyl-5,9-dihydro-6,8-dioxabenzocyclohepten-2-yl)-methanol and 1.27 g (18.6 mM) of imidazole in 20 ml of N,N-dimethylformamide was added 4.69 g (17.0 mM) of tert-butylchlorodiphenylsilane at room temperature and the mixture was stirred for 2 hours. This reaction mixture was poured in water and extracted with 3 portions of diethyl ether. The pooled organic layer was dried over MgSO$_4$ and the solvent was distilled off under reduced pressure. The residue was purified by silica gel column chromatography (hexane/ethyl acetate=30/1) to provide the title compound.

Colorless liquid. Yield 6.504 g (94%)

$^1$H-NMR (CDCl$_3$, 200 MHz) δ:1.079 (9 H, s), 1.511 (6H, s), 4.720 (2 H, s), 4.837 (2 H, s), 4.853 (2 H, s), 7.011 (1 H, s), 7.031 (1 H, d, 8.0 Hz), 7.157 (1 H, d, 7.8 Hz), 7.326 (6 H, m), 7.659–7.718 (4 H, m).

3) Synthesis of [4-(tert-butyldiphenylsiloxymethyl)-2-hydroxymethylphenyl]methanol To a solution of 6.175 g (13.825 mM) of tert-butyl-(7,7-dimethyl-5,9-dihydro-6,8-dioxabenzocyclohepten-2-yl) methoxydiphenylsilane in 50 ml of tetrahydrofuran-water (4:1) was added 2 ml of trifluoroacetic acid with ice-cooling and the mixture was stirred at room temperature for 4 hours. This reaction mixture was poured in aqueous solution of sodium hydrogen carbonate and extracted with 3 portions of ethyl acetate. The pooled organic layer was dried over MgSO$_4$ and the solvent was distilled off under reduced pressure to provide the title compound.

Colorless liquid. Yield 5.720 g (100%)

$^1$H-NMR (CDCl$_3$, 200 MHz) δ:1.090 (9 H, s), 2.973 (2 H, br s), 4.663 (4 H, s), 4.749 (2 H, s), 7.257–7.459 (14 H, m), 7.656–7.702 (4 H, m).

4) Synthesis of 5-(tert-butyldiphenylsiloxymethyl)-2-(3-phenylpropan-1-yl)-2,3-dihydro-1H-isoindole To a solution of 5.867 g (14.429 mM) of [4-(tert-butyldiphenylsiloxymethyl)-2-hydroxymethylphenyl]methanol and 12.6 ml (72.1 mM) of N,N-diisopropylethylamine in 100 ml of acetonitrile was added a solution of 3.47 g (30.3 mM) of methanesulfonyl chloride in 10 ml of acetonitrile dropwise with ice-cooling and the mixture was stirred at 0° C. for 0.5 hour. To this reaction mixture was added 2.15 g (15.9 mM) of 3-phenylpropylamine and the mixture was stirred at 80° C. overnight. The solvent was then distilled off under reduced pressure and the residue was diluted with aqueous solution of sodium hydrogen carbonate and extracted with 3 portions of ethyl acetate. The pooled organic layer was dried over MgSO$_4$ and the solvent was distilled off under reduced pressure. The residue was purified by silica gel column chromatography (hexane/ethyl acetate=6/1 to 3/1) to provide the title compound.

Brown liquid. Yield 3.710 g (51%)

$^1$H-NMR (CDCl$_3$, 200 MHz) δ:1.080 (9 H, s), 1.845–1.995 (2 H, m), 2.739 (2 H, t, 7.7 Hz), 2.754 (2 H, t, 7.3 Hz), 3.919 (4 H, s), 4.747 (2 H, s), 7.155–7.469 (14 H, m), 7.668–7.727 (4 H, m).

5) Synthesis of 2-(3-phenylpropan-1-yl)-2,3-dihydro-1H-isoindol-5-ylmethanol

To a solution of 3.699 g (7.316 mM) of 5-(tert-butyldiphenylsiloxymethyl)-2-(3-phenylpropan-1-yl)-2,3-dihydro-1H-isoindole in 50 ml of tetrahydrofuran was added 8.78 ml (8.78 mM) of 1.0N-tetrabutylammonium fluoride-tetrahydrofuran at room temperature and the mixture was stirred for 1 hour. This reaction mixture was poured in aqueous solution of sodium hydrogen carbonate and extracted with 3 portions of ethyl acetate. The pooled organic layer was dried over MgSO$_4$ and the solvent was distilled off under reduced pressure. The residue was purified by silica gel column chromatography (hexane/ethyl acetate=1/1 to ethyl acetate) to provide the title compound.

Brown liquid. Yield 1.840 g. (94%)

$^1$H-NMR (CDCl$_3$, 200 MHz) δ:1.846–1.998 (2 H, m), 2.414 (1 H, br s), 2.720 (2 H, t, 7.7 Hz), 2.736 (2 H, t, 7.5 Hz), 3.854 (2 H, s), 3.894 (2 H, s), 4.597 (2H, s), 7.078 (1 H, s), 7.123 (2 H, s), 7.154–7.336 (5H, m).

6) Synthesis of N-[2-(3-phenylpropan-1-yl)-2,3-dihydro-1H-isoindol-5-ylmethyl]phthalimide To a solution of 1.835 g (6.863 mM) of 2-(3-phenylpropan-1-yl)-2,3-dihydro-1H-isoindol-5-ylmethanol and 1.43 ml (10.3 mM) of triethylamine in 50 ml of tetrahydrofuran was added 0.64 ml (8.24 mM) of methanesulfonyl chloride dropwise with ice-cooling and the mixture was stirred at 0° C. for 0.5 hour. This reaction mixture was poured in aqueous solution of sodium hydrogen carbonate and extracted with 3 portions of diethyl ether. The pooled organic layer was dried over MgSO$_4$ and the solvent was distilled off under reduced pressure. The crude 2-(3-phenylpropan-1-yl)-2,3-dihydro-1H-isoindol-5-ylmethyl methanesulfonate thus obtained was dissolved in 60 ml of N,N-dimethylformamide, followed by addition of 1.40 g (7.55 mM) of potassium phthalimide, and the mixture was stirred at 100° C. for 4 hours. This reaction mixture was poured in aqueous solution of sodium hydrogen carbonate and extracted with 3 portions of ethyl acetate. The pooled organic solution was dried over MgSO$_4$ and the solvent was distilled off under reduced pressure. The residue was purified by silica gel flash column chromatography (hexane/ethyl acetate=3/1 to 2/1) to provide a mixture of the objective compound and phthalimide. This product was dissolved in ethyl acetate and the solution was washed serially with aqueous solution of sodium hydroxide and saturated aqueous solution of sodium chloride. It was then dried over anhydrous sodium sulfate (Na$_2$SO$_4$) and the solvent was distilled off under reduced pressure to provide the title compound.

Yellow liquid. Yield 0.401 g (15%)

$^1$H-NMR (CDCl$_3$, 200 MHz) δ:1.806–1.953 (2 H, m), 2.705 (4 H, t, 7.6 Hz), 3.876 (4 H, s), 4.817 (2 H, s), 7.112–7.319 (8 H, m), 7.673–7.755 (2 H, m), 7.794–7.873 (2 H, m).

Reference Example 8

Synthesis of N-[4-[4-(2-chlorobenzylidene)piperidino]-butyl]phthalimide

1) Synthesis of 1-(tert-butoxycarbonyl)-4-(2-chlorobenzylidene)piperidine

To a solution of 9.199 g (46.168 mM) of 1-(tert-butoxycarbonyl)-4-piperidone and 19.5 g (46.2 mM) of 2-chlorobenzyltriphenylphosphonium chloride in 50 ml of methanol was added 8.91 g (46.2 mM) of 28% sodium methoxide-methanol at room temperature and the mixture was refluxed for 36 hours. This reaction mixture was poured in water and extracted with 2 portions of ethyl acetate. The pooled organic layer was dried over Na$_2$SO$_4$ and the solvent was distilled off under reduced pressure. To the residue was added diethyl ether and the resulting precipitate (triphenylphosphine oxide) was filtered off and washed with diethyl ether. The filtrate and washes were combined and the solvent was distilled off under reduced pressure. The residue was purified by silica gel column chromatography (hexane/ethyl acetate=9/1 to 6/1) and crystallized from cold hexane to provide the title compound.

White solid. Yield 1.473 g (10%)

$^1$H-NMR (CDCl$_3$, 200 MHz) δ:1.474 (9 H, s), 2.277–2.396 (4 H, m), 3.405 (2 H, t, 5.8 Hz), 3.531 (2 H, t, 5.7 Hz), 6.356 (1 H, s), 7.193 (3 H, s), 7.354–7.402 (1 H, m).

2) Synthesis of N-[4-[4-(2-chlorobenzylidene)piperidino]butyl]phthalimide

To a solution of 1.428 g (4.639 mM) of 1-(tert-butoxycarbonyl)-4-(2-chlorobenzylidene)piperidine in 20 ml of methanol was added 3 ml of concentrated hydrochloric acid at room temperature and the mixture was stirred at 50° C. for 2 hours. The solvent was then distilled off under reduced pressure to recover crude 4-(2-chlorobenzylidene)piperidine hydrochloride. This crude product was not purified but used as it was in the next reaction.

The above crude 4-(2-chlorobenzylidene)piperidine hydrochloride, 1.31 g (4.64 mM) of 4-bromobutylphthalimide, and 1.28 g (9.28 mM) of potassium carbonate were stirred together in 20 ml of N,N-dimethylformamide at 100° C. overnight. This reaction mixture was poured in water and extracted with 2 portions of ethyl acetate. The organic layers were combined and dried over MgSO$_4$ and the solvent was distilled off under reduced pressure. The residue was purified by silica gel column chromatography (hexane/ethyl acetate=3/1 to 1/1) to provide the title compound.

Yellow liquid. Yield 1.560 g (82%)

$^1$H-NMR (CDCl$_3$, 200 MHz) δ:1.477–1.799 (4 H, m), 2.341–2.438 (8 H, m), 2.537 (2 H, t, 5.5 Hz), 3.715 (2H, t, 6.8 Hz), 6.265 (1 H, s), 7.098–7.197 (3 H, m), 7.345–7.378 (1 H, m), 7.682–7.748 (2 H, m), 7.796–7.862 (2 H, m).

Reference Example 9

Synthesis of N-[4-(4-hydroxy-4-phenylpiperidino)butyl]-phthalimide

A mixture of 2.501 g (14.110 mM) of 4-hydroxy-4-phenylpiperidine, 3.98 g (14.1 mM) of 4-bromobutylphthalimide, and 3.90 g (28.2 mM) of potassium carbonate was stirred in 30 ml of N,N-dimethylformamide at 100° C. for one day. To this reaction mixture was added water, followed by stirring, and the resulting precipitate was collected, rinsed with water, and dried to provide the title compound.

Light-yellow solid. Yield 3.835 g (72%)

$^1$H-NMR (CDCl$_3$, 200 MHz) δ:1.507–1.768 (7 H, m), 2.137 (2 H, dt, 4.3 Hz, 13.0 Hz), 2.361–2.476 (4 H, m), 2.773–2.830 (2 H, m), 3.727 (2 H, t, 6.9 Hz), 7.209–7.389 (3 H, m), 7.488–7.532 (2 H, m), 7.686–7.748 (2 H, m), 7.801–7.863 (2 H, m).

Reference Example 10

Synthesis of N-[2-hydroxy-3-(4-phenylpiperidino)propan-1-yl]phthalimide

A solution of 1.980 g (9.744 mM) of N-(2,3-epoxypropan-1-yl)phthalimide and 1.73 g (10.7 mM) of 4-phenylpiperidine in 50 ml of ethanol was refluxed for one hour, at the end of which time the solvent was distilled off under reduced pressure. The residue was purified by silica gel column chromatography (hexane/ethyl acetate=3/1 to 1/1) and crystallized from diethyl ether-hexane to provide the title compound.

White solid. Yield 2.113 g (60%)

$^1$H-NMR (CDCl$_3$, 200 MHz) δ: 1.560–1.835 (4 H, m), 2.083 (1 H, dt, 2.8 Hz, 11.6 Hz), 2.335–2.579 (4 H, m), 2.910–3.088 (2 H, m), 3.730 (1 H, dd, 5.0 Hz, 13.8 Hz), 3.841 (1 H, dd, 6.7 Hz, 13.7 Hz), 4.004–4.130 (1 H, m), 7.149–7.332 (5 H, m), 7.700–7.763 (2 H, m), 7.830–7.911 (2 H, m).

Reference Example 11

Synthesis of N-[2-[(4-phenylpiperidino)methyl]benzyl]-phthalimide

1) Synthesis of 2-(tert-butyldimethylsilyloxymethyl)-benzyl alcohol

To a solution of 14.074 g (101.86 mM) of 1,2-benzenedimethanol in 100 ml of 1,2-dimethoxyethane was added 4.07 g (102 mM) of a liquid paraffin suspension of 60% sodium hydride at room temperature and the mixture was stirred at the prevailing temperature for one hour. To this reaction mixture was added a solution of 15.4 g (102 mM) of tert-butylchlorodimethylsilane in 50 ml of 1,2-dimethoxyethane dropwise, and the mixture was stirred at room temperature overnight. This reaction mixture was poured in water and extracted with 3 portions of ethyl acetate. The organic layers were combined and dried over MgSO$_4$ and the solvent was distilled off under reduced pressure. The residue was purified by silica gel column chromatography (hexane/ethyl acetate=9/1 to 3/1) to provide the title compound.

Colorless liquid. Yield 22.792 g (89%)

¹H-NMR (CDCl₃, 200 MHz) δ:0.127 (6 H, s), 0.921 (9H, s), 3.219 (1 H, br t, 5.9 Hz), 4.681 (2 H, d, 5.2 Hz), 4.807 (2 H, s), 7.258–7.405 (4 H, m).

2) Synthesis of N-[2-(tert-butyldimethylsilyloxymethyl) benzyl]phthalimide

To a solution of 1.413 g (45.213 mM) of 2-(tert-butyldimethylsilyloxymethyl)benzyl alcohol and 7.56 ml (54.3 mM) of triethylamine in 150 ml of diethyl ether was added 5.70 g (49.7 mM) of methanesulfonyl chloride dropwise with ice-cooling and the mixture was stirred at 0° C. for 0.5 hour. This reaction mixture was poured in water and extracted with 2 portions of ethyl acetate. The organic layers were combined and dried over MgSO₄ and the solvent was distilled off under reduced pressure. The residue was dissolved in 150 ml of N,N-dimethylformamide, followed by addition of 9.21 g (49.7 mM) of potassium phthalimide, and the mixture was stirred at 100° C. for 3 hours. This reaction mixture was poured in water and extracted with 3 portions of ethyl acetate. The organic layers were combined and dried over MgSO₄ and the solvent was distilled off under reduced pressure. The residue was purified by silica gel column chromatography (hexane/ethyl acetate=9/1) to provide the title compound.

Colorless liquid. Yield 15.021 g (87%)

¹H-NMR (CDCl₃, 200 MHz) δ:0.112 (6 H, s), 0.938 (9H, s), 4.929 (2 H, s), 4.971 (2 H, s), 7.189–7.426 (4H, m), 7.693–7.755 (2 H, m), 7.818–7.880 (2 H, m).

3) Synthesis of N-[2-(hydroxymethyl)benzyl]phthalimide

To a solution of 15.021 g (39.368 mM) of N-[2-(tert-butyldimethylsilyloxymethyl)benzyl]phthalimide in 50 ml of methanol was added 5 ml of concentrated hydrochloric acid at room temperature and the mixture was stirred at the prevailing temperature for 10 minutes. This reaction mixture was poured in water-diethyl ether and the resulting precipitate was recovered, rinsed serially with water and diethyl ether, and dried to provide the title compound.

White solid. Yield 8.743 g (83%)

¹H-NMR (CDCl₃, 200 MHz) δ:3.033 (1 H, br s), 4.891 (2H, s), 5.004 (2 H, s), 7.219–7.310 (2 H, m), 7.362–7.418 (2 H, m), 7.699–7.761 (2 H, m), 7.809–7.871 (2 H, m).

4) Synthesis of N-[2-[(4-phenylpiperidino)methyl] benzyl]phthalimide

To a solution of 2.704 g (10.117 mM) of N-[2-(hydroxymethyl)benzyl]phthalimide and 1.69 ml (12.1 mM) of triethylamine in 50 ml of tetrahydrofuran was added 0.86 ml (11.1 mM) of methanesulfonyl chloride dropwise with ice-cooling and the mixture was stirred at 0° C. for 0.5 hour. This reaction mixture was poured in aqueous solution of sodium hydrogen carbonate and extracted with 3 portions of ethyl acetate. The organic layers were combined and dried over MgSO₄ and the solvent was distilled off under reduced pressure. The residue was dissolved in 50 ml of N,N-dimethylformamide, followed by addition of 1.79 g (11.1 mM) of 4-phenylpiperidine and 2.80 g (20.2 mM) of potassium carbonate, and the mixture was stirred at 100° C. overnight. This reaction mixture was poured in water and extracted with 2 portions of ethyl acetate. The organic layers were combined and dried over MgSO₄ and the solvent was distilled off under reduced pressure. The residue was purified by silica gel column chromatography (hexane/ethyl acetate=6/1 to 3/1) to provide the title compound.

White solid. Yield 2.722 g (66%)

¹H-NMR (CDCl₃, 200 MHz) δ:1.506–1.791 (4 H, m), 2.080 (2 H, dt, 2.3 Hz, 11.5 Hz), 2.482 (1 H, tt, 3.9 Hz, 11.9 Hz), 2.989 (2 H, br d, 11.4 Hz), 3.716 (2H, s), 5.123 (2 H, s), 7.134–7.376 (9 H, m), 7.671–7.759 (2 H, m), 7.819–7.882 (2 H, m).

Reference Example 12

Synthesis of 4-(4-phenylpiperidinomethyl)piperidine dihydrochloride

1) Synthesis of tert-butyl 4-(bromomethyl)piperidine-1-carboxylate

To a solution of 5.792 g (50.287 mM) of 4-piperidylmethanol in 150 ml of dichloromethane was added 12.1 g (55.3 mM) of di-tert-butyl dicarbonate dropwise at room temperature and the mixture was stirred at the prevailing temperature overnight. The solvent was then distilled off under reduced pressure to recover crude tert-butyl 4-(hydroxymethyl)piperidine-1-carboxylate. This crude product was not purified but used as it was in the next reaction. To a solution of the above crude tert-butyl 4-(hydroxymethyl)piperidine-1-carboxylate and 18.3 g (55.3 mM) of carbon tetrabromide in 100 ml of acetonitrile was added 14.5 g (55.3 mM) of triphenylphosphine at room temperature and the mixture was stirred at the prevailing temperature for 3 hours. The solvent was then distilled off under reduced pressure. To the residue was added diethyl ether, and after stirring, the resulting precipitate (triphenylphosphine oxide) was filtered off and washed with diethyl ether. The filtrate and washes were combined and concentrated and the residue was purified by silica gel column chromatography (hexane/ethyl acetate=30/1 to 15/1 to 9/1) to provide the title compound.

Colorless liquid. Yield 12.126 g (82%)

¹H-NMR (CDCl₃, 200 MHz) δ:1.075–1.284 (2 H, m), 1.454 (9 H, s), 1.702–1.854 (3 H, m), 2.693 (2 H, br t, 12.5 Hz), 3.294 (2 H, d, 5.8 Hz), 4.135 (2 H, br d, 12.8 Hz).

2) Synthesis of tert-butyl 4-(4-phenylpiperidinomethyl) piperidine-1-carboxylate A mixture of 3.081 g (11.075 mM) of tert-butyl 4-(bromomethyl)piperidine-1-carboxylate, 1.96 g (12.2 mM) of 4-phenylpiperidine, and 3.06 g (22.2 mM) of potassium carbonate was stirred in 20 ml of N,N-dimethylformamide at 110° C. for 4 hours. This reaction mixture was poured in water and extracted with 2 portions of diethyl ether. The organic layers were combined and dried over MgSO₄ and the solvent was distilled off under reduced pressure. The residue was purified by silica gel column chromatography (hexane/ethyl acetate=3/1) to provide the title compound.

Yellow liquid. Yield 3.550 g (89%)

¹H-NMR (CDCl₃, 200 MHz) δ:0.989–1.189 (2 H, m), 1.460 (9 H, s), 1.557–1.830 (7 H, m), 1.949–2.077 (2 H, m), 2.193 (2 H, d, 6.6 Hz), 2.403–2.559 (1 H, m), 2.696 (2 H, br t, 11.9 Hz), 2.970 (2 H, br d, 11.2 Hz), 4.068–4.174 (2 H, m), 7.153–7.339 (5 H, m).

3) Synthesis of 4-(4-phenylpiperidinomethyl)piperidine dihydrochloride

To a solution of 3.550 g (9.902 mM) of tert-butyl 4-(4-phenylpiperidinomethyl)piperidine-1-carboxylate in 30 ml of methanol was added 5 ml of concentrated hydrochloric acid and the mixture was stirred at room temperature for 3 hours. The solvent was then distilled off and the residue was crystallized from ethanol-diethyl ether to provide the title compound.

Light-yellow solid. Yield 2.972 g (91%)

¹H-NMR (CD₃OD, 200 MHz) δ:1.478–1.692 (2 H, m), 2.051–2.390 (7 H, m), 2.835–3.233 (7 H, m), 3.455 (2 H, br d, 12.8 Hz), 3.752 (2 H, br d, 12.8 Hz), 7.180–7.369 (5 H, m).

Reference Example 13

Synthesis of N-[[4-(4-phenylpiperidino)cyclohexyl]methyl]phthalimide

1) Synthesis of 1,5-dibromo-3-phenylpentane

To a suspension of 9.10 g (240 mM) of lithium aluminum hydride in tetrahydrofuran (500 ml)-diethyl ether (200 ml) was added a solution of 24.960 g (119.9 mM) of 3-phenylglutaric acid in 100 ml of tetrahydrofuran dropwise with ice-cooling and the mixture was stirred at room temperature overnight. To this reaction mixture was added water gradually dropwise under ice-cooling until a precipitate had formed. The precipitate was filtered off with the aid of celite and washed with ethyl acetate. The filtrate and washes were pooled and the solvent was distilled off under reduced pressure to provide crude 3-phenylpentane-1,5-diol. This crude product was not purified but used as it was in the next reaction. (Brown liquid, yield 19.19 g).

To a solution of the crude 3-phenylpentane-1,5-diol and 74.2 g (224 mM) of carbon tetrabromide in 300 ml of acetonitrile was added 58.7 g (224 mM) of triphenylphosphine with ice-cooling and the mixture was stirred at room temperature for one hour. The solvent was then distilled off under reduced pressure and the residue was diluted with diethyl ether and stirred. The resulting precipitate was filtered off and washed with diethyl ether. The filtrate and washes were pooled and the solvent was distilled off under reduced pressure. To the residue was added hexane, followed by stirring, and the precipitate was filtered off and washed with hexane. The filtrate and washes were combined and the solvent was distilled off under reduced pressure. The residue was purified by silica gel column chromatography (hexane/ethyl acetate=20/1) to provide the title compound.

Colorless liquid. Yield 25.963 g (71%)

$^1$H-NMR (CDCl$_3$, 200 MHz) δ:2.119–2.223 (4 H, m), 2.983–3.337 (5 H, m), 7.176–7.386 (5 H, m).

2) Synthesis of methyl 4-aminocyclohexanecarboxylate hydrochloride

To 5.109 g (35.680 mM) of 4-aminocyclohexanecarboxylic acid was added 50 ml of 10% HCl/methanol and the mixture was refluxed overnight. The solvent was then distilled off under reduced pressure and the residue was crystallized from methanol-diethyl ether to provide the title compound.

White solid. Yield 6.624 g (96%)

$^1$H-NMR (CD$_3$OD, 200 MHz) δ:1.460–1.936 (6 H, m), 2.073–2.187 (3 H, m), 2.639–2.702 (1 H, m), 3.187 (1 H, br s), 3.696 (3 H, s).

3) Synthesis of methyl 4-(4-phenylpiperidino)cyclohexanecarboxylate

A solution of 3.896 g (20.117 mM) of methyl 4-aminocyclohexanecarboxylate hydrochloride, 6.77 g (22.1 mM) of 1,5-dibromo-3-phenylpentane, and 14.0 ml (80.5 mM) of N,N-diisopropylethylamine in 100 ml of acetonitrile was refluxed for one day. This reaction mixture was poured in aqueous solution of sodium hydrogen carbonate and extracted with 3 portions of ethyl acetate. The organic layers were pooled and dried over MgSO$_4$ and the solvent was distilled off under reduced pressure. The residue was purified by silica gel column chromatography (hexane/ethyl acetate=3/1 to 1/1) to provide the title compound.

Yellow liquid. Yield 2.825 g (47%)

$^1$H-NMR (CDCl$_3$, 200 MHz) δ: 1.294–1.811 (10 H, m), 2.046–2.609 (7 H, m), 3.034 (2 H, d, 11.4 Hz), 3.668 (0.6 H, s), 3.691 (2.4 H, s), 7.150–7.336 (5 H, m).

4) Synthesis of 4-(4-phenylpiperidino)cyclohexylmethanol

To a suspension of 0.36 g (9.37 mM) of lithium aluminum hydride in 50 ml of tetrahydrofuran was added a solution of 2.825 g (9.372 mM) of methyl 4-(4-phenylpiperidino)cyclohexanecarboxylate in 50 ml of tetrahydrofuran dropwise with ice-cooling and the mixture was stirred at room temperature for one hour. To this reaction mixture was added ethyl acetate with ice-cooling to decompose the excess lithium aluminum hydride. Then, water was added until a white precipitate had formed. The precipitate was filtered off with the aid of celite and washed with ethyl acetate. The filtrate and washes were pooled and the solvent was distilled off under reduced pressure. The solid residue was rinsed with diethyl ether-hexane to provide the title compound.

White solid. Yield 2.160 g (84%)

$^1$H-NMR (CDCl$_3$, 200 MHz) δ:0.885–2.007 (15 H, m), 2.108–2.553 (4 H, m), 3.013–3.123 (2 H, m), 3.460 (0.4H, d, 6.2 Hz), 3.611 (1.6 H, d, 6.6 Hz), 7.140–7.341 (5 H, m).

5) Synthesis of N-[[4-(4-phenylpiperidino)cyclohexyl]methyl]phthalimide

To a solution of 1.986 g (7.264 mM) of 4-(4-phenylpiperidino)cyclohexylmethanol and 1.21 ml (8.72 mM) of triethylamine in 50 ml of tetrahydrofuran was added 0.62 ml (7.99 mM) of methanesulfonyl chloride dropwise with ice-cooling and the mixture was stirred at 0° C. for 5 hours. This reaction mixture was poured in water and extracted with 2 portions of ethyl acetate. The organic layers were pooled and dried over MgSO$_4$ and the solvent was distilled off under reduced pressure. The residue was dissolved in 50 ml of N,N-dimethylformamide, followed by addition of 1.48 g (7.99 mM) of potassium phthalimide, and the mixture was stirred at 100° C. overnight. After cooling to room temperature, this reaction mixture was poured in water and stirred and the resulting precipitate was collected by filtration, rinsed with water, and dried to provide the title compound.

Light-brown solid. Yield 0.567 g (19%)

$^1$H-NMR (CDCl$_3$, 200 MHz) δ:1.000–1.368 (2 H, m), 1.669–1.958 (12 H, m), 2.238–2.517 (3 H, m), 2.885–3.150 (2 H, m), 3.545 (1.6 H, d, 6.6 Hz), 3.699 (0.4 H, d, 7.6 Hz), 7.140–7.325 (5 H, m), 7.695–7.757 (2 H, m), 7.808–7.873 (2 H, m).

Reference Example 14

Synthesis of N-(1-benzhydrylpiperidin-4-ylmethyl)phthalimide

1) Synthesis of 1-benzhydrylpiperidin-4-ylmethanol

In 20 ml of N,N-dimethylformamide, 2.291 g (15.108 mM) of 4-piperidylmethanol hydrochloride, 4.48 g (18.1 mM) of bromodiphenylmethane, and 6.26 g (45.3 mM) of potassium carbonate were stirred together at 100° C. for 3.5 days and, then, at 150° C. for 2 hours. After cooling to room temperature, this reaction mixture was poured in water and extracted with 2 portions of ethyl acetate. The organic layers were pooled and dried over MgSO$_4$ and the solvent was distilled off under reduced pressure. The residue was purified by silica gel column chromatography (hexane/ethyl acetate=3/1 to 2/1 to 1/1) to provide the title compound.

White solid. Yield 0.347 g (8.2%)

$^1$H-NMR (CDCl$_3$, 200 MHz) δ: 1.209–1.696 (6 H, m) 1.841 (2 H, t, 11.7 Hz), 2.910 (2 H, d, 12.2 Hz), 3.500 (2 H, br s), 4.235 (1 H, s), 7.127–7.305 (6 H, m), 7.385–7.426 (4 H, m).

2) Synthesis of N-(1-benzhydrylpiperidin-4-ylmethyl)-phthalimide

To a solution of 0.450 g (1.599 mM) of 1-benzhydrylpiperidin-4-ylmethanol and 0.33 ml (2.40 mM) of triethylamine in 30 ml of tetrahydrofuran was added 0.15 ml (1.92 mM) of methanesulfonyl chlorine dropwise with ice-cooling and the mixture was stirred at 0° C. for 0.5 hour. This reaction mixture was poured in water and extracted with 2 portions of ethyl acetate. The organic layers were pooled and dried over $MgSO_4$ and the solvent was distilled off under reduced pressure. The residue was dissolved in 25 ml of N,N-dimethylformamide, followed by addition of 0.36 g (1.92 mM) of potassium phthalimide, and the mixture was stirred at 100° C. overnight. After cooling to room temperature, this reaction mixture was poured in water and extracted with 2 portions of ethyl acetate. The organic layers were pooled and dried over $MgSO_4$ and the solvent was distilled off under reduced pressure. The residue was purified by silica gel column chromatography (hexane/ethyl acetate=6/1 to 3/1) and crystallized from diethyl ether-hexane to provide the title compound.

White solid. Yield 0.178 g (27%)

$^1$H-NMR (CDCl$_3$, 200 MHz) δ:1.291–1.496 (2 H, m), 1.596 (2 H, br d, 13.0 Hz), 1.683–1.846 (3 H, m), 2.868 (2 H, d, 11.8 Hz), 3.595 (2 H, d, 7.0 Hz), 4.222 (1 H, s), 7.101–7.286 (6 H, m), 7.345–7.456 (4 H, m), 7.643–7.735 (2 H, m), 7.782–7.867 (2 H, m).

Reference Example 15

Synthesis of 1-(4-aminobutan-1-yl)-4-phenylpiperidine

1) Synthesis of 4-(4-phenylpiperidin-1-yl)butan-1-ylphthalimide

A solution of 5.00 g (31 mM) of 4-phenylpiperidine, 8.75 g (31 mM) of N-(4-bromobutyl)phthalimide, and 6.5 ml (46.6 mM) of triethylamine in acetonitrile (30 ml) was refluxed under nitrogen for 62 hours. The solvent was then distilled off under reduced pressure and the residue was diluted with water and extracted with chloroform. The organic layer was washed with saturated aqueous solution of sodium chloride and dried over $MgSO_4$. The resulting crude product was purified by column chromatography (methanol-ethyl acetate 5–10%) to provide the title compound.

White solid. Yield 10.38 g (92%)

$^1$H-NMR (200 MHz, CDCl$_3$) δ:1.49–1.88 (m, 8H), 1.95–2.14 (m, 2H), 2.32–2.57 (m, 3H), 3.04 (br d, J=11.4 Hz, 2H), 3.73 (d, J=6.8 Hz, 2H), 7.11–7.35 (m, 5H), 7.65–7.76 (m, 2H), 7.78–7.90 (m, 2H).

2) Synthesis of 1-(4-aminobutan-1-yl)-4-phenylpiperidine

To a solution of 10.38 g (28.64 mM) of 4-(4-phenylpiperidin-1-yl)butan-1-ylphthalimide in ethanol (160 ml) was added 4.2 ml (86.58 mM) of hydrazine monohydrate at room temperature and the mixture was refluxed for 1.5 hours. The white solid that formed was filtered off and the solvent was distilled off under reduced pressure. The residue was diluted with aqueous solution of sodium hydroxide and extracted with chloroform. The organic layer was washed with saturated aqueous solution of sodium chloride and dried over $MgSO_4$. The solvent was then distilled off under reduced pressure to provide the title compound.

Light-yellow solid. Yield 6.49 g (98%)

$^1$H-NMR (200 MHz, CDCl$_3$) δ:1.39–1.63 (m, 4H), 1.72–1.90 (m, 6H), 2.35–2.58 (m, 3H), 2.73 (t, J=6.6 Hz, 2H), 3.07 (br d, J=11.6 Hz, 2H), 7.15–7.35 (m, 5H).

Reference Example 16

Synthesis of 1-(3-aminopropan-1-yl)-4-phenylpiperidine

1) The procedure of Reference Example 15-1) was generally followed to provide 3-(4-phenylpiperidin-1-yl)propan-1-ylphthalimide as white solid.

$^1$H-NMR (200 MHz, CDCl$_3$) δ:1.40–1.79 (m, 4H), 1.83–2.04 m (m, 4H), 2.30–2.51 (m, 1H), 2.45 (t, J=6.9 Hz, 2H), 2.90–3.05 (m, 2H), 3.79 (t, J=7.0 Hz, 2H), 7.03–7.32 (m, 5H), 7.66–7.76 (m, 2H), 7.80–7.90 (m, 2H).

2) The procedure of Reference Example 15-2) was generally followed to provide 1-(3-aminopropan-1-yl)-4-phenylpiperidine as white solid.

$^1$H-NMR (200 MHz, CDCl$_3$) δ:1.61–1.90 (m, 6H), 1.94–2.12 (m, 2H), 2.29–2.59 (m, 5H), 2.81 (t, J=6.8 Hz, 2H), 3.00–3.15 (m, 2H), 7.07–7.38 (m, 5H).

Reference Example 17

Synthesis of 1-(4-aminobutan-1-yl)-4-benzylpiperidine dihydrochloride

1) The procedure of Reference Example 15-1) was generally followed to provide 4-(4-benzylpiperidin-1-yl)butan-1-ylphthalimide as yellow oil.

$^1$H-NMR (200 MHz, CDCl$_3$) δ: 1.17–1.96 (m, 11H), 2.26–2.38 (m, 2H), 2.51 (d, J=6.6 Hz, 2H), 2.83–2.96 (m, 2H), 3.70 (t, J=6.8 Hz, 2H), 7.10–7.31 (m, 5H), 7.67–7.73 (m, 2H), 7.78–7.86 (m, 2H).

2) Synthesis of 1-(4-aminobutan-1-yl)-4-benzylpiperidine dihydrochloride

To a solution of 9.66 g (25.7 mM) of 4-(4-benzylpiperidine-1-)butan-1-ylphthalimide in ethanol (30 ml) was added 1.9 ml (39.2 mM) of hydrazine monohydrate at room temperature and the mixture was refluxed for 2 hours. The white solid that formed was filtered off and the solvent was distilled off under reduced pressure. The residue was diluted with aqueous solution of sodium hydroxide and extracted with chloroform. The organic layer was washed with saturated aqueous solution of sodium chloride and dried over $MgSO_4$. The solvent was then distilled off under reduced pressure to provide a crude product (free compound). To a solution of this free compound (6.39 g) in ethanol (30 ml) was added 12N-hydrochloric acid (10 ml) at room temperature, followed by a few minutes' stirring. The solvent was then distilled off under reduced pressure and diethyl ether was added. The crystals that formed were collected by filtration and rinsed with ethanol and diethyl ether to provide the title compound.

White crystals. Yield 5.84 g (71%)

$^1$H-NMR (200 MHz, DMSO-d$_6$) δ:1.50–1.88 (m, 9H), 2.68–3.50 (m, 10 H), 7.14–7.36 (m, 5H), 7.92–8.24 (m, 2H).

Reference Example 18

Synthesis of 1-(3-aminopropan-1-yl)-4-benzylpiperidine dihydrochloride

1) The procedure of Reference Example 15-1) was generally followed to provide 3-(4-benzylpiperidin-1-yl)propan-1-ylphthalimide as white solid.

$^1$H-NMR (200 MHz, CDCl$_3$) δ:0.94–1.19 (m, 2H), 1.29–1.95 (m, 7H), 2.30–2.47 (m, 4H), 2.76–2.89 (m, 2H), 3.74 (t, J=6.8 Hz, 2H), 7.04–7.32 (m, 5H), 7.65–7.77 (m, 2H), 7.80–7.90 (m, 2H).

2) Synthesis of 1-(3-aminopropan-1-yl)-4-benzylpiperidine dihydrochloride

To a solution of 9.22 g (25.4 mM) of 3-(4-benzylpiperidin-1-yl)propan-1-ylphthalimide in ethanol (50 ml) was added 1.8 ml (37.1 mM) of hydrazine monohydrate at room temperature for 3 hours. After the white solid that formed was filtered off, 12.0 ml (52.2 mM) of di-tert-butyl dicarbonate was added and the mixture was stirred at room temperature for 14 hours. The solvent was then distilled off under reduced pressure and the residue was diluted with water and extracted with chloroform. The organic layer was washed with saturated aqueous solution of sodium chloride and dried over $MgSO_4$. The solvent was then distilled off under reduced pressure and the crude product was purified by column chromatography (methanol-ethyl acetate 10–20%). To this free compound was added 12N-hydrochloric acid (8 ml) at room temperature, followed by a few minutes' stirring. To this reaction mixture was added ethanol and the solvent was then distilled off under reduced pressure. The residue was treated with diethyl ether and the resulting crystals were collected by filtration and rinsed with ethanol and diethyl ether to provide the title compound.

White crystals. Yield 3.11 g (40%)

$^1$H-NMR (200 MHz, DMSO-$d_6$) δ:1.44–1.85 (m, 4H), 1.93–2.11 (m, 2H), 2.70–2.96 (m, 4H), 3.01–3.47 (m, 6H), 7.13–7.37 (m, 5H), 8.02–8.36 (m, 2H).

Reference Example 19

Synthesis of 1-(4-aminobutan-1-yl)-4-phenylpiperazine trihydrochloride

1) The procedure of Reference Example 15-1) was generally followed to provide 4-(4-phenylpiperazin-1-yl)butan-1-ylphthalimide as yellow-green crystals.

$^1$H-NMR (200 MHz, CDCl$_3$) δ:1.49–1.83 (m, 4H), 2.44 (t, J=7.3 Hz, 2H), 2.57 (m, 4H), 3.13–3.25 (m, 4H), 3.73 (t, J=6.9 Hz, 2H), 6.81–6.97 (m, 3H), 7.18–7.32 (m, 2H), 7.66–7.78 (m, 2H), 7.78–7.90 (m, 2H).

2) The procedure of Reference Example 17-2) was generally followed to provide 1-(4-aminobutan-1-yl)-4-phenylpiperazine trihydrochloride as white crystals.

$^1$H-NMR (200 MHz, DMSO-$d_6$) δ: 1.54–1.95 (m, 4H), 2.70–2.91 (m, 2H), 2.98–3.31 (m, 6H), 3.45–3.60 (m, 2H), 3.69–3.1 (m, 2H), 5.65–6.03 (m, 3H), 6.84–6.91 (m, 1H), 7.00–7.04 (m, 2H), 7.24–7.32 (m, 2H).

Reference Example 20

Synthesis of 1-(3-aminopropan-1-yl)-4-phenylpiperazine trihydrochloride

1) The procedure of Reference Example 15-1) was generally followed to provide 3-(4-phenylpiperazin-1-yl)-propan-1-ylphthalimide as white crystals.

$^1$H-NMR (200 MHz, CDCl$_3$) δ: 1.82–1.98 (m, 2H), 2.43–2.59 (m, 6H), 2.99–3.10 (m, 4H), 3.80 (t, J=7.0 Hz, 2H), 6.78–6.91 (m, 3H), 7.17–7.30 (m, 2H), 7.64–7.75 (m, 2H), 7.79–7.90 (m, 2H).

2) The procedure of Reference Example 17-2) was generally followed to provide 1-(3-aminopropan-1-yl)-4-phenylpiperazine trihydrochloride as white crystals.

$^1$H-NMR (200 MHz, DMSO-$d_6$) δ: 2.00–2.21 (m, 2H), 2.82–3.02 (m, 2H), 3.02–3.35 (m, 6H), 3.44–3.61 (m, 2H), 3.72–3.90 (m, 2H), 5.86–6.25 (m, 3H), 6.81–6.93 (m, 1H), 6.95–7.06 (tm, 2H), 7.20–7.32 (m, 2H), 8.12–8.38 (m, 2H).

Reference Example 21

Synthesis of 1-(4-aminobutan-1-yl)-4-benzylpiperazine trihydrochloride

1) The procedure of Reference Example 15-1) was generally followed to provide 4-(4-benzylpiperazin-1-yl)-butan-1-ylphthalimide as tan-colored oil.

$^1$H-NMR (200 MHz, CDCl$_3$) δ: 1.45–1.79 (m, 4H), 2.31–2.57 (m, 10H), 3.49 (s, 2H), 3.70 (t, J=6.9 Hz, 2H), 7.22–7.35 (m, 5H), 7.68–7.76 (m, 2H), 7.80–7.87 (m, 2H).

2) The procedure of Reference Example 17-2) was generally followed to provide 1-(4-aminobutan-1-yl)-4-benzylpiperazine trihydrochloride as white crystals.

$^1$H-NMR (200 MHz, DMSO-$d_6$) δ: 1.50–1.88 (m, 4H), 2.66–2.87 (m, 2H), 2.95–3.77 (m, 10H), 4.17–4.52 (m, 2H), 7.35–7.51 (m, 3H), 7.55–7.72 (m, 2H), 7.92–8.25 (m, 2H).

Reference Example 22

Synthesis of 1-(3-aminopropan-1-yl)-4-benzylpiperazine trihydrochloride

1) The procedure of Reference Example 15-1) was generally followed to provide 3-(4-benzylpiperazin-1-yl)-propan-1-ylphthalimide as tan-colored oil.

$^1$H-NMR (200 MHz, CDCl$_3$) δ: 1.78–1.93 (m, 2H), 2.23–2.53 (m, 10H), 3.40 (s, 2H), 3.75 (t, J=6.8 Hz, 2H), 7.19–7.31 (m, 5H), 7.65–7.76 (m, 2H), 7.78–7.88 (m, 2H).

2) The procedure of Reference Example 17-2) was generally followed to provide 1-(3-aminopropan-1-yl)-4-benzylpiperazine trihydrochloride as white crystals.

$^1$H-NMR (200 MHz, DMSO-$d_6$) δ: 1.93–2.13 (m, 2H), 2.80–3.01 (m, 2H), 3.11–3.93 (m, 10H), 4.29–4.52 (m, 2H), 7.41–7.52 (m, 3H), 7.59–7.73 (m, 2H), 8.00–8.28 (m, 2H).

Reference Example 23

Synthesis of 2-(4-aminobutan-1-yl)-1,2,3,4-tetrahydroisoquinoline dihydrochloride 1) The procedure of Reference Example 15-1) was generally followed to provide 4-(1,2,3,4-tetrahydroisoquinolin-2-yl)-butan-1-ylphthalimide as yellow solid.

$^1$H-NMR (200 MHz, CDCl$_3$) δ: 1.54–1.93 (m, 4H), 2.54 (t, J=7.4 Hz, 2H), 2.69–2.74 (m, 2H), 2.86–2.92 (m, 2H), 3.61 (s, 2H), 3.70 (t, J=7.0 Hz, 2H), 6.94–7.14 (m, 4H), 7.64–7.75 (m, 2H), 7.78–7.89 (m, 2H).

2) The procedure of Reference Example 17-2) was generally followed to provide 2-(4-aminobutan-1-yl)-1,2,3,4-tetrahydroisoquinoline dihydrochloride as white crystals.

$^1$H-NMR (200 MHz, DMSO-$d_6$) δ: 1.52–1.75 (m, 2H), 1.79–2.01 (m, 2H), 2.71–3.75 (m, 8H), 4.17–4.35 (m, 1H), 4.40–4.58 (m, 1H), 7.13–7.32 (m, 4H), 7.98–8.29 (m, 3H), 11.10–11.32 (m, $_1$H).

Reference Example 24

Synthesis of 2-(3-aminopropan-1-yl)-1,2,3,4-tetrahydroisoquinoline dihydrochloride 1) The procedure of Reference Example 15-1) was generally followed to provide 3-(1,2,3,4-tetrahydroisoquinolin-2-yl)-propan-1-ylphthalimide as white crystals.

$^1$H-NMR (200 MHz, CDCl$_3$) δ: 1.88–2.05 (m, 2H), 2.60 (t, J=7.0 Hz, 2H), 2.64–2.72 (m, 2H), 2.73–2.83 (m, 2H), 3.57 (s, 2H), 3.82 (t, J=7.0 Hz, 2H), 6.92–7.12 (m, 4H), 7.58–7.67 (m, 2H), 7.72–7.81 (m, 2H).

2) The procedure of Reference Example 17-2) was generally followed to provide 2-(3-aminopropan-1-yl)-1,2,3,4-tetrahydroisoquinoline dihydrochloride as white crystals.

$^1$H-NMR (200 MHz, DMSO-$d_6$) δ: 2.03–2.26 (m, 2H), 2.82–3.13 (m, 2H), 3.17–3.75 (m, 6H), 4.18–4.36 (m, 1H), 4.44–4.61 (m, 1H), 7.12–7.38 (m, 4H), 8.02–8.45 (m, 3H).

Reference Example 25

Synthesis of 3-(1-tert-butoxycarbonyl-4-piperidyl)-1-propylamine

1) Synthesis of 3-(1-tert-butoxycarbonyl-4-piperidyl)-1-propanol

To a solution of 35.8 g (250 mM) of 3-(4-piperidyl)-1-propanol in 500 ml of ethanol was added 54.6 g (250 mM) of di-tert-butyl dicarbonate dropwise and the mixture was stirred at room temperature for one hour. The solvent was then distilled off under reduced pressure and the residue was purified by column chromatography (ethyl acetate-hexane= 1/1 ethyl acetate) to provide the title compound as light-yellow oil (50.2 g, 82%).

$^1$H-NMR (200 MHz, CDCl$_3$) δ: 0.96–1.41 (m, 5H), 1.45 (s, 9H), 1.49–1.78 (m, 4H), 2.61–2.74 (m, 2H), 3.62 (t, J=6.4 Hz, 2H), 4.04–4.10 (m, 2H).

2) Synthesis of 3-(l-tert-butoxycarbonyl-4-piperidyl)-1-propylphthalimide

To a solution of 4.87 g (20.0 mM) of 3-(1-tert-butoxycarbonyl-4-piperidyl)-1-propanol and 5.6 ml (40.0 mM) of triethylamine in 50 ml of diethyl ether was added 1.86 ml (24.0 mM) of methanesulfonyl chloride at 0° C. and the mixture was stirred at 0° C. for 30 minutes. This reaction mixture was then poured in iced water and extracted with ether. The organic layer was washed with saturated aqueous solution of sodium chloride and dried over MgSO$_4$ and the solvent was distilled off under reduced pressure to provide 3-(1-tert-butoxycarbonyl-4-piperidyl)-1-propyl mesylate. To a solution of the above mesylate in 100 ml of N,N-dimethylformamide was added 3.70 g (20.0 mM) of potassium phthalimide and the mixture was heated at 100° C. for 90 minutes. After cooling to room temperature, this reaction mixture was poured in iced water and the resulting precipitate was collected by filtration, rinsed with water, and dried in vacuo to provide the title compound as white solid (20.24 g, 90%).

$^1$H-NMR (200 MHz, CDCl$_3$) δ: 0.94–1.37 (m, 5H), 1.45 (s, 9H), 1.57–1.80 (m, 4H), 2.61–2.73 (m, 2H), 3.68 (t, J=7.2 Hz, 2H), 4.04–4.10 (m, 2H), 7.70–7.87 (m, 4H)

3) Synthesis of 3-(1-tert-butoxycarbonyl-4-piperidyl)-1-propylamine

To a solution of 20.24 g (54.34 mM) of 3-(1-tert-butoxycarbonyl-4-piperidyl)-1-propylphthalimide in 350 ml of ethanol was added 7.9 ml (163 mM) of hydrazine monohydrate and the mixture was refluxed for one hour. After cooling to room temperature, the resulting precipitate (phthalide) was filtered off and washed with a small amount of ethanol. The filtrate and washes were pooled and the solvent was distilled off under reduced pressure. The residue was extracted with chloroform and the organic layer was washed with saturated aqueous solution of sodium chloride and dried over MgSO$_4$. The solvent was then distilled off under reduced pressure to provide the title compound. Light-yellow oil. Yield 13.08 g (99%)

$^1$H-NMR (200 MHz, CDCl$_3$) δ: 0.96–1.95 (m, 18H), 2.61–2.72 (m, 4H), 4.04–4.10 (m, 2H).

Reference Example 26

Synthesis of tert-butyl 4-[(methylamino)methyl]piperidine-1-carboxylate

1) Synthesis of N-(1-tert-butoxycarbonylpiperidin-4-ylmethyl)trifluoroacetamide

To a solution of 5.07 g (23.7 mM) of tert-butyl 4-aminomethylpiperidine-1-carboxylate and 5.0 ml (35.9 mM) of triethylamine in acetonitrile (40 ml) was added 5.6 ml (47.1 mM) of ethyl trifluoroacetate at room temperature and the mixture was stirred at room temperature for 1.5 hours. After the solvent was distilled off under reduced pressure, the residue was diluted with ethyl acetate and washed with water and saturated aqueous solution of sodium chloride. The solvent was then distilled off under reduced pressure to provide the title compound as light-yellow solid (6.40 g, 87%).

$^1$H-NMR (200 MHz, CDCl$_3$) δ: 1.04–1.30 (m, 2H), 1.45 (s, 9H), 1.60–1.82 (m, 3H), 2.62–2.76 (m, 2H), 2.78 (t, J=6.4 Hz, 2H), 4.07–4.18 (m, 2H), 6.33–6.48 (m, 1H).

2) Synthesis of N-methyl-N-(1-tert-butoxycarbonylpiperidin-4-ylmethyl)trifluoroacetamide Under nitrogen, 0.21 g (5.25 mM) of 60% sodium hydride-liquid paraffin was added to a solution of 1.51 g (4.87 mM) of N-(1-tert-butoxycarbonylpiperidin-4-ylmethyl)trifluoroacetamide in N,N-dimethylformamide (10 ml) at 0° C. and the mixture was stirred at the prevailing temperature for 40 minutes. To this reaction mixture was added 0.5 ml (5.90 mM) of methyl methanesulfonate and the mixture was stirred at room temperature for 112 hours. The mixture was further stirred at 100° C. for 2.5 hours, at the end of which time the reaction was stopped by adding saturated aqueous solution of sodium hydrogen carbonate. The reaction mixture was then extracted with ethyl acetate. The organic layer was washed with saturated aqueous solution of sodium chloride and dried over MgSO$_4$. The crude product thus obtained was purified by column chromatography (ethyl acetate-hexane 40%) to provide the title compound.

Colorless oil. Yield 1.32 g (84%)

$^1$H-NMR (200 MHz, CDCl$_3$) δ: 1.10–1.30 (m, 2H), 1.46 (s, 9H), 1.50–1.96 (m, 3H), 2.56–2.77 (m, 2H), 3.04 (s, 0.78 H), 3.15 (s, 2.22H), 3.26–3.40 (m, 2H), 4.04–4.25 (m, 2H).

3) Synthesis of tert-butyl 4-[(methylamino)methyl]-piperidine-1-carboxylate

To a solution of 1.32 g (4.07 mM) of N-methyl-N-(1-tert-butoxycarbonylpiperidin-4-ylmethyl)trifluoroacetamide in ethanol was added 0.23 g (6.08 mM) of sodium borohydride at room temperature and the mixture was stirred at room temperature for 2.5 hours. To this reaction mixture was further added 0.27 g (7.1 mM) of sodium borohydride and the mixture was stirred at room temperature for 20 hours. The mixture was then stirred at 60° C. for 1.5 hours. To this reaction mixture was added water to stop the reaction and methylene chloride was added for extraction. The organic layer was washed with saturated aqueous solution of sodium chloride and dried over MgSO$_4$. The solvent was then distilled off to provide the title compound as colorless oil (1.00 g, quantitative).

$^1$H-NMR (200 MHz, CDCl$_3$) δ: 0.96–1.24 (m, 2H), 1.45 (s, 9H), 1.50–1.78 (m, 3H), 2.44 (s, 3H), 2.47 (d, J=6.2 Hz, 2H), 2.63–2.76 (m, 2H), 3.98–4.21 (m, 2H).

Reference Example 27

Synthesis of tert-butyl 4-[(benzylamino)methyl]piperidin-1-carboxylate

1) The procedure of Reference Example 26-2) was generally followed to provide N-benzyl-N-[1-(tert-butoxycarbonylpiperidin-4-ylmethyl]trifluoroacetamide as colorless oil.

$^1$H-NMR (200 MHz, CDCl$_3$) δ: 1.02–1.30 (m, 2H), 1.44 (s, 9H), 1.50–1.63 (m, 2H), 1.69–1.99 (m, 1H), 2.52–2.74 (m, 2H), 3.98–4.24 (m, 2H), 4.59–4.72 (m, 2H), 7.16–7.42 (m, 5H).

2) The procedure of Reference Example 26-3) was generally followed to provide tert-butyl 4-(benzylamino) methylpiperidine-1-carboxylate as colorless oil.

$^1$H-NMR (200 MHz, CDCl$_3$) δ: 0.96–1.23 (m, 2H), 1.45 (s, 9H), 1.47–1.78 (m, 3H), 2.51 (d, J=6.4 Hz, 2H), 2.54–2.78 (m, 2H), 3.79 (s, 2H), 3.95–4.18 (m, 2H), 7.19–7.44 (m, 5H).

Reference Example 28

Synthesis of 2-[N-tert-butoxycarbonyl-N-(3-phenylpropan-1-yl)]aminoethylamine

1) Synthesis of 2-[N-tert-butoxycarbonyl-N-(3-phenylpropan-1-yl)]aminoethanol

A solution of 7.6 ml (50 mM) of 3-bromo-1-phenylpropane and 17.1 g (280 mM) of 2-aminoethanol in acetonitrile (100 ml) was refluxed for 16 hours. The solvent was then distilled off under reduced pressure and the residue was diluted with chloroform and washed with water and saturated aqueous solution of sodium chloride. The organic layer was dried over MgSO$_4$ and the solvent was distilled off under reduced pressure. The residue was dissolved in chloroform (100 ml), followed by addition of 11.5 ml (50 mM) of di-tert-butyl dicarbonate, and the mixture was stirred at room temperature for 2 hours. The solvent was distilled off under reduced pressure and the residue was purified by column chromatography (ethyl acetate-hexane 50%) to provide the title compound.

Yield 14.07 g (quantitative)

$^1$H-NMR (200 MHz, CDCl$_3$) δ: 1.45 (s, 9H), 1.73–1.95 (m, 2H), 2.61 (t, J=7.8 Hz, 2H), 3.15–3.44 (m, 4H), 3.67–3.80 (m, 2H), 7.12–7.35 (m, 5H).

2) Synthesis of 2-[N-tert-butoxycarbonyl-N-(3-phenylpropan-1-yl)]aminoethylphthalimide To a suspension of 14.07 g (50 mM) of 2-[N-tert-butoxycarbonyl-N-(3-phenylpropan-1-yl)]aminoethanol, 26.23 g (100 mM) of triphenylphosphine, and 14.71 g (100 mM) of phthalimide in tetrahydrofuran (100 ml) was added 15.8 ml (100 mM) of diethyl azodicarboxylate at 0° C. and the mixture was stirred for 4.5 hours. The solvent was then distilled off under reduced pressure and diethyl ether was added to the residue, followed by cooling. The resulting crystals were filtered off and the solvent was distilled off under reduced pressure. The residue was purified by column chromatography (ethyl acetate-hexane 20–30%) to provide the title compound.

Yield 13.34 g (65%)

$^1$H-NMR (200 MHz, CDCl$_3$) δ: 1.24–1.30 (s, 9H), 1.74–1.95 (m, 2H), 2.59 (t, J=7.8 Hz, 2H), 3.13–3.36 (m, 2H), 3.41–3.55 (m, 2H), 3.76–3.90 (m, 2H), 7.09–7.32 (m, 5H), 7.63–7.92 (m, 4H).

3) Synthesis of 2-[N-tert-butoxycarbonyl-N-(3-phenylpropan-1-yl)aminoethylamine

To a solution of 13.34 g (32.5 mM) of 2-[N-tert-butoxycarbonyl-N-(3-phenylpropan-1-yl)]aminoethylphthalimide in ethanol (200 ml) was added 4.8 ml (99 mM) of hydrazine monohydrate at room temperature and the mixture was refluxed for 1.5 hours. After cooling to room temperature, the precipitate was filtered off and the solvent was distilled off under reduced pressure. The residue was diluted with water and extracted with chloroform and the organic layer was washed with saturated aqueous solution of sodium chloride. The solvent was then distilled off under reduced pressure to provide the title compound in crude form as light-yellow oil.

Yield 9.84 g (quantitative)

$^1$H-NMR (200 MHz, CDCl$_3$) δ: 1.44 (s, 9H), 1.74–1.94 (m, 2H), 2.60 (t, J=7.8 Hz, 2H), 2.81 (t, J=6.6 Hz, 2H), 3.11–3.35 (m, 4H), 7.13–7.35 (m, 5H).

Reference Example 29

Synthesis of 3-[N-tert-butoxycarbonyl-N-(3-phenylpropan-1-yl)]aminopropylamine

1) The procedure of Reference Example 28-1) was generally followed to provide 3-[N-tert-butoxycarbonyl-N-(3-phenylpropan-1-yl)]aminopropanol.

$^1$H-NMR (200 MHz, CDCl$_3$) δ: 1.45 (s, 9H), 1.55–1.94 (m, 4H), 2.54–2.66 (m, 2H), 3.06–3.22 (m, 2H), 3.29–3.43 (m, 2H), 3.46–3.62 (m, 2H), 7.12–7.33 (m, 5H).

2) The procedure of Reference Example 28-2) was generally followed to provide 3-[N-tert-butoxycarbonyl-N-(3-phenylpropan-1-yl)]aminopropylphthalimide.

$^1$H-NMR (200 MHz, CDCl$_3$) δ: 1.41 (s, 9H), 1.78–1.96 (m, 4H), 2.55–2.63 (m, 2H), 3.13–3.31 (m, 4H), 3.68 (t, J=7.4 Hz, 2H), 7.12–7.31 (m, 5H), 7.68–7.87 (m, 4H).

3) The procedure of Reference Example 28-3) was generally followed to provide 3-[N-tert-butoxycarbonyl-N-(3-phenylpropan-1-yl)]aminopropylamine as light-yellow oil.

$^1$H-NMR (200 MHz, CDCl$_3$) δ: 1.44 (s, 9H), 1.52–1.95 (m, 4H), 2.56–2.72 (m, 4H), 3.10–3.35 (m, 4H), 7.14–7.35 (m, 5H).

Reference Example 30

Synthesis of 4-[N-tert-butoxycarbonyl-N-(3-phenylpropan-1-yl)]aminobutylamine

1) The procedure of Reference Example 28-1) was generally followed to provide 4-[N-tert-butoxycarbonyl-N-(3-phenylpropan-1-yl)]aminobutanol.

$^1$H-NMR (200 MHz, CDCl$_3$) δ: 1.44 (s, 9H), 1.47–1.65 (m, 4H), 1.74–1.95 (m, 2H), 2.60 (t, J=7.8 Hz, 2H), 3.11–3.29 (m, 4H), 3.60–3.72 (m, 2H), 7.12–7.33 (m, 5H).

2) The procedure of Reference Example 28-2) was generally followed to provide 4-[N-tert-butoxycarbonyl-N-(3-phenylpropan-1-yl)]aminobutylphthalimide.

$^1$H-NMR (200 MHz, CDCl$_3$) δ: 1.42 (s, 9H), 1.47–1.92 (m, 6H), 2.54–2.62 (m, 2H), 3.09–3.27 (m, 4H), 3.70 (t, J=6.8 Hz, 2H), 7.10–7.32 (m, 5H), 7.68–7.89 (m, 4H).

3) The procedure of Reference Example 28-3) was generally followed to provide 4-[N-tert-butoxycarbonyl-N-(3-phenylpropan-1-yl)]aminobutylamine as light-yellow oil.

$^1$H-NMR (200 MHz, CDCl$_3$) δ: 1.43 (s, 9H), 1.35–1.62 (m, 4H), 1.72–1.90 (m, 2H), 2.20–2.93 (m, 4H), 3.08–3.31 (m, 4H), 7.13–7.34 (m, 5H).

Reference Example 31

Synthesis of 3-[N-methyl-N-(3-phenylpropan-1-yl) amino]-propan-1-ylamine

1) Synthesis of N-(3-phenylpropan-1-yl) trifluoroacetamide

To a solution of 9.37 g (69.3 mM) of 3-phenylpropylamine and 14 ml (100.4 mM) of triethylamine in acetonitrile (70 ml) was added 16.4 ml (122.7 mM) of ethyl trifluoroacetate at room temperature and the mixture was stirred at the prevailing temperature for 2 hours. The solvent was then distilled off and the residue was diluted with ethyl acetate and washed with water and saturated aqueous solution of sodium chloride. The organic layer was dried over $MgSO_4$ and the solvent was distilled off under reduced pressure to provide the title compound.

White crystals. Yield 15.95 g (quantitative)

$^1$H-NMR (200 MHz, $CDCl_3$) δ: 1.86–2.04 (m, 2H), 2.69 (t, J=7.5 Hz, 2H), 3.39 (dd, J=6.6, 6.6 Hz, 2H), 6.16–6.43 (m, 1H), 7.09–7.41 (m, 5H).

2) Synthesis of N-methyl-N-(3-phenylpropan-1-yl) trifluoroacetamide

Under nitrogen, 1.5 g (37.5 mM) of a 60% suspension of sodium hydride in liquid paraffin was added to a solution of 8.0 g (34.6 mM) of N-(3-phenylpropan-1-yl) trifluoroacetamide in N,N-dimethylformamide (70 ml) at 0° C. and the mixture was stirred at the prevailing temperature for 40 minutes. To this reaction mixture was added 3.5 ml (41.3 mM) of methyl methanesulfonate and the mixture was stirred at room temperature for 1.5 hours. Then, water was added to the reaction system to stop the reaction and the reaction mixture was extracted with ethyl acetate. The organic layer was washed with saturated aqueous solution of sodium chloride, dried over $MgSO_4$, and purified by column chromatography (ethyl acetate-hexane 15%) to provide the title compound.

Light-yellow oil. Yield 7.48 g (88%)

$^1$H-NMR (200 MHz, $CDCl_3$) δ: 1.83–2.02 (m, 2H), 2.61–2.69 (m, 2H), 3.00 (s, 1.17H), 3.09 (s, 1.83H), 3.35–3.52 (m, 2H), 7.14–7.37 (m, 5H).

3) Synthesis of 3-[N-methyl-N-(3-phenylpropan-1-yl) amino]propan-1-ylphthalimide To a solution of 4.0 g (16.3 mM) of N-methyl-N-(3-phenylpropan-1-yl)trifluoroacetamide in ethanol (30 ml) was added 1.23 g (32.5 mM) of sodium borohydride at room temperature and the mixture was stirred at the prevailing temperature for 15 hours. This reaction mixture was diluted with water and extracted with methylene chloride. The organic layer was washed with saturated aqueous solution of sodium chloride and dried over $MgSO_4$. The solvent was then distilled off under reduced pressure to provide crude (3-phenylpropan-1-yl)methylamine (2.5 g) as light-yellow oil. A solution of 2.6 g (<16.3 mM) of this (3-phenylpropan-1-yl)methylamine, 4.81 g (17.9 mM) of N-(3-bromopropyl) phthalimide, and 3.0 ml (21.5 mM) of triethylamine was refluxed for 20 hours. The solvent was then distilled off under reduced pressure and the residue was diluted with water and extracted with methylene chloride. The organic layer was washed with saturated aqueous solution of sodium chloride, dried over $MgSO_4$, and purified by column chromatography (methanol-ethyl acetate 20%) to provide the title compound.

Colorless oil. Yield 3.49 g (64%)

$^1$H-NMR (200 MHz, $CDCl_3$) δ: 1.07–1.96 (m, 4H), 2.24 (s, 3H), 2.37–2.47 (m, 4H), 2.62 (t, J=7.7 Hz, 2H), 3.74 (t, J=7.3 Hz, 2H), 7.12–7.33 (m, 5H), 7.66–7.77 (m, 2H), 7.79–7.88 (m, 2H).

4) Synthesis of 3-[N-methyl-N-(3-phenylpropan-1-yl) amino]propan-1-ylamine

To a solution of 3.49 (10.37 mM) of 3-[N-methyl-N-(3-phenylpropan-1-yl)amino]propan-1-ylphthalimide in ethanol (50 ml) was added 1.5 ml (30.92 mM) of hydrazine monohydrate at room temperature and the mixture was refluxed for 40 minutes. The solid that formed was filtered off and the filtrate was concentrated. The residue was diluted with water, made strongly basic with sodium hydroxide, and, then, extracted with chloroform. The organic layer was washed with saturated aqueous solution of sodium chloride and dried over $MgSO_4$. The solvent was then distilled off under reduced pressure to provide the title compound.

Colorless oil. Yield 2.09 g (98%)

$^1$H-NMR (200 MHz, $CDCl_3$) δ: 1.55–1.87 (m, 4H), 2.22 (s, 3H), 2.34–2.43 (m, 4H), 2.59–2.67 (m, 2H), 2.75 (s, J=7.0 Hz, 2H.), 7.13–7.36 (m, 5H).

Reference Example 32

Synthesis of 4-[(3-phenylpropan-1-yl) aminomethyl]-piperidine

1) Synthesis of N-(3-phenylpropan-1-yl)-N-(1-tert-butoxycarbonylpiperidin-4-ylmethyl)trifluoroacetamide Under nitrogen, 0.25 g (6.25 mM) of a 60% suspension of sodium hydride in liquid paraffin was added to a solution of 1.73 g (5.57 mM) of N-(1-tert-butoxycarbonylpiperidin-4-ylmethyl)trifluoroacetoamide in N,N-dimethylformamide (20 ml) at 0° C. and the mixture was stirred at 0° C. for 30 minutes. To this mixture was added 1.0 ml (6.58 mM) of 1-bromo-3-phenylpropane and the mixture was stirred at room temperature for 2.5 hours and further at 60° C. for one hour. The reaction was stopped by adding water and the reaction mixture was extracted with ethyl acetate. The organic layer was washed with saturated aqueous solution of sodium chloride, dried over $MgSO_4$, and purified by column chromatography (ethyl acetate-hexane 30%) to provide the title compound.

Colorless liquid. Yield 1.49 g (62%)

$^1$H-NMR (200 MHz, $CDCl_3$) δ: 0.99–1.33 (m, 2H), 1.46 (s, 9H), 1.43–1.67 (m, 3H), 1.82–2.03 (m, 2H), 2.51–2.72 (m, 4H), 3.17–3.46 (m, 4H), 4.00–4.22 (m, 2H), 7.12–7.37 (m, 5H).

2) Synthesis of 4-[(3-phenylpropan-1-yl)aminomethyl]-piperidine

To a solution of 1.49 g (3.48 mM) of N-(3-phenylpropan-1-yl)-N-[1-tert-butoxycarbonylpiperidin-4-ylmethyl] trifluoroacetamide in ethanol (10 ml) was added 1.0 ml (12 mM) of 12N-hydrochloric acid at room temperature and the mixture was stirred for 20 hours. The solvent was then distilled off under reduced pressure and 3 ml (36 mM) of 12N-hydrochloric acid was added to the residue. This mixture was stirred at room temperature for 20 minutes. To this reaction mixture was added ethanol and the solvent was distilled off under reduced pressure to provide 1.29 g (quantitative) of a crude product as white solid. To a solution of 0.33 g (0.90 mM) of this crude product in ethanol (4 ml) was added 4 ml (4 mM) of 1N-aqueous solution of sodium hydroxide at room temperature and the mixture was stirred for 30 minutes. The ethanol was then distilled off under reduced pressure and the residue was extracted with chloroform. The organic layer was washed with saturated aqueous solution of sodium chloride and dried over $MgSO_4$. The solvent was then distilled off under reduced pressure to provide the title compound.

Colorless liquid. Yield 0.1858 g (89%)

$^1$H-NMR (200 MHz, CDCl$_3$) δ: 0.96–1.24 (m, 2H), 1.45–4.92 (m, 5H), 2.46 (d, J=6.6 Hz, 2H), 2.50–2.72 (m, 6H), 2.98–3.16 (m, 2H), 7.10–7.33 (m, 5H).

Reference Example 33

Synthesis of ethyl 5-thia-1,8b-diazaacenaphthylene-4-carboxylate

To a solution of ethyl (imidazo[1,2-a]pyridin-5-ylthio) acetate (11.8 g) in acetic acid (120 ml) was added hexamethylenetetramine (14.0 g) and the mixture was reacted at 90° C. for 10 hours. After this reaction mixture was allowed to cool, ethyl acetate (360 ml) was added and the mixture was washed with water. The organic layer was neutralized with 30% aqueous solution of sodium hydroxide under ice-cooling and washed again with water. The organic layer was concentrated and n-hexane (100 ml) was added to the crystalline residue, followed by 1 hour of stirring at room temperature. The crystals were collected by filtration and dried to provide the title compound (9.6 g, 78%).

$^1$H-NMR (300 MHz, CDCl$_3$) δ: 1.30 (t, J=7.1 Hz, 3H), 4.22 (q, J=7.1 Hz, 2H), 5.70 (m, 1H), 6.55–6.64 (m, 2H), 6.80 (s, 1H), 7.01 (s, 1H).

Reference Example 34

Synthesis of 5-chloro-3-formylimidazo[1,2-a] pyridine

A solution of 5-chloroimidazo[1,2-a]pyridine (997 mg) and hexamethylenetetramine (1.8 g) in acetic acid (10 ml) was stirred at 90° C. for 5 hours. After the reaction mixture was allowed to cool, ethyl acetate-tetrahydrofuran (4/1; 200 ml) was added and the mixture was washed with saturated aqueous solution of sodium chloride. The organic layer was neutralized with 2N-aqueous solution of sodium hydroxide, dried over MgSO$_4$, and concentrated. The resulting crystals were rinsed with diethyl ether to provide the title compound (440 mg, 37%).

$^1$H-NMR (300 MHz, CDCl$_3$) δ: 7.20 (d, J=7.4 Hz, 1H), 7.44 (dd, J=7.4, 8.9 Hz, 1H), 7.76 (d, J=8.9 Hz, 1H), 8.50 (s, 1H), 10.71 (s, 1H).

Reference Example 35

Synthesis of ethyl 5-thia-1,8b-diazaacenaphthylene-4-carboxylate

A solution of imidazo[1,2-a]pyridine-5-thiol (448 mg), ethyl thioglycolate (0.36 ml), and sodium ethoxide (210 mg) in ethanol (10 ml) was refluxed with stirring for 3 hours. The mixture was then allowed to cool and concentrated. The residue was diluted with ethyl acetate (10 ml) and extracted with 1N-hydrochloric acid. The aqueous layer was neutralized with 1N-NaOH/water and extracted with ethyl acetate, and the organic layer was washed with water and concentrated. The resulting crystals were collected, rinsed with diisopropyl ether (20 ml), and dried to provide the title compound (430 mg, 65%).

Reference Example 36

Synthesis of 6-tert-butyldimethylsiloxy-2-(2-hydroxyethyl)-2,5,7,8-tetramethylchroman 1) Synthesis of methyl 6-hydroxy-2,5,7,8-tetramethylchroman-2-acetate To a suspension of 10.0 g (37.83 mM) of 6-hydroxy-2,5,7,8-tetramethylchroman-2-acetic acid in methanol (50 ml) was added 0.5 ml (6 mM) of concentrated sulfuric acid at room temperature and the mixture was stirred for 3 days. To this reaction mixture was added a saturated aqueous solution of sodium hydrogen carbonate at 0° C. until the pH had been brought to 5–7 and the solvent was then distilled off under reduced pressure. The residue was diluted with water and extracted with diethyl ether. The organic layer was washed with saturated aqueous solution of sodium chloride and dried over MgSO$_4$. The solvent was then distilled off under reduced pressure to provide the title compound as tan-colored oil.

Yield 7.69 g (75%)

$^1$H-NMR (CDCl$_3$) δ: 1.41 (s, 3H), 1.82–2.06 (m, 2H), 2.09 (s, 3H), 2.11 (S, 3H), 2.16 (s, 3H), 2.60–2.68 (m, 4H), 3.69 (s, 3H).

IR (neat): 3494, 2933, 1730, 1450, 1329, 1252, 1165, 1092, 1028, 924 cm$^{-1}$

2) Synthesis of methyl 6-tert-butyldimethylsiloxy-2,5,7,8-tetramethylchroman-2-acetate Under nitrogen, 5.41 g (35.9 mM) of tert-butyldimethylsilyl chloride was added to a solution of 7.69 g (27.63 mM) of methyl 6-hydroxy-2,5,7,8-tetramethylchroman-2-acetate and 2.82 g (41.4 mM) of imidazole in DMF (54 ml) at room temperature and the mixture was stirred at 0° C. for 20 hours. This reaction mixture was poured in saturated aqueous sodium hydrogen carbonate-diethyl ether under intense agitation to stop the reaction and, then, extracted with diethyl ether. The organic layer was washed with water and saturated aqueous solution of sodium chloride and dried over MgSO$_4$. The resulting crude product was purified by column chromatography (ethyl acetate-hexane: 10%) to provide the title compound as yellow oil.

Yield 11.35 g (quant.)

$^1$H-NMR (CDCl$_3$) δ: 0.11 (s, 6H), 1.04 (s, 9H), 1.41 (s, 3H), 1.85–2.03 (m, 2H), 2.05 (s, 6H), 2.09 (s, 3H), 2.55–2.64 (m, 4H), 3.69 (s, 3H).

IR (neat): 2937, 2858, 1740, 1460, 1254, 1092, 941, 887, 837, 779 cm$^{-1}$.

3) Synthesis of 6-tert-butyldimethylsiloxy-2-(2-hydroxyethyl)-2,5,7,8-tetramethylchroman Under nitrogen, a solution of 11.35 g (28.91 mM) of methyl 6-tert-butyldimethylsiloxy-2,5,7,8-tetramethylchroman-2-acetate in diethyl ether (10 ml) was added to a suspension of 1.1 g (28.99 mM) of lithium aluminum hydride in diethyl ether (50 ml) at 0° C. and the mixture was stirred at the prevailing temperature for one hour. Then, water (1.1 ml), 15% aqueous solution of NaOH (1.1 ml), and water (1.1 ml) were added in that order and the mixture was stirred at room temperature for 30 minutes. To this mixture was added magnesium sulfate, and after the precipitate was filtered off, the solvent was distilled off under reduced pressure to provide a crude product. This crude product was purified by column chromatography (ethyl acetate-hexane: 20–30%) to provide the title compound as light-yellow oil (9.65 g, 92%).

$^1$H-NMR (CDCl$_3$) δ: 0.12 (s, 6H), 1.05 (s, 9H), 1.28 (s, 3H), 1.70–2.02 (m, 4H), 2.06 (s, 6H), 2.10 (s, 3H), 2.50–2.67 (m, 2H), 3.83–4.03 (m, 2H).

Reference Example 37

Synthesis of 1-(trans-4-aminomethyl-1-cyclohexylmethyl)-4-phenylpiperidine dihydrochloride 1)

Synthesis of trans-4-[N-(tert-butoxycarbonyl) aminomethyl]cyclohexane-1-carboxylic acid To a suspension of 47.16 g (300 mM) of trans-4-aminomethylcyclohexane-1-carboxylic acid in purified water (300 ml)-THF (300 ml) was added 41.8 ml (300 mM) of triethylamine as well as 65.48 g (300 mM) of di-tert-butyl dicarbonate and the mixture was stirred at room temperature for 2 hours. Then, 12N-hydrochloric acid was added until the aqueous layer had been brought to pH 2 and the mixture was then extracted with 200 ml of ethyl acetate. The organic layer was washed with 300 ml of saturated aqueous solution of sodium chloride and dried over $MgSO_4$ and the solvent was distilled off under reduced pressure to provide 67.3 g (yield 87.2%) of crude product as white solid. This crude product was not purified but used as it was in the next reaction.

$^1$H-NMR (200 MHz, DMSO-$d_6$) δ: 0.74–0.98 (m, 2H), 1.09–1.47 (m, 12H), 1.61–1.79 (m, 2H), 1.79–1.98 (m, 2H), 1.98–2.19 (m, 1H), 2.76 (t, 2H, J=6.2 Hz), 6.78 (t, 1H, J=5.4 Hz).

IR (KBr): 3375, 1694, 1529 $cm^{-1}$.

2) Synthesis of trans-4-[N-(tert-butoxycarbonyl)aminomethyl]cyclohexane-1-methanol To 400 ml of 1.0M borane-THF was added 51.7 g (200 mM) of trans-4-[N-(tert-butoxycarbonyl)aminomethyl]cyclohexane-1-carboxylic acid in small portions at 0° C. and the mixture was stirred at room temperature for 2 hours. This reaction mixture was then poured in iced water and, after thorough stirring, extracted with 200 ml of ethyl acetate. The organic layer was washed with 250 ml of saturated aqueous solution of sodium chloride and dried over $MgSO_4$ and the solvent was distilled off under reduced pressure to provide 47.06 g (yield 96.7%) of crude product as white solid. This crude product was not purified but used as it was in the next reaction.

$^1$H-NMR (200 MHz, DMSO-$d_6$) δ: 0.74–0.96 (m, 4H), 1.14–1.45 (m, 11H), 1.62–1.81 (m, 4H), 2.76 (t, 2H, J=6.2 Hz), 3.20 (t, 2H, J=6.0 Hz), 4.31 (t, 1H, OH, J=6.0 Hz), 6.72 (t, 1H, J=5.4 Hz).

IR (KBr): 3376, 1698, 1533 $cm^{-1}$.

3) Synthesis of N-(trans-4-bromomethyl-1-cyclohexylmethyl)-N-(tert-butoxycarbonyl)amine To a solution of 5.00 g (20.55 mM) of trans-4-[N-(tert-butoxycarbonyl)aminomethyl]cyclohexane-1-methanol and 6.42 g (24.48 mM) of triphenylphosphine in methylene chloride (30 ml) was added 13.63 g (41.1 mM) of carbon tetrabromide at 0° C. and the mixture was stirred at room temperature for 20 hours. This reaction mixture was purified by column chromatography (ethyl acetate-hexane: 10%) to provide the title compound as white solid.

Yield 2.53 g (40%)

$^1$H-NMR (200 MHz, $CDCl_3$) δ: 0.83–1.14 (m, 4H), 1.44 (s, 9H), 1.49–1.70 (m, 2H), 1.71–2.01 (m, 4H), 2.98 (t, J=6.4 Hz, 2H), 3.28 (d, J=6.2 Hz, 2H), 4.47–4.66 (m, 1H).

IR (KBr): 3390, 2921, 1685, 1524, 1257, 1174, 613 $cm^{-1}$.

4) Synthesis of 1-[trans-4-[N-(tert-butoxycarbonyl)aminomethyl]-1-cyclohexylmethyl]-4-phenylpiperidine A solution of 2.51 g (8.20 mM) of N-(trans-4-bromomethyl-1-cyclohexylmethyl)-N-(tert-butoxycarbonyl)amine, 1.32 g (8.19 mM) of 4-phenylpiperidine, and 2.3 ml (16.5 mM) of triethylamine in ethanol (10 ml) was refluxed under nitrogen for 64 hours. After cooling to room temperature, the reaction mixture was diluted with water and extracted with ethyl acetate. The organic layer was washed with saturated aqueous solution of sodium chloride and dried over $MgSO_4$. This crude product was purified by column chromatography (methanol-ethyl acetate: 10%) to provide the title compound as light-yellow solid.

Yield 1.02 g (32%)

$^1$H-NMR (200 MHz, $CDCl_3$) δ: 0.85–0.99 (m, 4H), 1.45 (s, 9H), 1.61–2.15 (m, 12H), 2.22 (d, J=6.8 Hz, 2H), 2.39–2.56 (m, 1H), 2.90–3.10 (m, 4H), 4.51–4.64 (m, 1H), 7.13–7.39 (m, 5H).

IR (KBr): 3386, 2937, 1691, 1522, 1443, 1279, 1250, 1171, 698 $cm^{-1}$.

5) Synthesis of 1-(trans-4-aminomethyl-1-cyclohexylmethyl)-4-phenylpiperidine dihydrochloride To a solution of 1.02 g (2.64 mM) of 1-[trans-4-[N-(tert-butoxycarbonyl)aminomethyl]-1-cyclohexylmethyl]-4-phenylpiperidine in ethanol (10 ml) was added 10 ml (120 mM) of 12N-hydrochloric acid at room temperature and the mixture was stirred for one hour. This reaction mixture was concentrated under reduced pressure (crystals separated out) and diethyl ether was added to the residue. The resulting crystal crop was harvested by filtration and rinsed with ethanol and diethyl ether to provide the title compound as light-purple crystals.

Yield 0.81 g (85%)

$^1$H-NMR (200 MHz, DMSO-$d_6$) δ: 0.85–1.11 (m, 4H), 1.68–2.08 (m, 6H), 2.14–2.40 (m, 2H), 2.55–3.17 (m, 7H), 3.40–3.64 (m, 4H), 7.18–7.41 (m, 5H), 7.92–8.16 (m, 3H), 10.17–10.44 (m, 1H).

IR (neat): 1603, 1504, 1433, 9985, 945, 754, 702 $cm^{-1}$.

Reference Example 38

Synthesis of 1-[4-(aminomethyl)benzyl]-4-phenylpiperidine dihydrochloride

1) Synthesis of 4-[N-(tert-butoxycarbonyl)aminomethyl]benzoic acid

To a suspension of 15 g (99.2 mM) of 4-(aminomethyl)benzoic acid in THF (100 ml) was added 100 ml (100 mM) of 1N-aqueous solution of NaOH at room temperature, followed by addition of 23.8 g (109 mM) of di-tert-butyl dicarbonate, and the mixture was stirred for 20 hours. To this reaction mixture was added 6N-hydrochloric acid so as to bring the pH to 4 and the mixture was extracted with ethyl acetate. The organic layer was washed with saturated aqueous solution of sodium chloride and dried over $MgSO_4$. The solvent was distilled off under reduced pressure and hexane was added to the crystalline residue. The crystals were collected by filtration and rinsed with hexane to provide the title compound as white crystals.

Yield 22.23 g (89%)

m.p. 161–162° C.

$^1$H-NMR (200 MHz, DMSO-$d_6$) δ: 1.40 (9H, s), 4.19 (2H, d, J=6.4 Hz), 7.34 (2H, d, J=8.2 Hz), 7.39–7.50 (1H, m), 7.89 (2H, d, J=8.2 Hz).

IR (KBr): 3357, 2982, 1686, 1510, 1431, 1292, 1246, 1171 $cm^{-1}$.

2) Synthesis of 4-[N-(tert-butoxycarbonyl)aminomethyl]-1-phenylmethanol

To 100 ml (100 mM) of 1M borane-THF complex was added 25.13 g (100 mM) of 4-[N-(tert-butoxycarbonyl)aminomethyl]benzoic acid at 0° C. and the mixture was stirred at room temperature for 1.5 hours. The reaction was stopped by adding iced water and the reaction mixture was extracted with ethyl acetate. The organic layer was washed with saturated aqueous solution of sodium chloride and dried over $MgSO_4$. The solvent was then distilled off under reduced pressure and the resulting crystal crop was harvested by filtration and rinsed with hexane to provide the title compound as white crystals.

Yield 11.07 g (47%)

m.p. 88–90° C.

$^1$H-NMR (200 MHz, CDCl$_3$) δ: 1.46 (9H, s), 4.31 (2H, d, J=6.0 Hz), 4.68 (2H, s), 4.76–5.06 (1H, s), 7.23–7.38 (m, 4H).

IR (KBr): 3347, 2980, 1686, 1514, 1248, 1171 cm$^{-1}$.

3) Synthesis of 1-[4-[N-(tert-butoxycarbonyl)aminomethyl]benzyl]-4-phenylpiperidine To a solution of 5.0 g (21.07 mM) of 4-[N-(tert-butoxycarbonyl)aminomethyl]-1-phenylmethanol and 5.9 ml (42.33 mM) of triethylamine in THF (42 ml) was added 2.5 ml (32.3 mM) of methanesulfonyl chloride at 0° C. and the mixture was stirred at the prevailing temperature for one hour. The reaction was then stopped by adding saturated aqueous solution of sodium hydrogen carbonate and the mixture was extracted with ethyl acetate. The organic layer was washed with water and saturated aqueous solution of sodium chloride and dried over MgSO$_4$. The solvent was then distilled off under reduced pressure to provide 6.72 g (21.07 mM) of crude product as light-brown solid. To a solution of 6.72 g (21.07 mM) of this crude mesylate in ethanol (42 ml) was added 5.9 ml (42.33 mM) of triethylamine as well as 3.40 g (21.09 mM) of 4-phenylpiperidine and the mixture was refluxed for 18 hours. After cooling to room temperature, the reaction mixture was diluted with water and extracted with ethyl acetate. The organic layer was washed with water and saturated aqueous solution of sodium chloride and dried over magnesium sulfate. After concentration, the crude product was purified by column chromatography (ethyl acetate-hexane: 50%) to provide the title compound as light-yellow solid.

Yield 5.77 g (72%)

m.p. 73–74° C.

$^1$H-NMR (200 MHz, CDCl$_3$) δ: 1.46 (9H, s), 1.73–1.88 (4H, m), 1.99–2.19 (1H, m), 2.94–3.08 (2H, m), 3.54 (2H, s), 4.31 (2H, d, J=5.8 Hz), 4.73–4.96 (1H, m), 7.13–7.36 (4H, m).

IR (KBr): 3389, 1690, 1518, 1269, 1171 cm$^{-1}$.

4) Synthesis of 1-[4-(aminomethyl)benzyl]-4-phenylpiperidine dihydrochloride

To 5.77 g (15.16 mM) of 1-[4-[N-(tert-butoxycarbonyl)aminomethyl]benzyl]-4-phenylpiperidine was added 10 ml (120 mM) of 12N-hydrochloric acid at room temperature and the mixture was stirred at the prevailing temperature for 2 hours. To this reaction mixture was added ethanol and the mixture was concentrated under reduced pressure. To the residue were added ethanol and diethyl ether and the resulting crystals were harvested by filtration. This crystal crop was rinsed with ethanol and diethyl ether to provide the title compound as white crystals.

Yield 4.72 g (88%)

m.p. 257–260° C. (dec.)

$^1$H-NMR (200 MHz, DMSO-d$_6$) δ: 1.82–2.01 (2H, m), 2.05–2.32 (2H, m), 2.68–2.88 (1H, m), 2.91–3.15 (2H, m), 3.28–3.56 (2H, m), 3.99–4.12 (2H, m), 4.32 (2H, d, J=5.0 Hz), 7.12–7.44 (5H, m), 7.59 (2H, d, J=8.0 Hz), 7.73 (2H, d, J=8.0 Hz), 8.34–8.74 (3H, m), 11.25–11.50 (1H, m).

IR (KBr): 2091, 1601, 1530, 1450, 1533, 1422, 1399, 939, 746, 700 cm$^{-1}$.

Reference Example 39

Synthesis of 1-[4-(aminomethyl)benzyl]-4-benzylpiperidine dihydrochloride

1) Synthesis of 1-[4-[N-(tert-butoxycarbonyl)aminomethyl]benzyl]-4-benzylpiperidine To a solution of 5.0 g (21.07 mM) of 4-[N-(tert-butoxycarbonyl)aminomethyl]-1-phenylmethanol and 5.9 ml (42.33 mM) of triethylamine in THF (42 ml) was added 2.5 ml (32.3 mM) of methanesulfonyl chloride at 0° C. and the mixture was stirred at the prevailing temperature for one hour. The reaction was stopped by adding saturated aqueous solution of sodium hydrogen carbonate and the reaction mixture was extracted with ethyl acetate. The organic layer was washed with water and saturated aqueous solution of sodium chloride and dried over MgSO$_4$. The solvent was then distilled off under reduced pressure to provide 7.21 g (21.07 mM) of crude product as light-brown solid. To a solution of 7.21 g (21.07 mM) of this crude mesylate in ethanol (42 ml) was added 5.9 g (42.33 mM) of triethylamine as well as 3.69 g (21.05 mM) of 4-phenylpiperidine and the mixture was refluxed for 18 hours. After cooling to room temperature, the reaction mixture was diluted with water and extracted with ethyl acetate. The organic layer was washed with water and saturated aqueous solution of sodium chloride and dried over MgSO$_4$. After concentration, the crude product was purified by column chromatography (ethyl acetate-hexane: 50%) to provide the title compound as light-yellow oil.

Yield 5.77 g (69%)

$^1$H-NMR (200 MHz, CDCl$_3$) δ: 1.20–1.40 (2H, m), 1.46 (9H, s), 1.85–2.01 (2H, m), 2.53 (2H, d, J=6.2 Hz), 2.78–2.93 (2H, m), 3.48 (2H, s), 4.29 (2H, d, J=6.0 Hz), 4.70–4.88 (1H, m), 7.07–7.34 (9H, m).

IR (neat): 3350, 2924, 1709, 1508, 1452, 1365, 1252, 1173 cm$^{-1}$.

2) Synthesis of 1-[4-(aminomethyl)benzyl]-4-benzylpiperidine dihydrochloride

To 5.77 g (14.6 mM) of 1-[4-[N-(tert-butoxycarbonyl)aminomethyl]benzyl]-4-benzylpiperidine was added 10 ml (120 mM) of 12N-hydrochloric acid at room temperature and the mixture was stirred at the prevailing temperature for one hour. After addition of ethanol, the mixture was concentrated under reduced pressure and ethanol and diethyl ether were added to the residue. The resulting crystal crop was harvested by filtration and rinsed with ethanol and diethyl ether to provide the title compound as white crystals.

Yield 4.25 g (79%)

m.p. 245–250° C.

$^1$H-NMR (200 MHz, DMSO-d$_6$) δ: 1.50–1.88 (5H, m), 2.65–2.98 (2H, m), 3.16–3.41 (4H, m), 3.98–4.14 (2H, m), 4.17–4.28 (2H, m), 7.12–7.36 (5H, m), 7.55 (2H, d, J=8.4 Hz), 7.65 (2H, d, J=8.4 Hz), 8.29–8.62 (3H, m), 10.70–10.98 (1H, m).

IR (KBr): 3395, 2980, 2500, 1593, 1512, 1454, 1078, 881, 860, 748, 700 cm$^{-1}$.

Reference Example 40

Synthesis of tert-butyl 4-[(dimethoxyphosphoryl)acetyl]piperidine-1-carboxylate

1) Synthesis of ethyl 1-(tert-butoxycarbonyl)piperidine-4-carboxylate

To a solution of 16.377 g (104.17 mM) of ethyl piperidine-4-carboxylate in 150 ml of tetrahydrofuran was added a solution of 25.0 g (115 mM) of di-tert-butyl dicarbonate in 50 ml of tetrahydrofuran dropwise at room temperature and the mixture was stirred at the prevailing temperature for 3 hours. The solvent was then distilled off under reduced pressure and the residue was purified by silica gel column chromatography (hexane-ethyl acetate:9/1 to 6/1) to provide the title compound.

Colorless liquid. Yield 26.631 g (99%)

¹H-NMR (CDCl₃, 200 MHz) δ: 1.258 (3H, t, 7.1 Hz), 1.456 (9H, s), 1.518–1.718 (2H, m), 1.880 (2H, br d, 13.3 Hz), 2.434 (1H, tt, 4.0 Hz, 11.0 Hz), 2.832 (2H, br t, 13.9 Hz), 4.031 (2H, br d, 13.4 Hz), 4.145 (2H, q, 7.1 Hz).

IR (neat): 2976, 1732, 1695, 1421, 1367, 1313, 1240, 1167, 1041 cm⁻¹.

2) Synthesis of tert-butyl 4-[(dimethoxyphosphoryl]acetyl piperidine-1-carboxylate To a solution of 10.1 g (81.3 mM) of dimethyl methylphosphonate in 100 ml of tetrahydrofuran was added 53.2 ml (85.2 mM) of 1.6M n-butyllithium-hexane dropwise at −78° C. and the mixture was stirred at the prevailing temperature for 10 minutes. To this mixture was added a solution of 9.964 g (38.721 mM) of ethyl 1-(tert-butoxycarbonyl)piperidine-4-carboxylate in 50 ml of tetrahydrofuran at −78° C. and the mixture was stirred until the temperature had recovered to room temperature. This reaction mixture was poured in aqueous solution of ammonium chloride and extracted with 3 portions of ethyl acetate. The organic layers were pooled and dried over MgSO₄ and the solvent was distilled off under reduced pressure. The residue was purified by silica gel column chromatography (hexane-ethyl acetate:1/1 to ethyl acetate) to provide the title compound.

Colorless liquid. Yield 11.487 g (88%)

¹H-NMR (CDCl₃, 200 MHz) δ: 1.453 (9H, s), 1.299–1.700 (2H, m), 1.865 (2H, br d, 11.0 Hz), 2.661–2.850 (3H, m), 3.147 (2H, d, 22.8 Hz), 3.793 (6H, d, 11.4 Hz), 4.109 (2H, br d, 12.8 Hz).

IR (neat): 3475, 2931, 1691, 1423, 1242, 1169, 1030, 810 cm⁻¹.

Reference Example 41

Synthesis of tert-butyl 4-[4-(dimethoxyphosphoryl)-3-oxobutyl]piperidine-1-carboxylate 1) Synthesis of tert-butyl (E)-4-(2-ethoxycarbonylvinyl)piperidine-1-carboxylate To a solution of 10.7 g (84.4 mM) of oxalyl chloride in 100 ml of tetrahydrofuran was added 12.0 ml (169 mM) of dimethyl sulfoxide dropwise at −78° C. and the mixture was stirred for 5 minutes. Then, a solution of [ ]g ( mM) of tert-butyl 4-(hydroxymethyl)piperidine-1-carboxylate in 100 ml of tetrahydrofuran was added dropwise and the mixture was stirred at −78° C. for 15 minutes. To this mixture was added 47.0 ml (338 mM) of triethylamine at −78° C. and the temperature was increased to room temperature. This reaction mixture was poured in water and extracted with 3 portions of ethyl acetate. The organic layers were pooled and dried over MgSO₄ and the solvent was distilled off under reduced pressure. The resulting crude tert-butyl 4-formylpiperidine-1-carboxylate was not purified but used as it was in the next reaction.

A 60% suspension of sodium hydride in liquid paraffin, 2.48 g (61.9 mM), was washed with hexane twice and suspended in 50 ml of toluene. Then, under ice-cooling, a solution of 15.1 g (67.5 mM) of ethyl diethylphosphonoacetate in 50 ml of toluene was added dropwise and the mixture was stirred at room temperature for 30 minutes. To this mixture was further added a solution of the crude-tert-butyl 4-formylpiperidine-1-carboxylate obtained above in 100 ml of toluene dropwise at room temperature and the mixture was stirred at room temperature overnight. (The stirring had to be discontinued after about 1 hour because of formation of a gum-like precipitate). This reaction mixture was poured in water and extracted with 2 portions of diethyl ether. The organic layers were pooled and dried over MgSO₄ and the solvent was distilled off under reduced pressure. The crude product thus obtained was purified by silica gel column chromatography (hexane-ethyl acetate:6/1) to provide the title compound.

Yellow liquid. Yield 14.281 g (90%)

¹H-NMR (CDCl₃, 200 MHz) δ: 1.236–1.420 (2H, m), 1.293 (3H, t, 7.0 Hz), 1.460 (9H, s), 1.737 (2H, br d, 13.8 Hz), 2.205–2.383 (1H, m), 2.762 (2H, br t, 11.9 Hz), 4.121 (2H, br d, 12.4 Hz), 4.193 (2H, q, 7.1 Hz), 5.801 (1H, dd, 1.2 Hz, 16.0 Hz), 6.897 (1H, dd, 6.6 Hz, 15.8 Hz).

IR (neat): 2978, 1718, 1693, 1421, 1275, 1169 cm⁻¹.

2) Synthesis of tert-butyl (E)-4-[4-(dimethoxyphosphoryl)-3-oxo-1-butenyl]piperidine-1-carboxylate To a solution of 13.1 g (106 mM) of dimethyl methylphosphonate in 100 ml of tetrahydrofuran was added 69.2 ml (111 mM) of 1.6M n-butyllithium-hexane dropwise at −78° C. and the mixture was stirred at the prevailing temperature for 10 minutes. To this reaction mixture was added a solution of 14.271 g (50.362 mM) of tert-butyl (E)-4-(2-ethoxycarbonylvinyl)piperidine-1-carboxylate in 100 ml of tetrahydrofuran at −78° C. and the mixture was stirred until the temperature had recovered to room temperature. This reaction mixture was poured in aqueous solution of ammonium chloride and extracted with 3 portions of ethyl acetate. The organic layers were pooled and dried over MgSO₄ and the solvent was distilled off under reduced pressure. The residue was purified by silica gel column chromatography (hexane-ethyl acetate:1/1 to ethyl acetate) to provide the title compound.

Yellow liquid. Yield 11.768 g (65%)

¹H-NMR (CDCl₃, 200 MHz) δ: 1.115–1.403 (2H, m), 1.462 (9H, s), 1.559–1.832 (2H, m), 2.271–2.394 (1H, m), 2.769 (2H, br t, 12.1 Hz), 3.228 (2H, d, 22.6 Hz), 3.786 (6H, d, 11.4 Hz), 3.962–4.189 (2H, m), 6.212 (1H, dd, 1.3 Hz, 15.9 Hz), 6.862 (1H, dd, 6.5 Hz, 15.7 Hz).

IR (neat): 3479, 2958, 1689, 1425, 1250, 1171, 1032, 970, 814 cm⁻¹.

3) Synthesis of tert-butyl 4-[4-(dimethoxyphosphoryl)-3-oxobutyl]piperidine-1-carboxylate A solution of 5.443 g (15.062 mM) of tert-butyl (E)-4-[4-(dimethoxyphosphoryl)-3-oxo-1-butenyl]piperidine-1-carboxylate in 50 ml of methanol was subjected to hydrogenation using 3 g of 10% palladium-on-carbon (50% hydrous) as a catalyst at room temperature and atmospheric pressure until the starting material had been no longer detected. The catalyst was removed by filtration with the aid of celite and the catalyst was washed with methanol. The filtrate and washes were pooled and the solvent was distilled off under reduced pressure. The residue was purified by silica gel column chromatography (hexane-ethyl acetate:1/1 to ethyl acetate) to provide the title compound.

Colorless liquid. Yield 4.732 g (87%)

¹H-NMR (CDCl₃, 200 MHz) δ: 0.994–1.691 (9H, m), 1.449 (9H, s), 2.659 (2H, br t, 12.1 Hz), 3.094 (2H, d, 22.6 Hz), 3.789 (6H, d, 11.4 Hz), 3.962–4.185 (2H, m).

IR (neat): 3479, 2927, 1689, 1423, 1246, 1167, 1030, 812 cm⁻¹.

Reference Example 42

Synthesis of tert-butyl 4-(diethoxyphosphorylmethylthiomethyl)piperidine-1-carboxylate 1) Synthesis of S-(diethoxyphosphorylmethyl) thioacetate To a solution of 17.527 g (93.938 mM) of diethyl chloromethylphosphonate in 50 ml of N,N-dimethylformamide was added 12.9 g (113 mM) of potassium thioacetate and the mixture was stirred at 100° C. for 3 hours. This reaction mixture was poured in water, saturated with sodium chloride, and extracted with 4 portions of ethyl acetate. The organic layers were pooled and dried over $MgSO_4$ and the solvent was distilled off under reduced pressure. The residue was purified by silica gel column chromatography (hexane-ethyl acetate:3/1 to 1/1) to provide the title compound.

Orange-colored liquid. Yield 13.059 g (61%)

$^1$H-NMR (CDCl$_3$, 200 MHz) δ: 1.330 (6H, t, 7.2 Hz), 2.398 (3H, s), 3.231 (2H, d, 14.0 Hz), 4.141 (4H, quint, 7.4 Hz).

IR (neat): 2983, 1701, 1252, 1051, .1024, 968, 623 cm$^{-1}$.

2) Synthesis of tert-butyl 4-(diethoxyphosphorylmethylthiomethyl)piperidine-1-carboxylate To a solution of 1.529 g (6.759 mM) of S-(diethoxyphosphorylmethyl) thioacetate in 30 ml of methanol was added 1.30 g (6.76 mM) of 28% sodium methoxide-methanol under ice-cooling and the mixture was stirred at the prevailing temperature for 20 minutes. To this reaction mixture was added crude tert-butyl 4-(mesyloxymethyl)piperidine-1-carboxylate [which was prepared by adding 0.73 ml (9.46 mM) of methanesulfonyl chloride to a solution of 1.75 g (8.11 mM) of tert-butyl 4-(hydroxymethylthiomethyl)piperidine-1-carboxylate and 1.51 ml (10.8 mM) of triethylamine in 30 ml of tetrahydrofuran with ice-cooling, stirring the mixture at the prevailing temperature for 0.5 hour, pouring the mixture in water, extracting it with 2 portions of ethyl acetate, drying the pooled organic layer over $MgSO_4$, and concentrating it], and the mixture was refluxed for 3 hours. The solvent was distilled off under reduced pressure and the residue was diluted with water and extracted with 2 portions of ethyl acetate. The organic layers were pooled and dried over $MgSO_4$ and the solvent was distilled off under reduced pressure. The residue was purified by silica gel column chromatography (hexane-ethyl acetate: 3/1 to ethyl acetate) to provide the title compound.

Yellow liquid. Yield 2.325 g (90%)

$^1$H-NMR (CDCl$_3$, 200 MHz) δ: 1.042–1.256 (2H, m), 1.353 (6H, t, 6.9 Hz), 1.454 (9H, s), 1.552–1.730 (1H, m), 1.804 (2H, br d, 13.8 Hz), 2.629–2.778 (6H, m), 4.060–4.130 (2H, m), 4.181 (4H, quint, 7.4 Hz).

IR (neat): 2978, 2929, 1691, 1423, 1246, 1163, 1053, 1026, 966, 827 cm$^{-1}$.

Reference Example 43

Synthesis of tert-butyl 4-(diethoxyphosphorylmethanesulfonylmethyl)piperidine-1-carboxylate A solution of 2.325 g (6.095 mM) of tert-butyl 4-(diethoxyphosphorylmethylthiomethyl)piperidine-1-carboxylate, 2.76 g (24.4 mM) of 30% aqueous solution of hydrogen peroxide, and 0.2 g of sodium tungstate in 50 ml of methanol was stirred at room temperature overnight. This reaction mixture was poured in water and extracted with 4 portions of ethyl acetate. The organic layers were pooled and dried over $MgSO_4$ and the solvent was distilled off under reduced pressure. The residue was purified by silica gel column chromatography (hexane-ethyl acetate:1/1 to ethyl acetate) to provide the title compound.

Colorless liquid. Yield 2.041 g (81%)

$^1$H-NMR (CDCl$_3$, 200 MHz) δ: 1.224–1.410 (2H, m), 1.376 (6H, t, 7.1 Hz), 1.452 (9H, s), 1.943 (2H, br d, 13.2 Hz), 2.203–2.335 (1H, m), 2.768 (2H, br t, 12.3 Hz), 3.325 (2H, d, 6.6 Hz), 3.567 (2H, d, 16.4 Hz), 4.090 (2H, br d, 12.4 Hz), 4.234 (4H, qd, 7.1 Hz, 8.3 Hz).

IR (neat): 2976, 1689, 1425, 1311, 1250, 1165, 1051, 1022, 972, 835, 798 cm$^{-1}$.

Reference Example 44

Synthesis of tert-butyl 4-(diphenoxyphosphorylmethanesulfonylaminomethyl)piperidine-1-carboxylate A solution of 2.405 g (5.947 mM) of phenyl di-phenoxyphosphorylmethanesulfonate and 1.66 g (7.73 mM) of 1-(tert-butoxycarbonyl)piperidine-4-ylmethylamine in 50 ml of toluene was refluxed overnight. The solvent was then distilled off under reduced pressure and the residue was purified by silica gel column chromatography (hexane-ethyl acetate:2/1 to 1/1) to provide the title compound.

Yellow liquid. Yield 2.245 g (72%)

$^1$H-NMR (CDCl$_3$, 200 MHz) δ: 1.000–1.181 (2H, m), 1.449 (9H, s), 1.524–1.724 (3H, m), 2.636 (2H, t, 13.0 Hz), 2.973 (2H, t, 6.4 Hz), 3.883 (2H, d, 16.0 Hz), 4.087 (2H, br d, 11.0 Hz), 5.409 (1H, t, 6.4 Hz), 7.186–7.264 (6H, m), 7.332–7.405 (4H, m).

IR (neat): 3207, 2934, 1687, 1489, 1425, 1338, 1277, 1213, 1182, 1163, 951, 766 cm$^{-1}$.

Reference Example 45

Synthesis of 5-thia-1,8b-diazaacenaphthylene-4-carboxylic acid

To a solution of 3.00 g (12.18 mM) of ethyl 5-thia-1,8b-diazaacenaphthylene-4-carboxylate in methanol (9 ml) was added 18 ml (18 mM) of 1N-aqueous solution of sodium hydroxide at room temperature and the mixture was stirred for 2.5 hours. This reaction mixture was cooled to 0° C. and 1N-hydrochloric acid was added until the pH had been brought to 5. The resulting crystals were harvested by filtration. This crystal crop was rinsed with water, ethanol and diethyl ether to provide the title compound as orange-colored solid (yield 1.98 g, 69%).

Elemental analysis for $C_{10}H_6N_2O_2S.1H_2O$ Calcd.: C, 50.84; H, 3.41; N, 11.86 Found: C, 50.59; H, 3.41; N, 11.62

Reference Example 46

Synthesis of 1-aminoacetyl-4-(3-phenylpropan-1-yl)piperazine dihydrochloride

1) Synthesis of tert-butyl 4-(3-phenylpropyl)piperazine-1-carboxylate

To a solution of 7.06 g (37.9 mmol.) of 1-tert-butoxycarbonylpiperazine in ethanol (50 ml) were added, at room temperature, 8.0 ml (57.4 mmol.) of triethylamine and 7.09 g (39.7 mmol.) of 1-bromo-3-phenylpropane. The mixture was heated under reflux for 16 hours under nitrogen atmosphere. To the reaction system was added ethyl acetate. The mixture was washed with water and a saturated aqueous saline solution, which was dried over magnesium sulfate. The solvent was distilled off under reduced pressure. The residue was purified by means of a column chromatography (ethyl acetate/hexane=25–50%). The solvent was distilled off under reduced pressure to give the object compound as a pale yellow liquid product. The yield was 8.69 g (75%).

¹H-NMR (CDCl₃, 200 MHz) δ: 1.46 (9H, 5), 1.75–1.90 (2H, m), 2.30–2.42 (6H, m), 2.64 (2H, t, J=7.6 Hz), 3.43 (4H, t, J=5.2 Hz), 7.11–7.30 (5H, m).

IR (neat): 1699, 1456, 1419, 1365, 1288, 1238, 1173, 1126, 1007, 866, 748, 700 cm⁻¹.

2) Synthesis of 1-(3-phenylpropyl)-piperazine dihydrochloride

To 8.45 g (27.8 mmol.) of tert-butyl 4-phenylpropylpiperazine-1-carboxylate was added, at room temperature, 10 ml (120 mmol.) of 12N hydrochloric acid. The mixture was stirred for one hour. To the reaction system was added ethanol, which was then concentrated under reduced pressure. To the resulting white crystalline precipitate was added diethyl ether, which was subjected to filtration to collect the crystals. The crystals were washed with ethanol and diethyl ether to give the object compound as white crystals. Further, from the filtrate, crystallization was conducted to give the object compound as white crystals.

Yield: first crop 5.41 g (70%)

second crop 1.77 g (23%)

m.p.182–189° C.

¹H-NMR (DMSO-d₆, 200 MHz) δ: 1.91–2.13 (2H, m), 2.65 (2H, t, J=7.8 Hz), 3.02–3.86 (10H, m), 7.15–7.37 (5H, m), 9.46–9.96 (2H, m).

IR (KBr): 3500, 3410, 3026, 2939, 2403, 1554, 1443, 1385, 966, 762, 706 cm⁻¹.

3) Synthesis of 1-[N-(tert-butoxycarbonyl)aminoacetyl]-4-(3-phenylpropan-1-yl)piperazine To a suspension of 1.90 g (10.8 mmol.) of N-tert-butoxycarbonylglycine and 2.48 g (16.2 mmol.) of 1-hydroxybenzotriazole monohydrate in acetonitrile (20 ml) was added, at room temperature, 3.11 g (16.2 mmol.) of N-ethyl-N'-3-(N,N-dimethylamino)propylcarbodiimide hydrochloride. The mixture was stirred for one hour. To the reaction system was added a solution of 3.00 g (10.8 mmol.) of 1-(3-phenylpropyl)-piperazine dihydrochloride, 3.29 g (21.6 mmol.) of 1,8-diazabicyclo[5.4.0]unde-7-cene (DBU) and 1.5 ml (10.8 mmol.) of triethylamine in acetonitrile (15 ml). The mixture was stirred for further one hour. The solvent was distilled off under reduced pressure. To the residue were added water and ethyl acetate, which was subjected to extraction with ethyl acetate. The organic layer was washed with a saturated aqueous solution of sodium hydrogencarbonate and a saturated aqueous saline solution, followed by drying over magnesium sulfate. The solvent was distilled off under reduced pressure to leave a crude product, which was purified by means of a column chromatography (ethyl acetate-methanol/ethyl acetate 10%). The solvent was distilled off under reduced pressure to give the object compound as a pale yellow oily product. The yield was 3.63 g (93%).

¹H-NMR (CDCl₃, 200 MHz) δ: 1.45 (9H, s), 1.73–1.90 (2H, m), 2.30–2.48 (6H, m), 2.65 (2H, t, J=7.6 Hz), 3.32–3.43 (2H, m), 3.59–3.69 (2H, m), 3.95 (2H, d, J=4.4 Hz), 5.46–5.58 (1H, m), 7.12–7.34 (5H, m).

IR (KBr): 3417, 2937, 1713, 1655, 1462, 1242, 1171, 1026, 752, 702 cm⁻¹.

4) Synthesis of 1-aminoacetyl-4-(3-phenylpropan-1-yl) piperazine dihydrochloride To 3.48 g (9.63 mmol.) of 1-[N-(tert-butoxycarbonyl) aminoacetyl]-4-(3-phenylpropan-1-yl)piperazine was added, at room temperature, 7 ml (84 mmol.) of 12N hydrochloric acid. The mixture was stirred for 30 minutes. To the reaction system was added ethanol to allow crystals to precipitate. The reaction mixture was concentrated under reduced pressure, to which were added diethyl ether and ethanol. The crystals were collected by filtration and washed with diethyl ether to give the object compound as white crystals. The yield was 2.81 g (87%).

m.p.223–227° C. (decomp.)

¹H-NMR (DMSO-d₆, 200 MHz) δ: 1.97–2.20 (2H, m), 2.65 (2H, t, J=7.8 Hz), 2.79–3.74 (8H, m), 3.78–4.09 (3H, m), 4.32–4.51 (1H, m), 7.15–7.38 (5H, m), 8.12–8.49 (3H, m), 11.61–11.84 (1H, m).

IR (KBr): 3423, 3361, 2995, 2931, 2559, 2465, 1670, 1498 cm⁻¹.

Reference Example 47

Synthesis of 1-Aminoacetyl-4-(2-phenethyl) piperazine dihydrochloride

1) Synthesis of tert-butyl 4-(2-phenethyl)piperazine-1-carboxylate

To a solution of 7.00 g (37.6 mmol.) of 1-tert-butoxycarbonylpiperazine in ethanol (50 ml) were added, at room temperature, 8.0 ml (57.4 mmol.) of triethylamine and 8.42 g (45.4 mmol.) of phenethyl bromide. The mixture was heated under reflux for 16 hours under nitrogen atmosphere.. To the reaction system were further added 2 ml (14.3 mmol.) of triethylamine and 2 ml (14.6 mmol.) of phenethyl bromide. The mixture was heated for further four hours under reflux. To the reaction system was added ethyl acetate, which was washed with water and a saturated aqueous saline solution, followed by drying over magnesium sulfate. The solvent was distilled off under reduced pressure. The residue was purified by means of a column chromatography (ethyl acetate/hexane 30–50%), followed by distilling off the solvent to give the object compound as a white crystalline product. The yield was 8.03 g (74%). m.p.62–65° C.

¹H-NMR (CDCl₃, 200 MHz) δ: 1.47 (9H, s), 2.44–2.49 (4H, m), 2.55–2.66 (2H, m), 2.74–2.88 (2H, m), 3.44–3.49 (2H, m), 7.15–7.36 (5H, m).

IR (KBr): 2976, 2868, 2818, 1687, 1414, 1252, 1174, 1120, 1001, 711, 735, 696 cm⁻¹.

2) Synthesis of 1-(2-phenethyl)piperazine dihydrochloride

To 7.94 g (27.34 mmol.) of tert-butyl 4-(2-phenethyl) piperazine-1-carboxylate was added, at room temperature, 10 ml (120 mmol.) of 12N hydrochloric acid. The mixture was stirred for 30 minutes. To the reaction system was added ethanol. To the resulting crystalline precipitate was further added diethyl ether, then the crystals were collected by filtration, followed by washing them with ethanol and diethyl ether to give the object compound as white crystals. The yield was 6.96 g (97%). m.p.206–210° C.

¹H-NMR (DMSO-d₆, 200 MHz) δ: 2.96–3.88 (12H, m), 7.17–7.42 (5H, m), 9.65–10.11 (2H, m).

IR (KBr): 3542, 3141, 2931, 2764, 2359, 1434, 1084 cm⁻¹.

3) Synthesis of 1-[N-(tert-butoxycarbonyl)aminoacetyl]-4-(2-phenethyl)piperazine To a suspension of 2.00 g (11.4 mmol.) of N-tert-butoxycarbonyl glycine and 2.62 g (17.1 mmol.) of 1-hydroxybenzotriazole monohydrate in acetonitrile (20 ml) was added, at room temperature, 3.28 g (17.1 mmol.) of N-ethyl-N'-3-(N,N-dimethylamino)propylcarbodiimide hydrochloride. The mixture was stirred for one hour. To the reaction system was added a solution of 3.00 g (11.4 mmol.) of 1-(2-phenethyl)piperazine dihydrochloride, 3.47 g (22.8 mmol.) of 1,8-diazabicyclo[5.5.0]unde-7-cene (DBU) and 1.6 ml (11.5 mmol.) of triethylamine in acetonitrile (20 ml). The mixture was stirred for further one hour. The solvent was distilled off under reduced pressure. To the residue was added water, which was subjected to extraction with ethyl acetate. The organic layer was washed with a saturated aqueous solution of hydrogencarbonate and a saturated aqueous saline solution, followed by drying over magnesium sulfate. The solvent was distilled off under reduced pressure to leave a crude product, which was purified by means of a column chromatography (methanol/ethyl acetate 5%). the solvent was distilled off under reduced pressure. The residue was recrystallized from ethyl acetate-petroleum ether to give the object compound as white crystals. The yield was 3.01 g (76%). m.p.109–110° C.

$^1$H-NMR (CDCl$_3$, 200 MHz) δ: 1.45 (9H, s), 2.45–2.56 (4H, m), 2.56–2.70 (2H, m), 2.74–2.87 (2H, m), 3.35–3.47 (2H, m), 3.60–3.73 (2H, m), 3.96 (2H, d, J=4.2 Hz), 5.45–5.60 (1H, m), 7.14–7.36 (5H, m).

IR (KBr): 3263, 2968, 2929, 1718, 1656, 1543, 1452, 1240, 1163, 1038, 739 cm$^{-1}$.

4) Synthesis of 1-aminoacetyl-4-(2-phenethyl)piperazine dihydrochloride

To 2.98 g (8.58 mmol.) of 1-[N-(tert-butoxycarbonyl) aminoacetyl]-4-(2-phenethyl)piperazine was added, at room temperature, 4 ml (48 mmol.) of 12N -hydrochloric acid. The mixture was stirred for 30 minutes. To the reaction system was added ethanol to allow crystals to precipitate. Diethyl ether was further added, then crystals were collected by filtration and washed with ethanol and diethyl ether to give the object compound as white crystals. The yield was 2.67 g (97%).

m.p.237–247° C. (decomp.)

$^1$H-NMR (DMSO-d$_6$, 200 MHz) δ: 2.88–3.47 (8H, m), 3.51–3.76 (2H, m), 3.83–4.11 (3H, m), 4.36–4.53 (1H, m), 7.21–7.42 (5H, m), 8.16–8.38 (3H, m).

IR (KBr): 3412, 2995, 2931, 2549, 1666, 1500, 1452 cm$^{-1}$.

Reference Example 48

Synthesis of 1-(aminoacetyl)-4-(3-phenylpropan-1-yl)-2,3,5,6-tetrahydro-7H-1,4-diazepine dihydrochloride 1) Synthesis of tert-butyl 4-(3-phenylpropan-1-yl)-2,3,5,6-tetrahydro-7H-1,4-diazepine-1-carboxylate To a solution of 4.50 g (22.47 mmol.) of 1-tert-butoxycarbonyl-2,3,5,6-tetrahydro-7H-1,4-diazepine in ethanol (50 ml) were added, at room temperature, 4.7 ml (33.72 mmol.) of triethylamine and 4.47 g (22.45 mmol.) of 1-bromo-3-phenylpropane. The mixture was heated under reflux for 8 hours under nitrogen atmosphere. To the reaction system were further added 4.7 ml (33.72 mmol.) of triethylamine and 4.47 g (22.45 mmol.) of 1-bromo-3-phenylpropane. The mixture was heated for 16 hours under reflux, which was cooled to room temperature. To the reaction system was added ethyl acetate, which was washed with water and a saturated aqueous saline solution, followed by drying over magnesium sulfate. The solvent was distilled off under reduced pressure. The residue was purified by means of a column chromatography. The solvent was distilled off under reduced pressure to give the object compound as a yellow liquid product. The yield was 5.41 g (76%).

$^1$H-NMR (CDCl$_3$, 200 MHz) δ: 1.46 (9H, s), 1.68–1.89 (4H, m), 2.46–2.53 (2H, m), 2.54–2.70 (6H, m), 3.36–3.55 (4H, m), 7.12–7.34 (5H, m).

IR (neat): 2937, 1693, 1464, 1412, 1365, 1173, 746, 700 cm$^{-1}$.

2) Synthesis of 1-(3-phenylpropan-1-yl)-2,3,5,6-tetrahydro-7H-1,4-diazepine dihydrochloride To 5.41 g (5.41 g (16.99 mmol.) of tert-butyl 4-(3-phenylpropan-1-yl)-2,3,5,6-tetrahydro-7H-1,4-diazepine-1-carboxylate was added, at room temperature, 5 ml (60 mmol.) of 12N hydrochloric acid. The mixture was stirred for 2 hours. To the reaction system was added ethanol, then the solvent was distilled off under reduced pressure to give the object compound as a pale yellow amorphous product. The yield was 5.65 g (100%).

$^1$H-NMR (DMSO-d$_6$, 200 MHz) δ: 1.91–2.33 (4H, m), 2.63 (2H, t, J=7.8 Hz), 3.02–3.84 (10H, m), 7.10–7.39 (5H, m), 9.38–10.08 (2H, m), 11.42–11.74 (1H, m).

3) Synthesis of 1-[N-(tert-butoxycarbonyl)aminoacetyl]-4-(3-phenylpropan-1-yl)-2,3,5,6-tetrahydro-7H-1,4-diazepine To a suspension of 2.8 g (15.98 mmol.) of N-tert-butoxycarbonyl glycine and 3.67 g (23.96 mmol.) of 1-hydroxybenzotriazole monohydrate was added, at room temperature, 4.6 g (24.0 mmol.) of N-ethyl-N'-3-(N,N-dimethylamino)propylcarbodiimide hydrochloride. The mixture was stirred for one hour. To the reaction system, was added an acetonitrile solution (20 ml) of 5.65 (16.99 mmol.) of 1-(3-phenylpropan-1-yl)-2,3,5,6-tetrahydro-7H-1,4-diazepine dihydrochloride, 5.17 g (33.96 mmol.) of 1,8-diazabicyclo[5.4.0]unde-7-cene (DBU) and 2.3 ml (16.5 mmol.) of triethylamine. The mixture was stirred for 2 hours. The solvent was distilled off under reduced pressure. To the residue was added water, which was subjected to extraction with ethyl acetate. The organic layer was washed with a saturated aqueous solution of sodium hydrogencarbonate and a saturated aqueous saline solution, which was dried over magnesium sulfate, followed by distilling off the solvent under reduced pressure. The crude product thus-obtained was purified by means of a column chromatography (methanol/ethyl acetate 10–20%). The solvent was distilled off under reduced pressure to afford the object compound as a pale yellow oily product. The yield was 5.64 g (94%).

$^1$H-NMR (CDCl$_3$, 200 MHz) δ: 1.45 (9H, s), 1.68–1.97 (4H, m), 2.42–2.55 (2H, m), 2.55–2.74 (6H, m), 3.36–3.49 (2H, m), 3.58–3.72 (2H, m), 3.90–3.99 (2H, m), 5.50–5.62 (1H, m), 7.12–7.35 (5H, m).

IR (neat): 3415, 2935, 1711, 1651, 1456, 1168 cm$^{-1}$.

4) Synthesis of 1-(aminoacetyl)-4-(3-phenylpropan-1-yl)-2,3,5,6-tetrahydro-7H-1,4-diazepine dihydrochloride To 5.64 g (15.02 mmol.) of 1-[N-(tert-butoxycarbonyl) aminoacetyl]-4-(3-phenylpropan-1-yl)-2,3,5,6-tetrahydro-7H-1,4-diazepine was added, at room temperature, 5 ml (60 mmol.) of 12N hydrochloric acid. The mixture was stirred for 20 minutes. To the reaction system was added ethanol. The solvent was distilled off under reduced pressure to leave the object compound as a pale yellow amorphous product. This compound was used for the subsequent reaction without purification. The yield was 4.69 g (90%).

$^1$H-NMR (DMSO-d$_6$, 200 MHz) δ: 1.94–2.18 (4H, m), 2.56–2.71 (2H, m), 2.90–4.15 (12H, m), 7.15–7.37 (5H, m), 8.14–8.42 (3H, m).

IR (KBr): 3353, 2949, 1661, 1470 cm$^{-1}$.

Reference Example 49

Synthesis of 1-(aminoacetyl)-4-(2-phenethyl)-2,3,5,6-tetrahydro-7H-1,4-diazepine dihydrochloride 1) Synthesis of tert-butyl 4-(2-phenethyl)-2,3,5,6-tetrahydro-7H-1,4-diazepine-1-carboxylate To a solution of 4.61 g (20.0 mmol.) of 1-tert-butoxycarbonyl-2,3,5,6-tetrahydro-7H-1,4-diazepine in ethanol (50 ml) were added, at room temperature, 6.5 ml (46.6 mmol.) of triethylamine and 6.3 g (34.0 mmol.) of phenethyl bromide. The mixture was heated under reflux for 16 hours under nitrogen atmosphere. To the reaction system were further added 3.0 ml (21.5 mmol.) of triethylamine and 1.0 ml (7.32 mmol.) of phenethyl bromide. The mixture was heated under reflux for 3 hours under nitrogen atmosphere. The reaction mixture was cooled to room temperature, to which was added ethyl acetate. The mixture was washed with water and a saturated aqueous saline solution, followed by drying over magnesium sulfate. The solvent was distilled off under reduced pressure. The residue was purified by means of a column chromatography (ethyl acetate/hexane 50%-ethyl acetate). The solvent was distilled off under reduced pressure to afford the object compound as a pale yellow oily product. The yield was 5.63 g (80%).

$^1$H-NMR (CDCl$_3$, 200 MHz) δ: 1.46 (9H, s), 1.75–1.94 (2H, m), 2.63–2.87 (8H, m), 3.37–3.58 (4H, m), 7.13–7.36 (5H, m).

IR (neat): 1691 cm$^{-1}$.

2) Synthesis of 1-(2-phenethyl-2,3,5,6-tetrahydro-7H-1,4-diazepine dihydrochloride To 5.63 g (18.5 mmol.) of tert-butyl 4-(2-phenethyl)-2,3,5,6-tetrahydro-7H-1,4-diazepine-1-carboxylate was added, at room temperature, 5 ml (60 mmol.) of 12N hydrochloric acid. The mixture was stirred for one hour. To the reaction system was added ethanol, which was concentrated under reduced pressure. To the resulting white crystals were added ethanol and diethyl ether. The crystals were collected by filtration and washed with ethanol and diethyl ether to give the object compound as a white crystalline product. The yield was 4.7 g (92%)

$^1$H-NMR (DMSO-d$_6$, 200 MHz) δ: 2.07–2.28 (2H, m), 2.90–3.90 (12H, m), 7.18–7.20 (5H, m), 9.36–10.09 (2H, m), 11.55–11.89 (1H, m).

IR (KBr): 2973, 2593, 1580, 1441, 1111, 1030, 1020, 747, 696 cm$^{-1}$.

3) Synthesis of 1-[N-(tert-butoxycarbonyl)aminoacetyl]-4-(2-phenethyl)-2,3,5,6-tetrahydro-7H-1,4-diazepine To a suspension of 2.71 g (15.47 mmol.) of N-tert-butoxycarbonyl glycine and 3.55 g (23.2 mmol.) of 1-hydroxybenzotriazole monohydrate in acetonitrile (30 ml) was added, at room temperature, 4.45 g (23.2 mmol.) of N-ethyl-N'-3-(N,N-dimethylamino)propylcarbodiimide hydrochloride. The mixture was stirred for one hour. To the reaction system was added a solution of 4.5 g (16.23 mmol.) of 1-(2-phenethyl)-2,3,5,6-tetrahydro-7H-1,4-diazepine dihydrochloride, 4.94 g (32.45 mmol.) of 1,8-diazabicyclo[5.4.0]unde-7-cene (DBU) and 2.2 ml (15.78 mmol.) of triethylamine in acetonitrile. The mixture was stirred for further one hour. the solvent was distilled off under reduced pressure. To the residue was added water, which was subjected to extraction with ethyl acetate. The organic layer was washed with a saturated aqueous solution of sodium hydrogencarbonate and a saturated aqueous saline solution, which was dried over magnesium sulfate, followed by distilling off the solvent under reduced pressure. The crude product was purified by means of a column chromatography (methanol/ethyl acetate 10–40%). The solvent was distilled off under reduced pressure to give the object compound as a pale yellow oily product. The yield was 5.18 g (93%).

$^1$H-NMR (CDCl$_3$, 200 MHz) δ: 1.45 (9H, s), 1.79–2.00 (2H, m), 2.61–2.82 (8H, m), 3.36–3.50 (2H, m), 3.59–3.74 (2H, m), 3.89–3.99 (2H, m), 5.50–5.63 (1H, m), 7.13–7.35 (5H, m).

IR (neat): 3415, 2974, 2935, 1712, 1651, 1493, 1458, 1365, 1250, 1171, 1053, 750, 702 cm$^{-1}$.

4) Synthesis of 1-(aminoacetyl)-4-(2-phenethyl)-2,3,5,6-tetrahydro-7H-1,4-diazepine dihydrochloride To 5.18 g (14.3 mmol.) of 1-[N-(tert-butoxycarbonyl)aminoacetyl]-4-(2-phenethyl)-2,3,5,6-tetrahydro-7H-1,4-diazepine was added, at room temperature, 5 ml (60 mmol.) of 12N hydrochloric acid. The mixture was stirred for one hour. To the reaction system was added ethanol, then the solvent was distilled off under reduced pressure. To the residue were added ethanol and diethyl ether. The resulting crystals were collected by filtration, followed by washing with diethyl ether, to give the object compound as white crystals. The yield was 4.64 g (97%).

m.p.257–260° C. (decomp.)

$^1$H-NMR (DMSO-d$_6$, 200 MHz) δ: 1.97–2.22 (2H, m), 2.93–4.14 (14H, m), 7.20–7.41 (5H, m), 8.15–8.42 (3H,

IR (KBr): 3374, 2948, 1661, 1470 cm$^{-1}$.

Reference Example 50

Synthesis of N-[1-(3-phenylpropan-1-yl)piperidin-4-yl]-aminoacetamide dihydrochloride 1) Synthesis of N-[1-(3-phenylpropan-1-yl)piperidin-4-yl]-(N-tert-butoxycarbonylamino)acetamide To a suspension of 4.21 g (24.03 mmol.) of N-tert-butoxycarbonyl glycine and 5.51 g (35.98 mmol.) of 1-hydroxybenzotriazole monohydrate in acetonitrile (30 ml) was added, at room temperature, 6.90 g (36.0 mmol.) of N-ethyl-N'-3-(N,N-dimethylamino)propylcarboxiimide hydrochloride. The mixture was stirred for one hour. To the reaction system was then added a solution of 7.00 g (24.03 mmol.) of 4-amino-1-(3-phenylpropan-1-yl)piperidine dihydrochloride, 7.32 g (48.08 mmol.) of 1,8-bicyclo[5.4.0]unde-7-cene (DBU) and 3.4 ml (24.4 mmol.) of triethylamine in acetonitrile (20 ml). The mixture was stirred for 2 hours at room temperature. The solvent was distilled off under reduced pressure. To the residue was added chloroform. The mixture was washed with water and a saturated aqueous saline solution, followed by drying over magnesium sulfate. The solvent was distilled off under reduced pressure. The residue was purified by means of a column chromatography (methanol/ethyl acetate 30%). The solvent was distilled off under reduced pressure to give the object compound as a yellowish orange liquid product. The yield was 5.35 g (59%).

$^1$H-NMR (CDCl$_3$, 200 MHz) δ: 1.45 (9H, s), 1.61–1.97 (6H, m), 2.03–2.20 (2H, m), 2.32–2.43 (2H, m), 2.63 (2H, t, J=7.6 Hz), 2.74–2.93 (2H, m), 3.66–3.87 (1H, m), 3.75 (2H, d, J=6.0 Hz), 4.99–5.15 (1H, m), 5.92–6.06 (1H, m), 7.12–7.33 (5H, m).

IR (neat): 3413, 3305, 2937, 1713, 1670, 1539, 1369, 1250, 1169 cm$^{-1}$.

2) Synthesis of N-[1-(3-phenylpropan-1-yl)piperidin-4-yl]-aminoacetamide dihydrochloride To 5.35 g (14.25 mmol.) of N-[1-(3-phenylpropan-1-yl)piperidin-4-yl]-(N-tert-butoxy-carbonylamino)acetamide was added, at room temperature, 10 ml (120 mmol.) of 12N hydrochloric acid. The mixture was stirred for one hour. To the reaction system was added ethanol, which was then concentrated under reduced pressure. To the concentrate were added 2-propanol and diethyl ether. The resulting crystals were collected by filtration, followed by washing with 2-propanol and diethyl ether, to give the object compound as a pale yellow crystalline product. The yield was 4.20 g (85%).

m.p.258–261° C.

¹H-NMR (DMSO-d$_6$, 200 MHz) δ: 1.67–2.21 (6H, m), 2.56–2.62 (2H, m), 2.64–3.12 (4H, m), 3.24–4.13 (5H, m), 7.11–7.37 (5H, m), 8.04–8.30 (3H, m), 8.65–8.76 (1H, m).

IR (KBr): 3175, 3054, 2996, 1690, 1568, 1505, 1437, 1269, 912, 764, 706 cm$^{-1}$.

Reference Example 51

Synthesis of 4-(4-aminobutan-1-yl)-1-benzoylpiperazine dihydrochloride

1) Synthesis of 1-benzoyl-4-benzylpiperazine

To a solution of 25.72 g (145.92 mmol.) of 1-benzylpiperazine and 31 ml (222.4 mmol.) of triethylamine in acetonitrile (250 ml) was added at 0° C. 21.44 g (152.5 mmol.) of benzoyl chloride. The mixture was stirred for 16 hours at room temperature. The solvent was distilled off under reduced pressure. To the residue were added water and a saturated aqueous solution of sodium hydrogencarbonate, followed by extraction with ethyl acetate. The organic layer was washed with a saturated aqueous saline solution, which was dried over magnesium sulfate, followed by concentration. The concentrate was purified by means of a column chromatography (ethyl acetate/hexane 50%-ethyl acetate). The solvent was distilled off under reduced pressure. The resulting crystals were collected by filtration and washed with hexane to give the object compound as a pale brown crystalline product. The yield was 38.41 g (94%)

¹H-NMR (CDCl$_3$, 200 MHz) δ: 2.82–2.62 (4H, m), 3.31–3.58 (2H, m), 3.54 (2H, s), 3.65–3.89 (2H, m), 7.18–7.36 (5H, m), 7.40 (5H, s).

IR (KBr): 1628, 1437, 1279, 997, 739, 704 cm$^{-1}$.

2) Synthesis of 1-benzoylpiperazine formate

To a suspension of 20.02 g (71.4 mmol.) of 1-benzoyl-4-benzylpiperazine and 1.0 g of 10% palladium carbon in methanol (200 ml) was added dropwise gradually, at room temperature, 9.9 g (215 mmol.) of formic acid. The mixture was stirred for 6 hours. The catalyst was filtered off, and the filtrate was concentrated under reduced pressure. To the concentrate was added ethyl acetate, and the mixture was concentrated. To the resulting crystals were added ethyl acetate and hexane. The mixture was subjected to filtration to collect the crystals, followed by washing with ethyl acetate and hexane to give the object compound as a white crystalline product. The yield was 15.97 g (95%).

m.p.88–90° C.

¹H-NMR (DMSO-d$_6$, 200 MHz) δ: 2.74–2.95 (4H, m), 3.24–3.73 (4H, m), 7.34–7.49 (5H, m), 8.29 (1H, s).

IR (KBr): 3433, 2937, 1660, 1626, 1446, 1249, 1404, 1282, 1242, 1007, 781, 739, 708 cm$^{-1}$.

3) Synthesis of 4-(4-aminobutan-1-yl)-1-benzoylpiperazine dihydrochloride

A solution of 5.0 g (21.16 mmol.) of 1-benzoylpiperazine formate, 5.97 g (21.16 mmol.) of 4-bromobutylphthalimide and 9.0 ml (64.57 mmol.) of triethylamine in ethanol (50 ml) was heated for 40 hours under reflux. The reaction mixture was cooled to room temperature, to which was added water. The mixture was subjected to extraction with ethyl acetate. The organic layer was washed with a saturated aqueous saline solution, which was then dried over magnesium sulfate, followed by distilling off the solvent under reduced pressure to leave a crude product. The crude product was purified by means of a column chromatography (methanol/ethyl acetate 5–10%). The solvent was distilled off under reduced pressure to give N-[4-(4-benzoylpiperazin-1-yl)butan-1-yl]phthalimide (6.99 g) as yellow oil. To a solution of 6.99 g of this compound in ethanol (50 ml) was added, at room temperature, 1.34 g (26.8 mmol.) of hydrazine monohydrate. The mixture was heated for 2 hours under reflux. The reaction mixture was cooled to room temperature. The resulting white solid substance was filtered off, and the filtrate was concentrated under reduced pressure. To the concentrate was added water, which was subjected to extraction with chloroform. The organic layer was washed with a saturated aqueous saline solution, which was dried over magnesium sulfate, followed by distilling off the solvent under reduced pressure to leave crude 4-(4-aminobutan-1-yl)-1-benzoylpiperazine. To an ethanol solution of this compound was added, at room temperature, 5 ml (60 mmol.) of 12N hydrochloric acid. The mixture was stirred for one hour at room temperature. The reaction mixture was concentrated under reduced pressure, to which was added diethyl ether. The resulting crystals were collected by filtration and washed with ethanol and diethyl ether to give the object compound as a white crystalline product. The yield was 2.92 g (41%).

m.p.257–260° C. (decomp.)

¹H-NMR (DMSO-d$_6$, 200 MHz) δ: 1.51–1.88 (4H, m), 2.71–2.92 (2H, m), 2.94–3.20 (4H, m), 3.27–3.65 (6H, m), 7.41–7.55 (5H, m), 7.88–8.13 (3H, m).

IR (KBr): 2931, 1632, 1460, 1429, 1284, 714 cm$^{-1}$.

Reference Example 52

Synthesis of 4-(3-aminopropan-1-yl)-1-benzoylpiperazine dihydrochloride

A solution of 5.0 g (21.16 mmol.) of 1-benzoylpiperazine.formate, 5.67 g (21.15 mmol.) of 3-bromopropylphthalimide and 9.0 ml (64.57 mmol.) of triethylamine in ethanol (50 ml) was heated under reflux for 18 hours under nitrogen atmosphere. The reaction mixture was cooled to room temperature, to which was added water. the mixture was subjected to extraction with ethyl acetate. The organic layer was washed with a saturated aqueous saline solution, which was dried over magnesium sulfate, followed by distilling off the solvent under reduced pressure. The resulting crude product was purified by means of a column chromatography (methanol/ethyl acetate 5%), followed by distilling off the solvent under reduced pressure, to give N-[3-(4-benzoylpiperazin-1-yl)propan-1-yl] phthalimide (6.22 g) as yellow oil. To an ethanol (50 ml) solution of this compound (6.22 g) was added, at room temperature, 1.24 g (24.8 mmol.) of hydrazine monohydrate. The mixture was heated for 2 hours under reflux. The reaction mixture was cooled to room temperature, then the resulting white solid substance was filtered off. The filtrate was concentrated under reduced pressure. To the concentrate was added water, which was subjected to extraction with chloroform. The organic layer was washed with a saturated aqueous saline solution, followed by drying over magnesium sulfate. the solvent was distilled off under reduced pressure to leave crude 4-(3-aminopropan-1-yl)-1-benzoylpiperazine. To an ethanol solution of this crude 4-(3-aminopropan-1-yl)-1-benzoylpiperazine was added, at room temperature, 3 ml (36 mmol.) of 12N hydrochloric acid. The mixture was stirred for one hour at room temperature. The reaction mixture was concentrated under reduced pressure. To the concentrate was added diethyl ether. The resulting crystals were collected by filtration and washed with ethanol and diethyl ether to give the object compound as a white crystalline product. The yield was 1.80 g (27%).

$^1$H-NMR (DMSO-d$_6$, 200 MHz) δ: 1.94–2.11 (2H, m), 2.83–3.64 (12H, m), 7.42–7.54 (5H, m).

IR (KBr): 3433, 2997, 2929, 1630, 1458, 1429, 1284 cm$^{-1}$.

Reference Example 53

Synthesis of cis-4-(1-benzyl-2,6-dimethyl-piperazin-1-yl) butan-1-ylamine

1) Synthesis of cis-1-tert-butoxycarbonyl-3,5-dimethyl piperazine

To an ethanol (42 ml) solution of 5.0 g (21.07 mmol.) of cis-3,5-dimethyl piperazine was added, at room temperature, 2.5 ml (32.3 mmol.) of di-tert-butyl dicarbonate. The mixture was stirred for one hour. The solvent was distilled off under reduced pressure. To the residue was added water, which was subjected to extraction with chloroform. The organic layer was washed with a saturated aqueous saline solution, which was dried over magnesium sulfate. The solvent was distilled off under reduced pressure to give the object compound as a pale yellow solid product. The yield was 5.77 g (72%).

$^1$H-NMR (CDCl$_3$, 200 MHz) δ: 1.06 (6H, d, J=6.4 Hz), 1.46 (9H, s), 2.21–2.40 (2H, m), 2.68–2.86 (2H, m), 3.79–4.09 (2H, m).

IR (KBr): 3319, 2972, 1680, 1425, 1367, 1315, 1267, 1173, 1144, 1072, 895, 866, 797 cm$^{-1}$.

2) Synthesis of cis-1-tert-butoxycarbonyl-3,5-dimethyl-4-benzyl piperazine

To a suspension of 10 g (46.66 mmol.) of cis-1-tert-butoxycarbonyl-3,5-dimethyl piperazine and 12.90 g (93.3 mmol.) of potassium carbonate in N,N-dimethylformamide (100 ml) was added, at room temperature, 11.97 g (70 mmol.) of benzyl bromide. The mixture was stirred for 16 hours at 120° C. To the reaction system was added water, which was subjected to extraction with ethyl acetate. The organic layer was washed with a saturated aqueous saline solution, which was dried over magnesium sulfate, followed by distilling off the solvent. The residue was purified by means of a column chromatography (ethyl acetate/hexane 30%) to give the object compound as a pale yellow oily product. The yield was 13.56 g (95%).

$^1$H-NMR (CDCl$_3$, 200 MHz) δ: 1.04 (6H, d, J=5.8 Hz), 1.45 (9H, s), 2.45–2.75 (4H, m), 3.67–3.92 (2H, m), 3.81 (2H, s), 7.15–7.39 (5H, m).

IR (neat): 2980, 1693, 1423, 1136, 1061, 924, 883, 766, 729, 700 cm$^{-1}$.

3) Synthesis of cis-1-benzyl-2,6-dimethyl piperazine

To 13.56 g (44.54 mmol.) of cis-1-tert-butoxycarbonyl-3,5-dimethyl-4-benzyl piperazine was added, at room temperature, 15 ml (180 mmol.) of 12N hydrochloric acid. The mixture was stirred for one hour. To the reaction system was added at 0° C., a 8N aqueous solution of sodium hydroxide to make pH of the reaction system alkaline, which was then subjected to extraction with ethyl acetate. The organic layer was washed with a saturated aqueous saline solution, which was dried over magnesium sulfate. The solvent was distilled off under reduced pressure to leave the object compound as a yellow oily product. This compound was used for the subsequent reaction without purification. The yield was 7.67 g (95%).

$^1$H-NMR (CDCl$_3$, 200 MHz) δ: 1.02 (6H, d, J=5.8 Hz), 2.39–2.63 (4H, m), 2.88 (2H, d, J=9.8 Hz), 3.83 (2H, s), 7.15–7.41 (5H, m).

IR (KBr): 3271, 2970, 2816, 1460, 1379, 1315, 1200, 1158, 1140, 1603, 729 cm$^{-1}$.

4) Synthesis of N-cis-[4-(1-benzyl-2,6-dimethyl piperazin-1-yl)butan-1-yl]phthalimide To a solution of 3.5 g (17.13 mmol.) of cis-1-benzyl-2, 6-dimethyl piperazine and 5.0 ml (35.87 mmol.) of triethylamine in ethanol (30 ml) was added, at room temperature, 4.83 g (17.12 mmol.) of 4-bromobutyl phthalimide. The mixture was heated under reflux for 18 hours under nitrogen atmosphere. The reaction mixture was cooled to room temperature, to which was added water, followed by extraction with ethyl acetate. The organic layer was washed with a saturated aqueous saline solution, which was dried over magnesium sulfate. The solvent was distilled off under reduced pressure. The residue was purified by means of a column chromatography (ethyl acetate/hexane 75%-ethyl acetate) to give the object compound as an orange oily product. The yield was 5.86 g (84%).

$^1$H-NMR (CDCl$_3$, 200 MHz) δ: 1.02 (6H, d, J=6.4 Hz), 1.44–1.87 (6H, m), 2.23–2.35 (2H, m), 2.55–2.78 (4H, m), 3.70 (2H, t, J=7.2 Hz), 3.81 (2H, s), 7.16–7.37 (5H, m), 7.66–7.75 (2H, m), 7.78–7.86 (2H, m).

IR (neat): 2939, 2812, 1772, 1714, 1396, 1369, 1155, 1076, 1047, 721 cm$^{-1}$.

5) Synthesis of cis-4-(1-benzyl-2,6-dimethylpiperazin-1-yl)butan-1-ylamine

To an ethanol (20 ml) solution of 5.86 g (14.45 mmol.) of N-cis-[4-(1-benzyl-2,6-dimethylpiperazin-1-yl) butan-1-yl] phthalimide was added, at room temperature, 1.08 g (21.57 mmol.) of hydrazine monohydrate. The mixture was heated for two hours under reflux. The reaction mixture was cooled to room temperature, then the resulting white solid matter was filtered off. From the filtrate, the solvent was distilled off under reduced pressure. To the residue were added an aqueous solution of sodium hydroxide and sodium chloride. The mixture was subjected to extraction with chloroform. The organic layer was washed with a saturated aqueous saline solution, which was dried over magnesium sulfate. The solvent was distilled off under reduced pressure to give the object compound as an orange oily product. This compound was used for the subsequent reaction without purification. The yield was 3.64 g (91%).

$^1$H-NMR (CDCl$_3$, 200 MHz) δ: 1.04 (6H, d, J=6.2 Hz), 1.36–1.63 (4H, m), 1.78–1.89 (2H, m), 2.22–2.33 (2H, m), 2.57–2.82 (6H, m), 3.83 (2H, s), 7.14–7.40 (5H, m).

IR (neat): 3359, 2936, 2812, 1468, 1323, 1153, 1076, 729, 698 cm$^{-1}$.

Reference Example 54

Synthesis of cis-4-(3-aminopropyl)-1-benzyl-2,6-dimethyl piperazine

1) Synthesis of N-cis-[3-(4-benzyl-3,5-dimethyl piperazine-1-yl)propan-1-yl]phthalimide To an ethanol (40 ml) solution of 4.06 g (19.87 mmol.) of cis-1-benzyl-2,6-dimethyl piperazine and 5.6 ml (40.18 mmol.) of triethylamine was added, at room temperature, 5.33 g (19.88 mmol.) of 3-bromomopropyl phthalimide. The mixture was heated under reflux for 20 hours under nitrogen atmosphere. The reaction mixture was cooled to room temperature. To the reaction system was added water, which was subjected to extraction with ethyl acetate. The organic layer was washed with a saturated aqueous saline solution and dried over magnesium sulfate, followed by distilling off the solvent under reduced pressure. The residue was purified by means of a column chromatography (ethyl acetate/hexane 50–75%) to give the object compound as a yellow oily product. The yield was 6.59 g (85%).

¹H-NMR (CDCl₃, 200 MHz) δ: 0.99 (6H, d, J=5.8 Hz), 1.71–1.93 (4H, m), 2.31–2.38 (2H, m), 2.41–2.55 (2H, m), 2.65–2.76 (2H, m), 3.71–3.78 (2H, m), 3.73 (2H, s), 7.13–7.37 (5H, m), 7.65–7.74 (2H, m), 7.78–7.86 (2H, m).

IR (neat): 2964, 2937, 2812, 1772, 1714, 1466, 1396, 1369, 1329, 1200, 1155, 1090, 1038, 721 cm⁻¹.

2) Synthesis of cis-4-(3-aminopropyl-1-benzyl-2,6-dimethyl piperazine

To an ethanol (30 ml) solution of 6.59 g (16.8 mmol.) of N-cis-[3-(4-benzyl-3,5-dimethylpiperazin-1-yl) propan-1-yl)phthalimide was added, at room temperature, 1.26 g (25.2 mmol.) of hydrazine monohydrate. The mixture was heated for one hour under reflux. The reaction mixture was cooled to room temperature. The resulting white solid matter was filtered off. From the filtrate, the solvent was distilled off under reduced pressure. To the residue was added an aqueous solution of sodium hydroxide, which was subjected to extraction with chloroform. The organic layer was washed with a saturated aqueous saline solution and dried over magnesium sulfate. The solvent was distilled off under reduced pressure to leave the object compound as a yellow oily product. This compound was used for the subsequent reaction without purification. The yield was 3.85 g (88%).

¹H-NMR (CDCl₃, 200 MHz) δ: 1.04 (6H, d, J=6.2 Hz), 1.57–1.70 (2H, m), 1.83 (2H, t, J=10.8 Hz), 2.29–2.37 (2H, m), 2.61–2.83 (6H, m), 3.83 (2H, s), 7.18–7.32 (5H, m).

IR (neat): 3361, 3284, 2937, 2812, 1603, 1493, 1375, 1323, 1153, 1076, 727, 698 cm⁻¹.

Reference Example 55

Synthesis of cis-1-(2-aminoethyl)-4-(3-phenylpropan-1-yl)-3,5-dimethyl piperazine 1) Synthesis of cis-1-tert-butoxycarbonyl-3,5-dimethyl-4-(3-phenylpropan-1-yl)piperazine To a suspension of 10 g (46.66 mmol.) of cis-1-tert-butoxycarbonyl-3,5-dimethyl piperazine and 12.90 g (93.3 mmol.) of potassium carbonate in N,N-dimethylformamide (50 ml) was added, at room temperature, 11.15 g (56 mmol.) of 1-bromo-3-phenylpropane. The mixture was stirred for 40 hours at 120° C., which was then cooled to room temperature. To the reaction system was added water, which was subjected to extraction with ethyl acetate. The organic layer was washed with a saturated aqueous saline solution and dried over magnesium sulfate. The solvent was distilled off under reduced pressure. The residue was purified by means of a column chromatography (ethyl acetate/hexane 20–30%) to give the object compound as a yellow oily product. The yield was 12.21 g (79%).

¹H-NMR (CDCl₃, 200 MHz) δ: 1.00 (6H, d, J=5.8 Hz), 1.45 (9H, s), 1.57–1.69 (2H, m), 2.43–2.62 (6H, m), 2.67–2.85 (2H, s), 3.68–3.96 (2H, m), 7.13–7.35 (5H, m).

IR (neat): 2974, 2931, 2856, 1695, 1454, 1427, 1273, 1248, 1174, 1142, 748, 700 cm⁻¹.

2) Synthesis of cis-1-(3-phenylpropan-1-yl)-2,6-dimethyl-piperazine

To 11.76 g (35.4 mmol.) of cis-1-tert-butoxycarbonyl-3,5-dimethyl-4-(3-phenylpropan-1-yl)piperazine was added, at room temperature, 10 ml (120 mmol.) of 12N hydrochloric acid. The mixture was stirred for one hour. To the reaction system was added water. Impurities were removed by extraction with ethyl acetate. The solution was made alkaline by the addition of an aqueous solution of sodium hydroxide, which was subjected to extraction with ethyl acetate. The organic layer was washed with a saturated aqueous saline solution, which was dried over magnesium sulfate. The solvent was distilled off under reduced pressure to give the object compound as a yellow oily product. This compound was used for the subsequent reaction without purification. The yield was 5.51 g (67%)

¹H-NMR (CDCl₃, 200 MHz) δ: 0.98 (6H,. d, J=5.8 Hz), 1.66–1.84 (2H, m), 2.43–2.59 (6H, m), 2.74–2.88 (4H, s), 7.13–7.35 (5H, m).

IR (neat): 3267, 2962, 2937, 2818, 1689, 1454, 1373, 1319, 1205, 1157, 1074, 924, 748, 700 cm⁻¹.

3) Synthesis of N-cis-[2-[4-(3-phenylpropan-1-yl)-3,5-dimethyl piperazin-1-yl]ethan-1-yl]phthalimide To a solution of 5.67 g (21.5 mmol.) of phthalimide acetaldehyde diethyl acetal in acetic acid (18 ml) was added, at room temperature, 2.1 ml (25.2 mmol.) of 12N hydrochloric acid. The mixture was stirred for 2 hours at 60° C. The reaction mixture was cooled to room temperature, which was neutralized with 2.54 g (30.2 mmol.) of sodium hydrogencarbonate. To the reaction system was added a solution of 5.00 g (21.5 mmol.) of cis-1-(3-phenylpropan-1-yl)-2,6-dimethyl piperazine in methanol (40 ml). The mixture was stirred for one hour. To the reaction system was added 6.84 g (32.27 mmol.) of sodium triacetoxyborohydride divided into three portions with the interval of 30 minutes. The mixture was stirred for 18 hours. The solvent was distilled off under reduced pressure. The residue was neutralized with acetic acid, which was subjected to extraction with ethyl acetate. The organic layer was washed with a saturated aqueous saline solution and dried over magnesium sulfate, followed by concentration to leave a crude product. The crude product was purified by means of a column chromatography (methanol/ethyl acetate 5%) to give the object compound as a pale brown oily product. The yield was 7.37 g (85%).

¹H-NMR (CDCl₃, 200 MHz) δ: 0.99 (6H, d, J=6.2 Hz), 1.54–1.74 (2H, m), 1.81–1.93 (2H, m), 2.44–2.63 (6H, m), 2.68–2.86 (2H, m), 3.79 (2H, t, J=6.8 Hz), 7.11–7.32 (5H, m), 7.64–7.74 (2H, m), 7.80–7.87 (2H, m).

IR (neat): 2945, 2814, 1774, 1713, 1394, 1327, 1242, 1159, 1076, 1026, 721 cm⁻¹.

4) Synthesis of cis-1-(2-aminoethyl)-4-(3-phenylpropan-1-yl)-3,5-dimethyl piperazine To an ethanol (50 ml) solution of 7.28 g (17.95 mmol.) of N-cis-[2-[4-(3-phenylpropan-1-yl)-3,5-dimethyl piperazin-1-yl]ethan-1-yl]phthalimide was added, at room temperature, 1.3 ml (26.8 mmol.) of hydrazine monohydrate. The mixture was heated under reflux for 2 hours, which was cooled to room temperature. The resulting white solid matter was filtered off. From the filtrate, the solvent was distilled off under reduced pressure. To the residue was added an aqueous solution of sodium hydroxide, which was subjected to extraction with chloroform. The organic layer was washed with a saturated aqueous saline solution and dried over magnesium sulfate. The solvent was then distilled off under reduced pressure to give the object compound as a yellow oily product. This compound was used for the subsequent reaction without purification. The yield was 4.35 g (88%).

¹H-NMR (CDCl₃, 200 MHz) δ: 1.00 (6H, d, J=6.2 Hz), 1.65–1.90 (4H, m), 2.34 (2H, t, J=6.3 Hz), 2.54 (2H, t, J=7.5 Hz), 2.61–2.85 (8H, m), 7.13–7.34 (5H, m).

IR (neat): 3359, 3262, 2960, 2810, 1691, 1603, 1456, 1371, 1323, 1153, 1076, 748, 700 cm⁻¹.

Reference Example 56

Synthesis of trans-1-(4-aminobutyl)-4-benzyl-2,5-dimethyl piperazine

1) Trans-1-tert-butoxycarbonyl-2,5-dimethyl piperazine

To an ethanol (200 ml) solution of 25.18 g (220.5 mmol.) of trans-2,5-dimethyl piperazine was added, at room temperature, 9.63 g (44.1 mmol.) of di-tert-butyl dicarbonate. The mixture was stirred for 2 hours. The solvent was distilled off under reduced pressure. To the residue was added water, which was subjected to extraction with ethyl acetate. The organic layer was washed with a saturated aqueous saline solution, which was dried over magnesium sulfate. The solvent was distilled off under reduced pressure to give the object compound as a pale brown oily product. The yield was 9.36 g (99%).

$^1$H-NMR (CDCl$_3$, 200 MHz) δ: 1.17 (3H, d, J=7.0 Hz), 1.21 (3H, d, J=6.6 Hz), 1.46 (9H, s), 2.48 (1H, dd, J=12.8 & 3.0 Hz), 3.05–3.26 (3H, m), 3.55 (1H, dd, J=13.2 & 1.6 Hz), 4.03–4.19 (1H, m).

2) Synthesis of trans-1-butoxycarbonyl-2,5-dimethyl-4-benzyl piperazine

To an acetonitrile (40 ml) solution of 4.5 g (21.0 mmol.) of trans-1-tert-butoxycarbonyl-2,5-dimethyl piperazine and 5.9 ml (42.3 mmol.) of triethylamine was added, at room temperature, 3.2 ml (26.9 mmol.) of benzyl bromide. The mixture was heated for 24 hours under reflux. The solvent was distilled off under reduced pressure. To the residue was added water. The mixture was subjected to extraction with ethyl acetate. The organic layer was washed with a saturated aqueous saline solution, which was dried over magnesium sulfate. The solvent was distilled off under reduced pressure. The residue was purified by means of a column chromatography (ethyl acetate/hexane 10%) to give the object compound as a pale yellow oily product. The yield was 5.17 g (81%).

$^1$H-NMR (CDCl$_3$, 200 MHz) δ: 0.98 (3H, d, J=6.6 Hz), 1.23 (3H, d, J=7.0 Hz), 1.46 (9H, s), 2.19 (1H, d, J=13.0 Hz), 2.70 (1H, dd, J=12.0 & 4.4 Hz), 2.85–3.04 (1H, m), 3.31 (1H, dd, J=12.8 & 3.8 Hz), 3.46 (1H, d, J=13.6 Hz), 3.62 (1H, d, J=13.6 Hz), 3.65 (1H, dd, J=13.0 & 0.8 Hz), 4.10–4.28 (1H, m), 7.18–7.42 (5H, m).

IR (neat): 2929, 2819, 1691, 1417, 1367, 1317, 1267, 1163, 1059, 864, 756, 708 cm$^{-1}$.

3) Synthesis of trans-1-benzyl-2,5-dimethylpiperazine dihydrochloride

To 9.76 g (32.06 mmol.) of trans-1-tert-butoxycarbonyl-2,5-dimethyl-4-benzyl piperazine was added, at room temperature, 10 ml (120 mmol.) of 12N hydrochloric acid. The mixture was stirred for one hour. The solvent was distilled off under reduced pressure. To the residue was added 2-propanol, which was further concentrated. To the concentrate was added diethyl ether. The resulting crystals were collected by filtration and washed with 2-propanol and diethyl ether to give the object compound as white crystals. The yield was 7.97 g (90%).

$^1$H-NMR (DMSO-d$_6$, 200 MHz) δ: 1.22 (3H, d, J=6.6 Hz), 1.59 (3H, d, J=5.4 Hz), 2.84–3.83 (6H, m), 3.96–4.29 (1H, m), 4.57–4.74 (1H, m), 7.36–7.52 (3H, m), 7.56–7.72 (2H, m), 9.93–10.25 (2H, m).

IR (neat): 2767, 2694, 2507, 2266, 1454, 1333, 1186, 1061, 991, 928, 766, 706 cm$^{-1}$.

4) Synthesis of N-trans-[4-(4-benzyl-2,5-dimethylpiperazin-1-yl)butan-1-yl]phthalimide A To a suspension of 4.00 g (14.43 mmol.) of trans-1-benzyl-2,5-dimethylpiperazine dihydrochloride, 4.88 g (17.3 mmol.) of 4-bromobutyl phthalimide and 8.0 ml (57.4 mmol.) of triethylamine in acetonitrile (50 ml) was added, at room temperature, 2.59 g (17.3 mmol.) of sodium iodide. The mixture was heated under reflux for 20 hours under nitrogen atmosphere. The solvent was distilled off under reduced pressure. To the residue was added water. The mixture was subjected to extraction with ethyl acetate. The organic layer was washed with a saturated aqueous saline solution and dried over magnesium sulfate, followed by distilling off the solvent. The residue was purified by means of a column chromatography (ethyl acetate-methanol/ethyl acetate 5%) to give the object compound as a brown oily product. The yield was 3.97 g (68%).

$^1$H-NMR (CDCl$_3$, 200 MHz) δ: 0.95 (3H, d, J=5.8 Hz), 1.15 (3H, d, J=6.0 Hz), 1.43–1.77 (4H, m), 1.82–1.93 (2H, m), 2.08 (2H, t, J=10.8 Hz), 2.16–2.51 (3H, m), 2.59 (1H, dd, J=11.4 & 2.8 Hz), 2.70–2.79 (1H, m), 2.82 (1H, dd, J=11.4 & 2.8 Hz), 3.06 (1H, d, J=13.2 Hz), 3.70 (2H, t, J=7.0 Hz), 4.08 (1H, d, J=13.2 Hz), 7.16–7.34 (5H, m), 7.65–7.76 (2H, m), 7.78–7.89 (2H, m).

IR (neat): 2939, 2800, 1770, 1713, 1441, 1396, 1371, 1336, 1182, 1066, 1041, 719 cm$^1$.

5) Synthesis of trans-1-(4-aminobutyl)-4-benzyl-2,5-dimethyl piperazine

To an ethanol (20 ml) solution of 3.97 g (9.79 mmol.) of N-trans-[4-(4-benzyl-2,5-dimethyl-piperazin-1-yl)butan-1-yl]phthalimide was added, at room temperature, 0.74 g (14.8 mmol.) of hydrazine monohydrate. The mixture was heated for 2 hours under reflux. The reaction mixture was cooled to room temperature. The resulting white solid matter was filtered off. From the filtrate, the solvent was distilled off. To the residue was added an aqueous solution of sodium hydroxide. The mixture was subjected to extraction with chloroform. The organic layer was washed with a saturated aqueous saline solution and dried over magnesium sulfate. The solvent was distilled off under reduced pressure to leave the object compound as a yellow oily product. This compound was used for the subsequent reaction without purification. The yield was 2.31 g (86%).

$^1$H-NMR (CDCl$_3$, 200 MHz) δ: 0.95 (3H, d, J=6.2 Hz), 1.16 (3H, d, J=5.8 Hz), 1.34–1.55 (4H, m), 1.81–1.91 (1H, m), 2.02–2.13 (1H, m), 2.14–2.52 (4H, m), 2.60 (1H, dd, J=11.4 & 2.6 Hz), 2.65–2.76 (2H, m), 2.83 (1H, dd, J=1.0 & 3.0 Hz), 3.07 (1H, d, J=13.6 Hz), 4.08 (1H, d, J=13.2 Hz), 7.19–7.36 (5H, m).

IR (neat): 3363, 3280, 2935, 2802, 1603, 1450, 1377, 1336, 1178, 1153, 1068, 833, 739, 700 cm$^{-1}$.

Reference Example 57

Synthesis of 1-(2-aminoethan-1-yl)-2,6-dioxo-4-(3-phenylpropan-1-yl)piperazine dihydrochloride 1) Synthesis of 4-benzyl-1-(2-(tert-butoxycarbonylamino) ethan-1-yl)-2,6-dioxopiperazine To a suspension of 9.75 g (43.68 mmol.) of benzyl iminodiacetic acid in tetrahydrofuran (129 ml) was added, at room temperature under nitrogen atmosphere, 15.58 g (96.08 mmol.) of carbonyldiimidazole. The mixture was heated for one hour under reflux. To the reaction system was added a solution of 7.00 g (43.69 mmol.) of 1-tert-butoxycarbonyl ethylenediamine in tetrahydrofuran (20 ml). The mixture was heated for 21 hours under reflux. The solvent was distilled off under reduced pressure. The residue was dissolved in ethyl acetate. The solution was washed twice with 0.5 N hydrochloric acid (200 ml, 50 ml), which was further washed with water and a saturated aqueous saline solution, followed by drying over magnesium sulfate and concentration. The concentrate was washed by means of a column chromatography (ethyl acetate/hexane 50%) to give the object compound as a colorless crystals. The yield was 8.65 g (57%).

$^1$H-NMR (CDCl$_3$, 200 MHz) δ: 1.41 (9H, s), 3.26–3.45 (2H, m), 3.41 (4H, s), 3.62 (2H, s), 3.91 (2H, t, J=5.6 Hz), 4.66–4.81 (1H, m), 7.24–7.41 (5H, m).

IR (KBr): 3404, 2976, 1768, 1687, 1680, 1516, 1352, 1228, 1164, 704 cm$^{-1}$.

2) Synthesis of 1-[2-(tert-butoxycarbonylamino)ethan-1-yl]-2,6-dioxopiperazine

A solution of 4.0 g (11.5 mmol.) of 4-benzyl-1-[2-(tert-butoxycarbonylamino)ethan-1-yl]-2,6-dioxopiperazine and 0.37 g of 10% palladium carbon in methanol (100 ml) was stirred for 20 hours under hydrogen atmosphere. The palladium carbon was filtered off, followed by distilling off the solvent under reduced pressure to give the object compound as colorless crystals. The yield was 3.4 g (100%).

$^1$H-NMR (CDCl$_3$, 200 MHz) δ: 1.41 (9H, s), 3.26–3.40 (2H, m), 3.68 (4H, s), 3.95 (2H, t, J=5.4 Hz), 4.74–4.90 (1H, m).

IR (KBr): 3369, 2981, 1730, 1687, 1664, 1537, 1367, 1340, 1267, 1254, 1180, 868 cm$^{-1}$.

4) Synthesis of 1-(tert-butoxycarbonylamino)-2,6-dioxo-4-(3-phenylpropan-1-yl)piperazine To a solution of 3.01 g (11.7 mmol.) of 1-[2-(tert-butoxycarbonylamino)ethan-1-yl]-2,6-dioxopiperazine and 1.57 g (11.7 mmol.) of dihydrocinnamic aldehyde in tetrahydrofuran (50 ml) was added 3.72 g (17.6 mmol.) of sodium triacetoxyborohydride. The mixture was stirred for 18 hours at room temperature. The reaction mixture was poured into water to suspend the reaction, which was subjected to extraction with ethyl acetate. The organic layer was washed with a saturated aqueous saline solution, which was dried over magnesium sulfate, followed by concentration. The concentrate was purified by means of a column chromatography (ethyl acetate/hexane 30–50%), followed by recrystallization (ethyl acetate-hexane) to give the object compound as colorless crystals. The yield was 2.77 g (63%).

$^1$H-NMR (CDCl$_3$, 200 MHz) δ: 1.42 (9H, s), 1.73–1.88 (2H, m), 2.65 (2H, t, J=7.5 Hz), 3.20–3.42 (2H, m), 3.39 (4H, m), 3.92 (2H, t, J=5.7 Hz), 4.68–4.82 (1H, m), 7.10–7.35 (5H, m).

IR (KBr): 3365, 2983, 1740, 1689, 1682, 1672, 1531, 1365, 1348, 1265, 1228, 1174, 1138, 964, 748, 696, 642 cm$^{-1}$.

5) Synthesis of 1-(2-aminoethan-1-yl)-2,6-dioxo-4-(3-phenylpropan-1-yl)piperazine dihydrochloride To a solution of 2.67 g (7.11 mmol.) of 1-(tert-butoxycarbonylamino)-2,6-dioxo-4-(3-phenylpropan-1-yl) piperazine in ethanol (30 ml) was added, at room temperature, 5 ml (60 mmol.) of 12N hydrochloric acid. The mixture was stirred for 16 hours, which was then concentrated under reduced pressure. The resulting crystals were collected by filtration and washed with ethanol and diethyl ether to give the object compound as colorless crystals. The yield was 2.41 g (97%).

$^1$H-NMR (DMSO-d$_6$, 200 MHz) δ: 1.91–2.11 (2H, m), 2.61–2.68 (2H, m), 2.88–3.05 (2H, m), 3.08–3.26 (2H, m), 3.96 (2H, t, J=5.9 Hz), 4.25 (4H, br s), 7.13–7.38 (5H, m), 8.05–8.32 (3H, m).

IR (KBr): 2974, 1751, 170, 1379, 1261, 1165, 962, 760, 702 cm$^{-1}$.

Reference Example 58

Synthesis of 2-amino-6-fluoropyridine

A solution of 30.0 g of 2,6-difluoropyridine in 150 mL (4.6 equivalents) was stirred in a sealed tube (inner pressure 12.1 kgcm$^{-2}$) for 5 hours at 130° C. The reaction mixture was cooled to 0° C., which was left standing for two hours. Resulting crude crystals (plates) were collected by filtration with a glass filter, which were dried at 40° C. for 2 hours under reduced pressure (24.2 g, yield 82.6%).

$^1$H-NMR (CDCl$_3$, 300 MHz) δ: 4.33–4.74 (2H, br s), 6.20 (1H, m), 6.30 (1H, m), 7.48 (1H, m).

Elemental analysis for C$_5$H$_5$H$_2$F Calcd.: C, 53.57; H, 4.50; N, 24.97; F, 16.95 Found: C, 53.44; H, 4.45; N, 24.97; F, 17.25

Reference Example 59

Synthesis of 6-(2-fluoropyridinyl)thioacetic acid ethyl ester

To a solution of 2,6-difluoropyridine (5 mL) in DMF (10 mL) were added potassium carbonate (1 equivalent) and thioglycolic acid ethyl ester (1 equivalent). The mixture was stirred overnight at room temperature. To the reaction mixture were added ethyl acetate (100mL×3) and water (100 mL). The aqueous layer was subjected to extraction. The extract was combined with the ethyl acetate solution, which was washed with a saturated aqueous saline solution (100 mL×3), dried over anhydrous magnesium sulfate and concentrated under reduced pressure to afford 6-(2-fluoropyridinyl)thioacetic acid ethyl ester (10 g, yield 84%) as an oily product.

$^1$H-NMR (CDCl$_3$, 300 MHz) δ: 1.28 (3H, t, J =7.1 Hz), 3.93 (2H, s), 4.22 (2H, q, J=7.1 Hz), 6.60 (1H, ddd, J=2.6, 7.9 & 7.9 Hz), 7.11 (1H, ddd, J=2.3, 7.9 & 7.9 Hz), 7.59 (1H, ddd, J=7.9, 7.9 & 7.9 Hz).

Reference Example 60

Synthesis of 2-fluoro-6-(formylamino)pyridine

A solution of 0.63 g of 2,6-difluoropyridine in 0.2 mL of formamide was stirred for 3 hours at 150° C. The reaction mixture was cooled to room temperature, to which were added water (100 mL) and ethyl acetate (100 mL×3) for extraction. The extract solution was dried over anhydrous magnesium sulfate, followed by concentration to give powdery precipitate of 2-fluoro-6-(formylamino)pyridine. The powdery product was collected by filtration and dried for 2 hours at 40° C. under reduced pressure (0.4 g).

$^1$H-NMR (CDCl$_3$, 300 MHz) δ: 6.64–6.73 (128/93H, m), 7.72–7.88 (1H, m), 8.11 (58/93H, m), 8.51 (58/93H, s), 8.77 (1H, br s), 9.32 (35/93H, d, J=10.6 Hz).

Reference Example 61

Synthesis of 5-fluoroimidazo[1,2-a]pyridine

2-Amino-6-fluoropyridine (12 g) was completely dissolved in 120 mL of distilled water at 60° C. To the solution was added 35 mL (2 equivalents) of 40% chloroacetaldehyde. The mixture was stirred for 3 hours at 60° C. The reaction mixture was gradually cooled to room temperature, to which were added a 1N—HCl aqueous solution (50 mL) and ethyl acetate (150 mL). The ethyl acetate solution was subjected to extraction with a 1N—HCl aqueous solution (100 mL). The extract was mixed with the aqueous solution. To this aqueous solution was added NaHCO$_3$ for neutralization (pH 0.35–7.30). To the neutralized aqueous solution was added a mixture of ethyl acetate and THF (4:1) (150 mL×3) to extract the product. The extract solutions were combined and dried over anhydrous magnesium sulfate, which was concentrated under reduced pressure to afford 5-fluoroimidazo[1,2-a]pyridine as a black liquid product (9.5 g, yield 65%).

$^1$H-NMR (CDCl$_3$, 300 MHz) δ: 6.52 (1H, m), 7.26 (1H, m), 7.49 (2H, d, J=9.1 Hz), 7.66 (2H, m). MS (SIMS), 137(MH$^+$).

Reference Example 62

Synthesis of 5-fluoroimidazo[1,2-a]pyridine

2-Fluoro-6-formylaminopyridine (5 g) was dissolved in 50 mL of ethanol. To the solution was added 23.5 mL (4 equivalents) of 40% chloroacetaldehyde. The mixture was stirred for one hour under reflux. The reaction mixture was gradually cooled to room temperature, to which were added a 1N—HCl aqueous solution (100 mL) and ethyl acetate (100 mL). The ethyl acetate solution was subjected to extraction with a 1N—HCl aqueous solution (100 mL×2). The aqueous solutions were combined, to which was added NaHCO$_3$ for neutralization (pH 0.35–7.30). To the neutralized aqueous solution was added ethyl acetate (100 mL×3) to extract the product. The extract solutions were combined and dried over magnesium sulfate, which was concentrated under reduced pressure to afford 5-fluoroimidazo[1,2-a]pyridine as a black liquid product (1.5 g, yield 31%).

Reference Example 63

Synthesis of 5-fluoroimidazo[1,2-a]pyridine monohydrochloride

To the black liquid 5-fluoroimidazo[1,2-a]pyridine (650 mg) was added conc. hydrochloric acid (5 mL). The mixture was concentrated, which was crystallized from a mixture of ethanol, THF and ethyl acetate (10 mL:50 mL:200 mL) to afford 5-fluoroimidazo[1,2-a]pyridine monohydrochloride as a powdery product (690 mg, yield 83%).

$^1$H-NMR (D$_2$O, 300 MHz) δ: 7.24 (1H, m), 7.78 (1H, d, J=9.1 Hz), 7.98–8.10 (2H, m), 8.15 (1H, m).

Reference Example 64

Synthesis of (imidazo[1,2-a]pyridin-5-ylthio) ethyl acetate

In 10 mL of dimethylformamide was dissolved 1.2 g of 5-fluoroimidazo[1,2-a]pyridine. To the solution were added 1.8 g of potassium carbonate and 1.5 mL of thioglycolic acid ethyl ester. The mixture was stirred for 4 hours at room temperature. To the reaction mixture were added a 1N—HCl aqueous solution (100 mL) and ethyl acetate (100 mL). The ethyl acetate solution was subjected to extraction with a 1N—HCl aqueous solution (100 mL×2). The aqueous solutions were combined, to which was added NaHCO$_3$ to neutralize (pH 0.35–7.30). To the thus-neutralized aqueous solution was added ethyl acetate (100 mL×3) to extract the product. These extract solutions were combined and washed with a saturated aqueous saline solution (100 mL×3), which was dried over anhydrous magnesium sulfate, followed by concentration under reduced pressure to afford (imidazo[1,2-a]pyridin-5-ylthio) ethyl acetate as a black liquid product (1.7 g, 80%).

$^1$H-NMR (CDCl$_3$, 300 MHz) δ: 1.17 (3H, t, J=7.2 Hz), 3.68 (2H, s), 4.12 (2H, q, J=7.2 Hz), 7.07 (1H, dd, J=1.0 & 7.0 Hz), 7.16 (1H, dd, J=7.0 & 8.9 Hz), 7.65 (1H, d, J=8.9 Hz), 7.71 (1H, s), 7.91 (1H, s).

Reference Example 65

Synthesis of (imidazo[1,2-a]pyridin-5-ylthio) ethyl acetate from 5-chloroimidazo[1,2-a]pyridine monohydrochloride In a 50 mL-capacity reaction vessel, 1 g of 5-chloroimidazo[1,2-a]pyridine monohydrochloride was suspended in 10 mL of dimethylformamide under argon atmosphere. To the reaction vessel was added 1.5 mL of triethylamine. The mixture was stirred for 15 minutes, to which was added 2.4 mL of thioglycolic acid ethyl ester. The mixture was stirred for 2 hours at 60° C. and for further 2 hours at 80° C. The reaction mixture was left standing for cooling, to which were added a 1N—HCl aqueous solution (50 mL) and ethyl acetate (100 mL). The ethyl acetate layer was subjected to extraction with a 1N—HCl aqueous solution (50 mL×2). The acid aqueous solutions were combined, to which was added NaHCO$_3$ to neutralize (pH 0.35–7.30). To the thus-neutralized aqueous solution was added ethyl acetate (50 mL×3) to extract the product. The extract solutions were combined, which was washed with a saturated aqueous saline solution (50 mL×3), dried over anhydrous magnesium sulfate and subjected to filtration. The filtrate was concentrated under reduced pressure to afford (imidazo[1,2-a]pyridin-5-ylthio) ethyl acetate as a black liquid product (1.8 g, quantitative yield 62.1%, HPLC 87.5%).

Reference Example 66

Synthesis of (imidazo[1,2-a]pyridin-5-ylthio ethyl acetate from 5-bromoimidazo[1,2-a]pyridine In a 50 mL-capacity reaction vessel, 103.2 mg of 5-bromoimidazo[1,2-a]pyridine was dissolved in 1 mL of dimethylformamide under argon atmosphere. To the reaction vessel was added 0.11 mL of triethylamine, to which was added 0.085 mL of thioglycolic acid ethyl ester. The mixture was stirred for 1.5 hour at room temperature, for 2 hours at 60° C. and for 9 hours at 80° C. The reaction mixture was left standing for cooling, to which were added a 1N—HCl aqueous solution (50 ml) and ethyl acetate (100 mL). The ethyl acetate layer was subjected to extraction with a 1N—HCl aqueous solution (50 mL×2). The acid solutions were combined, to which was added NaHCO$_3$ for neutralization (pH 0.35–7.30). To the thus-neutralized solution was added ethyl acetate (50 mL×3) for extracting the product. The extract solutions were combined and dried over anhydrous magnesium sulfate, which was subjected to filtration. The filtrate was concentrated under reduced pressure to afford (imidazo[1,2-a]pyridin-5-ylthio) ethyl acetate as a black liquid product (150 mg, quantitative yield 56.9%, HPLC 79.1%).

Reference Example 67

Synthesis of 2-fluoro-6-methyl thiopyridine

To a solution of 2,6-difluoropyridine (1 g) in THF (10 mL) was added sodium thiomethoxide (731 mg, 1,2 equivalent) at 0° C. under argon atmosphere. The mixture was stirred overnight. To the reaction mixture were added ethyl acetate (30 mL×2) and water (30 mL) to conduct extraction from the aqueous layer. The ethyl acetate solutions were combined and washed with water (20 mL×2), which was dried over anhydrous sodium sulfate, followed by filtration. The filtrate was concentrated under reduced pressure to afford 2-fluoro-6-methyl thiopyridine (1.09 g, yield 88%).

$^1$H-NMR (CDCl$_3$, 300 MHz) δ: 2.55 (3H, s), 3.93 (2H, s), 3.57 (1H, m), 7.05 (1H, m), 7.56 (1H, m).

Reference Example 68

Synthesis of 2-amino-6-methyl thiopyridine

In a sealed reaction vessel (inner pressure 12,1 kgcm$^{-2}$), a solution of 900 mg of 2-fluoro-6-methyl thiopyridine in 5 mL of a 28% aqueous ammonia was stirred for one hour at 150° C. and for 6 hours at 180° C. The reaction mixture was cooled to room temperature, to which were added ethyl acetate (50 mL) and water (50 mL). The aqueous layer was subjected to extraction with ethyl acetate (50 mL). The ethyl acetate layers were combined and washed with water (50 mL×2), which was dried over anhydrous sodium sulfate, followed by filtration. The filtrate was concentrated under reduced pressure to leave a yellow oily product. (crystallized by leaving standing overnight) (873 g, yield 99%).

$^1$H-NMR (CDCl$_3$, 300 MHz) δ: 2.49 (3H, s), 4.40 (2H, br s), 6.18 (1H, dd, J=0.5 & 8.1 Hz), 6.53 (1H, dd, J=0.5 & 7.7 Hz), 7.26 (1H, dd, J=7.7 & 8.1 Hz).

Reference Example 69

Synthesis of 2-amino-6-methyl thiopyridine

To 2-amino-6-fluoropyridine (300 mg) was added an aqueous solution of sodium thiomethoxide (13 ml, 10 equivalents). The suspension was stirred for one hour at 80° C. and for 5 hours at 100° C. The reaction mixture was cooled to room temperature, to which were added ethyl acetate (40 mL×2) and water (30 mL). The aqueous layer was subjected to extraction. Ethyl acetate solutions were combined and washed with water (40 mL), which was dried over anhydrous sodium sulfate, followed by filtration. The filtrate was concentrated under reduced pressure to give an oily product (crystallized by leaving standing overnight) (237 mg, yield 63%).

Reference Example 70

Synthesis of 5-methyl thioimidazo[1,2-a]pyridine

A solution of 3.094 g of 2-amino-6-methyl thiopyridine in 31 mL of ethanol was heated to 60° C. To the solution was added dropwise 14.6 mL of 40% chloroacetaldehyde. The mixture was stirred for one hour, which was cooled and concentration. To the concentrate was added 60 mL of 1N—HCl, which was washed with ethyl acetate (20 mL×2) to the aqueous layer was added 50 mL of 2N-sodium hydroxide, which was subjected to extraction with ethyl acetate (30 mL×3). The ethyl acetate layers were combined and washed with water (20 mL×2), which was dried over sodium sulfate, followed by filtration and concentration to afford 5.01 g of a brown oily product (yield 83.0%).

$^1$H-NMR (CDCl$_3$, 300 MHz) δ: 2.61 (3H, s), 6.76 (1H, m), 7.18 (1H, m), 7.55 (1H, m), 7.73 (2H, m).

Reference Example 71

Synthesis of imidazo[1,2-a]pyridine-5-thiol

A flask was charged, under argon atmosphere, 2 mL of xylene, 0.1 mL of hexamethyl phosphoric triamide and 24.4 mg of sodium hydride. The mixture was heated to 45° C., to which was added 0.06 mL of diethylamine. The mixture was stirred for 20 minutes, to which was added a solution of 57 mg of 5-methyl thioimidazo [1,2-a]pyridine in 1 mL of xylene. The mixture was heated to 150° C., which was stirred for 2.5 hours. The reaction mixture was cooled, to which were added 5 mL of water and 10 mL of 1N—HCl. The mixture was washed with 20 mL of ethyl acetate. The aqueous layer was adjusted to pH 8.5 with 2N—NaOH, which was subjected to extraction with ethyl acetate. The extract solution was dried over Na$_2$SO$_4$ which was subjected to filtration. The filtrate was concentrated to leave imidazo [1,2-a]pyridine-5-thiol (10 mg, 19%) as a brown oily product.

$^1$H-NMR (DMSO-d$_6$, 300 MHz) δ: 6.93 (2H, m), 7.30 (1H, m), 7.85 (1H, m), 8.32 (1H, m).

Reference Example 72

Synthesis of 5-thia-1,8b-diazaacenaphthylene-4-carboxylic acid

To a solution of 120.02 g (0.7991 mol.) of imidazo[1,2-a]pyridine-5-thiol and 134 mL (0.959 mol.) of triethylamine in 500 mL ethanol was added dropwise, at room temperature, 88.6 mL (0.799 mol.) of ethyl bromoacetate. The mixture was stirred for 2 hours at room temperature. The solvent of the reaction mixture was distilled off under reduced pressure. To the residue was added ethyl acetate, then resulting precipitate (principally triethylamine-hydrochloride) was collected by filtration and washed with ethyl acetate. The filtrate and the washing were combined, from which the solvent was distilled off to leave (imidazo [1,2-a]pyridin-5-ylthio) ethyl acetate as a crude product. This crude product was used for the subsequent reaction without purification. Brown liquid product Yield 199.7 g A solution of 199.7 g of the crude (imidazo[1,2-a]pyridin-5-ylthio) ethyl acetate and 224 g (1.60 mol.) of hexamethylene tetramine in 500 mL of acetic acid was stirred for one day at 90° C. The reaction mixture was poured into water, which was subjected to extraction twice with ethyl acetate. The organic layers were combined and washed with water, which was dried over anhydrous magnesium sulfate, followed by distilling off the solvent under reduced pressure to leave a solid matter. The solid matter was washed with diethyl ether to give ethyl 5-thia-1,8b-diazaacenaphthylene-4-carboxylate as a crude product. This crude product was used for the subsequent reaction without purification. Blackish purple solid product Yield 193.69 g To a solution of 193.69 g of ethyl 5-thia-1,8b-diazaacenaphthylene-4-carboxylate in 1 liter of ethanol was added a solution of 62.9 g (1.57 mol.) of sodium hydroxide in 50 mL of water. The mixture was stirred for 0.5 hour at room temperature. To the reaction mixture was added about 130 mL of conc. hydrochloric acid while stirring until the pH became about 4–5. The resulting precipitate was collected by filtration. which was washed with ethanol, acetone and diethyl ether successively to give 5-thia-1,8b-diazaacenaphthylene-4-carboxylic acid.

Orange solid Yield 96.3 g (55%)

$^1$H-NMR (DMSO-d$_6$, 200 MHz) δ: 5.97 (1H, dd, J=6.6 & 1.2 Hz), 6.57–6.73 (2H, m), 6.88 (1H, s), 7.12 (1H, s).

Reference Example 73

Synthesis of 4-amino-1-(3-phenylpropyl)piperidine

5%-Palladium/carbon(2.5 g) and 28%-sodium methoxide (32.9 g) were added into the methanol solution (467 ml) of 1-(3-phenylpropyl)-4-aminopyridinium bromide (50 g). The mixture was subjected by catalytic reduction for 5 hours under hydrogen pressure (6–8 atm) and at 40° C. After this mixture was cooled, the filtrate removed the catalyst was concentrated. Ethyl acetate (1 L) and water (200 mL), and further 2N-sodium hydroxide with cooling with ice were added into the concentrated solution. The separate solution was washed with water (300 mL), dried over sodium sulfate, and concentrated.

Acetonitrile (476 mL), and 3.5N-hydrochloric acid/ethyl acetate (195 mL) with cooling with ice were added into the concentrated solution. After stirring for 40 minutes at room temperature, the mixture was filtrated, and washed with acetonitrile (70 mL). This was dried under reduced pressure to obtain 4-amino-1-(3-phenylpropyl)piperidine 2 hydrochloride (42.86, 86.3%).

$^1$H-NMR (D$_2$O, 300MHz) δ: 1.7–2.0 (m, 6H), 2.5 (t, 2H, J=7.5 Hz), 2.8–3.2 (m, 4H), 3.3–3.6 (m, 3H), 7.1–7.3 (m, 5H).

Reference Example 74

Synthesis of 4-amino-1-(3-phenylpropyl)piperidine

The mixture of 1-(3-phenylpropyl)-4-aminopyridinium bromide (10 g), 2-propanol (200 mL), sodium methoxide (1.84 g) and sodium borohydride (10 g) were refluxed under heating. Methanol (50 mL) was added dropwise to the mixture per 30 minutes. The solution was refluxed for 2 hours, cooled to room temperature, and water (150 mL) and concentrated hydrochloric acid (35 mL) were added into this. The mixture was stirred for 1.5 hours at room temperature. After adding 30%-sodium hydroxide (50 mL), the solution was concentrated. The concentrated solution was extracted by ethyl acetate (100 mL×3), washed with water (50 mL×2), dried over sodium sulfate, filtered, and concentrated. This was dissolved in methanol-denatured alcohol (23 mL) with cooling with ice. 3.96N-Hydrochloric acid/methanol-denatured alcohol (15 mL) was added dropwise to this solution. This was stirred for 30 minutes with cooling with ice, and stirred for 1 hour at room temperature. After dropping diisopropyl ether (60 mL), the solution was stirred for 2 hours at room temperature, and stirred for 1 hour with cooling with ice. The crystal filtered under reduced pressure was washed with isopropyl ether (20 mL×2). This was dried under reduced pressure to obtain 4-amino-1-(3-phenylpropyl)piperidine 2 hydrochloride (8.54 g, 86%).

$^1$H-NMR (D$_2$O, 300 MHz) δ: 1.7–2.0 (m, 6H), 2.5 (t, 2H, J=7.5 Hz), 2.8–3.2 (m, 4H), 3.3–3.6 (m, 3H), 7.1–7.3 (m, 5H).

Reference Example 75

Synthesis of 1-(3-Aminopropan-1-yl)-4-tert-butoxycarbonyl-2-oxopiperazine

1) Syntheis of 4-tert-Butoxycarbonyl-2-oxopiperazine

Di-tert-butyl dicarbonate (10.4 g, 47.6 mmol) was added to a stirred solution of 2-oxopiperazine (4.77 g, 47.6 mmol) in ethanol (100 ml) at room temperature. After stirring at room temperature for 1 hour, the reaction mixture was concentrated in vacuo to give 4-tert-butoxycarbonyl-2-oxopiperazine as colorless crystals (8.00 g, 84%), which were collected by filtration and washed with hexane.

$^1$H-NMR (200 MHz, CDCl$_3$) δ: 6.90–6.56 (1H, m), 4.09 (2H, s), 3.64 (2H, t, J=5.2 Hz), 3.44–3.34 (2H, m), 1.48 (9H, s).

IR (KBr) : 3265, 3195, 2981, 1691, 1666, 1635, 1419, 1398, 1365, 1338, 1243, 1176, 1131, 1002 cm$^{-1}$.

2) Syntheis of 4-tert-Butoxycarbonyl-1-(3-phthalimidopropan-1-yl)-2-oxopiperazine Sodium hydride (60% in oil, 1.78 g, 44.5 mmol) was added in a small portions to a stirred solution of 4-tert-butoxycarbonyl-2-oxopiperazine (8.00 g, 40.0 mmol) in N,N-dimethylformamide (100 ml) at room temperature and the mixture was stirred at room temperature for 1 hour. Then, N-(3-bromopropyl)phthalimide (12.5 g, 46.6 mmol) was added to the mixture. After stirring at room temperature for 1 hour, the reaction mixture was poured into water and extracted with ethyl acetate. The extract was successively washed with water, brine, dried over MgSO$_4$ and concentrated in vacuo. The residue was chromatographed on silica gel (150 g) with hexane-ehtyl acetate (1:1) to give 4-tert-butoxycarbonyl-1-(3-phthalimidopropan-1-yl)-2-oxopiperazine as a colorless oil (9.02 g, 55%).

$^1$H-NMR (200 MHz, CDCl$_3$) δ: 7.90–7.80 (2H, m), 7.80–7.68 (2H, m), 4.07 (2H, s), 3.72 (2H, t, J=5.2 Hz), 3.67 (2H, t, J=5.2 Hz), 3.50 (2H, t, J=7.2 Hz), 3.37 (2H, t, J=5.2 Hz), 1.98 (2H, tt, J=7.2 and 7.2 Hz), 1.47 (9H, s).

IR (neat) : 2976, 2935, 1772, 1714, 1652, 1398, 1367, 1239, 1170, 1126, 722 cm$^{-1}$.

3) Synthesis of 1-(3-Aminopropan-1-yl)-4-tert-butoxycarbonyl-2-oxopiperazine

Hydrazine monohydrate (1.75 g, 46.6 mmol) was added to a stirred solution of 4-tert-butoxycarbonyl-1-(3-phthalimidopropan-1-yl)-2-oxopiperazine (9.02 g, 23.3 mmol) in ethanol (50 ml) at room temperature. The reaction mixture was refluxed for 1 hour. The precipitates were removed off by filtration and the filtrate was concentrated in vacuo. The residue was dissolved in 2N-sodium hydroxide and extracted with chloroform. The extract was washed with brine, dried over MgSO$_4$ and concentrated in vacuo to give 1-(3-aminopropan-1-yl)-4-tert-butoxycarbonyl-2-oxopiperazine as a colorless oil (5.43 g, 91%).

$^1$H-NMR (200 MHz, CDCl$_3$) δ: 4.29 (2H, m), 4.07 (2H, s), 3.69–3.60 (2H, m), 3.51–3.20 (4H, m), 2.71 (2H, t, J=7.0 Hz), 2.03–1.92 (2H, m), 1.47 (9H, s).

IR (neat): 2977, 1695, 1652, 1419, 1367, 1326, 1247, 1168 cm$^{-1}$.

Reference Example 76

Synthesis of 3-(4-tert-Butoxycarbonylaminophenyl) propyl methanesulfonate

1) Synthesis of (E)-Ethyl 3-(4-Nitrophenyl)acrylate

Sodium hydride (60% in oil, 2.22 g, 55.5 mmol) was added to a stirred solution of 4-nitrobenzaldehyde (8.00 g, 52.9 mmol) and triethyl phosphonoacetate (12.4 g, 55.5 mmol) in N,N-dimethylformamide (50 ml) at 0° C. After stirring at 0° C. for 30 minutes, the reaction mixture was poured into water to give (E)-ethyl 3-(4-nitrophenyl)acrylate as colorless crystals (11.7 g, quant.), which were collected by filtration and successively washed with water and hexane.

mp 133–135° C.

$^1$H-NMR (200 MHz, CDCl$_3$) δ: 8.26 (2H, d, J=8.8 Hz), 7.72 (1H, d, J=16.0 Hz), 7.68 (2H, d, J=8.8 Hz), 6.57 (1H, d, J=16.0 Hz), 4.30 (2H, q, J=7.0 Hz), 1.36 (3H, t, J=7.0 Hz).

IR (KBr): 3107, 3080, 2985, 2908, 1714, 1646, 1594, 1517, 1342, 1313, 1180, 979, 844 cm$^{-1}$.

2) Synthesis of Ethyl 3-(4-Aminophenyl)propionate (E)-Ethyl 3-(4-nitrophenyl)acrylate (11.7 g, 52.9 mmol) in tetrahydrofuran (100 ml) was hydrogenated over 10% Palladium-Carbon (1.20 g) at atmospheric pressure. After removal of the catalyst, the filtrate was concentrated in vacuo to give ethyl 3-(4-aminophenyl)propionate as a yellow oil (9.66 g, 95%).

$^1$H-NMR (200 MHz, CDCl$_3$) δ: 6.99 (2H, d, J=8.4 Hz), 6.62 (2H, d, J=8.4 Hz), 4.12 (2H, q, J=7.0 Hz), 3.60–3.00 (2H, m), 2.84 (2H, t, J=7.6 Hz), 2.55 (2H, t, J=7.6 Hz), 1.23 (3H, t, J=7.0 Hz).

IR (neat): 3371, 2981, 2925, 1729, 1627, 1519, 1372, 1282, 1180, 1155, 1037, 825 cm$^{-1}$.

3) Synthesis of Ethyl 3-(4-tert-butoxycarbonylaminophenyl)propionate

A mixture of ethyl 3-(4-aminophenyl)propionate (9.66 g, 50.0 mmol), di-tert-butyl dicarbonate (13.1 g, 60.0 mmol), triethylamine (6.07 g, 60.0 mmol) and tetrahydrofuran (50 ml) was stirred at room temperature for 17 hours. The reaction mixture was poured into water and extracted with ethyl acetate. The extract was successively washed with water and brine, dried over $MgSO_4$ and concentrated in vacuo. The residue was chromatographed on silica gel (150 g) with hexane-ethyl acetate (5:1) to give ethyl 3-(4-tert-butoxycarbonylaminophenyl)propionate as a yellow oil (14.7 g, quant.).

$^1$H-NMR (200 MHz, $CDCl_3$) δ: 7.27 (2H, d, J=8.6 Hz), 7.12 (2H, d, J=8.6 Hz), 6.42 (1H, brs), 4.12 (2H, q, J=7.0 Hz), 2.90 (2H, t, J=8.0 Hz), 2.58 (2H, t, J=8.0 Hz), 1.53 (9H, s), 1.23 (3H, t, J=7.0 Hz).

IR (neat): 3344, 2981, 1808, 1729, 1527, 1372, 1315, 1215, 1160, 1118, 1072 $cm^{-1}$.

4) Synthesis of 3-(4-tert-Butoxycarbonylaminophenyl)propanol

Diisobutylaluminium hydride(1.5 M in toluene, 30.5 ml, 45.8 mmol) was added dropwise to a stirred solution of ethyl 3-(4-tert-butoxycarbonylaminophenyl)propionate (6.10 g, 20.8 mmol) in tetrahydrofuran (60 ml) at 0° C. and the mixture was stirred at 0° C. for 1 hour. 2N-hydrochloric acid was added to the mixture and the mixture was extracted with ethyl acetate. The extract was successively washed with water, saturated aqueous $NaHCO_3$ and brine, dried over $MgSO_4$ and concentrated in vacuo. The residue was chromatographed on silica gel (100 g) with hexane-ethyl acetate (3:2) to give 3-(4-tert-butoxycarbonylaminophenyl)propanol as a colorless oil (2.66 g, 51%).

$^1$H-NMR (200 MHz, $CDCl_3$) δ: 7.34–7.00 (4H, m), 6.44 (1H, brs), 3.67 (2H, t, J=6.4 Hz), 2.80–2.60 (2H, m), 2.00–1.80 (2H, m), 1.43 (9H, s).

IR (neat): 3311, 2979, 2933, 1726, 1521, 1369, 1243, 1158, 1116, 1054 $cm^{-1}$.

5) Synthesis of 3-(4-tert-Butoxycarbonylaminophenyl)propyl methanesulfonate

A mixture of 3-(4-tert-butoxycarbonylaminophenyl)propanol (2.66 g, 10.6 mmol), methanesulfonylchloride (1.33 g, 11.6 mmol), triethylamine (1.18 g, 11.7 mmol) and ethyl acetate (10 ml) was stirred at room temperature for 1 hour. Then the reaction mixture was diluted with ethyl acetate and successively washed with water and brine, dried over $MgSO_4$ and concentrated in vacuo. The residue was chromatographed on silica gel (50 g) with hexane-ethyl acetate (3:1) to give 3-(4-tert-butoxycarbonylaminophenyl)propyl methanesulfonate as colorless crystals (2.75 g, 79%).

$^1$H-NMR (200 MHz, $CDCl_3$) δ: 7.35–7.00 (4H, m), 6.44 (1H, brs), 4.21 (2H, t, J=6.4 Hz), 2.99 (3H, s), 2.70 (2H, t, J=7.4 Hz), 2.15–1.95 (2H, m), 1.52 (9H, s).

IR (KBr): 3381, 2979, 1706, 1529, 1349, 1237, 1168, 952 $cm^{-1}$.

Reference Example 77

Synthesis of 3-(3-tert-Butoxycarbonylaminophenyl) propyl Methanesulfonate

1) Synthesis of (E)-Ethyl 3-(3-Nitrophenyl)acrylate

Sodium hydride (60% in oil, 2.22 g, 55.5 mmol) was added to a stirred solution of 3-nitrobenzaldehyde (8.00 g, 52.9 mmol) and triethyl phosphonoacetate (12.4 g, 55.5 mmol) in N,N-dimethylformamide (50 ml) at 0° C. After stirring at 0° C. for 1.5 hours, the reaction mixture was poured into water to give (E)-ethyl 3-(3-nitrophenyl)acrylate as colorless crystals (11.7 g, quant.), which were collected by filtration and washed with water and hexane.

mp 65–66° C.

$^1$H-NMR (200 MHz, $CDCl_3$) δ: 8.42–8.35 (1H, m), 8.24 (1H, dd, J=8.0 and 2.2 Hz), 7.88–7.80 (1H, m), 7.73 (1H, d, J=15.6 Hz), 7.59 (1H, dd, J=8.0 and 8.0 Hz), 6.57 (1H, d, J=15.6 Hz), 4.30 (2H, q, J=6.0 Hz), 1.36 (3H, t, J=6.0 Hz).

2) Synthesis of Ethyl 3-(3-Aminophenyl)propionate (E)-Ethyl 3-(3-nitrophenyl)acrylate (12.1 g, 52.9 mmol) in tetrahydrofuran (100 ml) was hydrogenated over 10% palladium-Carbon (2.80 g) at atmospheric pressure. After removal of the catalyst, the filtrate was concentrated in vacuo. The residue was chromatographed on silica gel (100 g) with hexane-ethyl acetate (3:1) to give ethyl 3-(3-aminophenyl)propionate as a yellow oil (6.21 g, 61%).

$^1$H-NMR (200 MHz, $CDCl_3$) δ: 7.12–7.00 (1H, m), 6.65–6.50 (3H, m), 4.13 (2H, q, J=7.0 Hz), 3.62 (2H, brs), 2.86 (2H, t, J=7.0 Hz), 2.58 (2H, t, J=7.0 Hz), 1.24 (3H, t, J=7.0 Hz).

3) Synthesis of Ethyl 3-(3-tert-butoxycarbonylaminophenyl)propionate

A mixture of ethyl 3-(3-aminophenyl)propionate (6.21 g, 32.1 mmol), di-tert-butyl dicarbonate (8.41 g, 38.5 mmol), triethylamine (3.90 g, 38.5 mmol) and tetrahydrofuran (30 ml) was stirred at room temperature for 19 hours. The reaction mixture was poured into water and extracted with ethyl acetate. The extract was successively washed with water and brine, dried over $MgSO_4$ and concentrated in vacuo. The residue was chromatographed on silica gel (100 g) with hexane-ethyl acetate (8:1) to give ethyl 3-(3-tert-butoxycarbonylaminophenyl)propionate as a yellow oil (9.35 g, 99%).

$^1$H-NMR (200 MHz, $CDCl_3$) δ: 7.40–7.10 (3H, m), 6.90–6.80 (1H, m), 6.44 (1H, brs), 4.13 (2H, q, J=7.2 Hz), 2.92 (2H, t, J=7.8 Hz), 2.60 (2H, t, J=7.8 Hz), 1.51 (9H, s), 1.24 (3H, t, J=7.2 Hz).

IR (neat): 3346, 2981, 2933, 1733, 1612, 1594, 1538, 1494, 1442, 1369, 1236, 1162, 1056, 871, 788 $cm^{-1}$.

4) Synthesis of 3-(3-tert-Butoxycarbonylaminophenyl)propanol

Diisobutylaluminium hydride (1.5 M in toluene, 57.0 ml, 85.5 mmol) was added dropwise to a stirred solution of ethyl 3-(3-tert-butoxycarbonylaminophenyl)propionate (9.35 g, 31.9 mmol) in tetrahydrofuran (100 ml) at 0° C. and the mixture was stirred at room temperature for 24 hours. 2N-hydrochloric acid was added to the mixture and the mixture was extracted with ethyl acetate. The extract was successively washed with water saturated aqueous $NaHCO_3$ and brine, dried over $MgSO_4$ and concentrated in vacuo. The residue was chromatographed on silica gel (100 g) with hexane-ethyl acetate (2:1) to give 3-(3-tert-butoxycarbonylaminophenyl)propanol as a colorless oil (3.24 g, 40%).

$^1$H-NMR (200 MHz, $CDCl_3$) δ: 7.30–7.05 (3H, m), 7.00–6.80 (1H, m), 6.47 (1H, brs), 3.66 (2H, t, J=6.4 Hz), 2.68 (2H, t, J=7.6 Hz), 2.00–1.80 (2H, m), 1.52 (9H, s).

IR (neat): 3317, 2979, 2933, 1699, 1610, 1592, 1538, 1490, 1442, 1369, 1245, 1160, 1056, 778 $cm^{-1}$.

5) Synthesis of 3-(3-tert-Butoxycarbonylaminophenyl) propyl Methanesulfonate

A mixture of 3-(3-tert-butoxycarbonylaminophenyl) propanol (3.24 g, 12.9 mmol), methanesulfonylchloride (1.63 g, 14.2 mmol), triethylamine (1.44 g, 14.2 mmol) and ethyl acetate (50 ml) was stirred at room temperature for 1 hour. Then the reaction mixture was diluted with ethyl acetate and successively washed with water and brine, dried over MgSO$_4$ and concentrated in vacuo. The residue was chromatographed on silica gel (50 g) with hexane-ethyl acetate (3:1) to give 3-(3-tert-butoxycarbonylaminophenyl) propyl methanesulfonate as a colorless oil (3.50 g, 82%).

$^1$H-NMR (200 MHz, CDCl$_3$) δ: 7.40–7.00 (3H, m), 6.86 (1H, d, J=6.6 Hz), 6.46 (1H, brs), 4.22 (2H, t, J=6.0 Hz), 3.01 (3H, s), 2.73 (2H, t, J=7.6 Hz), 2.20–1.98 (2H, m), 1.51 (9H, s).

Reference Example 78

Synthsis of 3-(4-Cyanophenyl)propyl Methanesulfonate

1) Synthesis of (E)-Ethyl 3-(4-Cyanophenyl)acrylate

Sodium hydride (60% in oil, 3.20 g, 80.0 mmol) was added to a stirred solution of 4-cyanobenzaldehyde (10.0 g, 76.3 mmol) and triethyl phosphonoacetate (18.0 g, 80.1 mmol) in N,N-dimethylformamide (80 ml) at 0° C. After stirring at 0° C. for 1 hour, the reaction mixture was poured into water to give (E)-ethyl 3-(4-cyanophenyl)acrylate as colorless crystals (13.9 g, 91%), which were collected by filtration and washed with water and hexane.

$^1$H-NMR (200 MHz, CDCl$_3$) δ: 7.74–7.54 (4H, m ), 7.63 (1H, d, J=16.2 Hz), 6.52 (1H, d, J=16.2 Hz), 4.29 (2H, q, J=7.0 Hz), 1.34 (3H, t, J=7.0 Hz).

IR (KBr): 3402, 2987, 2227, 1706, 1641, 1560, 1473, 1369, 1166, 1002, 850 cm$^{-1}$.

2) Synthesis of Ethyl 3-(4-Cyanophenyl)propionate (E)-Ethyl 3-(4-cyanophenyl)acrylate (13.9 g, 69.1 mmol) in tetrahydrofuran (100 ml) was hydrogenated over 10% Palladium-Carbon (4.00 g) at atmospheric pressure. After removal of the catalyst, the filtrate was concentrated in vacuo to give ethyl 3-(4-cyanophenyl)propionate as a yellow oil (13.7 g, 98%).

$^1$H-NMR (200 MHz, CDCl$_3$) δ: 7.59 (2H, d, J=8.2 Hz), 7.33 (2H, d, J=8.2 Hz), 4.13 (2H, q, J=7.0 Hz), 3.01 (2H, t, J=7.6 Hz), 2.64 (2H, t, J=7.6 Hz), 1.23 (3H, t, J=7.0 Hz).

IR (neat): 2981, 2933, 2229, 1733, 1608, 1506, 1446, 1417, 1374, 1297, 1185, 1041, 827 cm$^{-1}$.

3) Synthesis of 3-(4-Cyanophenyl)propionic Acid

A mixture of ethyl 3-(4-cyanophenyl)propionate (6.00 g, 29.5 mmol), 2N-sodium hydroxide (30 ml, 60.0 mmol) and ethanol (60 ml) was stirred at room temperature for 1 hour. The reaction mixture was acidified with 1N-hydrochloric acid and extracted with ethyl acetate. The extract was washed with brine, dried over MgSO$_4$ and concentrated in vacuo to give 3-(4-cyanophenyl)propionic acid as colorless crystals (4.40 g, 85%).

$^1$H-NMR (200 MHz, CDCl$_3$) δ: 7.60 (2H, d, J=8.0 Hz), 7.33 (2H, d, J=8.0 Hz), 3.02 (2H, t, J=7.6 Hz), 2.71 (2H, t, J=7.6 Hz).

IR (KBr): 3060, 2922, 2227, 1710, 1608, 1434, 1411, 1330, 1309, 1224, 935, 840 cm$^{-1}$.

4) Synthesis of 3-(4-Cyanophenyl)propanol Borane-tetrahydrofuran complex (1.0 M in tetrahydrofuran, 33.0 ml, 33.0 mmol) was added dropwise to a stirred solution of 3-(4-cyanophenyl)propionic acid (4.40 g, 25.1 mmol) in tetrahydrofuran (50 ml) at OüÅ and the stirring was continued at room temperature for 14 hours. Water (50 ml) and potassium carbonate (10.0 g, 72.4 mmol) was added to the mixture. The mixture was extracted with ethyl acetate and the extract was washed with brine, dried over MgSO$_4$ and concentrated in vacuo to give 3-(4-cyanophenyl)propanol as a yellow oil (3.20 g, 79%).

$^1$H-NMR (200 MHz, CDCl$_3$) δ: 7.58 (2H, d, J=8.2 Hz), 7.31 (2H, d, J=8.2 Hz), 3.68 (2H, t, J=6.2 Hz), 2.79 (2H, t, J=7.8 Hz), 2.00–1.75 (2H, m).

IR (neat): 3319, 2943, 2229, 1608, 1505, 1415, 1054, 854, 817 cm$^{-1}$.

5) Synthesis of 3-(4-Cyanophenyl)propyl Methanesulfonate

A mixture of 3-(4-cyanophenyl)propanol (3.77 g, 23.4 mmol), methanesulfonylchloride (2.96 g, 25.8 mmol), triethylamine (2.60 g, 25.7 mmol) and ethyl acetate (100 ml) was stirred at room temperature for 30 minutes. Then the reaction mixture was diluted with ethyl acetate and successively washed with water and brine, dried over MgSO$_4$ and concentrated in vacuo. The residue was chromatographed on silica gel (60 g) with hexane-ethyl acetate (1:1) to give 3-(4-cyanophenyl)propane methanesulfonate as a colorless oil (4.79 g, 86%).

$^1$H-NMR (200 MHz, CDCl$_3$) δ: 7.61 (2H, d, J=8.4 Hz), 7.31 (2H, d, J=8.4 Hz), 4.24 (2H, t, J=6.2 Hz), 3.02 (3H, s), 2.83 (2H, t, J=7.8 Hz), 2.09 (2H, tt, J=7.8 and 6.2 Hz).

IR (neat): 3028, 2941, 2227, 1608, 1506, 1351, 1172, 975, 929, 836, 815 cm$^{-1}$.

Reference Example 79

Synthesis of 4-(3-Aminopropan-1-yl)-1-(3-phenylpropan-1-yl)-2-oxopiperazine

1) Synthesis of 4-tert-Butoxycarbonyl-1-(3-phenylpropan-1-yl)-2-oxopiperazine Sodium hydride (60% in oil, 630 mg, 15.8 mmol) was added to a stirred solution of 4-tert-butoxycarbonyl-2-oxopiperazine (3.00 g, 15.0 mmol) in N,N-dimethylformamide (40 ml) at room temperature and the stirring was continued at room temperature for 30 minutes. 1-Bromo-3-phenylpropane (3.29 g, 16.5 mmol) was added to the mixture and the stirring was continued at room temperature for 1 hour. The reaction mixture was poured into water and extracted with ethyl acetate. The extract was successively washed with water, brine, dried over MgSO$_4$ and concentrated in vacuo. The residue was chromatographed on silica gel (50 g) with hexane-ethyl acetate (1:1) to give 4-tert-butoxycarbonyl-1-(3-phenylpropan-1-yl)-2-oxopiperazine as colorless crystals (3.85 g, 81%), which were collected by filtration and washed with hexane.

$^1$H-NMR (200 MHz, CDCl$_3$) δ: 7.35–7.15 (5H, m), 4.04 (2H, s), 3.57 (2H, t, J=5.4 Hz), 3.46 (2H, t, J=7.2 Hz), 3.28 (2H, t, J=5.4 Hz), 2.65 (2H, t, J=7.2 Hz), 1.90 (2H, tt, J=7.2 and 7.2 Hz), 1.46 (9H, IR (KBr): 2975, 2916, 1699, 1656, 1419, 1367, 1239, 1170, 1128, 992, 701 cm$^{-1}$.

2) Synthesis of 1-(3-Phenylpropan-1-yl)-2-oxopiperazine

Concentrated hydrochloric acid (4.2 ml) was added to 4-tert-butoxycarbonyl-1-(3-phenylpropan-1-yl)-2-oxopiperazine (3.85 g, 12.1 mmol) at room temperature and the mixture was stirred at room temperature for 1 hour. The reaction mixture was basified with 8N-sodium hydroxide and extracted with ethyl acetate. The extract was washed with brine, dried over MgSO$_4$ and concentrated in vacuo to give 1-(3-phenylpropan-1-yl)-2-oxopiperazine as a colorless oil (2.49 g, 94%).

$^1$H-NMR (200 MHz, CDCl$_3$) δ: 7.30–7.05 (5H, m), 3.48 (2H, s), 3.44 (2H, t, J=7.6 Hz), 3.25 (2H, t, J=5.4 Hz), 3.01 (2H, t, J=5.4 Hz), 2.65 (2H, t, J=7.6 Hz), 1.91 (2H, tt, J=7.6 and 7.6 Hz).

IR (neat): 3290, 2927, 1635, 1496, 1454, 1344, 1315, 751, 701 cm$^{-1}$.

3) Synthesis of 1-(3-Phenylpropan-1-yl)-4-(3-phthaloylpropan-1-yl)-2-oxopiperazine A mixture of 1-(3-phenylpropan-1-yl)-2-oxopiperazine (2.49 g, 11.4 mmol), N-(3-bromopropyl)phthalimide (3.67 g, 13.7 mmol), potassium carbonate (1.89 g, 13.7 mmol) and N,N-dimethylformamide (20 ml) was stirred at room temperature for 4 hours. The reaction mixture was poured into water and extracted with ethyl acetate. The extract was successively washed with water, brine, dried over MgSO$_4$ and concentrated in vacuo. The residue was chromatogrphed on silica gel (60 g) with hexane-ethyl acetate (1:4) to give 1-(3-phenylpropan-1-yl)-4-(3-phthaloylpropan-1-yl)-2-oxopiperazine as a colorless oil (2.05 g, 44%).

$^1$H-NMR (200 MHz, CDCl$_3$) δ: 7.82 (2H, dd, J=5.2 and 3.2 Hz), 7.64 (2H, dd, J=5.2 and 3.2 Hz), 7.35–7.10 (5H, m), 3.77 (2H, t, J=6.6 Hz), 3.30 (2H, t, J=7.6 Hz), 3.16 (2H, t, J=5.4 Hz), 3.07 (2H, s), 2.70–2.52 (4H, m), 2.45 (2H, t, J=6.6 Hz), 2.00–1.70 (4H, m).

4) Synthesis of 4-(3-Aminopropan-1-yl)-1-(3-phenylpropan-1-yl)-2-oxopiperazine

Hydrazine monohydrate (382 mg, 7.63 mmol) was added to a stirred solution of 1-(3-phenylpropan-1-yl)-4-(3-phthaloylpropan-1-yl)-2-oxopiperazine (2.05 g, 5.05 mmol) in ethanol (10 ml) at room temperature. The reaction mixture was refluxed for 1 hour. The precipitates were removed off by filtration and the filtrate was concentrated in vacuo. The residue was dissolved in 2N-sodium hydroxide and extracted with chloroform. The extract was washed with brine, dried over MgSO$_4$ and concentrated in vacuo to give 4-(3-aminopropan-1-yl)-1-(3-phenylpropan-1-yl)-2-oxopiperazine as a colorless oil (1.38 g, 99%).

$^1$H-NMR (200 MHz, CDCl$_3$) δ: 7.35–7.15 (5H, m), 3.43 (2H, t, J=7.6 Hz), 3.30 (2H, t, J=5.4 Hz), 3.13 (2H, s), 2.78 (2H, t, J=6.8 Hz), 2.71–2.58 (4H, m), 2.46 (2H, t, J=7.2 Hz), 2.05–1.75 (2H, m), 1.65 (2H, tt, J=6.8 and 6.8 Hz).

EXAMPLE 1

Synthesis of (R)-N-[1-(1,4-benzodioxan-2-ylmethyl) piperidin-4-ylmethyl]-5-thia-1,8b-diazaacenaphthylene-4-carboxamide dihydrochloride 1) Synthesis of ethyl imidazo[1,2-a]pyridin-5-ylthioacetate To a solution of 100.55 g (669.4 mM) of imidazo[1,2-a]pyridine-5-thiol and 112 ml (803 mM) of triethylamine in 500 ml of ethanol was added 81.7 ml (736 mM) of ethyl bromoacetate at room temperature and the mixture was stirred at room temperature for 2 hours. The solvent was then distilled off under reduced pressure and ethyl acetate was added to the residue. The resulting precipitate (triethylamine hydrochloride) was filtered off and washed with ethyl acetate. The filtrate and washes were pooled, the solvent was distilled off under reduced pressure, and the residue was purified by silica gel column chromatography (hexane-ethyl acetate=1:1 to ethyl acetate) to provide the title compound.

Brown liquid. Yield 132.34 g (84%)

$^1$H-NMR (CDCl$_3$, 200 MHz) δ: 1.169 (3H, t, 7.1 Hz), 3.678 (2H, s), 4.122 (2H, q, 7.1 Hz), 7.066 (1H, dd, 1.5 Hz, 6.9 Hz), 7.160 (1H, dd, 7.0 Hz, 8.8 Hz), 7.642 (1H, ddd, 0.7 Hz, 1.5 Hz, 8.8 Hz), 7.724 (1H, d, 1.0 Hz), 7.919 (1H, d, 0.6 Hz).

IR (neat): 3390, 2983, 1734, 1487, 1294, 1180, 1147, 1026, 783, 739 cm$^1$.

2) Synthesis of ethyl 5-thia-1,8b-diazaacenaphthylene-4-carboxylate

Process A

To 250 ml of N,N-dimethylformamide was added 93.2 ml (1.0 M) of phosphorus oxychloride dropwise at 0° C. with constant stirring over 10 minutes and the mixture was further stirred at 0° C. for 1 hour. To this solution was added a solution of 47.26 g (0.2 M) of ethyl imidazo[1,2-a]pyridin-5-ylthioacetate in 50 ml of N,N-dimethylformamide over 5 minutes and the mixture was stirred at 80° C. for 16 hours. This reaction mixture was then poured in 1 lf of iced water and, after thorough stirring, 1 l of ethyl acetate was added. To this mixture was added 50% aqueous solution of sodium hydroxide with ice-cooling and stirring until the aqueous layer had become neutral. The organic layer was washed with three 500 ml portions of water and further with 500 ml of saturated aqueous solution of sodium chloride and dried over MgSO$_4$. The solvent was then distilled off under reduced pressure to provide a deep-purple residue. This residue was rinsed with 250 ml of diethyl ether to provide the title compound as crude product. This crude product was not further purified but used as it was in the next reaction 3).

Deep-purple solid. Yield 11.58 g (23.5%)

$^1$H-NMR (CDCl$_3$, 200 MHz) δ: 1.299 (3H, t, 7.1 Hz), 4.224 (2H, q, 7.1 Hz), 5.629–5.731 (1H, m), 6.506–6.609 (2H, m), 6.807 (1H, s), 7.006 (1H, s).

IR (nujol):1693, 1614, 1267, 1227, 1043, 773, 735 cm$^{-1}$.

Process B

A 60% suspension of sodium hydride in liquid paraffin, 22.4 g (560 mM), was washed with two 100 ml portions of hexane followed by addition of 60 ml of N,N-dimethylformamide and the mixture was suspended in 500 ml of tetrahydrofuran. With the reaction vessel being cooled on a water bath, a solution of 132.34 g (560.1 mM) of ethyl imidazo[1,2-a]pyridin-5-ylthioacetate in 200 ml of tetrahydrofuran was added dropwise at room temperature and the mixture was stirred at the prevailing temperature for 2 hours. Then, on a water bath, 67.9 ml (840 mM) of ethyl formate was added and the mixture was stirred at the prevailing temperature overnight. The resulting precipitate was recovered by filtration, washed serially with ethyl acetate and diethyl ether, and dried to provide ethyl 2-(imidazo[1,2-a]pyridin-5-ylthio)-3-oxo-2-sodiopropionate.

Yellow solid. Yield 114.37 g (71%)

$^1$H-NMR (CD$_3$OD, 200 MHz) δ: 1.222 (3H, t, 7.1 Hz), 4.119 (2H, q, 7.1 Hz), 6.676 (1H, d, 6.6 Hz), 7.207 (1H, dd, 7.0 Hz, 8.8 Hz), 7.291 (1H, d, 8.4 Hz), 7.590 (1H, s), 7.933 (1H, s), 9.400 (1H, s).

IR (nujol): 1662, 1558, 1273, 1065, 771, 732, 692 cm$^{-1}$.

Elemental analysis for C$_{12}$H$_{11}$N$_2$O$_3$SNa.0.3H$_2$O Calcd.: C, 49.41; H, 4.01; N, 9.60 Found: C, 49.55; H, 4.14; N, 9.35

While 500 ml of acetic acid was heated at 120–130° C. and stirred, 106.64 g (372.5 mM) of the above ethyl 2-(imidazo[1,2-a]pyridin-5-ylthio)-3-oxo-2-sodiopropionate was added portionwise and the mixture was stirred at 100° C. overnight. The solvent was then distilled off under reduced pressure and the residue was diluted with water, neutralized with potassium carbonate with caution, and extracted with 4 portions of chloroform. The organic layers were pooled and dried over MgSO$_4$ and the solvent was distilled off under reduced pressure. The residue was purified by silica gel column chromatography (hexane-ethyl acetate=1/1 to ethyl acetate) and the solid product was rinsed with diethyl ether to provide the title compound.

Deep-purple solid. Yield 50.33 g (55%)

3) Synthesis of 5-thia-1,8b-diazaacenaphthylene-4-carboxylic acid

To a solution of 64.047 g (260.0 mM) of ethyl 5-thia-1,8b-diazaacenaphthylene-4-carboxylate in 400 ml of ethanol was added 156 ml (312 mM) of 2N-aqueous solution of sodium hydroxide and the mixture was stirred at room temperature for one hour. To this reaction mixture was added concentrated hydrochloric acid with stirring to bring pH into the range of 4–5 and the resulting precipitate was recovered by filtration and rinsed serially with ethanol and diethyl ether to provide the title compound.

Red solid. Yield 61.16 g (100%)

$^1$H-NMR (DMSO-$d_6$, 200 MHz) δ: 5.97 (1H, dd, 6.6 Hz, 1.2 Hz), 6.57–6.73 (2H, m), 6.88 (1H, s), 7.12 (1H, s).

IR (KBr): 3413, 1632, 1338 cm$^{-1}$.

4) Synthesis of (piperidin-4-ylmethyl)-5-thia-1,8b-diazaacenaphthylene-4-carboxamide dihydrochloride While 26.48 g (121.3 mM) of 5-thia-1,8b-diazaacenaphthylene-4-carboxylic acid and 15.4 g (133 mM) of N-hydroxysuccinimide were stirred together in 250 ml of acetonitrile, 25.6 g (133 mM) of 1-ethyl-3-(3-dimethylaminopropyl)carbodiimide hydrochloride was added and the mixture was stirred at room temperature for 6 hours. To this reaction mixture was added 20.3 ml (146 mM) of triethylamine as well as 27.3 g (127 mM) of 1-(tert-butoxycarbonyl)piperidin-4-ylmethylamine and the mixture was stirred at room temperature overnight. This reaction mixture was poured in aqueous solution of sodium hydrogen carbonate and extracted with 3 portions of ethyl acetate. The organic layers were pooled and dried over MgSO$_4$ and the solvent was distilled off under reduced pressure. The residue was subjected to silica gel column chromatography (ethyl acetate to ethyl acetate-methanol=9:1) to provide crude N-[1-(tert-butoxycarbonyl)piperidin-4-ylmethyl]-5-thia-1,8b-diazaacenaphthylene-4-carboxamide. To this crude N-[1-(tert-butoxycarbonyl)piperidin-4-ylmethyl]-5-thia-1,8b-diazaacenaphthylene-4-carboxamide was added 30 ml of concentrated hydrochloric acid and the mixture was stirred at room temperature for one hour. To this reaction mixture was added ethanol, followed by stirring, and the resulting precipitate was recovered by filtration and rinsed serially with ethanol and diethyl ether to provide the title compound.

Orange-colored solid. Yield 33.347 g (71%)

$^1$H-NMR (DMSO-$d_6$, 200 MHz) δ: 1.19–1.54 (2H, m), 1.58–1.92 (3H, m), 2.66–2.96 (2H, m), 2.96–3.15 (2H, m), 3.16–3.35 (2H, m), 6.65 (1H, d, 7.4 Hz), 7.01 (1H, d, 9.2 Hz), 7.26 (1H, s), 7.32 (1H, dd, 9.2 Hz, 7.4 Hz), 7.70 (1H, s), 8.70–9.28 (3H, m, NH).

IR (KBr): 3358, 1641, 1535 cm$^{-1}$.

5) Synthesis of (R)-N-[1-(1,4-benzodioxan-2-ylmethyl)piperidin-4-ylmethyl)-5-thia-1,8b-diazaacenaphthylene-4-carboxamide To a solution of 0.410 g (2.467 mM) of (R)-2-hydroxymethyl-1,4-benzodioxane and 0.52 ml (3.70 mM) of triethylamine in 30 ml of diethyl ether was added 0.21 ml (2.71 mM) of methanesulfonyl chloride dropwise with ice-cooling and the mixture was stirred for 0.5 hour. This reaction mixture was poured in aqueous solution of sodium hydrogen carbonate and extracted with 2 portions of ethyl acetate. The organic layers were combined and dried over MgSO$_4$ and the solvent was distilled off under reduced pressure. The residue was passed through a short silica gel column (hexane-ethyl acetate=3/1 to 2/1) to provide crude (S)-2-methanesulfonyloxymethyl-1,4-benzodioxane.

A solution of the above crude (S)-2-methanesulfonyloxymethyl-1,4-benzodioxane, 1.05 g (2.71 mM) of N-(piperidin-4-ylmethyl)-5-thia-1,8b-diazaacenaphthylene-4-carboxamide dihydrochloride, and 1.20 ml (8.64 mM) of triethylamine in 30 ml of ethanol was refluxed for 3 days. The solvent was then distilled off under reduced pressure and the residue was purified by silica gel column chromatography (ethyl acetate to ethyl acetate-methanol=4/1 to 3/1) to provide the title compound and triethylamine hydrochloride as a mixture. This mixture was diluted with ethyl acetate and washed serially with aqueous solution of sodium hydrogen carbonate, water, and saturated aqueous solution of NaCl. The organic layer was dried over MgSO$_4$ and the solvent was distilled off to provide the title compound.

Red foam. Yield 0.452 g (40%)

$^1$H-NMR (CDCl$_3$, 200 MHz) δ: 1.222–1.368 (2H, m), 1.493–1.702 (3H, m), 2.011–2.187 (2H, m), 2.543 (1H, dd, 6.4 Hz, 13.0 Hz), 2.663 (1H, dd, 5.4 Hz, 13.2 Hz), 2.885–3.035 (2H, m), 3.182 (2H, t, 6.1 Hz), 3.957 (1H, dd, 7.7 Hz, 11.7 Hz), 4.249–4.317 (2H, m), 5.759 (1H, dd, 2.5 Hz, 5.5 Hz), 6.371 (1H, br t, 5.9 Hz), 6.600–6.654 (3H, m), 6.788–6.896 (4H, m), 6.990 (1H, s).

IR (neat): 3313, 2924, 1618, 1549, 1491, 1265, 1153, 731 cm$^{-1}$.

6) Synthesis of (R)-N-[1-(1,4-benzodioxan-2-ylmethyl)piperidin-4-ylmethyl]-5-thia-1,8b-diazaacenaphthylene-4-carboxamide dihydrochloride In 1 ml of methanol was dissolved 0.452 g of (R)-N-[1-(1,4-benzodioxan-2-ylmethyl)piperidin-4-ylmethyl]-5-thia-1,8b-diazaacenaphthylene-4-carboxamide, followed by addition of an excess of methanolic HCl. The mixture was stirred and concentrated to provide the title compound.

Orange-colored foam. Yield 0.530 g $^1$H-NMR (CD$_3$OD, 200 MHz) δ: 1.641–2.042 (5H, m), 3.114–3.588 (6H, m), 3.687–3.881 (2H, m), 4.037 (1H, dd, 6.6 Hz, 11.8 Hz), 4.346 (1H, dd, 2.3 Hz, 11.5 Hz), 4.828–4.905 (1H, m), 6.636 (1H, d, 7.2 Hz), 6.827–6.904 (3H, m), 6.931–6.992 (1H, m), 7.038 (1H, d, 9.2 Hz), 7.098 (1H, s), 7.401 (1H, dd, 7.6 Hz, 8.8 Hz), 7.563 (1H, s).

IR (nujol): 3228, 2650, 1630, 1493, 1294, 1263, 756 cm$^{-1}$.

Elemental analysis for C$_{25}$H$_{28}$Cl$_2$N$_4$O$_3$S.2.5H$_2$O Calcd.: C, 51.72; H, 5.73; N, 9.65 Found: C, 51.66; H, 5.97; N, 9.62

EXAMPLE 2

Synthesis of (S)-N-(1-(1,4-benzodioxan-2-ylmethyl)piperidin-4-ylmethyl]-5-thia-1,8b-diazaacenaphthylene-4-carboxamide dihydrochloride The procedure of Example 1–5) was generally followed to provide (S)-N-[1-(1,4-benzodioxan-2-ylmethyl)piperidin-4-ylmethyl]-5-thia-1,8b-diazaacenaphthylene-4-carboxamide as red foam.

$^1$H-NMR (CDCl$_3$, 200 MHz) δ: 1.245–1.395 (2H, m), 1.468–1.719 (3H, m), 2.018–2.210 (2H, m), 2.561 (1H, dd, 5.8 Hz, 13.4 Hz), 2.679 (1H, dd, 5.7 Hz, 13.3 Hz), 2.901–3.059 (2H, m), 3.211 (2H, t, 6.2 Hz), 3.973 (1H, dd, 7.7 Hz, 11.7 Hz), 4.253–4.350 (2H, m), 5.798 (1H, br t, 6.2 Hz), 5.800 (1H, dd, 1.8 Hz, 6.2 Hz), 6.594–6.719 (3H, m), 6.801–6.909 (4H, m), 7.062,(1H, s).

IR (neat): 3311, 2924, 1618, 1549, 1491, 1265, 1153, 735 cm$^{-1}$.

Using the above compound, the procedure of Example 1–6) was generally followed to provide the title compound as orange-colored foam.

¹H-NMR (CD₃OD, 200 MHz) δ: 1.643–2.040 (5H, m),, 3.116–3.238 (4H, m), 3.418–3.594 (2H, m), 3.685–3.879 (2H, m), 4.037 (1H, dd, 6.6 Hz, 11.8 Hz), 4.349 (1H, dd, 2.2 Hz, 11.4 Hz), 4.832–4.907 (1H, m), 6.638 (1H, d, 7.2 Hz), 6.829–6.905 (3H, m), 6.933–6.995 (1H, m), 7.040 (1H, d, 9.2 Hz), 7.105 (1H, s), 7.404 (1H, dd, 7.6 Hz, 9.0 Hz), 7.569 (1H, s).

IR (nujol): 3230, 2667, 1630, 1493, 1298, 1263, 756 cm⁻¹.

Elemental analysis for $C_{25}H_{28}Cl_2N_4O_3S \cdot 2.0H_2O$ Calcd.: C, 52.54; H, 5.64; N, 9.80 Found: C, 52.53; H, 5.86; N, 9.75

EXAMPLE 3

Synthesis of N-[1-(1,4-benzodioxan-2-ylmethyl) piperidin-4-ylmethyl]-5-thia-1,8b-diazaacenaphthylene-4-carboxamide dihydrochloride The procedure of Example 1–5) was generally followed to provide N-[1-(1,4-benzodioxan-2-ylmethyl)piperidin-4-ylmethyl)-5-thia-1,8b-diazaacenaphthylene-4-carboxamide as red foam.

¹H-NMR (CDCl₃, 200 MHz) δ: 1.273–1.396 (2H, m), 1.478–1.713 (3H, m), 2.015–2.204 (2H, m), 2.553 (1H, dd, 5.8 Hz, 13.6 Hz), 2.674 (1H, dd, 5.8 Hz, 13.6 Hz), 2.894–3.066 (2H, m), 3.204 (2H, t, 6.1 Hz), 3.968 (1H, dd, 7.8 Hz, 11.6 Hz), 4.242–4.348 (2H, m), 5.788 (1H, dd, 1.6 Hz, 6.0 Hz), 5.865 (1H, br t, 6.2 Hz), 6.583–6.711 (3H, m), 6.794–6.902 (4H, m), 7.047 (1H, s).

IR (neat): 3313, 2926, 1618, 1549, 1491, 1267, 1153, 731 cm⁻¹.

Using the above compound, the procedure of Example 1–6) was generally followed to provide the title compound as orange-colored foam.

¹H-NMR (CD₃OD, 200 MHz) δ: 1.577–2.042 (5H, m), 3.083–3.246 (4H, m), 3.403–3.530 (2H, m), 3.656–3.845 (2H, m), 4.034 (1H, dd, 6.5 Hz, 11.5 Hz), 4.326 (1H, dd, 2.4 Hz, 11.4 Hz), 4.832–4.907 (1H, m), 6.615 (1H, dd, 0.8 Hz, 7.6 Hz), 6.861–6.896 (3H, m), 6.929–6.973 (1H, m), 7.007 (1H, dd, 0.8 Hz, 9.2 Hz), 7.045 (1H, s), 7.393 (1H, dd, 7.5 Hz, 8.9 Hz), 7.539 (1H, s).

IR (nujol): 3217, 2663, 1629, 1493, 1294, 1261, 756 cm⁻¹.

Elemental analysis for $C_{25}H_{28}Cl_2N_4O_3S \cdot 3.0H_2O$ Calcd.: C, 50.93; H, 5.81; N, 9.50 Found: C, 51.11; H, 5.86; N, 9.55

EXAMPLE 4

Synthesis of N-[1-(3-phenylpropan-1-yl)piperidin-3-ylmethyl]-5-thia-1,8b-diazaacenaphthylene-4-carboxamide dihydrochloride 1) Synthesis of N-[1-(3-phenylpropan-1-yl)piperidin-3-ylmethyl)-5-thia-1,8b-diazaacenaphthylene-4-carboxamide To a solution of 0.406 g (1.860 mM) of 5-thia-1,8b-diazaacenaphthylene-4-carboxylic acid, 0.62 g (2.05 mM) of 1-(3-phenylpropan-1-yl)piperidin-3-ylmethylamine dihydrochloride, and 1.04 ml (7.44 mM) of triethylamine in 10 ml of N,N-dimethylformamide was added 0.34 ml (2.23 mM) of diethyl cyanophosphate at room temperature and the mixture was stirred at the prevailing temperature overnight. This reaction mixture was poured in aqueous solution of sodium hydrogen carbonate and extracted with 3 portions of ethyl acetate. The organic layers were pooled and dried over MgSO₄ and the solvent was distilled off under reduced pressure. The residue was purified by silica gel column chromatography (ethyl acetate to ethyl acetate-methanol= 4/1 to 2/1) to provide the title compound.

Red foam Yield 0.300 g (37%)

¹H-NMR (CDCl₃, 200 MHz) δ: 1.072–1.187 (1H, m), 1.497–2.045 (8H, m), 2.188 (1H, t, 9.0 Hz), 2.390 (2H, t, 7.8 Hz), 2.628 (2H, t, 7.7 Hz), 2.708–2.901 (3H, in), 3.202 (1H, dd, 5.2 Hz, 13.6 Hz), 3.324 (1H, dd, 6.1 Hz, 13.3 Hz), 5.702 (1H, dd, 1.6 Hz, 6.2 Hz), 6.537–6.679 (3H, m), 6.859 (1H, br s), 6.975 (1H, s), 7.144–7.325 (5H, m).

IR (neat): 3278, 2931, 1618, 1549, 1481, 1281, 1155, 1053, 773, 733, 700 cm⁻¹.

2) Synthesis of N-[1-(3-phenylpropan-1-yl)piperidin-3-ylmethyl]-5-thia-1,8b-diazaacenaphthylene-4-carboxamide dihydrochloride The procedure of Example 1–6) was generally followed to provide the title compound as orange-colored foam.

¹H-NMR (CD₃OD, 200 MHz) δ: 1.145–1.350 (1H, m), 1.830–2.214 (6H, m), 2.709 (2H, t, 7.5 Hz), 2.784–2.964 (2H, m), 3.108–3.372 (4H, m), 3.509–3.559 (2H, m), 6.627 (1H, d, 7.2 Hz), 7.035 (1H, d, 8.8 Hz), 7.120–7.325 (6H, m), 7.391 (1H, dd, 7.7 Hz, 9.1 Hz), 7.556 (1H, s).

IR (neat): 3390, 2949, 2679, 1633, 1566, 1537, 1450, 1296, 1215, 754, 702 cm⁻¹.

Elemental analysis for $C_{25}H_{30}Cl_2N_4OS \cdot 2.5H_2O$ Calcd.: C, 54.54; H, 6.41; N, 10.18 Found: C, 54.52; H, 6.40; N, 9.96

EXAMPLE 5

Synthesis of 4-[1'-(3-phenylpropan-1-yl)-4,4'-bipiperidin-1-ylcarbonyl]-5-thia-1,8b-diazaacenaphthylene dihydrochloride The procedure of Example 4-1) was generally followed to provide 4-[1'-(3-phenylpropan-1-yl)-4,4'-bipiperidin-1-ylcarbonyl)-5-thia-1,8b-diazaacenaphthylene as red foam.

¹H-NMR (CDCl₃, 200 MHz) δ: 1.049–1.382 (6H, m), 1.644–1.903 (8H, m), 2.346 (2H, t, 7.6 Hz), 2.619 (2H, t, 7.7 Hz), 2.817 (2H, br t, 12.3 Hz), 2.964 (2H, br d, 11.2 Hz), 4.354 (2H, br d, 13.4 Hz), 5.705 (1H, dd, 1.5 Hz, 6.3 Hz), 6.045 (1H, s), 6.587 (1H, dd, 9.2 Hz, 16.8 Hz), 6.607 (1H, dd, 9.2 Hz, 12.0 Hz), 6.921 (1H, s), 7.127–7.312 (5H, m).

IR (neat): 2937, 1618, 1483, 1439, 1279, 1149, 731 cm⁻¹.

Using the above compound, the procedure of Example 1–6) was generally followed to provide the title compound as orange-colored foam.

¹H-NMR (CD₃OD, 200 MHz) δ: 1.145–2.194 (12H, m), 2.707 (2H, t, 7.7 Hz), 2.903–3.154 (6H, m), 3.587 (2H, br d, 11.8 Hz), 4.342 (2H, br d, 12.8 Hz), 6.521 (1H, s), 7.666 (1H, d, 7.4 Hz), 7.096 (1H, d, 8.8 Hz), 7.140–7.330 (5H, m), 7.424 (2H, dd, 7.6 Hz, 9.2 Hz), 7.499 (1H, s).

IR (neat): 2947, 2721, 1630, 1500, 1448, 1390, 1275, 1215, 972, 754, 702 cm⁻¹.

Elemental analysis for $C_{29}H_{36}Cl_2N_4OS \cdot 2.5H_2O$ Calcd.: C, 57.61; H, 6.83; N, 9.27 Found: C, 57.56; H, 7.10; N, 8.88

EXAMPLE 6

Synthesis of N-[2-[1-(3-phenylpropan-1-yl) piperidin-4-ylidene]ethyl]-5-thia-1,8b-diazaacenaphthylene-4-carboxamide dihydrochloride 1) Synthesis of N-[2-(piperidin-4-ylidene)ethyl]-5-thia-1, 8b-diazaacenaphthylene-4-carboxamide dihydrochloride To a solution of 2.555 g (7.169 mM) of N-[2-(1-(tert-butoxycarbonyl)piperidin-4-ylidene]ethyl]phthalimide in 30 ml of ethanol was added 0.38 ml (7.89 mM) of hydrazine monohydrate and the mixture was refluxed for one hour. After cooling to room temperature, this reaction mixture was poured in aqueous solution of sodium hydroxide and extracted with 3 portions of ethyl acetate. The organic layers were pooled and dried over $MgSO_4$ and the solvent was distilled off under reduced pressure. The resulting crude 2-[1-(tert-butoxycarbonyl)piperidin-4-ylidene]ethylamine was not purified but used as it was in the next reaction.

While 1.56 g (7.17 mM) of 5-thia-1,8b-diazaacenaphthylene-4-carboxylic acid and 0.83 g (7.17 mM) of N-hydroxysuccinimide were stirred together in 50 ml of acetonitrile, 1.51 g (7.89 mM) of 1-ethyl-3-(3-dimethylaminopropyl)carbodiimide hydrochloride was added and the mixture was stirred at room temperature for 2 hours. To this reaction mixture was added 1.50 ml (10.8 mM) of triethylamine as well as a solution of the above crude 2-[1-(tert-butoxycarbonyl)piperidin-4-ylidene] ethylamine in 20 ml of acetonitrile and the mixture was stirred at room temperature for 2 hours. This reaction mixture was poured in aqueous solution of sodium hydrogen carbonate and extracted with 3 portions of ethyl acetate. The organic layers were pooled and dried over $MgSO_4$ and the solvent was distilled off under reduced pressure. The residue was subjected to silica gel column chromatography (ethyl acetate to ethyl acetate-methanol=9/1) to provide crude N-[2-(1-(tert-butoxycarbonyl)piperidin-4-ylidene]ethyl]-5-thia-1,8b-diazaacenaphthylene-4-carboxamide. To this crude N-[2-(1-(tert-butoxycarbonyl)piperidin-4-ylidene) ethyl]-5-thia-1,8b-diazaacenaphthylene-4-carboxamide was added 4 ml of concentrated hydrochloric acid and the mixture was stirred at room temperature for 0.5 hour. After addition of ethanol, the mixture was stirred and the resulting precipitate was recovered and rinsed serially with ethanol and diethyl ether to provide the title compound.

Orange-colored solid. Yield 1.117 g (39%)

$^1$H-NMR ($CD_3OD$, 200 MHz) δ: 2.460 (2H, t, 5.8 Hz), 2.614 (2H, t, 5.8 Hz), 3.169–3.248 (4H, m), 3.856–3.909 (2H, m), 5.427 (1H, t, 7.2 Hz), 6.607 (1H, d, 7.2 Hz), 6.927 (1H, s), 6.987 (1H, d, 9.2 Hz), 7.384 (1H, dd, 7.8 Hz, 9.2 Hz), 7.503 (1H, s).

IR (Nujol): 3498, 3446, 3251, 3190, 3064, 2792, 2476, 1626, 1564, 1500, 1281, 1213, 775 $cm^{-1}$.

2) Synthesis of N-[2-[1-(3-phenylpropan-1-yl)piperidin-4-ylidene]ethyl]-5-thia-1,8b-diazaacenaphthylene-4-carboxamide A solution of 0.508 g (1.272 mM) of N-[2-(piperidin-4-ylidene)ethyl]-5-thia-1,8b-diazaacenaphthylene-4-carboxamide dihydrochloride, 0.38 g (1.91 mM) of 1-bromo-3-phenylpropane, and 0.62 ml (4.45 mM) of triethylamine in 20 ml of ethanol was refluxed overnight. The solvent was then distilled off under reduced pressure and the residue was purified by silica gel column chromatography (ethyl acetate to ethyl acetate-methanol=4/1) to provide the objective compound and triethylamine hydrochloride as a mixture. This mixture was diluted with ethyl acetate and washed serially with aqueous solution of sodium hydrogen carbonate, water, and saturated aqueous solution of sodium chloride. The organic layer was dried over $MgSO_4$ and the solvent was distilled off under reduced pressure to provide the title compound.

Red liquid. Yield 0.395 g (70%)

$^1$H-NMR ($CDCl_3$, 200 MHz) δ: 1.749–1.901 (2H, m), 2.196–2.467 (10H, m), 2.630 (2H, t, 7.7 Hz), 3.870 (2H, t, 6.2 Hz), 5.178 (1H, t, 7.2 Hz), 5.737 (1H, dd, 2.2 Hz, 5.8 Hz), 6.171 (1H, t, 5.2 Hz), 6.534–6.698 (3H, m), 6.968 (1H, s), 7.133–7.308 (5H, m).

IR (neat): 3300, 2941, 1616, 1543, 1510, 1481, 1279, 1155, 773, 731, 700 $cm^{-1}$.

3) Synthesis of N-[2-[1-(3-phenylpropan-1-yl)piperidin-4-ylidene]ethyl]-5-thia-1,8b-diazaacenaphthylene-4-carboxamide dihydrochloride The procedure of Example 1–6) was generally followed to provide the title compound as orange-colored solid.

$^1$H-NMR ($CD_3OD$, 200 MHz) δ: 2.026–2.183 (2H, m), 2.310–2.590 (3H, m), 2.724 (2H, t, 7.5 Hz), 2.936–3.019 (3H, m), 3.097–3.182 (2H, m), 3.539–3.645 (2H, m), 3.805 (1H, dd, 7.0 Hz, 15.4 Hz), 3.922 (1H, dd, 7.8 Hz, 15.2 Hz), 5.431 (1H, t, 7.3 Hz), 6.605 (1H, d, 7.2 Hz), 6.949 (1H, s), 6.991 (1H, d, 8.8 Hz), 7.160–7.305 (5H, m), 7.386 (1H, dd, 7.5 Hz, 8.9 Hz), 7.508 (1H, s).

IR (Nujol): 3331, 3250, 3064, 2705–2460, 1632, 1562, 1529, 1498, 1275, 1215, 775, 727 $cm^{-1}$.

Elemental analysis for $C_{26}H_{30}Cl_2N_4OS \cdot 2.0H_2O$ Calcd.: C, 56.41; H, 6.19; N, 10.12 Found: C, 56.39; H, 6.12; N, 10.10

EXAMPLE 7

Synthesis of N-[1-(3-phenylpropan-1-yl)piperidin-2-ylmethyl]-5-thia-1,8b-diazaacenaphthylene-4-carboxamide dihydrochloride 1) Synthesis of N-(piperidin-2-ylmethyl)-5-thia-1,8b-diazaacenaphthylene-4-carboxamide dihydrochloride While 3.605 g (16.519 mM) of 5-thia-1,8b-diazaacenaphthylene-4-carboxylic acid and 2.09 g (18.2 mM) of N-hydroxysuccinimide were stirred together in 100 ml of acetonitrile, 3.48 g (18.2 mM) of 1-ethyl-3-(3-dimethylaminopropyl)carbodiimide hydrochloride was added and the mixture was stirred at room temperature for 2 hours. To this reaction mixture was added 3.45 ml (24.8 mM) of triethylamine as well as 2.83 g (24.8 mM) of 2-aminomethylpiperidine and the mixture was stirred at room temperature for one hour. Then, 5.41 g (24.8 mM) of di-tert-butyl dicarbonate was added and the mixture was stirred at room temperature for another hour. This reaction mixture was poured in aqueous solution of sodium hydrogen carbonate and extracted with 3 portions of ethyl acetate. The organic layers were pooled and dried over $MgSO_4$ and the solvent was distilled off under reduced pressure. The residue was subjected to silica gel column chromatography (ethyl acetate to ethyl acetate-methanol=9/1) to provide crude N-[1-(tert-butoxycarbonyl)piperidin-2-ylmethyl]-5-thia-1,8b-diazaacenaphthylene-4-carboxamide. To this crude N-[1-(tert-butoxycarbonyl)piperidin-2-ylmethyl]-5-thia-1,8b-diazaacenaphthylene-4-carboxamide was added 5 ml of concentrated hydrochloric acid and the mixture was stirred at room temperature for 0.5 hour. After addition of ethanol, the mixture was stirred and the resulting precipitate was recovered and rinsed serially with ethanol and diethyl ether to provide the title compound.

Orange-colored solid. Yield 3.476 g (54%)

$^1$H-NMR ($CD_3OD$, 200 MHz) δ: 1.476–1.909 (6H, m), 2.898–3.022 (1H, m), 3.290–3.504 (4H, m), 6.615 (1H, d, 7.6 Hz), 6.993 (1H, d, 8.8 Hz), 7.068 (1H, s), 7.390 (1H, dd, 7.6 Hz, 8.8 Hz), 7.547 (1H, s).

IR (Nujol): 3300, 3199, 3032, 2713, 1633, 1564, 1539, 1500, 1294, 795 $cm^{-1}$.

2) Synthesis of N-[1-(3-phenylpropan-1-yl)piperidin-2-ylmethyl]-5-thia-1,8b-diazaacenaphthylene-4-carboxamide The procedure of Example 6-2) was generally followed to provide the title compound.

Red liquid. Yield 0.164 g (15%)

$^1$H-NMR (CDCl$_3$, 200 MHz) δ: 1.256–1.909 (7H, m), 2.218–2.819 (7H, m), 2.980–3.042 (1H, m), 3.367 (2H, t, 4.3 Hz), 5.705 (1H, dd, 1.4 Hz, 6.2 Hz), 6.532–6.689 (4H, m), 7.001 (1H, s), 7.149–7.318 (5H, m).

IR (neat): 3319, 2935, 1618, 1545, 1483, 1281, 1153, 773, 733, 700 cm$^{-1}$.

3) Synthesis of N-[1-(3-phenylpropan-1-yl)piperidin-2-ylmethyl]-5-thia-1,8b-diazaacenaphthylene-4-carboxamide dihydrochloride The procedure of Example 1–7) was generally followed to provide the title compound as orange-colored foam.

$^1$H-NMR (CD$_3$OD, 200 MHz) δ: 1.558–2.261 (8H, m), 2.627–2.862 (2H, m), 3.012–3.747 (7H, m), 6.621 (1H, dd, 0.8 Hz, 7.6 Hz), 7.010 (1H, dd, 0.8 Hz, 9.2 Hz), 7.147–7.301 (6H, m), 7.399 (1H, dd, 7.6 Hz, 9.2 Hz), 7.550 (1H, s).

IR (Nujol): 3392, 3061–2545, 1633, 1566, 1537, 1500, 1450, 1294, 1215, 785, 752, 702 cm$^{-1}$.

Elemental analysis for C$_{25}$H$_{30}$Cl$_2$N$_4$OS.2.OH$_2$Calcd.: C, 55.45; H, 6.33; N, 10.35 Found: C, 55.61; H, 6.35; N, 10.14

EXAMPLE 8

Synthesis of N-[2-[1-(3-phenylpropan-1-yl)-1,2,3,6-tetrahydropyridin-4-yl]ethyl]-5-thia-1,8b-diazaacenaphthylene-4-carboxamide dihydrochloride The procedure of Example 6-1) was generally followed to provide N-[2-(1,2,3,6-tetrahydropyridin-4-yl)ethyl]-5-thia-1,8b-diazaacenaphthylene-4-carboxamide dihydrochloride as orange-colored solid.

$^1$H-NMR (CD$_3$OD, 200 MHz) δ: 2.271–2.392 (4H, m), 3.193–3.429 (4H, m), 3.639 (2H, br s), 5.529 (1H, br s), 6.606 (1H, d, 7.8 Hz), 6.988 (1H, d, 8.6 Hz), 6.991 (1H, s), 7.383 (1H, dd, 8.0 Hz, 8.8 Hz), 7.513 (1H, s).

IR (Nujol): 3516, 3454, 3244, 3061, 2791–2339, 1633, 1566, 1533, 1498, 1304, 1263, 1213, 829, 773, 735 cm$^{-1}$.

Using the above compound, the procedure of Example 6-2) was generally followed to provide N-[2-[1-(3-phenylpropan-1-yl)-1,2,3,6-tetrahydropyridin-4-yl]ethyl]-5-thia-1,8b-diazaacenaphthylene-4-carboxamide as red foam.

$^1$H-NMR (CDCl$_3$, 200 MHz) δ: 1.797–1.951 (2H, m), 2.143–2.227 (4H, m), 2.467 (2H, t, 7.7 Hz), 2.573 (2H, d, 5.4 Hz), 2.650 (2H, t, 7.5 Hz), 2.986 (2H, br s), 3.385 (2H, q, 6.4 Hz), 5.455 (1H, s), 5.720 (1H, dd, 1.8 Hz, 6.2 Hz), 6.259 (1H, t, 5.5 Hz), 6.524–6.609 (2H, m), 6.651 (1H, s), 6.975 (1H, s), 7.133–7.323 (5H, m).

IR (neat): 3277, 2939, 1618, 1549, 1481, 1281, 1155, 773, 731, 700 cm$^{-1}$.

Using the above compound, the procedure of Example 1–6) was generally followed to provide the title compound as orange-colored foam.

$^1$H-NMR (CD$_3$OD, 200 MHz) δ: 2.061–2.220 (3H, m), 2.269–2.379,(2H, m), 2.606 (1H, br s), 2.738 (2H, t, 7.7 Hz), 3.176–3.350 (4H, m), 3.407–3.661 (3H, m), 3.880 (1H, br d, 15.4 Hz), 5.493 (1H, br s), 6.606 (1H, d, 7.6 Hz), 7.027 (1H, d, 9.2 Hz), 7.145–7.294 (6H, m), 7.381 (1H, dd, 7.7 Hz, 8.7 Hz), 7.537 (1H, s).

IR (neat): 3390, 3060–2602, 1633, 1566, 1535, 1500, 1446, 1296, 1215, 785, 754, 702 cm$^{-1}$.

Elemental analysis for C$_{26}$H$_{30}$Cl$_2$N$_4$OS.2.5H$_2$O Calcd.: C, 55.51; H, 6.27; N, 9.96 Found: C, 55.37; H, 6.42; N, 9.94

EXAMPLE 9

Synthesis of N-[1-(3-phenylpropan-1-yl)piperidin-4-ylmethyl]-3-(5-thia-1,8b-diazaacenaphthylen-4-yl) acrylamide dihydrochloride 1) Synthesis of 5-thia-1,8b-diazaacenaphthylene-4-methanol To 10.757 g (43.676 mM) of ethyl 5-thia-1,8b-diazaacenaphthylene-4-carboxylate in 200 ml of dichloromethane was added a 20 ml (approx.) portion of 87.4 ml (131 mM) of 1.5M diisobutylaluminum hydride-toluene at −78° C. and the temperature was increased to about 0° C. After this mixture was cooled to −78° C. again, about 30 ml of 1.5M diisobutylaluminum hydride-toluene was added and the temperature was increased to about 0° C. This reaction mixture was further cooled to −78° C. and the remainder of 1.5M diisobutylaluminum hydride-toluene was added. The mixture was stirred at the prevailing temperature for 0.5 hour. To this reaction mixture was added methanol at −78° C. to decompose the excess diisobutylaluminum hydride. Then, water was added with caution under ice-cooling until a precipitate had formed. The precipitate was filtered off with the aid of celite and washed with aqueous dimethyl sulfoxide. From the pooled filtrate, the solvent was distilled off under reduced pressure and the solid residue was rinsed with diethyl ether to provide the title compound.

Yellow solid. Yield 7.777 g (87%)

$^1$H-NMR (DMSO-d$_6$, 200 MHz) δ: 3.804 (2H, s), 5.330 (1H, br s), 5.945 (1H, dd, 2.2 Hz, 5.6 Hz), 6.123 (1H, s), 6.596–6.706 (2H, m), 6.883 (1H, s).

IR (Nujol): 3429, 3084, 1481, 1090, 1028, 851, 767, 727 cm$^{-1}$.

2) Synthesis of 3-(5-thia-1,8b-diazaacenaphthylen-4-yl) acrylic acid

To a solution of 7.777 g (38.076 mM) of 5-thia-1,8b-diazaacenaphthylene-4-methanol in ethyl acetate (50 ml)-N,N-dimethylformamide (50 ml) was added 23 g of active manganese dioxide and the mixture was stirred at room temperature for 4 hours. The reaction mixture was filtered and the precipitate was washed with N,N-dimethylformamide. The pooled filtrate was distilled under reduced pressure to remove the solvent. The crude 5-thia-1,8b-diazaacenaphthylene-4-carbaldehyde thus obtained was not purified but used as it was in the next reaction. To a solution of 9.39 g (41.9 mM) of ethyl diethylphosphonoacetate in 50 ml of toluene was added 1.68 g (41.9 mM) of a 60% suspension of sodium hydride in liquid paraffin at room temperature and the mixture was stirred for 0.5 hour. This mixture was added to a solution of the above crude 5-thia-1,8b-diazaacenaphthylene-4-carbaldehyde in N,N-dimethylformamide (50 ml)-toluene (200 ml) under ice cooling and the mixture was stirred at room temperature for one hour. This reaction mixture was poured in water and extracted with 3 portions of ethyl acetate. The organic layers were pooled and dried over MgSO$_4$ and the solvent was distilled off under reduced pressure. The resulting crude ethyl 3-(5-thia-1,8b-diazaacenaphthylen-4-yl)acrylate was not purified but used as it was in the next reaction. To a solution of the above crude ethyl 3-(5-thia-1,8b-diazaacenaphthylen-4-yl)acrylate in 300 ml of ethanol was added 60 ml (120 mM) of 2N-aqueous solution of sodium hydroxide and the mixture was stirred at room temperature for 3 hours. To this reaction mixture was added concentrated hydrochloric acid (ca 10 ml) with stirring to bring the pH into the range of 4–5 and the resulting precipitate was recovered by filtration and rinsed serially with ethanol and diethyl ether to provide the title compound.

Red solid. Yield 7.777 g (84%)

$^1$H-NMR (DMSO-d$_6$, 200 MHz) δ: 5.529 (1H, d, 15.8 Hz), 6.262 (1H, dd, 1.4 Hz, 6.6 Hz), 6.795–6.939 (3H, m), 7.226 (1H, d, 16.0 Hz), 7.266 (1H, s).

IR (Nujol): 2521, 1711, 1587, 1309, 1255, 1136, 1107, 947, 970 cm$^{-1}$.

3) Synthesis of N-(piperidin-4-ylmethyl)-3-(5-thia-1,8b-diazaacenaphthylen-4-yl)acrylamide dihydrochloride While 0.708 g (2.898 mM) of 3-(5-thia-1,8b-diazaacenaphthylen-4-yl)acrylic acid, 0.68 g (3.19 mM) of 1-(tert-butoxycarbonyl)piperidin-4-ylmethylamine, and 0.48 ml (3.48 mM) of triethylamine were stirred together in 10 ml of N,N-dimethylformamide, 0.53 ml (3.48 mM) of diethyl cyanophosphate was added dropwise at room temperature and the mixture was stirred at the prevailing temperature overnight. This reaction mixture was poured in aqueous solution of sodium hydrogen carbonate and extracted with 3 portions of ethyl acetate. The organic layers were pooled and dried over $MgSO_4$ and the solvent was distilled off under reduced pressure. The residue was subjected to silica gel column chromatography (ethyl acetate to ethyl acetate-methanol=9/1) to provide crude N-[1-(tert-butoxycarbonyl)piperidin-4-ylmethyl]-3-(5-thia-1,8b-diazaacenaphthylen-4-yl)acrylamide.

To this crude N-[1-(tert-butoxycarbonyl)piperidin-4-ylmethyl]-3-(5-thia-1,8b-diazaacenaphthylen-4-yl)acrylamide was added 1 ml of concentrated hydrochloric acid and the mixture was stirred at room temperature for 0.5 hour. After addition of ethanol, the mixture was stirred and the resulting precipitate was collected and washed serially with ethanol and diethyl ether to provide the title compound.

Orange-colored solid. Yield 1.099 g (92%)

$^1$H-NMR ($CD_3OD$, 200 MHz) δ: 1.335–1.635 (2H, m), 1.794–2.072 (3H, m), 2.907–3.035 (2H, m), 3.227–3.438 (4H, m), 6.173 (1H, d, 15.4 Hz), 6.743 (1H, s), 6.751 (1H, d, 7.4 Hz), 7.141 (1H, d, 8.8 Hz), 7.195 (1H, d, 15.4 Hz), 7.504 (1H, dd, 7.8 Hz, 9.2 Hz), 7.546 (1H, s).

IR (Nujol): 3373, 2735, 1666, 1637, 1606, 1552, 1381, 1344, 1302, 1261, 1215, 962, 777 $cm^{-1}$.

4) Synthesis of N-[1-(3-phenylpropan-1-yl)piperidin-4-ylmethyl]-3-(5-thia-1,8b-diazaacenaphthylen-4-yl)acrylamide A solution of 0.502 g (1.214 mM) of N-(piperidin-4-ylmethyl)-3-(5-thia-1,8b-diazaacenaphthylen-4-yl)acrylamide dihydrochloride, 0.36 g (1.82 mM) of 1-bromo-3-phenylpropane, and 0.59 ml (4.25 mM) of triethylamine in 20 ml of ethanol was refluxed for one day. The solvent was then distilled off under reduced pressure and the residue was purified by silica gel column chromatography (ethyl acetate to ethyl acetate-methanol=4/1), whereby a mixture of the objective compound and triethylamine hydrochloride was obtained. This mixture was diluted with ethyl acetate and washed serially with aqueous solution of sodium hydrogen carbonate, water, and saturated aqueous solution of sodium chloride. The organic layer was dried over $MgSO_4$ and the solvent was distilled off under reduced pressure to provide the title compound.

Red foam. Yield 0.305 g (55%)

$^1$H-NMR ($CDCl_3$, 200 MHz) δ: 1.229–1.401 (2H, m), 1.482–1.958 (7H, m), 2.354 (2H, t, 7.7 Hz), 2.612 (2H, t, 7.7 Hz), 2.896–2.954 (2H, m), 3.231 (2H, t, 6.0 Hz), 5.659 (1H, d, 15.2 Hz), 5.859 (1H, dd, 1.2 Hz, 6.6 Hz), 6.222 (1H, br t, 5.8 Hz), 6.255 (1H, s), 6.598–6.746 (2H, m), 7.048–7.305 (7H, m).

IR (neat): 3273, 2926, 1651, 1614, 1585, 1554, 1344, 1265, 1213, 1142, 964, 773, 731, 700 $cm^{-1}$.

5) Synthesis of N-[1-(3-phenylpropan-1-yl)piperidin-4-ylmethylj-3-(5-thia-1,8b-diazaacenaphthylen-4-yl)acrylamide dihydrochloride In 2 ml of methanol was dissolved 0.305 g of N-[1-(3-phenylpropan-1-yl)piperidin-4-ylmethyl]-3-(5-thia-1,8b-diazaacenaphthylen-4-yl)acrylamide, followed by addition of a stoichiometric excess of methanolic hydrochloric acid. The mixture was stirred and concentrated and the residue was crystallized from ethanol-diethyl ether to provide the title compound.

Orange-colored solid. Yield 0.342 g $^1$H-NMR ($CD_3OD$, 200 MHz) δ: 1.405–2.610 (2H, m), 1.790–2.140 (5H, m), 2.711 (2H, t, 7.5 Hz), 2.868–3.244 (6H, m), 3.553–3.616 (2H, m), 6.149 (1H, d, 15.4 Hz), 6.735 (1H, s), 6.792 (1H, d, 7.2 Hz), 7.109–7.334 (7H, m), 7.496 (1H, dd, 7.8 Hz, 9.2 Hz), 7.537 (1H, s).

IR (Nujol): 3255, 2669, 1637, 1601, 1545, 1301, 1263, 1215, 1159, 970, 777, 752, 727, 700 $cm^{-1}$.

Elemental analysis for $C_{27}H_{32}C_{12}N_4OS·2.0H_2O$ Calcd.: C, 57.14; H, 6.39; N, 9.87 Found: C, 57.44; H, 6.27; N, 9.80

EXAMPLE 10

Synthesis of N-[1-(3-phenylpropan-1-yl)piperidin-4-yl]-3-(5-thia-1,8b-diazaacenaphthylen-4-yl)acrylamide dihydrochloride The procedure of Example 9-3) was generally followed to provide N-(piperidin-4-yl)-3-(5-thia-1,8b-diazaacenaphthylen-4-yl)acrylamide dihydrochloride as orange-colored solid.

$^1$H-NMR ($CD_3OD$, 200 MHz) δ: 1.641–1.844 (2H, m), 2.123–2.174 (2H, m), 3.072–3.466 (4H, m), 3.978–4.132 (1H, m), 6.138 (1H, d, 15.4 Hz), 6.741 (1H, s), 6.789 (1H, d, 7.4 Hz), 7.128 (1H, d, 8.4 Hz), 7.211 (1H, d, 15.8 Hz), 7.494 (1H, dd, 7.8 Hz, 9.2 Hz), 7.536 (1H, s).

IR (Nujol): 3485, 3413, 3230, 2725, 1664, 1639, 1605, 1549, 1302, 1263, 1213, 993, 781 $cm^{-1}$.

Using the above compound, the procedure of Example 6-2) was generally followed to provide N-[1-(3-phenylpropan-1-yl)piperidin-4-yl]-3-(5-thia-1,8b-diazaacenaphthylen-4-yl)acrylamide as red foam.

$^1$H-NMR ($CDCl_3$, 200 MHz) δ: 1.423–1.597 (2H, m), 1.731–2.147 (6H, m), 2.366 (2H, t, 7.7 Hz), 2.616 (2H, t, 7.7 Hz), 2.834–2.892 (2H, m), 3.799–3.944 (1H, m), 5.665 (1H, d, 15.0 Hz), 5.845 (1H, d, 6.6 Hz), 6.171 (1H, d, 8.0 Hz), 6.253 (1H, s), 6.590–6.737 (2H, m), 7.043 (1H, s), 7.118–7.307 (6H, m).

IR (neat): 3265, 2943, 1649, 1614, 1585, 1551, 1348, 1267, 1213, 1142, 1113, 960, 910, 773, 731, 700 $cm^{-1}$.

Using the above compound, the procedure of Example 1–6) was generally followed to provide the title compound as orange-colored solid.

$^1$H-NMR ($CD_3OD$, 200 MHz) δ: 1.711–1.908 (2H, m), 2.048–2.218 (4H, m), 2.720 (2H, t, 7.5 Hz), 3.011–3.222 (4H, m), 3.590–3.654 (2H, m), 3.929–4.205 (1H, m), 6.113 (0.8H, d, 15.4 Hz), 6.321 (0.2H, d, 16.0 Hz), 6.737 (1H, s), 6.790 (1H, d, 7.2 Hz), 7.109–7.339 (7H, m), 7.495 (1H, dd, 7.6 Hz, 9.2 Hz), 7.539 (1H, s).

IR (Nujol): 3369, 3184, 1486, 1655, 1637, 1597, 1552, 1215, 1159, 980, 837, 783, 758, 727 $cm^{-1}$.

Elemental analysis for $C_{26}H_{30}Cl_2N_4OS·1.4H_2O$ Calcd.: C, 57.54; H, 6.09; N, 10.32 Found C, 57.74; H, 6.07; N, 10.17

EXAMPLE 11

Synthesis of N-[2-(3-phenylpropan-1-yl)-2,3-dihydro-1H-isoindol-5-ylmethyl]-5-thia-1,8b-diazaacenaphthylene-4-carboxamide dihydrochloride 1) Synthesis of N-[2-(3-phenylpropan-1-yl)-2,3-dihydro-1H-isoindol-5-ylmethyl]-5-thia-1,8b-diazaacenaphthylene-4-carboxamide To a solution of 0.401 g (1.011 mM) of N-[2-(3-phenylpropan-1-yl)-2,3-dihydro-1H-isoindol-5-ylmethyl]- phthalimide in 20 ml of ethanol was added 0.05 ml (1.11 mM) of hydrazine monohydrate and the mixture was refluxed for 2 hours. After cooling to room temperature, the precipitate that had formed was filtered off and washed with ethanol. From the pooled filtrate, the solvent was distilled off. The resulting crude N-[2-(3-phenylpropan-1-yl)-2,3-dihydro-1H-isoindol-5-yl]methylamine was not purified but used as it was in the next reaction. To a solution of 0.22 g (1.21 mM) of 5-thia-1,8b-diazaacenaphthylene-4-carboxylic acid, the above crude N-t2-(3-phenylpropan-1-yl)-2,3-dihydro-1H-isoindol-5-yl]methylamine, and 0.17 ml (1.21 mM) of triethylamine in 20 ml of N,N-dimethylformamide was added 0.18 ml (1.21 mM) of diethyl cyanophosphate dropwise at room temperature with constant stirring and the mixture was stirred at the prevailing temperature for 3 days. This reaction mixture was poured in aqueous solution of sodium hydrogen carbonate and extracted with 3 portions of ethyl acetate. The organic layers were pooled and dried over $MgSO_4$ and the solvent was distilled off under reduced pressure. The residue was purified by silica gel column chromatography (ethyl acetate to ethyl acetate-methanol=9/1) to provide the title compound.

Red liquid. Yield 0.109 g (23%)

$^1$H-NMR (CDCl$_3$, 200 MHz) δ: 1.870–1.985 (2H, m), 2.714 (2H, t, 8.0 Hz), 2.751 (2H, t, 7.3 Hz), 3.913 (4H, s), 4.399 (2H, d, 5.8 Hz), 5.715 (1H, dd, 2.9 Hz, 4.9 Hz), 6.571 (1H, dd, 9.2 Hz, 11.2 Hz), 6.591 (1H, s), 6.664 (1H, s), 6.672 (1H, br t, 5.3 Hz), 6.907 (1H, s), 7.058–7.332 (8H, m).

IR (neat): 3275, 2935, 1618, 1545, 1481, 1281, 1153, 1032, 771, 731, 700 cm$^{-1}$.

2) Synthesis of N-[2-(3-phenylpropan-1-yl)-2,3-dihydro-1H-isoindol-5-ylmethyl]-5-thia-1,8b-diazaacenaphthylene-4-carboxamide dihydrochloride The procedure of Example 1–6) was generally followed to provide the title compound as brown solid.

$^1$H-NMR (CD$_3$OD, 200 MHz) δ: 1.070–2.227 (2H, m), 2.764 (2H, t, 7.7 Hz), 3.401–3.482 (2H, m), 4.427 (2H, s), 4.482–4.553 (2H, m), 4.836–4.878 (2H, m), 6.587 (1H, d, 7.4 Hz), 6.991 (1H, d, 8.8 Hz), 6.995 (1H, s), 7.149–7.415 (9H, m), 7.512 (1H, s).

IR (neat): 3251, 3131, 2924, 2515, 1633, 125, 1498, 1443, 1296, 1219 cm$^{-1}$.

Elemental analysis for $C_{28}H_{28}Cl_2N_4OS.4.5H_2O$ Calcd.: C, 54.19; H, 6.01; N, 9.03 Found: C, 53.99; H, 5.63; N, 9.38

EXAMPLE 12

Synthesis of N-[2-[1-(3-phenylpropan-1-yl)-2,5-dihydro-1H-pyrrol-3-yl]ethyl]-5-thia-1,8b-diazaacenaphthylene-4-carboxamide dihydrochloride The procedure of Example 6-1) was generally followed to provide N-[2-(2,5-dihydro-lH-pyrrol-3-yl)ethyl]-5-thia-1,8b-diazaacenaphthylene-4-carboxamide dihydrochloride as orange-colored solid.

$^1$H-NMR (CD$_3$OD, 200 MHz) δ: 2.445 (2H, t, 6.4 Hz), 3.440 (2H, t, 6.8 Hz), 4.048 (4H, s), 5.645 (1H, s), 6.614 (1H, d, 7.8 Hz), 6.996 (1H, d, 8.4 Hz), 7.006 (1H, s), 7.389 (1H, dd, 7.6 Hz, 9.2 Hz), 7.528,(1H, s).

IR (Nujol): 3358, 3226, 2665, 1657, 1633, 1564, 1535, 1498, 1282, 1209, 777 cm$^{-1}$.

Using the above compound, the procedure of Example 6-2) was generally followed to provide N-[2-[1-(3-phenylpropan-1-yl)-2,5-dihydro-1-pyrrol-3-yl]ethyl]-5-thia-1,8b-diazaacenaphthylene-4-carboxamide as red liquid.

$^1$H-NMR (CDCl$_3$, 200 MHz) δ: 1.742–1.894 (2H, m), 2.291 (2H, t, 6.2 Hz), 2.645 (2H, t, 7.5 Hz), 2.667 (2H, t, 7.7 Hz), 3.367–3.460 (6H, m), 5.489 (1H, s), 5.721 (1H, dd, 2.2 Hz, 5.4 Hz), 6.524 (1H, t, 5.1 Hz), 6.570–6.627 (3H, m), 6.960 (1H, s), 7.134–7.327 (5H, m).

IR (neat): 3242, 2937, 1618, 1549, 1510, 1481, 1281, 1153, 910, 773, 731, 700 cm$^{-1}$.

Using the above compound, the procedure of Example 1–6) was generally followed to provide the title compound as orange-colored foam.

$^1$H-NMR (CD$_3$OD, 200 MHz) δ: 1.991–2.149 (2H, m), 2.421 (2H, t, 6.2 Hz), 2.747 (2H, t, 7.7 Hz), 3.290–3.513 (4H, m), 3.914–4.052 (2H, m), 4.240–4.334 (2H, m), 5.634 (1H, s), 6.598 (1H, d, 7.4 Hz), 6.993 (1H, d, 9.0 Hz), 7.043 (1H, s), 7.144–7.299 (5H, m), 7.385 (1H, dd, 7.4 Hz, 9.2 Hz), 7.517 (1H, s).

IR (neat): 3062, 2945, 2675, 2486, 1633, 1566, 1537, 1500, 1448, 1296, 1215, 785, 756, 702 cm$^{-1}$.

Elemental analysis for $C_{25}H_{28}Cl_2N_4OS.2.0H_2O$ Calcd.: C, 55.66; H, 5.98; N, 10.38 Found: C, 55.88; H, 6.33; N, 10.32

EXAMPLE 13

Synthesis of N-[4-[4-(2-chlorobenzylidene)piperidino]-butyl]-5-thia-1,8b-diazaacenaphthylene-4-carboxamide dihydrochloride The procedure of Example 11-1) was generally followed to provide N-[4-[4-(2-chlorobenzylidene)piperidino]butyl]-5-thia-1,8b-diazaacenaphthylene-4-carboxamide as red liquid.

$^1$H-NMR (CDCl$_3$, 200 MHz) δ: 1.565–1.628 (4H, m), 2.377–2.500 (8H, m), 2.598 (2H, t, 5.2 Hz), 3.282–3.339 (2H, m), 5.759 (1H, dd, 2.0 Hz, 6.0 Hz), 6.307 (1H, s), 6.551–6.689 (4H, m), 7.007 (1H, s), 7.116–7.247 (3H, m), 7.352–7.408 (1H, m).

IR (neat): 3304, 2941, 1618, 1549, 1510, 1479, 1281, 1155, 910, 773, 731 cm$^{-1}$.

Using the above compound, the procedure of Example 1–6) was generally followed to provide the title compound as orange-colored solid.

$^1$H-NMR (CD$_3$OD, 200 MHz) δ: 1.577–1.705 (2H, m), 1.764–1.916 (2H, m), 2.469–3.103 (6H, m), 3.193 (2H, br t, 8.1 Hz), 3.317 (2H, t, 6.6 Hz), 3.552–3.762 (2H, m), 6.556 (1H, s), 6.609 (1H, d, 7.4 Hz), 6.997 (1H, d, 8.8 Hz), 7.037 (1H, s), 7.239–7.448 (5H, m), 7.526 (1H, s).

IR (Nujol): 3213, 2721, 1632, 1498, 1292, 1215, 750, 725 cm$^{-1}$.

Elemental analysis for $C_{26}H_{29}Cl_3N_4OS.3.5H_2O$ Calcd.: C, 50.78; H, 5.90; N, 9.11 Found: C, 51.04; H, 5.74; N, 9.30

EXAMPLE 14

Synthesis of N-[4-(4-hydroxy-4-phenylpiperidino)butyl]-5-thia-1,8b-diazaacenaphthylene-4-carboxamide dihydrochloride The procedure of Example 11-1) was generally followed to provide N-[4-(4-hydroxy-4-phenylpiperidino)butyl]-5-thia-1,8b-diazaacenaphthylene-4-carboxamide as red foam.

$^1$H-NMR (CDCl$_3$, 200 MHz) δ: 1.584–1.826 (7H, m), 2.186 (2H, dt, 4.1 Hz, 13.1 Hz), 2.392–2.546 (4H, m), 2.812–2.867 (2H, m), 3.260–3.337 (2H, m), 5.716 (1H, dd, 1.8 Hz, 5.8 Hz), 6.539–6.656 (4H, m), 6.942 (1H, s), 7.213–7.402 (3H, m), 7.501–7.548 (2H, m).

IR (neat): 3305, 2943, 1618, 1547, 1510, 1481, 1282, 1153, 910, 770, 731, 700 cm$^{-1}$.

Using the above compound, the procedure of Example 1-6) was generally followed to provide the title compound as orange-colored solid.

$^1$H-NMR (CD$_3$OD, 200 MHz) δ: 1.593–2.012 (6H, m), 2.425 (2H, dt, 4.8 Hz, 13.7 Hz), 3.218 (2H, t, 8.2 Hz), 3.292–3.576 (6H, m), 6.616 (1H, d, 7.6 Hz), 6.999 (1H, d, 10.4 Hz), 7.025 (1H, s), 7.231–7.436 (4H, m), 7.507–7.584 (3H, m).

IR (Nujol): 3211, 2673, 1630, 1497, 1292, 1213, 976, 766, 725, 700 cm$^{-1}$.

Elemental analysis for C$_{25}$H$_{30}$Cl$_2$N$_4$O$_2$S.1.5H$_2$O Calcd.: C, 54.74; H, 6.06; N, 10.21 Found: C, 54.42; H, 6.44; N, 10.10

EXAMPLE 15

Synthesis of N-[2-hydroxy-3-(4-phenylpiperidino) propan-1-yl]-5-thia-1,8b-diazaacenaphthylene-4-carboxamide dihydrochloride The procedure of Example 11-1) was generally followed to provide N-[2-hydroxy-3-(4-phenylpiperidino)propan-1-yl]-5-thia-1,8b-diazaacenaphthylene-4-carboxamide as red foam.

$^1$H-NMR (CDCl$_3$, 200 MHz) δ: 1.623–1.890 (4H, m), 2.126 (1H, dt, 2.4 Hz, 11.5 Hz), 2.293–2.620 (5H, m), 2.919–3.131 (2H, m), 3.236 (1H, td, 6.0 Hz, 13.7 Hz), 3.558 (1H, ddd, 3.7 Hz, 5.6 Hz, 13.7 Hz), 3.813–3.932 (1H, m), 5.759 (1H, dd, 1.6 Hz, 6.2 Hz), 6.525 (1H, br t, 5.0 Hz), 6.561–6.684 (3H, m), 7.031 (1H, s), 7.172–7.352 (5H, m).

IR (neat): 3311, 2933, 2808, 1618, 1543, 1506, 1483, 1281, 1155, 910, 773, 731, 700 cm$^{-1}$.

Using the above compound, the procedure of Example 1-6) was generally followed to provide the title compound as orange-colored solid.

$^1$H-NMR (CD$_3$OD, 200 MHz) δ: 2.092 (4H, br s), 2.820–2.970 (1H, m), 3.147–3.425 (6H, m), 3.724–3.786 (2H, m), 4.190–4.300 (1H, m), 6.619 (1H, d, 7. Hz), 7.000 (1H, d, 9.2 Hz), 7.078 (1H, s), 7.221–7.437 (6H, m), 7.550 (1H, s).

IR (Nujol): 3242, 2723, 1633, 1498, 1296, 1215, 1113, 783, 702 cm$^{-1}$.

Elemental analysis for C$_{24}$H$_{28}$Cl$_2$N$_4$O$_2$S.2.0H$_2$O Calcd.: C, 53.04; H, 5.93; N, 10.31 Found: C, 53.09; H, 6.11; N, 10.31

EXAMPLE 16

Synthesis of N-[2-oxo-3-(4-phenylpiperidino) propan-1-yl]-5-thia-1,8b-diazaacenaphthylene-4-carboxamide dihydrochloride 1) Synthesis of N-[2-oxo-3-(4-phenylpiperidino)propan-1-yl]-5-thia-1,8b-diazaacenaphthylene-4-carboxamide To a solution of 0.39 g (3.05 mM) of oxalyl chloride in 20 ml of dichloromethane was added 0.43 ml (6.11 mM) of dimethyl sulfoxide dropwise at −78° C. The mixture was stirred for 5 minutes, at the end of which time a solution of 0.885 g (2.037 mM) of N-[2-hydroxy-3-(4-phenylpiperidino)propan-1-yl]-5-thia-1,8b-diazaacenaphthylene-4-carboxamide in 20 ml of dichloromethane was added and the mixture was stirred at −78° C. for 15 minutes. To this mixture was added 1.70 ml (12.2 mM) of triethylamine and the temperature was increased to room temperature. This reaction mixture was poured in water and extracted with 3 portions of ethyl acetate. The organic layers were pooled and dried over MgSO$_4$ and the solvent was distilled off under reduced pressure. The resulting crude product was purified by silica gel column chromatography (ethyl acetate to ethyl acetate-methanol=9/1 to 4/1) to provide the title compound.

Red foam. Yield 0.652 g (74%)

$^1$H-NMR (CDCl$_3$, 200 MHz) δ: 1.812–1.903 (4H, m), 2.195–2.324 (2H, m), 2.423–2.580 (1H, m), 2.910–2.967 (2H, m), 3.278 (2H, s), 4.354 (2H, d, 4.6 Hz), 5.789 (1H, dd, 1.9 Hz, 6.1 Hz), 6.581–6.722 (4H, m), 7.063 (1H, s), 7.166–7.357 (5H, m).

IR (neat): 3257, 2935, 1731, 1616, 1539, 1504, 1483, 1282, 1153, 910, 773, 731, 700 cm$^{-1}$.

2) Synthesis of N-[2-oxo-3-(4-phenylpiperidino)propan-1-yl]-5-thia-1,8b-diazaacenaphthylene-4-carboxamide dihydrochloride The procedure of Example 1-6) was generally followed to provide the title compound as orange-colored solid.

$^1$H-NMR (CD$_3$OD, 200 MHz) δ: 2.050–2.150 (4H, m), 2.841–3.000 (1H, m), 3.180–3.321 (2H, m), 3.629–3.691 (2H, m), 4.215 (2H, s), 4.444 (2H, s), 6.625 (1H, 7.2 Hz), 7.007 (1H, d, 9.2 Hz), 7.039 (1H, s), 7.195–7.442 (6H, m), 7.557 (1H, s).

IR (Nujol): 3234, 2723, 1743, 1633, 1498, 1300, 1215, 968, 779, 725, 700 cm$^{-1}$.

Elemental analysis for C$_{24}$H$_{26}$Cl$_2$N$_4$O$_2$S.2.5H$_2$O Calcd.: C, 52.36; H, 5.68; N, 10.18 Found: C, 52.65; H, 5.72; N, 10.08

EXAMPLE 17

Synthesis of N-[2-f(4-phenylpiperidino)methyl] benzyl]-5-thia-1,8b-diazaacenaphthylene-4-carboxamide dihydrochloride The procedure of Example 11-1) was generally followed to provide N-[2-[(4-phenylpiperidino)methyl]-benzyl]-5-thia-1,8b-diazaacenaphthylene-4-carboxamide as red solid.

$^1$H-NMR (CDCl$_3$, 200 MHz) δ: 1.787–2.030 (4H, m), 2.207 (2H, dt, 2.3 Hz, 11.8 Hz), 2.619 (1H, tt, 3.9 Hz, 12.0 Hz), 3.109 (2H, br d, 11.6 Hz), 3.549 (2H, s), 4.484 (2H, d, 5.0 Hz), 5.418 (1H, dd, 0.8 Hz, 6.8 Hz), 6.460 (1H, dd, 6.8 Hz, 9.2 Hz), 6.535 (1H, s), 6.598 (1H, dd, 0.9 Hz, 9.2 Hz), 6.768 (1H, s), 7.154–7.453 (9H, m), 8.127 (1H, br s).

IR (Nujol): 3296, 1647, 1597, 1516, 1485, 1244, 1140, 741 cm$^{-1}$.

Using the above compound, the procedure of Example 1-6) was generally followed to provide the title compound as orange-colored solid.

$^1$H-NMR (CD$_3$OD, 200 MHz) δ: 2.053–2.125 (4H, m), 2.883–3.044 (1H, m), 3.224–3.367 (2H, m), 3.585–3.667 (2H, m), 4.566 (4H, s), 6.584 (1H, d, 7.6 Hz), 7.017 (1H, d, 8.8 Hz), 7.182–7.631 (12H, m).

IR (Nujol): 3392, 2698, 1610, 1572, 1311, 1207, 760 cm$^{-1}$.

Elemental analysis for C$_{29}$H$_{30}$Cl$_2$N$_4$OS.1.0H$_2$O Calcd.: C, 60.94; H, 5.64; N, 9.80 Found: C, 60.67; H, 5.78; N, 9.74

EXAMPLE 18

Synthesis of N-(1-phenethylpiperidin-4-yl)-3-(5-thia-1,8b-diazaacenaphthylen-4-yl)acrylamide dihydrochloride 1) Synthesis of N-(1-phenethylpiperidin-4-yl)-3-(5-thia-1,8b-diazaacenaphthylen-4-yl)acrylamide In 10 ml of ethanol was suspended 0.998 g (2.5 mM) of N-(piperidin-4-yl)-3-(5-thia-1,8b-diazaacenaphthylen-4-yl)

acrylamide dihydrochloride as well as 0.703 g (3.8 mM) of phenethyl bromide, followed by addition of 1.74 ml (12.5 mM) of triethylamine, and the mixture was refluxed for 5 hours. To this reaction mixture was further added 0.070 g (0.38 mM) of phenethyl bromide, and the mixture was refluxed overnight. This reaction mixture was diluted with 5% aqueous solution of sodium hydrogen carbonate and extracted with dichloromethane. The organic layer was washed with saturated aqueous solution of sodium chloride and dried over $Na_2SO_4$ and the solvent was distilled off under reduced pressure. The residue was purified by silica gel column chromatography (ethyl acetate-methanol=4/1) and concentrated and the residue was crystallized from ether to provide the title compound.

Red solid. Yield 0.544 g (51%)

$^1$H-NMR (CDCl$_3$) δ: 1.45–1.80 (4H, m), 1.90–2.10 (2H, m), 2.15–2.35 (2H, m), 2.60–2.75 (2H, m), 2.80–2.90 (2H, m), 2.93–3.10 (2H, m), 3.83–4.05 (1H, m), 5.44–5.48 (1H, m), 5.61 (1H, d, 15.0 Hz), 5.88 (1H, d, 6.2 Hz), 6.29 (1H, s), 6.63–6.78 (2H, m), 7.08 (1H, s), 7.15–7.35 (4H, m).

IR (KBr): 3392, 3224, 3035, 2941, 1647, 1614, 1578, 1363, 1263, 1142, 1111, 995, 966, 750, 702 cm$^{-1}$.

2) Synthesis of N-(1-phenethylpiperidin-4-yl)-3-(5-thia-1,8b-diazaacenaphthylen-4-yl)acrylamide dihydrochloride The procedure of Example 1-7) was generally followed to provide the title compound as orange-colored solid.

$^1$H-NMR (CD$_3$OD) δ: 1.75–2.00 (2H, m), 2.05–2.35 (4H, m), 3.00–3.25 (4H, m), 3.30–3.50 (2H, m), 3.65–3.80 (2H, m), 3.90–4.30 (1H, m), 6.12 (0.8H, d, 15.4 Hz), 6.33 (0.2H, d, 15.0 Hz), 6.94 (1H, s), 6.77 (1H, d, 7.4 Hz), 7.10–7.48 (6H, m), 7.53 (1H, s).

IR (KBr): 3425, 3240, 3052, 2947, 2684, 1659, 1605, 1551, 1504, 1394, 1360, 1217, 1151, 966, 764 cm$^{-1}$.

Elemental analysis for $C_{25}H_{28}N_4OSCl_2.0.5H_2O$ Calcd.: C, 58.59; H, 5.70; N, 10.93 Found C, 58.65; H, 5.81; N, 11.11

Example 19

Synthesis of N-(1-phenethylpiperidin-4-ylmethyl)-3-(5-thia-1,8b-diazaacenaphthylen-4-yl)acrylamide Dihydrochloride The procedure of Example 18-1) was generally followed to provide N-(1-phenethylpiperidin-4-ylmethyl)-3-(5-thia-1,8b-diazaacenaphthylen-4-yl)acrylamide as red solid.

$^1$H-NMR (CDCl$_3$) δ: 1.25–1.50 (2H, m), 1.50–1.80 (3H, m), 1.95–2.20 (4H, m), 2.56–2.64 (2H, m), 2.78–2.86 (2H, m), 3.04 (2H, br d, 11.8 Hz), 3.27 (2H, t, 6.1 Hz), 5.61 (1H, d, 15.2 Hz), 5.80–5.95 (2H, m), 6.63–6.77 (2H, m), 7.08 (1H, s), 7.15–7.32 (4H, m).

IR (KBr): 3427, 3292, 2924, 1641, 1614, 1587, 1543, 1344, 1267, 1144, 951, 770, 702 cm$^{-1}$.

Using the above compound, the procedure of Example 1–6) was generally followed to provide the title compound as orange-colored solid.

$^1$H-NMR (CD$_3$OD) δ: 1.40–1.70 (2H, m), 1.80–2.10 (3H, m), 2.90–3.50 (8H, m), 3.69 (2H, br d, 12.8 Hz), 6.17 (1H, d, 15.4 Hz), 6.74 (1H, s), 6.80 (1H, d, 7.4 Hz), 7.11–7.40 (5H, m), 7.45–7.50 (1H, m), 7.55 (1H, s).

IR (KBr): 3427, 3230, 3059, 2943, 2681, 1657, 1639, 1603, 1552, 1500, 1456, 1392, 1358, 1304, 1267, 1217, 1157, 968, 839, 783, 702 cm$^{-1}$.

Elemental analysis for $C_{26}H_{30}N_4OSCl_2.0.5H_2O$ Calcd.: C, 59.31; H, 5.93; N, 10.64 Found: C, 59.29; H, 5.88; N, 10.59

Example 20

Synthesis of 4-(4-phenylpiperidinomethyl)-1-(5-thia-1,8b-diazaacenaphthylen-4-ylcarbonyl)piperidine Dihydrochloride The procedure of Example 4-1) was generally followed to provide 4-(4-phenylpiperidinomethyl)-1-(5-thia-1,8b-diazaacenaphthylen-4-ylcarbonyl)piperidine as red foam.

$^1$H-NMR (CDCl$_3$, 200 MHz) δ: 1.061–1.240 (2H, m), 1.672–2.103 (9H, m), 2.222 (2H, d, 6.6 Hz), 2.409–2.566 (1H, m), 2.826–2.995 (4H, m), 4.338 (2H, br d, 13.6 Hz), 5.714 (1H, dd, 1.4 Hz, 6.2 Hz), 6.061 (1H, s), 6.530–6.669 (2H, m), 6.926 (1H, s), 7.158–7.343 (5H, m).

IR (neat): 2933, 1616, 1483, 1435, 1281, 1265, 1149, 910, 771, 729, 700 cm$^{-1}$.

Using the above compound, the procedure of Example 1–6) was generally followed to provide the title compound as orange-colored foam.

$^1$H-NMR (CD$_3$OD, 200 MHz) δ: 1.280–1.449 (2H, m), 2.002–2.321 (7H, m), 2.870–3.238 (7H, m), 3.752 (2H, br d, 12.0 Hz), 4.383 (2H, br d, 13.2 Hz), 6.528 (1H, s), 6.658 (1H, d, 7.2 Hz), 7.069 (1H, d, 9.2 Hz), 7.173–7.473 (7H, m).

IR (Nujol): 2669, 1624, 1498, 1213, 970 cm$^{-1}$.

Elemental analysis for $C_{27}H_{32}C_{12}N_4OS.2.0H_2O$ Calcd.: C, 57.14; H, 6.39; N, 9.87 Found: C, 57.02; H, 6.45; N, 9.98

Example 21

Synthesis of N-[[4-(4-phenylpiperidino)cyclohexyl]methyl]- 5-thia-1,8b-diazaacenaphthylene-4-carboxamide Dihydrochloride The procedure of Example 11-1) was generally followed to provide N-[[4-(4-phenylpiperidino)cyclohexyl]methyl]-5-thia-1,8b-diazaacenaphthylene-4-carboxamide as red foam.

$^1$H-NMR (CDCl$_3$, 200 MHz) δ: 0.842–1.071 (2H, m), 1.214–1.987 (12H, m), 2.144–2.535 (3H, m), 2.991–3.316 (4H, m), 5.716–5.771 (1H, m), 6.542–6.676 (4H, m), 6.976 (1H, s), 7.138–7.330 (5H, m).

IR (neat): 3307, 2927, 1616, 1551, 1510, 1483, 1279, 1153, 910, 771, 731, 700 cm$^{-1}$.

Using the above compound, the procedure of Example 1–6) was generally followed to provide the title compound as orange-colored solid.

$^1$H-NMR (CD$_3$OD, 200 MHz) δ: 1.048–1.246 (2H, m), 1.501–2.227 (12H, m), 2.824–2.972 (1H, m), 3.108–3.344 (4H, m), 3.533–3.675 (2H, m), 6.618 (1H, d, 8.4 Hz), 6.903–7.015 (2H, m), 7.195–7.434 (6H, m), 7.516 (1H, s).

IR (Nujol): 3379, 3215, 2644, 1633, 1500, 1286, 1219 cm$^{-1}$.

Example 22

Synthesis of N-[1-(3-phenylpropan-1-yl)piperidin-4-ylmethyl]-5-thia-1,8b-diazaacenaphthylene-4-carboxamide Dihydrochloride The procedure of Example 18-1) was generally followed to provide N-[1-(3-phenylpropan-1-yl)piperidin-4-ylmethyl]-5-thia-1,8b-diazaacenaphthylene-4-carboxamide as red foam.

¹H-NMR (CDCl₃, 200 Mz) δ: 1.32–1.81 (5H, m), 1.81–1.97 (2H, m), 1.97–2.18 (2H, m), 2.41–2.56 (2H, m), 2.64 (2H, t, 7.6 Hz), 2.98–3.14 (2H, m), 3.19 (2H, t, 5.8 Hz), 5.76 (1H, dd, 5.6 Hz, 3.4 Hz), 6.44 (1H, t, 5.6 Hz), 6.55–6.68 (2H, m), 6.77 (1H, s), 7.02 (1H, s), 7.11–7.34 (5H, m).

IR (KBr): 3289, 1620, 1546, 1279 cm⁻¹.

Using the above compound, the procedure of Example 1–6) was generally followed to provide the title compound as orange-colored solid.

¹H-NMR (DMSO-d6, 200 Mz) δ: 1.42–1.70 (3H, m), 1.72–1.92 (2H, m), 2.01–2.22 (2H, m), 2.62–2.78 (2H, m), 2.78–2.97 (2H, m), 2.97–3.33 (4H, m), 3.44–3.60 (2H, m), 6.66 (1H, d, 7.2 Hz), 7.03 (1H, d, 8.8 Hz), 7.20–7.46 (2H, m), 7.71 (1H, s), 8.97 (1H, t, 5.4 Hz).

IR (KBr): 3379, 1641, 1535, 1294 cm⁻¹.

Elemental analysis for C₂₅H₃₀N₄OSCl₂.2H₂O Calcd.: C, 55.45; H, 6.33; N, 10.35; Cl, 13.09 Found: C, 55.18; H, 6.29; N, 10.35; Cl, 13.05

Example 23

Synthesis of N-[1-(3,3'-bithiophen-5-ylmethyl)piperidin-4-ylmethyl]-5-thia-1,8b-diazaacenaphthylene-4-carboxamide Dihydrochloride The procedure of Example 18-1) was generally followed to provide N-[1-(3,3'-bithiophen-5-ylmethyl)piperidin-4-ylmethyl]-5-thia-1,8b-diazaacenaphthylene-4-carboxamide as reddish brown solid.

¹H-NMR (CDCl₃) δ: 1.20–1.85 (5H, m), 1.90–2.15 (2H, m), 2.98 (2H, br d, 11.2 Hz), 3.21 (2H, t, 6.2 Hz), 3.71 (2H, s), 5.79 (1H, dd, 1.7 Hz, 6.3 Hz), 5.80–5.90 (1H, m), 6.58–6.71 (3H, m), 7.05 (1H, s), 7.14 (1H, s), 7.20–7.40 (4H, m).

IR (KBr): 3332, 3093, 2922, 2796 1618, 1539, 1506, 1481, 1367, 1340, 1277, 1155, 968, 840, 771, 737, 594 cm⁻¹.

Using the above compound, the procedure of Example 1–6) was generally followed to provide the title compound as light orange-colored solid.

¹H-NMR (CD₃OD) δ: 1.45–1.70 (2H, m), 1.80–2.10 (3H, m), 2.95–3.40 (4H, m), 3.50–3.70 (2H, m), 4.57 (2H, s), 6.60 (1H, d, 7.4 Hz), 6.99 (2H, t, 4.3 Hz), 7.30–7.80 (7H, m).

IR (KBr): 3388, 3064, 2927, 2729, 1633, 1566, 1537, 1502, 1452, 1394, 1296, 939, 839, 777, 600 cm⁻¹.

Elemental analysis for C₂₅H₂₆N₄OS₃Cl₂.2.8H₂O Calcd.: C, 48.74; H, 5.17; N, 9.09 Found: C, 49.10; H, 5.40; N, 8.70

Example 24

Synthesis of N-[1-(benzo[b]furan-2-ylmethyl)piperidin-4-ylmethyl]-5-thia-1,8b-diazaacenaphthylene-4-carboxamide Dihydrochloride The procedure of Example 18-1) was generally followed to provide N-[1-(benzo[b]furan-2-ylmethyl)piperidin-4-ylmethyl]-5-thia-1,8b-diazaacenaphthylene-4-carboxamide as deep red foam.

¹H-NMR (CDCl₃) δ: 1.25–1.80 (5H, m), 1.95–2.15 (2H, m), 2.90–3.05 (2H, m), 3.20 (2H, t, 6.0 Hz), 3.68 (2H, s), 5.79 (1H, dd, 1.7 Hz, 6.1 Hz), 5.80–5.90 (1H, m), 6.59–6.72 (4H, m), 7.05 (1H, s), 7.16–7.30 (2H, m), 7.46–7.55 (2H, m).

IR (KBr): 3429, 3062, 2924, 1618, 1543, 1510, 1454, 1282, 1155, 1105, 970, 773, 752 cm⁻¹.

Using the above compound, the procedure of Example 1–6) was generally followed to provide the title compound as orange-colored solid.

¹H-NMR (CD₃OD) δ: 1.40–1.60 (2H, m), 1.80–2.10 (3H, m), 3.00–3.40 (4H, m), 3.50–3.70 (2H, m), 4.57 (2H, s), 6.60 (1H, d, 7.8 Hz), 6.96–7.00 (2H, m), 7.16 (1H, s), 7.26–7.42 (3H, m), 7.51–7.58 (2H, m), 7.68 (1H, d, 8.2 Hz).

IR (KBr): 3429, 3061, 2926, 2719, 2667, 1633, 1564, 1539, 1502, 1452, 1392, 1290, 1215, 1107, 939, 787, 756 cm⁻¹.

Elemental analysis for C₂₅H₂₆N₄O₂SCl₂.1.3H₂O Calcd.: C, 55.51; H, 5.33; N, 10.36 Found: C, 55.75; H, 5.32; N, 10.36

Example 25

Synthesis of N-(1-benzhydrylpiperidin-4-ylmethyl)-5-thia-1,8b-diazaacenaphthylene-4-carboxamide Dihydrochloride The procedure of Example 11-1) was generally followed to provide N-(1-benzhydrylpiperidin-4-ylmethyl)-5-thia-1,8b-diazaacenaphthylene-4-carboxamide as red foam.

¹H-NMR (CDCl₃, 200 MHz) δ: 1.216–1.629 (5H, m), 1.809 (2H, t, 11.0 Hz), 2.882 (2H, d, 11.4 Hz), 3.175 (2H, t, 6.1 Hz), 4.224 (1H, s), 5.723 (1H, dd, 2.0 Hz, 6.0 Hz), 6.301 (1H, t, 5.7 Hz), 6.522–6.650 (3H, m), 6.967 (1H, s), 7.112–7.294 (6H, m), 7.361–7.455 (4H, m).

IR (neat): 3313, 2922, 1616, 1549, 1483, 1281, 1153, 908, 731, 704 cm⁻¹.

Using the above compound, the procedure of Example 1–6) was generally followed to provide the title compound as orange-colored foam.

¹H-NMR (CD₃OD, 200 MHz) δ: 1.711–1.970 (5H, m), 3.051 (2H, br t, 12.1 Hz), 3.219 (2H, d, 5.4 Hz), 3.413 (2H, br d, 12.2 Hz), 4.910 (1H, s), 6.600 (1H, d, 7.6 Hz), 6.961–7.029 (2H, m), 7.337–7.512 (8H, m), 7.725–7.773 (4H, m).

IR (Nujol): 3352, 3194, 2719–2530, 1630, 1562, 1533, 1290, 1213, 754, 708 cm⁻¹.

Elemental analysis for C₂₉H₃₀Cl₂N₄OS.1.5H₂O Calcd.: C, 60.00; H, 5.73; N, 9.65 Found: C, 60.00; H, 6.11; N, 9.43

Example 26

Synthesis of N-[4-(4-phenylpiperidin-1-yl)butan-1-yl]-5-thia-1,8b-diazaacenaphthylene-4-carboxamide Dihydrochloride 1) Synthesis of N-[4-(4-phenylpiperidin-1-yl)butan-1-yl]-5-thia-1,8b-diazaacenaphthylene-4-carboxamide To a suspension of 1.0 g (4.58 mM) of 5-thia-1,8b-diazaacenaphthylene-4-carboxylic acid and 1.05 g (9.12 mM) of N-hydroxysuccinimide in acetonitrile (10 ml) was added 1.76 g (9.18 mM) of N-ethyl-N'-3-(N,N-dimethylamino)propylcarbodiimide hydrochloride at room temperature and the mixture was stirred at the prevailing temperature for 2 hours. To this reaction mixture was added a solution of 1.60 g (6.89 mM) of 1-(4-aminobutan-1-yl)-4-phenylpiperidine and 1.3 ml (9.33 mM) of triethylamine in acetonitrile (5 ml) and the mixture was further stirred for one hour. The solvent was then distilled off under reduced pressure and the residue was diluted with water and extracted with chloroform. The organic layer was washed with saturated aqueous solution of sodium chloride and dried over MgSO₄. This crude product was purified by column chromatography (methanol/ethyl acetate 20–50–80%) to provide the title compound as red-purple solid.

Yield 1.76 g (89%)

$^1$H-NMR (200 MHz, CDCl$_3$) δ: 1.50–1.68 (m, 4H), 1.73–1.92 (m, 4H), 1.99–2.18 (m, 2H), 2.36–2.57 (m, 3H), 3.03–3.16 (m, 2H), 3.25–3.39 (m, 2H), 5.73 (dd, J=1.6, 6.0, 1H), 6.50–6.72 (m, 4H), 6.98 (s, 1H), 7.10–7.29 (m, 5H).

2) Synthesis of N-[4-(4-phenylpiperidin-1-yl)butan-1-yl]-5-thia-1,8b-diazaacenaphthylene-4-carboxamide Dihydrochloride To a solution of 1.76 g (4.07 mM) of N-[4-(4-phenylpiperidin-1-yl)butan-1-yl]-5-thia-1,8b-diazaacenaphthylene-4-carboxamide in ethanol (15 ml) was added 6 ml (24 mM) of 4N-HCl/methanol at room temperature and the mixture was stirred at the same temperature for several minutes. The solvent was then distilled off under reduced pressure and diethyl ether was added to the residue. The resulting crystals were collected by filtration and rinsed with diethyl ether to provide the title compound as orange-colored crystals.

Yield 1.78 g (81%)

$^1$H-NMR (200 MHz, DMSO-d$_6$) δ: 1.42–1.61 (m, 2H), 1.65–1.86 (m, 2H), 1.87–2.26 (m, 4H), 2.73–3.31 (m, 7H), 3.28–3.61 (m, 2H), 6.61 (d, J=7.2 Hz, 1H), 6.98 (d, J=8.4 Hz, 1H), 7.17–7.40 (m, 7H), 7.65 (s, 1H), 8.84–8.97 (m, 1H).

IR (KBr): 1635, 1568, 1533, 1500, 1294, 1217, 787 cm$^{-1}$.

Elemental analysis for C$_{25}$H$_{30}$N$_4$OSCl$_2$·2.3H$_2$O Calcd.: C, 54.90; H, 6.38; N, 10.24 Found: C, 54.97; H, 6.37; N, 10.16

Example 27

Synthesis of N-[3-(4-phenylpiperidin-1-yl)propan-1-yl]-5-thia-1,8b-diazaacenaphthylene-4-carboxamide Dihydrochloride 1) The procedure of Example 26-1) was generally followed to provide N-[3-(4-phenylpiperidin-1-yl)propan-1-yl]-5-thia-1,8b-diazaacenaphthylene-4-carboxamide as red-purple solid.

$^1$H-NMR (200 MHz, CDCl$_3$) δ: 1.63–12.19 (m, 8H), 2.55–2.60 (m, 3H), 3.10–3.23 (m, 2H), 3.37–3.49 (m, 2H), 5.57 (dd, J=1.2, 6.6 Hz, 1H), 6.47–6.65 (m, 3H), 6.67 (s, 1H), 6.91 (s, 1H), 7.16–7.35 (m, 5H).

2) The procedure of Example 26-2) was generally followed to provide N-[3-(4-phenylpiperidin-1-yl)propan-1-yl]-5-thia-1,8b-diazaacenaphthylene-4-carboxamide dihydrochloride as orange-colored crystals.

$^1$H-NMR (200 MHz, DMSO-d$_6$) δ: 1.82–2.23 (m, 6H), 2.72–3.34 (m, 7H), 3.46–3.61 (m, 2H), 6.58 (d, J=7.2 Hz, 1H), 6.96 (d, J=8.8 Hz, 1H), 7.16–7.40 (m, 7H), 7.63 (s, 1H), 8.92–9.04 (m, 1H).

IR (KBr): 1635, 1566, 1533, 1500, 1294, 1213, 785 cm$^{-1}$.

Elemental analysis for C$_{24}$H$_{28}$N$_4$OSCl$_2$·3.0H$_2$O Calcd.: C, 52.84; H, 6.28; N, 10.27 Found: C, 52.78; H, 6.08; N, 10.05

Example 28

Synthesis of N-[4-(4-benzylpiperidin-1-yl)butan-1-yl]-5-thia-1,8b-diazaacenaphthylene-4-carboxamide Dihydrochloride 1) Synthesis of N-[4-(4-benzylpiperidin-1-yl)butan-1-yl]-5-thia-1,8b-diazaacenaphthylene-4-carboxamide To a suspension of 1.0 g (4.58 mM) of 5-thia-1,8b-diazaacenaphthylene-4-carboxylic acid and 1.05 g (9.12 mM) of N-hydroxysuccinimide in acetonitrile (10 ml) was added 1.76 g (9.18 mM) of N-ethyl-N'-3-(N,N-dimethylamino)propylcarbodiimide hydrochloride at room temperature and the mixture was stirred at the prevailing temperature for 2 hours. To this reaction mixture was added a suspension of 2.19 g (6.86 mM) of 1-(4-aminobutan-1-yl)-4-benzylpiperidine dihydrochloride and 3.87 ml (27.8 mM) of triethylamine m in acetonitrile (5 ml) and the mixture was further stirred for one hour. The solvent was then distilled off under reduced pressure and the residue was diluted with water and extracted with chloroform. The organic layer was washed with saturated aqueous solution of sodium chloride, dried over MgSO$_4$, and purified by column chromatography (methanol/ethyl acetate 30–50%) to provide the title compound as red-purple amorphous substance.

Yield 2.00 g (98%)

$^1$H-NMR (200 MHz, CDCl$_3$) δ: 1.51–1.92 (m, 9H), 2.23–2.43 (m, 2H), 2.53–2.78 (m, 4H), 3.22–3.42 (m, 4H), 5.72 (dd, J=2.2, 5.8 Hz, 1H), 6.52–6.62 (m, 2H), 6.94 (s, 1H), 7.04 (s, 1H), 7.10–7.48 (m, 6H).

2) Synthesis of N-[4-(4-benzylpiperidin-1-yl)butan-1-yl]-5-thia-1,8b-diazaacenaphthylene-4-carboxamide Dihydrochloride To a solution of 2.00 g (4.48 mM) of N-[4-(4-benzylpiperidin-1-yl)butan-1-yl]-5-thia-1,8b-diazaacenaphthylene-4-carboxamide in ethanol (20 ml) was added 10 ml (40 mM) of 4N-HCl/methanol at room temperature and the mixture was stirred at room temperature for several minutes. After the solvent was distilled off under reduced pressure, diethyl ether was added to the residue and the mixture was cooled to 0° C. The resulting crystals were collected by filtration and rinsed with ethanol and diethyl ether to provide the title compound as orange-colored crystals.

Yield 1.76 g (70%)

$^1$H-NMR (200 MHz, DMSO-d6) δ: 1.34–1.86 (m, 9H), 2.61–3.50 (m, 10H), 6.64 (d, J=7.4 Hz, 1H), 6.99 (d, J=9.0 Hz, 1H), 7.17–7.35 (m, 7H), 7.67 (s, 1H), 8.89–9.02 (m, 1H).

IR (KBr): 1635, 1566, 1533, 1500, 1294, 1215, 787 cm$^{-1}$.

Elemental analysis for C$_{26}$H$_{32}$N$_4$OSCl$_2$·2.3H$_2$O Calcd.: C, 55.67; H, 6.58; N, 9.99 Found C, 55.75; H, 6.74; N, 9.84

Example 29

Synthesis of N-[3-(4-benzylpiperidin-1-yl)propan-1-yl]-5-thia-1,8b-diazaacenaphthylene-4-carboxamide Dihydrochloride 1) Synthesis of N-[3-(4-benzylpiperidin-1-yl)propan-1-yl]-5-thia-1,8b-diazaacenaphthylene-4-carboxamide To a suspension of 1.0 g (4.58 mM) of 5-thia-1,8b-diazaacenaphthylene-4-carboxylic acid and 1.05 g (9.12 mM) of N-hydroxysuccinimide in acetonitrile (10 ml) was added 1.76 g (9.18 mM) of N-ethyl-N'-3-(N,N-dimethylamino)propylcarbodiimide hydrochloride at room temperature and the mixture was stirred at the prevailing temperature for 2 hours. To this mixture was added a suspension of 2.09 g (6.85 mM) of 1-(3-aminopropan-1-yl)-4-benzylpiperidine dihydrochloride and 3.87 ml (27.8 mM) of triethylamine in acetonitrile (5 ml) and the mixture was further stirred for 30 minutes. The solvent was then distilled off under reduced pressure and the residue was diluted with water and extracted with chloroform. The organic layer was washed with saturated aqueous solution of sodium chloride, dried over MgSO$_4$, and purified by column chromatography (methanol/ethyl acetate 20–40–60%) to provide the title compound as red-purple amorphous substance.

Yield 1.84 g (93%)

$^1$H-NMR (200 MHz, CDCl$_3$) δ: 1.22–2.05 (m, 9H), 2.45–2.57 (m, 4H), 2.93–3.10 (m, 2H), 3.34–3.46 (m, 2H), 5.75 (dd, J=2.0, 6.0 Hz, 1H), 6.54–6.67 (m, 3H), 7.03 (s, 1H), 7.06–7.34 (m, 5H), 8.32–8.46 (m, 1H).

2) Synthesis of N-[3-(4-benzylpiperidin-1-yl)propan-1-yl]-5-thia-1,8b-diazaacenaphthylene-4-carboxamide Dihydrochloride To a solution of 1.84 g (4.25 mM) of N-[3-(4-benzylpiperidin-1-yl)propan-1-yl]-5-thia-1,8b-diazaacenaphthylene-4-carboxamide in ethanol (10 ml) was added 6 ml (24 mM) of 4N-HCl/methanol at room temperature and the mixture was stirred at room temperature for several minutes. After the solvent was distilled off under reduced pressure, ethanol and diethyl ether were added to the crystalline residue. The crystal crop was then harvested by filtration and rinsed with ethanol and diethyl ether to provide the title compound as orange-colored crystals.

Yield 1.81 g (84%)

$^1$H-NMR (200 MHz, DMSO-d$_6$) δ: 1.37–1.96 (m, 7H), 2.59–3.47 (m, 10H), 6.56 (d, J=6.8 Hz, 1H), 6.94 (d, J=8.4 Hz, 1H), 7.14–7.37 (m, 7H), 7.61 (s, 1H), 8.90–9.04 (m, 1H).

IR (KBr): 1633, 1568, 1300, 1217, 787 cm$^{-1}$.

Example 30

Synthesis of N-[4-(4-phenyl-1-piperazinyl)butan-1-yl]-5-thia-1,8b-diazaacenaphthylene-4-carboxamide Trihydrochloride 1) Synthesis of N-[4-(4-phenyl-1-piperazinyl)butan-1-yl]-5-thia-1,8b-diazaacenaphthylene-4-carboxamide To a suspension of 1.0 g (4.58 mM) of 5-thia-1,8b-diazaacenaphthylene-4-carboxylic acid and 0.90 g (7.82 mM) of N-hydroxysuccinimide in acetonitrile (10 ml) was added 1.51 g (7.88 mM) of N-ethyl-N'-3-(N,N-dimethylamino)propylcarbodiimide hydrochloride at room temperature and the mixture was stirred at the prevailing temperature for 2 hours. To this reaction mixture was added a solution of 2.02 g (5.89 mM) of 1-(4-aminobutan-1-yl)-4-phenylpiperazine trihydrochloride and 4.1 ml (29.4 mM) of triethylamine in ethanol (10 ml) and the mixture was further stirred for one hour. The solvent was distilled off under reduced pressure and the residue was diluted with water and extracted with chloroform. The organic layer was washed with saturated aqueous solution of sodium chloride, dried over MgSO$_4$, and purified by column chromatography (methanol/ethyl acetate 50% methanol-chloroform=1:10). After concentration, ethanol was added to the residue and the resulting crystal crop was harvested by filtration to provide the title compound as rouge-colored crystals.

Yield 1.37 g (69%)

$^1$H-NMR (200 MHz, CDCl$_3$) δ: 1.48–1.67 (m, 4H), 2.36–2.48 (m, 2H), 2.57–2.66 (m, 4H), 3.17–3.40 (m, 6H), 5.73 (dd, J=1.6, 6.4 Hz, 1H), 6.28–6.40 (m, 1H), 6.56–6.69 (m, 3H), 6.82–6.99 (m, 4H), 7.22–7.33 (m, 2H).

IR (KBr): 3267, 3054, 3949, 2816, 1612, 1547, 1495, 1279, 1232, 1147, 761 cm$^{-1}$.

2) Synthesis of N-[4-(4-phenyl-1-piperazinyl)butan-1-yl]-5-thia-1,8b-diazaacenaphthylene-4-carboxamide Trihydrochloride To a solution of 1.37 g (3.16 mM) of N-[4-(4-phenyl-1-piperazinyl)butan-1-yl]-5-thia-1,8b-diazaacenaphthylene-4-carboxamide in ethanol (20 ml) was added 10 ml (40 mM) of 4N-HCl/methanol at room temperature and the mixture was stirred at room temperature for 3 hours (crystals separated out). After the solvent was distilled off under reduced pressure, ethanol and diethyl ether were added to the residue and the resulting crystals were collected by filtration and rinsed with ethanol and diethyl ether to provide the title compound.

Orange-colored crystals. Yield 1.7252 g (97%)

$^1$H-NMR (200 MHz, DMSO-d$_6$) δ: 1.40–1.62 (m, 2H), 1.64–1.87 (m, 2H), 2.96–3.28 (m, 8H), 3.46–3.59 (m, 2H), 3.70–3.89 (m, 2H), 6.69 (d, J=7.0 Hz, 1H), 6.87 (d, J=7.2 Hz, 1H), 6.99–7.04 (m, 3H), 7.23–7.40 (m, 4H), 7.72 (s, 1H), 8.92–9.07 (m, 1H), 10.90–11.11 (m, 1H).

IR (KBr): 3404, 2914, 2503, 1635, 1566, 1533, 1497, 1441, 1288, 1215, 779 cm$^{-1}$.

Elemental analysis for C$_{24}$H$_{30}$N$_5$OSCl$_3$·1.0H$_2$O Calcd.: C, 51.39; H, 5.75; N, 12.48 Found: C, 51.37; H, 5.86; N, 12.23

Example 31

Synthesis of N-[3-(4-phenyl-1-piperazinyl)propan-1-yl]-5-thia-1,8b-diazaacenaphthylene-4-carboxamide Trihydrochloride 1) The procedure of Example 30-1) was generally followed to provide N-[3-(4-phenyl-1-piperazinyl)propan-1-yl]-5-thia-1,8b-diazaacenaphthylene-4-carboxamide as red-purple solid.

$^1$H-NMR (200 MHz, CDCl$_3$) δ: 1.58–1.84 (m, 2H), 2.54–2.66 (m, 2H), 2.66–2.77 (m, 4H), 3.26–3.38 (m, 4H), 3.38–3.53 (m, 2H), 5.37 (d, J=7.0 Hz, 1H), 6.42 (dd, J=7.0, 9.2 Hz, 1H), 6.60 (dd, J=0.8, 9.2 Hz, 1H), 6.72 (s, 1H), 6.86 (s, 1H), 6.87–6.99 (m, 3H), 7.20–7.35 (m, 2H), 8.10–8.23 (m, 1H).

IR (KBr): 3177, 2949, 2831, 1643, 1606, 1495, 1279, 1238, 1149, 768, 687 cm$^{-1}$.

2) The procedure of Example 30-2) was generally followed to provide N-[3-(4-phenyl-1-piperazinyl)propan-1-yl]-5-thia-1,8b-diazaacenaphthylene-4-carboxamide trihydrochloride as orange-colored crystals.

$^1$H-NMR (200 MHz, DMSO-d$_6$) δ: 1.82–2.03 (m, 2H), 2.98–3.30 (m, 8H), 3.44–3.60 (m, 2H), 3.71–3.90 (m, 2H), 6.59 (d, J=7.0 Hz, 1H), 6.81–7.04 (m, 4H), 7.15–7.33 (m, 4H), 7.64 (m, 1H), 8.94–9.07 (m, 1H), 10.86–11.02 (m, 1H).

IR (KBr): 3248, 3035, 2673, 2565, 1639, 1531, 1502, 1446, 1394, 1296, 1215 cm$^{-1}$.

Example 32

Synthesis of N-[4-(4-benzyl-1-piperazinyl)butan-1-yl]-5-thia-1,8b-diazaacenaphthylene-4-carboxamide Trihydrochloride 1) The procedure of Example 30-1) was generally followed to provide N-[4-(4-benzyl-1-piperazinyl)butan-1-yl]-5-thia-1,8b-diazaacenaphthylene-4-carboxamide as red amorphous substance.

$^1$H-NMR (200 MHz, CDCl$_3$) δ: 1.48–1.65 (m, 4H), 2.31–2.63 (m, 10H), 3.23–3.36 (m, 2H), 3.51 (s, 2H), 5.77 (dd, J=1.2, 6.2 Hz, 1H), 6.43–6.53 (m, 1H), 6.56–6.71 (m, 3H), 7.02 (s, 1H), 7.23–35 (m, 5H).

IR (KBr): 3415, 2937, 2812, 1624, 1549, 1281, 1151, 739 cm$^{-1}$.

2) The procedure of Example 30-2) was generally followed to provide N-[4-(4-benzyl-1-piperazinyl)butan-1-yl]-

5-thia-1,8b-diazaacenaphthylene-4-carboxamide trihydrochloride as orange-colored crystals.

$^1$H-NMR (200 MHz, DMSO-d$_6$) δ: 1.41–1.79 (m, 4H), 3.01–4.41 (m, 14H), 6.56 (d, J=7.4 Hz, 1H), 6.94 (d, J=8.8 Hz, 1H), 7.12 (br s, 1H), 7.16–7.28 (m, 1H), 7.38–7.65 (m, 6H), 8.72–8.86 (m, 1H).

IR (KBr): 3253, 2951, 2519, 1630, 1529, 1450, 1304, 1217, 791 cm$^{-1}$.

Elemental analysis for $C_{25}H_{32}N_5OSCl_3.1.0H_2O$ Calcd.: C, 52.22; H, 5.96; N, 12.18 Found: C, 52.07; H, 6.05; N, 11.88

Example 33

Synthesis of N-[3-(4-benzyl-1-piperazinyl)propan-1-yl]-5-thia-1,8b-diazaacenaphthylene-4-carboxamide Trihydrochloride 1) The procedure of Example 30-1) was generally followed to provide N-[3-(4-benzyl-1-piperazinyl)propan-1-yl]-5-thia-1,8b-diazaacenaphthylene-4-carboxamide as red amorphous substance.

$^1$H-NMR (200 MHz, CDCl$_3$) δ: 1.57–1.78 (m, 2H), 2.38–2.71 (m, 10H), 3.35–3.46 (m, 2H), 3.50 (s, 2H), 5.76 (dd, J=2.0, 6.0 Hz, 1H), 6.56–6.68 (m, 3H), 7.04 (s, 1H), 7.23–7.36 (m, 5H), 8.15–8.27 (m, 1H).

IR (KBr): 3346, 2941, 2812, 1622, 1545, 1279, 1149, 739 cm$^{-1}$.

2) The procedure of Example 30-2) was generally followed to provide N-[3-(4-benzyl-1-piperazinyl)propan-1-yl]-5-thia-1,8b-diazaacenaphthylene-4-carboxamide trihydrochloride as reddish orange-colored crystals.

$^1$H-NMR (200 MHz, DMSO-d$_6$) δ: 1.80–2.01 (m, 2H), 3.03–3.32 (m, 2H), 3.32–3.82 (m, 10H), 4.35–4.51 (m, 2H), 6.64 (d, J=7.4 Hz, 1H), 6.99 (d, J=9.2 Hz, 1H), 7.20 (br s, 1H), 7.31 (dd, J=7.4, 9.2 Hz, 1H), 7.42–7.55 (m, 3H), 7.61–7.76 (m, 3H), 8.93–9.09 (m, 1H).

IR (KBr): 3396, 3053, 2649, 2561, 1635, 1444, 1296, 1213, 945, 791 cm$^{-1}$.

Elemental analysis for $C_{24}H_{30}N_5OSCl_3.2.0H_2O$ Calcd.: C, 49.79; H, 5.92; N, 12.10 Found: C, 49.66; H, 5.80; N, 12.09

Example 34

Synthesis of N-[4-(1,2,3,4-tetrahydroisoquinolin-2-yl)butan-1-yl]-5-thia-1,8b-diazaacenaphthylene-4-carboxamide Dihydrochloride 1) Synthesis of N-[4-(1,2,3,4-tetrahydroisoquinolin-2-yl)butan-1-yl]-5-thia-1,8b-diazaacenaphthylene-4-carboxamide To a suspension of 1.0 g (4.58 mM) of 5-thia-1,8b-diazaacenaphthylene-4-carboxylic acid and 1.05 g (9.12 mM) of N-hydroxysuccinimide in acetonitrile (10 ml) was added 1.76 g (9.18 mM) of N-ethyl-N'-3-(N,N-dimethylamino)propylcarbodiimide hydrochloride at room temperature and the mixture was stirred at the prevailing temperature for 2 hours. To this reaction mixture was added a solution of 1.90 g (6.85 mM) of 2-(4-aminobutan-1-yl)-1,2,3,4-tetrahydroisoquinoline dihydrochloride and 4.0 ml (28.7 mM) of triethylamine in ethanol (10 ml) and the mixture was further stirred for one hour. The solvent was then distilled off under reduced pressure and the residue was diluted with water and extracted with methylene chloride. The organic layer was washed with saturated aqueous solution of sodium chloride, dried over MgSO$_4$, and purified by column chromatography (methanol/ethyl acetate 30%) to provide the title compound as red-purple amorphous substance.

Yield 1.76 g (95%)

$^1$H-NMR (200 MHz, CDCl$_3$) δ: 1.57–1.92 (m, 4H), 2.58 (t, J=6.2 Hz, 2H), 2.73–2.79 (m, 2H), 2.95 (t, J=5.8 Hz, 2H), 3.25–3.37 (m, 2H), 3.69 (s, 2H), 5.55 (dd, J=2.0, 6.2 Hz, 1H), 6.30 (s, 1H), 6.48–6.60 (m, 3H), 6.97–7.16 (m, 4H), 7.41–7.55 (m, 1H).

2) Synthesis of N-[4-(1,2,3,4-tetrahydroisoquinolin-2-yl)butan-1-yl]-5-thia-1,8b-diazaacenaphthylene-4-carboxamide Dihydrochloride To a solution of 1.76 g (4.35 mM) of N-[4-(1,2,3,4-tetrahydroisoquinolin-2-yl)butan-1-yl]-5-thia-1,8b-diazaacenaphthylene-4-carboxamide in ethanol (10 ml) was added 6 ml (24 mM) of 4N-HCl/methanol at room temperature and the mixture was stirred at room temperature for several minutes. After the solvent was distilled off under reduced pressure, ethanol was added to the residue and the mixture was concentrated. Then, diethyl ether was added and the crystal crop was harvested by filtration and rinsed with ethanol and diethyl ether to provide the title compound.

Orange-colored crystals. Yield 1.65 g (78%)

$^1$H-NMR (200 MHz, DMSO-d$_6$) δ: 1.42–1.62 (m, 2H), 1.70–1.93 (m, 2H), 2.91–3.39 (m, 7H), 3.56–3.77 (m, 1H), 4.18–4.35 (m, 1H), 4.43–4.59 (m, 1H), 6.57 (d, J=6.8 Hz, 1H), 6.95 (d, J=8.4 Hz, 1H), 7.09–7.32 (m, 6H), 7.61 (s, 1H), 8.83–8.95 (m, 1H).

IR (KBr): 3400, 3045, 2939, 1635, 1562, 1535, 1500, 1440, 1292, 1211, 756 cm$^{-1}$.

Elemental analysis for $C_{23}H_{26}N_4OSCl_2.0.5H_2O$ Calcd.: C, 56.79; H, 5.59; N, 11.52 Found: C, 56.67; H, 5.73; N, 11.40

Example 35

Synthesis of N-[3-(1,2,3,4-tetrahydroisoquinolin-2-yl)-propan-1-yl]-5-thia-1,8b-diazaacenaphthylene-4-carboxamide Dihydrochloride 1) The procedure of Example 34-1) was generally followed to provide N-[3-(1,2,3,4-tetrahydroisoquinolin-2-yl)propan-1-yl]-5-thia-1,8b-diazaacenaphthylene-4-carboxamide as red-purple amorphous substance.

$^1$H-NMR (200 MHz, CDCl$_3$) δ: 1.65–1.90 (m, 2H), 2.67–2.83 (m, 4H), 2.93–3.03 (m, 2H), 3.39–3.52 (m, 2H), 3.71 (s, 2H), 5.23 (dd, J=1.6, 6.6 Hz, 1H), 6.13 (s, 1H), 6.31 (s, 1H), 6.44–6.53 (m, 2H), 6.97–7.13 (m, 4H), 8.71–8.94 (m, 1H).

2) The procedure of Example 34-2) was generally followed to provide N-[3-(1,2,3,4-tetrahydroisoquinolin-2-yl)propan-1-yl]-5-thia-1,8b-diazaacenaphthylene-4-carboxamide dihydrochloride as orange-colored crystals.

$^1$H-NMR (200 MHz, DMSO-d$_6$) δ: 1.88–2.12 (m, 2H), 2.88–3.36 (m, 7H), 3.56–3.75 (m, 1H), 4.17–4.37 (m, 1H), 4.45–4.60 (m, 1H), 6.59 (d, J=7.4 Hz, 1H), 6.96 (d, J=9.0 Hz, 1H), 7.14–7.35 (m, 6H), 7.64 (s, 1H), 8.96–9.11 (m, 1H).

IR (KBr): 3390, 3047, 295, 2684, 2600, 1637, 1531, 1442, 1294, 1211 cm$^{-1}$.

Example 36

Synthesis of N-[1-(3-phenylpropan-1-yl)piperidin-4-yl]-5-thia-1,8b-diazaacenaphthylene-4-carboxamide Dihydrochloride 1) Synthesis of N-(1-ethoxycarbonylpiperidin-4-yl)-5-thia-1,8b-diazaacenaphthylenecarboxamide To a suspension of 10.76 g (38.45 mM) of 5-thia-1,8b-diazaacenaphthylene-4-carboxylic acid hydrochloride and 11.35 g (98.62 mM) of N-hydroxysuccinimide in acetonitrile (150 ml) was added 18.9 g (98.59 mM) of N-ethyl-N'-3-(N,N-dimethylamino)propylcarbodiimide hydrochloride and the mixture was stirred at room temperature for 2 hours. Then, at room temperature, a solution of 10 ml (58.3 mM) of ethyl 4-aminopiperidine-1-carboxylate and 13 ml (92.3 mM) of triethylamine in acetonitrile (30 ml) was added and the mixture was stirred for 2 hours. The solvent was then distilled off under reduced pressure and the residue was diluted with water and extracted with chloroform. The organic layer was washed with saturated aqueous solution of sodium chloride and dried over $MgSO_4$. The crude product thus obtained was purified by column chromatography (methanol/ethyl acetate 20%) to provide the title compound. Red amorphous substance. Yield 19.47 g (quantitative)

$^1$H-NMR (200 MHz, $CDCl_3$) δ: 1.16–1.46 (m, 2H), 1.26 (t, J=7.0 Hz, 3H), 1.93–2.02 (m, 2H), 2.84–2.97 (m, 2H), 3.87–4.21 (m, 3H), 4.13 (q, J=7.0 Hz, 2H), 5.67 (br d, J=8.0 Hz, 1H), 5.80 (dd, J=1.8, 6.2 Hz, 1H), 6.59–6.71 (m, 3H), 7.05 (s, 1H).

2) Synthesis of N-(1-tert-butoxycarbonylpiperidin-4-yl)-5-thia-1,8b-diazaacenaphthylenecarboxamide Under argon gas, 21 ml (147.6 mM) of trimethylsilyl iodide was added to a solution of 19.47 g (<38.45 mM) of N-(1-ethoxycarbonylpiperidin-4-yl)-5-thia-1,8b-diazaacenaphthylenecarboxamide in acetonitrile (350 ml) at room temperature and the mixture was stirred for 84 hours. The reaction was stopped by adding methanol to the reaction system and 30 ml (215 mM) of triethylamine and 9.8 ml (42.7 mM) of di-tert-butyl dicarbonate were added at room temperature, followed by 1 hour of stirring. The solvent was then distilled off under reduced pressure and the residue was diluted with water and extracted with chloroform. The organic layer was washed with saturated aqueous solution of sodium chloride and dried over $MgSO_4$. The crude product thus obtained was purified by column chromatography (methanol/ethyl acetate 20%) to provide the title compound as red amorphous substance (14.59 g, 95%).

$^1$H-NMR (200 MHz, $CDCl_3$) δ: 1.13–1.99 (m, 2H), 1.46 (s, 9H), 1.73–1.98 (m, 2H), 2.74–2.95 (m, 2H), 3.84–4.18 (m, 3H), 5.70–5.85 (m, 1H), 5.79 (dd, J=1.9, 5.7 Hz, 1H), 6.58–6.72 (m, 3H), 7.04 (s, 1H).

3) Synthesis of N-(piperidin-4-yl)-5-thia-1,8b-diazaacenaphthylenecarboxamide Dihydrochloride To 14.59 g (36.4 mM) of N-(1-tert-butoxycarbonyl-piperidin-4-yl)-5-thia-1,8b-diazaacenaphthylenecarboxamide was added 20 ml (240 mM) of 12N-hydrochloric acid at room temperature and the mixture was stirred at room temperature for one hour. To this reaction mixture was added ethanol and the resulting crystal crop was harvested by filtration and rinsed with ethanol and diethyl ether to provide the title compound.

Orange-colored crystals. Yield 10.08 g (74%)

$^1$H-NMR (200 MHz, $D_2O$) δ: 1.64–1.87 (m, 2H), 2.03–2.19 (m, 2H), 3.03–3.21 (m, 2H), 3.42–3.58 (m, 2H), 3.82–4.02 (m, 1H), 5.98 (d, J=7.0 Hz, 1H), 6.60 (d, J=9.2 Hz, 1H), 6.67 (s, 1H), 6.78 (dd, J=7.2, 9.2 Hz, 1H), 6.98 (s, 1H).

IR (KBr): 3481, 3223, 2935, 2798, 2717, 1633, 1529 1302, 1257, 1211, 787 cm$^{-1}$.

4) Synthesis of N-[1-(3-phenylpropan-1-yl)piperidin-4-yl]-5-thia-1,8b-diazaacenaphthylene-4-carboxamide To a solution of 0.40 g (1.07 mM) of N-(piperidin-4-yl)-5-thia-1,8b-diazaacenaphthylenecarboxamide dihydrochloride and 0.75 ml (5.38 mM) of triethylamine in ethanol (5 ml) was added 0.20 ml (1.32 mM) of 1-bromo-3-phenylpropane at room temperature and the mixture was refluxed under nitrogen for 15 hours. The solvent was then distilled off under reduced pressure and the residue was diluted with water and extracted with methylene chloride. The organic layer was washed with saturated aqueous solution of sodium chloride, dried over $MgSO_4$, and purified by column chromatography (methanol/ethyl acetate 20–40%) to provide the title compound.

Red-purple amorphous substance. Yield 356 mg (80%)

$^1$H-NMR (200 MHz, $CDCl_3$) δ: 1.41–1.64 (m, 2H), 1.75–2.21 (m, 6H), 2.31–2.47 (m, 2H), 2.63 (t, J=7.7 Hz, 2H), 7.79–2.96 (m, 2H), 3.72–3.92 (m, 1H), 5.75–5.80 (m, 2H), 6.57–6.69 (m, 3H), 7.03 (s, 1H), 7.16–7.32 (m, 5H).

5) Synthesis of N-[1-(3-phenylpropan-1-yl)piperidin-4-yl]-5-thia-1,8b-diazaacenaphthylene-4-carboxamide Dihydrochloride To a solution of 356.2 mg (0.85 mM) of N-[1-(3-phenylpropan-1-yl)piperidin-4-yl]-5-thia-1,8b-diazaacenaphthylene-4-carboxamide in ethanol (6 ml) was added 2.0 ml (8.0 mM) of 4N-HCl/methanol at room temperature and the mixture was stirred at room temperature for several minutes. After the solvent was distilled off under reduced pressure, diethyl ether was added to the residue and the resulting crystals were collected by filtration and rinsed with ethanol and diethyl ether to provide the title compound.

Orange-colored crystals. Yield 399 mg (96%)

$^1$H-NMR (200 MHz, DMSO-$d_6$) δ: 1.80–2.14 (m, 6H), 2.63 (t, J=7.5 Hz, 2H), 2.82–3.11 (m, 4H), 3.38–3.56 (m, 2H), 3.72–3.93 (m, 1H), 6.64 (d, J=6.6 Hz, 1H), 6.99 (d, J=9.2 Hz, 1H), 7.15–7.38 (m, 7H), 7.67 (s, 1H), 8.80–8.90 (m, 1H).

IR (KBr): 3412, 3051, 1635, 1564, 1535, 1495, 1304 cm$^{-1}$.

Elemental analysis for $C_{24}H_{28}N_4OSCl_2 \cdot 2.5H_2O$ Calcd.: C, 53.73; H, 6.20; N, 10.44 Found: C, 54.03; H, 5.96; N, 10.46

Example 37

Synthesis of N-(1-phenethylpiperidin-4-yl)-5-thia-1,8b-diazaacenaphthylene-4-carboxamide Dihydrochloride 1) The procedure of Example 36-4) was generally followed to provide N-(1-phenethylpiperidin-4-yl)-5-thia-1,8b-diazaacenaphthylene-4-carboxamide as red-purple solid.

m.p. 216.0–217.0° C.

$^1$H-NMR (200 MHz, $CDCl_3$) δ: 1.40–1.70 (2H, m), 1.80–2.20 (4H, m), 2.50–3.10 (6H, m), 3.70–4.00 (1H, m), 5.60–5.90 (2H, m), 6.50–6.80 (3H, m), 7.04 (1H, s), 7.10–7.40 (5H, m).

IR (KBr): 3292, 2947, 1612, 1537, 1279, 1159, 771, 735, 696 cm$^{-1}$.

2) The procedure of Example 36-5) was generally followed to provide N-(1-phenethylpiperidin-4-yl)-5-thia-1,8b-diazaacenaphthylene-4-carboxamide dihydrochloride as orange-colored crystals.

$^1$H-NMR (200 MHz, $CD_3OD$) δ: 1.80–2.30 (m, 6H), 3.00–3.60 (m, 4H), 3.73 (br d, J=12.8 Hz, 2H), 3.90–4.20 (m, 1H), 6.61 (d, J=7.0 Hz, 1H), 6.90–7.10 (m, 2H), 7.20–7.50 (m, 6H), 7.53 (s, 1H).

IR (KBr): 3427, 3244, 3030, 2935, 2727, 1632, 1562, 1537, 1502, 1458, 1308, 791, 758, 704 cm$^{-1}$.

Elemental analysis for $C_{23}H_{26}N_4OSCl_2 \cdot 1.0H_2O$ Calcd.: C, 55.76; H, 5.70; N, 11.31 Found: C, 56.06; H, 5.47; N, 11.51

Example 38

Synthesis of N-[1-[3-(2-fluorophenyl)propan-1-yl]piperidin-4-yl]-5-thia-1,8b-diazaacenaphthylene-4-carboxamide Dihydrochloride 1) Synthesis of N-[1-[3-(2-fluorophenyl)propan-1-yl)piperidin-4-yl]-5-thia-1,8b-diazaacenaphthylene-4-carboxamide To a solution of 616.7 mg (4.0 mM) of 3-(2-fluorophenyl)propanol and 809.5 mg (8.0 mM) of triethylamine in ether (20 ml) was added 687.3 mg (6.0 mM) of methanesulfonyl chloride gradually with ice-cooling and the mixture was stirred at the prevailing temperature for 5 minutes and, then at room temperature for 1 hour. Then, 405 mg (4.0 mM) of triethylamine and 344 mg (3.0 mM) of methanesulfonyl chloride were further added and the mixture was further stirred at room temperature for 1 hour. To this reaction mixture was added 5% aqueous solution of sodium hydrogen carbonate and the reaction product was extracted into ethyl acetate. The organic layer was washed with water and dried over $Na_2SO_4$ and the solvent was distilled off under reduced pressure. To the mesyl compound thus obtained was added a solution of 746.6 mg (2.0 mM) of N-(piperidin-4-yl)-5-thia-1,8b-diazaacenaphthylenecarboxamide dihydrochloride and 1.15 g (10 mM) of triethylamine in ethanol (10 ml) and the mixture was refluxed overnight. To this reaction mixture was added 5% aqueous solution of sodium hydrogen carbonate and the reaction product was extracted into ethyl acetate. The organic layer was washed with water and dried over $Na_2SO_4$ and the solvent was distilled off under reduced pressure. The residue was purified by silica gel column chromatography (ethyl acetate/methanol=3/1). After concentration, ether was added to the residue and the resulting crystals were collected by filtration to provide the title compound as reddish orange-colored solid (553.6 mg, 63.4%).

$^1$H-NMR (200 MHz, $CDCl_3$) δ: 1.35–1.57 (2H, m), 1.70–2.15 (6H, m), 2.40 (2H, t, J=7.5 Hz), 2.66 (2H, t, J=8.0 Hz), 2.85 (2H, br d, J=12.0 Hz), 3.70–3.90 (1H, m), 5.67 (1H, d, J=7.8 Hz), 5.78 (1H, dd, J=1.5, 6.1 Hz), 6.58–6.70 (3H, m), 6.95–7.22 (5H, m).

IR (KBr): 3429, 3394, 3217, 3049, 2939, 2804, 2771, 1632, 1614, 1552, 1512, 1479, 1454, 1311, 1281, 1246, 1228, 1140, 1099, 781, 758, 735 cm$^{-1}$.

2) Synthesis of N-[1-[3-(2-fluorophenyl)propan-1-yl]piperidin-4-yl]-5-thia-1,8b-diazaacenaphthylene-4-carboxamide Dihydrochloride To a solution of 553.6 mg (1.3 mM) of N-[1-[3-(2-fluorophenyl)propan-1-yl]piperidin-4-yl]-5-thia-1,8b-diazaacenaphthylene-4-carboxamide in ethanol (20 ml) was added 2 ml (8.0 mM) of 4N-HCl/ethyl acetate and the mixture was stirred for several minutes. The solvent was then distilled off under reduced pressure and ether was added to the residue. The resulting crystal crop was harvested by filtration to provide orange-colored crystals (666.6 mg, 94%).

$^1$H-NMR (200 MHz, $CD_3OD$) δ: 1.80–2.20 (m, 6H), 2.77 (t, J=7.4 Hz, 2H), 3.00–3.22 (m, 3H), 3.40–3.50 (m, 1H), 3.63 (br d, J=12.4 Hz, 2H), 3.90–4.10 (m, 1H), 6.61 (d, J=7.6 Hz, 1H), 6.98–7.43 (m, 7H), 7.53 (s, 1H).

IR (KBr): 3427, 3390, 3062, 2940, 2717, 1633, 1564, 1539, 1504, 1456, 1304, 1217, 771 cm$^{-1}$.

Elemental analysis for $C_{24}H_{27}N_4OSCl_2F \cdot 2H_2O$ Calcd.: C, 52.84; H, 5.73; N, 10.27 Found: C, 52.66; H, 5.83; N, 10.20

Example 39

Synthesis of N-(1-[3-(2-chlorophenyl)propan-1-yl]-piperidin-4-yl]-5-thia-1,8b-diazaacenaphthylene-4-carboxamide Dihydrochloride 1) The procedure of Example 38-1) was generally followed to provide N-[1-[3-(2-chlorophenyl)propan-1-yl]piperidin-4-yl]-5-thia-1,8b-diazaacenaphthylene-4-carboxamide as red solid.

$^1$H-NMR (200 MHz, $CDCl_3$) δ: 1.39–1.59 (2H, m), 1.73–2.16 (6H, m), 2.40 (2H, t, J=7.5 Hz), 2.75 (2H, t, J=7.7 Hz), 2.86 (2H, br d, J=12.2 Hz), 3.70–3.95 (1H, m), 5.64 (1H, d, J=7.6 Hz), 5.79 (1H, dd, J=1.8, 6.2 Hz), 6.58–6.70 (3H, m), 7.05 (1H, s), 7.10–7.36 (4H, m).

IR (KBr): 3230, 2949, 1633, 1614, 1541, 1508, 1479, 1311, 1281, 1246, 1140, 779, 758 cm$^{-1}$.

2) The procedure of Example 38-2) was generally followed to provide N-[1-[3-(2-chlorophenyl)propan-1-yl]piperidin-4-yl]-5-thia-1,8b-diazaacenaphthylene-4-carboxamide dihydrochloride as reddish orange-colored crystals.

$^1$H-NMR (200 MHz, $CD_3OD$) δ: 1.80–2.20 (6H, m), 2.82–2.90 (2H, m), 3.03–3.22 (3H, m), 3.40–3.50 (1H, m), 3.65 (2H, br d, J=12.2 Hz), 3.90–4.10 (1H, m), 6.61 (1H, d, J=7.2 Hz), 6.97–7.04 (2H, m), 7.19–7.43 (5H, m), 7.53 (1H, s).

IR (KBr): 3400, 3066, 2945, 2717, 1633, 1568, 1539, 1504, 1473, 1456, 1302, 1215, 758 cm$^{-1}$.

Elemental analysis for $C_{24}H_{27}N_4OSCl_3 \cdot 2H_2O$ Calcd.: C, 51.30; H, 5.56; N, 9.97 Found: C, 51.47; H, 5.69; N, 9.87

Example 40

Synthesis of N-[1-[2-(thiophen-3-yl)ethan-1-yl]piperidin-4-yl]-5-thia-1,8b-diazaacenaphthylene-4-carboxamide Dihydrochloride 1) The procedure of Example 38-1) was generally followed to provide N-[1-[2-(thiophen-3-yl)ethan-1-yl]piperidin-4-yl]-5-thia-1,8b-diazaacenaphthylene-4-carboxamide as rouge-colored solid.

$^1$H-NMR (200 MHz, $CDCl_3$) δ: 1.40–1.60 (2H, m), 1.90–2.05 (2H, m), 2.12–2.23 (2H, m), 2.58–2.65 (2H, m), 2.79–2.95 (4H, m), 3.75–3.95 (1H, m), 5.60–5.80 (2H, m), 6.58–6.70 (3H, m), 6.94–7.04 (3H, m), 7.23–7.25 (1H, m).

IR (KBr): 3292, 2949, 1608, 1539, 1508, 1481, 1308, 1279, 1236, 1161, 1119, 771, 737, 646 cm$^{-1}$.

2) The procedure of Example 38-2) was generally followed to provide N-[1-[2-(thiophen-3-yl)ethan-1-yl]piperidin-4-yl]-5-thia-1,8b-diazaacenaphthylene-4-carboxamide dihydrochloride as orange-colored crystals.

$^1$H-NMR (200 MHz, $CD_3OD$) δ: 1.85–2.25 (4H, m), 3.05–3.20 (4H, m), 3.23–3.50 (2H, m), 3.60–3.75 (2H, m), 3.90–4.15 (1H, m), 6.61 (1H, d, J=7.2 Hz), 6.96–7.10 (3H, m), 7.10–7.45 (3H, m), 7.52 (1H, s).

IR (KBr): 3392, 3059, 2910, 2721, 2675, 2551, 1633, 1564, 1529, 1502, 1458, 1394, 1304, 1263, 1215, 787 cm$^{-1}$.

Example 41

Synthesis of N-[1-(1,4-benzodioxan-2-ylmethyl)piperidin-4-yl]-5-thia-1,8b-diazaacenaphthylene-4-carboxamide Dihydrochloride 1) The procedure of Example 38-1) was generally followed to provide N-[1-(1,4-benzodioxan-2-ylmethyl)

piperidin-4-yl]-5-thia-1,8b-diazaacenaphthylene-4-carboxamide as red amorphous substance.

$^1$H-NMR (200 MHz, CDCl$_3$) δ: 1.38–1.53 (m, 2H), 1.86–2.02 (m, 2H), 2.18–2.21 (m, 2H), 2.52–2.76 (m, 2H), 2.80–3.02 (m, 2H), 23.72–3.91 (m, 1H), 3.98 (dd, J=7.6, 11.6 Hz, 1H), 4.22–4.35 (m, 2H), 5.48–5.60 (m, 1H), 5.80 (dd, J=1.6, 6.4 Hz, 1H), 6.59–6.72 (m, 3H), 6.80–6.91 (m, 4H), 7.06 (s, 1H).

IR (KBr): 1620, 1543, 1493, 1267, 1149, 782 cm$^{-1}$.

2) The procedure of Example 38-2) was generally followed to provide N-[1-(1,4-benzodioxan-2-ylmethyl)piperidin-4-yl)-5-thia-1,8b-diazaacenaphthylene-4-carboxamide dihydrochloride as orange-colored crystals.

$^1$H-NMR (200 MHz, DMSO-d$_6$) δ: 1.81–2.09 (m, 4H), 2.95–4.39 (m, 9H), 4.85–5.00 (m, 1H), 6.48–6.53 (m, 1H), 6.77–6.98 (m, 5H), 7.10–7.23 (m, 2H), 7.55 (s, 1H), 8.71–8.79 (m, 1H).

IR (KBr): 1637, 1497, 1304, 1263, 762 cm$^{-1}$.

Elemental analysis for C$_{24}$H$_{26}$N$_4$O$_3$SCl$_2$.2.0H$_2$O Calcd.: C, 51.71; H, 5.42; N, 10.05 Found: C, 51.74; H, 5.34; N, 9.91

Example 42

Synthesis of N-[2-(1-(3-phenylpropan-1-yl)piperidin-4-yl)ethan-1-yl]-5-thia-1,8b-diazaacenaphthylene-4-carboxamide Dihydrochloride 1) Synthesis of N-[2-(1-tert-butoxycarbonyl-4-piperidyl)ethyl]-5-thia-1,8b-diazaacenaphthylene-4-carboxamide In 50 ml of acetonitrile were suspended 4.37 g (20.0 mM) of 5-thia-1,8b-diazaacenaphthylene-4-carboxylic acid and 4.60 g (40.0 mM) of N-hydroxysuccinimide, followed by addition of 7.67 g (40.0 mM) of N-ethyl-N'-3-(N,N-dimethylamino)propylcarbodiimide hydrochloride, and the mixture was stirred at room temperature for 1 hour. The solvent was then distilled off under reduced pressure and the residue was extracted with chloroform. The organic layer was washed with saturated aqueous solution of sodium chloride and dried over MgSO$_4$ and the solvent was distilled off under reduced pressure. The active ester thus obtained was dissolved in 100 ml of chloroform. To this solution were added 5.6 ml (40.0 mM) of triethylamine and 3.08 g (24.0 mM) of 4-(2-aminoethyl)piperidine, and the mixture was stirred at room temperature for 30 minutes. Then, 4.37 g (20.0 mM) of di-tert-butyl dicarbonate was added dropwise and the mixture was further stirred at room temperature for 1 hour. This reaction mixture was washed with water and the organic layer was further washed with saturated aqueous solution of sodium chloride. The organic layer was dried over MgSO$_4$ and the solvent was distilled off under reduced pressure. The residue was purified by column chromatography (ethyl acetate/ethanol=10/1) to provide the title compound.

Red oil. Yield 3.37 g (39%)

$^1$H-NMR (200 MHz, CDCl$_3$) δ: 1.01–1.28 (m, 2H), 1.41–1.58 (m, 12H), 1.62–1.76 (m, 2H), 2.62–2.74 (m, 2H), 3.34 (m, 2H), 4.04–4.11 (m, 2H), 5.79 (dd, J=2.0, 6.0 Hz, 1H), 5.85 (t, J=5.6 Hz, 1H), 6.62–6.71 (m, 3H), 7.04 (s, 1H).

IR (KBr): 1684, 1622, 1547, 1281, 1159 cm$^{-1}$.

2) Synthesis of N-[2-(4-piperidyl)ethyl]-5-thia-1,8b-diazaacenaphthylene-4-carboxamide Dihydrochloride To a solution of 3.37 g (7.86 mM) of N-[2-(1-tert-butoxycarbonyl-4-piperidyl)ethyl]-5-thia-1,8b-diazaacenaphthylene-4-carboxamide in ethanol (100 ml) was added 12N-hydrochloric acid (3.2 ml, 39.3 mM) and the mixture was stirred at room temperature for 1 hour. The resulting crystals were collected by filtration and rinsed with small amounts of ethanol and ether to provide the title compound.

Orange-colored crystals. Yield 2.52 g (80.0%)

$^1$H-NMR (200 MHz, DMSO-d$_6$) δ: 1.22–1.68 (m, 5H), 1.78–1.85 (m, 2H), 2.68–2.91 (m, 2H), 3.10–3.31 (m, 4H), 6.63 (d, J=6.8 Hz, 1H), 7.00 (d, J=9.2 Hz, 1H), 7.24 (s, 1H), 7.31 (dd, J=6.8, 9.2 Hz, 1H), 7.68 (s, 1H), 8.91 (t, J=5.6 Hz, 1H), 9.08 (br s, 2H).

IR (KBr): 1643, 1533, 1290 cm$^{-1}$.

3) Synthesis of N-[2-(1-(3-phenylpropan-1-yl)piperidin-4-yl)ethan-1-yl]-5-thia-1,8b-diazaacenaphthylene-4-carboxamide To a solution of 0.60 g (1.49 mM) of N-[2-(4-piperidyl)ethyl]-5-thia-1,8b-diazaacenaphthylene-4-carboxamide dihydrochloride and 1.0 ml (7.17 mM) of triethylamine in ethanol (6 ml) was added 0.27 ml (1.78 mM) of 3-phenyl-1-bromopropane at room temperature and the mixture was refluxed under nitrogen for 24 hours. The solvent was then distilled off under reduced pressure and the residue was diluted with water and extracted with chloroform. The organic layer was washed with saturated aqueous solution of sodium chloride, dried over MgSO$_4$, and purified by column chromatography (methanol/ethyl acetate 30–50–80%) to provide the title compound.

Red-purple amorphous substance. Yield 514 mg (77%)

$^1$H-NMR (200 MHz, CDCl$_3$) δ: 1.08–2.01 (m, 11H), 2.31–2.39 (m, 2H), 2.62 (t, J=7.7 Hz, 2H), 2.92 (br d, J=11.2 H, 2H), 3.28–3.38 (m, 2H), 5.55–5.68 (m, 1H), 5.78 (dd, J=1.7, 6.5 Hz, 1H), 6.58–6.70 (m, 3H), 7.05 (s, 1H), 7.12–7.33 (m, 5H).

4) Synthesis of N-[2-(1-(3-phenylpropan-1-yl)piperidin-4-yl)ethan-1-yl]-5-thia-1,8b-diazaacenaphthylene-4-carboxamide Dihydrochloride To a solution of 0.5142 g (1.15 mM) of N-[2-(1-(3-phenylpropan-1-yl)piperidin-4-yl)ethan-1-yl]-5-thia-1,8b-diazaacenaphthylene-4-carboxamide in ethanol (10 ml) was added 4 ml (16 mM) of 4N-HCl/methanol at room temperature and the mixture was stirred at room temperature for several minutes. The solvent was distilled off under reduced pressure and diethyl ether was added to the residue. The resulting crystals were collected by filtration and rinsed with ethanol and diethyl ether to provide the title compound.

Orange-colored crystals. Yield 546 mg (88%)

$^1$H-NMR (200 MHz, DMSO-d$_6$) δ: 1.31–1.61 (m, 5H), 1.70–2.14 (m, 4H), 2.63 (t, J=7.5 Hz, 2H), 2.70–3.23 (m, 6H), 3.36–3.52 (m, 2H), 6.59 (d, J=7.4 Hz, 1H), 6.96 (d, J=8.8 Hz, 1H), 7.16 (s, 1H), 7.19–7.37 (m, 6H), 7.63 (s, 1H), 8.74–9.88 (m, 1H).

IR (KBr): 1639, 1560, 1537, 1500, 1444, 1290, 1217, 831, 785 cm$^{-1}$.

Elemental analysis for C$_{26}$H$_{32}$N$_4$OSCl$_2$.1.0H$_2$O Calcd.: C, 58.09; H, 6.38; N, 10.42 Found: C, 58.22; H, 6.12; N, 10.45

Example 43

Synthesis of N-[2-(1-phenethylpiperidin-4-yl)ethan-1-yl]-5-thia-1,8b-diazaacenaphthylene-4-carboxamide Dihydrochloride 1) The procedure of Example 42-3) was generally followed to provide N-[2-(1-phenethylpiperidin-4-yl)ethan-1- yl]-5-thia-1,8b-diazaacenaphthylene-4-carboxamide as red-purple amorphous substance.

$^1$H-NMR (200 MHz, CDCl$_3$) δ: 1.32–1.58 (m, 4H), 1.69–2.20 (m, 5H), 2.63–2.71 (m, 2H), 2.84–2.92 (m, 2H), 3.04–3.18 (m, 2H), 3.31–3.41 (m, 2H), 5.71–5.85 (m, 1H), 5.79 (dd, J=1.8, 6.2 Hz, 1H), 6.59–6.67 (m, 2H), 6.71 (s, 1H), 7.06 (s, 1H), 7.16–7.39 (m, 5H).

2) The procedure of Example 42-4) was generally followed to provide N-[2-(1-phenethylpiperidin-4-yl)ethan-1-yl]-5-thia-1,8b-diazaacenaphthylene-4-carboxamide dihydrochloride as orange-colored crystals.

$^1$H-NMR (200 MHz, DMSO-d$_6$) δ: 1.31–1.62 (m, 5H), 1.77–1.96 (m, 2H), 2.72–3.30 (m, 8H), 3.46–3.60 (m, 2H), 6.61 (d, J=7.4 Hz, 1H), 6.97 (d, J=9.2 Hz, 1H), 7.17 (s, 1H), 7.20–7.42 (m, 6H), 7.65 (s, 1H), 8.80–8.90 (m, 1H).

IR (KBr): 1632, 1564, 1535, 1441, 1290, 1211, 795, 770 cm$^{-1}$.

Example 44

Synthesis of N-[2-(1-(3-(2-chlorophenyl)propan-1-yl)piperidin-4-yl)ethan-1-yl]-5-thia-1,8b-diazaacenaphthylene-4-carboxamide Dihydrochloride 1) Synthesis of N-[2-(1-(3-(2-chlorophenyl)propan-1-yl)piperidin-4-yl)ethan-1-yl]-5-thia-1,8b-diazaacenaphthylene-4-carboxamide To a solution of 409.5 mg (2.4 mM) of 3-(2-chlorophenyl)propanol and 0.7 ml (4.8 mM) of triethylamine in ether (20 ml) was added 412.4 mg (3.6 mM) of methanesulfonyl chloride gradually with ice-cooling and the mixture was stirred at room temperature for 2 hours. To the reaction mixture was added 5% aqueous solution of sodium hydrogen carbonate and the product was extracted into ethyl acetate. The organic layer was washed with saturated aqueous solution of sodium chloride and dried over Na$_2$SO$_4$ and the solvent was distilled off under reduced pressure. To the mesyl compound thus obtained was added a solution of 481.6 mg (1.2 mM) of 2-(piperidin-4-yl)ethan-1-yl-5-thia-1,8b-diazaacenaphthylene-4-carboxamide dihydrochloride and 0.85 ml (6.0 mM) of triethylamine in ethanol (10 ml) and the mixture was refluxed overnight. To this reaction mixture was added 5% aqueous solution of sodium hydrogen carbonate and the reaction product was extracted into ethyl acetate. The organic layer was washed with saturated aqueous solution of sodium chloride and dried over Na$_2$SO$_4$ and the solvent was distilled off under reduced pressure. The residue was purified by silica gel column chromatography (ethyl acetate/methanol=3/1), concentrated, and treated with ether, whereby the title compound was obtained as deep-red amorphous substance (327.9 mg, 56.8%).

$^1$H-NMR (200 MHz, CDCl$_3$) δ: 1.10–1.55 (5H, m), 1.60–2.10 (6H, m), 2.37–2.44 (2H, m), 2.74 (2H, t, J=7.6 Hz), 2.95 (2H, br d, J=11.0 Hz), 3.28–3.38 (2H, m), 5.65–5.80 (1H, m), 5.78 (1H, dd, J=1.9, 6.3 Hz), 6.60–6.70 (3H, m), 7.05 (1H, s), 7.10–7.20 (4H, m).

IR (KBr): 3286, 3057, 2926, 1618, 1545, 1512, 1479, 1442, 1280, 1153, 1053, 970, 870, 754, 677, 650 cm$^{-1}$.

2) Synthesis of N-[2-(1-(3-(2-chlorophenyl)propan-1-yl)piperidin-4-yl)ethan-1-yl]-5-thia-1,8b-diazaacenaphthylene-4-carboxamide Dihydrochloride To a solution of 327.9 mg (0.68 mM) of N-[2-(1-(3-(2-chlorophenyl)propan-1-yl)piperidin-4-yl)ethan-1-yl]-5-thia-1,8b-diazaacenaphthylene-4-carboxamide in ethanol (10 ml) was added 2 ml (8.0 mM) of 4N-HCl/ethyl acetate and the mixture was stirred for several minutes. The solvent was then distilled off under reduced pressure and ether was added to the residue. The resulting crystals were collected by filtration and rinsed with ethanol and diethyl ether to provide the title compound as orange-colored crystals (364.0 mg, 91%).

$^1$H-NMR (200 MHz, CD$_3$OD) δ: 1.30–1.80 (5H, m), 1.90–2.10 (4H, m), 2.90–3.40 (8H, m), 3.50–3.70 (2H, m), 6.60 (1H, d, J=6.8 Hz), 6.96–7.00 (2H, m), 7.10–7.45 (5H, m), 7.51 (1H, s).

IR (KBr): 3427, 3057, 2939, 2727, 1632, 1566, 1535, 1502, 1473, 1439, 1390, 1292, 1215, 1051, 951, 762 cm$^{-1}$.

Elemental analysis for C$_{26}$H$_{31}$N$_4$OSCl$_2$.2.0H$_2$O Calcd.: C, 52.93; H, 5.98; N, 9.50 Found: C, 52.95; H, 5.75; N, 9.41

Example 45

Synthesis of N-[2-(1-(2-chlorophenethyl)piperidin-4-yl)ethan-1-yl]-5-thia-1,8b-diazaacenaphthylene-4-carboxamide Dihydrochloride 1) The procedure of Example 44-1) was generally followed to provide N-[2-(1-(2-chlorophenethyl)piperidin-4-yl)ethan-1-yl]-5-thia-1,8b-diazaacenaphthylene-4-carboxamide as deep red amorphous substance.

$^1$H-NMR (200 MHz, CDCl$_3$) δ: 1.25–1.55 (5H, m), 1.60–1.85 (2H, m), 1.95–2.15 (2H, m), 2.54–2.62 (2H, m), 2.91–3.06 (4H, m), 3.30–3.40 (2H, m), 6.60–6.75 (1H, m), 5.79 (1H, dd, J=1.6, 6.0 Hz), 6.59–6.71 (3H, m), 7.05 (1H, s), 7.10–7.36 (4H, m).

IR (KBr): 3334, 3062, 2927, 1618, 1543, 1512, 1479, 1441, 1371, 1342, 1281, 1211, 1153, 1111, 1051, 970, 771, 752, 729 cm$^{-1}$.

2) The procedure of Example 44-2) was generally followed to provide N-[2-(1-(2-chlorophenethyl)piperidin-4-yl)ethan-1-yl]-5-thia-1,8b-diazaacenaphthylene-4-carboxamide dihydrochloride as orange-colored crystals.

$^1$H-NMR (200 MHz, CD$_3$OD) δ: 1.40–1.90 (5H, m), 1.95–2.20 (2H, m), 3.00–3.40 (8H, m), 3.60–3.80 (2H, m), 6.61 (1H, d, J=7.4 Hz), 6.97–7.01 (2H, m), 7.25–7.50 (5H, m), 7.52 (1H, s).

IR (KBr): 3425, 2941, 2665, 2532, 1632, 1566, 1537, 1502, 1473, 1394, 1338, 1286, 1215, 1111, 783 cm$^{-1}$.

Elemental analysis for C$_{25}$H$_{29}$N$_4$OSCl$_3$.1.0H$_2$O Calcd.: C, 53.82; H, 5.60; N, 10.04 Found: C, 54.06; H, 5.66; N, 9.97

Example 46

Synthesis of N-[3-(1-(3-phenylpropan-1-yl)piperidin-4-yl)propan-1-yl]-5-thia-1,8b-diazaacenaphthylene-4-carboxamide Dihydrochloride 1) Synthesis of N-[3-(1-tert-butoxycarbonyl-4-piperidyl)propan-1-yl]-5-thia-1,8b-diazaacenaphthylene-4-carboxamide In acetonitrile (120 ml) was suspended 6.55 g (30.0 mM) of 5-thia-1,8b-diazaacenaphthylene-4-carboxylic acid as well as 6.91 g (60.0 mM) of N-hydroxysuccinimide, followed by additino of 11.50 g (60.0 mM) of N-ethyl-N'-3-(N,N-dimethylamino)propylcarbodiimide hydrochloride, and the mixture was stirred at room temperature for 1 hour. The solvent was then distilled off under reduced pressure and the residue was extracted with chloroform. The organic layer was washed with saturated aqueous solution of sodium chloride and dried over MgSO$_4$ and the solvent was distilled off under reduced pressure to provide the active ester. To a solution of this active ester in chloroform (100 ml) was added 8.4 ml (60.0 mM) m of triethylamine as well as 8.72 g (36.0 mM) of 3-(1-tert-butoxycarbonyl-4-piperidyl)propylamine and the mixture was stirred at room temperature for 30 minutes. This reaction mixture was washed with purified water and the organic layer was further washed with saturated m aqueous solution of sodium chloride. After the organic layer was dried over MgSO$_4$, the solvent was distilled off under reduced pressure and the residue was purified by column chromatography (ethyl acetate/ethanol= 10/1) to provide the title compound. Red solid. Yield 10.16 g (76%)

$^1$H-NMR (200 MHz, CDCl$_3$) δ: 0.95–1.41 (m, 4H), 1.45 (s, 9H), 1.48–1.72 (m, 5H), 2.61–2.73 (m, 2H), 3.28 (m, 2H), 4.05–4.14 (m, 2H), 5.79 (dd, J=2.2, 5.8 Hz, 1H), 6.02 (t, J=5.6 Hz, 1H), 6.63–6.70 (m, 3H), 7.02 (s, 1H).

IR (KBr): 1684, 1624, 1278, 1161 cm$^{-1}$.

2) Synthesis of N-[3-(4-piperidyl)propan-1-yl]-5-thia-1,8b-diazaacenaphthylene-4-carboxamide Dihydrochloride To a solution of 10.12 g (22.87 mM) of N-[3-(1-tert-butoxycarbonyl-4-piperidyl)propan-1-yl]-5-thia- 1,8b-diazaacenaphthylene-4-carboxamide in 100 ml of ethanol was added 9.4 ml (114.33 mM) of 12N-hydrochloric acid and the mixture was stirred at room temperature for 1 hour. The resulting precipitate was recovered by filtration and rinsed with small amounts of ethanol and ether to provide 8.79 g (92.5%) of the title compound as orange-colored crystals.

$^1$H-NMR (200 MHz, DMSO-d$_6$) δ: 1.13–1.59 (m, 7H), 1.74–1.80 (m, 2H), 2.68–2.93 (m, 2H), 3.04–3.30 (m, 4H), 6.62 (d, 1H), 7.00 (d, J=9.2 Hz, 1H), 7.18 (s, 1H), 7.30 (dd, J=7.4, 9.2 Hz, 1H), 7.67 (s, 1H), 8.84 (t, J=5.6 Hz, 1H), 8.88–9.15 (br s, 2H).

IR (KBr): 1637, 1564, 1518 cm$^{-1}$.

3) Synthesis of N-[3-(1-(3-phenylpropan-1-yl)piperidin-4-yl)propan-1-yl]-5-thia-1,8b-diazaacenaphthylene-4-carboxamide To a solution of 1.0 g (2.41 mM) of N-[3-(4-piperidyl)propan-1-yl]-5-thia-1,8b-diazaacenaphthylene-4-carboxamide dihydrochloride and 1.7 ml (12.2 mM) of triethylamine in ethanol (10 ml) was added 0.45 ml (2.96 mM) of 1-bromo-3-phenylpropane at room temperature and the mixture was refluxed under nitrogen for 20 hours. The solvent was then distilled off under reduced pressure and the residue was diluted with water and extracted with chloroform. The organic layer was washed with saturated aqueous solution of sodium chloride, dried over MgSO$_4$, and purified by column chromatography (methanol/ethyl acetate 30–50–100%) to provide the title compound.

Red-purple amorphous substance. Yield 811 mg (73%)

$^1$H-NMR (200 MHz, CDCl$_3$) δ: 1.17–1.38 (m, 4H), 1.44–2.03 (m, 9H), 2.34–2.41 (m, 2H), 2.62 (t, J=7.7 Hz, 2H), 2.86–3.02 (m, 2H), 3.29 (q, J=6.6 Hz, 2H), 5.61–5.73 (m, 1H), 5.79 (dd, J=1.6, 6.4 Hz, 1H), 6.58–6.70 (m, 3H), 7.05 (s, 1H), 7.11–7.33 (m, 5H).

4) Synthesis of N-(3-(1-(3-phenylpropan-1-yl)piperidin-4-yl)propan-1-yl]-5-thia-1,8b-diazaacenaphthylene-4-carboxamide Dihydrochloride To a solution of 0.8113 g (1.76 mM) of N-[3-(1-(3-phenylpropan-1-yl)piperidin-4-yl)propan-1-yl]-5-thia-1,8b-diazaacenaphthylene-4-carboxamide in ethanol (10 ml) was added 6 ml (24 mM) of 4N-HCl/methanol at room temperature and the mixture was stirred at room temperature for several minutes. The solvent was then distilled off under reduced pressure, and after addition of diethyl ether to the crystalline residue, the crystal crop was harvested by filtration and rinsed with ethanol and diethyl ether to provide the title compound.

Orange-colored crystals. Yield 821 mg (85%)

$^1$H-NMR (200 MHz, DMSO-d$_6$) δ: 1.04–1.28 (m, 2H), 1.32–1.62 (m, 5H), 1.65–1.88 (m, 2H), 1.93–2.12 (m, 2H), 2.37–2.68 (m, 2H), 2.72–3.20 (m, 6H), 3.31–3.51 (m, 2H), 6.53 (d, J=7.2 Hz, 1H), 6.93 (d, J=8.8 Hz, 1H), 7.07 (s, 1H), 7.12–7.38 (m, 6H), 7.58 (s, 1H), 8.61–8.77 (m, 1H).

IR (KBr): 1635, 1562, 1529, 1446, 1300, 1217 cm$^{-1}$.

Elemental analysis for $C^{27}H_{34}N_4OSCl_2 \cdot 1.0H_2O$ Calcd.: C, 58.79; H, 6.58; N, 10.16 Found C, 58.66; H, 6.74; N, 10.12

Example 47

Synthesis of N-[3-(1-phenethylpiperidin-4-yl)propan-1-yl]-5-thia-1,8b-diazaacenaphthylene-4-carboxamide Dihydrochloride 1) The procedure of Example 46-3) was generally followed to provide N-[3-(1-phenethylpiperidin-4-yl)propan-1-yl]-5-thia-1,8b-diazaacenaphthylene-4-carboxamide as red-purple amorphous substance.

$^1$H-NMR (200 MHz, CDCl$_3$) δ: 1.21–2.16 (m, 11H), 2.57–2.66 (m, 2H), 2.81–2.89 (m, 2H), 2.92–3.12 (m, 2H), 3.24–3.34 (m, 2H), 5.66–5.77 (m, 1H), 5.80 (dd, J=1.71 6.3 Hz, 1H), 6.58–6.73 (m, 3H), 7.06 (s, 1H), 7.14–7.37 (m, 5H).

2) The procedure of Example 46-4) was generally followed to provide N-[3-(1-phenethylpiperidin-4-yl)propan-1-yl]-5-thia-1,8b-diazaacenaphthylene-4-carboxamide dihydrochloride as orange-colored crystals.

$^1$H-NMR (200 MHz, DMSO-d$_6$) δ: 1.94–2.21 (m, 2H), 2.66 (br t, J=7.7 Hz, 2H), 3.09–3.90 (m, 14H), 6.60 (d, J=7.4 Hz, 1H), 6.97 (d, J=9.0 Hz, 1H), 7.16–7.37 (m, 7H), 7.65 (s, 1H), 9.03–9.16 (m, 1H).

IR(KBr):1639, 1564, 1535, 1500, 1446, 1292, 1217 cm$^{-1}$.

Elemental analysis for $C_{26}H_{32}N_4OSCl_2 \cdot 0.5H_2O$ Calcd.: C, 59.08; H, 6.29; N, 10.60 Found: C, 59.03; H, 6.21; N, 10.52

Example 48

Synthesis of N-[3-(1-(3-(2-chlorophenyl)propan-1-yl)piperidin-4-yl)propan-1-yl]-5-thia-1,8b-diazaacenaphthylene-4-carboxamide Dihydrochloride 1) Synthesis of N-[3-(1-(3-(2-chlorophenyl)propan-1-yl)piperidin-4-yl)propan-1-yl)-5-thia-1,8b-diazaacenaphthylene-4-carboxamide To a solution of 682.6 mg (4.0 mM) of 3-(2-chlorophenyl)propanol and 809.5 mg (8.0 mM) of triethylamine in ether (20 ml) was added 687.3 mg (6.0 mM) of methanesulfonyl chloride gradually with ice cooling and the mixture was stirred at that temperature for 5 minutes and further at room temperature for 30 minutes. To this reaction mixture was added 5% aqueous solution of sodium hydrogen carbonate and the reaction product was extracted into ethyl acetate. The organic layer was washed with water and dried over Na$_2$SO$_4$ and the solvent was distilled off under reduced pressure. To the resulting mesyl compound was added a solution of 830.8 mg (2.0 mM) of N-[3-(4-piperidyl)propan-1-yl]-5-thia-1,8b-diazaacenaphthylene-4-carboxamide dihydrochloride and 1.15 g (10 mM) of triethylamine in ethanol (10 ml) and the mixture was refluxed overnight. To this reaction mixture was added 5% aqueous solution of sodium hydrogen carbonate and the reaction product was extracted into ethyl acetate. The organic layer was washed with water and dried over $Na_2SO_4$ and the solvent was then distilled off under reduced pressure. The residue was purified by silica gel column chromatography (ethyl acetate/methanol=3/1) to provide the title compound as reddish orange-colored amorphous substance (580.0 mg, 58.6%).

$^1$H-NMR (200 MHz, $CDCl_3$) δ: 1.10–1.40 (4H, m), 1.40–2.00 (9H, m), 2.38 (2H, t, J=7.5 Hz), 2.69 (2H, t, J=7.8 Hz), 2.93 (2H, br d, J=11.0 Hz), 3.22–3.32 (2H, m), 5.78 (1H, dd, J=1.8, 6.2 Hz), 5.80–5.90 (1H, m), 6.57–6.70 (3H, m), 7.03 (1H, s), 7.05–7.35 (4H, m).

IR (neat): 3307, 2927, 1618, 1556, 1477, 1443, 1281, 1151, 1055, 754 $cm^{-1}$.

2) Synthesis of N-[3-(1-(3-(2-chlorophenyl)propan-1-yl)piperidin-4-yl)propan-1-yl]-5-thia-1,8b-diazaacenaphthylene-4-carboxamide Dihydrochloride To a solution of 580.0 mg (1.2 mM) of N-[3-(1-(3-(2-chlorophenyl)propan-1-yl)piperidin-4-yl)propan-1-yl]-5-thia-1,8b-diazaacenaphthylene-4-carboxamide in ethanol (10 ml) was added 2 ml (8.0 mM) of 4N-HCl/ethyl acetate and the mixture was stirred for several minutes. The solvent was then distilled off under reduced pressure and ether was added to the residue. The resulting crystal crop was harvested by filtration and rinsed with ethanol and diethyl ether to provide the title compound as orange-colored crystals (605.4 mg, 91%).

$^1$H-NMR (200 MHz, $CD_3OD$) δ: 1.25–1.80 (8H, m), 1.90–2.20 (4H, m), 2.75–3.05 (4H, m), 3.05–3.35 (3H, m), 3.54–3.60 (2H, m), 6.60 (1H, d, J=7.4 Hz), 6.92–7.00 (2H, m), 7.15–7.45 (5H, m), 7.50 (1H, s).

IR (KBr): 3464, 3215, 3049, 2939, 2656, 1635, 1568, 1539, 1502, 1473, 1437, 1298, 1219, 781, 756 $cm^{-1}$.

Elemental analysis for $C_{27}H_{33}N_4OSCl_3.0.5H_2O$ Calcd.: C, 56.20; H, 5.94; N, 9.71 Found C, 56.29; H, 5.80; N, 9.61

Example 49

Synthesis of N-[3-(1-(2-chlorophenethylpiperidin-4-yl)-propan-1-yl)-5-thia-1,8b-diazaacenaphthylene-4-carboxamide Dihydrochloride 1) The procedure of Example 48-1) was generally followed to provide N-[3-(1-(2-chlorophenethyl)piperidin-4-yl)propan-1-yl]-5-thia-1,8b-diazaacenaphthylene-4-carboxamide as deep-red solid.

$^1$H-NMR (200 MHz, $CDCl_3$) δ: 1.10–1.40 (2H, m), 1.40–1.80 (4H, m), 1.90–2.30 (3H, m), 2.50–2.65 (2H, m), 2.80–3.15 (4H, m), 3.20–3.40 (2H, m), 3.43–3.54 (2H, m), 5.75–6.00 (2H, m), 6.55–6.80 (3H, m), 7.04 (1H, s), 7.05–7.40 (4H, m).

IR (KBr): 3390, 3265, 2927, 1740, 1697, 1643, 1618, 1558, 1514, 1481, 1371, 1286, 1153, 1119, 889, 771, 727, 675 $cm^{-1}$.

2) The procedure of Example 48-2) was generally followed to provide N-[3-(1-(2-chlorophenethyl)piperidin-4-yl)propan-1-yl]-5-thia-1,8b-diazaacenaphthylene-4-carboxamide dihydrochloride as light-orange-colored crystals.

$^1$H-NMR (200 MHz, $CD_3OD$) δ: 1.25–1.70 (7H, m), 1.90–2.10 (2H, m), 2.95–3.40 (8H, m), 3.60–3.75 (2H, m), 6.60 (1H, d, J=7.8 Hz), 6.90 (1H, s), 6.98 (1H, d, J=9.2 Hz), 7.25–7.55 (6H, m).

IR (KBr): 3427, 3053, 2937, 2856, 2652, 1635, 1564, 1537, 1504, 1292, 1217, 771 $cm^{-1}$.

Elemental analysis for $C_{26}H_{31}N_4OSCl_3.0.5H_2O$ Calcd.: C, 55.47; H, 5.73; N, 9.95 Found: C, 55.72; H, 5.79; N, 9.96

Example 50

Synthesis of N-[3-(1-(1,4-benzodioxan-2-ylmethyl) piperidin-4-yl)propan-1-yl]-5-thia-1,8b-diazaacenaphthylene-4-carboxamide Dihydrochloride 1) The procedure of Example 48-1) was generally followed to provide N-[3-(1-(1,4-benzodioxan-2-ylmethyl) piperidin-4-yl)propan-1-yl]-5-thia-1,8b-diazaacenaphthylene-4-carboxamide as reddish orange-colored amorphous substance.

$^1$H-NMR (200 MHz, $CDCl_3$)δ: 1.10–1.40 (4H, m), 1.40–1.80 (5H, m), 1.90–2.20 (2H, m), 2.49–2.71 (2H, m), 2.86–2.30 (2H, m), 3.23–3.33 (2H, m), 3.92–4.01 (1H, m), 4.20–4.40 (2H, m), 5.79 (1H, dd, J=1.8, 6.0 Hz), 5.80–5.95 (1H, m), 6.58–6.72 (3H, m), 6.75–6.98 (4H, m), 7.04 (1H, s).

IR (KBr): 3321, 2926, 1616, 1543, 1495, 1265, 1155, 1082, 1041, 750 $cm^{-1}$.

2) The procedure of Example 48-2) was generally followed to provide N-[3-(1-(1,4-benzodioxan-2-ylmethyl) piperidin-4-yl)propan-1-yl]-5-thia-1,8b-diazaacenaphthylene-4-carboxamide dihydrochloride as orange-colored crystals.

$^1$H-NMR (200 MHz, $CD_3OD$) δ: 1.25–1.80 (7H, m), 1.85–2.10 (2H, m), 3.05–3.32 (5H, m), 3.35–3.40 (2H, m), 3.60–3.85 (2H, m), 4.03 (1H, dd, J=6.3 Hz, 11.3 Hz), 4.32 (1H, dd, J=2.4, 11.6 Hz), 6.61 (1H, d, J=7.6 Hz), 6.80–7.05 (6H, m), 7.34–7.43 (1H, m), 7.51 (1H, s).

IR (KBr): 3425, 3062, 2933, 1632, 1564, 1537, 1495, 1265, 758 $cm^{-1}$.

Elemental analysis for $C_{27}H_{32}N_4O_3SCl_2.0.5H_2O$ Calcd.: C, 56.20; H, 5.94; N, 9.71 Found C, 56.29; H, 5.80; N, 9.61

Example 51

Synthesis of N-methyl-N-[1-(3-phenylpropan-1-yl) piperidin-4-ylmethyl]-5-thia-1,8b-diazaacenaphthylene- 4-carboxamide Dihydrochloride 1) Synthesis of N-methyl-N-(1-tert-butoxycarbonylpiperidin-4-ylmethyl)-5-thia-1,8b-diazaacenaphthylene-4-carboxamide To a solution of 0.58 g (1.84 mM) of 5-thia-1,8b-diazaacenaphthylene-4-carboxylic acid N-hydroxysuccinimide ester, synthesized in the same manner as Example 42-1), in acetonitrile (6 ml) was added a solution of 0.50 g (2.19 mM) of tert-butyl 4-[(methylamino) methyl]piperidine-1-carboxylic acid and 1.0 ml (7.2 mM) of triethylamine in acetonitrile (3 ml) at room temperature and the mixture was stirred at room temperature for 13 hours. The solvent was then distilled off under reduced pressure and the residue was diluted with water and extracted with methylene chloride. The organic layer was washed with saturated aqueous solution of sodium chloride, dried over $MgSO_4$, and purified by column chromatography (methanol/ethyl acetate 30%) to provide the title compound.

Red-purple solid. Yield 771 mg (98%)

$^1$H-NMR (200 MHz, $CDCl_3$) δ: 1.06–1.31 (m, 2H), 1.45 (s, 9H), 1.51–1.98 (m, 3H), 2.58–2.78 (m, 2H), 3.11 (br s, 3H), 3.21–3.40 (m, 2H), 4.01–4.22 (m, 2H), 5.74 (dd, J=1.8, 6.1 Hz, 1H), 6.06 (s, 1H), 6.55–6.68 (m, 2H), 6.94 (s, 1H).

2) Synthesis of N-methyl-N-(piperidin-4-ylmethyl)-5-thia-1,8b-diazaacenaphthylene-4-carboxamide Dihydrochloride To a solution of 0.7716 g (1.8 mM) of N-methyl-N-(1-tert-butoxycarbonylpiperidin-4-ylmethyl)-5-thia-1,8b-diazaacenaphthylene-4-carboxamide in ethanol (5 ml) was added 0.8 ml (9.6 mM) of 12N-hydrochloric acid at room temperature and the mixture was stirred for 18 hours. The solvent was then distilled off under reduced pressure, and 2 ml (24 mM) of 12N-hydrochloric acid was added to the residue. The mixture was stirred for 5 minutes, after which ethanol was added and the solvent was distilled off under reduced pressure. To the residue was further added ethanol and the ethanol, was distilled off under reduced pressure. The resulting crystals were collected by filtration and rinsed serially with ethanol, acetone, and diethyl ether to provide the title compound.

Orange-colored solid. Yield 494.1 mg (68%)

$^1$H-NMR (200 MHz, $D_2O$) δ: 1.30–1.61 (m, 2H), 1.70–1.96 (m, 2H), 2.02–2.23 (m, 1H), 2.86–3.08 (m, 3H), 3.15–3.53 (m, 6H), 6.13 (d, J=7.4 Hz, 1H), 6.37 (s, 1H), 6.75 (d, J=9.2 Hz, 1H), 6.94 (dd, J=7.4 Hz, 9.2 Hz, 1H), 7.07 (s, 1H).

3) Synthesis of N-methyl-N-[1-(3-phenylpropan-1-yl)piperidin-4-ylmethyl]-5-thia-1,8b-diazaacenaphthylene-4-carboxamide To a solution of 464.3 mg (1.16 mM) of N-methyl-N-(piperidin-4-ylmethyl)-5-thia-1,8b-diazaacenaphthylene-4-carboxamide dihydrochloride and 0.8 ml (5.74 mM) of triethylamine in ethanol was added 0.21 ml (1.38 mM) of 1-bromo-3-phenylpropane at room temperature, and the mixture was refluxed under nitrogen for 15 hours. The solvent was then distilled off under reduced pressure and the residue was diluted with water and extracted with methylene chloride. The organic layer was washed with saturated aqueous solution of sodium chloride, dried over $MgSO_4$, and purified by column chromatography (methanol/ethyl acetate 20–50%) to provide the title compound.

Red-purple solid. Yield 346 mg (67%)

$^1$H-NMR (200 MHz, $CDCl_3$) δ: 1.20–1.45 (m, 2H), 1.50–1.98 (m, 7H), 2.32–2.39 (m, 2H), 2.62 (t, J=7.7 Hz, 2H), 2.84–3.00 (m, 2H), 3.06 (br s, 3H), 3.35 (d, J=7.0 Hz, 2H), 5.71 (dd, J=1.6, 6.4 Hz, 1H), 6.04 (s, 1H), 6.53–6.67 (m, 2H), 6.93 (s, 1H), 7.13–7.32 (m, 5H).

4) Synthesis of N-methyl-N-[1-(3-phenylpropan-1-yl)piperidin-4-ylmethyl]-5-thia-1,8b-diazaacenaphthylene-4-carboxamide Dihydrochloride To a solution of 346.1 mg (0.77 mM) of N-methyl-N-[1-(3-phenylpropan-1-yl)piperidin-4-ylmethyl]-5-thia-1,8b-diazaacenaphthylene-4-carboxamide in ethanol (4 ml) was added 2.0 ml (8.0 mM) of 4N-HCl/methanol and the mixture was stirred at room temperature for 20 minutes. The solvent was then distilled off under reduced pressure to provide the title compound.

Orange-colored amorphous solid. Yield 397 mg (90%)

$^1$H-NMR (200 MHz, DMSO-$d_6$) δ: 1.40–2.18 (m, 7H), 2.63 (t, J=7.7 Hz, 2H), 2.73–3.55 (m, 11H), 6.65 (d, J=7.6 Hz, 1H), 6.60 (br s, 1H), 7.03 (d, J=9.2 Hz, 1H), 7.21–7.35 (m, 6H), 7.50 (s, 1H).

IR (KBr): 3417, 2935, 2721, 1628, 1498, 1448 cm$^{-1}$.

Elemental analysis for $C_{26}H_{32}N_4OSCl_2 \cdot 3.0H_2O$ Calcd.: C, 54.44; H, 6.68; N, 9.77 Found: C, 54.32; H, 6.62; N, 9.64

Example 52

Synthesis of N-benzyl-N-[1-(3-phenylpropan-1-yl)piperidin-4-ylmethyl]-5-thia-1,8b-diazaacenaphthylene Dihydrochloride 1) Synthesis of N-benzyl-N-(1-tert-butoxycarbonylpiperidin-4-ylmethyl)-5-thia-1,8b-diazaacenaphthylene To a solution of 1.26 g (4.0 mM) of 5-thia-1,8b-diazaacenaphthylene-4-carboxylic acid N-hydroxysuccinimide ester, synthesized in the same manner as Example 42-1), in acetonitrile (12 ml) was added a solution of 1.40 g (4.79 mM) of tert-butyl 4-benzylaminomethyl)piperidine-1-carboxylic acid and 1.2 ml (8.6 mM) of triethylamine in acetonitrile (6 ml) at room temperature and the mixture was stirred at room temperature for 17 hours and further at 40° C. for 3 days. The solvent was then distilled off under reduced pressure and the residue was diluted with water and extracted with methylene chloride. The organic layer was washed with saturated aqueous solution of sodium chloride and dried over $MgSO_4$. The attempt made to purify the residue by column chromatography (methanol/ethyl acetate 20% methanol/chloroform=1/15) failed. Thus, a crude product (0.5162 g) was obtained.

2) Synthesis of N-benzyl-N-(piperidin-4-ylmethyl)-5-thia-1,8b-diazaacenaphthylene Dihydrochloride To a solution of crude N-benzyl-N-(1-tert-butoxycarbonylpiperidin-4-ylmethyl)-5-thia-1,8b-diazaacenaphthylene (0.5162 g) in ethanol (2 ml) was added 1.0 ml (12 mM) of 12N-hydrochloric acid and the mixture was -stirred at room temperature for 15 hours. The solvent was then distilled off under reduced pressure and the residue was diluted with water and washed with chloroform. Then, water was distilled off under reduced pressure to provide a crude product (0.451 g) as orange-colored solid.

3) Synthesis of N-benzyl-N-[1-(3-phenylpropan-1-yl)piperidin-4-ylmethyl]-5-thia-1,8b-diazaacenaphthylene To a solution of crude N-benzyl-N-(piperidin-4-ylmethyl)-5-thia-1,8b-diazaacenaphthylene dihydrochloride (0.451 g) and 0.7 ml (5.0 mM) of triethylamine in ethanol (4 ml) was added 0.17 ml (1.1 mM) of 1-bromo-3-phenylpropane at room temperature, and the mixture was refluxed under nitrogen for 15 hours. The solvent was then distilled off under reduced pressure and the residue was diluted with water and extracted with methylene chloride. The organic layer was washed with saturated aqueous solution of sodium chloride and dried over $MgSO_4$. The attempt to purify the residue by column chromatography (methanol/chloroform=1/50–1/15, 1/20) failed. Thus, the crude product was recovered as red-purple solid (245 mg).

$^1$H-NMR (200 MHz, $CDCl_3$) δ: 1.14–1.44 (m, 2H), 1.51–2.01 (m, 7H), 2.32–2.39 (m, 2H), 2.61 (t, J=7.7 Hz, 2H), 2.93 (br d, J=11.4 Hz, 2H), 3.25 (d, J=6.6 Hz, 2H), 4.69 (br s, 2H), 5.70 (dd, J=1.4, 6.4 Hz, 1H), 6.04 (s, 1H), 6.52–6.65 (m, 2H), 6.88 (s, 1H), 7.09–7.42 (m, 10H).

4) Synthesis of N-benzyl-N-[1-(3-phenylpropan-1-yl)-piperidin-4-ylmethyl]-5-thia-1,8b-diazaacenaphthylene Dihydrochloride To a solution of 245.4 mg (ca 0.47 mM) of crude N-benzyl-N-[1-(3-phenylpropan-1-yl)piperidin-4-ylmethyl]-5-thia-1,8b-diazaacenaphthylene in ethanol (4 ml) was added 1.0 ml (4.0 mM) of 4N-HCl/methanol at room temperature, and the mixture was stirred for 20 minutes. The solvent was then distilled off under reduced pressure and diethyl ether was added to the crystalline residue. The crystal crop was then harvested by filtration to provide the title compound as orange-colored solid.

Orange-colored crystals. Yield 174 mg (7%, 4 steps)

$^1$H-NMR (200 MHz, DMSO-$d_6$) δ: 1.40–1.78 (m, 4H), 1.89–2.13 (m, 3H), 2.63 (t, J=7.7 Hz, 2H), 2.71–3.53 (m, 8H), 4.66–4.87 (m, 2H), 6.64 (d, J=7.4 Hz, 1H), 6.69 (s, 1H), 7.02 (d, J=9.2 Hz, 1H), 7.16–7.50 (m, 12H).

IR (KBr): 3425, 2937, .2667, 1630, 1498, 1439 cm$^{-1}$.

Elemental analysis for $C_{32}H_{36}N_4OSCl_2 \cdot 2.5H_2O$ Calcd.: C, 59.99; H, 6.45; N, 8.75 Found: C, 60.26; H, 6.59; N, 8.53

Example 53

Synthesis of N-[2-(3-phenylpropan-1-ylamino) ethan-1-yl]-5-thia-1,8b-diazaacenaphthylene-4-carboxamide Dihydrochloride

To a suspension of 1.09 g (ca 3.2 mM) of 5-thia-1,8b-diazaacenaphthylene-4-carboxylic acid and 1.15 g (10 mM) of N-hydroxysuccinimide in acetonitrile (15 ml) was added 1.92 g (10 mM) of N-ethyl-N'-3-(N,N-dimethylamino) propylcarbodiimide hydrochloride at room temperature, and the mixture was stirred for 2 hours. The solvent was then distilled off under reduced pressure and the residue was diluted with water and extracted with chloroform. The organic layer was washed with saturated aqueous solution of sodium chloride and dried over $MgSO_4$ and the solvent was distilled off under reduced pressure to provide a crude active ester (1.63 g). To a solution of this crude active ester (1.63 g) and 1.4 ml (10 mM) of triethylamine in acetonitrile (15 ml) was added 1.67 g (6.00 mM) of tert-butyl N-(2-aminoethan-1-yl)-3-phenylpropan-1-ylaminocarboxylate at room temperature, and the mixture was stirred at room temperature for 1 hour. The solvent was then distilled off under reduced pressure and the residue was diluted with water and extracted with methylene chloride. The organic layer was washed with saturated aqueous solution of sodium chloride and dried over $MgSO_4$ and the solvent was distilled off under reduced pressure. The crude residue was subjected to column chromatography (methanol/ethyl acetate 10%), whereby a crude product (2.13 g, containing impurities) was obtained. To 413 mg (0.80 mM) of this crude product was added 1.5 ml (18 mM) of 12N-hydrochloric acid, and the mixture was stirred for several minutes. Then, ethanol and diethyl ether were added to the reaction mixture and the resulting crystals were collected by filtration and rinsed serially with ethanol, acetone, and diethyl ether to provide the title compound.

Orange-colored crystals. Yield 329 mg (91%)

$^1$H-NMR (200 MHz, DMSO-$d_6$) δ: 1.84–2.03 (m, 2H), 2.67 (t, J=7.7 Hz, 2H), 2.84–3.09 (m, 4H), 3.39–3.51 (m, 2H), 6.60 (d, J=6.8 Hz, 1H), 6.96 (d, J=8.4 Hz, 1H), 7.16–7.37 (m, 7H), 7.65 (s, 1H), 9.00– 9.18 (m, 2H).

IR (KBr): 3431, 3236, 1636, 1568, 1502, 1292, 785 $cm^{-1}$.

Elemental analysis for $C_{21}H_{24}N_4OSCl_2 \cdot 0.1H_2O$ Calcd.: C, 55.65; H, 5.38; N, 12.36 Found: C, 55.44; H, 5.19; N, 12.35

Example 54

The procedure of Example 53 was generally followed to provide N-[3-(3-phenylpropan-1-ylamino)propan-1-yl]-5-thia-1,8b-diazaacenaphthylene-4-carboxamide dihydrochloride as orange-colored crystals.

$^1$H-NMR (200 MHz, DMSO-$d_6$) δ: 1.73–2.01 (m, 4H), 2.67 (t, J=7.7 Hz, 2H), 2.81–2.97 (m, 4H), 3.15–3.26 (m, 2H), 6.61 (d, J=7.4 Hz, 1H), 6.97 (d, J=9.0 Hz, 1H), 7.20–7.33 (m, 7H), 7.65 (s, 1H), 8.95–9.15 (m, 1H).

IR (KBr): 3436, 2947, 2792, 1635, 1294 $cm^{-1}$.

Example 55

The procedure of Example 53 was generally followed to provide N-[4-(3-phenylpropan-1-ylamino)butan-1-yl]-5-thia-1,8b-diazaacenaphthylene-4-carboxamide dihydrochloride as orange-colored crystals.

$^1$H-NMR (200 MHz, DMSO-$d_6$) δ: 1.32–1.70 (m, 4H), 1.86–2.01 (m, 2H), 2.66 (t, J=7.7 Hz, 2H), 2.77–2.93 (m, 4H), 3.06–3.19 (m, 2H), 6.60 (d, J=6.8 Hz, 1H), 6.97 (d, J=8.4 Hz, 1H), 7.15–7.34 (m, 7H), 7.64 (s, 1H), 8.82–9.10 (m, 1H).

IR (KBr): 3411, 2944, 2786, 1637, 1565, 1292 $cm^{-1}$.

Elemental analysis for $C_{23}H_{28}N_4OSCl_2$ Calcd.: C, 57.62; H, 5.89; N, 11.69 Found: C, 57.32; H, 5.91; N, 11.57

Example 56

Synthesis of N-[3-(N-methyl-N-(3-phenylpropan-1-yl)amino)propan-1-yl]-5-thia-1,8b-diazaacenaphthylene-4-carboxamide Dihydrochloride

1) Synthesis of N-[3-(N-methyl-N-(3-phenylpropan-1-yl)amino)propan-1-yl]-5-thia-1,8b-diazaacenaphthylene-4-carboxamide To a solution of 0.50 g (1.59 mM) of 5-thia-1,8b-diazaacenaphthylene-4-carboxylic acid N-hydroxysuccinimide ester, synthesized in the same manner as Example 42-1), in acetonitrile (6 ml) was added a solution of 0.39 g (1.89 mM) of [3-(N-methyl-N-(3-phenylpropan-1-yl)amino)propan-1-yl]amine and 0.5 ml (3.59 mM) of triethylamine in acetonitrile (4 ml) at room temperature, and the mixture was stirred for 5 minutes. The solvent was then distilled off under reduced pressure and the residue was diluted with water and extracted with methylene chloride. The organic layer was washed with saturated aqueous solution of sodium chloride, dried over $MgSO_4$, and purified by column chromatography (methanol/ethyl acetate 80–100%) to provide the title compound.

Red-purple oil. Yield 577 mg (89%)

$^1$H-NMR (200 MHz, $CDCl_3$) δ: 1.57–1.73 (m, 2H), 1.77–1.95 (m, 2H), 2.25 (s, 3H), 2.40–2.55 (m, 4H), 2.66 (t, J=7.7 Hz, 2H), 3.37–3.45 (m, 2H), 5.58 (d, J=6.4 Hz, 1H), 6.49–6.64 (m, 3H), 6.89 (s, 1H), 7.12–7.3 (m, 5H), 8.37–8.60 (m, 1H).

2) Synthesis of N-[3-(N-methyl-N-(3-phenylpropan-1-yl)amino)propan-1-yl]-5-thia-1,8b-diazaacenaphthylene-4-carboxamide Dihydrochloride To a solution of 577.3 mg (1.42 mM) of N-[3-(N-(3-phenylpropan-1-yl)amino)propan-1-yl]-5-thia-1,8b-diazaacenaphthylene-4-carboxamide in ethanol (6 ml) was added 2.0 ml (8.0 mM) of 4N-HCl/methanol at room temperature and the mixture was stirred for several minutes. The solvent was then distilled off under reduced pressure to provide the title compound.

Orange-colored amorphous substance. Yield 670 mg (87%)

$^1$H-NMR (200 MHz, DMSO-$d_6$) δ: 1.71–2.07 (m, 4H), 2.60–2.73 (m, 5H), 2.89–3.25 (m, 6H), 6.62 (d, J=7.4 Hz, 1H), 6.98 (d, J=9.2 Hz, 1H), 7.16–7.36 (m, 7H), 7.66 (s, 1H), 8.92–9.03 (m, 1H).

IR (KBr): 3433, 3059, 2951, 2715, 1637, 1296 $cm^{-1}$.

Elemental analysis for $C_{23}H_{28}N_4O_2SCl_2 \cdot 2.5H_2O$ Calcd.: C, 52.67; H, 6.34; N, 10.68 Found: C, 52.40; H, 6.25; N, 10.39

Example 57

Synthesis of 4-[4-(3-phenylpropan-1-yl)piperazino-1-carbonyl]-5-thia-1,8b-diazaacenaphthylene Dihydrochloride

1) Synthesis of 4-(4-tert-butoxycarbonylpiperazino-1-carbonyl)-5-thia-1,8b-diazaacenaphthylene To a solution of 0.85 g (2.7 mM) of 5-thia-1,8b-diazaacenaphthylene-4-carboxylic acid N-hydroxysuccinimide ester, synthesized in the same manner as Example 42-1), in acetonitrile (10 ml) was added a suspension of 0.28 g (3.25 mM) of piperazine and 0.75 ml (5.38 mM) of triethylamine in acetonitrile (3 ml) at room temperature, and the mixture was stirred at room temperature for 30 minutes. To this reaction mixture was added 1.0 ml (4.3 mM) of di-tert-butyl dicarbonate, and the mixture was stirred at room temperature for 2.5 hours. The solvent was then distilled off under reduced pressure and the residue was diluted with water and extracted with methylene chloride. The organic layer was washed with saturated aqueous solution of sodium chloride and dried over $MgSO_4$. The attempt to purify the residue by column chromatography (methanol/ethyl acetate 10%) failed. As a consequence, a crude product was recovered as red-purple amorphous substance.

$^1$H-NMR (200 MHz, $CDCl_3$) δ: 1.48 (s, 9H), 3.25–3.73 (m, 8H), 5.74 (dd, J=1.8, 5.8 Hz, 1H), 6.12 (s, 1H), 6.56–6.67 (m, 2H), 6.95 (s, 1H).

2) Synthesis of 4-(piperazino-1-carbonyl)-5-thia-1,8b-diazaacenaphthylene Dihydrochloride To a solution of 0.5092 g (ca 1.3 mM) of crude 4-(4-tert-butoxycarbonylpiperazino-1-carbonyl)-5-thia-1,8b-diazaacenaphthylene in ethanol (4 ml) was added 0.54 ml (6.48 mM) of 12N-hydrochloric acid at room temperature, and the mixture was stirred for 15 hours. The resulting crystals were filtered off and the filtrate was concentrated to provide a crude product as orange-colored solid (333 mg).

$^1$H-NMR (200 MHz, $D_2O$) δ: 3.20–3.48 (m, 4H), 3.90–4.03 (m, 4H), 6.17 (d, J=7.0 Hz, 1H), 6.43 (s, 1H), 6.78 (d, J=9.4 Hz, 1H), 6.94–7.02 (m, 1H), 7.11 (s, 1H).

3) Synthesis of 4-[4-(3-phenylpropan-1-yl)piperazino-1-carbonyl]-5-thia-1,8b-diazaacenaphthylene To a solution of 333 mg (ca 0.927 mM) of 4-(piperazino-1-carbonyl)-5-thia-1,8b-diazaacenaphthylene dihydrochloride and 0.65 ml (4.66 mM) of triethylamine in ethanol (6 ml) was added 0.17 ml (1.1 mM) of 1-bromo-3-phenylpropane at room temperature and the mixture was refluxed under nitrogen for 48 hours. The solvent was then distilled off under reduced pressure and the residue was diluted with water and extracted with methylene chloride. The organic layer was washed with saturated aqueous solution of sodium chloride, dried over $MgSO_4$, and purified by column chromatography (methanol/ethyl acetate 20–40%) to provide the title compound.

Red-purple amorphous substance. Yield 160 mg (15%, 3 steps)

$^1$H-NMR (200 MHz, $CDCl_3$) δ: 1.78–1.90 (m, 2H), 2.40–2.47 (m, 6H), 2.65 (t, J=7.7 Hz, 2H), 3.63–3.68 (m, 4H), 5.71 (dd, J=1.6, 6.2 Hz, 1H), 6.01 (s, 1H), 6.53–6.66 (m, 2H), 6.93 (s, 1H), 7.15–7.34 (m, 5H).

IR (KBr): 3425, 2595, 1632, 1498, 1431, 1273, 1211, 966 $cm^{-1}$.

4) Synthesis of 4-[4-(3-phenylpropan-1-yl)piperazino-1-carbonyl]-5-thia-1,8b-diazaacenaphthylene Dihydrochloride To a solution of 160 mg (0.40 mM) of 4-[4-(3-phenylpropan-1-yl)piperazino-1-carbonyl]-5-thia-1,8b-diazaacenaphthylene in ethanol (2 ml) was added 0.5 ml (2.0 mM) of 4N-HCl/methanol. The solvent was then distilled off under reduced pressure to provide the title compound.

Orange-colored amorphous substance. Yield 183 mg (90%)

$^1$H-NMR (200 MHz, DMSO-$d_6$) δ: 1.96–2.13 (m, 2H), 2.65 (t, J=7.8 Hz, 2H), 2.94–3.16 (m, 4H), 3.42–3.63 (m, 4H), 4.20–4.36 (m, 2H), 6.65 (d, J=8.6 Hz, 1H), 6.67 (s, 1H), 7.03 (d, J=9.2 Hz, 1H), 7.17–7.36 (m, 6H), 7.52 (s, 1H).

IR (KBr): 3439, 3060, 2942, 1637, 1329, 1120, 791 $cm^{-1}$.

Elemental analysis for $C_{23}H_{26}N_4OSCl_2 \cdot 1.5H_2O$ Calcd.: C, 54.76; H, 5.79; N, 11.11 Found: C, 54.72; H, 6.03; N, 10.87

Example 58

Synthesis of N-12-(4-(3-phenylpropan-1-yl) piperazin-1-yl)ethan-1-yl]-5-thia-1,8b-diazaacenaphthylene-4-carboxamide Trihydrochloride 1) Synthesis of N-[2-(4-tert-butoxycarbonyl-1-piperazinyl)ethan-1-yl]-5-thia-1,8b-diazaacenaphthylene-4-carboxamide In 50 ml of acetonitrile were suspended 3.27 g (15.0 mM) of 5-thia-1,8b-diazaacenaphthylene-4-carboxylic acid and 3.45 g (30.0 mM) of N-hydroxysuccinimide, followed by addition of 5.75 g (30.0 mM) of N-ethyl-N'-3-(N,N-dimethylamino)propylcarbodiimide hydrochloride, and the mixture was stirred at room temperature for 1 hour. The solvent was then distilled off under reduced pressure and the residue was extracted with chloroform (150 ml). The organic layer was washed with 100 ml of saturated aqueous solution of sodium chloride and dried over $MgSO_4$ and the solvent was distilled off under reduced pressure to provide the active ester. To a solution of this active ester in 100 ml of chloroform were added 4.2 ml (30.0 mM) of triethylamine and 1.94 g (15.0 mM) of 1-(2-aminoethyl)piperazine and the mixture was stirred at room temperature for 30 minutes. Then, 3.28 g (15.0 mM) of di-tert-butyl dicarbonate was added dropwise and the mixture was further stirred at room temperature for 1 hour. This reaction mixture was washed with 100 ml of purified water and the organic layer was further washed with 150 ml of saturated aqueous solution of sodium chloride. The organic layer was dried over $MgSO_4$ and the solvent was distilled off under reduced pressure. The residue was purified by silica gel column chromatography (eluent: ethyl acetate/ethanol=10/1) to provide the title compound.

Yield 3.64 g (56.5%, red liquid).

$^1$H-NMR (200 MHz, $CDCl_3$) δ: 1.47 (s, 9H), 2.42 (m, 4H), 2.53 (t, 2H, J=6.0 Hz), 3.35–3.48 (m, 6H), 5.80 (dd, 1H, J=6.2, 4.4 Hz), 6.42 (br s, 1H, NH), 6.62–6.70 (m, 3H), 7.05 (s, 1H).

IR (KBr): 1687, 1622, 1280, 1161 $cm^{-1}$.

2) Synthesis of N-[2-(piperazinyl)ethan-1-yl]-5-thia-1,8b-diazaacenaphthylene-4-carboxamide Trihydrochloride To a solution of 3.60 g (8.38 mM) of N-[2-(4-tert-butoxycarbonyl-1-piperazinyl)ethan-1-yl]-5-thia-1,8b-diazaacenaphthylene-4-carboxamide in 100 ml of ethanol was added 3.4 ml (41.90 mM) of 12N-hydrochloric acid and the mixture was stirred at room temperature for one hour. The resulting crystals were collected by filtration and rinsed with small amounts of ethanol and ether to provide the title compound. Yield 3.36 g (91.4%, orange-colored crystals).

$^1$H-NMR (200 MHz, DMSO-$d_6$) δ: 3.30–3.59 (m, 12H), 6.64 (d, 1H, J=7.0 Hz), 7.01 (d, 1H, J=8.2 Hz), 7.28–7.36 (m, 2H), 7.69 (s, 1H), 9.18 (t, 1H, NH, J=5.6 Hz), 9.90 (br s, 2H, NH).

IR (KBr): 1641, 1568, 1298 $cm^{-1}$.

3) Synthesis of N-[2-(4-(3-phenylpropan-1-yl)piperazin-1-yl)ethan-1-yl]-5-thia-1,8b-diazaacenaphthylene-4-carboxamide To a solution of 1.63 g (3.71 mM) of N-[2-(1-piperazinyl) ethan-1-yl]-5-thia-1,8b-diazaacenaphthylene-4- carboxamide trihydrochloride and 3.0 ml (21.5 mM) of triethylamine in ethanol (16 ml) was added 0.68 ml (4.47 mM) of 1-bromo-3-phenylpropane at room temperature, and the mixture was refluxed under nitrogen for 20 hours. The solvent was then distilled off under reduced pressure and the residue was diluted with water and extracted with chloroform. The organic layer was washed with saturated aqueous solution of sodium chloride, dried over $MgSO_4$, and purified by column chromatography (methanol/ethyl acetate 20–50%) to provide the title compound.

Red-purple amorphous substance. Yield 1.15 g (69%)

$^1$H-NMR (200 MHz, $CDCl_3$) δ: 1.73–1.93 (m, 2H), 2.36–2.68 (m, 14H), 3.33–3.42 (m, 2H), 5.78 (dd, J=1.8, 6.2 Hz, 1H), 6.46–6.66 (m, 4H), 7.04 (s, 1H), 7.15–7.31 (m, 5H).

4) Synthesis of N-[2-(4-(3-phenylpropan-1-yl)piperazin-1-yl)ethan-1-yl]-5-thia-1,8b-diazaacenaphthylene-4-carboxamide Trihydrochloride To a solution of 1.15 g (2.57 mM) of N-[2-(4-(3-phenylpropan-1-yl)piperazin-1-yl)ethan-1-yl]-5-thia-1,8b-diazaacenaphthylene-4-carboxamide in ethanol (10 ml) was added 4 ml (16 mM) of 4N-HCl/methanol at room temperature and the mixture was stirred at room temperature for several minutes. The solvent was then distilled off under reduced pressure and diethyl ether was added to the residue. The resulting crystals were collected by filtration and rinsed with ethanol and diethyl ether to provide the title compound.

Orange-colored crystals. Yield 1.27 g (85%)

$^1$H-NMR (200 MHz, DMSO-$d_6$) δ: 1.94–2.21 (m, 2H), 2.66 (br t, J=7.7 Hz, 2H), 3.09–3.90 (m, 14H), 6.60 (d, J=7.4 Hz, 1H), 6.97 (d, J=9.0 Hz, 1H), 7.16–7.37 (m, 7H), 7.65 (s, 1H), 9.03–9.16 (m, 1H).

IR (KBr): 1641, 1560, 1535, 1497, 1443, 1288, 1215, 1107, 958, 794 cm$^{-1}$.

Elemental analysis for $C_{25}H_{32}N_5OSCl_3 \cdot 1.5H_2O$ Calcd.: C, 51.42; H, 6.04; N, 11.99 Found: C, 51.51; H, 5.79; N, 11.81

Example 59

Synthesis of N-[3-(4-(3-phenylpropan-1-yl)piperazin-1-yl)propan-1-yl]-5-thia-1,8b-diazaacenaphthylene-4-carboxamide Trihydrochloride 1) The procedure of Example 58-1) was generally followed to provide N-[3-(4-tert-butoxycarbonyl-1-piperazinyl)propan-1-yl]-5-thia-1,8b-diazaacenaphthylene-4-carboxamide as red oil.

$^1$H-NMR (200 MHz, $CDCl_3$) δ: 1.47 (s, 9H), 1.62–1.80 (m, 2H), 2.33–2.59 (m, 6H), 3.35–3.48 (m, 2H), 3.48–3.59 (m, 4H), 5.74 (dd, J=1.4, 6.4 Hz, 1H), 6.57–6.71 (m, 3H), 7.02 (s, 1H), 7.70 (t, J=5.4 Hz, 1H).

IR (KBr): 3327, 1695, 1626 cm$^{-1}$.

2) The procedure of Example 58-2) was generally followed to provide N-[3-(1-piperazinyl)propan-1-yl]-5-thia-1,8b-diazaacenaphthylene-4-carboxamide trihydrochloride as orange-colored crystals.

$^1$H-NMR (200 MHz, DMSO-$d_6$) δ: 1.83–2.05 (m, 2H), 3.04–3.32 (m, 6H), 3.32–3.77 (m, 6H), 6.68 (d, J=7.2 Hz, 1H), 7.03 (d, J=8.8 Hz, 1H), 7.27 (s, 1H), 7.35 (dd, J=7.2, 8.8 Hz, 1H), 7.73 (s, 1H), 9.06 (t, J=5.6 Hz, 1H), 9.94 (br s, 2H).

IR (KBr): 3363, 1639, 1556 cm$^{-1}$.

3) The procedure of Example 58-3) was generally followed to provide N-[3-(4-(3-phenylpropan- 1-yl)piperazin-1-yl)propan-1-yl]-5-thia-1,8b-diazaacenaphthylene-4-carboxamide as red oil.

$^1$H-NMR (200 MHz, $CDCl_3$) δ: 1.51–1.92 (m, 4H), 2.29–2.71 (m, 14H), 3.37–3.45 (m, 2H), 5.69 (dd, J=1.2, 6.4 Hz, 1H), 6.51–6.66 (m, 3H), 6.98 (s, 1H), 7.12–7.35 (m, 5H), 8.07–8.24 (m, 1H).

IR (KBr):3255, 2939, 2814, 1620, 1545, 1279, 1151 cm$^{-1}$.

4) The procedure of Example 58-4) was generally followed to provide N-[3-(4-(3-phenylpropan-1-yl)piperazin-1-yl)propan-1-yl]-5-thia-1,8b-diazaacenaphthylene-4-carboxamide trihydrochloride as orange-colored crystals.

$^1$H-NMR (200 MHz, DMSO-$d_6$) δ: 1.78–2.10 (m, 4H), 2.56–2.72 (m, 2H), 2.98–4.09 (m, 14H), 6.51 (d, J=7.4 Hz, 1H), 6.91 (d, J=9.2 Hz, 1H), 7.04–7.38 (m, 7H), 7.57 (s, 1H), 8.76–8.89 (m, 1H).

IR (KBr): 3174, 3035, 2366, 1630, 1441, 1296, 1211, 795 cm$^{-1}$.

Elemental analysis for $C_{26}H_{34}N_5OSCl_3 \cdot 0.5H_2O$ Calcd.: C, 53.84; H, 6.08; N, 12.07 Found,: C, 53.84; H, 5.80; N, 12.29

Example 60

Synthesis of N-[1-(3-phenylpropan-1-yl)pyrrolidin-3-yl]-5-thia-1,8b-diazaacenaphthylene-4-carboxamide Dihydrochloride 1) Synthesis of N-[3-(1-tert-butoxycarbonyl)pyrrolidinyl)-5-thia-1,8b-diazaacenaphthylene-4-carboxamide In 50 ml of acetonitrile were suspended 3.27 g (15.0 mM) of 5-thia-1,8b-diazaacenaphthylene-4-carboxylic acid and 3.45 g (30.0 mM) of N-hydroxysuccinimide, followed by addition of 5.75 g (30.0 mM) of N-ethyl-N'-3-(N,N-dimethylamino)propylcarbodiimide hydrochloride, and the mixture was stirred at room temperature for 1 hour. The solvent was then distilled off under reduced pressure and the residue was extracted with 150 ml of chloroform. The organic layer was washed with 100 ml of saturated aqueous solution of sodium chloride and dried over $MgSO_4$ and the solvent was distilled off under reduced pressure to provide the active ester. To a solution of this active ester in 100 ml of chloroform were added 4.2 ml (30.0 mM) of triethylamine and 1.55 g (15.0 mM) of 3-aminopyrrolidine, and the mixture was stirred at room temperature for 30 minutes. Then, 3.28 g (15.0 mM) of di-tert-butyl dicarbonate was added dropwise and the mixture was further stirred at room temperature for 1 hour. This reaction mixture was then washed by adding 100 ml of purified water and the organic layer was further washed with 150 ml of saturated aqueous solution of sodium chloride. The organic layer was dried over $MgSO_4$ and the solvent was distilled off under reduced pressure. The residue was purified by silica gel column chromatography (eluent: ethyl acetate/ethanol=10/1) to provide the title compound. Yield 3.22 g (55.5%, red solid).

$^1$H-NMR (200 MHz, $CDCl_3$) δ: 1.46 (s, 9H), 1.81–2.02 (m, 1H), 2.08–2.28 (m, 1H), 3.43–3.88 (m, 4H), 4.12–4.27 (m, 1H), 4.74 (d, 1H, NH, J=6.0 Hz), 5.73 (dd, 1H, J=5.6, 3.2 Hz), 6.23 (s, 1H), 6.58–6.66 (m, 2H), 6.95 (s, 1H).

IR (KBr): 1697, 1608, 1163 cm$^{-1}$.

2) Synthesis of N-(3-pyrrolidinyl)-5-thia-1,8b-diazaacenaphthylene-4-carboxamide Dihydrochloride To a solution of 3.2 g (8.28 mM) of N-[3-(1-tert-butoxycarbonyl)pyrrolidinyl]-5-thia-1,8b-diazaacenaphthylene-4-carboxamide in 100 ml of ethanol was added 3.4 ml (41.40 mM) of 12N-hydrochloric acid and the mixture was stirred at room temperature for 1 hour. The resulting crystals were collected by filtration and rinsed with small amounts of ethanol and ether to provide the title compound. Yield 2.12 g (89.4%, orange-colored crystals).

$^1$H-NMR (200 MHz, DMSO-d$_6$) δ: 2.04–2.32 (m, 2H), 3.61–3.84 (m, 5H), 6.65 (d, 1H, J=7.4 Hz), 6.87 (s, 1H), 7.04 (d, 1H, J=9.2 Hz), 7.32 (t, 1H, J=7.6 Hz), 7.59 (s, 1H), 8.51 (br s, 2H, NH).

IR (KBr): 1605, 1497, 1427 cm$^{-1}$.

3) Synthesis of N-[1-(3-phenylpropan-1-yl)pyrrolidin-3-yl]-5-thia-1,8b-diazaacenaphthylene-4-carboxamide To a solution of 0.50 g (1.39 mM) of N-(3-pyrrolidinyl)-5-thia-1,8b-diazaacenaphthylene-4-carboxamide dihydrochloride and 1.0 ml (7.17 mM) of triethylamine in ethanol (5 ml) was added 0.25 ml (1.64 mM) of 1-bromo-3-phenylpropane at room temperature, and the mixture was refluxed under nitrogen for 18 hours. To this reaction mixture was further added 0.2 ml (1.32 mM) of 1-bromo-3-phenylpropane, and the mixture was further refluxed for 3 hours. The solvent was then distilled off under reduced pressure and the residue was diluted with water and extracted with chloroform. The organic layer was washed with saturated aqueous solution of sodium chloride, dried over MgSO$_4$, and purified by column chromatography (methanol/ethyl acetate 20–30%) to provide N-[1-(3-phenylpropan-1-yl)pyrrolidin-3-yl]-5-thia-1,8b-diazaacenaphthylene-4-carboxamide.

Red-purple amorphous substance. Yield 242 mg (43%)

$^1$H-NMR (200 MHz, CDCl$_3$) δ: 1.67–2.20 (m, 4H), 2.61–2.71 (m, 4H), 3.24–3.41 (m, 2H), 3.49–3.83 (m, 3H), 5.71 (dd, J=2.2, 5.8 Hz, 1H), 6.22 (s, 1H), 6.51–6.62 (m, 2H), 6.93 (s, 1H), 7.16–7.32 (m, 6H).

4) Synthesis of N-[1-(3-phenylpropan-1-yl)pyrrolidin-3-yl]-5-thia-1,8b-diazaacenaphthylene-4-carboxamide Dihydrochloride To a solution of 242.4 mg (0.60 mM) of N-[1-(3-phenylpropan-1-yl)pyrrolidin-3-yl]-5-thia-1,8b-diazaacenaphthylene-4-carboxamide in ethanol (2 ml) was added 1.5 ml (6.0 mM) of 4N-HCl/methanol at room temperature and the mixture was stirred at room temperature for several minutes. The solvent was then distilled off under reduced pressure and diethyl ether was added to the residue. The resulting crystals were collected by filtration and rinsed with diethyl ether to provide the title compound.

Orange-colored crystals. Yield 253 mg (88%)

$^1$H-NMR (200 MHz, DMSO-d$_6$) δ: 1.88–2.09 (m, 2H), 2.14–2.31 (m, 2H), 2.69 (t, J=7.6 Hz, 2H), 2.88–3.03 (m, 2H), 3.46–4.07 (m, 5H), 6.62 (d, J=7.4 Hz, 1H), 6.86 (s, 1H), 7.09 (d, J=9.2 Hz, 1H), 7.15–7.37 (m, 6H), 7.55 (s, 1H), 9.41–9.82 (m, 1H).

IR (KBr): 1624, 1498, 1437, 1390, 1211, 785 cm$^{-1}$.

Example 61

Synthesis of N-[(3R)-1-(3-phenylpropan-1-yl) pyrrolidin-3-yl]-5-thia-1,8b-diazaacenaphthylene-4-carboxamide Dihydrochloride 1) The procedure of Example 60-1) was generally followed to provide N-[(3R)-1-tert-butoxycarbonylpyrrolidinyl]-5-thia-1,8b-diazaacenaphthylene-4-carboxamide as red solid.

$^1$H-NMR (200 MHz, CDCl$_3$) δ: 1.46 (s, 9H), 1.78–1.98 (m, 1H), 2.04–2.28 (m, 1H), 3.36–3.92 (m, 4H), 4.12–4.30 (m, 1H), 4.56–4.72 (m, 1H), 5.72 (dd, J=2.2, 5.6 Hz, 1H), 6.23 (s, 1H), 6.58–6.71 (m, 2H), 6.95 (s, 1H).

IR (KBr): 1697, 1608, 1163 cm$^{-1}$.

2) The procedure of Example 60-2) was generally followed to provide N-[(3R)-pyrrolidinyl)-5-thia-1,8b-diazaacenaphthylene-4-carboxamide dihydrochloride as orange-colored crystals.

$^1$H-NMR (200 MHz, DMSO-d$_6$) δ: 2.07–2.29 (m, 1H), 2.34–2.55 (m, 1H), 3.39–4.16 (m, 5H), 6.08 (d, J=7.3 Hz, 1H), 6.53 (s, 1H), 6.70 (d, J=8.9 Hz, 1H), 6.89 (dd, 7.3, 8.9 Hz, 1H), 7.08 (s, 1H).

IR (KBr): 1603, 1500, 1433 cm$^{-1}$.

3) The procedure of Example 60-3) was generally followed to provide N-[(3R)-1-(3-phenylpropan-1-yl) pyrrolidin-3-yl]-5-thia-1,8b-diazaacenaphthylene-4-carboxamide as red-purple amorphous substance.

$^1$H-NMR (200 MHz, CDCl$_3$) δ: 1.67–2.20 (m, 4H), 2.61–2.71 (m, 4H), 3.24–3.41 (m, 2H), 3.49–3.83 (m, 3H), 5.71 (dd, J=2.2, 5.6 Hz, 1H), 6.22 (s, 1H), 6.51–6.62 (m, 2H), 6.93 (s, 1H), 7.16–7.32 (m, 6H).

4) The procedure of Example 60-4) was generally followed to provide N-[(3R)-1-(3-phenylpropan-1-yl) pyrrolidin-3-yl]-5-thia-1,8b-diazaacenaphthylene-4-carboxamide dihydrochloride as orange-colored crystals.

$^1$H-NMR (200 MHz, DMSO-d$_6$) δ: 1.87–2.07 (m, 2H), 2.12–2.33 (m, 2H), 2.69 (t, J=7.6 Hz, 2H), 2.88–3.04 (m, 2H), 3.46–4.07 (m, 5H), 6.58 (d, J=7.2 Hz, 1H), 6.83 (s, 1H), 6.98 (d, J=9.2 Hz, 1H), 7.16–7.38 (m, 6H), 7.51 (s, 1H), 9.31–9.70 (m, 1H).

IR (KBr): 1624, 1498, 1437, 1390, 1211, 785 cm$^{-1}$.

Elemental analysis for $C_{23}H_{26}N_4OSCl_2 \cdot 1.6H_2O$ Calcd.: C, 54.56; H, 5.81; N, 11.07 Found: C, 54.44; H, 6.09; N, 11.04

Example 62

Synthesis of N-[(3S)-1-(3-phenylpropan-1-yl) pyrrolidin-3-yl]-5-thia-1,8b-diazaacenaphthylene-4-carboxamide Dihydrochloride 1) The procedure of Example 60-1) was generally followed to provide N-[(3s)-(1-tert-butoxycarbonyl) pyrrolidinyl]-5-thia-1,8b-diazaacenaphthylene-4-carboxamide as red solid.

$^1$H-NMR (200 MHz, CDCl$_3$) δ: 1.46 (s, 9H), 1.78–1.91 (m, 1H), 2.04–2.28 (m, 1H), 3.36–3.92 (m, 4H), 4.12–4.30 (m, 1H), 4.56–4.72 (m, 1H), 5.72 (dd, J=2.2, 5.6 Hz, 1H), 6.23 (s, 1H), 6.53–6.71 (m, 2H), 6.95 (s, 1H).

IR (KBr): 1697, 1608, 1163 cm$^{-1}$.

2) The procedure of Example 60-2) was generally followed to provide N-[(3s)-pyrrolidinyl)-5-thia-1,8b-diazaacenaphthylene-4-carboxamide dihydrochloride as orange-colored crystals.

$^1$H-NMR (200 MHz, DMSO-d$_6$) δ: 2.07–2.29 (m, 1H), 2.34–2.55 (m, 1H), 3.39–4.16 (m, 5H), 6.08 (d, J=7.3 Hz, 1H), 6.53 (s, 1H), 6.70 (d, J=8.9 Hz, 1H), 6.89 (dd, 7.3, 8.9 Hz, 1H), 7.08 (s, 1H).

IR (KBr): 1606, 1496, 1425 cm$^{-1}$.

3) The procedure of Example 60-3) was generally followed to provide N-[(3S)-1-(3-phenylpropan-1-yl) pyrrolidin-3-yl]-5-thia-1,8b-diazaacenaphthylene-4-carboxamide as red-purple amorphous substance.

$^1$H-NMR (200 MHz, CDCl$_3$) δ: 1.67–2.20 (m, 4H), 2.61–2.71 (m, 4H), 3.24–3.41 (m, 2H), 3.49–3.83 (m, 3H), m 5.71 (dd, J=2.2, 5.6 Hz, 1H), 6.22 (s, 1H), 6.51–6.62 (m, 2H), 6.93 (s, 1H), 7.16–7.32 (m, 6H).

4) The procedure of Example 60-4) was generally followed to provide N-[(3S)-1-(3-phenylpropan-1-yl)

pyrrolidin-3-yl]-5-thia-1,8b-diazaacenaphthylene-4-carboxamide dihydrochloride as orange-colored crystals.

$^1$H-NMR (200 MHz, DMSO-d$_6$) δ: 1.88–2.08 (m, 2H), 2.14–2.33 (m, 2H), 2.68 (t, J=7.6 Hz, 2H), 2.88–3.05 (m, 2H), 3.28–4.32 (m, 5H), 6.56 (d, J=7.0 Hz, 1H), 6.82 (s, 1H), 6.96 (d, J=9.2 Hz, 1H), 7.16–7.37 (m, 6H), 7.50 (s, 1H), 9.22–9.63 (m, 1H).

IR (KBr): 1624, 1498, 1437, 1390, 1211, 785 cm$^{-1}$.

Elemental analysis for C$_{23}$H$_{26}$N$_4$OSCl$_2$·1.5H$_2$O Calcd.: C, 54.76; H, 5.79; N, 11.11 Found: C, 54.46; H, 5.83; N, 11.01

Example 63

Synthesis of 4-[4-(3-phenylpropan-1-ylaminomethyl)piperidino-1-carbonyl]-5-thia-1,8b-diazaacenaphthylene Dihydrochloride 1) Synthesis of 4-[4-(3-phenylpropan-1-ylaminomethyl)piperidino-1-carbonyl]-5-thia-1,8b-diazaacenaphthylene To a solution of 0.21 g (0.67 mM) of 5-thia-1,8b-diazaacenaphthylene-4-carboxylic acid N-hydroxysuccinimide ester, synthesized in the same manner as Example 42-1), in acetonitrile (2 ml) was added a solution of 0.1858 g (0.8 mM) of 4-[(3-phenylpropan-1-yl)aminomethyl]piperidine and 0.15 ml (1.08 mM) of triethylamine in acetonitrile (2 ml) at 0° C. and the mixture was stirred at the prevailing temperature for 4 hours. The solvent was then distilled off under reduced pressure and the residue was diluted with water and extracted with chloroform. The organic layer was washed with saturated aqueous solution of sodium chloride, dried over MgSO$_4$, and purified by column chromatography (methanol/ethyl acetate 20–50–100%) to provide the title compound.

Red-purple amorphous substance. Yield 180 mg (62%)

$^1$H-NMR (200 MHz, CDCl$_3$) δ: 1.02–1.30 (m, 2H), 1.57–1.91 (m, 5H), 2.50 (d, J=6.2 Hz, 2H), 2.59–2.70 (m, 4H), 2.81–2.93 (m, 2H), 4.30–4.37 (m, 2H), 5.71 (dd, J=1.6, 6.2 Hz, 1H), 6.05 (s, 1H), 6.53–6.66 (m, 2H), 6.92 (s, 1H), 7.15–7.32 (m, 5H).

2) Synthesis of 4-[4-(3-phenylpropan-1-ylaminomethyl)piperidino-1-carbonyl]-5-thia-1,8b-diazaacenaphthylene Dihydrochloride To a solution of 180.9 mg (0.42 mM) of 4-[4-(3-phenylpropan-1-ylaminomethyl)piperidino-1-carbonyl]-5-thia-1,8b-diazaacenaphthylene in ethanol (2 ml) was added 1.0 ml (4 mM) of 4N-HCl/methanol at room temperature and the mixture was stirred for several minutes. The solvent was then distilled off under reduced pressure to provide the title compound.

Orange-colored amorphous substance. Yield 201 mg (86%)

$^1$H-NMR (200 MHz, DMSO-d$_6$) δ: 1.09–1.28 (m, 2H), 1.77–2.08 (m, 5H), 2.58–3.04 (m, 8H), 4.06–4.24 (m, 2H), 6.52 (s, 1H), 6.65 (d, J=7.2 Hz, 1H), 7.03 (d, J=9.2 Hz, 1H), 7.15–7.37 (m, 6H), 7.50 (s, 1H), 8.93–9.19 (m, 1H).

IR (KBr): 3421, 2945, 2794, 1628, 1500, 1444, 1387, 1281, 1215 cm$^{-1}$.

Elemental analysis for C$_{25}$H$_{30}$N$_4$OSCl$_2$·3.0H$_2$O Calcd.: C, 53.66; H, 6.48; N, 10.01 Found C, 53.88; H, 6.59; N, 10.04

Example 64

Synthesis of N-[3-(4-benzyl-1,4-diazepan-1-yl)propan-1-yl]-5-thia-1,8b-diazaacenaphthylene-4-carboxamide Trihydrochloride 1) Synthesis of N-[3-(1-tert-butoxycarbonyl-1,4-diazepan-1-yl)propan-1-yl]-5-thia-1,8b-diazaacenaphthylene-4-carboxamide In acetonitrile (50 ml) was suspended 2619 mg (12 mM) of 5-thia-1,8b-diazaacenaphthylene-4-carboxylic acid and 2762 mg (24 mM) of N-hydroxysuccinimide, followed by addition of 4601 mg (24 mM) of N-ethyl-N'-3-(N,N-dimethylamino)propylcarbodiimide hydrochloride, and the mixture was stirred at room temperature for 1 hour. The solvent was then distilled off under reduced pressure and the residue was extracted with chloroform. The organic layer was washed with saturated aqueous solution of sodium chloride and dried over MgSO$_4$. The solvent was then distilled off under reduced pressure to provide the active ester. To a solution of this active ester in chloroform (100 ml) were added 4.2 ml (30 mM) of triethylamine and 3710 mg (14 mM) of 1-tert-butoxycarbonyl-4-(3-aminopropyl)-1,4-diazepane, and the mixture was stirred at room temperature for 30 minutes. This reaction mixture was washed with purified water and the organic layer was further washed with saturated aqueous solution of sodium chloride. The organic layer was dried over MgSO$_4$ and the solvent was distilled off under reduced pressure. The residue was purified by column chromatography (ethyl acetate/ethanol=10/1) to provide the title compound as red solid. Yield 4291 mg (78.2%).

$^1$H-NMR (200 MHz, CDCl$_3$) δ: 1.47 (s, 9H), 1.62–1.83 (m, 2H), 1.83–2.16 (m, 2H), 2.51–2.83 (m, 6H), 3.29–3.55 (m, 6H), 5.71 (dd, 1H, J=5.8, 2.2 Hz), 6.54–6.77 (m, 3H), 7.03 (d, 1H, J=4.0 Hz), 7.76 (d, 1H, J=14.8 Hz).

2) Synthesis of N-[3-(hexahydro-1,4-diazepin-1-yl)propan-1-yl]-5-thia-1,8b-diazaacenaphthylene-4-carboxamide Trihydrochloride To a solution of 4250 mg (9.29 mM) of N-[3-(4-tert-butoxycarbonyl-2,3,5,6-tetrahydro-7H-1,4-diazepin-1-yl)propan-1-yl]-5-thia-1,8b-diazaacenaphthylene-4-carboxamide in 100 ml of ethanol was added 3.8 ml (46.44 mM) of 12N-hydrochloric acid, and the mixture was stirred at room temperature for 1 hour. The resulting precipitate was recovered by filtration and rinsed with small amounts of ethanol and ether to provide the title compound. Yield 4020 mg (92.8%).

$^1$H-NMR (200 MHz, DMSO-d$_6$) δ: 1.82–2.06 (m, 2H), 2.09–2.31 (m, 2H), 3.02–3.42 (m, 6H), 3.46–3.82 (m, 6H), 6.65 (d, 1H, J=7.4 Hz), 7.02 (d, 1H, J=9.2 Hz), 7.28 (s, 1H), 7.32 (dd, 1H, J=9.2, 7.4 Hz), 7.70 (s, 1H), 9.07 (t, 1H, J=5.6 Hz).

3) Synthesis of N-[3-(4-benzyl-2,3,5,6-tetrahydro-7H-1,4-diazepin-1-yl)propan-1-yl]-5-thia-1,8b-diazaacenaphthylene-4-carboxamide In 10 ml of ethanol were suspended 606.9 mg (1.3 mM) of N-[3-(hexahydro-1,4-diazepin-1-yl)propan-1-yl]-5-thia-1,8-diazaacenaphthylene-4-carboxamide trihydrochloride and 342.1 mg (2.0 mM) of benzyl bromide, followed by addition of 0.91 ml (6.5 mM) of triethylamine, and the mixture was refluxed overnight. This reaction mixture was diluted with 5% aqueous solution of sodium hydrogen carbonate and and extracted with ethyl acetate. The organic layer was washed with saturated aqueous solution of sodium chloride and dried over Na$_2$SO$_4$. The solvent was then distilled off under reduced pressure and the residue was purified by silica gel column chromatography (ethyl acetate/methanol=2/3) to provide the title compound as deep-red liquid (320.0 mg, 55.0%).

$^1$H-NMR (200 MHz, CDCl$_3$) δ: 1.60–1.75 (2H, m), 1.75–1.95 (2H, m), 2.60–2.85 (10H, m), 3.37–3.45 (2H, m), 3.63 (2H, s), 5.71 (1H, dd, J=1.7, 6.1 Hz), 6.54–6.66 (3H, m), 6.96 (1H, s), 7.20–7.35 (5H, m), 8.40 (1H, br s).

IR (neat): 3286, 3059, 2933, 2818, 1618, 1547, 1508, 1481, 1452, 1348, 1281, 1213, 1155, 1120, 773, 733, 700, 650 cm$^{-1}$.

4) Synthesis of N-[3-(4-benzyl-2,3,5,6-tetrahydro-7H-1,4-diazepin-1-yl)propan-1-yl]-5-thia-1,8b-diazaacenaphthylene-4-carboxamide Trihydrochloride To a solution of 320.0 mg (0.71 mM) of N-[3-(4-benzyl-2,3,5,6-tetrahydro-7H-1,4-diazepin-1-yl)propan-1-yl]-5-thia-1,8b-diazaacenaphthylene-4-carboxamide in ethanol (10 ml) was added 2 ml (8.0 mM) of 4N-HCl/ethyl acetate, and the mixture was stirred under heating for 2 hours. To the ethanolic solution containing crystals was added ether and the crystal crop was harvested by filtration and rinsed with ethanol and diethyl ether to provide the title compound as light-orange-colored crystals (390.9 mg, 94%).

$^1$H-NMR (200 MHz, CD$_3$OD) δ: 1.90–2.20 (2H, m), 2.20–2.50 (2H, m), 3.15–4.10 (12H, m), 4.40–4.60 (2H, m), 6.50–6.70 (1H, m), 6.90–7.10 (2H, m), 7.30–7.70 (7H, m).

IR (KBr): 3425, 3064, 2949, 2603, 1633, 1566, 1535, 1500, 1454, 1389, 1296, 1215, 785, 700, 631, 599, 525 cm$^{-1}$.

Elemental analysis for C$_{25}$H$_{32}$N$_5$OSCl$_3$.1.5H$_2$O Calcd.: C, 51.42; H, 6.04; N, 11.99 Found: C, 51.20; H, 5.96; N, 11.75

Example 65

Synthesis of N-[3-(4-phenethyl-2,3,5,6-tetrahydro-7H-1,4-diazepin-1-yl)propan-1-yl]-5-thia-1,8b-diazaacenaphthylene-4-carboxamide Trihydrochloride 1) The procedure of Example 64-3) was generally followed to provide N-[3-(4-phenethyl-2,3,5,6-tetrahydro-7H-1,4-diazepin-1-yl)propan-1-yl]-5-thia-1,8b-diazaacenaphthylene-4-carboxamide as deep-red solid.

$^1$H-NMR (200 MHz, CDCl$_3$) δ: 1.60–1.75 (2H, m), 1.80–1.95 (2H, m), 2.60–2.90 (14H, m), 3.35–3.50 (2H, m), 5.71 (1H, d, J=6.6 Hz), 6.50–6.70 (3H, m), 6.97 (1H, s), 7.10–7.35 (5H, m), 8.25–8.35 (1H, m).

IR (KBr): 3269, 3055, 2933, 2806, 1643, 1620, 1556, 1514, 1481, 1454, 1369, 1282, 1225, 1151, 1117, 777, 750, 700, 669 cm$^{-1}$.

2) The procedure of Example 64-4) was generally followed to provide N-[3-(4-phenethyl-2,3,5,6-tetrahydro-7H-1,4-diazepin-1-yl)propan-1-yl]-5-thia-1,8b-diazaacenaphthylene-4-carboxamide trihydrochloride as orange-colored crystals.

$^1$H-NMR (200 MHz, CD$_3$OD) δ: 1.95–2.20 (2H, m), 2.30–2.50 (2H, m), 3.10–3.25 (2H, m), 3.25–4.10 (14H, m), 6.62 (1H, d, J=7.6 Hz), 6.97–7.03 (2H, m), 7.20–7.45 (6H, m), 7.54 (1H, s).

IR (KBr): 3425, 3062, 2945, 2659, 2727, 1632, 1564, 1537, 1502, 1456, 1392, 1296, 1215, 1107, 785, 702 cm$^{-1}$.

Elemental analysis for C$_{26}$H$_{34}$N$_5$OSCl$_3$.2.0H$_2$O Calcd.: C, 51.44; H, 6.31; N, 11.54 Found: C, 51.48; H, 6.24; N, 11.62

Example 66

Synthesis of N-[3-(4-(3-phenylpropan-1-yl)-2,3,5,6-tetrahydro-7H-1,4-diazepin-1-yl)propan-1-yl]-5-thia-1,8b-diazaacenaphthylene-4-carboxamide Trihydrochloride 1) The procedure of Example 64-3) was generally followed to provide N-[3-(4-(3-phenylpropan-1-yl)-2,3,5,6-tetrahydro-7H-1,4-diazepin-1-yl)propan-1-yl]-5-thia-1,8b-diazaacenaphthylene-4-carboxamide as deep red oil.

$^1$H-NMR (200 MHz, CDCl$_3$) δ: 1.60–1.95 (6H, m), 2.45–2.80 (14H, m), 3.37–3.45 (2H, m), 5.72 (1H, dd, J=1.4, 6.4 Hz), 6.52–6.66 (3H, m), 6.98 (1H, s), 7.10–7.35 (5H, m), 8.36 (1H, br s).

IR (neat): 3280, 3059, 3024, 2937, 2818, 1616, 1545, 1481, 1342, 1281, 1215, 1155, 1120, 1034, 966, 868, 752, 700, 652, 606, 503, 473 cm$^{-1}$.

2) The procedure of Example 64-4) was generally followed to provide N-[3-(4-(3-phenylpropan-1-yl)-2,3,5,6-tetrahydro-7H-1,4-diazepin-1-yl)propan-1-yl]-5-thia-1,8b-diazaacenaphthylene-4-carboxamide trihydrochloride as light-orange-colored crystals.

$^1$H-NMR (200 MHz, CD$_3$OD) δ: 1.95–2.55 (6H, m), 2.65–2.90 (2H, m), 3.20–4.20 (14H, m), 6.50–6.70 (1H, m), 6.90–7.15 (2H, m), 7.15–7.45 (6H, m), 7.50–7.60 (1H, m).

IR (KBr): 3394, 3061, 2947, 2659, 1633, 1564, 1537, 1502, 1456, 1392, 1296, 1215, 1107, 787, 756, 702 cm$^{-1}$.

Elemental analysis for C$_{27}$H$_{36}$N$_5$OSCl$_3$.1.0H$_2$O Calcd.: C, 52.98; H, 6.42; N, 11.44 Found: C, 52.79; H, 6.61; N, 11.37

Example 67

Synthesis of N-[1-(3-(2-fluorophenyl)propan-1-yl)piperidin-4-ylmethyl]-5-thia-1,8b-diazaacenaphthylene-4-carboxamide Dihydrochloride 1) Synthesis of N-[1-(3-(2-fluorophenyl)propan-1-yl)piperidin-4-ylmethyl]-5-thia-1,8b-diazaacenaphthylene-4-carboxamide Under nitrogen gas, 0.38 ml (4.90 mM) of methanesulfonyl chloride was added to a solution of 499 mg (3.24 mM) of 2-fluorophenylpropanol and 0.90 ml (6.47 mM) of triethylamine in methylene chloride (6 ml) at 0° C. and the mixture was stirred at the prevailing temperature for 20 minutes. The reaction was stopped by adding saturated aqueous solution of sodium hydrogen carbonate. The reaction mixture was then extracted with diethyl ether. The organic layer was washed with water and saturated aqueous solution of sodium chloride and dried over MgSO$_4$. The solvent was then distilled off under reduced pressure to provide 0.722 g (3.24 mM) of 2-fluorophenylpropyl mesylate. To a solution of 0.58 g (1.5 mM) of N-(piperidin-4-ylmethyl)-5-thia-1,8b-diazaacenaphthylene-4-carboxamide dihydrochloride and 1.0 ml (7.2 mM) of triethylamine in ethanol was added 0.60 g (2.69 mM) of 2-fluorophenylpropyl mesylate at room temperature, and the mixture was refluxed under nitrogen for 16 hours. The solvent was then distilled off under reduced pressure and the residue was diluted with water and extracted with chloroform. The organic -layer was washed with saturated aqueous solution of sodium chloride and dried over MgSO$_4$. The resulting crude product was purified by column chromatography (methanol/ethyl acetate 20–50%) to provide the title compound.

Reddish purple amorphous substance. Yield 347 mg (54%)

$^1$H-NMR (200 MHz, CDCl$_3$) δ: 1.21–2.05 (m, 9H), 2.38 (t, J=7.7 Hz, 2H), 2.65 (t, J=7.5 Hz, 2H), 2.94 (br d, J=11.8 Hz, 2H), 3.20 (t, J=6.1 Hz, 2H), 5.78 (dd, J=1.8, 6.0 Hz, 1H), 5.89–6.03 (m, 1H), 6.57–6.69 (m, 3H), 6.92–7.21 (m, 5H).

2) Synthesis of N-[1-(3-(2-fluorophenyl)propan-1-yl)piperidin-4-ylmethyl]-5-thia-1,8b-diazaacenaphthylene-4-carboxamide Dihydrochloride To a solution of 347 mg (0.8 mM) of N-[1-(3-(2-fluorophenyl)propan-1-yl)piperidin-4-ylmethyl]-5-thia-1,8b-diazaacenaphthylene-4-carboxamide in ethanol (4 ml)

was added 1.0 ml (4.0 mM) of 4N-HCl/methanol. After the solvent was distilled off under reduced pressure, ethanol and diethyl ether were added to the residue and the resulting crystals were collected by filtration and rinsed with ethanol and diethyl ether to provide the title compound.

Orange-colored crystals. Yield 360 mg (86%)

$^1$H-NMR (200 MHz, DMSO-$d_6$) δ: 1.36–2.09 (m, 7H), 2.66 (t, J=7.9 Hz, 2H), 2.72–3.48 (m, 8H), 6.57 (d, J=7.4 Hz, 1H), 6.95 (d, J=8.8 Hz, 1H), 7.11–7.39 (m, 6H), 7.61 (s, 1H), 8.83–8.90 (m, 1H).

IR (KBr): 3462, 3057, 2951, 2696, 1643, 1535, 1497, 1443, 1290, 1221, 800 cm$^{-1}$.

Elemental analysis for $C_{25}H_{29}N_4OSCl_2F.1.0H_2O$ Calcd.: C, 55.45; H, 5.77; N, 10.35 Found: C, 55.60; H, 5.80; N, 10.13

Example 68

Synthesis of N-[1-(2-fluorophenethyl)piperidin-4-ylmethyl]-5-thia-1,8b-diazaacenaphthylene-4-carboxamide Dihydrochloride 1) The procedure of Example 67-1) was generally followed to provide N-[1-(2-fluorophenethyl)piperidin-4-ylmethyl]-5-thia-1,8b-diazaacenaphthylene-4-carboxamide as rouge-colored solid.

$^1$H-NMR (200 MHz, CDCl$_3$) δ: 1.20–1.45 (2H, m), 1.45–1.80 (3H, m), 1.95–2.15 (2H, m), 2.50–2.65 (2H, m), 2.82–2.90 (2H, m), 3.04 (2H, br d, J=11.8 Hz), 3.22 (2H, t, J=6.0 Hz), 5.79 (1H, dd, J=1.8, 6.2 Hz), 5.85–5.95 (1H, m), 6.59–6.71 (3H, m), 6.96–7.24 (5H, m).

IR (KBr): 3250, 3086, 2927, 1639, 1618, 1558, 1485, 1286, 1153, 760 cm$^{-1}$.

2) The procedure of Example 67-2) was generally followed to provide N-[1-(2-fluorophenethyl)piperidin-4-ylmethyl]-5-thia-1,8b-diazaacenaphthylene-4-carboxamide dihydrochloride as light-orange-colored crystals.

$^1$H-NMR (200 MHz, CD$_3$OD) δ: 1.45–1.70 (2H, m), 1.80–2.10 (3H, m), 2.95–3.50 (8H, m), 3.71 (2H, br d, J=12.4 Hz), 6.60 (1H, d, J=7.6 Hz), 6.99 (1H, d, J=7.8 Hz), 7.01 (1H, s), 7.07–7.20 (2H, m), 7.27–7.43 (3H, m), 7.52 (1H, s).

IR (KBr): 3427, 3250, 2933, 2688, 1635, 1566, 1539, 1497, 1439, 1390, 1284, 1209, 779, 761 cm$^{-1}$.

Elemental analysis for $C_{24}H_{27}N_4OSFCl_2.0.5H_2O$ Calcd.: C, 55.60; H, 5.44; N, 10.81 Found: C, 55.42; H, 5.40; N, 10.73

Example 69

Synthesis of N-[1-(3-fluorophenethyl)piperidin-4-ylmethyl]-5-thia-1,8b-diazaacenaphthylene-4-carboxamide Dihydrochloride 1) The procedure of Example 67-1) was generally followed to provide N-[1-(3-fluorophenethyl)piperidin-4-ylmethyl)-5-thia-1,8b-diazaacenaphthylene-4-carboxamide as rouge-colored solid.

$^1$H-NMR (200 MHz, CDCl$_3$) δ: 1.20–1.45 (2H, m), 1.45–1.80 (3H, m), 1.90–2.10 (2H, m), 2.55–2.63 (2H, m), 2.77–2.85 (2H, m), 3.01 (2H, br d, J=11.4 Hz), 3.21 (2H, t, J=6.0 Hz), 5.78 (1H, dd, J=2.2, 5.5 Hz), 6.20 (1H, br t, J=5.5 Hz), 6.57–6.69 (3H, m), 6.85–7.02 (4H,m), 7.18–7.25 (1H, m).

IR (KBr): 3315, 2924, 1618, 1547, 1483, 1281, 1148, 775, 733, 692 cm$^{-1}$.

2) The procedure of Example 67-2) was generally followed to provide N-[1-(3-fluorophenethyl)piperidin-4-ylmethyl]-5-thia-1,8b-diazaacenaphthylene-4-carboxamide dihydrochloride as orange-colored crystals.

$^1$H-NMR (200 MHz, CD$_3$OD) δ: 1.45–1.70 (2H, m), 1.75–2.10 (3H, m), 2.90–3.50 (8H, m), 3.60–3.75 (2H, m), 6.62 (1H, d, J=7.6 Hz), 6.95–7.20 (5H, m), 7.30–7.43 (2H, m), 7.53 (1H, s).

IR (KBr): 1633, 1566, 1539, 1292, 785 cm$^{-1}$.

Elemental analysis for $C_{24}H_{27}N_4OSFCE_2.1.5H_2O$ Calcd.: C, 53.73; H, 5.64; N, 10.44 Found: C, 53.54; H, 5.91; N, 10.36

Example 70

Synthesis of N-[1-(4-fluorophenethyl)piperidin-4-ylmethyl]-5-thia-1,8b-diazaacenaphthylene-4-carboxamide Dihydrochloride 1) The procedure of Example 67-1) was generally followed to provide N-[1-(4-fluorophenethyl)piperidin-4-ylmethyl]-5-thia-1,8b-diazaacenaphthylene-4-carboxamide as reddish orange-colored amorphous substance.

$^1$H-NMR (200 MHz, CDCl$_3$) δ: 1.20–1.45 (2H, m), 1.45–1.80 (3H, m), 1.90–2.10 (2H, m)1 2.50–2.59 (2H, m), 2.74–2.82 (2H, m), 3.01 (2H, br d, J=11.8 Hz), 3.21 (2H, t, J=6.0 Hz), 5.78 (1H, dd, J=2.0, 5.6 Hz), 6.09 (1H, br t, J=5.6 Hz), 6.58–6.69 (3H, m), 6.91–7.03 (3H, m), 7.11–7.27 (2H, m).

IR (KBr): 3352, 2927, 1618, 15456, 1510, 1481, 1282, 1219, 1153, 827, 773, 731 cm$^{-1}$.

2) The procedure of Example 67-2) was generally followed to provide N-[1-(4-fluorophenethyl)piperidin-4-ylmethyl]-5-thia-1,8b-diazaacenaphthylene-4-carboxamide dihydrochloride as orange-colored crystals.

$^1$H-NMR (200 MHz, CD$_3$OD) δ: 1.45–1.75 (2H, m), 1.75–2.10 (3H, m), 2.90–3.45 (8H, m), 3.60–3.75 (2H, m), 6.61 (1H, d, J=7.8 Hz), 6.97–7.11 (4H, m), 7.29–7.42 (3H, m), 7.52 (1H, s).

IR (KBr): 3431, 3246, 3061, 2935, 2690, 1632, 1566, 1541, 1510, 1439, 1389, 1288, 1215, 831, 783 cm$^{-1}$.

Elemental analysis for $C_{24}H_{27}N_4OSFCl_2.0.5H_2O$ Calcd.: C, 55.60; H, 5.44; N, 10.81 Found: C, 55.83; H, 5.27; N, 11.02

Example 71

Synthesis of N-[1-(2-chlorophenethyl)piperidin-4-ylmethyl]-5-thia-1,8b-diazaacenaphthylene-4-carboxamide Dihydrochloride 1) The procedure of Example 67-1) was generally followed to provide N-[1-(2-chlorophenethyl)piperidin-4-ylmethyl]-5-thia-1,8b-diazaacenaphthylene-4-carboxamide as reddish orange-colored amorphous substance.

$^1$H-NMR (200 MHz, CDCl$_3$) δ: 1.25–1.47 (2H, m), 1.47–1.80 (3H, m), 2.00–2.20 (2H, m), 2.56–2.64 (2H, m), 2.90–3.09 (4H, m), 3.23 (2H, t, J=5.8 Hz), 5.79 (1H, dd, J=1.8, 6.0 Hz), 5.94 (1H, br t, J=5.5 Hz), 6.59–6.71 (3H, m), 7.05 (1H, s), 7.10–7.40 (4H, m).

IR (KBr): 3309, 2924, 1618, 1543, 1510, 1479, 1282, 1155, 771, 754, 732 cm$^{-1}$.

2) The procedure of Example 67-2) was generally followed to provide N-[1-(2-chlorophenethyl)piperidin-4- ylmethyl]-5-thia-1,8b-diazaacenaphthylene-4-carboxamide dihydrochloride as orange-colored crystals.

¹H-NMR (200 MHz, CD₃OD) δ: 1.45–1.75 (2H, m), 1.80–2.10 (3H, m), 2.95–3.45 (8H, m), 3.65–3.80 (2H, m), 6.61 (1H, d, J=7.8 Hz), 6.99 (1H, d, J=7.8 Hz), 7.01 (1H, s), 7.25–7.50 (5H, m), 7.53 (1H, s).

IR (KBr): 3429, 2945, 2710, 1653, 1635, 1564, 1537, 1502, 1282, 773, 754 cm⁻¹.

Elemental analysis for $C_{24}H_{27}N_4OSCl_3 \cdot 0.5H_2O$ Calcd.: C, 53.89; H, 5.28; N, 10.47 Found: C, 53.74; H, 5.09; N, 10.52

Example 72

Synthesis of N-[1-(3-chlorophenethyl)piperidin-4-ylmethyl]-5-thia-1,8b-diazaacenaphthylene-4-carboxamide Dihydrochloride 1) The procedure of Example 67-1) was generally followed to provide N-[1-(3-chlorophenethyl)piperidin-4-ylmethyl]-5-thia-1,8b-diazaacenaphthylene-4-carboxamide as reddish orange-colored amorphous substance.

¹H-NMR (200 MHz, CDCl₃) δ: 1.20–1.45 (2H, m), 1.45–1.80 (3H, m), 1.90–2.15 (2H, m), 2.53–2.60 (2H, m), 2.74–2.82 (2H, m), 3.00 (2H, br d, J=11.8 Hz), 3.21 (2H, t, J=6.0 Hz), 5.78 (1H, dd, J=1.8, 6.0 Hz), 5.95–6.05 (1H, m), 6.58–6.69 (3H, m), 7.03–7.09 (2H, m), 7.10–7.20 (3H, m).

IR (KBr): 3327, 2926, 1618, 1545, 1481, 1282, 1153, 687 cm⁻¹.

2) The procedure of Example 67-2) was generally followed to provide N-[1-(3-chlorophenethyl)piperidin-4-ylmethyl)-5-thia-1,8b-diazaacenaphthylene-4-carboxamide dihydrochloride as orange-colored crystals.

¹H-NMR (200 MHz, CD₃OD) δ: 1.45–1.75 (2H, m), 1.75–2.10 (3H, m), 2.90–3.50 (8H, m), 3.60–3.75 (2H, m), 6.62 (1H, d, J=7.6 Hz), 6.97–7.02 (2H, m), 7.20–7.45 (5H, m), 7.53 (1H, s).

IR (KBr): 1633, 1566, 1537, 1504, 1292, 1215, 785 cm⁻¹.

Elemental analysis for $C_{24}H_{27}N_4OSCl_3 \cdot 1.5H_2O$ Calcd.: C, 52.13; H, 5.47; N, 10.13 Found: C, 52.47; H, 5.53; N, 10.23

Example 73

Synthesis of N-[1-(4-chlorophenethyl)piperidin-4-ylmethyl]-5-thia-1,8b-diazaacenaphthylene-4-carboxamide Dihydrochloride 1) The procedure of Example 67-1) was generally followed to provide N-[1-(4-chlorophenethyl)piperidin-4-ylmethyl]-5-thia-1,8b-diazaacenaphthylene-4-carboxamide as reddish orange-colored amorphous substance.

¹H-NMR (200 MHz, CDCl₃) δ: 1.20–1.45 (2H, m), 1.45–1.80 (3H, m), 1.90–2.10 (2H, m), 2.50–2.60 (2H, m), 2.70–2.85 (2H, m), 3.00 (2H, br d, J=11.4 Hz), 3.22 (2H, t, J=6.1 Hz), 5.79 (1H, dd, J=1.9, 6.1 Hz), 5.94 (1H, br t, J=5.9 Hz), 6.59–6.72 (3H, m), 7.05–7.14 (3H, m), 7.22–7.27 (2H, m).

IR (KBr): 3282, 3055, 2924, 2806, 1616, 1549, 1485, 1282, 1153, 1119, 1092, 970, 773, 731 cm⁻¹.

2) The procedure of Example 67-2) was generally followed to provide N-[1-(4-chlorophenethyl)piperidin-4-ylmethyl]-5-thia-1,8b-diazaacenaphthylene-4-carboxamide dihydrochloride as orange-colored crystals.

¹H-NMR (200 MHz, CD₃OD) δ: 1.40–1.75 (2H, m), 1.75–2.10 (3H, m), 2.90–3.50 (8H, m), 3.60–3.75 (2H, m), 6.61 (1H, d, J=7.4 Hz), 6.99 (1H, d, J=8.8 Hz), 7.00 (1H, s), 7.25–7.45 (5H, m), 7.53 (1H, s).

IR (KBr): 3425, 3061, 2935, 2731, 1633, 1566, 1537, 1498, 1292, 1215, 785 cm⁻¹.

Elemental analysis for $C_{24}H_{27}N_4OSCl_3 \cdot 1.5H_2O$ Calcd.: C, 52.13; H, 5.47; N, 10.13 Found C, 51.90; H, 5.54; N, 10.10

Example 74

Synthesis of N-[1-(3-(3-fluorophenyl)propan-1-yl) piperidin-4-ylmethyl]-5-thia-1,8b-diazaacenaphthylene-4-carboxamide Dihydrochloride 1) The procedure of Example 67-1) was generally followed to provide N-[1-(3-(3-fluorophenyl)propan-1-yl) piperidin-4-ylmethyl]-5-thia-1,8b-diazaacenaphthylene-4-carboxamide as red-purple amorphous substance.

¹H-NMR (200 MHz, CDCl₃) δ: 1.30–1.97 (m, 9H), 2.31–2.38 (m, 2H), 2.62 (t, J=7.5 Hz, 2H), 2.93 (br d, J=11.8 Hz, 2H), 3.21 (t, J=6.0 Hz, 2H), 5.79 (dd, J=1.7, 6.1 Hz, 1H), 5.77–5.85 (m, 1H), 6.58–6.70 (m, 3H), 6.81–6.96 (m, 3H), 7.05 (s, 1H), 7.11–7.25 (m, 1H).

2) The procedure of Example 67-2) was generally followed to provide N-[1-(3-(3-fluorophenyl)propan-1-yl) piperidin-4-ylmethyl]-5-thia-1,8b-diazaacenaphthylene-4-carboxamide dihydrochloride as orange-colored crystals.

¹H-NMR (200 MHz, DMSO-d₆) δ: 1.45–2.13 (m, 7H), 2.66 (t, J=7.6 Hz, 2H), 2.70–3.28 (m, 8H), 6.62 (d, J=7.2 Hz, 1H), 6.93–7.40 (m, 7H), 7.66 (s, 1H), 8.86–8.97 (m, 1H).

IR (KBr): 3417, 3064, 2941, 1635, 1574, 1535, 1294, 787 cm⁻¹.

Example 75

Synthesis of N-[1-(3-(4-fluorophenyl)propan-1-yl) piperidin-4-ylmethyl]-5-thia-1,8b-diazaacenaphthylene-4-carboxamide Dihydrochloride 1) The procedure of Example 67-1) was generally followed to provide N-[1-(3-(4-fluorophenyl)propan-1-yl) piperidin-4-ylmethyl]-5-thia-1,8b-diazaacenaphthylene-4-carboxamide as red-purple amorphous substance.

¹H-NMR (200 MHz, CDCl₃) δ: 1.30–2.47 (m, 11H), 2.61 (t, J=7.7 Hz, 2H), 3.02 (br d, J=12 Hz, 2H), 3.21 (t, J=5.9 Hz, 2H), 5.76–5.80 (m, 1H), 6.04–6.20 (m, 1H), 6.57–6.68 (m, 2H), 6.74 (s, 1H), 6.92–7.17 (m, 5H).

2) The procedure of Example 67-2) was generally followed to provide N-[1-(3-(4-fluorophenyl)propan-1-yl) piperidin-4-ylmethyl]-5-thia-1,8b-diazaacenaphthylene-4-carboxamide dihydrochloride as orange-colored crystals.

¹H-NMR (200 MHz, DMSO-d₆) δ: 1.40–2.04 (m, 6H), 2.53–3.10 (m, 11H), 6.55 (d, J=7.6 Hz, 1H), 6.94 (d, J=9.2 Hz, 1H), 7.08–7.31 (m, 6H), 7.57 (d, J=1.2 Hz, 1H), 8.78–8.88 (m, 1H).

IR (KBr): 1639, 1508, 1294, 1221 cm⁻¹.

Elemental analysis for $C_{25}H_{29}N_4OSCl_2F \cdot 0.5H_2O$ Calcd.: C, 56.39; H, 5.68; N, 10.52 Found: C, 56.47; H, 5.85; N, 10.61

Example 76

Synthesis of N-[1-(3-(2,4-difluorophenyl)propan-1-yl)piperidin-4-ylmethyl]-5-thia-1,8b-diazaacenaphthylene-4-carboxamide Dihydrochloride 1) The procedure of Example 67-1) was generally followed to provide N-[1-(3-(2,4-difluorophenyl)propan-1-yl)

piperidin-4-ylmethyl]-5-thia-1,8b-diazaacenaphthylene-4-carboxamide as red-purple amorphous substance.

$^1$H-NMR (200 MHz, CDCl$_3$) δ: 1.16–2.05 (m, 8H), 2.34 (t, J=7.7 Hz, 2H), 2.60 (t, J=7.7 Hz, 2H), 2.69 (m, 1H), 2.91 (br d, J=12 Hz, 2H), 3.18 (t, J=6.1 Hz, 2H), 5.76 (dd, J=2.8, 5.0 Hz, 1H), 6.39 (m, 1H), 6.56–6.82 (m, 5H), 6.98 (s, 1H), 7.07–7.18 (m, 1H).

2) The procedure of Example 67-2) was generally followed to provide N-[1-(3-(2,4-difluorophenyl)propan-1-yl) piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.35–2.06 (m, 7H), 2.60–13.49 (m, 10H), 6.56 (d, J=7.6 Hz, 1H), 6.95 (d, J=8.8 Hz, 1H), 7.00–7.46 (m, 5H), 7.60 (s, 1H), 8.82–8.90 (m, 1H).

IR (KBr):3415, 3056, 2943, 2700, 1635, 1504, 1288 cm$^{-1}$.

Elemental analysis for C$_{25}$H$_{28}$N$_4$OSCl$_2$F$_2$.1.0H$_2$O Calcd.: C, 53.67; H, 5.40; N, 10.01 Found: C, 53.97; H, 5.28; N, 10.11

Example 77

Synthesis of N-[1-(3-(2-chlorophenyl)propan-1-yl) piperidin-4-ylmethyl]-5-thia-1,8b-diazaacenaphthylene-4-carboxamide Dihydrochloride 1) The procedure of Example 67-1) was generally followed to provide N-[1-(3-(2-chlorophenyl)propan-1-yl) piperidin-4-ylmethyl]-5-thia-1,8b-diazaacenaphthylene-4-carboxamide as red-purple amorphous substance.

$^1$H-NMR (200 MHz, CDCl$_3$) δ: 1.17–2.05 (m, 9H), 2.39 (t, J=7.6 Hz, 2H), 2.74 (t, J=7.7 Hz, 2H), 2.94 (br d, J=11.4 Hz, 2H), 3.20 (t, J=6.1 Hz, 2H), 5.78 (dd, J=1.8, 6.0 Hz, 1H), 5.97 (m, 1H), 6.57–6.70 (m, 3H), 7.03 (s, 1H), 7.06–7.37 (m, 4H).

2) The procedure of Example 67-2) was generally followed to provide N-[1-(3-(2-chlorophenyl)propan-1-yl) piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.40–2.23 (m, 7H), 2.65–3.70 (m, 10H), 6.49–6.53 (d, J=7.4 Hz, 1H), 6.92 (d, J=9.4 Hz, 1H), 7.08–7.46 (m, 6H), 7.55 (s, 1H), 8.75–8.80 (m, 1H).

IR (KBr): 3452, 3375, 3055, 2951, 2690, 1641, 1531, 1439, 1288, 1217, 800 cm$^{-1}$.

Elemental analysis for C$_{25}$H$_{29}$N$_4$OSCl$_3$.0.6H$_2$O Calcd.: C, 54.51; H, 5.52; N, 10.17 Found: C, 54.70; H, 5.71; N, 9.90

Example 78

Synthesis of N-[1-(3-(3-chlorophenyl)propan-1-yl) piperidin-4-ylmethyl]-5-thia-1,8b-diazaacenaphthylene-4-carboxamide Dihydrochloride 1) The procedure of Example 67-1) was generally followed to provide N-[1-(3-(3-chlorophenyl)propan-1-yl) piperidin-4-ylmethyl]-5-thia-1,8b-diazaacenaphthylene-4-carboxamide as red-purple amorphous substance.

$^1$H-NMR (200 MHz, CDCl$_3$) δ: 1.18–2.00 (m, 9H), 2.29–2.37 (m, 2H), 2.59 (t, J=7.5 Hz, 2H), 2.91 (br d, J=11.4 Hz, 2H), 3.18 (t, J=6.1 Hz, 2H), 5.76 (dd, J=2.4, 5.4 Hz, 1H), 6.29 (br t, J=5.9 Hz, 1H), 6.59–6.66 (m, 3H), 7.00 (s, 1H), 7.03–7.07 (m, 1H), 7.12–7.24 (m, 3H).

2) The procedure of Example 67-2) was generally followed to provide N-[1-(3-(3-chlorophenyl)propan-1-yl) piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.40–2.12 (m, 7H), 2.65 (t, J=7.7 Hz, 2H), 2.72–3.26 (m, 6H), 3.38–3.50 (m, 2H), 6.61 (d, J=7.4 Hz, 1H), 6.97 (d, J=9.2 Hz, 1H), 7.21–7.39 (m, 6H), 7.65 (s, 1H), 8.89–8.99 (m, 1H).

IR (KBr): 3442, 1637, 1292, 1213, 793 cm$^{-1}$.

Elemental analysis for C$_{25}$H$_{29}$N$_4$OSCl$_3$.1.0H$_2$O Calcd.: C, 53.82; H, 5.60; N, 10.04 Found: C, 54.07; H, 5.80; N, 9.79

Example 79

Synthesis of N-[1-[3-(4-chlorophenyl)propan-1-yl]-piperidin-4-ylmethyl]-5-thia-1,8b-diazaacenaphthylene-4-carboxamide Dihydrochloride 1) The procedure of Example 67-1) was generally followed to provide N-[1-[3-(4-chlorophenyl)propan-1-yl] piperidin-4-ylmethyl]-5-thia-1,8b-diazaacenaphthylene-4-carboxamide as red oil.

$^1$H-NMR (200 MHz, CDCl$_3$) δ: 1.45–1.83 (5H, m), 1.85–2.03 (2H, m), 2.15–2.30 (2H, m), 2.53–2.67 (4H, m), 3.10–3.24 (4H, m), 5.754 (1H, dd, J=2.4, 5.3 Hz), 6.50–6.70 (3H, m), 6.822 (1H, s), 7.05–7.15 (3H, m), 7.22–7.30 (2H, m).

2) The procedure of Example 67-2) was generally followed to provide N-[1-[3-(4-chlorophenyl)propan-1-yl] piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.45–1.95 (4H, m), 1.90–2.15 (2H, m), 2.58–2.70 (2H, m), 2.70–3.30 (5H, m), 3.40–3.55 (2H, m), 6.685 (1H, d, J=7.6 Hz), 7.017 (1H, d, J=7.6 Hz), 7.017 (1H, d, J=9.2 Hz), 7.24–7.39 (5H, m), 7.720 (1H, s), 8.90–9.10 (1H, m), 10.588 (1H, br s).

IR (KBr): 3420, 3250, 3050, 2950, 2850, 2720, 2670, 2600, 2550, 1650, 1630, 1560, 1530, 1500, 1440, 1280, 1220, 1090, 780 cm$^{-1}$.

Elemental analysis for C$_{25}$H$_{29}$N$_4$OSCl$_3$.1.5H$_2$O Calcd.: C, 52.96; H, 5.69; N, 9.88 Found: C, 53.43; H, 5.71; N, 9.59

Example 80

Synthesis of N-[1-(3-(2-methoxyphenyl)propan-1-yl)piperidin-4-ylmethyl]-5-thia-1,8b-diazaacenaphthylene-4-carboxamide Dihydrochloride 1) The procedure of Example 67-1) was generally followed to provide N-[1-(3-(2-methoxyphenyl)propan-1-yl) piperidin-4-ylmethyl]-5-thia-1,8b-diazaacenaphthylene-4-carboxamide as red-purple amorphous substance.

$^1$H-NMR (200 MHz, CDCl$_3$) δ: 1.20–2.00 (m, 9H), 2.35–2.43 (m, 2H), 2.61 (t, J=7.7 Hz, 2H), 2.96 (br d, J=11.4 Hz, 2H), 3.18 (t, J=5.9 Hz, 2H), 3.81 (s, 3H), 5.74–5.78 (m, 1H), 6.16–6.30 (m, 1H), 6.55–6.67 (m, 3H), 6.78–6.89 (m, 2H), 6.99–7.20 (m, 3H).

2) The procedure of Example 67-2) was generally followed to provide N-[1-(3-(2-methoxyphenyl)propan-1-yl) piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.35–2.00 (m, 7H), 2.53–3.26 (m, 8H), 3.38–3.47 (m, 2H), 3.79 (s, 3H), 6.56 (d,

J=7.2 Hz, 1H), 6.83–6.98 (m, 3H), 7.13–7.27 (m, 4H), 7.60 (s, 1H), 8.80–8.92 (m, 1H).

IR (KBr): 3463, 3390, 2948, 2702, 1638, 1533, 1498, 1441, 1290, 802, 764 cm$^{-1}$.

Elemental analysis for $C_{26}H_{32}N_4OSCl_2 \cdot 1.0H_2O$ Calcd.: C, 56.41; H, 6.19; N, 10.12 Found: C, 56.69; H, 6.24; N, 10.07

Example 81

Synthesis of N-[1-[3-(4-methoxyphenyl)propan-1-yl]piperidin-4-ylmethyl]-5-thia-1,8b-diazaacenaphthylene-4-carboxamide Dihydrochloride 1) The procedure of Example 67-1) was generally followed to provide N-[1-[3-(4-methoxyphenyl)propan-1-yl]piperidin-4-ylmethyl]-5-thia-1,8b-diazaacenaphthylene-4-carboxamide as red oil.

$^1$H-NMR (200 MHz, CDCl$_3$) δ: 1.25–1.95 (9H, m), 2.29–2.36 (2H, m), 2.52–2.60 (2H, m), 2.86–2.96 (2H, m), 3.204 (2H, t, J=6.2 Hz), 3.786 (3H, s), 5.791 (1H, dd, J=1.8, 6.2 Hz), 5.70–5.82 (1H, m), 6.632–6.692 (3H, m), 6.818 (2H, d, J=8.6 Hz), 7.054 (1H, s), 7.093 (2H, d, J=8.8 Hz).

2) The procedure of Example 67-2) was generally followed to provide N-[1-[3-(4-methoxyphenyl)propan-1-yl]piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.45–2.10 (7H, m), 2.50–2.60 (2H, m), 2.70–3.30 (6H, m), 3.37–3.51 (2H, m), 3.728 (3H, s), 6.604 (1H, d, J=7.4 Hz), 6.867 (2H, d, J=8.0 Hz), 6.973 (1H, d, J=9.2 Hz), 7.13–7.32 (4H, m), 7.643 (1H, s), 8.90–8.96 (1H, m).

IR (KBr): 3420, 3280, 2980, 2930, 2670, 1635, 1560, 1530, 1510, 1460, 1280, 1260, 1240, 1220, 1030, 780 cm$^{-1}$.

Elemental analysis for $C_{26}H_{32}N_4O_2SCl_2 \cdot 1H_2O$ Calcd.: C, 56.41; H, 6.19; N, 10.12 Found: C, 56.09; H, 6.36; N, 10.00

Example 82

Synthesis of N-[1-(3-(2,3-dimethoxyphenyl)propan-1-yl)piperidin-4-ylmethyl]-5-thia-1,8b-diazaacenaphthylene-4-carboxamide Dihydrochloride 1) The procedure of Example 67-1) was generally followed to provide N-[1-[3-(2,3-dimethoxyphenyl)propan-1-yl)piperidin-4-ylmethyl]-5-thia-1,8b-diazaacenaphthylene-4-carboxamide as red-purple amorphous substance.

$^1$H-NMR (200 MHz, CDCl$_3$) δ: 1.15–1.98 (m, 9H), 2.34–2.42 (m, 2H), 2.54–2.69 (m, 2H), 2.85–2.99 (m, 2H), 3.17 (t, J=6.0 Hz, 2H), 3.81 (s, 3H), 3.85 (s, 3H), 5.73–5.78 (m, 1H), 6.52–6.65 (m, 4H), 6.75–6.79 (m, 2H), 6.92–6.99 (m, 2H).

2) The procedure of Example 67-2) was generally followed to provide N-[1-[3-(2,3-dimethoxyphenyl)propan-1-yl)piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.35–2.03 (m, 7H), 2.55–3.07 (m, 8H), 3.38–3.49 (m, 2H), 3.73 (s, 3H), 3.80 (s, 3H), 6.58 (d, J=7.8 Hz, 1H), 6.78–7.03 (m, 4H), 7.14–7.29 (m, 2H), 7.61 (s, 1H), 8.81–8.90 (m, 1H).

Elemental analysis for $C_{27}H_{34}N_4O_3SCl_2 \cdot 2.0H_2O$ Calcd.: C, 53.91; H, 6.37; N, 9.31 Found: C, 53.98; H, 6.66; N, 9.06

Example 83

Synthesis of N-[1-(3-(2,4-dimethoxyphenyl)propan-1-yl)piperidin-4-ylmethyl]-5-thia-1,8b-diazaacenaphthylene-4-carboxamide Dihydrochloride 1) The procedure of Example 67-1) was generally followed to provide N-[1-(3-(2,4-dimethoxyphenyl)propan-1-yl)piperidin-4-ylmethyl]-5-thia-1,8b-diazaacenaphthylene-4-carboxamide as red-purple amorphous substance.

$^1$H-NMR (200 MHz, CDCl$_3$) δ: 1.20–1.97 (m, 9H), 2.33–2.41 (m, 2H), 2.53 (t, J=7.6 Hz, 2H), 2.95 (br d, J=11.4 Hz, 2H), 3.18 (t, J=6.0 Hz, 2H), 3.78 (s, 3H), 3.79 (s, 3H), 5.76 (dd, J=2.4, 5.6 Hz, 1H), 6.26–6.43 (m, 3H), 6.60–6.68 (m, 3H), 6.99–7.03 (m, 2H).

2) The procedure of Example 67-2) was generally followed to provide N-[1-(3-(2,4-dimethoxyphenyl)propan-1-yl)piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.39–1.95 (m, 7H), 2.65–3.25 (m, 8H), 3.37–3.45 (m, 2H), 3.74 (s, 3H), 3.78 (s, 3H), 6.43–6.55 (m, 3H), 6.92 (d, J=9.0 Hz, 1H), 7.04–7.24 (m, 3H), 7.57 (s, 1H), 8.77–8.84 (m, 1H).

IR (KBr): 3429, 1633, 1508, 1292, 1209, 787 cm$^{-1}$.

Elemental analysis for $C_{27}H_{34}N_4O_3SCl_2 \cdot 2.5H_2O$ Calcd.: C, 53.11; H, 6.44; N, 9.18 Found C, 53.30; H, 6.65; N, 9.18

Example 84

Synthesis of N-[1-[3-(4-ethylphenyl)propan-1-yl]piperidin-4-ylmethyl]-5-thia-1,8b-diazaacenaphthylene-4-carboxamide Dihydrochloride 1) The procedure of Example 67-1) was generally followed to provide N-[1-[3-(4-ethylphenyl)propan-1-yl]piperidin-4-ylmethyl]-5-thia-1,8b-diazaacenaphthylene-4-carboxamide as red oil.

$^1$H-NMR (200 MHz, CDCl$_3$) δ: 1.220 (3H, t, J=7.6 Hz), 1.25–1.38 (1H, m), 1.40–2.05 (8H, m), 2.32–2.39 (2H, m), 2.54–2.67 (4H, m), 2.88–2.95 (2H, m), 3.196,(2H, t, J=6.1 Hz), 5.778 (1H, dd, J=1.8, 6.1 Hz), 5.85–5.93 (1H, m), 6.573–6.695 (3H, m), 7.034 (1H, s), 7.097 (4H, s).

2) The procedure of Example 67-2) was generally followed to provide N-[1-[3-(4-ethylphenyl)propan-1-yl]piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.159 (3H, t, J=7.5 Hz), 1.43–1.85 (5H, m), 1.90–2.10 (2H, m), 2.45–2.65 (4H, m), 2.75–3.25 (5H, m), 3.35–3.55 (3H, m), 6.603 (1H, d, J=7.4 Hz), 6.970 (1H, d, J=9.2 Hz), 7.14–7.31 (5H, m), 7.643 (1H, s), 8.85–9.00 (1H, m), 10.47 (1H, br s).

IR (KBr): 3400, 3250, 3050, 2950, 2920, 2730, 1630, 1560, 1530, 1500, 1440, 1390, 1290, 1110, 1045, 945, 780 cm$^{-1}$.

Elemental analysis for $C_{27}H_{34}N_4O_2SCl_2 \cdot 1H_2O$ Calcd.: C, 58.79; H, 6.58; N, 10.16 Found C, 58.64; H, 6.62; N, 9.62

Example 85

Synthesis of N-[1-(3-(2-trifluoromethylphenyl)propan-1-yl)piperidin-4-ylmethyl]-5-thia-1,8b-diazaacenaphthylene-4-carboxamide Dihydrochloride 1) The procedure of Example 67-1) was generally followed to provide N-[1-(3-(2-trifluoromethylphenyl)propan-1-yl)piperidin-4-ylmethyl]-5-thia-1,8b-diazaacenaphthylene-4-carboxamide as red-purple amorphous substance.

$^1$H-NMR (200 MHz, CDCl$_3$) δ: 1.18–2.05 (m, 9H), 2.30–2.38 (m, 2H), 2.68 (t, J=7.5 Hz, 2H), 2.85–3.01 (m, 2H), 3.21 (t, J=6.2 Hz, 2H), 5.79 (dd, J=1.8, 6.0 Hz, 1H), 5.65–5.90 (m, 1H), 6.59–6.71 (m, 3H), 7.05 (s, 1H), 7.28 (d, J=8.0 Hz, 2H), 7.53 (d, J=8.0 Hz, 2H).

2) The procedure of Example 67-2) was generally followed to provide N-[1-(3-(2-trifluoromethylphenyl)propan-1-yl)piperidin-4-ylmethyl]-5-thia-1,8b-diazaacenaphthylene-4-carboxamide dihydrochloride as orange-colored crystals.

$^1$H-NMR (200 MHz, DMSO-$d_6$) δ: 1.30–2.10 (m, 7H), 2.68–3.52 (m, 10H), 6.51 (d, J=7.4 Hz, 1H), 6.91 (d, J=8.8 Hz, 1H), 7.08 (s, 1H), 7.14–7.22 (m, 1H), 7.41–7.73 (m, 5H), 8.72–8.86 (m, 1H).

IR (KBr): 3425, 3250, 3059, 2947, 2710, 1637, 1308, 1115, 779 cm$^{-1}$.

Elemental analysis for $C_{26}H_{29}N_4OSCl_2F_3 \cdot 1.5H_2O$
Calcd.: C, 52.00; H, 5.37; N, 9.33 Found: C, 51.77; H, 5.28; N, 9.10

Example 86

Synthesis of N-[1-(3-(3-trifluoromethylphenyl)propan-1-yl)piperidin-4-ylmethyl]-5-thia-1,8b-diazaacenaphthylene- 4-carboxamide Dihydrochloride 1) The procedure of Example 67-1) was generally followed to provide N-[1-(3-(3-trifluoromethylphenyl)propan-1-yl)piperidin-4-ylmethyl]-5-thia-1,8b-diazaacenaphthylene-4-carboxamide as red-purple amorphous substance.

$^1$H-NMR (200 MHz, CDCl$_3$) δ: 1.18–2.03 (m, 9H), 2.30–2.37 (m, 2H), 2.68 (t, J=7.6 Hz, 2H), 2.88–2.94 (m, 2H), 3.20 (t, J=6.0 Hz, 2H), 5.78 (dd, J=1.9, 5.9 Hz, 1H), 6.07 (br t, J=5.9 Hz, 1H), 6.62–6.68 (m, 3H), 7.02 (s, 1H), 7.35–7.48 (m, 4H).

2) The procedure of Example 67-2) was generally followed to provide N-[1-(3-(3-trifluoromethylphenyl)propan-1-yl)piperidin-4-ylmethyl]-5-thia-1,8b-diazaacenaphthylene-4-carboxamide dihydrochloride as orange-colored crystals.

$^1$H-NMR (200 MHz, DMSO-$d_6$) δ: 1.19–2.08 (m, 7H), 2.68–3.52 (m, 10H), 6.60 (d, J=7.2 Hz, 1H), 6.96 (d, J=8.6 Hz, 1H), 7.17–7.31 (m, 2H), 7.58–7.64 (m, 5H), 8.86–8.97 (m, 1H).

IR (KBr): 3423, 3060, 2942, 1637, 1329, 1120, 791 cm$^{-1}$.

Elemental analysis for $C_{26}H_{29}N_4OSCl_2F_3 \cdot 2.0H_2O$
Calcd.: C, 51.23; H, 5.46; N, 9.19 Found: C, 51.25; H, 5.45; N, 9.17

Example 87

Synthesis of N-[1-(3-(4-trifluoromethylphenyl)propan-1-yl)piperidin-4-ylmethyl]-5-thia-1,8b-diazaacenaphthylene-4-carboxamide Dihydrochloride 1) The procedure of Example 67-1) was generally followed to provide N-[1-(3-(4-trifluoromethylphenyl)propan-1-yl)piperidin-4-ylmethyl]-5-thia-1,8b-diazaacenaphthylene-4-carboxamide as red-purple amorphous substance.

$^1$H-NMR (200 MHz, CDCl$_3$) δ: 1.18–2.05 (m, 9H), 2.30–2.38 (m, 2H), 2.68 (t, J=7.5 Hz, 2H), 2.85–3.01 (m, 2H), 3.21 (t, J=6.2 Hz, 2H), 5.79 (dd, J=1.8, 6.0 Hz, 1H), 5.65–5.90 (m, 1H), 6.59–6.71 (m, 3H), 7.05 (s, 1H), 7.28 (d, J=8.0 Hz, 2H), 7.53 (d, J=8.0 Hz, 2H).

2) The procedure of Example 67-2) was generally followed to provide N-[1-(3-(4-trifluoromethylphenyl)propan-1-yl)piperidin-4-ylmethyl]-5-thia-1,8b-diazaacenaphthylene-4-carboxamide dihydrochloride as orange-colored crystals.

$^1$H-NMR (200 MHz, DMSO-$d_6$) δ: 1.36–2.18 (m, 7H), 2.74 (t, J=7.6 Hz, 2H), 2.70–3.23 (m, 6H), 3.41–3.53 (m, 2H), 6.64 (d, J=7.0 Hz, 1H), 6.99 (d, J=8.4 Hz, 1H), 7.16–7.23 (m, 1H), 7.30 (dd, J=7.0, 8.4 Hz, 1H), 7.49 (d, J=8.0 Hz, 2H), 7.677 (s, 1H), 2.782 (d, J=8.0 Hz, 2H), 8.87–9.00 (m, 1H).

IR (KBr): 3398, 3057, 2941, 2673, 1635, 1327, 1119, 785 cm$^{-1}$.

Elemental analysis for $C_{26}H_{29}N_4OSCl_2F_3 \cdot 1.5H_2O$
Calcd.: C, 52.00; H, 5.37; N, 9.33 Found C, 51.87; H, 5.16; N, 9.47

Example 88

Synthesis of N-[1-(3-(3-trifluoromethoxyphenyl)propan-1-yl)piperidin-4-ylmethyl]-5-thia-1,8b-diazaacenaphthylene-4-carboxamide Dihydrochloride 1) The procedure of Example 67-1) was generally followed to provide N-[1-(3-(3-trifluoromethoxyphenyl)propan-1-yl)piperidin-4-ylmethyl]-5-thia-1,8b-diazaacenaphthylene-4-carboxamide as red oil.

$^1$H-NMR (200 MHz, CDCl$_3$) δ: 1.20–1.38 (2H, m), 1.42–1.60 (1H, m), 1.62–2.00 (6H, m), 2.335 (2H, t, J=7.5 Hz), 2.645 (2H, t, J=7.7 Hz), 2.915 (2H, d, J=11.8 Hz), 3.207 (2H, t, J=6.1 Hz), 5.790 (1H, dd, J=1.8, 6.2 Hz), 5.78–5.85 (1H, m), 6.58–6.71 (3H, m), 7.00–7.13 (4H, m), 7.23–7.339 (1H, m).

2) The procedure of Example 67-2) was generally followed to provide N-[1-(3-(3-trifluoromethoxyphenyl)propan- 1-yl)piperidin-4-ylmethyl]-5-thia-1,8b-diazaacenaphthylene-4-carboxamide dihydrochloride as orange-colored crystals.

$^1$H-NMR (200 MHz, DMSO-$d_6$) δ: 1.42–1.95 (5H, m), 1.95–2.15 (2H, m), 2.61–3.23 (8H, m), 3.451 (2H, d like, J=11.4 Hz), 6.685 (1H, d, J=7.6 Hz), 7.020 (1H, d, J=9.2 Hz), 7.15–7.50 (6H, m), 7.719 (1H, s), 9.065 (1H, t like, J=5.5 Hz), 10.5 (1H, br s).

IR (KBr): 3420, 2950, 2720, 2550, 1635, 1565, 1535, 1500, 1440, 1395, 1280, 1220, 1150, 790, 740, 700, 630, 600 cm$^{-1}$.

Elemental analysis for $C_{26}H_{29}N_4O_2SCl_2F_3 \cdot 1.5H_2O$
Calcd.: C, 50.65; H, 5.23; N, 9.09 Found: C, 50.32; H, 5.63; N, 8.81

Example 89

Synthesis of N-[1-(3-(4-trifluoromethoxyphenyl)propan-1-yl)piperidin-4-ylmethyl]-5-thia-1,8b-diazaacenaphthylene-4-carboxamide dihydrochloride 1) The procedure of Example 67-1) was generally followed to provide N-[1-(3-(4-trifluoromethoxyphenyl)propan-1-yl)piperidin-4-ylmethyl]-5-thia-1,8b-diazaacenaphthylene-4-carboxamide as red-purple amorphous substance.

$^1$H-NMR (200 MHz, CDCl$_3$) δ: 1.32–2.21 (m, 9H), 2.44–2.52 (m, 2H), 2.64 (t, J=7.6 Hz, 2H), 3.03–3.09 (m, 2H), 3.19 (t, J=5.5 Hz, 2H), 5.75 (dd, J=2.6, 5.4 Hz, 1H), 6.41–6.69 (m, 3H), 6.77 (s, 1H), 7.01–7.22 (m, 5H).

2) The procedure of Example 67-2) was generally followed to provide N-[1-(3-(4-trifluoromethoxyphenyl)propan-1-yl)piperidin-4-ylmethyl]-5-thia-1,8b-diazaacenaphthylene-4-carboxamide dihydrochloride as orange-colored crystals.

¹H-NMR (200 MHz, DMSO-d₆) δ: 1.38–2.16 (m, 7H), 2.67 (t, J=7.6 Hz, 2H), 2.70–3.26 (m, 6H), 3.38–3.52 (m, 2H), 6.62 (d, J=7.4 Hz, 1H), 6.98 (d, J=9.0 Hz, 1H), 7.19–7.41 (m, 6H), 7.65 (s, 1H), 8.90–8.96 (m, 1H).

IR (KBr): 3375, 3062, 2942, 2710, 1637, 1506, 1269, 1217, 1161, 787 cm⁻¹.

Elemental analysis for $C_{26}H_{29}N_4O_2SCl_2F_3 \cdot 1.5H_2O$ Calcd.: C, 50.65; H, 5.23; N, 9.09 Found C, 50.38; H, 5.20; N, 8.87

Example 90

Synthesis of N-[1-[3-(4-hydroxyphenyl)propan-1-yl]piperidin-4-ylmethyl]-5-thia-1,8b-diazaacenaphthylene-4-carboxamide Dihydrochloride 1) The procedure of Example 67-1) was generally followed to provide N-[1-[3-(4-tert-butyldimethylsiloxyphenyl)propan-1-yl]piperidin-4-ylmethyl]-5-thia-1,8b-diazaacenaphthylene-4-carboxamide as red oil.

¹H-NMR (200 MHz, CDCl₃) δ: 0.178 (6H, s), 0.978 (9H, 5), 1.20–1.42 (2H, m), 1.42–2.05 (7H, m), 2.28–2.90 (2H, m), 2.544 (2H, t like, J=7.5 Hz), 2.88–3.00 (2H, m), 3.202 (2H, t like, J=6.0 Hz), 5.785 (1H, d, J=6.6 Hz), 5.80–5.95 (1H, m), 6.59–6.76 (5H, m), 6.90–7.05 (3H, m).

2) The procedure of Example 67-2) was generally followed to provide N-[1-[3-(4-hydroxyphenyl)propan-1-yl]piperidin-4-ylmethyl]-5-thia-1,8b-diazaacenaphthylene-4-carboxamide dihydrochloride as orange-colored crystals.

¹H-NMR (200 MHz, DMSO-d₆) δ: 1.40–2.10 (7H, m), 2.65–3.20 (7H, m), 3.33–3.53 (3H, m), 6.61–6.78 (3H, m), 6.90–7.05 (3H, m), 7.15–7.35 (2H, m), 7.671 (1H, s), 8.85–9.03 (1H, m), 10.4 (1H, br s).

IR (KBr): 3420, 3250, 2950, 2930, 1650, 1635, 1610, 1560, 1540, 1520, 1500, 1290, 1220, 800 cm⁻¹.

Elemental analysis for $C_{25}H_{30}N_4O_2SCl_2 \cdot 1.0H_2O$ Calcd.: C, 55.66; H, 5.98; N, 10.38 Found: C, 55.81; H, 5.91; N, 10.07

Example 91

Synthesis of N-[1-(3-(4-biphenyl)propan-1-yl)piperidin-4-ylmethyl]-5-thia-1,8b-diazaacenaphthylene-4-carboxamide Dihydrochloride 1) The procedure of Example 67-1) was generally followed to provide N-[1-(3-(4-biphenyl)propan-1-yl)piperidin-4-ylmethyl]-5-thia-1,8b-diazaacenaphthylene-4-carboxamide as red-purple amorphous substance.

¹H-NMR (200 MHz, CDCl₃) δ: 1.33–2.16 (m, 9H), 2.49–2.56 (m, 2H), 2.68 (t, J=7.7 Hz, 2H), 3.08 (br d, J=11.8 Hz, 2H), 3.19 (t, J=5.9 Hz, 2H), 5.73 (dd, J=2.2, 5.6 Hz, 1H), 6.53–6.72 (m, 3H), 6.77 (s, 1H), 7.01 (s, 1H), 7.23–7.60 (m, 9H).

2) The procedure of Example 67-2) was generally followed to provide N-[1-(3-(4-biphenyl)propan-1-yl)piperidin-4-ylmethyl]-5-thia-1,8b-diazaacenaphthylene-4-carboxamide dihydrochloride as orange-colored crystals.

¹H-NMR (200 MHz, DMSO-d₆) δ: 1.35–2.17 (m, 7H), 2.60–3.52 (m, 10H), 6.52 (d, J=7.4 Hz, 1H), 6.92 (d, J=8.2 Hz, 1H), 7.10–7.66 (m, 12H), 8.72–8.84 (m, 1H).

IR (KBr): 3425, 1635, 1292, 1213, 775 cm⁻¹.

Elemental analysis for $C_{31}H_{34}N_4OSCl_2 \cdot 2.0H_2O$ Calcd.: C, 60.28; H, 6.20; N, 9.07 Found: C, 60.10; H, 6.28; N, 8.79

Example 92

Synthesis of N-[1-(1-naphthylmethyl)piperidin-4-ylmethyl]-5-thia-1,8b-diazaacenaphthylene-4-carboxamide Dihydrochloride 1) The procedure of Example 67-1) was generally followed to provide N-[1-(1-naphthylmethyl)piperidin-4-ylmethyl]-5-thia-1,8b-diazaacenaphthylene-4-carboxamide as deep-red amorphous substance.

¹H-NMR (200 MHz, CDCl₃) δ: 1.15–1.40 (2H, m), 1.45–1.80 (3H, m), 1.90–2.10 (2H, m), 2.96 (2H, br d, J=11.0 Hz), 3.19 (2H, t, J=6.1 Hz), 3.88 (2H, s), 5.77 (1H, dd, J=1.5, 6.3 Hz), 5.75–5.90 (1H, m), 6.57–6.70 (3H, m), 7.04 (1H, s), 7.35–7.65 (4H, m), 7.70–7.90 (2H, m), 8.20–8.350 (1H, m).

IR (KBr): 3319, 3049, 2922, 2806, 2764, 1618, 1541, 1510, 1481, 1367, 1281, 1151, 1113, 970, 773, 733, 652 cm⁻¹.

2) The procedure of Example 67-2) was generally followed to provide N-[1-(1-naphthylmethyl)piperidin-4-ylmethyl]-5-thia-1,8b-diazaacenaphthylene-4-carboxamide dihydrochloride as light-orange-colored crystals.

¹H-NMR (200 MHz, CD₃OD) δ: 1.35–1.65 (2H, m), 1.80–2.05 (3H, m), 3.10–3.40 (4H, m), 3.50–3.65 (2H, m), 4.83 (2H, s), 6.60 (1H, d, J=7.6 Hz), 6.95–7.00 (2H, m), 7.34–7.81 (6H, m), 7.98–8.08 (2H, m), 8.26 (1H, d, J=8.0 Hz).

IR (KBr): 3427, 3062, 2935, 2729, 1633, 1564, 1537, 1504, 1394, 1296, 1217, 779, 602 cm⁻¹.

Elemental analysis for $C_{27}H_{28}N_4OSCl_2 \cdot 4.0H_2O$ Calcd.: C, 54.09; H, 6.05; N, 9.34 Found: C, 54.15; H, 5.79; N, 9.38

Example 93

Synthesis of N-[1-(2-naphthylmethyl)piperidin-4-ylmethyl]-5-thia-1,8b-diazaacenaphthylene-4-carboxamide Dihydrochloride 1) The procedure of Example 67-1) was generally followed to provide N-[1-(2-naphthylmethyl)piperidin-4-ylmethyl]-5-thia-1,8b-diazaacenaphthylene-4-carboxamide as reddish orange-colored solid.

¹H-NMR (CDC) δ: 1.20–1.45 (2H, m), 1.45–1.75 (3H, m), 1.80–2.15 (2H, m), 2.95 (2H, br d, J=11.4 Hz), 3.20 (2H, t, J=5.9 Hz), 3.66 (2H, s), 5.77 (1H, d, J=6.2 Hz), 5.80–5.95 (1H, m), 6.57–6.70 (3H, m), 7.03 (1H, s), 7.40–7.55 (3H, m), 7.70–7.90 (4H, m).

IR (KBr): 3292, 3257, 3051, 2912, 2800, 1630, 1545, 1512, 1481, 1365, 1335, 1279, 1146, 771, 730 cm⁻¹.

2) The procedure of Example 67-2) was generally followed to provide N-[1-(2-naphthylmethyl)piperidin-4-ylmethyl]-5-thia-1,8b-diazaacenaphthylene-4-carboxamide dihydrochloride as orange-colored crystals.

¹H-NMR (200 MHz, CD₃OD) δ: 1.40–1.70 (2H, m), 1.80–2.05 (3H, m), 2.95–3.30 (4H, m), 3.45–2.65 (2H, m), 4.48 (2H, s), 6.59 (1H, d, J=7.0 Hz), 6.96 (1H, s), 6.97 (1H, d, J=8.4 Hz), 7.33–7.41 (1H, m), 7.50 (1H, s), 7.50–7.65 (3H, m), 7.90–8.05 (3H, m), 8.07 (1H, s).

IR (KBr): 3427, 3228, 3055, 2933, 2669, 2530, 1632, 1566, 1537, 1502, 1433, 1389, 1290, 1213, 781, 598, 478 cm⁻¹.

Elemental analysis for $C_{27}H_{28}N_4OSCl_2 \cdot 1.0H_2O$ Calcd.: C, 59.45; H, 5.54; N, 10.27 Found: C, 59.52; H, 5.54; N, 10.27

Example 94

Synthesis of N-[1-(3-(2-naphthyl)propan-1-yl)piperidin-4-ylmethyl]-5-thia-1,8b-diazaacenaphthylene-4-carboxamide Dihydrochloride 1) The procedure of Example 67-1) was generally followed to provide N-[1-(3-(2-naphthyl)propan-1-yl)

piperidin-4-ylmethyl]-5-thia-1,8b-diazaacenaphthylene-4-carboxamide as red-purple amorphous substance.

$^1$H-NMR (200 MHz, CDCl$_3$) δ: 1.35–1.81 (m, 5H), 1.97–2.21 (m, 4H), 2.55–2.64 (m, 2H), 3.03–3.22 (m, 6H), 5.73 (dd, J=2.0, 6.0 Hz, 1H), 6.51–6.63 (m, 3H), 6.79 (s, 1H), 7.01 (s, 1H), 7.27–7.54 (m, 4H), 7.71 (br d, J=8.0 Hz, 1H), 7.82–7.87 (m, 1H), 7.97–8.04 (m, 1H).

2) The procedure of Example 67-2) was generally followed to provide N-[1-(3-(2-naphthyl)propan-1-yl)piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.39–1.71 (m, 5H), 2.03–2.23 (m, 2H), 2.70–3.28 (m, 8H), 3.37–3.50 (m, 2H), 6.60 (d, J=7.2 Hz, 1H), 6.97 (d, J=8.8 Hz, 1H), 7.20–7.31 (m, 2H), 7.40–7.58 (m, 4H), 7.65 (s, 1H), 7.78–7.83 (m, 1H), 7.91–7.96 (m, 1H), 8.09–8.13 (m, 1H), 8.90–9.01 (m, 1H).

IR (KBr): 3489, 3394, 3253, 2951, 2698, 1637, 1535, 1292, 1211, 793 cm$^{-1}$.

Elemental analysis for C$_{29}$H$_{32}$N$_4$OSCl$_2$.1.5H$_2$O Calcd.: C, 59.79; H, 6.06; N, 9.62 Found: C, 59.65; H, 6.06; N, 9.46

Example 95

Synthesis of N-[1-[2-(thiophen-2-yl)ethan-1-yl]piperidin-4-ylmethyl]-5-thia-1,8b-diazaacenaphthylene-4-carboxamide Dihydrochloride 1) The procedure of Example 67-1) was generally followed to provide N-[1-[2-(thiophen-2-yl)ethan-1-yl]piperidin-4-ylmethyl]-5-thia-1,8b-diazaacenaphthylene-4-carboxamide as red solid.

$^1$H-NMR (200 MHz, CDCl$_3$) δ: 1.23–1.41 (2H, m), 1.45–1.8 (3H, m), 1.95–2.13 (2H, m), 2.58–2.68 (2H, m), 2.96–3.08 (4H, m), 3.212 (2H, t, J=6.1 Hz), 5.789 (1H, dd, J=1.9, 5.9 Hz), 5.95–6.09 (1H, m), 6.58–6.71 (3H, m), 6.81–6.94 (1H, m), 7.035 (1H, s), 7.129 (1H, dd, J=1.0, 5.0 Hz).

2) The procedure of Example 67-2) was generally followed to provide N-[1-[2-(thiophen-2-yl)ethan-1-yl]piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.40–1.95 (5H, m), 2.80–3.10 (4H, m), 3.15–3.40 (4H, m), 3.549 (2H, d like, J=12.2 Hz), 6.633 (1H, d, J=7.4 Hz), 6.96–7.03 (3H, m), 7.227 (1H, s), 7.22–7.34 (1H, m), 7.420 (1H, d, J=4.8 Hz), 7.672 (1H, s), 8.95–9.00 (1H, m), 10.83 (1H, br s).

IR (KBr): 3430, 3250, 3050, 2930, 2700, 1635, 1585, 1540, 1500, 1440, 1390, 1290, 1280, 1210, 780, 700 cm$^{-1}$.

Elemental analysis for C$_{22}$H$_{26}$N$_4$OS$_2$Cl$_2$.0.5H$_2$O Calcd.: C, 52.17; H, 5.37; N, 11.06 Found: C, 52.05; H, 5.56; N, 10.88

Example 96

Synthesis of N-[1-[2-(thiophen-3-yl)ethan-1-yl)piperidin-4-ylmethyl]-5-thia-1,8b-diazaacenaphthylene-4-carboxamide Dihydrochloride 1) The procedure of Example 67-1) was generally followed to provide N-[1-[2-(thiophen-3-yl)ethan-1-yl]piperidin-4-ylmethyl]-5-thia-1,8b-diazaacenaphthylene-4-carboxamide as red solid.

$^1$H-NMR (200 MHz, CDCl$_3$) δ: 1.21–1.45 (2H, m), 1.45–1.68 (1H, m), 1.68–1.88 (2H, m), 1.93–2.08 (2H, m), 2.56–2.68 (2H, m), 2.80–2.88 (2H, m), 3.011 (2H, d like, J=11.6 Hz), 3.224 (2H, t like, J=6.0 Hz) 5.800, (1H, dd, J=1.8, 6.2 Hz), 5.75–6.85 (1H, m), 6.59–6.72 (3H, m), 6.94–7.00 (2H, m), 7.064 (1H, s), 7.23–7.26 (1H, m).

2) The procedure of Example 67-2) was generally followed to provide N-[1-[2-(thiophen-3-yl)ethan-1-yl]piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.40–1.90 (5H, m), 2.78–2.95 (2H, m), 3.00–3.18 (4H, m), 3.18–3.35 (2H, m), 3.48–3.60 (2H, m), 6.576 (1H, d, J=7.4 Hz), 6.953 (1H, d, J=8.4 Hz), 7.056 (1H, dd, J=1.2, 5.0 Hz), 7.17–7.32 (3H, m), 7.52–7.56 (1H, m), 7.621 (1H, s), 8.87–8.93 (1H, m), 10.53 (1H, br s).

IR (KBr): 3430, 3250, 3050, 2930, 2680, 1635, 1565, 1540, 1500, 1440, 1390, 1290, 1280, 1220, 780 cm$^{-1}$.

Elemental analysis for C$_{22}$H$_{26}$N$_4$OS$_2$Cl$_2$.0.5H$_2$O Calcd.: C, 52.17; H, 5.37; N, 11.06 Found: C, 52.52; H, 5.16; N, 10.98

Example 97

Synthesis of N-[1-[2-(furan-3-yl)ethan-1-yl]piperidin-4-ylmethyl]-5-thia-1,8b-diazaacenaphthylene-4-carboxamide Dihydrochloride 1) The procedure of Example 67-1) was generally followed to provide N-[1-[2-(furan-3-yl)ethan-1-yl]piperidin-4-ylmethyl]-5-thia-1,8b-diazaacenaphthylene-4-carboxamide as red oil.

$^1$H-NMR (200 MHz, CDCl$_3$) δ: 1.23–1.40 (2H, m), 1.43–1.60 (1H, m), 1.62–1.78 (2H, m), 1.985 (2H, J=1.6, 11.6 Hz), 2.48–2.66 (4H, m), 2.991 (2H, d like, J=11.4 Hz), 3.216 (2H, t, J=6.1 Hz), 5.792 (1H, dd, J=1.7, 6.1 Hz), 5.78–5.90 (1H, m), 6.284 (1H, s), 6.58–6.72 (3H, m), 7.052 (1H, s), 7.255 (1H, s), 7.347 (1H, t, J=1.6 Hz).

2) The procedure of Example 67-2) was generally followed to provide N-[1-[2-(furan-3-yl)ethan-1-yl]piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.45–1.90 (5H, m), 2.80–2.95 (4H, m), 3.00–3.10 (2H, m), 3.15–3.30 (2H, m), 3.43–3.60 (2H, m), 6.42–6.45 (1H, m), 6.590 (1H, d, J=7.2 Hz), 6.964 (1H, d, J=8.8 Hz), 7.19–7.31 (2H, m), 7.56–7.64 (3H, m), 8.85–9.00 (1H, m), 10.6 (1H, br s).

IR (KBr): 3420, 3250, 3070, 3000, 2940, 2680, 2640, 1635, 1585, 1540, 1500, 1470, 1440, 1395, 1310, 1300, 1280, 1220, 1160, 1020, 940, 875, 800, 780, 630, 600 cm$^{-1}$.

Elemental analysis for C$_{22}$H$_{26}$N$_4$O$_2$SCl$_2$.1.0H$_2$O Calcd.: C, 52.91; H, 5.65; N, 11.22 Found: C, 53.27; H, 5.38; N, 11.22

Example 98

Synthesis of N-[1-[(thiazol-4-yl)methyl]piperidin-4-ylmethyl]-5-thia-1,8b-diazaacenaphthylene-4-carboxamide Trihydrochloride 1) Synthesis of N-(1-[(thiazol-4-yl)methyl]piperidin-4-ylmethyl]-5-thia-1,8b-diazaacenaphthylene-4-carboxamide To a solution of 255 mg (1.5 mM) of 4-chloromethylthiazole, 387 mg (1 mM) of N-(piperidin-4-ylmethyl)-5-thia-1,8b-diazaacenaphthylene-4-carboxamide dihydrochloride, and 697 ml (5 mM) of triethylamine in ethanol (10 ml) was added 225 mg (1.5 mM) of sodium iodide at room temperature and the mixture was refluxed on an oil bath at 90° C. overnight. To this reaction mixture was added water and the reaction product was extracted into ethyl acetate. The organic layer was washed with water and saturated aqueous solution of sodium chloride and dried over $Na_2SO_4$. The solvent was then distilled off under reduced pressure and the residue was subjected to silica gel column chromatography. The fractions eluting with ethyl acetate/ethanol/triethylamine (20/20/1) were pooled to provide the title compound as red oil (150 mg).

$^1$H-NMR (200 MHz, CDCl$_3$) δ: 1.25–1.45 (2H, m), 1.45–1.60 (1H, m), 1.60–1.72 (2H, m), 2.049 (2H, t like, J=11.4 Hz), 2.966 (2H, d like, J=11.8 Hz), 3.206 (2H, t like, J=6.0 Hz), 3.722 (2H, s), 5.791 (1H, dd, J=1.8, 6.2 Hz), 5.75–5.90 (1H, m), 6.59–6.71 (3H, m), 7.050 (1H, s), 7.184 (1H, d, J=2.2 Hz), 8.786 (1H, d, J=2.0 Hz).

2) Synthesis of N-[1-[(thiazol-4-yl)methyl]piperidin-4-ylmethyl]-5-thia-1,8b-diazaacenaphthylene-4-carboxamide Trihydrochloride To a solution of N-[1-[(thiazol-4-yl)methyl]piperidin-4-ylmethyl]-5-thia-1,8b-diazaacenaphthylene-4-carboxamide in ethanol was added 2 ml (8.0 mM) of 4N-HCl/ethyl acetate. The solvent was distilled off under reduced pressure and the residue was diluted with ether. The crystals that formed were harvested by filtration and rinsed with ethanol and diethyl ether to provide the title compound as orange-colored crystals (150 mg, 28%).

$^1$H-NMR (200 MHz, DMSO-d$_6$) δ: 1.35–1.90 (5H, m), 2.80–3.25 (4H, m), 3.30–3.45 (2H, m), 4.431 (2H, d, J=4.6 Hz), 6.674 (1H, d, J=6.8 Hz), 7.010 (1H, d, J=9.2 Hz), 7.21–7.38 (2H, m), 7.707 (1H, s), 8.052 (1H, d, J=1.8 Hz), 8.90–9.10 (1H, m), 9.232 (1H, d, J=2.0 Hz), 10.6 (1H, br s).

IR (KBr): 3400, 2950, 1635, 1560, 1540, 1500, 1290, 1220, 1110, 940, 890, 820, 780 cm$^{-1}$.

Elemental analysis for $C_{20}H_{24}N_5OS_2Cl_3$.0.5H$_2$O Calcd.: C, 45.33; H, 4.75; N, 13.22 Found: C, 45.31; H, 5.07; N, 13.09

Example 99

Synthesis of N-[1-(3-cyclohexylpropan-1-yl)piperidin-4-ylmethyl]-5-thia-1,8b-diazaacenaphthylene-4-carboxamide Dihydrochloride 1) The procedure of Example 67-1) was generally followed to provide N-[1-(3-cyclohexylpropan-1-yl)piperidin-4-ylmethyl]-5-thia-1,8b-diazaacenaphthylene-4-carboxamide as red-purple amorphous substance.

$^1$H-NMR (200 MHz, CDCl$_3$) δ: 0.75–1.87 (m, 20H), 2.30 (t, J=11.0 Hz, 2H), 2.53–2.62 (m, 2H), 3.13–3.25 (m, 4H), 5.75 (dd, J=2.6, 5.4 Hz, 1H), 6.52–6.64 (m, 2H), 6.90 (s, 1H), 7.02 (m, 2H).

2) The procedure of Example 67-2) was generally followed to provide N-[1-(3-cyclohexylpropan-1-yl)piperidin-4-ylmethyl)-5-thia-1,8b-diazaacenaphthylene-4-carboxamide dihydrochloride as orange-colored crystals.

$^1$H-NMR (200 MHz, DMSO-d$_6$) δ: 0.75–1.82 (m, 20H), 2.63–3.48 (m, 8H), 6.60 (d, J=7.2 Hz, 1H), 6.97 (d, J=8.6 Hz, 1H), 7.19–7.31 (m, 2H), 7.64 (s, 1H), 8.85–8.94 (m, 1H).

IR (KBr): 3438, 2924, 1635, 1535, 1298, 788 cm$^{-1}$.

Elemental analysis for $C_{25}H_{36}N_4OSCl_2$.2.1H$_2$O Calcd.: C, 54.65; H, 7.38; N, 10.20 Found C, 54.41; H, 7.37; N, 10.11

Example 100

Synthesis of N-[1-[(quinolin-2-yl)methyl]piperidin-4-ylmethyl]-5-thia-1,8b-diazaacenaphthylene-4-carboxamide Trihydrochloride 1) The procedure of Example 98-1) was generally followed to provide N-[1-[(quinolin-2-yl)methyl]piperidin-4-ylmethyl]-5-thia-1,8b-diazaacenaphthylene-4-carboxamide as red oil.

$^1$H-NMR (200 MHz, CDCl$_3$) δ: 1.23–1.44 (2H, m), 1.45–1.72 (3H, m), 2.128 (2H, t like J=11.5 Hz), 2.940 (2H, d like, J=11.6 Hz), 3.222 (2H, t like, J=6.0 Hz), 3.823 (2H, s), 5.781 (1H, dd, J=1.8, 6.2 Hz), 5.78–5.90 (1H, m), 6.57–6.70 (3H, m), 7.037 (1H, s), 7.47–7.82 (4H, m), 8.05–8.14 (2H, m).

2) The procedure of Example 98-2) was generally followed to provide N-[1-[(quinolin-2-yl)methyl]piperidin-4-ylmethyl]-5-thia-1,8b-diazaacenaphthylene-4-carboxamide trihydrochloride as orange-colored crystals.

$^1$H-NMR (200 MHz, DMSO-d$_6$) δ: 1.45–1.90 (5H, m), 3.00–3.25 (4H, m), 3.45–3.60 (2H, m), 4.654 (2H, br s), 6.672 (1H, d, J=6.8 Hz), 7.008 (1H, d, J=9.0 Hz), 7.245 (1H, s), 7.336 (1H, dd, J=7.6, 9.1 Hz), 7.16–7.22 (2H, m), 7.80–7.88 (2H, m), 8.02–8.12 (2H, m), 8.523 (1H, d, J=8.4 Hz), 8.98–9.05 (1H ,m), 10.6 (1H, br s).

IR (KBr): 3420, 2620, 1630, 1550, 1530, 1500, 1390, 1300, 1210, 940, 790 cm$^{-1}$.

Elemental analysis for $C_{26}H_{28}N_5OSCl_3$.2.0H$_2$O Calcd.: C, 51.96; H, 5.37; N, 11.65 Found C, 52.12; H, 5.47; N, 11.81

Example 101

Synthesis of N-[1-[3-(4-pyridyl)propan-1-yl]piperidin-4-ylmethyl]-5-thia-1,8b-diazaacenaphthylene-4-carboxamide Trihydrochloride 1) The procedure of Example 98-1) was generally followed to provide N-[1-[3-(4-pyridyl)propan-1-yl]piperidin-4-ylmethyl]-5-thia-1,8b-diazaacenaphthylene-4-carboxamide as red oil.

$^1$H-NMR (200 MHz, CDCl$_3$) δ: 1.23–1.38 (2H, m), 1.42–1.60 (1H, m), 1.60–1.78 (2H, m), 1.80–1.98 (3H, m), 2.05–2.13 (1H, m), 2.341 (2H, t like J=7.5 Hz), 2.627 (2H, t, J=7.7 Hz), 2.911 (2H, d like, J=11.8 Hz), 3.200 (2H, t, J=6.2 Hz), 5.783 (1H, dd, J=2.0, 6.2 Hz), 5.92–6.05 (1H, m), 6.58–6.69 (3H, m), 7.030 (1H, s), 7.114 (2H, dd, J=1.4, 4.8 Hz), 8.481 (2H, dd, J=1.4, 4.4 Hz).

2) The procedure of Example 98-2) was generally followed to provide N-[1-[3-(4-pyridyl)propan-1-yl]piperidin-4-ylmethyl]-5-thia-1,8b-diazaacenaphthylene-4-carboxamide trihydrochloride as orange-colored crystals.

$^1$H-NMR (200 MHz, DMSO-d$_6$) δ: 1.45–1.90 (5H, m), 2.08–2.20 (2H, m), 2.70–3.28 (8H, m), 3.471 (2H, d like), 6.530 (1H, d, J=7.2 Hz), 6.928 (1H, d, J=9.0 Hz), 7.12–7.25 (2H, m), 7.575 (1H, s), 7.944 (2H, d, J=5.8 Hz), 8.851 (2H, d, J=5.4 Hz), 8.80–8.91 (1H, m), 10.6 (1H, br s).

IR (KBr): 3420, 2920, 2700, 1635, 1500, 1295, 1220, 790, 780 cm$^{-1}$.

Elemental analysis for $C_{24}H_{30}N_5OSCl_3$.1.5H$_2$O Calcd.: C, 50.57; H, 5.84; N, 12.29 Found: C, 50.59; H, 5.89; N, 12.10

Example 102

Synthesis of N-[1-(2-(3-indolyl)ethan-1-yl)piperidin-4-ylmethyl]-5-thia-1,8b-diazaacenaphthylene-4-carboxamide Dihydrochloride 1) The procedure of Example 67-1) was generally followed to provide N-[1-(2-(3-indolyl)ethan-1-yl)piperidin-4-ylmethyl]-5-thia-1,8b-diazaacenaphthylene-4-carboxamide as deep-red amorphous substance.

$^1$H-NMR (200 MHz, CDCl$_3$) δ: 1.20–1.45 (2H, m), 1.45–1.90 (3H, m), 1.95–2.15 (2H, m), 2.60–2.80 (2H, m), 2.90–3.15 (4H, m), 3.23 (2H, t, J=6.0 Hz), 5.79 (1H, dd, J=1.7, 6.1 Hz), 5.91 (1H, br t, J=6.1 Hz), 6.58–6.75 (3H, m), 7.00–7.25 (4H, m), 7.36 (1H, d, J=7.2 Hz), 7.62 (1H, d, J=7.2 Hz), 8.14 (1H, br s).

IR (KBr): 3334, 2922, 1618, 1541, 1510, 1481, 1456, 1342, 1281, 1153, 744 cm$^{-1}$.

2) The procedure of Example 67-2) was generally followed to provide N-[1-(2-(3-indolyl)ethan-1-yl)piperidin-4-ylmethyl]-5-thia-1,8b-diazaacenaphthylene-4-carboxamide dihydrochloride as orange-colored crystals.

$^1$H-NMR (200 MHz, CD$_3$OD) δ: 1.40–1.70 (2H, m), 1.70–2.10 (3H, m), 2.90–3.15 (2H, m), 3.15–3.50 (6H, m), 3.60–3.80 (2H, m), 6.59 (1H, d, J=7.8 Hz), 6.95–7.23 (5H, m), 7.34–7.41 (2H, m), 7.51 (1H, s), 7.61 (1H, d, J=7.0 Hz).

IR (KBr): 3392, 3062, 2935, 2727, 1633, 1564, 1539, 1504, 1456, 1292, 1216, 1105, 748 cm$^{-1}$.

Elemental analysis for C$_{26}$H$_{29}$N$_5$OSCl$_2$.2.0H$_2$O Calcd.: C, 55.12; H, 5.87; N, 12.36 Found: C, 55.16; H, 6.03; N, 12.01

Example 103

Synthesis of N-(1-benzylpiperidin-4-ylmethyl)-5-thia-1,8b-diazaacenaphthylene-4-carboxamide Dihydrochloride 1) Synthesis of N-(1-benzylpiperidin-4-ylmethyl)-5-thia-1,8b-diazaacenaphthylene-4-carboxamide To a solution of 0.58 g (1.5 mM) of N-(piperidin-4-ylmethyl)-5-thia-1,8b-diazaacenaphthylene-4-carboxamide dihydrochloride and 1.0 ml (7.5 mM) of triethylamine in ethanol was added 0.19 ml (1.6 mM) of benzyl bromide at room temperature, and the mixture was refluxed under nitrogen for 6 hours. The solvent was then distilled off under reduced pressure and the residue was diluted with water and extracted with methylene chloride. The organic layer was washed with saturated aqueous solution of sodium chloride and dried over MgSO$_4$. The resulting crude product was purified by column chromatography (methanol/ethyl acetate 40%) to provide the title compound.

Yield 479 mg (79%)

$^1$H-NMR (200 MHz, CDCl$_3$) δ: 1.17–1.69 (m, 5H), 1.94 (t, J=11.0 Hz, 2H), 2.88 (br d, J=11.6 Hz, 2H), 3.17 (t, J=5.9 Hz, 2H), 3.48 (s, 2H), 5.72–5.76 (m, 1H), 6.35–6.50 (m, 1H), 6.59–6.64 (m, 3H), 6.96–6.97 (m, 2H), 7.18–7.38 (m, 5H).

2) Synthesis of N-(1-benzylpiperidin-4-ylmethyl)-5-thia-1,8b-diazaacenaphthylene-4-carboxamide Dihydrochloride In a solution of 479 mg (1.18 mmol) of N-(1-benzylpiperidin-4-ylmethyl)-5-thia-1,8b-diazaacenaphthylene-4-carboxamide in ethanol (4 ml) was added 1.0 ml (4 mM) of 4N-HCl/methnol and the mixture was stirred at room temperature for several minutes. The solvent was then distilled off under reduced pressure and the residue was diluted with ethanol and diethyl ether. The resulting crystals were collected by filtration and rinsed with ethanol and diethyl ether to provide the title compound.

Orange-colored crystals. Yield 424 mg (73%)

$^1$H-NMR (200 MHz, DMSO-d$_6$) δ: 1.42–1.87 (m, 5H), 2.79–3.35 (m, 6H), 4.25 (br s, 2H), 6.59 (d, J=7.2 Hz, 1H), 6.96 (d, J=9.0 Hz, 1H), 7.17–7.30 (m, 2H), 7.44–7.47 (m, 3H), 7.59–7.65 (m, 3H), 8.83–8.89 (m, 1H).

Elemental analysis for C$_{23}$H$_{26}$N$_4$OSCl$_2$.1.0H$_2$O Calcd.: C, 55.76; H, 5.70; N, 11.31 Found: C, 55.71; H, 5.70; N, 11.57

Example 104

Synthesis of N-(1-phenethylpipridin-4-ylmethyl)-5-thia-1,8b-diazaacenaphthylene-4-carboxamide Dihydrochloride 1) The procedure of Example 103-1) was generally followed to provide N-(1-phenethylpiperidin-4-ylmethyl)-5-thia-1,8b-diazaacenaphthylene-4-carboxamide as red-purple amorphous substance.

$^1$H-NMR (200 MHz, CDCl$_3$) δ: 1.23–2.10 (m, 5H), 2.01 (t, J=11.3 Hz, 2H), 2.54–2.62 (m, 2H), 2.77–2.85 (m, 2H), 3.02 (br d, J=11.2 Hz, 2H), 3.22 (t, J=5.3 Hz, 2H), 5.76–5.81 (m, 1H), 5.92–6.13 (m, 1H), 6.56–6.69 (m, 3H), 7.02–7.05 (s, 1H), 7.16–7.32 (m, 5H).

2) The procedure of Example 103-2) was generally followed to provide N-(1-phenethylpiperidin-4-ylmethyl)-5-thia-1,8b-diazaacenaphthylene-4-carboxamide m dihydrochloride as orange-colored crystals.

$^1$H-NMR (200 MHz, DMSO-d$_6$) δ: 1.40–1.87 (m, 7H), 2.79–3.59 (m, 8H), 6.55 (d, J=7.0 Hz, 1H), 6.94 (d, J=9.2 Hz, 1H), 7.15–7.39 (m, 7H), 7.60 (s, 1H), 8.80–8.91 (m, 1H).

IR (KBr): 3415, 3057, 2941, 2702, 1637, 1535, 1294, 1215, 789 cm$^{-1}$.

Elemental analysis for C$_{24}$H$_{28}$N$_4$OSCl$_2$.0.5H$_2$O Calcd.: C, 57.60; H, 5.84; N, 11.19 Found: C, 57.52; H, 5.75; N, 11.00

Example 105

Synthesis of N-[1-(4-phenylbutan-1-yl)piperidin-4-yl-methyl]-5-thia-1,8b-diazaacenaphthylene-4-carboxamide Dihydrochloride 1) The procedure of Example 103-1) was generally followed to provide N-[1-(4-phenylbutan-1-yl)piperidin 4-ylmethyl]-5-thia-1,8b-diazaacenaphthylene-4-carboxamide as red-purple amorphous substance.

$^1$H-NMR (200 MHz, CDCl$_3$) δ: 1.18–1.94 (m, 11H), 2.32 (t, J=7.4 Hz, 2H), 2.62 (t, J=7.2 Hz, 2H), 2.91 (br d, J=11.2 Hz, 2H), 3.20 (t, J=6.2 Hz, 2H), 5.79 (dd, J=1.6, 6.2 Hz, 1H), 5.75–5.90 (m, 1H), 6.56–6.70 (m, 3H), 7.04–7.30 (m, 6H).

2) The procedure of Example 103-2) was generally followed to provide N-[1-(4-phenylbutan-1-yl)piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.30–1.85 (m, 9H), 2.53–3.20 (m, 10H), 6.53 (d, J=7.6 Hz, 1H), 6.93 (d, J=9.2 Hz, 1H), 7.11–7.32 (m, 7H), 7.57 (s, 1H), 8.75–8.86 (m, 1H).

IR (KBr): 1635, 1566, 1533, 1502, 1294, 1217, 787 cm$^{-1}$.

Elemental analysis for C$_{26}$H$_{32}$N$_4$OSCl$_2$.2.1H$_2$O Calcd.: C, 56.03; H, 6.55; N, 10.05 Found C, 55.78; H, 6.55; N, 10.05

Example 106

Synthesis of N-[1-(5-phenylpentan-1-yl)piperidin-4-ylmethyl]-5-thia-1,8b-diazaacenaphthylene-4-carboxamide Dihydrochloride 1) The procedure of Example 103-1) was generally followed to provide N-[1-(5-phenylpentan-1-yl)piperidin-4-ylmethyl]-5-thia-1,8b-diazaacenaphthylene-4-carboxamide as red-purple amorphous substance.

$^1$H-NMR (200 MHz, CDCl$_3$) δ: 1.25–1.90 (m, 10H), 2.34–3.31 (m, 11H), 5.74 (dd, J=2.2, 5.8 Hz, 1H), 6.51–6.63 (m, 2H), 6.90–7.31 (m, 7H).

IR (KBr): 3440, 1628, 1551, 1281, 1151 cm$^{-1}$.

2) The procedure of Example 103-2) was generally followed to provide N-[1-(5-phenylpentan-1-yl)piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.25–1.85 (m, 11H), 2.65–3.20 (m, 10H), 2.59 (t, J=7.5 Hz, 2H), 6.55 (d, J=8.0 Hz, 1H), 6.95 (d, J=8.8 Hz, 1H), 7.13–7.32 (m, 7H), 7.60 (s, 1H), 8.75–8.86 (m, 1H).

IR(KBr):1635, 1566, 1535, 1500, 1444, 1294, 1217 cm$^{-1}$.

Elemental analysis for $C_{27}H_{34}N_4OSCl_2 \cdot 1.8H_2O$ Calcd.: C, 57.30; H, 6.70; N, 9.90 Found C, 57.51; H, 9.96; N, 9.96

Example 107

Synthesis of N-[1-(3-phenyl-2-propan-1-yl)piperidin-4-ylmethyl]-5-thia-1,8b-diazaacenaphthylene-4-carboxamide Dihydrochloride 1) Synthesis of N-[1-(3-phenyl-2-propan-1-yl)piperidin-4-ylmethyl]-5-thia-1,8b-diazaacenaphthylene-4-carboxamide To a solution of 0.58 g (1.5 mM) of N-(piperidin-4-ylmethyl)-5-thia-1,8b-diazaacenaphthylene-4-carboxamide dihydrochloride and 1.0 ml (7.2 mM) of triethylamine in ethanol (6 ml) was added 0.355 g (1.8 mM) of cinnamyl bromide at room temperature and the mixture was refluxed under nitrogen for 24 hours. To this reaction mixture was further added 0.29 g (1.47 mM) of cinnamyl bromide and the mixture was refluxed for 2 hours. The solvent was then distilled off under reduced pressure and the residue was diluted with water and extracted with chloroform. The organic layer was washed with saturated aqueous solution of sodium chloride and dried over MgSO$_4$. The resulting crude product was purified by column chromatography (methanol-chloroform=1:19–1:10–1:5) to provide the title compound.

Red-purple amorphous substance. Yield 379 mg (59%)

$^1$H-NMR (200 MHz, CDCl$_3$) δ: 1.27–1.80 (m, 5H), 2.03 (br t, J=10.9 Hz, 2H), 2.90–3.25 (m, 6H), 5.75 (dd, J=2.5, 5.3 Hz, 1H), 6.28 (dt, J=6.7, 15.8 Hz, 1H), 6.49–6.65 (m, 4H), 6.69 (s, 1H), 6.99 (s, 1H), 7.23–7.41 (m, 5H).

2) Synthesis of N-[1-(3-phenyl-2-propan-1-yl)piperidin-4-ylmethyl]-5-thia-1,8b-diazaacenaphthylene-4-carboxamide Dihydrochloride To a solution of 0.3919 g (0.84 mM) of N-[1-(3-phenyl-2-propan-1-yl)piperidin-4-ylmethyl]-5-thia-1,8b-diazaacenaphthylene-4-carboxamide in ethanol (4 ml) was added 1.0 ml (4 mM) of 4N-HCl/methanol. The solvent was distilled off under reduced pressure and the residue was diluted with ethanol and diethyl ether. The resulting crystals were collected by filtration and rinsed with ethanol and diethyl ether to provide the title compound.

Orange-colored crystals. Yield 330.2 mg (77%)

$^1$H-NMR (200 MHz, DMSO-d$_6$) δ: 1.38–1.91 (m, 5H), 2.81–3.10 (m, 4H), 3.41–3.53 (m, 2H), 3.84 (br d, J=6.8 Hz, 2H), 6.32–6.49 (m, 1H), 6.57 (d, J=7.2 Hz, 1H), 6.82 (d, J=16 Hz, 1H), 6.95 (d, J=8.8 Hz, 1H), 7.15–7.53 (m, 7H), 7.61 (s, 1H), 8.80–8.93 (m, 1H).

IR (KBr): 3452, 1639, 1292, 1215 cm$^{-1}$.

Elemental analysis for $C_{25}H_{28}N_4OSCl_2 \cdot 0.5H_2O$ Calcd.: C, 58.59; H, 5.70; N, 10.93 Found: C, 58.37; H, 5.84; N, 10.66

Example 108

Synthesis of N-[1-(2-phenoxyethan-1-yl)piperidin-4-yl-methyl]-5-thia-1,8b-diazaacenaphthylene-4-carboxamide Dihydrochloride 1) Synthesis of N-[1-(2-phenoxyethan-1-yl)piperidin-4-ylmethyl]-5-thia-1,8b-diazaacenaphthylene-4-carboxamide Under nitrogen gas, 0.37 ml (4.78 mM) of methanesulfonyl chloride was added to a solution of 0.44 g (3.18 mM) of phenoxyethanol and 0.89 ml (6.39 mM) of triethylamine in methylene chloride (6 ml) at 0° C. and the mixture was stirred at the prevailing temperature for 35 minutes. The reaction was stopped by adding saturated aqueous solution of sodium hydrogen carbonate and the reaction mixture was extracted with diethyl ether. The organic layer was washed serially with water and saturated aqueous solution of sodium chloride and dried over MgSO$_4$. The solvent was then distilled off under reduced pressure to provide 0.6989 g (<3.18 mM) of phenoxyethyl mesylate. To a solution of 0.58 g (1.5 mM) of N-(piperidin-4-ylmethyl)-5-thia-1,8b-diazaacenaphthylene-4-carboxamide dihydrochloride and 1.0 ml (7.2 mM) of triethylamine in ethanol (6.0 ml) was added 0.6989 g (<3.18 mM) of the above phenoxyethyl mesylate at room temperature and the mixture was refluxed under nitrogen for 17 hours. The solvent was then distilled off under reduced pressure and the residue was diluted with water and extracted with chloroform. The organic layer was washed with saturated aqueous solution of sodium chloride and dried over MgSO$_4$. The resulting crude product was purified by column chromatography (methanol/ethyl acetate 30–40%) to provide the title compound.

Red-purple amorphous substance. Yield 414 mg (63%)

$^1$H-NMR (200 MHz, CDCl$_3$) δ: 1.21–2.18 (m, 7H), 2.80 (t, J=5.9 Hz, 2H), 3.02 (br d, J=11.6 Hz, 2H), 3.20 (t, J=6.1 Hz, 2H), 4.10 (t, J=5.9 Hz, 2H), 5.78 (dd, J=2.0, 6.0 Hz, 1H), 6.01 (br t, J=5.8 Hz, 1H), 6.57–6.70 (m, 3H), 6.86–6.98 (m, 3H), 7.03 (s, 1H), 7.24–7.32 (m, 2H).

2) Synthesis of N-[1-(2-phenoxyethan-1-yl)piperidin-4-ylmethyl]-5-thia-1,8b-diazaacenaphthylene-4-carboxamide Dihydrochloride To a suspension of 414 mg (0.95 mM) of N-[1-(2-phenoxyethan-1-yl)piperidin-4-ylmethyl]-5-thia-1,8b-diazaacenaphthylene-4-carboxamide in ethanol (9 ml) was added 1.0 ml (4 mM) of 4N-HCl/methanol and the mixture was stirred at room temperature for 30 minutes. The resulting crystals were collected by filtration and rinsed with ethanol and ether to provide the title compound.

Orange-colored crystals. Yield 363 mg (70%)

$^1$H-NMR (200 MHz, DMSO-d$_6$) δ: 1.41–1.90 (m, 5H), 2.93–3.60 (m, 8H), 4.36–4.45 (m, 2H), 6.60 (d, J=6.8 Hz, 1H), 6.94–7.02 (m, 4H), 7.21–7.37 (m, 4H), 7.64 (s, 1H), 8.91–8.97 (m, 1H).

IR (KBr): 3388, 3238, 3057, 2638, 2514, 1639, 1294, 1230, 797, 764 cm$^{-1}$.

Elemental analysis for $C_{24}H_{28}N_4O_2SCl_2 \cdot 0.5H_2O$ Calcd.: C, 55.81; H, 5.66; N, 10.85 Found: C, 55.84; H, 5.69; N, 10.69

Example 109

Synthesis of N-[1-(4-phenoxybutan-1-yl)piperidin-4-ylmethyl]-5-thia-1,8b-diazaacenaphthylene-4-carboxamide Dihydrochloride 1) Synthesis of N-[1-(4-phenoxybutan-1-yl)piperidin-4-ylmethyl]-5-thia-1,8b-diazaacenaphthylene-4-carboxamide To a solution of 0.58 g (1.5 mM) of N-(piperidin-4-ylmethyl)-5-thia-1,8b-diazaacenaphthylene-4-carboxamide dihydrochloride and 1.0 ml (27.5 mM) of triethylamine in ethanol (6 ml) was added 0.45 g (1.96 mM) of 4-phenoxybutyl bromide at room temperature and the mixture was refluxed under nitrogen for 14 hours. To this reaction mixture was further added 0.23 g (1.0 mM) of 4-phenoxybutyl bromide and the mixture was refluxed for 6 hours. The solvent was then distilled off under reduced pressure and the residue was diluted with water and extracted with chloroform. The organic layer was washed with saturated aqueous solution of sodium chloride and dried over $MgSO_4$. The resulting crude product was purified by column chromatography (methanol/chloroform=1/15–1/10–1/5) to provide the title compound.

Red-purple amorphous substance. Yield 324 mg (47%)
$^1$H-NMR (200 MHz, $CDCl_3$) δ: 1.40–1.92 (m, 9H), 2.15–2.28 (m, 2H), 2.53–2.67 (m, 2H), 3.12–3.22 (m, 4H), 3.97 (br t, J=5.3 Hz, 2H), 5.74.(dd, J=2.4, 5.6 Hz, 1H), 6.58–6.61 (m, 2H), 6.65–6.76 (m, 1H), 6.81–6.97 (m, 3H), 7.02 (s, 1H), 7.23–7.31 (m, 3H).

2) Synthesis of N-[1-(4-phenoxybutan-1-yl)piperidin-4-ylmethyl]-5-thia-1,8b-diazaacenaphthylene-4-carboxamide Dihydrochloride To a solution of 0.3241 g (0.70 mM) of N-[1-(4-phenoxybutan-1-yl)piperidin-4-ylmethyl]-5-thia-1,8b-diazaacenaphthylene-4-carboxamide in ethanol (4 ml) was added 1.0 ml (4 mM) of 4N-HCl/methanol. The solvent was distilled off under reduced pressure and the residue was diluted with ethanol and ether. The resulting crystals were collected by filtration and rinsed with ethanol and diethyl ether to provide the title compound.

Orange-colored crystals. Yield 270 mg (70%)
$^1$H-NMR (200 MHz, DMSO-$d_6$) δ: 1.35–1.93 (m, 9H), 2.65–3.21 (m, 6H), 3.43–3.49 (m, 2H), 3.99 (t, J=5.6 Hz, 2H), 6.58 (d, J=7.4 Hz, 1H), 6.89–6.98 (m, m 4H), 7.19–7.33 (m, 4H), 7.63 (s, 1H), 8.89–8.94 (m, 1H).
IR (KBr): 3435, 3051, 2943, 1635, 1294, 1241, 764 $cm^{-1}$.
Elemental analysis for $C_{26}H_{32}N_4O_2SCl_2 \cdot 1.0H_2O$ Calcd.: C, 56.41; H, 6.19; N, 10.12 Found C, 56.57; H, 6.07; N, 10.19

Example 110

Synthesis of N-[1-(3-phenoxypropan-1-yl)piperidin-4-yl-methyl]-5-thia-1,8b-diazaacenaphthylene-4-carboxamide Dihydrochloride 1) The procedure of Example 109-1) was generally followed to provide N-[1-(3-phenoxypropan-1-yl)piperidin-4-ylmethyl]-5-thia-1,8b-diazaacenaphthylene-4-carboxamide as red-purple amorphous substance.

$^1$H-NMR (200 MHz, $CDCl_3$) δ: 1.20–1.73 (m, 5H), 1.90–2.08 (m, 4H), 2.50–2.57 (m, 2H), 2.98 (br d, J=11.2 Hz, 2H), 3.18 (t, J=6.1 Hz, 2H), 3.99 (t, J=6.2 Hz, 2H), 5.74 (dd, J=3.0, 5.0 Hz, 1H), 6.52–6.68 (m, 4H), 6.82–6.97 (m, 4H), 7.17–7.32 (m, 2H).

2) The procedure of Example 109-2) was generally followed to provide N-[1-(3-phenoxypropan-1-yl)piperidin-4-ylmethyl]-5-thia-1,8b-diazaacenaphthylene-4-carboxamide dihydrochloride as orange-colored crystals.

$^1$H-NMR (200 MHz, DMSO-$d_6$) δ: 1.42–1.95 (m, 5H), 2.10–2.28 (m, 2H), 2.81–3.29 (m, 6H), 3.43–3.56 (m, 2H), 4.05 (t, J=6.0 Hz, 2H), 6.61 (d, J=7.4 Hz, 1H), 6.91–6.9 (m, 4H), 7.21–7.34 (m, 4H), 7.65 (s, 1H), 8.87–9.00 (m, 1H).
IR (KBr): 3421, 3236, 3049, 2941, 2642, 2532, 1635, 1295, 1294, 1240, 762 $cm^{-1}$.
Elemental analysis for $C_{25}H_{30}N_4O_2SCl_2 \cdot 0.5H_2O$ Calcd.: C, 56.60; H, 5.89; N, 10.56 Found: C, 56.38; H, 5.79; N, 10.56

Example 111

Synthesis of N-[1-(3-(2-fluorophenoxy)propan-1-yl)piperidin-4-ylmethyl]-5-thia-1,8-diazaacenaphthylene-4-carboxamide Dihydrochloride 1) Synthesis of N-[1-(3-(2-fluorophenoxy)propan-1-yl)piperidin-4-ylmethyl]-5-thia-1,8b-diazaacenaphthylene-4-carboxamide To a solution of 0.58 g (1.5 mM) of N-(piperidin-4-ylmethyl)-5-thia-1,8b-diazaacenaphthylene-4-carboxamide dihydrochloride and 1.0 ml (7.5 mM) of triethylamine in ethanol were added 0.37 g (2.0 mM) of 3-(2-fluorophenoxy)-propyl chloride and 0.28 g (1.9 mM) of sodium iodide at room temperature and the mixture was refluxed under nitrogen for 20 hours. The solvent was then distilled off under reduced pressure and the residue was diluted with water and extracted with chloroform. The organic layer was washed with saturated aqueous solution of sodium chloride and dried over $MgSO_4$. The resulting crude product was purified by column chromatography (methanol/ethyl acetate 30–50%) to provide the title compound.

Red-purple amorphous substance. Yield 244 mg (35%)
$^1$H-NMR (200 MHz, $CDCl_3$) δ: 1.16–2.06 (m, 9H), 2.48–2.55 (m, 2H), 2.94 (br d, J=11.6 Hz, 2H), 3.19 (t, J=6.2 Hz, 2H), 4.07 (t, J=6.4 Hz, 2H), 5.77 (dd, J=2.5, 5.3 Hz, 1H), 6.25 (br t, J=5.8 Hz, 1H), 6.61–6.67 (m, 3H), 6.84–7.14 (m, 5H).

2) Synthesis of N-[1-(3-(2-fluorophenoxy)propan-1-yl)piperidin-4-ylmethyl]-5-thia-1,8b-diazaacenaphthylene-4-carboxamide Dihydrochloride To a solution of 244 mg (0.52 mM) of N-[1-(3-(2-fluorophenoxy)propan-1-yl)piperidin-4-ylmethyl]-5-thia-1,8b-diazaacenaphthylene-4-carboxamide in ethanol (4 ml) was added 1.0 ml (4.0 mM) of 4N-HCl/methanol. The solvent was distilled off under reduced pressure and the residue was purified by recrystallization to provide the title compound.

Orange-colored crystals. Yield 218 mg (75%)
$^1$H-NMR (200 MHz, DMSO-$d_6$) δ: 1.35–1.90 (m, 5H), 2.13–2.30 (m, 2H), 2.80–3.60 (m, 8H), 4.14 (t, J=5.8 Hz, 2H), 6.57 (d, J=7.4 Hz, 1H), 6.93–7.02 (m, 2H), 7.10–7.28 (m, 5H), 7.61 (s, 1H), 8.87 (m, 1H).
IR (KBr): 3429, 1635, 1506, 1290 $cm^{-1}$.
Elemental analysis for $C_{25}H_{29}N_4O_2SCl_2 \cdot 1.0H_2O$ Calcd.: C, 53.86; H, 5.60; N, 10.05 Found: C, 53.91; H, 5.46; N, 10.00

Example 112

Synthesis of N-[1-(3-(3-fluorophenoxy)propan-1-yl)piperidin-4-ylmethyl]-5-thia-1,8b-diazaacenaphthylene-4-carboxamide Dihydrochloride 1) The procedure of Example 111-1) was generally followed to provide N-[1-(3-(3-fluorophenoxy)propan-1-yl)piperidin-4-ylmethyl]-5-thia-1,8b-diazaacenaphthylene-4-carboxamide as red-purple amorphous substance.

$^1$H-NMR (200 MHz, $CDCl_3$) δ: 1.20–2.13 (m, 9H), 2.56 (br t, J=6.8 Hz, 2H), 3.00 (br d, J=11.0 Hz, 2H), 3.19 (t, J=5.7 Hz, 2H), 3.98 (t, J=6.0 Hz, 2H), 5.60–5.71 (m, 1H), 6.35–6.83 (m, 7H), 6.98–7.05 (m, 1H), 7.13–7.29 (m, 1H).

2) The procedure of Example 111-2) was generally followed to provide N-[1-(3-(3-fluorophenoxy)propan-1-yl)piperidin-4-ylmethyl]-5-thia-1,8b-diazaacenaphthylene-4-carboxamide dihydrochloride as orange-colored crystals.

$^1$H-NMR (200 MHz, DMSO-$d_6$) δ: 1.36–1.87 (m, 5H), 2.10–2.25 (m, 2H), 2.78–3.80 (m, 8H), 4.07 (t, J=5.9 Hz, 2H), 6.57 (d, J=6.8 Hz, 1H), 6.72–6.85 (m, 3H), 6.95 (d, J=9.0 Hz, 1H), 7.14–7.37 (m, 3H), 7.61 (s, 1H), 8.80–8.90 (m, 1H).
IR (KBr): 3413, 2948, 2648, 1635, 1491, 1288, 1136, 779 $cm^{-1}$.
Elemental analysis for $C_{25}H_{29}N_4O_2SCl_2 \cdot 1.5H_2O$ Calcd.: C, 53.00; H, 5.69; N, 9.89 Found: C, 53.01; H, 5.72; N, 9.65

Example 113

Synthesis of N-[1-(3-(4-fluorophenoxy)propan-1-yl)piperidin-4-ylmethyl]-5-thia-1,8b-diazaacenaphthylene-4-carboxamide Dihydrochloride 1) The procedure of Example 111-1) was generally followed to provide N-[1-(3-(4-fluorophenoxy)propan-1-yl)piperidin-4-ylmethyl]-5-thia-1,8b-diazaacenaphthylene-4-carboxamide as red-purple amorphous substance.

$^1$H-NMR (200 MHz, CDCl$_3$) δ: 1.25–2.13 (m, 7H), 2.55–2.62 (m, 2H), 3.00–3.06 (m, 4H), 3.19 (t, J=5.9 Hz, 2H), 3.96 (t, J=6.2 Hz, 2H), 5.75 (dd, J=3.0, 5.0 Hz, 1H), 6.58–6.65 (m, 3H), 6.72 (s, 1H), 6.77–7.00 (m, 5H).

2) The procedure of Example 111-2) was generally followed to provide N-[1-(3-(4-fluorophenoxy)propan-1-yl)piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.40–2.22 (m, 7H), 2.77–3.54 (m, 8H), 4.03 (t, J=6.1 Hz, 2H), 6.54 (d, J=7.8 Hz, 1H), 6.89–7.24 (m, 7H), 7.58 (s, 1H), 8.78–8.86 (m, 1H).

IR (KBr): 3461, 3400, 2711, 1637, 1504, 1294, 1211, 835, 790 cm$^{-1}$.

Elemental analysis for C$_{25}$H$_{29}$N$_4$O$_2$SCl$_2$.1.0H$_2$O Calcd.: C, 53.86; H, 5.60; N, 10.05 Found: C, 53.65; H, 5.57; N, 9.81

Example 114

Synthesis of N-[1-(2-(2-fluorophenoxy)ethan-1-yl)piperidin-4-ylmethyl]-5-thia-1,8b-diazaacenaphthylene-4-carboxamide Dihydrochloride 1) The procedure of Example 108-1) was generally followed to provide N-[1-(2-(2-fluorophenoxy)ethan-1-yl)piperidin-4-ylmethyl]-5-thia-1,8b-diazaacenaphthylene-4-carboxamide as red oil.

$^1$H-NMR (200 MHz, CDCl$_3$) δ: 1.25–2.21 (7H, m), 2.847 (2H, t like, J=6.0 Hz), 3.00–3.10 (2H, d like), 3.217 (2H, t, J=6.0 Hz), 4.10–4.20 (2H, m), 5.799 (1H, dd, J=1.8, 6.2 Hz), 5.75–5.88 (1H, m), 6.60–6.73 (2H, m), 6.85–7.15 (6H, m).

2) The procedure of Example 108-2) was generally followed to provide N-[1-(2-(2-fluorophenoxy)ethan-1-yl)piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.40–1.95 (4H, m), 2.90–3.35 (5H, m), 3.40–3.65 (4H, m), 4.45–4.55 (2H, m), 6.645 (1H, d, J=7.6 Hz), 6.95–7.08 (2H, m), 7.13–7.35 (5H, m), 7.678 (1H, s), 8.85–8.98 (1H, m), 10.70 (1H, br s).

IR (KBr): 3420, 3050, 2950, 1635, 1560, 1535, 1280, 1260, 1220, 1150, 780, 760 cm$^{-1}$.

Elemental analysis for C$_{24}$H$_{27}$N$_4$O$_2$SCl$_2$.2.5H$_2$O Calcd.: C, 50.53; H, 5.65; N, 9.82 Found: C, 50.81; H, 5.68; N, 9.65

Example 115

Synthesis of N-[1-(2-(3-fluorophenoxy)ethan-1-yl)piperidin-4-ylmethyl]-5-thia-1,8b-diazaacenaphthylene-4-carboxamide Dihydrochloride 1) The procedure of Example 108-1) was generally followed to provide N-[1-(2-(3-fluorophenoxy)ethan-1-yl)piperidin-4-ylmethyl]-5-thia-1,8b-diazaacenaphthylene-4-carboxamide as red oil.

$^1$H-NMR (200 MHz, CDCl$_3$) δ: 1.25–1.45 (2H, m), 1.45–1.63 (1H, m), 1.63–1.78 (2H, m), 2.05–2.18 (2H, m), 2.798 (2H, t, J=6.0 Hz), 3.017 (2H, d like, J=11.8 Hz), 3.212 (2H, t, J=6.0 Hz), 4.080 (2H, t, J=5.7 Hz), 5.800 (1H, dd, J=1.8, 6.1 Hz), 5.75–5.90 (1H, m), 6.58–6.73 (6H, m), 7.054 (1H, s), 7.16–7.27 (1H, m).

2) The procedure of Example 108-2) was generally followed to provide N-[1-(2-(3-fluorophenoxy)ethan-1-yl)piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.45–1.95 (4H, m), 2.92–3.15 (4H, m), 3.18–3.35 (1H, m), 3.42–3.65 (4H, m), 4.38–4.52 (2H, m), 6.603 (1H, d, J=7.2 Hz), 6.78–6.99 (4H, m), 7.20–7.42 (3H, m), 7.647 (1H, s), 8.90–9.00 (1H, m), 10.70 (1H, br s).

IR (KBr): 3420, 3250, 3050, 2950, 1635, 1610, 1590, 1560, 1540, 1500, 1490, 1290, 1260, 1220, 1170, 1140, 780 cm$^{-1}$.

Elemental analysis for C$_{24}$H$_{27}$N$_4$O$_2$SCl$_2$F.1.0H$_2$O Calcd.: C, 53.04; H, 5.38; N, 10.31 Found C, 53.32; H, 5.59; N, 10.32

Example 116

Synthesis of N-[1-(2-(4-fluorophenoxy)ethan-1-yl)piperidin-4-ylmethyl]-5-thia-1,8b-diazaacenaphthylene-4-carboxamide Dihydrochloride 1) The procedure of Example 108-1) was generally followed to provide N-[1-(2-(4-fluorophenoxy)ethan-1-yl)piperidin-4-ylmethyl]-5-thia-1,8b-diazaacenaphthylene-4-carboxamide as red oil.

$^1$H-NMR (200 MHz, CDCl$_3$) δ: 1.20–1.42 (2H, m), 1.45–1.65 (1H, m), 1.63–1.77 (2H, m), 2.03–2.16 (2H, m), 2.783 (2H, t, J=5.9 Hz), 3.015 (2H, d like, J=11.8 Hz), 3.214 (2H, t, J=6.2 Hz), 4.055 (2H, t, J=5.9 Hz), 5.798 (1H, dd, J=1.6, 6.2 Hz), 5.75–5.85 (1H, m), 6.59–6.72 (3H, m), 6.80–6.88 (2H, m), 6.89–7.01 (2H, m), 7.058 (1H, s).

2) The procedure of Example 108-2) was generally followed to provide N-[1-(2-(4-fluorophenoxy)ethan-1-yl)piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.40–1.90 (5H, m), 2.90–3.15 (3H, m), 3.15–3.30 (1H, m), 3.40–3.60 (4H, m), 4.33–4.42 (2H, m), 6.599 (1H, d, J=7.4 Hz), 6.94–7.06 (3H, m), 7.13–7.31 (4H, m), 7.644 (1H, s), 8.85–8.95 (1H, m), 10.56 (1H, br s).

IR (KBr): 3420, 3250, 3050, 2950, 1635, 1560, 1540, 1500, 1290, 1250, 1210, 830, 780, 760 cm$^{-1}$.

Elemental analysis for C$_{24}$H$_{27}$N$_4$O$_2$SCl$_2$.1.5H$_2$O Calcd.: C, 52.17; H, 5.47; N, 10.14 Found: C, 52.28; H, 5.53; N, 10.06

Example 117

Synthesis of N-[1-(3-(2,4-difluorophenoxy)propan-1-yl)piperidin-4-ylmethyl]-5-thia-1,8b-diazaacenaphthylene-4-carboxamide Dihydrochloride 1) The procedure of Example 111-1) was generally followed to provide N-[1-(3-(2,4-difluorophenoxy)propan-1-yl)piperidin-4-ylmethyl]-5-thia-1,8b-diazaacenaphthylene-4-carboxamide as red-purple amorphous substance.

$^1$H-NMR (200 MHz, CDCl$_3$) δ: 1.21–1.73 (m, 4H), 1.90–2.08 (m, 5H), 2.54 (t, J=7.4 Hz, 2H), 2.96 (br d, J=12.2

Hz, 2H), 3.21 (t, J=6.2 Hz, 2H), 4.04 (t, J=6.3 Hz, 2H), 5.79 (dd, J=1.8, 6.2 Hz, 1H), 5.82–5.89 (m, 1H), 6.58–6.93 (m, 6H), 7.05 (s, 1H).

2) The procedure of Example 111-2) was generally followed to provide N-[1-(3-(2,4-difluorophenoxy)propan-1-yl)piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.42–1.95 (m, 5H), 2.14–2.29 (m, 2H), 2.80–3.26 (m, 6H), 3.46–3.55 (m, 2H), 4.12 (t, J=5.9 Hz, 2H), 6.60 (d, J=7.2 Hz, 1H), 6.96 (d, J=8.8 Hz, 1H), 6.96–7.05 (m, 1H), 7.15–7.42 (m, 4H), 7.64 (s, 1H), 8.86–8.97 (m, 1H).

IR (KBr): 3460, 3381, 3246, 2951, 2702, 1639, 1510, 1294, 1215, 798 cm$^{-1}$.

Elemental analysis for $C_{25}H_{28}N_4O_2SCl_2F_2 \cdot 1.0H_2O$ Calcd.: C, 52.18; H, 5.25; N, 9.74 Found C, 52.31; H, 5.29; N, 9.67

Example 118

Synthesis of N-[1-(3-(4-chlorophenoxy)propan-1-yl) piperidin-4-ylmethyl]-5-thia-1,8b-diazaacenaphthylene-4-carboxamide Dihydrochloride 1) The procedure of Example 111-1) was generally followed to provide N-[1-(3-(4-chlorophenoxy)propan-1-yl) piperidin-4-ylmethyl]-5-thia-1,8b-diazaacenaphthylene-4-carboxamide as red-purple amorphous substance.

$^1$H-NMR (200 MHz, CDCl$_3$) δ: 1.19–2.01 (m, 9H), 2.50 (t, J=7.5 Hz, 2H), 2.95 (br d, J=11.4 Hz, 2H), 3.20 (t, J=6.2 Hz, 2H), 3.97 (t, J=6.4 Hz, 2H), 5.78 (dd, J=2.2, 5.8 Hz, 1H), 6.07 (br t, J=5.9 Hz, 1H), 6.63–6.68 (m, 3H), 6.80–6.85 (m, 2H), 7.02 (s, 1H), 7.20–7.26 (m, 2H).

2) The procedure of Example 111-2) was generally followed to provide N-[1-(3-(4-chlorophenoxy)propan-1-yl) piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.39–1.90 (m, 5H), 2.10–2.26 (m, 2H), 2.76–3.31 (m, 6H), 3.43–3.58 (m, 2H), 4.05 (t, J=6.0 Hz, 2H), 6.57 (d, J=7.4 Hz, 1H), 6.92–7.01 (m, 3H), 7.16–7.37 (m, 4H), 7.61 (s, 1H), 8.87 (m, 1H).

IR (KBr): 3404, 1635, 1495, 1292, 1242 cm$^{-1}$.

Elemental analysis for $C_{25}H_{29}N_4O_2SCl_3 \cdot 0.5H_2O$ Calcd.: C, 53.15; H, 5.35; N, 9.92 Found: C, 53.40; H, 5.23; N, 9.92

Example 119

Synthesis of N-[1-(3-(2-methoxyphenoxy)propan-1-yl)piperidin-4-ylmethyl]-5-thia-1,8b-diazaacenaphthylene-4-carboxamide Dihydrochloride 1) The procedure of Example 111-1) was generally followed to provide N-[1-(3-(2-methoxyphenoxy)propan-1-yl) piperidin-4-ylmethyl]-5-thia-1,8b-diazaacenaphthylene-4-carboxamide as red oil.

$^1$H-NMR (200 MHz, CDCl$_3$) δ: 1.26–2.15 (9H, m), 2.630 (2H, t, J=7.3 Hz), 3.02–3.08 (2H, m), 3.218 (2H, t, J=6.1 Hz), 3.861 (3H, s), 4.079 (2H, t, J=6.4 Hz), 5.786 (1H, dd, J=1.8, 6.2 Hz), 5.90–6.05 (1H, m), 6.60–6.75 (3H, m), 6.907 (4H, s), 7.056 (1H, s).

2) The procedure of Example 111-2) was generally followed to provide N-[1-(3-(2-methoxyphenoxy)propan-1-yl) piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.40–1.85 (5H, m), 2.10–2.30 (2H, m), 2.80–3.30 (6H, m), 3.45–3.60 (2H, m), 3.762 (3H, s), 4.00–4.06 (2H, m), 6.571 (1H, d, J=6.6 Hz), 6.86–7.01 (5H, m), 7.16–7.28 (2H, m), 7.611 (1H, s), 8.82–8.90 (1H, m).

IR (KBr): 3420, 2920, 1630, 1500, 1285, 1250, 1220, 1120, 780, 740 cm$^{-1}$.

Elemental analysis for $C_{26}H_{32}N_4O_3SCl_2 \cdot 1.5H_2O$ Calcd.: C, 53.98; H, 6.10; N, 9.68 Found: C, 53.86; H, 6.14; N, 9.51

Example 120

Synthesis of N-[1-(3-(4-methoxyphenoxy)propan-1-yl)piperidin-4-ylmethyl]-5-thia-1,8b-diazaacenaphthylene-4-carboxamide Dihydrochloride 1) The procedure of Example 111-1) was generally followed to provide N-[1-(3-(4-methoxyphenoxy)propan-1-yl) piperidin-4-ylmethyl]-5-thia-1,8b-diazaacenaphthylene-4-carboxamide as red-purple amorphous substance.

$^1$H-NMR (200 MHz, CDCl$_3$) δ: 1.38–2.25 (m, 9H), 2.63–2.71 (m, 2H), 3.11 (br d, J=11.4 Hz, 2H), 3.17–3.26 (m, 2H), 3.77 (s, 3H), 3.97 (t, J=6.1 Hz, 2H), 5.77 (dd, J=2.0, 5.8 Hz, 1H), 6.15–6.27 (m, 1H), 6.60–6.67 (m, 2H), 6.77–6.83 (m, 5H), 7.05 (s, 1H).

2) The procedure of Example 111-2) was generally followed to provide N-[1-(3-(4-methoxyphenoxy)propan-1-yl) piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.40–1.95 (m, 5H), 2.11–2.24 (m, 2H), 2.78–3.30 (m, 6H), 3.43–3.53 (m, 2H), 3.70 (s, 3H), 3.98 (t, J=5.9 Hz, 2H), 6.56 (d, J=7.3 Hz, 1H), 6.87–6.97 (m, 5H), 7.15–7.28 (m, 2H), 7.61 (s, 1H), 8.80–8.92 (m, 1H).

IR (KBr): 3425, 3051, 2947, 2708, 2507, 1635, 1506, 1227 cm$^{-1}$.

Example 121

Synthesis of N-[1-(3-(4-tert-butylphenoxy)propan-1-yl)piperidin-4-ylmethyl]-5-thia-1,8b-diazaacenaphthylene-4-carboxamide Dihydrochloride 1) The procedure of Example 111-1) was generally followed to provide N-[1-(3-(4-tert-butylphenoxy)propan-1-yl) piperidin-4-ylmethyl]-5-thia-1,8b-diazaacenaphthylene-4-carboxamide as red-purple amorphous substance.

$^1$H-NMR (200 MHz, CDCl$_3$) δ: 1.29 (s, 9H), 1.40–2.36 (m, 9H), 2.62–2.70 (m, 2H), 3.04–3.13 (m, 2H), 3.21 (t, J=6.2 Hz, 2H), 3.99 (t, J=6.0 Hz, 2H), 5.74 (dd, J=2.2, 5.8 Hz, 1H), 6.36–6.67 (m, 3H), 6.79–6.84 (m, 2H), 6.90 (s, 1H), 7.05 (s, 1H), 7.26–7.31 (m, 2H).

2) The procedure of Example 111-2) was generally followed to provide N-[1-(3-(4-tert-butylphenoxy)propan-1-yl) piperidin-4-ylmethyl]-5-thia-1,8b-diazaacenaphthylene-4-carboxamide dihydrochloride as orange-colored solid.

$^1$H-NMR (200 MHz, DMSO-d$_6$) δ: 1.25 (s, 9H), 1.35–1.92 (m, 5H), 2.06–2.23 (m, 2H), 2.80–3.56 (m, 8H), 4.02 (t, J=6.0 Hz, 2H), 6.56 (d, J=7.4 Hz, 1H), 6.83–6.89 (m, 2H), 6.94 (d, J=9.0 Hz, 1H), 7.10 (s, 1H), 7.19–7.32 (m, 3H), 7.60 (s, 1H), 8.72–8.82 (m, 1H).

IR (KBr): 3429, 2954, 1635, 1510, 1294, 1244, 831, 785 cm$^{-1}$.

Example 122

Synthesis of N-[1-(3-(2,4,6-trimethylphenoxy) propan-1-yl)piperidin-4-ylmethyl]-5-thia-1,8b-diazaacenaphthylene-4-carboxamide Dihydrochloride 1) The procedure of Example 111-1) was generally followed to provide N-[1-(3-(2,4,6- trimethylphenoxy)propan- 1-yl)piperidin-4-ylmethyl]-5-thia-1,8b-diazaacenaphthylene-4-carboxamide as red-purple amorphous substance.

¹H-NMR (200 MHz, CDCl₃) δ: 1.37–1.86 (m, 4H), 2.00–2.30 (m, 5H), 2.21 (s, 9H), 2.75–2.83 (m, 2H), 3.12–3.19 (m, 4H), 3.76 (t, J=5.8 Hz, 2H), 5.69–5.73 (m, 1H), 6.56–6.58 (m, 2H), 6.80 (s, 2H), 6.89 (s, 1H), 6.99 (s, 1H), 7.14–7.29 (m, 1H).

2) The procedure of Example 111-2) was generally followed to provide N-[1-(3-(2,4,6-trimethylphenoxy)propan-1-yl)piperidin-4-ylmethyl]-5-thia-1,8b-diazaacenaphthylene-4-carboxamide dihydrochloride as orange-colored solid.

¹H-NMR (200 MHz, DMSO-d₆) δ: 1.40–1.95 (m, 4H), 2.05–2.40 (m, 3H), 2.17 (s, 9H), 2.80–3.36 (m, 6H), 3.52 (br d, J=12.4 Hz, 2H), 3.74 (t, J=5.7 Hz, 2H), 6.60 (d, J=7.0 Hz, 1H), 6.82 (s, 2H), 6.97 (d, J=9.2 Hz, 1H), 7.20–7.31 (m, 2H), 7.65 (s, 1H), 8.87–8.95 (m, 1H).

IR (KBr): 3392, 2947, 2715, 1635, 1492, 1294, 1215 cm⁻¹.

Example 123

Synthesis of N-[1-[2-(phenylthio)ethan-1-yl]piperidin-4-ylmethyl]-5-thia-1,8b-diazaacenaphthylene-4-carboxamide dihydrochloride 1) The procedure of Example 108-1) was generally followed to provide N-[1-[2-(phenylthio)ethan-1-yl]piperidin-4-ylmethyl]-5-thia-1,8b-diazaacenaphthylene-4-carboxamide as red solid.

1H-NMR (200 MHz, CDCl₃) δ: 1.20–1.40 (2H, m), 1.40–1.60 (1H, m), 1.60–1.75 (2H, m), 1.92–2.08 (2H, m), 2.58–2.66 (2H, m), 2.945 (2H, d like, J=11.2 Hz), 3.02–3.10 (2H, m), 3.201 (2H, t, J=6.1 Hz), 5.791 (1H, dd, J=1.7, 6.2 Hz), 6.58–6.71 (3H, m), 7.053 (1H, s), 7.10–7.37 (5H, m).

2) The procedure of Example 108-2) was generally followed to provide N-[1-[2-(phenylthio)ethan-1-yl]piperidin-4-ylmethyl]-5-thia-1,8b-diazaacenaphthylene-4-carboxamide dihydrochloride as orange-colored crystals.

¹H-NMR (200 MHz, DMSO-d₆) δ: 1.30–1.90 (5H, m), 2.75–3.30 (7H, m), 3.38–3.60 (3H, m), 6.600 (1H, d, J=6.8 Hz), 6.966 (1H, d, J=9.2 Hz), 7.17–7.46 (7H, m), 7.641 (1H, s), 8.83–8.93 (1H, m), 10.84 (1H, br s).

IR (KBr): 3420, 3250, 3050, 2680, 1650, 1635, 1565, 1540, 1500, 1440, 1390, 1290, 1220, 750 cm⁻¹.

Elemental analysis for $C_{24}H_{28}N_4OS_2Cl_2 \cdot 0.5H_2O$ Calcd.: C, 54.13; H, 5.49; N, 10.52 Found: C, 53.68; H, 5.83; N, 10.22

Example 124

Synthesis of N-[1-(phenylaminocarbonylmethyl)piperidin-4-ylmethyl]-5-thia-1,8b-diazaacenaphthylene-4-carboxamide dihydrochloride 1) Synthesis of N-[1-(phenylaminocarbonylmethyl)piperidin-4-ylmethyl]-5-thia-1,8b-diazaacenaphthylene-4-carboxamide To a solution of 581 mg (1.5 mM) of N-(piperidin-4-ylmethyl)-5-thia-1,8b-diazaacenaphthylene-4-carboxamide dihydrochloride and 759 mg (7.5 mM) of triethylamine in ethanol (30 ml) was added 254 mg (1.5 mM) of chloroacetylaniline at room temperature, and the mixture was refluxed for 18 hours. The solvent was then distilled off under reduced pressure and the residue was diluted with water and extracted with methylene chloride. The organic layer was washed with saturated aqueous solution of sodium chloride and dried over Na₂SO₄. The resulting crude product was purified by column chromatography (methanol/ethyl acetate=½) to provide the title compound as red oil.

¹H-NMR (200 MHz, CDCl₃) δ: 1.25–1.45 (2H, m), 1.45–2.68 (1H, m), 1.70–1.80 (2H, m), 2.246 (2H, dt, J=2.2 11.65 Hz), 2.936 (2H, br d, J=11.8 Hz), 3.109 (2H, s), 3.248 (2H, t, J=6.4 Hz), 5.791 (1H, dd, J=1.6, 6.0 Hz), 5.88–5.95 (1H, m), 6.59–6.71 (3H, m), 7.05–7.15 (2H, m), 7.29–7.38 (2H, m), 7.52–7.58 (2H, m), 9.117 (1H, br s).

2) Synthesis of N-[1-phenylaminocarbonylmethyl)piperidin-4-ylmethyl]-5-thia-1,8b-diazaacenaphthylene-4-carboxamide dihydrochloride To a solution of N-[1-(phenylaminocarbonylmethyl)-piperidin-4-ylmethyl]-5-thia-1,8b-diazaacenaphthylene-4-carboxamide in chloroform-methanol (1:1) was added 2 ml (8.0 mM) of 4N-HCl/ethyl acetate. The solvent was distilled off under reduced pressure and the residue was diluted with ethanol/ether (¹⁄₁₀). The resulting crystals were collected by filtration and rinsed with ethanol and diethyl ether to provide the title compound as orange-colored crystals (506 mg, 60%).

¹H-NMR (200 MHz, DMSO-d₆) δ: 1.40–1.80 (5H, m), 3.00–3.30 (4H, m), 3.45–3.60 (2H, m), 4.152 (2H, s), 6.618 (1H, d, J=7.2 Hz), 6.977 (1H, d, J=8.8 Hz), 7.114 (1H, t, J=7.5 Hz), 7.24–7.39 (4H, m), 7.627 (1H, s), 7.666 (2H, s), 8.95–9.10 (1H, m), 10.00 (1H, br s), 11.016 (1H, s).

IR (KBr): 3400, 3250, 3050, 2950, 1690, 1630, 1600, 1560, 1540, 1500, 1440, 1390, 1300, 1210, 1110, 940, 780, 760 cm⁻¹.

Elemental analysis for $C_{24}H_{27}N_5O_2SCl_2 \cdot 2.5H_2O$ Calcd.: C, 50.97; H, 5.70; N, 12.38 Found: C, 51.17; H, 5.68; N, 12.13

Example 125

Synthesis of N-[1-[[3,5-bis(trifluoromethyl)phenyl]amino-carbonylmethyl]piperidin-4-ylmethyl]-5-thia-1,8b-diazaacenaphthylene-4-carboxamide dihydrochloride 1) Synthesis of N-[1-[[3,5-bis(trifluoromethyl)phenyl]-aminocarbonylmethyl]piperidin-4-ylmethyl]-5-thia-1,8b-diazaacenaphthylene-4-carboxamide To a solution of 709 mg (3 mM) of 3,5-bis(trifluoromethyl)aniline and 455 mg (4.5 mM) of triethylamine in dichloromethane (20 ml) was added 386 mg (3.3 mM) of chloroacetyl chloride gradually with ice-cooling and the mixture was stirred at room temperature for 30 minutes. This reaction mixture was washed with 5% aqueous solution of sodium hydrogen carbonate and the organic layer was dried over Na₂SO₄. The solvent was then distilled off under reduced pressure to recover crystals (830 mg). This chloride was dissolved in ethanol (30 ml), followed by addition of 759 mg (7.5 mM) of triethylamine and 581 mg (1.5 mM) of N-(piperidin-4-ylmethyl)-5-thia-1,8b-diaza-acenaphthylene-4-carboxamide dihydrochloride, and the mixture was refluxed at 90° C. overnight. After removal of excess ethanol by concentration to about half the initial volume, the residue was diluted with water (20 ml) and extracted with dichloromethane. The organic layer was washed with water and dried and the solvent was distilled off. The residue was purified by silica gel column chromatography (methanol/ethyl acetate=½) to provide the title compound as red oil (570 mg, 0.98 mM).

$^1$H-NMR (200 MHz, CDCl$_3$) δ: 1.33–1.49 (2H, m), 1.50–1.70 (1H, m), 1.73–1.85 (2H, m), 2.22–2.38 (2H, m), 2.85–3.00 (2H, m), 3.161 (2H, s), 3.282 (2H, t, J=6.4 Hz), 5.75–5.85 (2H, m), 6.60–6.73 (3H, m), 7.081 (1H, s), 7.616 (1H, s), 8.081 (2H, s), 9.458 (1H, br s).

2) Synthesis of N-[1-[[3,5-bis(trifluoromethyl)phenyl]-aminocarbonylmethyl]piperidin-4-ylmethyl]-5-thia-1,8b-diazaacenaphthylene-4-carboxamide dihydrochloride To a solution of N-[1-[[3,5-bis(trifluoromethyl)-phenyl]aminocarbonylmethyl]piperidin-4-ylmethyl]-5-thia-1,8b-diazaacenaphthylene-4-carboxamide in chloroform-methanol (1:1) was added 2 ml (8.0 mM) of 4N-HCl/ethyl acetate. The solvent was distilled off under reduced pressure and the residue was diluted with ether. The resulting crystals were collected by filtration and rinsed with ethanol and diethyl ether to provide the title compound as orange-colored crystals (404 mg, 41%).

$^1$H-NMR (200 MHz, DMSO-d$_6$) δ: 1.45–1.95 (5H, m), 3.00–3.40 (4H, m), 3.50–3.68 (2H, m), 4.268 (2H, s), 6.647 (1H, d, J=7.4 Hz), 6.996 (1H, d, J=9.2 Hz), 7.24–7.35 (2H, m), 7.698 (1H, s), 7.854 (1H, s), 8.392 (2H, s), 9.017 (1H, br s), 10.179 (1H, br s), 12.225 (1H, s).

IR (KBr): 3420, 3230, 3050, 2950, 1700, 1635, 1560, 1540, 1500, 1470, 1440, 1380, 1280, 1215, 1180, 1130, 940, 890, 840, 780, 700, 680 cm$^{-1}$.

Elemental analysis for C$_{26}$H$_{25}$N$_5$O$_2$SCl$_2$F$_6$·0.2H$_2$O. Calcd.: C, 47.31; H, 3.88; N, 10.61 Found: C, 47.59; H, 4.19; N, 10.45

Example 126

Synthesis of N-[1-[[2,6-bis(trifluoromethyl) phenyl] aminocarbonylmethyl]piperidin-4-ylmethyl]-5-thia-1,8b-diazaacenaphthylene-4-carboxamide dihydrochloride 1) The procedure of Example 125-1) was generally followed to provide N-[1-[[2,6-bis(trifluoromethyl)phenyl] amino-carbonylmethyl]piperidin-4-ylmethyl]-5-thia-1,8b-diazaacenaphthylene-4-carboxamide as red solid.

$^1$H-NMR (200 MHz, CDCl$_3$) δ: 1.25–1.45 (2H, m), 1.55–1.85 (3H, m), 2.26–2.40 (2H, m), 2.88–2.90 (2H, m), 3.172 (2H, s), 3.266 (2H, t, J=6.1 Hz), 5.75–5.80 (1H, m), 5.809 (1H, dd, J=6.3, 1.8 Hz), 6.61–6.75 (3H, m), 7.075 (1H, s), 7.452 (1H, d like), 7.744 (1H, d like), 8.896 (1H, s), 10.20 (1H, br s).

2) The procedure of Example 125-2) was generally followed to provide N-[1-[[2,6-bis(trifluoromethyl)phenyl] amino-carbonylmethyl]piperidin-4-ylmethyl]-5-thia-1,8b-diazaacenaphthylene-4-carboxamide dihydrochloride as yellow crystals.

$^1$H-NMR (200 MHz, DMSO-d$_6$) δ: 1.40–1.70 (3H, m), 1.70–1.95 (3H, m), 3.00–3.20 (2H, m), 3.50–3.65 (2H, m), 4.15–4.40 (3H, m), 6.564 (1H, d, J=7.6 Hz), 6.950 (1H, d, J=9.2 Hz), 7.18–7.28 (2H, m), 7.616 (1H, s), 7.928 (1H, d-like), 8.85–9.00 (1H, m), 10.04 (1H, br s), 10.80 (1H, br s).

IR (KBr): 3400, 3230, 3050, 2950, 1700, 1630, 1580, 1560, 1540, 1500, 1430, 1390, 1330, 1315, 1600, 1210, 1180, 1130, 1080, 1040, 940, 840, 780, 740, 630 cm$^{-1}$.

Elemental analysis for C$_{26}$H$_{25}$N$_5$O$_2$SCl$_2$F$_6$·1.0H$_2$O. Calcd.: C, 46.30; H, 4.03; N, 10.38 Found: C, 46.16; H, 3.91; N, 10.40

Example 127

Synthesis of N-[1-[(4-fluorophenyl) aminocarbonylmethyl]piperidin-4-ylmethyl]-5-thia-1,8b-diazaacenaphthylene-4-carboxamide dihydrochloride 1) The procedure of Example 125-1) was generally followed to provide N-[1-[(4-fluorophenyl) aminocarbonylmethyl]piperidin-4-ylmethyl]-5-thia-1,8b-diazaacenaphthylene-4-carboxamide as red oil.

$^1$H-NMR (200 MHz, CDCl$_3$) δ: 1.20–1.45 (2H, m), 1.50–1.70 (1H, m), 1.70–1.95 (2H, m), 2.18–2.35 (2H, m), 2.85–3.00 (2H, m), 3.107 (2H, s), 3.20–3.35 (2H, m), 5.797 (1H, dd, J=2.2, 5.5 Hz), 5.98–6.15 (1H, m), 6.59–6.77 (3H, m), 6.98–7.15 (3H, m), 7.45–7.65 (2H, m), 9.123 (1H, br s).

2) The procedure of Example 125-2) was generally followed to provide N-[1-[(4-fluorophenyl) aminocarbonylmethyl]piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.40–1.95 (6H, m), 2.98–3.30 (3H, m), 3.48–3.60 (2H, m), 4.157 (2H, s), 6.639 (1H, d, J=6.8 Hz), 6.990 (1H, d, J=9.2 Hz), 7.15–7.35 (3H, m), 7.63–7.75 (3H, m), 8.96–9.08 (1H, m), 10.026 (1H, br s), 11.162 (1H, s).

IR (KBr): 3400, 3230, 3050, 2950, 1695, 1630, 1560, 1535, 1500, 1300, 1210, 840, 780, 700, 620 cm$^{-1}$.

Elemental analysis for C$_{24}$H$_{26}$N$_5$O$_2$SCl$_2$F·2.2H$_2$O. Calcd.: C, 49.86; H, 5.30; N, 12.11 Found: C, 50.29; H, 5.31; N, 11.65

Example 128

Synthesis of N-[1-(benzylaminocarbonylmethyl) piperidin-4-ylmethyl]-5-thia-1,8b-diazaacenaphthylene-4-carboxamide dihydrochloride 1) The procedure of Example 125-1) was generally followed to provide N-[1-(benzylaminocarbonylmethyl) piperidin-4-ylmethyl]-5-thia-1,8b-diazaacenaphthylene-4-carboxamide as red oil.

$^1$H-NMR (200 MHz, CDCl$_3$) δ: 1.05–1.30 (2H, m), 1.40–1.60 (1H, m), 1.655 (2H, br d like, J=12.8 Hz), 2.127 (2H, t like, J=10.7 Hz), 2.828 (2H, br d, J=11.4 Hz), 3.020 (2H, s), 3.152 (2H, t, J=6.4 Hz), 4.468 (2H, d, J=5.8 Hz), 5.741 (1H, dd, J=3.0, 5.2 Hz), 6.490 (1H, t, J=5.9 Hz), 6.59–6.65 (3H, m), 6.949 (1H, s), 7.239–7.385 (5H, m), 7.526–7.58 (1H, t, J=5.9 Hz).

2) The procedure of Example 125-2) was generally followed to provide N-[1-(benzylaminocarbonylmethyl) piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.40–1.90 (4H, m), 2.95–3.51 (7H, m), 3.983 (2H, br s), 4.352 (2H, d, J=5.8 Hz), 6.649 (1H, d, J=7.4 Hz), 7.003 (1H, d, J=9.2 Hz), 7.20–7.39 (6H, m), 7.693 (1H, s), 9.05–9.15 (1H, m), 9.316 (1H, t, J=5.9 Hz), 10.00 (1H, br s).

IR (KBr): 3420, 3220, 3050, 2930, 1680, 1630, 1560, 1540, 1500, 1450, 1430, 1390, 1285, 1210, 1110, 950, 780, 740, 700 cm$^{-1}$.

Elemental analysis for C$_{25}$H$_{29}$N$_5$O$_2$SCl$_2$·0.5H$_2$O. Calcd.: C, 55.25; H, 5.56; N, 12.89 Found: C, 55.02; H, 6.29; N, 12.22

Example 129

Synthesis of N-[1-(N-methyl-N-phenylaminocarbonylmethyl)piperidin-4-ylmethyl]-5-thia-1,8b-diazaacenaphthylene-4-carboxamide dihydrochloride 1) The procedure of Example 125-1) was generally followed to provide N-[1-(N-methyl-N- phenylaminocarbonylmethyl)piperidin-4-ylmethyl]-5-thia-1,8b-diazaacenaphthylene-4-carboxamide as red oil.

$^1$H-NMR (200 MHz, CDCl$_3$) δ: 1.18–1.53 (3H, m), 1.55–1.68 (2H, m), 1.88–2.05 (2H, m), 2.78–2.95 (2H, m), 2.912 (2H, s), 3.150 (2H, t like, J=5.9 Hz), 3.266 (3H, s), 5.763 (1H, dd, J=2.8, 5.4 Hz), 6.433 (1H, br s), 6.60–6.63 (2H, m), 6.700 (1H, s), 6.991 (1H, s), 7.16–7.22 (2H, m), 7.29–7.48 (3H, m).

2) The procedure of Example 125-2) was generally followed to provide N-[1-(N-methyl-N-phenylaminocarbonylmethyl)piperidin-4-ylmethyl]-5-thia-1,8b-diazaacenaphthylene-4-carboxamide dihydrochloride as orange-colored crystals.

$^1$H-NMR (200 MHz, DMSO-d$_6$) δ: 1.40–1.95 (4H, m), 2.82–3.10 (3H, m), 3.10–3.55 (4H, m), 3.243 (3H, s), 3.80–3.91 (2H, m), 6.651 (1H, d, J=7.6 Hz), 7.003 (1H, d, J=9.2 Hz), 7.25–7.60 (6H, m), 7.694 (1H, s), 9.00–9.15 (1H, m), 9.632 (1H, br s).

IR (KBr): 3400, 3230, 3050, 2950, 1650, 1630, 1590, 1560, 1535, 1500, 1455, 1435, 1360, 1290, 1210, 1130, 1110, 1040, 950, 780, 700, 620 cm$^{-1}$.

Example 130

Synthesis of N-[1-(3,3-diphenylpropan-1-yl) piperidin-4-ylmethyl]-5-thia-1,8b-diazaacenaphthylene-4-carboxamide dihydrochloride 1) The procedure of Example 38-1) was generally followed to provide N-[1-(3,3-diphenylpropan-1-yl)piperidin-4-ylmethyl]-5-thia-1,8b-diazaacenaphthylene-4-carboxamide as deep red foam.

$^1$H-NMR (CDCl$_3$) δ: 1.30–1.75 (5H, m), 1.90–2.05 (2H, m), 2.20–2.60 (4H, m), 2.98 (2H, br d, 11.4 Hz), 3.19 (2H, t, J=5.9 Hz), 3.95 (1H, br t, 6.6 Hz), 5.78 (1H, dd, 1.8, 5.8 Hz), 5.95–6.05 (1H, m), 6.57–6.70 (2H, m), 6.72 (1H, s), 7.04 (1H, s), 7.10–7.35 (10H, m).

IR (KBr): 3359, 3059, 3026, 2927, 2810, 1618, 1543, 1510, 1481, 1452, 1282, 1155, 970, 771, 752, 735, 702 cm$^{-1}$.

2) Synthesis of N-[1-(3,3-diphenylpropan-1-yl)piperidin-4-ylmethyl]-5-thia-1,8b-diazaacenaphthylene-4-carboxamide dihydrochloride Using the above compound, the procedure of Example 1-6) was generally followed to provide the title compound as orange-colored solid.

$^1$H-NMR (CD$_3$OD) δ: 1.40–1.70 (2H, m), 1.80–2.00 (3H, m), 2.50–2.65 (2H, m), 2.80–3.10 (4H, m), 3.19 (2H, d, 5.8 Hz), 3.50–3.65 (2H, m), 4.02 (1H, t, 7.7 Hz), 6.60 (1H, d, 7.6 Hz), 6.96–7.01 (2H, m), 7.15–7.45 (11H, m), 7.51 (1H, s).

IR (KBr): 3388, 3061, 2933, 2694, 1635, 1564, 1535, 1498, 1454, 1394, 1290, 1215, 1103, 781, 704 cm$^{-1}$.

Elemental analysis for C$_{31}$H$_{34}$N$_4$OSCl$_2$·1.5H$_2$O. Calcd.: C, 61.18; H, 6.13; N, 9.21 Found: C, 61.15; H, 6.21; N, 9.32

Example 131

Synthesis of N-[1-(3-phenylpropan-1-yl)piperidin-4-yl]-5-thia-1,8b-diazaacenaphthylene-4-carboxamide dihydro-chloride 1) Synthesis of N-[(1-ethoxycarbonyl)piperidin-4-yl]-5-thia-1,8b-diazaacenaphthylenecarboxamide To a solution of 2.02 g (9.26 mM) of 5-thia-1,8b-diazaacenaphthylenecarboxylic acid in acetonitrile (30 ml) was added 2.13 g (18.51 mM) of N-hydroxysuccinimide and 3.55 g (18.52 mM) of N-ethyl-N'-3-(N,N-dimethylamino) propylcarbodiimide hydrochloride, and the mixture was stirred at room temperature for 2 hours. The solvent was then distilled off under reduced pressure and the residue was diluted with water and extracted with chloroform. The extract was washed with saturated aqueous solution of sodium chloride and dried over MgSO$_4$ and the solvent was distilled off under reduced pressure. To a solution of the residue in acetonitrile (27 ml) was added a mixture of 1.9 ml (11.08 mM) of ethyl 4-aminopiperidinecarboxylate and 2.5 ml (17.9 mM) of triethylamine in acetonitrile (5 ml), and the mixture was stirred at room temperature for 2 hours. The solvent was then distilled off under reduced pressure and the residue was diluted with water and extracted with methylene chloride. The organic layer was washed with saturated aqueous solution of sodium chloride and dried over MgSO$_4$ and the solvent was distilled off under reduced pressure. The residue was purified by silica gel column chromatography (methanol/ethyl acetate 20%) to provide 3.12 g (91%) of N-[(1-ethoxycarbonyl)piperidin-4-yl]-5-thia-1,8b-diazaacenaphthylenecarboxamide as red amorphous substance.

$^1$H-NMR (CDCl$_3$) δ: 1.16–1.46 (m, 2H), 1.26 (t, J=7.0 Hz, 3H), 1.93–2.02 (m, 2H), 2.84–2.97 (m, 2H), 3.87–4.21 (m, 2H), 4.13 (q, J=7.0 Hz, 2H), 5.67 (br d, J=8.0 Hz, 1H), 5.80 (dd, J=1.8, 6.2 Hz, 1H), 6.59–6.71 (m, 3H), 7.05 (s, 1H).

2) Synthesis of N-(1-tert-butoxycarbonylpiperidin-4-yl)-5-thia-1,8b-diazaacenaphthylenecarboxamide Under argon gas, 1.8 ml (12.65 mM) of trimethylsilyl iodide was added to a solution of 1.58 g (4.24 mM) of N-[(N-ethoxycarbonyl)piperidin-4-yl]-5-thia-1,8b-diazaacenaphthylenecarboxamide in acetonitrile (35 ml) at room temperature and the mixture was stirred for 16 hours. Then, 1.2 ml (8.43 mM) of trimethylsilyl iodide was further added and the mixture was stirred at room temperature for 2 days. The reaction was stopped by adding methanol and the reaction mixture was stirred at room temperature for 2 hours. To this mixture were added 4 ml (28.7 mM) of triethylamine and 1.07 ml (4.66 mM) of di-tert-butyl dicarbonate at room temperature and the mixture was stirred for 10 minutes. The solvent was then distilled off under reduced pressure and the residue was diluted with water and extracted with methylene chloride. The organic layer was washed with saturated aqueous solution of sodium chloride and dried over MgSO$_4$ and the solvent was distilled off under reduced pressure. The residue was purified by silica gel column chromatography (methanol/ethyl acetate 10%) to provide 2.12 g of N-(1-tert-butoxycarbonylpiperidin-4-yl)-5-thia-1,8b-diazaacenaphthylenecarboxamide as red amorphous substance.

$^1$H-NMR (CDCl$_3$) δ: 1.13–1.99 (m, 2H), 1.46 (s, 9H), 1.73–1.98 (m, 2H), 2.74–2.95 (m, 2H), 3.84–4.18 (m, 3H), 5.70–5.85 (m, 1H), 5.79 (dd, J=1.9, 5.7 Hz, 1H), 6.58–6.72 (m, 3H), 7.04 (s, 2H).

3) Synthesis of N-(piperidin-4-yl)-5-thia-1,8b-diazaacenaphthylenecarboxamide dihydrochloride To 2.12 g of N-(1-tert-butoxycarbonylpiperidin-4-yl)-5-thia-1,8b-diazaacenaphthylenecarboxamide was added 10 ml of concentrated hydrochloric acid and the mixture was stirred at room temperature for 2 hours. The solid matter was filtered off and ethanol was added to the filtrate. After the solvent was distilled off under reduced pressure, ethanol was added again and the mixture was concentrated. The above procedure was repeated a few times and the resulting crystals were collected by filtration. This crystal crop was rinsed with ethanol and diethyl ether to provide 0.95 g (60%) of N-(piperidin-4-yl)-5-thia-1,8b-diazaacenaphthylenecarboxamide dihydrochloride as orange-colored solid.

$^1$H-NMR (D$_2$O) δ: 1.64–1.87 (m, 2H), 2.03–2.19 (m, 2H), 3.03–3.21 (m, 2H), 3.42–3.58 (m, 2H), 3.82–4.02 (m, 1H), 5.98 (d, J=7.0 Hz, 1H), 6.60 (d, J=9.2 Hz, 1H), 6.67 (s, 1H), 6.78 (dd, J=7.2, 9.2 Hz, 1H), 6.98 (s, 1H).

4) Synthesis of N-[1-(3-phenylpropan-1-yl)piperidin-4-yl]-5-thia-1,8b-diazaacenaphthylene-4-carboxamide dihydrochloride To a solution of 3.0 g (8.84 mM) of N-(piperidin-4-yl)-5-thia-1,8b-diazaacenaphthylenecarboxamide dihydrochloride and 4.1 ml (29.4 mM) of triethylamine in ethanol (40 ml) was added 1.6 ml (10.53 mM) of 3-phenyl-1-bromopropane at room temperature and the mixture was refluxed under nitrogen for 16 hours. The solvent was then distilled off under reduced pressure and the residue was diluted with water and extracted with chloroform. The organic layer was washed with saturated aqueous solution of sodium chloride and dried over MgSO$_4$ and the solvent was distilled off under reduced pressure. The residue was purified by silica gel column chromatography (methanol/ethyl acetate 20–40%) to provide 2.91 g (86%) of N-[1-(3-phenylpropan-1-yl)piperidin-4-yl]-5-thia-1,8b-diazaacenaphthylene-4-carboxamide as red-purple amorphous substance.

$^1$H-NMR (CDCl$_3$) δ: 1.41–1.64 (m, 2H), 1.75–2.21 (m, 6H), 2.31–2.47 (m, 2H), 2.63 (t, J=7.7 Hz, 2H), 7.79–2.96 (m, 2H), 3.72–3.92 (m, 1H), 5.75–5.80 (m, 2H), 6.57–6.69 (m, 1H), 7.03 (s, 1H), 7.16–7.32 (m, 5H).

5) Synthesis of N-[1-(3-phenylpropan-1-yl)piperidin-4-yl]-5-thia-1,8b-diazaacenaphthylene-4-carboxamide dihydrochloride To a solution of 2.91 g (6.95 mM) of N-[1-(3-phenylpropan-1-yl)piperidin-4-yl]-5-thia-1,8b-diazaacenaphthylene-4-carboxamide in ethanol (10 ml) was added 10 ml (40 mM) of 4N-HCl/methanol at room temperature and the mixture was stirred at room temperature for several minutes. After the solvent was distilled off under reduced pressure, ethanol and diethyl ether were added to the residue. The resulting crystals were collected by filtration and rinsed with ethanol and diethyl ether to provide 3.08 g (90%) of N-[1-(3-phenylpropan-1-yl)piperidin-4-yl]-5-thia-1,8b-diazaacenaphthylene-4-carboxamide dihydrochloride as orange-colored solid.

$^1$H-NMR (DMSO-d$_6$) δ: 1.80–2.14 (m, 6H), 2.63 (t, J=7.5 Hz, 2H), 2.82–3.11 (m, 4H), 3.38–3.56 (m, 2H), 3.72–3.93 (m, 1H), 6.64 (d, J=6.6 Hz, 1H), 6.99 (d, J=9.2 Hz, 1H), 7.15–7.38 (m, 7H), 7.67 (s, 1H), 8.80–8.90 (m, 1H).

Elemental analysis for C$_{24}$H$_{28}$N$_4$OSCl$_2$·2.5H$_2$O. Calcd.: C, 53.73; H, 6.20; N, 10.44 Found: C, 53.84; H, 6.06; N, 10.28

Example 132

Synthesis of N-[1-(3-phenylpropan-1-yl)piperidin-4-yl]-5-thia-1,8b-diazaacenaphthylene-4-carboxamide 1) Synthesis of tert-butyl 4-aminopiperidine-1-carboxylate ½ potassium hydrogen sulfate salt To a solution of 50 g (262.8 mM) of 4-amino-1-benzylpiperidine in 500 ml of methanol was added 5 g of 5% palladium-on-carbon (hydrous) and catalytic reduction was carried out at the hydrogen pressure of 5 kg/cm$^2$ at 35° C. for 15 hours. The catalyst Pd/carbon was then filtered off and the filtrate was concentrated under reduced pressure to provide 4-aminopiperidine. To a solution of this 4-aminopiperidine in toluene (500 ml) was added 27.89 g (262.8 mM) of benzaldehyde and the mixture was refluxed for 3 hours, with the byproduct water being removed with a Dean-Stark trap. After cooling to room temperature, 63.08 g (289 mM) of di-tert-butyl dicarbonate was added dropwise gradually over about 1 hour and the mixture was stirred at room temperature overnight. After the solvent was distilled off under reduced pressure, 290 ml of 1N-aqueous solution of potassium hydrogen sulfate was added to the residue at room temperature and the mixture was stirred for 2 hours. The resulting crystal crop was harvested by filtration and rinsed with water, ethanol, and diethyl ether to provide tert-butyl 4-aminopiperidine-1-carboxylate ½ potassium hydrogen sulfate salt as colorless crystals (49.02 g, 71%).

$^1$H-NMR (200 MHz, CD$_3$CO$_2$D) δ: 1.47 (s, 9H), 1.52–1.73 (m, 2H), 2.01–2.18 (m, 2H), 2.75–2.98 (m, 2H), 3.41–3.59 (m, 1H), 4.10–4.32 (m, 2H).

IR (KBr): 1689, 1621, 1543, 1429, 1369, 1252, 1151, 1065, 862, 766, 617 cm$^{-1}$.

2) Synthesis of N-(1-tert-butoxycarbonylpiperidin-4-yl)-5-thia-1,8b-diazaacenaphthylenecarboxamide dihydrochloride To a suspension of 12.88 g (53.8 mM) of 5-thia-1,8b-diazaacenaphthylene carboxylic acid in acetonitrile (27 ml) were added 12.38 g (107.6 mM) of N-hydroxysuccinimide and 20.63 g (107.6 mM) of N-ethyl-N'-3-(N,N-dimethylamino)propylcarbodiimide hydrochloride, and the mixture was stirred at room temperature for 2 hours. To this reaction mixture was added a solution of 17.3 g (64.5 mM) of tert-butyl 4-aminopiperidine-1-carboxylate ½ potassium hydrogen sulfate salt, 19.6 g (128.7 mM) of 1,8-diazabicyclo[5.4.0]-7-undecene, and 7.5 ml (53.8 mM) of triethylamine in acetonitrile (80 ml) and the mixture was stirred for 64 hours. After the solvent was distilled off under reduced pressure, small amounts of ethanol and ethyl acetate were added to the residue. The organic layer was washed serially with water and saturated aqueous solution of sodium chloride and dried over MgSO$_4$ and the solvent was distilled off under reduced pressure. The residue was purified by silica gel column chromatography (methanol/ethyl acetate 10%) to provide 22.48 g of N-(1-tert-butoxycarbonylpiperidin-4-yl)-5-thia-1,8b-diazaacenaphthylenecarboxamide as red amorphous substance.

$^1$H-NMR (CDCl$_3$) δ: 1.16–1.46 (m, 2H), 1.26 (t, J=7.0 Hz, 3H), 1.93–2.02 (m, 2H), 2.84–2.97 (m, 2H), 3.87–4.21 (m, 2H), 4.13 (q, J=7.0 Hz, 2H), 5.67 (br d, J=8.0 Hz, 1H), 5.80 (dd, J=1.8, 6.2 Hz, 1H), 6.59–6.71 (m, 3H), 7.05 (s, 1H).

3) Synthesis of N-(piperidin-4-yl)-5-thia-1,8b-diazaacenaphthylenecarboxamide dihydrochloride To 22.48 g of N-(1-tert-butoxycarbonylpiperidin-4-yl)-5-thia-1,8b-diazaacenaphthylenecarboxamide was added 40 ml of concentrated hydrochloric acid and the mixture was stirred at room temperature for 2 hours. To this reaction mixture was added ethanol and the resulting crystals were collected by filtration. This crystal crop was rinsed with ethanol and diethyl ether to provide 14.68 g (73%) of N-(piperidin-4-yl)-5-thia-1,8b-diazaacenaphthylenecarboxamide dihydrochloride as orange-colored crystals.

$^1$H-NMR (D$_2$O) δ: 1.64–1.87 (m, 2H), 2.03–2.19 (m, 2H), 3.03–3.21 (m, 2H), 3.42–3.58 (m, 2H), 3.82–4.02 (m, 1H), 5.98 (d, J=7.0 Hz, 1H), 6.60 (d, J=9.2 Hz, 1H), 6.67 (s, 1H), 6.78 (dd, J=7.2, 9.2 Hz, 1H), 6.98 (s, 1H).

4) Synthesis of N-[1-(3-phenylpropan-1-yl)piperidin-4-yl]-5-thia-1,8b-diazaacenaphthylene-4-carboxamide To a solution of 12.0 g (32.1 mM) of N-(piperidin-4-yl)-5-thia-1,8b-diazaacenaphthylenecarboxamide dihydrochloride and 22.4 ml (160.7 mM) of triethylamine was added 5.9 ml (38.8 mM) of 3-phenyl-1-bromopropane at room temperature and the mixture was refluxed under nitrogen for 20 hours. The solvent was then distilled off under reduced pressure and the residue was diluted with water and extracted with ethyl acetate. The organic layer was washed with saturated aqueous solution of sodium chloride and dried over $MgSO_4$ and the solvent was distilled off under reduced pressure. The residue was purified by silica gel column chromatography (methanol/ethyl acetate 20–40%). The crystals obtained were dissolved in ethanol (100 ml)-chloroform (100 ml) and the chloroform was distilled off by heating under atmospheric pressure. After concentration to about 80 ml, the residue was allowed to stand at room temperature and the resulting crystals were collected by filtration to provide 7.04 g (52%) of N-[1-(3-phenylpropan-1-yl)piperidin-4-yl]-5-thia-1,8b-diazaacenaphthylene-4-carboxamide as red crystals.

m.p. 187–188° C.

$^1$H-NMR (CDCl$_3$) δ: 1.41–1.64 (m, 2H), 1.75–2.21 (m, 6H), 2.31–2.47 (m, 2H), 2.63 (t, J=7.7 Hz, 2H), 7.79–2.96 (m, 2H), 3.72–3.92 (m, 1H), 5.75–5.80 (m, 2H), 6.57–6.69 (m, 1H), 7.03 (s, 1H), 7.16–7.32 (m, 5H).

Elemental analysis for $C_{24}H_{26}N_4OS$. Calcd.: C, 68.87; H, 6.26; N, 13.39 Found: C, 68.62; H, 6.25; N, 13.42

Example 133

Synthesis of N-[1-[2-(6-hydroxy-2,5,7,8-tetramethyl-chroman-2-yl)ethyl]piperidin-4-ylmethyl]-5-thia-1,8b-diazaacenaphthylene-4-carboxamide dihydrochloride 1) Synthesis of N-[1-[2-(6-tert-butyldimethylsiloxy-2,5,7,8-tetramethylchroman-2-yl)ethyl]piperidin-4-yl-methyl]-5-thia-1,8b-diazaacenaphthylene-4-carboxamide Under nitrogen gas, 0.46 ml (5.94 mM) of methanesulfonyl chloride was added to a solution of 1.46 g (4.00 mM) of 6-tert-butyldimethylsiloxy-2-(2-hydroxyethyl)-2,5,7,8-tetramethylchroman and 1.11 ml (7.96 mM) of triethylamine in diethyl ether (8 ml) at 0° C. and the mixture was stirred at the prevailing temperature for 30 minutes. The reaction was stopped by adding saturated aqueous solution of sodium hydrogen carbonate and the reaction mixture was extracted with diethyl ether. The organic layer was washed serially with water and saturated aqueous solution of sodium chloride and dried over $MgSO_4$. The solvent was then distilled off under reduced pressure to provide the crude mesylate (1.76 g) as light-yellow oil. This crude mesylate (1.76 g, 3.98 mM) was added to a solution of 0.77 g (1.99 mM) of N-(piperidin-4-ylmethyl)-5-thia-1,8b-diazaacenaphthylene-4-carboxamide dihydrochloride and 1.4 ml (10.0 mM) of triethylamine in ethanol (7 ml) and the mixture was refluxed under nitrogen for 18 hours. This reaction mixture was diluted with water and extracted with ethyl acetate. The organic layer was washed with saturated aqueous solution of sodium chloride and dried over $MgSO_4$. After concentration, the crude product was purified by column chromatography (methanol/ethyl acetate 20–40%) to provide the title compound as red amorphous substance.

Yield 1.00 g (76%)

$^1$H-NMR (CDCl$_3$) δ: 0.11 (s, 6H), 1.04 (s, 9H), 1.24 (s, 3H), 1.42–2.01 (m, 11H), 2.04 (s, 3H), 2.06 (s, 3H), 2.09 (s, 3H), 2.45–2.61 (m, 4H), 2.84–3.00 (m, 2H), 3.17–3.23 (m, 2H), 5.72–5.84 (m, 1H), 5.80 (dd, J=1.6, 6.2 Hz, 1H), 6.59–6.74 (m, 3H), 7.06 (s, 1H).

IR (KBr): 3442, 2929, 1622, 1545, 1468, 1257, 1153, 1092, 837, 773 cm$^{-1}$.

2) Synthesis of N-[1-[2-(6-hydroxy-2,5,7,8-tetramethyl-chroman-2-yl)ethyl]piperidin-4-ylmethyl]-5-thia-1,8b-diazaacenaphthylene-4-carboxamide dihydrochloride To a solution of 1.00 g (1.51 mM) of N-[1-[2-(6-tert-butyldimethylsiloxy-2,5,7,8-tetramethylchroman-2-yl)ethyl]piperidin-4-ylmethyl]-5-thia-1,8b-diazaacenaphthylene-4-carboxamide in ethanol (4 ml) was added 4.0 ml (16 mM) of 4N—HCl/methanol and the mixture was stirred at room temperature for 63 hours. After the solvent was distilled off under reduced pressure, ethanol was added and the mixture was stirred at room temperature for 1 hour. The resulting crystal crop was harvested by filtration and rinsed with ethanol and diethyl ether to provide the title compound as orange-colored crystals.

Yield 789.4 mg (84%)

$^1$H-NMR (DMSO-d$_6$) δ: 1.19 (s, 3H), 1.36–2.08 (m, 11H), 1.99 (s, 3H), 2.02 (s, 3H), 2.05 (s, 3H), 2.76–3.55 (m, 8H), 6.58 (d, J=7.0 Hz, 1H), 6.96 (d, J=8.4 Hz, 1H), 7.17–7.30 (m, 2H), 7.63 (s, 1H), 8.84–8.96 (m, 1H), 10.07–10.32 (m, 1H).

IR (KBr): 3392, 1635, 1564, 1450, 1294, 1253, 1161, 1088, 995, 789 cm$^{-1}$.

Elemental analysis for $C_{31}H_{40}N_4O_3SCl_2·2.0H_2O$. Calcd.: C, 56.79; H, 6.76; N, 8.54 Found: C, 56.93; H, 6.79; N, 8.35

Example 134

Synthesis of N-[1-[2-(6-hydroxy-2,5,7,8-tetramethyl-chroman-2-yl)ethyl]piperidin-4-yl]-5-thia-1,8b-diazaacenaphthylene-4-carboxamide dihydrochioride 1) Synthesis of N-[1-[2-(6-tert-butyldimethylsiloxy-2,5,7,8-tetramethylchroman-2-yl)ethyl]piperidin-4-yl]-5-thia-1,8b-diazaacenaphthylene-4-carboxamide Under nitrogen gas, 0.46 ml (5.94 mM) of methanesulfonyl chloride was added to a solution of 1.46 g (4.00 mM) of 6-tert-butyldimethylsiloxy-2-(2-hydroxyethyl)-2,5,7,8-tetramethylchroman and 1.11 ml (7.96 mM) of triethylamine in diethyl ether (8 ml) at 0° C. and the mixture was stirred at the prevailing temperature for 30 minutes. The reaction was stopped by adding saturated aqueous solution of sodium hydrogen carbonate and the reaction mixture was extracted with diethyl ether. The organic layer was washed serially with water and saturated aqueous solution of sodium chloride and dried over $MgSO_4$. The solvent was then distilled off under reduced pressure to provide crude mesylate (1.75 g) as light-yellow oil. To a solution of 0.93 g (2.4 mM) of N-(piperidin-4-yl)-5-thia-1,8b-diazaacenaphthylene-4-carboxamide dihydrochloride and 1.7 ml (12.2 mM) of triethylamine in ethanol (10 ml) was added the above mesylate (1.75 g) at room temperature and the mixture was refluxed under nitrogen for 16 hours. This reaction mixture was diluted with water and extracted with ethyl acetate. The organic layer was washed with saturated aqueous solution of sodium chloride and dried over $MgSO_4$. After concentration, the crude product obtained was purified by column chromatography (methanol/-ethyl acetate 20–30%) to provide the title compound as red amorphous substance.

$^1$H-NMR (200 MHz, CDCl$_3$) δ: 0.11 (s, 6H), 1.04 (s, 9H), 1.25 (s, 3H), 1.68–2.22 (m, 8H), 2.05 (s, 6H), 2.09 (s,

3H), 2.24–2.90 (m, 6H), 3.03–3.22 (m, 2H), 3.79–4.02 (m, 2H), 5.79 (dd, J=1.8, 5.8 Hz), 5.97–6.09 (m, 1H), 6.57–6.69 (m, 2H), 6.73 (s, 1H), 7.06 (s, 1H).

IR (KBr): 3444, 2943, 1624, 1251, 1153, 1092, 837, 773 cm$^{-1}$.

2) Synthesis of N-[1-[2-(6-hydroxy-2,5,7,8-tetramethylchroman-2-yl)ethyl]piperidin-4-yl]-5-thia-1,8b-diazaacenaphthylene-4-carboxamide dihydrochloride To a solution of 1.17 g (1.78 mM) of N-[1-[2-(6-tert-butyldimethylsiloxy-2,5,7,8-tetramethylchroman-2-yl)ethyl]piperidin-4-yl]-5-thia-1,8b-diazaacenaphthylene-4-carboxamide in ethanol (5 ml) was added 5.0 ml (20 mM) of 4N—HCl/methanol and the mixture was stirred at room temperature for 90 hours. After the solvent was distilled off under reduced pressure, ethanol and diethyl ether were added and the resulting crystals were collected by filtration and rinsed with ethanol and diethyl ether to provide the title compound as orange-colored crystals.

Yield 867.3 mg (80%)

$^1$H-NMR (200 MHz, DMSO-d$_6$) δ: 1.19 (s, 3H), 1.62–2.13 (m, 8H), 2.00 (s, 3H), 2.02 (s, 3H), 2.06 (s, 3H), 2.43–2.65 (m, 2H), 2.80–3.59 (m, 6H), 3.71–4.08 (m, 1H), 6.62 (d, J=7.8 Hz, 1H), 6.98 (d, J=8.8 Hz, 1H), 7.22 (s, 1H), 7.29 (dd, J=7.6, 8.8 Hz, 2H), 7.65 (s, 1H), 8.72–8.91 (m, 1H), 10.37–10.79 (m, 1H).

IR (KBr): 3396, 1635, 1533, 1450, 1306, 1257, 1219 cm$^{-1}$.

Example 135

Synthesis of N-[1-(3-phenylpropan-1-yl)piperidin-4-yl-methyl]-3,4-dihydro-5-thia-1,8b-diazaacenaphthylene-4-carboxamide dihydrochloride 1) Synthesis of ethyl 3,4-dihydro-5-thia-1,8b-diazaacenaphthylene-4-carboxylate To a solution of 11.8 g (50 mM) of ethyl imidazo-[1,2-a]pyridine-5-thiaacetate in acetonitrile (250 ml) was added 13.9 g (75 mM) of N,N-dimethylmethyleneammonium iodide and the mixture was refluxed for 2 hours. After cooling to room temperature, the solvent was distilled off under reduced pressure and the residue was dissolved in dichloromethane. This solution was washed with saturated aqueous solution of sodium hydrogen carbonate and saturated aqueous solution of sodium chloride, dried over MgSO$_4$, and concentrated under reduced pressure. The residue was purified by column chromatography (hexane/ethyl acetate 10–20%) to provide the title compound as red-purple oil.

Yield 5.13 g (41%)

$^1$H-NMR (200 MHz, CDCl$_3$) δ: 1.19 (t, 3H, J=7.2 Hz), 3.63–3.80 (m, 2H), 4.05–4.22 (m, 3H), 6.78 (d, J=7.0 Hz, 1H), 7.09–7.17 (m, 1H), 7.48 (d, J=8.4 Hz, 1H), 7.53 (s, 1H).

2) Synthesis of N-[(1-tert-butoxycarbonyl-4-piperidyl)-methyl]-3,4-dihydro-5-thia-1,8b-diazaacenaphthylene-4-carboxamide To a solution of 5.13 g (20.7 mM) of ethyl 3,4-dihydro-5-thia-1,8b-diazaacenaphthylene-4-carboxylate in ethanol (20 ml) was added 12 ml (24 mM) of 2N-aqueous solution of sodium hydroxide at room temperature and the mixture was stirred for 1 hour. To this reaction mixture was added 4 ml (24 mM) of 6N-hydrochloric acid and the resulting crystals were collected by filtration. This crystal crop was rinsed with ethanol and diethyl ether to provide 3,4-dihydro-5-thia-1,8b-diazaacenaphthylene-4-carboxylic acid as light-brown crystals. This carboxylic acid was not purified but used as it was in the next reaction. To 2.2 ml (30.0 mM) of thionyl chloride was added 661 mg (3.0 mM) of the above 3,4-dihydro-5-thia-1,8b-diazaacenaphthylene-4-carboxylic acid and the mixture was heated at 60° C. for 1 hour. Then, the excess thionyl chloride was distilled off under reduced pressure and 10 ml of toluene was added to the residue. After thorough mixing, the solvent was distilled off under reduced pressure to provide 3,4-dihydro-5-thia-1,8b-diazaacenaphthylene-4-carboxylic acid chloride hydrochloride. To a solution of this acid chloride in 30 ml of THF was added 2.5 ml (40.0 mM) of triethylamine as well as 1286 mg (6.0 mM) of 1-(tert-butoxycarbonyl)-4-aminomethylpiperidine at 0° C. and the mixture was stirred at room temperature for 30 minutes. The reaction mixture was then poured in 50 ml of iced water and extracted with 100 ml of ethyl acetate. The organic layer was washed with 100 ml of saturated aqueous solution of sodium chloride and dried over MgSO$_4$ and the solvent was distilled off under reduced pressure. The residue was purified by silica gel column chromatography (eluent: ethyl acetate/ethanol=10/1) to provide 801 mg (yield 64.1%) of the title compound as brown amorphous substance.

$^1$H-NMR (200 MHz, CDCl$_3$) δ: 0.72–1.01 (m, 2H), 1.25–1.38 (m, 3H), 2.38–2.61 (m, 2H), 2.83–3.02 (m, 1H), 3.08–3.27 (m, 1H), 3.62 (dd, 1H, J=17.4 Hz, 7.0 Hz), 3.87–4.09 (m, 4H), 6.66 (t, 1H, NH, J=5.8 Hz), 6.77 (d, 1H, J=7.2 Hz), 7.11 (dd, 1H, J=9.2, 7.2 Hz), 7.45 (d, 1H, J=9.2 Hz), 7.51 (s, 1H).

IR (KBr): 1666, 1385, 1188 cm$^{-1}$.

3) Synthesis of N-(4-piperidyl)methyl-3,4-dihydro-5-thia-1,8b-diazaacenaphthylene-4-carboxamide dihydrochloride To a solution of 480 g (1.15 mM) of N-[(1-tert-butoxycarbonyl-4-piperidyl)methyl]-3,4-dihydro-5-thia-1,8b-diazaacenaphthylene-4-carboxamide in 20 ml of 2-propanol was added 0.47 ml (5.76 mM) of 12N-hydrochloric acid and the mixture was stirred at room temperature for 1 hours. This reaction mixture was concentrated under reduced pressure and the resulting crystals were collected by filtration and rinsed with a small amount of ether to provide 404 mg (90.2%) of the title compound as white crystals.

$^1$H-NMR (200 MHz, DMSO-d$_6$) δ: 1.18–1.53 (m, 2H), 1.58–1.85 (m, 3H), 2.64–2.88 (m, 2H), 3.12–3.36 (m, 4H), 3.63–3.75 (m, 2H), 4.65 (t, 1H, J=5.8 Hz), 7.51 (dd, 1H, J=6.4, 2.2 Hz), 7.77–7.92 (m, 2H), 8.18 (s, 1H), 9.04 (t, 1H, NH, J=5.4 Hz), 9.20 (br s, 2H, NH).

IR (KBr): 1649, 1554, 1504 cm$^{-1}$.

4) Synthesis of N-[1-(3-phenylpropan-1-yl)piperidin-4-ylmethyl]-3,4-dihydro-5-thia-1,8b-diazaacenaphthylene-4-carboxamide To a solution of 746.4 mg (1.91 mM) of N-(4-piperidyl)methyl-3,4-dihydro-5-thia-1,8b-diazaacenaphthylene-4-carboxamide dihydrochloride and 1.4 ml (10.0 mM) of triethylamine in ethanol (5 ml) was added 0.35 ml (2.30 mM) of 1-bromo-3-phenylpropane at room temperature and the mixture was refluxed under nitrogen for 64 hours. This reaction mixture was diluted with water and extracted with chloroform, and the organic layer was washed with saturated aqueous solution of sodium chloride and dried over MgSO$_4$. The residue was purified by column chromatography (methanol/ethyl acetate 20–30–50%) to provide the title compound as red amorphous substance.

Yield 583.9 mg (70%)

$^1$H-NMR (200 MHz, CDCl$_3$) δ: 1.06–1.38 (m, 4H), 1.70–1.92 (m, 3H), 1.96–2.25 (m, 2H), 2.33–2.41 (m,

2H), 2.56–2.64 (m, 2H), 2.79–3.00 (m, 3H), 3.08–3.26 (m, 1H), 3.57–3.72 (m, 1H), 3.97–4.10 (m, 2H), 6.53–6.69 (m, 1H), 6.78 (dd, J=7.0, 1.0 Hz, 1H), 7.03–7.34 (m, 6H), 7.45 (dd, J=9.2, 1.0 Hz, 1H), 7.53 (s, 1H).

IR (KBr): 3304, 2926, 1657, 1620, 1556, 1481, 1306, 1140 cm$^{-1}$.

5) Synthesis of N-[1-(3-phenylpropan-1-yl)piperidin-4-ylmethyl]-3,4-dihydro-5-thia-1,8b-diazaacenaphthylene-4-carboxamide dihydrochloride To a solution of 583.9 mg (1.34 mM) of N-[1-(3-phenylpropan-1-yl)piperidin-4-ylmethyl]-3,4-dihydro-5-thia-1,8b-diazaacenaphthylene-4-carboxamide in ethanol (5 ml) was added 10 ml (40 mM) of 4N-HCl/methanol and the mixture was stirred at room temperature for several minutes. After the solvent was distilled off under reduced pressure, 2-propanol was added and the resulting crystals were filtered off. The filtrate was concentrated to provide the title compound as light-brown amorphous substance.

Yield 542.5 mg (80%)

$^1$H-NMR (200 MHz, DMSO-d$_6$) δ: 1.35–1.86 (m, 3H), 1.94–2.20 (m, 2H), 2.44–3.23 (m, 10H), 3.32–4.00 (m, 4H), 4.51–4.68 (m, 1H), 7.10–7.41 (m, 5H), 7.43–7.59 (m, 1H), 7.72–7.92 (m, 2H), 8.16 (s, 1H), 8.87–9.08 (m, 1H), 10.53–10.82 (m, 1H).

IR (KBr): 3421, 3064, 2933, 2721, 1662, 1551, 1502, 1441, 1365, 1215 cm$^{-1}$.

Example 136

Synthesis of N-[trans-4-(4-phenylpiperidin-1-ylmethyl)-1-cyclohexylmethyl]-5-thia-1,8b-diazaacenaphthylene-4-carboxamide dihydrochloride 1) Synthesis of N-[trans-4-(4-phenylpiperidin-1-ylmethyl)-1-cyclohexylmethyl]-5-thia-1,8b-diazaacenaphthylene-4-carboxamide To a solution of 0.41 g (1.88 mM) of 5-thia-1,8b-diazaacenaphthylene-4-carboxylic acid and 0.37 g (3.21 mM) of N-hydroxysuccinimide in acetonitrile (5 ml) was added 0.62 g (3.23 mM) of N-ethyl-N'-3-(N,N-dimethylamino)propylcarbodiimide at room temperature, and the mixture was stirred for 1 hour. To this reaction mixture was added a suspension of 0.70 g (1.95 mM) of 1-(trans-4-aminomethyl-1-cyclohexylmethyl)-4-phenylpiperidine dihydrochloride and 1.0 ml (7.71 mM) of triethylamine in chloroform (10 ml) and the mixture was further stirred for 2 hours. The solvent was then distilled off under reduced pressure and the residue was diluted with water and a small amount of ethanol and extracted with ethyl acetate. The organic layer was washed with saturated aqueous solution of sodium chloride and dried over MgSO$_4$. After concentration, the crude product obtained was purified by column chromatography (methanol/ethyl acetate 30–50%) and recrystallization from ethyl acetate to provide the title compound as red-purple crystals.

Yield 576.9 mg (63%)

$^1$H-NMR (200 MHz, CDCl$_3$) δ: 0.78–1.03 (m, 4H), 1.62–2.03 (m, 12H), 2.20 (d, J=7.0 Hz, 2H), 2.39–2.59 (m, 1H), 2.94–3.08 (m, 2H), 3.11–3.23 (m, 2H), 5.72–5.84 (m, 1H), 5.79 (dd, J=6.2, 1.6 Hz, 1H), 6.58–6.74 (m, 3H), 7.06 (s, 1H), 7.12–7.36 (m, 5H).

IR (KBr): 3336, 2922, 1618, 1533, 1277, 1161 cm$^{-1}$.

2) Synthesis of N-[trans-4-(4-phenylpiperidin-1-ylmethyl)-1-cyclohexylmethyl]-5-thia-1,8b-diazaacenaphthylene-4-carboxamide dihydrochloride To a solution of 549.7 mg (1.13 mM) of N-[trans-4-(4-phenylpiperidin-1-ylmethyl)-1-cyclohexylmethyl]-5-thia-1, 8b-diazaacenaphthylene-4-carboxamide in ethanol (5 ml) was added 1.0 ml (12.0 mM) of 12N-hydrochloric acid and the mixture was stirred at room temperature for several minutes. After the reaction mixture was concentrated under reduced pressure, diethyl ether was added to the residue and the resulting crystals were collected by filtration and rinsed with ethanol and diethyl ether to provide the title compound as orange-colored crystals.

Yield 541.1 mg (86%)

$^1$H-NMR (200 MHz, DMSO-d$_6$) δ: 0.80–1.12 (m, 4H), 1.29–2.09 (m, 8H), 2.14–2.41 (m, 2H), 2.65–3.17 (m, 7H), 3.44–3.62 (m, 2H), 6.63 (d, J=6.8 Hz, 1H), 6.99 (d, J=8.2 Hz, 1H), 7.19 (s, 1H), 7.21–7.42 (m, 6H), 7.67 (s, 1H), 8.81 (t, J=5.6 Hz, 1H), 10.14–10.40 (m, 1H).

IR (KBr): 3417, 2924, 1635, 1564, 1535, 1500, 1441, 1292 cm$^{-1}$.

Elemental analysis for $C_{29}H_{36}N_4OSCl_2 \cdot 1.5H_2O$. Calcd.: C, 59.38; H, 6.70; N, 9.55 Found: C, 59.10; H, 6.65; N, 9.55

Example 137

Synthesis of N-[1-(4-phenylbutan-1-yl)piperidin-4-yl]-5-thia-1,8b-diazaacenaphthylene-4-carboxamide dihydro-chloride 1) Synthesis of N-[1-(4-phenylbutan-1-yl)piperidin-4-yl]-5-thia-1,8b-diazaacenaphthylene-4-carboxamide To a solution of 72.5 mg (1.94 mM) of N-(piperidin-4-yl)-5-thia-1,8b-diazaacenaphthylene-4-carboxamide dihydrochloride and 1.4 ml (10.0 mM) of triethylamine in ethanol (7 ml) was added 0.61 g (2.33 mM) of 1-iodo-4-phenylbutane at room temperature and the mixture was refluxed under nitrogen for 6 hours. After cooling to room temperature, the reaction mixture was diluted with water and extracted with ethyl acetate. The organic layer was washed with saturated aqueous solution of sodium chloride, dried over MgSO$_4$, and concentrated. The resulting crude product was purified by column chromatography (methanol/ethyl acetate 30%) and recrystallization from ethyl acetate to provide the title compound as light-purple crystals.

Yield 495.2 mg (59%)

m.p. 183–185° C.

$^1$H-NMR (200 MHz, CDCl$_3$) δ: 1.47–1.68 (6H, m), 1.86–2.03 (2H, m), 2.12–2.29 (2H, m), 2.39–2.51 (2H, m), 2.57–2.72 (2H, m), 2.89–3.05 (2H, m), 3.74–3.97 (1H, m), 5.78 (1H, dd, J=6.2, 1.8 Hz), 5.81–5.92 (1H, m), 6.58–6.70 (3H, m), 7.05 (1H, s), 7.11–7.35 (5H, m).

IR (KBr): 3298, 2941, 1612, 1535, 1277, 1159 cm$^{-1}$.

2) Synthesis of N-[1-(4-phenylbutan-1-yl)piperidin-4-yl]-5-thia-1,8b-diazaacenaphthylene-4-carboxamide dihydro-chloride To a solution of 437.4 mg (1.01 mM) of N-[1-(4-phenylbutan-1-yl)piperidin-4-yl]-5-thia-1,8b-diazaacenaphthylene-4-carboxamide in ethanol (10 ml) was added 0.5 ml (6 mM) of 12N-hydrochloric acid and the mixture was stirred at room temperature for 16 hours. After this reaction mixture was concentrated, a small amount of ethanol was added to the residue and the crystals were collected by filtration and rinsed with ethanol and diethyl ether to provide the title compound as orange-colored crystals.

Yield 431.1 mg (84%)

m.p. 232–237° C. (dec.)

$^1$H-NMR (200 MHz, DMSO-$d_6$) δ: 1.48–2.02 (8H, m), 2.54–2.67 (2H, m), 2.77–3.15 (4H, m), 3.24–3.53 (2H, m), 3.70–4.08 (1H, m), 6.54 (1H, d, J=7.4 Hz), 6.93 (1H, d, J=9.2 Hz), 7.10–7.36 (7H, m), 7.58 (1H, s), 8.64–8.71 (0.2H, m), 8.78 (0.8H, d, J=7.2 Hz), 10.06–10.25 (0.2H, m), 10.38–10.60 (0.8H, m).

IR (KBr): 3415, 2939, 1632, 1566, 1535, 1500, 1304, 1213 cm$^{-1}$.

Elemental analysis for $C_{25}H_{30}N_4OSCl_2 \cdot 2.0H_2O$. Calcd.: C, 55.45; H, 6.33; N, 10.35 Found: C, 55.46; H, 6.21; N, 10.56

Example 138

Synthesis of N-[1-[3-(4-fluorophenyl)propan-1-yl]-piperidin-4-yl]-5-thia-1,8b-diazaacenaphthylene-4-carboxamide dihydrochloride 1) Synthesis of N-[1-[3-(4-fluorophenyl)propan-1-yl]-piperidin-4-yl]-5-thia-1,8b-diazaacenaphthylene-4-carboxamide Under nitrogen gas, 0.47 ml (6.07 mM) of methanesulfonyl chloride was added to a solution of 0.62 g (4.02 mM) of 3-(4-fluorophenyl)propanol and 1.1 ml (7.89 mM) of triethylamine in diethyl ether (8 ml) at 0° C. and the mixture was stirred at the prevailing temperature for 1 hour. The reaction was stopped by adding saturated aqueous solution of sodium hydrogen carbonate and the reaction mixture was extracted with diethyl ether. The organic layer was washed with saturated aqueous solution of sodium chloride and dried over $MgSO_4$. The solvent was then distilled off under reduced pressure to recover the crude mesylate. This crude product was not purified but used as it was in the next reaction. To a solution of 0.75 g (2.00 mM) of N-(piperidin-4-yl)-5-thia-1,8b-diazaacenaphthylene-4-carboxamide dihydrochloride and 1.4 ml (10.0 mM) of triethylamine in ethanol (8 ml) was added 0.94 g (<4.02 mM) of the above crude mesylate at room temperature and the mixture was refluxed under nitrogen for 16 hours. After cooling, the reaction mixture was diluted with water and extracted with ethyl acetate. The organic layer was washed with saturated aqueous solution of sodium chloride, dried over $MgSO_4$, and concentrated. The crude product thus obtained was purified by column chromatography (methanol/ethyl acetate 20–30–40%) and recrystallization from ethyl acetate-ethanol to provide the title compound as red-purple crystals.

Yield 405.2 mg (46%)

m.p. 117–119° C.

$^1$H-NMR (200 MHz, CDCl$_3$) δ: 1.35–1.65 (2H, m), 1.70–2.21 (6H, m), 2.31–2.42 (2H, m), 2.60 (2H, t, J=7.6 Hz), 2.72–2.96 (2H, m), 3.71–3.92 (1H, m), 5.66 (1H, br d, J=8.8 Hz), 5.78 (1H, dd, J=5.8, 1.6 Hz), 6.58–6.71 (3H, m), 6.91–7.16 (5H, m).

IR(KBr): 3284, 2941, 1614, 1535, 1508, 1281, 1160 cm$^{-1}$.

2) Synthesis of N-[1-[3-(4-fluorophenyl)propan-1-yl]-piperidin-4-yl)-5-thia-1,8b-diazaacenaphthylene-4-carboxamide dihydrochloride To a solution of 378.4 mg (0.86 mM) of N-[1-[(4-fluorophenyl)butan-1-yl]piperidin-4-yl]-5-thia-1,8b-diazaacenaphthylene-4-carboxamide in 5 ml of ethanol was added 0.5 ml (6.0 mM) of 12N-hydrochloric acid at room temperature and the mixture was stirred for several minutes. After the solvent was distilled off under reduced pressure, 2-propanol and ethanol were added to the residue. After concentration, diethyl ether was added and the resulting crystals were collected by filtration and rinsed with 2-propanol and diethyl ether to provide the objective compound as orange-colored crystals. This crystal crop was dissolved in ethanol and, after concentration, diethyl ether was added. The resulting crystals were collected by filtration and rinsed with ethanol and diethyl ether to provide the title compound as orange-colored crystals.

Yield 433.5 mg (65%)

m.p. 164–174° C. (dec.)

$^1$H-NMR (200 MHz, DMSO-$d_6$) δ: 1.75–2.13 (6H, m), 2.54–2.70 (2H, m), 2.82–3.10 (4H, m), 3.23–3.57 (2H, m), 3.71–4.06 (1H, m), 6.58 (1H, d, J=7.0 Hz), 6.96 (1H, d, J=9.2 Hz), 7.05–7.36 (6H, m), 7.62 (1H, s), 8.68–8.78 (0.14H, m), 8.81 (0.86H, d, J=7.8 Hz), 10.45–10.62 (0.14H, m), 10.68–10.94 (0.86H, m).

IR (KBr): 3412, 1633, 1506, 1217 cm$^{-1}$.

Elemental analysis for $C_{24}H_{27}N_4OSCl_2F \cdot 1.0H_2O$. Calcd.: C, 54.65; H, 5.54; N, 10.62 Found: C, 54.29; H, 5.83; N, 10.37

Example 139

Synthesis of N-[4-(4-phenylpiperidin-1-ylmethyl) benzyl]-5-thia-1,8b-diazaacenaphthylene-4-carboxamide dihydrochloride 1) Synthesis of N-[4-(4-phenylpiperidin-1-ylmethyl)-benzyl]-5-thia-1,8b-diazaacenaphthylene-4-carboxamide To a suspension of 1.0 g (4.58 mM) of 5-thia-1,8b-diazaacenaphthylene-4-carboxylic acid and 0.90 g (7.82 mM) of N-hydroxysuccinimide in acetonitrile (10 ml) was added 1.51 g (7.88 mM) of N-ethyl-N'-3-(N,N-dimethylamino)propylcarbodiimide hydrochloride at room temperature, and the mixture was stirred for 1 hour. To this reaction mixture was added a solution of 1.67 g (4.73 mM) of 1-[4-(aminomethyl)benzyl]-4-phenylpiperidine dihydrochloride, 1.44 g (9.46 mM) of DBU, and 0.55 ml (3.95 mM) of triethylamine in acetonitrile (20 ml), and the mixture was further stirred for 4 hours. The solvent was then distilled off under reduced pressure and the residue was diluted with water and extracted with ethyl acetate (a small amount of ethanol was additionally used). The organic layer was washed with saturated aqueous solution of sodium chloride and dried over $MgSO_4$. This crude product was purified by column chromatography (methanol/ethyl acetate 20–30%) to provide the title compound as red amorphous substance.

Yield 1.59 g (72%)

$^1$H-NMR (200 MHz, CDCl$_3$) δ: 1.68–1.89 (4H, m), 2.03–2.21 (2H, m), 2.39–2.60 (1H, m), 2.93–3.10 (2H, m), 3.56 (2H, s), 4.47 (2H, d, J=6.0 Hz), 5.77 (1H, dd, J=6.2, 1.8 Hz), 5.95–6.08 (1H, m), 6.62–6.70 (3H, m), 7.03 (1H, s), 7.17–7.21 (9H, m).

IR (KBr): 3295, 1615, 1543, 1481, 1281, 1155 cm$^{-1}$.

2) Synthesis of N-[4-(4-phenylpiperidin-1-ylmethyl)-benzyl]-5-thia-1,8b-diazaacenaphthylene-4-carboxamide dihydrochloride To a solution of 1.59 g (3.31 mM) of N-[4-(4-phenylpiperidin-1-ylmethyl)benzyl]-5-thia-1,8b-diazaacenaphthylene-4-carboxamide in ethanol was added 1 ml (12 mM) of 12N-hydrochloric acid at room temperature, and the mixture was stirred for several minutes. This reaction mixture was concentrated and, after addition of ethanol and diethyl ether, the crystal crop was harvested by filtration and rinsed with ethanol and diethyl ether to provide the title compound as orange-colored crystals.

Yield 1.26 g (69%)

m.p. 269–275° C. (dec.)

1H-NMR (200 MHz, DMSO-d$_6$) δ: 1.83–2.00 (2H, m), 2.02–2.29 (2H, m), 2.69–2.87 (1H, m), 2.90–3.14 (2H, m), 3.30–3.46 (2H, m), 4.29 (2H, d, J=4.8 Hz), 4.37 (2H, d, J=6.0 Hz), 6.59 (1H, d, J=7.4 Hz), 6.96 (1H, d, J=8.8 Hz), 7.13–7.22 (9H, m), 7.55–7.69 (3H, m), 9.35–9.47 (1H, m), 11.00–11.22 (1H, m).

IR (KBr): 3391, 1642, 15001, 1298, 770 cm$^{-1}$.

Elemental analysis for $C_{29}H_{30}N_4OSCl_2 \cdot 1.0H_2O$. Calcd.: C, 60.94; H, 5.64; N, 9.80 Found: C, 60.84; H, 5.73; N, 9.71

Example 140

Synthesis of N-[4-(4-benzylpiperidin-1-ylmethyl)benzyl]-5-thia-1,8b-diazaacenaphthylene-4-carboxamide dihydrochloride 1) Synthesis of N-[4-(4-benzylpiperidin-1-ylmethyl)benzyl]-5-thia-1,8b-diazaacenaphthylene-4-carboxamide To a suspension of 1.0 g (4.58 mM) of 5-thia-1,8b-diazaacenaphthylene-4-carboxylic acid hydrochloride and 0.90 g (7.82 mM) of N-hydroxysuccinimide in acetonitrile (10 ml) was added 1.51 g (7.88 mM) of N-ethyl-N'-3-(N,N-dimethylamino)propylcarbodiimide hydrochloride at room temperature, and the mixture was stirred for 2 hours. To this reaction mixture was added a solution of 1.88 g (5.12 mM) of 1-[4-(aminomethyl)benzyl]-4-benzylpiperidine dihydrochloride and 0.55 ml (3.95 mM) of triethylamine in acetonitrile (20 ml) and the mixture was further stirred for 4 hours. The solvent was then distilled off under reduced pressure and the residue was diluted with water and extracted with ethyl acetate (a small amount of ethanol was additionally used). The organic layer was washed with saturated aqueous solution of sodium chloride and dried over MgSO$_4$. The resulting crude product was purified by column chromatography (methanol/ethyl acetate 20%) to provide the title compound as red amorphous substance.

Yield 1.73 g (77%)

1H-NMR (200 MHz, CDCl$_3$) δ: 1.20–2.03 (7H, m), 2.53 (2H, d, J=6.4 Hz), 2.79–2.93 (2H, m), 3.49 (2H, s), 4.46 (2H, d, J=5.4 Hz), 5.77 (1H, dd, J=6.2, 1.8 Hz), 5.93–6.08 (1H, m), 6.56–6.71 (3H, m), 7.03 (1H, s), 7.07–7.37 (9H, m).

IR (KBr): 3204, 1643, 1615, 1537, 1481, 1281, 1155, 772, 700 cm$^{-1}$.

2) Synthesis of N-[4-(4-benzylpiperidin-1-ylmethyl)benzyl]-5-thia-1,8b-diazaacenaphthylene-4-carboxamide dihydrochloride To a solution of 1.73 g (3.50 mM) of N-[4-(4-benzylpiperidin-1-ylmethyl)benzyl]-5-thia-1,8b-diazaacenaphthylene-4-carboxamide in ethanol (12 ml) was added 1 ml (12 mM) of 12N-hydrochloric acid at room temperature, and the mixture was stirred for several minutes (crystals separated out). This reaction mixture was concentrated under reduced pressure and ethanol and diethyl ether were added to the residue. The crystal crop was then harvested by filtration and rinsed with ethanol and diethyl ether to provide the title compound as orange-colored crystals.

Yield 1.48 g (75%)

m.p. 164–172° C.

1H-NMR (200 MHz, DMSO-d$_6$) δ: 1.42–1.87 (5H, m), 2.68–2.95 (3H, m), 3.02–3.17 (1H, m), 3.18–3.33 (2H, m), 4.12–4.25 (2H, m), 4.35 (2H, d, J=4.6 Hz), 6.57 (1H, d, J=7.4 Hz), 6.96 (1H, d, J=9.2 Hz), 7.11–7.39 (9H, m), 7.50–7.65 (3H, m), 9.31–9.43 (1H, m), 10.49–10.79 (1H, m).

IR (KBr): 3217, 1634, 1566, 1537, 1505, 1298, 1217, 774, 700 cm$^{-1}$.

Elemental analysis for $C_{30}H_{32}N_4OSCl_2 \cdot 0.5C_2OH \cdot 1.5 \cdot H_2O$. Calcd.: C, 60.28; H, 6.20; N, 9.07 Found: C, 60.27; H, 5.89; N, 9.08

Example 141

Synthesis of N-[1-(3-phenylpropan-1-yl)piperidin-4-yl]-5-thia-1,8b-diazaacenaphthylene-4-carboxamide 1) Synthesis of 5-thia-1,8b-diazaacenaphthylene-4-carboxylic acid To a solution of 120.02 g (0.7991 mol) of imidazo-[1,2-a]pyridine-5-thiol and 134 ml (0.959 mol) of triethylamine in 500 ml of ethanol was added 88.6 ml (0.799 mol) of ethyl bromoacetate dropwise at room temperature, and the mixture was stirred at the same temperature for 2 hours. The solvent was then distilled off under reduced pressure and ethyl acetate was added to the residue. The resulting precipitate (for the most part, triethylamine hydrochloride) was filtered off and washed with ethyl acetate. The filtrate and washes were pooled and the solvent was distilled off under reduced pressure to provide ethyl (imidazo[1,2-a]pyridin-5-ylthio)acetate as crude product. This crude product was not purified but used as it was in the next reaction.

Brown liquid. Yield 199.7 g

To a solution of 199.7 g of crude ethyl imidazo[1,2-a]pyridin-5-ylthioacetate and 224 g (1.60 mol) of hexamethylenetetramine in 500 ml of acetic acid was stirred at 90° C. for 1 day. This reaction mixture was poured in water and extracted with 2 portions of ethyl acetate. The organic layers were pooled, washed with water, and dried over MgSO$_4$ and the solvent was distilled off under reduced pressure. The solid residue was rinsed with diethyl ether to provide crude ethyl 5-thia-1,8b-diazaacenaphthylene-4-carboxylate. This crude product was not purified but used as it was in the next reaction.

Blackish purple solid. Yield 193.69 g

To a solution of 193.69 g of the above ethyl 5-thia-1,8b-diazaacenaphthylene-4-carboxylate in 1 l of ethanol was added a solution of 62.9 g (1.57 mol) of sodium hydroxide in 500 ml of water, and the mixture was stirred at room temperature for 0.5 hour. To this reaction mixture was added about 130 ml of concentrated hydrochloric acid with stirring to bring the pH into the range of 4–5 and the resulting precipitate was recovered by filtration and rinsed with ethanol, acetone, and diethyl ether in that order to provide the title compound.

Orange-colored solid. Yield 96.3 g (55%)

1H-NMR (DMSO-d$_6$, 200 MHz) δ: 5.97 (1H, dd, J=6.6, 1.2 Hz), 6.57–6.73 (2H, m), 6.88 (1H, s), 7.12 (1H, s).

IR (KBr): 3413, 1632, 1338 cm$^{-1}$.

2) Synthesis of N-[1-(3-phenylpropan-1-yl)piperidin-4-yl]-5-thia-1,8b-diazaacenaphthylene-4-carboxamide While 39.11 g (0.1792 mol) of 5-thia-1,8b-diazaacenaphthylene-4-carboxylic acid and 21.7 g (0.188 mol) of N-hydroxysuccinimide were stirred together in 500 ml of acetonitrile, 36.1 g (0.188 mol) of 1-ethyl-3-(3-dimethylaminopropyl)carbodiimide hydrochloride was added, and the mixture was stirred at room temperature overnight. To this reaction mixture was added 30.0 ml (0.215 mol) of triethylamine and, then, a solution of 39.1 g (0.179 mol) of 4-amino-1-(3-phenylpropan-1-yl)piperidine in acetonitrile (100 ml)-chloroform (50 ml) was added. The mixture was stirred at room temperature for 1 hour and the resulting orange-colored precipitate was recovered by filtration and rinsed with acetonitrile (yield 55.75 g). This crude product was purified by silica gel column chromatography (ethyl acetate to ethyl acetate/methanol : 4/1~1/1) and recrystallization from chloroform-ethanol to provide the title compound.

Red crystals. Yield 49.5 g (66%)

m.p. 189.5–191.0° C.

$^1$H-NMR (CDCl$_3$, 200 MHz) δ: 1.350–1.568 (2H, m), 1.760–2.134 (6H, m), 2.359 (2H, t, J=7.7 Hz), 2.623 (2H, t, J=7.7 Hz), 2.804–2.865 (2H, m), 3.720–3.920 (1H, m), 5.584 (1H, d, J=8.4 Hz), 6.787 (1H, dd, J=1.6, 6.0 Hz), 6.578–6.702 (3H, m), 7.045 (1H, s), 7.156–7.325 (5H, m).

IR (KBr): 2995, 1622, 1545, 1479, 1282 cm$^{-1}$.

Elemental analysis for C$_{24}$H$_{26}$N$_4$OS. Calcd.: C, 68.87; H, 6.26; N, 13.39 Found: C, 68.83; H, 6.39; N, 13.39

Example 142

Synthesis of (E)-1-[1-(3-phenylpropan-1-yl)piperidin-4-yl]-3-(5-thia-1,8b-diazaacenaphthylen-4-yl)propen-1-one dihydrochloride To a solution of 2.541 g (12.441 mM) of 5-thia-1,8b-diazaacenaphthylene-4-methanol in 30 ml of N,N-dimethylformamide was added 6 g of activated manganese dioxide (Aldrich), and the mixture was stirred at room temperature overnight. This reaction mixture was filtered and the filter cake was washed with N,N-dimethylformamide. The filtrate and washes were combined and the solvent was distilled off under reduced pressure. The crude 5-thia-1,8b-diazaacenaphthylene-4-carbaldehyde thus obtained was not purified but used as it was in the next reaction.

To a solution of 5.30 g (14.9 mM) of tert-butyl 4-[(dimethoxyphosphoryl)acetyl]piperidine-1-carboxylate in 50 ml of toluene was added 0.55 g (13.7 mM) of a 60% suspension of sodium hydride in liquid paraffin at room temperature, and the mixture was stirred at the prevailing temperature for 2.5 hours. To this reaction mixture was added a solution of the above crude 5-thia-1,8b-diazaacenaphthylene-4-carbaldehyde in 50 ml of N,N-dimethylformamide at room temperature, and the mixture was stirred at the prevailing temperature for 2 hours. This reaction mixture was poured in water and extracted with 3 portions of ethyl acetate. The organic layers were pooled and dried over MgSO$_4$ and the solvent was distilled off under reduced pressure. The resulting crude (E)-1-[1-(tert-butoxycarbonyl)piperidin-4-yl]-3-(5-thia-1,8b-diazaacenaphthylen-4-yl)propen-1-one was not purified but used as it was in the next reaction.

To the above crude (E)-1-(1-(tert-butoxycarbonyl)-piperidin-4-yl]-3-(5-thia-1,8b-diazaacenaphthylen-4-yl) propen-1-one was added 5 ml of concentrated hydrochloric acid, and the mixture was stirred at room temperature for 10 minutes. To this reaction mixture was added ethanol, and the resulting precipitate was recovered by filtration and rinsed with ethanol and diethyl ether to provide the title compound.

Orange-colored solid. Yield 2.596 g (54%)

$^1$H-NMR (CD$_3$OD-DMSO-d$_6$, 200 MHz) δ: 1.672–1.881 (2H, m), 2.050–2.123 (2H, m), 3.017–3.158 (3H, m), 3.422 (2H, t d, J=4.0, 13.2 Hz), 6.381 (1H, d, J=15.8 Hz), 6.787 (1H, d, J=7.4 Hz), 6.876 (1H, s), 7.133 (1H, d, J=8.8 Hz), 7.354 (1H, d, J=15.8 Hz), 7.494 (1H, dd, J=7.8, 9.2 Hz), 7.594 (1H, s).

IR (Nujol): 3431, 2686, 1680, 1635, 1587, 1215, 1027, 785 cm$^{-1}$.

2) Synthesis of (E)-1-[1-(3-phenylpropan-1-yl)piperidin-4-yl]-3-(5-thia-1,8b-diazaacenaphthylen-4-yl)propen-1-one A solution of 0.675 g (1.756 mM) of (E)-1-(piperidin-4-yl)-3-(5-thia-1,8b-diazaacenaphthylen-4-yl)propen-1-one dihydrochloride, 0.52 g (2.63 mM) of 1-bromo-3-phenylpropane, and 0.86 ml (6.15 mM) of triethylamine in 30 ml of acetonitrile, and the mixture was refluxed for 1 day. This reaction mixture was poured in aqueous solution of sodium hydrogen carbonate and extracted with 3 portions of ethyl acetate. The organic layers were pooled and dried over MgSO$_4$ and the solvent was distilled off under reduced pressure. The residue was purified by silica gel column chromatography (ethyl acetate~ethyl acetate/methanol: 4/1) to provide the title compound.

Deep-purple liquid. Yield 0.159 g (21%)

$^1$H-NMR (CDCl$_3$, 200 MHz) δ: 1.619–2.110 (8H, m), 2.339–2.526 (3H, m), 2.634 (2H, t, J=7.7 Hz), 2.962 (2H, t d, J=3.2, 11.3 Hz), 5.894 (1H, dd, J=1.8, 6.4 Hz), 6.050 (1H, d, J=15.0 Hz), 6.345 (1H, s), 6.651–6.786 (2H, m), 7.028–7.325 (7H, m).

IR (neat): 2941, 1676, 1564, 1498, 1340, 1261, 1144, 1066, 773, 750, 700 cm$^{-1}$.

3) Synthesis of (E)-1-[1-(3-phenylpropan-1-yl)piperidin-4-yl]-3-(5-thia-1,8b-diazaacenaphthylen-4-yl)propen-1-one dihydrochloride In 2 ml of methanol was dissolved 0.159 g of (E)-1-[1-(3-phenylpropan-1-yl)piperidin-4-yl]-3-(5-thia-1,8b-diazaacenaphthylen-4-yl)propen-1-one, followed by addition of a stoichiometric excess of methanolic hydrochloric acid, and the mixture was stirred for 10 minutes. This reaction mixture was concentrated and crystallized from ethanol-diethyl ether to provide the title compound.

Orange-colored solid. Yield 0.151 g $^1$H-NMR (CD$_3$OD, 200 MHz) δ: 1.722–1.921 (2H, m), 2.008–2.171 (4H, m), 2.726 (2H, t, J=7.5 Hz), 3.006–3.178 (5H, m), 3.449 (0.4H, br d, J=12.4 Hz), 3.648 (1.6H, br d, J=11.4 Hz), 6.367 (0.8H, d, J=15.4 Hz), 6.420 (0.2H, d, J=15.8 Hz), 6.794 (1H, d, J=7.4 Hz), 6.883 (1H, s), 7.134 (1H, d, J=9.0 Hz), 7.199–7.418 (6H, m), 7.499 (1H, dd, J=7.6, 9.2 Hz), 7.592 (1H, s).

IR (Nujol): 2457, 1678, 1635, 1581, 1209, 1126, 1082, 972, 783, 754, 725 cm$^{-1}$.

Elemental analysis for C$_{26}$H$_{29}$Cl$_2$N$_3$OS·1.28H$_2$O. Calcd.: C, 59.42; H, 6.05; N, 8.00 Found: C, 59.05; H, 5.65; N, 7.93

Example 143

Synthesis of (E)-5-[1-(3-phenylpropan-1-yl) piperidin-4-yl]-1-(5-thia-1,8b-diazaacenaphthylen-4-yl)-1-penten-3-one dihydrochloride 1) Synthesis of (E)-5-(piperidin-4-yl)-1-(5-thia-1,8b-diazaacenaphthylen-4-yl)-1-penten-3-one dihydrochloride To a solution of 2.234 g (10.938 mM) of 5-thia-1,8b-diazaacenaphthylene-4-methanol in 25 ml of N,N-dimethylformamide was added 6 g of active manganese dioxide, and the mixture was stirred at room temperature overnight. This reaction mixture was filtered and the filter cake was washed with N,N-dimethylformamide. The filtrate and washes were pooled and concentrated to remove the solvent. The resulting crude 5-thia-1,8b-diazaacenaphthylene-4-carbaldehyde was not purified but used as it was in the next reaction.

To a solution of 4.77 g (13.1 mM) of tert-butyl 4-[4-(dimethoxyphosphoryl)-3-oxobutyl]piperidine-1-carboxylate in 50 ml of toluene was added 0.48 g (12.0 mM) of a 60% suspension of sodium hydride in liquid paraffin at room temperature, and the mixture was stirred at the prevailing temperature for 2 hours. This reaction mixture was added to a solution of the above crude 5-thia-1,8b-diazaacenaphthylene-4-carbaldehyde in N,N-dimethylformamide (30 ml)-toluene (50 ml) with ice-cooling and the mixture was stirred at the prevailing temperature for 3 hours. This reaction mixture was poured in water and extracted with 3 portions of ethyl acetate. The organic layers were pooled and dried over $MgSO_4$ and the solvent was distilled off under reduced pressure. The residue was purified by silica gel column chromatography (ethyl acetate to ethyl acetate/methanol : 9/1) to provide crude (E)-5-[1-(tert-butoxycarbonyl)piperidin-4-yl]-1-(5-thia-1,8b-diazaacenaphthylen-4-yl)-1-penten-3-one. This crude product was not purified but used as it was in the next reaction.

To the above crude (E)-5-[1-(tert-butoxycarbonyl)-piperidin-4-yl]-1-(5-thia-1,8b-diazaacenaphthylen-4-yl)-1-penten-3-one was added 5 ml of concentrated hydrochloric acid and the mixture was stirred at room temperature for 15 minutes. To this reaction mixture was added ethanol, followed by stirring, and the resulting precipitate was recovered by filtration and rinsed serially with ethanol and diethyl ether to provide the title compound.

Orange-colored solid. Yield 0.673 g (15%)

$^1$H-NMR (CD$_3$OD, 200 MHz) δ: 1.294–1.479 (2H, m), 1.583–1.646 (3H, m), 1.967 (2H, d, J=13.6 Hz), 2.756 (2H, t, J=7.1 Hz), 2.961 (2H, t, J=13.1 Hz), 3.381 (2H, d, J=12.6 Hz), 6.270 (1H, d, J=15.8 Hz), 6.803 (1H, d, J=7.4 Hz), 6.848 (1H, s), 7.138 (1H, d, J=9.2 Hz), 7.296 (1H, d, J=15.8 Hz), 7.507 (1H, dd, J=7.6, 9.0 Hz), 7.588 (1H s).

IR (Nujol): 3413, 2717, 1680, 1635, 1579, 1211, 1074, 972, 792 cm$^{-1}$.

2) Synthesis of (E)-5-[1-(3-phenylpropan-1-yl)piperidin-4-yl]-1-(5-thia-1,8b-diazaacenaphthylen-4-yl)-1-penten-3-one A solution of 0.362 g (0.878 mM) of (E)-5-(piperidin-4-yl]-1-(5-thia-1,8b-diazaacenaphthylen-4-yl)-1-penten-3-one dihydrochloride, 0.26 g (1.32 mM) of 1-bromo-3-phenylpropane, and 0.43 ml (3.07 mM) of triethylamine in 30 ml of ethanol was refluxed for 1 day. The reaction mixture was then poured in aqueous solution of sodium hydrogen carbonate and extracted with 3 portions of ethyl acetate. The organic layers were pooled and dried over $MgSO_4$ and the solvent was distilled off under reduced pressure. The residue was purified by silica gel column chromatography (ethyl acetate to ethyl acetate/methanol : 9/1) to provide the title compound.

Dark-purple liquid. Yield 0.281 g (70%)

$^1$H-NMR (CDCl$_3$, 200 MHz) δ: 1.158–1.366 (2H, m), 1.524–1.987 (9H, m), 2.345 (2H, t, J=7.7 Hz), 2.561 (2H, t, J=7.7 Hz), 2.617 (2H, t, J=7.7 Hz), 2.913 (2H, d, J=11.0 Hz), 5.898 (1H, dd, J=1.8, 6.2 Hz), 5.948 (1H, d, J=15.4 Hz), 6.334 (1H, s), 6.649–6.785 (2H, m), 7.003 (1H, d, J=15.4 Hz), 7.107 (1H, s), 7.127–7.319 (5H, m).

IR (neat): 2923, 1570, 1500, 1342, 1261, 1144, 1076, 964, 773, 733, 700 cm$^{-1}$.

3) Synthesis of (E)-5-[1-(3-phenylpropan-1-yl)piperidin-4-yl]-1-(5-thia-1,8b-diazaacenaphthylen-4-yl)-1-penten-3-one dihydrochloride In 2 ml of methanol was dissolved 0.281 g (E)-5-[1-(3-phenylpropan-1-yl)piperidin-4-yl]-1-(5-thia-1,8b-diazaacenaphthylen-4-yl)-1-penten-3-one, followed by addition of a stoichiometric excess of methanolic hydrochloric acid, and the mixture was stirred for 10 minutes. This reaction mixture was concentrated and crystallized from ethanol-diethyl ether to provide the title compound.

Orange-colored solid. Yield 0.309 g $^1$H-NMR (CD$_3$OD, 200 MHz) δ: 1.403–1.733 (5H, m), 1.952–2.148 (4H, m), 2.672–2.780 (4H, m), 2.910 (2H, t, J=12.1 Hz), 3.041–3.125 (2H, m), 3.555 (2H, d, J=13.2 Hz), 6.254 (1H, d, J=16.2 Hz), 6.791 (1H, d, J=7.6 Hz), 6.841 (1H, s), 7.130 (1H, d, J=9.2 Hz), 7.171–7.336 (6H, m), 7.496 (1H, dd, J=7.5, 8.9 Hz), 7.579 (1H, s).

IR (Nujol): 3408, 3165, 2679, 1668, 1641, 1184, 972, 762, 723 cm$^{-1}$.

Elemental analysis for $C_{28}H_{33}Cl_2N_3OS \cdot 1.0H_2O$. Calcd.: C, 61.31; H, 6.43; N, 7.66 Found: C, 61.01; H, 6.53; N, 7.58

Example 144

Synthesis of (E)-4-[2-[1-(3-phenylpropan-1-yl) piperidin-4-ylmethanesulfonyl]vinyl]-5-thia-1,8b-diazaacenaphthylene dihydrochloride 1) Synthesis of (E)-4-[2-(piperidin-4-ylmethanesulfonyl) vinyl]-5-thia-1,8b-diazaacenaphthylene dihydrochloride To a solution of 0.904 g (4.426 mM) of 5-thia-1,8b-diazaacenaphthylene-4-methanol in 30 ml of N,N-dimethylformamide was added 2 g of activated manganese dioxide (Aldrich), and the mixture was stirred at room temperature for 4 hours. This reaction mixture was filtered and the filter cake was washed with N,N-dimethylformamide. The filtrate and washes were pooled and the solvent was distilled off under reduced pressure. The resulting crude 5-thia-1,8b-diazaacenaphthylene-4-carbaldehyde was not purified but used as it was in the next reaction.

To a solution of 2.01 g (4.87 mM) of tert-butyl 4-(diethoxyphosphorylmethanesulfonylmethyl)piperidine-1-carboxylate in 30 ml of toluene was added 0.18 g (4.43 mM) of a 60% suspension of sodium hydride in liquid paraffin at room temperature, and the mixture was stirred at the prevailing temperature for 1 hour. This reaction mixture was added to a solution of the above crude 5-thia-1,8b-diazaacenaphthylene-4-carbaldehyde in N,N-dimethylformamide (10 ml)-toluene (30 ml) at room temperature and the mixture was stirred at the prevailing temperature for 0.5 hour. This reaction mixture was poured in water and extracted with 3 portions of ethyl acetate. The organic layers were pooled and dried over $MgSO_4$ and the solvent was distilled off under reduced pressure. The residue was purified by silica gel column chromatography (ethyl acetate~ethyl acetate/methanol=9/1) to provide crude (E)-4-[2-[1-(tert-butoxycarbonyl)piperidin-4-ylmethane-sulfonyl]viny]-5-thia-1,8b-diazaacenaphthylene. This crude product was not purified but used as it was in the next reaction.

To the above crude (E)-4-[2-[1-(tert-butoxycarbon-yl) piperidin-4-ylmethanesulfonyl]vinyl]-5-thia-1,8b-diazaacenaphthylene was added 3 ml of concentrated hydrochloric acid, and the mixture was stirred at room temperature for 10 minutes. To this reaction mixture was added ethanol, and the resulting precipitate was recovered by filtration and rinsed serially with ethanol and diethyl ether to provide the title compound.

Orange-colored solid. Yield 1.398 g (73%)

$^1$H-NMR (CD$_3$OD, 200 MHz) δ: 1.520–1.734 (2H, m), 2.189 (2H, br d, J=15.4 Hz), 2.278–2.410 (1H, m), 3.068 (2H, t, J=12.6 Hz), 3.226 (2H, d, J=6.6 Hz), 3.398 (2H, d, J=12.4 Hz), 6.801 (1H, d, J=7.2 Hz), 6.805 (1H, d, J=15.4 Hz), 6.920 (1H, s), 7.149 (1H, d, J=8.8 Hz), 7.274 (1H, d, J=15.4 Hz), 7.514 (1H, dd, J=7.6, 9.0 Hz), 7.625 (1H, s).

IR (Nujol): 2715, 1633, 1597, 1308, 1201, 1134, 945, 854, 785, 737 cm$^{-1}$.

2) Synthesis of (E)-4-[2-[1-(3-phenylpropan-1-yl)-piperidin-4-ylmethanesulfonyl]vinyl]-5-thia-1,8b-diazaacenaphthylene A solution of 0.402 g (0.925 mM) of (E)-4-[2-(piperidin-4-ylmethanesulfonyl)vinyl]-5-thia-1,8b-diazaacenaphthylene dihydrochloride, 0.28 g (1.39 mM) of 1-bromo-3-phenylpropane, and 0.45 ml (3.24 mM) of triethylamine in 20 ml of ethanol was refluxed for 1 day. This reaction mixture was poured in aqueous solution of sodium hydrogen carbonate and extracted with 2 portions of ethyl acetate. The organic layers were pooled and dried over MgSO$_4$ and the solvent was distilled off under reduced pressure. The residue was purified by silica gel column chromatography (ethyl acetate~ethyl acetate/methanol : 9/1-1/1) to provide the title compound.

Red liquid. Yield 0.373 g (94%)

$^1$H-NMR (CDCl$_3$, 200 MHz) δ: 1.681–1.822 (2H, m), 1.887–2.311 (7H, m), 2.542 (2H, t, J=7.8 Hz), 2.653 (2H, t, J=7.6 Hz), 2.977 (2H, d, J=6.2 Hz), 3.072–3.182 (2H, m), 5.929 (1H, dd, J=1.8, 6.2 Hz), 6.060 (1H, d, J=15.0 Hz), 6.396 (1H, s), 6.692–6.814 (2H, m), 7.023 (1H, d, J=15.0 Hz), 7.161–7.326 (6H, m).

IR (neat): 2939, 1581, 1498, 1294, 1126, 837, 777, 731 cm$^{-1}$.

3) Synthesis of (E)-4-[2-[1-(3-phenylpropan-1-yl)-piperidin-4-ylmethanesulfonyl]vinyl]-5-thia-1,8b-diazaacenaphthylene dihydrochloride In 2 ml of methanol was dissolved 0.418 g of (E)-4-[2-[1-(3-phenylpropan-1-yl)piperidin-4-ylmethanesulfonyl]vinyl]-5-thia-1,8b-diazaacenaphthylene, followed by addition of a stoichiometric excess of methanolic hydrochloric acid, and the mixture was stirred for 10 minutes. This reaction mixture was concentrated and crystallized from ethanol-diethyl ether to provide the title compound.

Orange-colored solid. Yield 0.373 g $^1$H-NMR (CD$_3$OD, 200 MHz) δ: 1.584–1.799 (2H, m), 2.000–2.258 (5H, m), 2.711 (2H, t, J=7.5 Hz), 2.962–3.141 (4H, m), 3.218 (2H, d, J=6.2 Hz), 3.550–3.619 (2H, m), 6.800 (1H, d, J=7.6 Hz), 6.802 (1H, d, J=15.0 Hz), 6.924 (1H, s), 7.125–7.307 (7H, m), 7.510 (1H, dd, J=7.4, 9.0 Hz), 7.627 (1H, s).

IR (Nujol): 2638–2360, 1633, 1591, 1306, 1269, 1122, 847, 816, 768 cm$^{-1}$.

Elemental analysis for C$_{26}$H$_{31}$Cl$_2$N$_3$O$_2$S$_2$·3.0H$_2$O. Calcd.: C, 51.48; H, 6.15; N, 6.93 Found: C, 51.69; H, 6.20; N, 6.55

Example 145

Synthesis of (E)-4-[2-[1-(3-phenylpropan-1-yl)piperidin-4-ylmethylthio]vinyl]-5-thia-1,8b-diazaacenaphthylene dihydrochloride 1) Synthesis of (E)-4-[2-(piperidin-4-ylmethylthio)vinyl]-5-thia-1,8b-diazaacenaphthylene dihydrochloride To a solution of 1.073 g (5.253 mM) of 5-thia-1,8b-diazaacenaphthylene-4-methanol in 30 ml of chloroform was added 3 g of activated manganese dioxide (Aldrich) and the mixture was stirred at room temperature for 4 hours. This reaction mixture was filtered and the filter cake was washed with chloroform. The filtrate and washes were pooled and the solvent was distilled off under reduced pressure. The crude 5-thia-1,8b-diazaacenaphthylene-4-carbaldehyde thus obtained was not purified but used as it was in the next reaction.

To a solution of 2.20 g (5.78 mM) of tert-butyl 4-(diethoxyphosphorylmethylthiomethyl)piperidine-1-carboxylate and the above crude 5-thia-1,8b-diazaacenaphthylene-4-carbaldehyde in N,N-dimethylformamide (10 ml)-toluene (50 ml) was added 0.59 g (5.25 mM) of tert-butoxypotassium and the mixture was stirred at room temperature for 15 minutes. This reaction mixture was poured in water and extracted with 3 portions of ethyl acetate. The organic layers were pooled and dried over MgSO$_4$ and the solvent was distilled off under reduced pressure. To the residue was added 4 ml of concentrated hydrochloric acid, and the mixture was stirred at room temperature for 10 minutes. To this reaction mixture was added ethanol, followed by stirring, and the resulting precipitate was recovered by filtration and rinsed serially with ethanol and diethyl ether to provide the title compound.

Yellow solid. Yield 0.667 g (32%)

$^1$H-NMR (CD$_3$OD, 200 MHz) δ: 1.409–1.612 (2H, m), 1.859–2.017 (1H, m), 2.098 (2H, d, J=13.6 Hz), 2.894 (2H, d, J=6.2 Hz), 3.004 (2H, t, J=12.4 Hz), 3.418 (2H, d, J=13.2 Hz), 6.318 (1H, d, J=15.4 Hz), 6.321 (1H, s), 6.644 (1H, d, J=15.4 Hz), 6.767 (1H, d, J=7.6 Hz), 7.119 (1H, d, J=9.2 Hz), 7.405 (1H, s), 7.473 (1H, dd, J=7.8, 8.8 Hz).

IR (Nujol): 2706, 1637, 1500, 1207, 937, 773 cm$^{-1}$.

2) Synthesis of (E)-4-[2-[1-(3-phenylpropan-1-yl)-piperidin-4-ylmethylthio]vinyl]-5-thia-1,8b-diazaacenaphthylene A solution of 0.314 g (0.780 mM) of (E)-4-[2-(piperidin-4-ylmethylthio)vinyl]-5-thia-1,8b-diazaacenaphthylene dihydrochloride, 0.19 g (0.94 mM) of 1-bromo-3-phenylpropane, and 0.38 ml (2.73 mM) of triethylamine in 20 ml of ethanol was refluxed for 1 day. This reaction mixture was poured in aqueous solution of sodium hydrogen carbonate and extracted with 2 portions of ethyl acetate. The organic layers were pooled and dried over MgSO$_4$ and the solvent was distilled off under reduced pressure. The residue was purified by silica gel column chromatography (ethyl acetate to ethyl acetate/methanol : 4/1) to provide the title compound.

Red liquid. Yield 0.233 g (67%)

$^1$H-NMR (CDCl$_3$, 200 MHz) δ: 1.255–1.614 (3H, m), 1.795–2.004 (6H, m), 2.381 (2H, t, J=7.7 Hz), 2.584–2.683 (4H, m), 2.956 (2H, d, 11.6 Hz), 5.862 (1H, dd, J=1.0, 6.8 Hz), 5.891 (1H, s), 5.986 (1H, d, J=15.4 Hz), 6.113 (1H, d, J=15.4 Hz), 6.625 (1H, dd, J=6.8, 9.4 Hz), 6.737 (1H, dd, J=1.1, 9.1 Hz), 6.951 (1H, s), 7.134–7.317 (5H, m).

IR (neat): 2933, 1610, 1475, 1290, 1246, 1136, 916, 851, 771, 700 cm$^{-1}$.

3) Synthesis of (E)-4-[2-[1-(3-phenylpropan-1-yl)-piperidin-4-ylmethylthio]vinyl]-5-thia-1,8b-diazaacenaphthylene dihydrochloride In 2 ml of methanol was dissolved 0.233 g of (E)-4-[2-[1-(3-phenylpropan-1-yl)piperidin-4-ylmethylthio]-vinyl]-5-thia-1,8b-diazaacenaphthylene, followed by addition of a stoichiometric excess of methanolic hydrochloric acid, and the mixture was stirred for 10 minutes. This reaction mixture was concentrated to provide the title compound.

Orange-colored foam. Yield 0.253 g $^1$H-NMR (CD$_3$OD, 200 MHz) δ: 1.504–1.700 (2H, m), 1.840–2.167 (5H, m), 2.713 (2H, t, J=7.1 Hz), 2.882 (2H, d, J=6.6 Hz), 2.969–3.141 (4H, m), 3.552–3.654 (2H, m), 6.312 (1H, d, J=15.4 Hz), 6.321 (1H, s), 6.632 (1H, d, J=15.8 Hz), 6.765 (1H, d, J=7.4 Hz), 7.121 (1H, d, J=9.2 Hz), 7.167–7.340 (5H, m), 7.405 (1H, s), 7.470 (1H, dd, J=7.8, 9.2 Hz).

IR (neat): 2949, 2717-2553, 1635, 1574, 1498, 1448, 1304, 1213, 783, 752, 702 cm$^{-1}$.

Elemental analysis for C$_{26}$H$_{31}$Cl$_2$N$_3$S$_2$·2.0H$_2$O. Calcd.: C, 56.10; H, 6.34; N, 7.55 Found: C, 55.99; H, 6.50; N, 7.57

Example 146

Synthesis of (E)-N-[1-(3-phenylpropan-1-yl)piperidin-4-ylmethyl]-2-(5-thia-1,8b-diazaacenaphthylen-4-yl)vinyl-sulfonamide dihydrochloride 1) Synthesis of (E)-N-(piperidin-4-ylmethyl)-2-(5-thia-1,8b-diazaacenaphthylen-4-yl)vinylsulfonamide dihydrochloride To a solution of 0.800 g (3.917 mM) of 5-thia-1,8b-diazaacenaphthylene-4-methanol in 30 ml of chloroform was added 3 g of activated manganese dioxide (Aldrich) and the mixture was stirred at room temperature for 4 hours. This reaction mixture was filtered and the filter cake was washed with chloroform. The filtrate and washes were pooled and the solvent was distilled off under reduced pressure. The resulting crude 5-thia-1,8b-diazaacenaphthylene-4-carbaldehyde was not purified but used as it was in the next reaction.

To a solution of 2.16 g (4.11 mM) of tert-butyl 4-(diphenoxyphosphorylmethanesulfonylaminomethyl)-piperidine-1-carboxylate in toluene (20 ml)-tetrahydrofuran (20 ml) was added 0.33 g (8.23 mM) of a 60% suspension of sodium hydride in liquid paraffin at room temperature and the mixture was stirred at the prevailing temperature for 1 hour. This reaction mixture was added to a solution of the above crude 5-thia-1,8b-diazaacenaphthylene-4-carbaldehyde in N,N-dimethylformamide (10 ml)-toluene (50 ml) at room temperature and the mixture was stirred at the prevailing temperature for 0.5 hour. This reaction mixture was poured in water and extracted with 3 portions of ethyl acetate. The organic layers were pooled and dried over MgSO$_4$ and the solvent was distilled off under reduced pressure. The residue was subjected to silica gel column chromatography (ethyl acetate to ethyl acetate/methanol : 9/1) to provide crude (E)-N-[1-(tert-butoxycarbonyl)piperidin-4-ylmethyl]-2-(5-thia-1,8b-diazaacenaphthylen-4-yl)vinylsulfonamide. To this crude product was added 1 ml of concentrated hydrochloric acid, and the mixture was stirred at room temperature for 30 minutes. To this reaction mixture was added ethanol, followed by stirring, and the resulting precipitate was recovered and washed serially with ethanol and diethyl ether to provide the title compound.

Yellow solid. Yield 0.384 g (22%)

$^1$H-NMR (CD$_3$OD, 200 MHz) δ: 1.339–1.631 (2H, m), 1.727–2.186 (3H, m), 2.910–3.063 (4H, m), 3.360–3.452 (2H, m), 6.546 (1H, d, J=14.8 Hz), 6.809 (1H, d, J=7.6 Hz), 6.840 (1H, s), 7.119 (1H, d, J=14.6 Hz), 7.151 (1H, d, J=9.2 Hz), 7.516 (1H, dd, J=7.6, 9.2 Hz), 7.594 (1H, s).

IR (Nujol): 3064, 2727-2505, 1637, 1601, 1138, 1061, 851, 787 cm$^{-1}$.

2) Synthesis of (E)-N-[1-(3-phenylpropan-1-yl)piperidin-4-ylmethyl]-2-(5-thia-1,8b-diazaacenaphthylen-4-yl)vinylsulfonamide A solution of 0.285 g (0.634 mM) of (E)-N-(piperidin-4-ylmethyl)-2-(5-thia-1,8b-diazaacenaphthylen-4-yl)vinylsulfonamide dihydrochloride, 0.15 g (0.76 mM) of 1-bromo-3-phenylpropane, and 0.31 ml (2.22 mM) of triethylamine in 20 ml of ethanol was refluxed for 1 day. This reaction mixture was then poured in aqueous solution of sodium hydrogen carbonate and extracted with 2 portions of ethyl acetate. The organic layers were combined and dried over MgSO$_4$ and the solvent was distilled off under reduced pressure. The residue was purified by silica gel column chromatography (ethyl acetate~ethyl acetate/methanol : 9/1) to provide the title compound.

Red foam. Yield 0.217 g (69%)

$^1$H-NMR (CDCl$_3$, 200 MHz) δ: 1.230–1.623 (3H, m), 1.726–2.036 (6H, m), 2.333–2.496 (2H, m), 2.624 (2H, t, 7.7 Hz), 2.875–3.029 (4H, m), 5.130 (1H, br s), 5.895 (1H, dd, 1.4, 6.6 Hz), 6.003 (1H, d, 15.0 Hz), 6.322 (1H, s), 6.638–6.800 (2H, m), 6.901 (1H, d, 15.0 Hz), 7.120–7.315 (6H, m).

IR (neat): 3030, 2931, 1585, 1329, 1140, 731 cm$^{-1}$.

3) Synthesis of (E)-N-[1-(3-phenylpropan-1-yl)piperidin-4-ylmethyl]-2-(5-thia-1,8b-diazaacenaphthylen-4-yl)vinylsulfonamide dihydrochloride In 2 ml of methanol was dissolved 0.217 g of (E)-N-[1-(3-phenylpropan-1-yl)piperidin-4-ylmethyl]-2-(5-thia-1,8b-diazaacenaphthylen-4-yl)vinylsulfonamide, followed by addition of a stoichiometric excess of methanolic hydrochloric acid, and the mixture was stirred for 10 minutes. This reaction mixture was concentrated to provide the title compound.

Orange-colored foam. Yield 0.247 g $^1$H-NMR (CD$_3$OD, 200 MHz) δ: 1.434–1.628 (2H, m), 1.714–2.165 (5H, m), 2.709 (2H, t, J=7.5 Hz), 2.911 (2H, d, J=6.6 Hz), 3.008–3.141 (4H, m), 3.522–3.621 (2H, m), 6.536 (1H, d, J=15.4 Hz), 6.803 (1H, d, J=7.2 Hz), 6.838 (1H, s), 7.106 (1H, d, J=15.4 Hz), 7.150 (1H, d, J=9.2 Hz), 7.155–7.332 (5H, m), 7.506 (1H, dd, J=7.8, 9.0 Hz), 7.590 (1H, s).

IR (Nujol): 3351, 2667, 1632, 2331, 1144, 725 cm$^{-1}$.

Elemental analysis for C$_{26}$H$_{32}$Cl$_2$N$_4$O$_2$S$_2$·1.0H$_2$O. Calcd.: C, 53.33; H, 5.85; N, 9.57 Found: C, 53.24; H, 5.59; N, 9.64

Example 147

Synthesis of N-[1-(3-phenylpropan-1-yl)piperidin-4-yl]-5-thia-1,8b-diazaacenaphthylene-4-carboxamide 1) Synthesis of 5-thia-1,8b-diazaacenaphthylene-4-carboxylic acid To a suspension of 2.2 g of ethyl 5-thia-1,8b-diazaacenaphthylene-4-carboxylate in methanol (6.6 ml) was added 1N-aqueous solution of sodium hydroxide (13 ml), and the mixture was stirred at room temperature for 2 hours. This reaction mixture was adjusted to pH 5 with 1N-hydrochloric acid under ice-cooling. Then, the mixture was stirred at room temperature for 1 hour. The resulting crystal cropwas harvested by filtration and dried to provide 5-thia-1,8b-diazaacenaphthylene-4-carboxylic acid (1.8 g, 94%).

¹H-NMR (300 MHz, DMSO-d₆) δ: 5.97 (1H, d, J=7.0 Hz), 6.60 (2H, d, J=9.1 Hz), 6.67 (1H, dd, J=7.0, 9.1 Hz), 6.89 (1H, s), 7.12 (1H, s).

2) Synthesis of N-[1-(3-phenylpropan-1-yl)piperidin-4-yl]5-thia-1,8b-diazaacenaphthylene-4-carboxamide (i) Process (A)

A suspension of 5-thia-1,8b-diazaacenaphthylene-4-carboxylic acid (1.2 g), 4-amino-1-(3-phenylpropan-1-yl)piperidine dihydrochloride (1.5 g), triethylamine (1.5 ml), 1-hydroxy-1H-benzotriazole monohydrate (0.8 g), and 1-ethyl-3-(3-diethylaminopropyl)carbodiimide hydrochloride (1.0 g) in N,N-dimethylformamide (15 ml) was stirred at 50° C. for 2 hours. After spontaneous cooling, this reaction mixture was extracted with ethyl acetate/tetrahydrofuran (4/1; 90 ml). The organic layer was washed with 1N-aqueous solution of sodium hydroxide (10 ml) and water (30 ml) and concentrated. The resulting crystal crop was rinsed with diisopropyl ether (20 ml) and dried to provide the title compound (2.0 g, 95%).

ii) Process (B)

To a suspension of 5-thia-1,8b-diazaacenaphthylene-4-carboxylic acid (10 g) and N,N-dimethylformamide (1.8 ml) in tetrahydrofuran (100 ml) was added oxalyl chloride (8 ml) dropwise with ice-cooling. Then, at room temperature, the mixture was stirred for 24 hours. This reaction mixture was concentrated and dissolved in N,N-dimethylformamide (40 ml).

To a solution of 4-amino-1-(3-phenylpropyl)-piperidine dihydrochloride (13.4 g), 1,8-diazabicyclo-[5.4.0]-7-undecene (13.7 ml), triethylamine (25.6 ml), and N,N-dimethylformamide (60 ml) was added the solution prepared above under ice-cooling using care not to allow the temperature to rise beyond 10° C. The mixture was then stirred at room temperature for 1.5 hours. This reaction mixture was diluted with water (400 ml) and extracted with ethyl acetate/tetrahydrofuran (4/1; 200 ml). The organic layer was washed with 1N-aqueous solution of sodium hydroxide (100 ml) and water (300 ml) and concentrated. The resulting crystals were rinsed with diisopropyl ether (20 ml) and dried to provide the title compound (12.9 g, 67%).

¹H-NMR (300 MHz, CDCl₃) δ: 1.45–1.53 (2H, m), 1.69–1.83 (2H, m), 1.85–1.92 (2H, m), 1.96–2.08 (2H, m), 2.33–2.38 (2H, m), 2.60–2.65 (2H, m), 2.81–2.85 (2H, m), 3.79–3.82 (1H, m), 5.53 (1H, d, J=7.8 Hz), 5.78 (1H, d, J=6.6 Hz), 6.59–6.69 (3H, m), 7.05 (1H, s), 7.16–7.19 (3H, m), 7.25–7.30 (2H, m).

Example 148

Synthesis of N-[4-(3-phenylpropan-1-yl)piperazin-1-ylcarbonylmethyl]-5-thia-1,8b-diazaacenaphthylene-4-carboxamide dihydrochloride 1) Synthesis of N-[4-(3-phenylpropan-1-yl)piperazin-1-ylcarbonylmethyl]-5-thia-1,8b-diazaacenaphthylene-4-carboxamide To a suspension of 1.0 g (4.58 mmol.) of 5-thia-1,8b-diazaacenaphthylene-4-carboxylic acid and 1.05 g (9.12 mmol.) of N-hydroxysuccinimide in acetonitrile (20 ml) was added, at room temperature, 1.76 g (9.18 mmol.) of N-ethyl-N'-3-(N,N-dimethylamino)propylcarbodiimide.hydrochloride. The mixture was stirred for 1.5 hour. To the reaction system was added a solution of 1.68 g (5.03 mmol.) of 1-aminoacetyl-4-(3-phenylpropan-1-yl)piperazine dihydrochloride, 1.53 g (10.05 mmol.) of 1,8-diazabicyclo[5.4.0]unde-7-cene (DBU) and 0.7 ml (5.02 mmol.) of triethylamine in acetonitrile (15 ml). The mixture was stirred for further 2 hours. The solvent was distilled off under reduced pressure. To the residue was added water. The mixture was subjected to extraction with ethyl acetate (a small volume of ethanol was also used). The organic layer was washed with a saturated aqueous solution of sodium hydrogencarbonate and a saturated aqueous saline solution, which was dried over magnesium sulfate. The solvent was distilled off under reduced pressure to leave a crude product, which was purified by means of a column chromatography (methanol/ethyl acetate 30–50%) to afford the object compound as a reddish amorphous substance. The yield was 1.32 g (62%).

¹H-NMR (CDCl₃, 200 MHz) δ: 1.71–1.91 (2H, m), 2.31–2.51 (6H, m), 2.65 (2H, t, J=7.6 Hz), 3.36–3.45 (2H, m), 3.59–3.73 (2H, m), 4.06 (2H, d, J=3.8 Hz), 5.78 (1H, dd, J=6.0 & 1.8 Hz), 6.58–6.72 (3H, m), 6.90–7.00 (1H, m), 7.05 (1H, s), 7.13–7.35 (5H, m).

IR (KBr): 1637, 1622, 1481, 1282, 1238, 1155, 773, 731, 700 cm⁻¹.

2) Synthesis of N-[4-(3-phenylpropan-1-yl)piperazin-1-ylcarbonylmethyl]-5-thia-1,8b-diazaacenaphthylene-4-carboxamide dihydrochloride To a solution of 1.306 g (2.83 mmol.) of N-[4-(3-phenylpropan-1-yl)piperazin-1-ylcarbonylmethyl]-5-thia-1,8b-diazaacenaphthylene-4-carboxamide in ethanol (10 ml) was added, at room temperature, 1.5 ml (18 mmol.) of 12N hydrochloric acid. The mixture was stirred for several minutes, which was concentrated under reduced pressure. To the resulting crystals were added ethanol and diethyl ether. The crystals were collected by filtration, which were washed with ether and diethyl ether to afford the object compound as orange crystals. The yield was 1.26 g (83%). m.p.189–196° C. (decomp.)

¹H-NMR (DMSO-d₆, 200 MHz) δ: 1.93–2.17 (2H, m), 2.65 (2H, t, J=7.6 Hz), 2.80–3.29 (6H, m), 3.39–3.68 (2H, m), 3.91–4.48 (4H, m), 6.59 (1H, d, J=7.0 Hz), 6.96 (1H, d, J=8.4 Hz), 7.17 (1H, s), 7.19–7.36 (6H, m), 7.66 (1H, s), 8.81–8.91 (1H, m), 11.18–11.45 (1H, m).

IR (KBr): 3260, 1667, 1638, 1503 cm⁻¹.

Elemental analysis for $C_{25}H_{29}N_5O_2S Cl_2 \cdot 1.5H_2O$. Calcd.: C, 53.47; H, 5.74; N, 12.47 Found: C, 53.47; H, 5.65; N. 12.46.

Example 149

Synthesis of N-[4-(2-phenethyl)piperazin-1-ylcarbonylmethyl]-5-thia-1,8b-diazaacenaphthylene-4-carboxamide dihydrochloride 1) Synthesis of N-[4-(2-phenethyl)piperazin-1-ylcarbonylmethyl]-5-thia-1,8b-diazaacenaphthylene-4-carboxamide To a suspension of 1.0 g (4.58 mmol.) of 5-thia-1,8b-diazaacenaphthylene-4-carboxylic acid and 1.05 g (9.12 mmol.) of N-hydroxysuccinimide in acetonitrile (20 ml) was added, at room temperature, 1.76 g (9.18 mmol.) of N-ethyl-N'-3-(N,N-dimethylamino)propylcarbodiimide hydrochloride. The mixture was stirred for 2 hours. To the reaction system was added a solution of 1.76 g (5.50 mmol.) of 1-aminoacetyl-4-(2-phenethyl)piperazine dihydrochloride, 1.67 g (10.97 mmol.) of 1,8-diazabicyclo[5.4.0]unde-7-cene (DBU) and 0.64 ml (4.59 mmol.) of triethylamine in acetonitrile (15 ml). The mixture was stirred for further one hour. The solvent was distilled off under reduced pressure. To the residue was added water. The mixture was subjected to extraction with ethyl acetate (a small volume of ethanol was also used). The organic layer was washed with a saturated aqueous solution of sodium hydrogencarbonate and a saturated aqueous saline solution, which was dried over magnesium sulfate to give a crude product. The crude product was purified by means of a column chromatography (methanol/ethyl acetate 30–40%), followed by crystallization from ethyl acetate to afford the object product as purple crystals. The yield was 1.18 g (57%). m.p.137–139° C.

$^1$H-NMR (CDCl$_3$, 200 MHz) δ: 2.46–2.58 (4H, m), 2.58–2.71 (2H, m), 2.75–2.87 (2H, m), 3.38–3.49 (2H, m), 3.63–3.75 (2H, m), 4.07 (2H, d, J=4.0 Hz), 5.78 (1H, dd, J=6.0 & 1.8 Hz), 6.55–6.67 (2H, m), 6.71 (1H, s), 6.92–7.01 (1H, m), 7.05 (1H, s), 7.16–7.36 (5H, m).

IR (KBr): 3423, 3255, 1632, 1618, 1556, 1481, 1282, 1246, 1157 cm$^{-1}$.

2) Synthesis of N-[4-(2-phenethyl)piperazin-1-ylcarbonylmethyl]-5-thia-1,8b-diazaacenaphthylene-4-carboxamide dihydrochloride To a solution of 1.13 g (2.52 mmol.) of N-[4-(2-phenethyl)piperazin-1-ylcarbonylmethyl]-5-thia-1,8b-diazaacenaphthylene-4-carboxamide in ethanol (10 ml) was added, at room temperature, 1.5 ml (18 mmol.) of 12N hydrochloric acid. The mixture was stirred for several minutes. The reaction mixture was concentrated under reduced pressure. To the resulting crystals were added ethanol and diethyl ether. The crystals were collected by filtration, followed by washing with ethanol and diethyl ether to give the object compound as orange crystals. The yield was 1.20 g (91%).

m.p.165–175° C. (decomp.)

$^1$H-NMR (DMSO-d$_6$, 200 MHz) δ: 2.84–3.42 (8H, m), 3.49–3.73 (2H, m), 3.92–4.52 (4H, m), 6.61 (1H, d, J=7.2 Hz), 6.98 (1H, d, J=9.2 Hz), 7.19 (1H, s), 7.20–7.42 (6H, m), 7.68 (1H, s), 8.85–8.96 (1H, m), 11.42–11.72 (1H, m).

IR (KBr): 3260, 1669, 1634 cm$^{-1}$.

Elemental analysis for $C_{24}H_{27}N_5O_2SCl_2 \cdot 2.0H_2O$. Calcd.: C, 51.80; H, 5.61; N, 12.58 Found: C, 51.86; H, 5.34; N, 12.54.

Example 150

Synthesis of N-[4-(3-phenylpropan-1-yl)-2,3,5,6-tetrahydro-7H-1,4-diazepin-1-ylcarbonylmethyl]-5-thia-1,8b-diazaacenaphthylene-4-carboxamide dihydrochloride 1) Synthesis of N-[4-(3-phenylpropan-1-yl)-2,3,5,6-tetrahydro-7H-1,4-diazepin-1-ylcarbonylmethyl]-5-thia-1,8b-diazaacenaphthylene-4-carboxamide To a suspension of 1.0 g (4.58 mmol.) of 5-thia-1,8b-diazaacenaphthylene-4-carboxylic acid and 1.05 g (9.12 mmol.) of N-hydroxysuccinimide in acetonitrile (20 ml) was added, at room temperature, 1.76 g (9.18 mmol.) of N-ethyl-N'-3-(N,N-dimethylamino)propylcarbodimide hydrochloride. The mixture was stirred for one hour. To the reaction system was added a solution of 1.91 g (5.48 mmol.) of 1-(aminoacetyl)-4-(3-phenylpropan-1-yl)-2,3,5,6-tetrahydro-7H-1,4-diazepine dihydrochloride, 1.67 g (10.97 mmol.) of 1,8-diazabicyclo[5.4.0]unde-7-cene (DBU) and 0.7 ml (5.0 mmol.) of triethylamine in acetonitrile (20 ml). The mixture was stirred for further one hour. The solvent was distilled off under reduced pressure. To the residue was added water. The mixture was subjected to extraction with ethyl acetate. The organic layer was washed with a saturated aqueous solution of sodium hydrogencarbonate and a saturated aqueous saline solution, followed by drying over magnesium sulfate. The solvent was distilled off under reduced pressure to leave a crude product, which was purified by means of a column chromatography (methanol/ethyl acetate 30–50%) to afford the object compound as an amorphous substance.

The yield was 1.00 g (46%).

$^1$H-NMR (CDCl$_3$, 200 MHz) δ: 1.68–1.97 (4H, m), 2.42–2.55 (2H, m), 2.55–2.75 (6H, m), 3.39–3.50 (2H, m), 3.60–3.72 (2H, m), 4.03–4.08 (2H, m), 5.77 (1H, dd, J=6.2 & 1.8 Hz), 6.55–6.65 (2H, m), 6.70 (1H, s), 6.95–7.06 (1H, m), 7.04 (1H, s), 7.13–7.34 (5H, m).

IR (KBr): 3243, 1644, 1622, 1454, 1283, 1157, 772, 702 cm$^{-1}$.

2) Synthesis of N-[4-(3-phenylpropan-1-yl)-2,3,5,6-tetrahydro-7H-1,4-diazepin-1-ylcarbonylmethyl]-5-thia-1,8b-diazaacenaphthylene-4-carboxamide dihydrochloride To a solution of 1.00 g (2.1 mmol.) of N-[4-(3-phenylpropan-1-yl)-2,3,5,6-tetrahydro-7H-1,4-diazepin-1-ylcarbonylmethyl]-5-thia-1,8b-diazaacenaphthylene-4-carboxamide in ethanol (10 ml) was added, at room temperature, 1 ml (12 mmol.) of 12N hydrochloric acid. The mixture was stirred for several minutes, followed by concentration under reduced pressure. To the resulting crystals was added diethyl ether. The crystals were collected by filtration, which were washed with ethanol and diethyl ether to give the object product as orange crystals. The yield was 0.996 g (86%).

m.p.269–275° C. (decomp.)

$^1$H-NMR (DMSO-d$_6$, 200 MHz) δ: 1.90–2.19 (4H, m), 2.54–2.70 (2H, m), 2.85–3.36 (4H, m), 3.38–3.65 (5H, m), 3.77–4.19 (3H, m), 6.63 (1H, d, J=7.4 Hz), 6.99 (1H, d, J=8.2 Hz), 7.15–7.38 (7H, m), 7.69 (1H, s), 8.83–8.96 (1H, m), 11.04–11.31 (1H, m).

IR (KBr): 3268, 1661, 1638, 1501 cm$^{-1}$.

Elemental analysis for $C_{26}H_{31}N_5O_2SCl_2 \cdot 1.0H_2O$. Calcd.: C, 55.12; H, 5.87; N, 12.36 Found: C, 54.82; H, 5.59; N, 12.54.

Example 151

Synthesis of N-[4-(2-phenethyl)-2,3,5,6-tetrahydro-7H-1,4-diazepin-1-ylcarbonylmethyl]-5-thia-1,8b-diazaacenaphthylene-4-carboxamide dihydrochloride 1) Synthesis of N-[4-(2-phenethyl)-2,3,5,6-tetrahydro-7H-1,4-diazepin-1-ylcarbonylmethyl]-5-thia-1,8b-diazaacenaphthylene-4-carboxamide To a suspension of 1.0 g (4.58 mmol.) of 5-thia-1,8b-diazaacenaphthylene-4-carboxylic acid and 1.05 g (9.12 mmol.) of N-hydroxysuccinimide in acetonitrile (20 ml) was added, at room temperature, 1.76 g (9.18 mmol.) of N-ethyl-N'-3-(N,N-dimethylamino)propylcarbodiimide hydrochloride. The mixture was stirred for one hour. To the reaction system was added a solution of 1.84 g (5.50 mmol.) of 1-(aminoacetyl)-4-(2-phenethyl)-2,3,5,6-tetrahydro-7H-1,4-diazepine dihydrochloride, 1.68 g (11.0 mmol.) of 1,8-diazabicyclo[5.4.0]unde-7-cene (DBU) and 0.7 ml (5.0 mmol.) of triethylamine in acetonitrile (20 ml). The mixture was stirred for further one hour. The solvent was distilled off under reduced pressure. To the residue was added water. The mixture was subjected to extraction with ethyl acetate (a small volume of ethanol was also used). The organic layer was washed with a saturated aqueous solution of sodium hydrogencarbonate and a saturated aqueous saline solution, which was dried over magnesium sulfate, followed by distilling off the solvent to leave a crude product. The crude product was purified by means of a column chromatography (methanol/ethyl acetate 20–50%) to afford the object compound as a reddish amorphous product. The yield was 0.91 g (43%).

$^1$H-NMR (CDCl$_3$, 200 MHz) δ: 1.78–1.99 (2H, m), 2.64–2.85 (8H, m), 3.40–3.50 (2H, m), 3.61–3.76 (2H, m), 4.01–4.09 (2H, m), 5.78 (1H, dd, J=5.8 & 1.8 Hz), 6.55–6.68 (2H, m), 6.72 (1H, s), 6.96–7.05 (1H, m), 7.05 (1H, s), 7.13–7.34 (5H, m).

2) Synthesis of N-[4-(2-phenethyl)-2,3,5,6-tetrahydro-7H-1,4-diazepin-1-ylcarbonylmethyl]-5-thia-1,8b-diazaacenaphthylene-4-carboxamide dihydrochloride To a solution of 0.91 g (1.97 mmol.) of N-[4-(2-phenethyl)-2,3,5,6-tetrahydro-7H-1,4-diazepin-1-ylcarbonylmethyl]-5-thia-1,8b-diazaacenaphthylene-4-carboxamide in ethanol (10 ml) was added, at room temperature, 1 ml (12 mmol.) of 12N hydrochloric acid. The mixture was stirred for one hour. To the resulting crystals was added diethyl ether, and the crystals were collected by filtration and washed with ethanol and diethyl ether to give the object compound as orange crystals. The yield was 0.9181 g (87%).

m.p.269–275° C. (decomp.)

$^1$H-NMR (DMSO-d$_6$, 200 MHz) δ: 1.99–2.23 (2H, m), 2.96–4.21 (14H, m), 6.59 (1H, d, J=7.4 Hz), 6.96 (1H, d, J=9.0 Hz), 7.14–7.41 (7H, m), 7.65 (1H, s), 8.80–8.90 (1H, m), 10.99–11.23 (1H, m).

IR (KBr): 3425, 1633, 1566, 1500, 1458, 1296, 1121, 783 cm$^{-1}$.

Elemental analysis for C$_{25}$H$_{29}$N$_5$O$_2$SCl$_2$·1.5H$_2$O. Calcd.: C, 53.47; H, 5.74; N, 12.47 Found: C, 53.37; H, 5.65; N, 12.69.

Example 152

Synthesis of N-[1-(3-phenylpropan-1-yl)piperidin-4-ylaminocarbonylmethyl]-5-thia-1,8b-diazaacenaphthylene-4-carboxamide dihydrochloride 1) Synthesis of N-[1-(3-phenylpropan-1-yl)piperidin-4-ylaminocarbonylmethyl]-5-thia-1,8b-diazaacenaphthylene-4-carboxamide To a suspension of 0.5 g (2.29 mmol.) of 5-thia-1,8b-diazaacenaphthylene-4-carboxylic acid and 0.53 g (4.61 mmol.) of N-hydroxysuccinimide in acetonitrile (10 ml) was added, at room temperature, 0.88 g (4.59 mmol.) of N-ethyl-N'-3-(N,N-dimethylamino)propylcarbodiimide hydrochloride. The mixture was stirred for 2 hours. To the reaction system was added a solution of 0.96 g (2.76 mmol.) of N-[1-(3-phenylpropan-1-yl)piperidin-4-yl]-aminoacetamide dihydrochloride, 0.84 g (5.52 mmol.) of 1,8-diazabicyclo[5.4.0]unde-7-cene (DBU) and 0.4 ml (2.87 mmol.) of triethylamine in acetonitrile (10 ml). The mixture was stirred for further one hour. The solvent was distilled off under reduced pressure. To the residue was added water, and the mixture was subjected to extraction with chloroform. The organic layer was washed with a saturated aqueous saline solution and dried over magnesium sulfate, followed by distilling off the solvent under reduced pressure to leave a crude product. The crude product was purified by means of a column chromatography (methanol/ethyl acetate 1:3→1:1→3:1), followed by recrystallization from ethyl acetate to afford the object compound as purple crystals. The yield was 303.2 mg (28%).

m.p.202–205° C.

$^1$H-NMR (CDCl$_3$, 200 MHz) δ: 1.36–2.00 (6H, m), 2.00–2.17 (2H, m), 2.30–2.42 (2H, m), 2.63 (2H, t, J=7.6 Hz), 2.76–2.92 (2H, m), 3.66–3.87 (1H, m), 3.91 (2H, d, J=4.8 Hz), 5.78 (1H, dd, J=6.0 & 1.8 Hz), 5.80–5.90 (1H, m), 6.56–6.74 (4H, m), 7.05 (1H, s), 7.13–7.33 (5H, m).

IR (KBr): 3281, 3065, 2946, 1649, 1622, 1553, 1483, 1287, 1267, 1159, 775 cm$^{-1}$.

2) Synthesis of N-[1-(3-phenylpropan-1-yl)piperidin-4-ylaminocarbonylmethyl]-5-thia-1,8b-diazaacenaphthylene-4-carboxamide dihydrochloride To a solution of 303.2 mg (0.64 mmol.) of N-[1-(3-phenylpropan-1-yl)piperidin-4-ylaminocarbonylmethyl]-5-thia-1,8b-diazaacenaphthylene-4-carboxamide in ethanol (5 ml) was added, at room temperature, 0.5 ml (6.0 mmol.) of 12N hydrochloric acid. The mixture was stirred for one hour. The mixture was concentrated under reduced pressure. To the concentrate were added ethanol and diethyl ether. The resulting crystals were collected by filtration and washed with ethanol and diethyl ether to afford the object compound as orange crystals. The yield was 257.5 mg (73%).

m.p.178–183° C. (decomp.)

$^1$H-NMR (DMSO-d$_6$, 200 MHz) δ: 1.61–2.11 (6H, m), 2.54–2.71 (2H, m), 2.77–3.87 (9H, m), 6.54 (1H, d, J=7.4 Hz), 6.93 (1H, d, J=8.8 Hz), 7.09 (1H, s), 7.10–7.36 (6H, m), 7.61 (1H, s), 8.16–8.25 (1H, m), 8.80–8.95 (1H, m).

IR (KBr): 3220, 3059, 1649, 1636, 1566, 1535, 1501, 1298 cm$^{-1}$.

Elemental analysis for C$_{26}$H$_{21}$N$_5$O$_2$SCl$_2$·1.5H$_2$O. Calcd.: C, 54.26; H, 5.95; N, 12.17 Found: C, 54.01; H, 5.74; N, 12.18.

Example 153

Synthesis of N-[4-(4-benzoylpiperazin-1-yl)butan-1-yl]-5-thia-1,8b-diazaacenaphthylene-4-carboxamide dihydrochloride 1) Synthesis of N-[4-(4-benzoylpiperazin-1-yl)butan-1-yl]-5-thia-1,8b-diazaacenaphthylene-4-carboxamide To a suspension of 1.0 g (4.58 mmol.) of 5-thia-1,8b-diazaacenaphthylene-4-carboxylic acid and 1.05 g (9.12 mmol.) of N-hydroxysuccinimide in acetonitrile (15 ml) was added, at room temperature, 1.76 g (9.18 mmol.) of N-ethyl-N'-3-(N,N-dimethylamino)propylcarbodiimide hydrochloride. The mixture was stirred for 2 hours. To the reaction system was added a solution of 1.68 g (5.5 mmol.) of 4-(4-aminobutan-1-yl)-1-benzoylpiperazine dihydrochloride, 1.68 g (11.04 mmol.) of 1,8-diazabicyclo[5.4.0]undecene (DBU) and 1.5 ml (10.76 mmol.) of triethylamine in acetonitrile (10 ml). The mixture was stirred for further 2 hours. The solvent was distilled off under reduced pressure. To the residue was added water, which was subjected to extraction with ethyl acetate (a small volume of ethanol was also used). The organic layer was washed with a saturated aqueous saline solution and dried over magnesium sulfate, followed by distilling off the solvent. The residue was purified by means of a column chromatography (methanol/ethyl acetate 20–30%) to give the object compound as a reddish amorphous product. The yield was 1.25 g (59%).

$^1$H-NMR (CDCl$_3$, 200 MHz) δ: 1.42–1.63 (4H, m), 2.24–2.56 (6H, m), 3.19–3.55 (4H, m), 3.63–3.88 (2H, m), 5.76–5.80 (1H, m), 5.96–6.08 (1H, m), 6.55–6.69 (3H, m), 7.02 (1H, s), 7.34–7.45 (5H, m).

IR (KBr): 3309, 1616, 1547, 1437, 1281, 1155, 1012, 775, 733, 712 cm$^{-1}$.

2) Synthesis of N-[4-(4-benzoylpiperazin-1-yl)butan-1-yl]-5-thia-1,8b-diazaacenaphthylene-4-carboxamide dihydrochloride To a solution of 1.16 g (2.51 mmol.) of N-[4-(4-benzoylpiperazin-1-yl)butan-1-yl]-5-thia-1,8b-diazaacenaphthylene-4-carboxamide in ethanol was added, at room temperature, 1 ml (12 mmol.) of 12N hydrochloric acid. The mixture was stirred for several minutes. The resulting crystals were collected by filtration and washed with ethanol and diethyl ether to give the object compound as orange crystals. The yield was 0.918 g (69%).

m.p.247–253° C. (decomp.)

$^1$H-NMR (DMSO-$d_6$, 200 MHz) δ: 1.40–1.58 (2H, m), 1.62–1.84 (2H, m), 2.96–3.24 (8H, m), 3.31–3.64 (4H, m), 6.61 (1H, d, J=6.8 Hz), 6.97 (1H, d, J=8.6 Hz), 7.22 (1H, s), 7.28 (1H, dd, J=7.6 & 9.2 Hz), 7.42–7.55 (5H, m), 7.64 (1H, s), 8.85–8.97 (1H, m).

IR (KBr): 3398, 1632, 1568, 1533, 1500, 1429, 1288 cm$^{-1}$.

Elemental analysis for $C_{25}H_{29}N_5O_2SCl_2 \cdot 1.5H_2O$. Calcd.: C, 53.47; H, 5.74; N, 12.47 Found: C, 53.28; H, 5.74; N, 12.73.

Example 154

Synthesis of N-[3-(4-benzoylpiperazin-1-yl)propan-1-yl]-5-thia-1,8b-diazaacenaphthylene-4-carboxamide dihydrochloride 1) Synthesis of N-[3-(4-benzoylpiperazin-1-yl)propan-1-yl]-5-thia-1,8b-diazaacenaphthylene-4-carboxamide To a suspension of 0.8 g (3.67 mmol.) of 5-thia-1,8b-diazaacenaphthylene-4-carboxylic acid and 0.84 g (8.8 mmol.) of N-hydroxysuccinimide in acetonitrile (15 ml) was added, at room temperature, 1.41 g (7.36 mmol.) of N-ethyl-N'-3-(N,N-dimethylamino)propylcarbodiimide hydrochloride. The mixture was stirred for 2 hours. To the reaction system was added a solution of 1.41 g (4.4 mmol.) of 4-(3-aminopropan-1-yl)-1-benzoylpiperazin dihydrochloride, 1.34 g (8.8 mmol.) of 1,8-diazabicyclo[5.4.0]unde-7-cene (DBU) and 1.0 ml (7.17 mmol.) of triethylamine in acetonitrile (15 ml). The mixture was stirred for further 2 hours. The solvent was distilled off under reduced pressure. To the residue was added water, which was subjected to extraction with ethyl acetate (a small volume of ethanol was also used). The organic layer was washed with a saturated aqueous saline solution, dried over magnesium sulfate and subjected to to distillation under reduced pressure. The residue was subjected to fractional purification by means of a column chromatography (methanol/ethyl acetate 30–40%), followed by distilling off the solvent under reduced pressure to afford the object compound as a reddish purple crystalline product. The yield was 0.738 g (45%).

$^1$H-NMR (CDCl$_3$, 200 MHz) δ: 1.68–1.81(2H,m), 2.43–2.63 (6H, m), 3.37–3.49 (2H, m), 3.55–3.92 (4H, m), 5.77 (1H, dd, J=1.8 & 6.6 Hz), 6.60–6.69 (1H, m), 6.73 (1H, s), 7.05 (1H, s), 7.25–7.35 (1H, m), 7.35–7.47 (5H, m).

IR (KBr): 3319, 1612, 1545, 1444, 1273, 1153 cm$^{-1}$.

2) Synthesis of N-[3-(4-benzoylpiperazin-1-yl)propan-1-yl]-5-thia-1,8b-diazaacenaphthylene-4-carboxamide dihydrochloride To a solution of 0.715 g (1.60 mmol.) of N-[3-(4-benzoylpiperazin-1-yl)propan-1-yl]-5-thia-1,8b-diazaacenaphthylene-4-carboxamide in ethanol (10 ml) was added, at room temperature, 10 ml (120 mmol.) of 12N hydrochloric acid. The mixture was stirred for 16 hours, which was concentrated under reduced pressure. To the concentrate were added ethanol and diethyl ether. The resulting crystals were collected by filtration and washed with ethanol and diethyl ether to give the object compound as orange crystals. The yield was 0.715 g (86%).

m.p.277–282° C. (decomp.)

$^1$H-NMR (DMSO-$d_6$, 200 MHz) δ: 1.82–2.01 (2H, m), 2.96–3.28 (8H, m), 3.34–3.61 (4H, m), 6.55 (1H, d, J=7.8 Hz), 6.93 (1H, d, J=9.2 Hz), 7.13 (1H, s), 7.18–7.26 (1H, m), 7.41–7.51 (5H, m), 7.60 (1H, s), 8.84–8.96 (1H, m).

IR (KBr): 3344, 1632, 1529, 1423, 1302, 800 cm$^{-1}$.

Elemental analysis for $C_{24}H_{27}N_5O_2SCl_2 \cdot 1.5H_2O$. Calcd.: C, 52.65; H, 5.52; N, 12.79 Found: C, 52.95; H, 5.30; N, 12.95.

Example 155

Synthesis of N-cis-[4-(4-benzyl-3,5-dimethylpiperazin-1-yl)butan-1-yl]-5-thia-1,8b-diazaacenaphthylene-4-carboxamide trihydrochloride 1) Synthesis of N-cis-[4-(1-benzyl-2,6-dimethylpiperazin-1-yl)butan-1-yl]-5-thia-1,8b-diazaacenaphthylene-4-carboxamide To a suspension of 1.0 g (4.58 mmol.) of 5-thia-1,8b-diazaacenaphthylene-4-carboxylic acid and 1.05 g (9.12 mmol.) of N-hydroxysuccinimide in acetonitrile (15 ml) was added, at room temperature, 1.76 g (9.18 mmol.) of N-ethyl-N'-3-(N,N-dimethylamino)propyl carbodiimide hydrochloride. The mixture was stirred for 2 hours. To the reaction system was added a solution of 1.64 g (5.95 mmol.) of cis-4-(1-benzyl-2,6-dimethylpiperazin-1-yl)butan-1-ylamine and 1.5 ml (10.76 mmol.) of triethylamine in acetonitrile (15 ml). The mixture was stirred for further 2 hours. The solvent was distilled off under reduced pressure. To the residue was added water, which was subjected to extraction with chloroform. The organic layer was washed with a saturated aqueous saline solution and dried over magnesium sulfate. The solvent was distilled off under reduced pressure to leave a crude product, which was subjected to fractional purification by means of a column chromatography (methanol/ethyl acetate 30%) to afford the object compound as a reddish amorphous product. The yield was 1.55 g (91%).

$^1$H-NMR (CDCl$_3$, 200 MHz) δ: 1.05 (6H, d, J=6.0 Hz), 1.47–1.63 (4H, m), 1.73–1.93 (2H, m), 2.24–2.36 (2H, m), 2.61–2.82 (4H, m), 3.23–3.36 (2H, m), 3.83 (2H, m), 5.74 (1H, dd, J=6.2 & 1.8 Hz), 6.56 (1H, s), 6.57–6.69 (3H, m), 6.97 (1H, s), 7.13–7.39 (5H, m).

IR (KBr): 3319, 1618, 1549, 1479, 1281, 1153, 773, 729 cm$^{-1}$.

2) Synthesis of N-cis-[4-(1-benzyl-2,6-dimethylpiperazin-1-yl)butan-1-yl]-5-thia-1,8b-diazaacenaphthylene-4-carboxamide trihydrochloride To a solution of 1.55 g (3.21 mmol.) of N-cis-[4-(1-benzyl-2,6-dimethylpiperazin-1-yl)butan-1-yl]-5-thia-1,8b-diazaacenaphthylene-4-carboxamide in ethanol (10 ml) was added 3.0 ml (36 mmol.) of 12N hydrochloric acid. The mixture was stirred for several minutes. The solvent was distilled off under reduced pressure. To the residue was added 2-propanol. The resulting crystals were collected by filtration and washed with 2-propanol and diethyl ether to give the object compound as orange crystals. The yield was 1.274 g (67%).

$^1$H-NMR (DMSO-$d_6$, 200 MHz) δ: 1.35–1.84 (10H, m), 3.00–3.45 (6H, m), 3.56–3.84 (4H, m), 4.42–4.64 (2H, m), 6.62 (1H, d, J=7.4 Hz), 6.98 (1H, d, J=9.2 Hz), 7.22 (1H, s), 7.29 (1H, dd, J=9.2 & 7.6 Hz), 7.38–7.62 (5H, m), 7.65 (1H, s), 8.82–8.95 (1H, m).

IR (KBr): 3423, 1635, 1537, 1498, 1448, 1296, 1215, 783, 746 cm$^{-1}$.

Elemental analysis for $C_{27}H_{36}N_5OSCl_3 \cdot 1.0H_2O$. Calcd.: C, 53.78; H. 6.39; N, 11.61 Found: C, 53.54; H, 6.39; N, 11.48.

Example 156

Synthesis of N-cis-[3-(4-benzyl-3,5-dimethylpiperazin-1-yl)propan-1-yl]-5-thia-1,8b-diazaacenaphthylene-4-carboxamide trihydrochloride 1) Synthesis of N-cis-[3-(4-benzyl-3,5-dimethylpiperazin-1-yl)propan-1-yl]-5-thia-1,8b-diazaacenaphthylene-4-carboxamide To a suspension of 1.0 g (4.58 mmol.) of 5-thia-1,8b-diazaacenaphthylene-4-carboxylic acid and 1.05 g (9.12 mmol.) of N-hydroxysuccinimide in acetonitrile (30 ml) was added, at room temperature, 1.76 g (9.18 mmol.) of N-ethyl-N'-3-(N,N-dimethylamino)propylcarbodimide hydrochloride. The mixture was stirred for 2 hours. To the reaction system was added a solution of 1.56 g (5.97 mmol.) of cis-4-(3-aminopropyl)-1-benzyl-2,6-dimethylpiperazine and 2.0 ml (14.3 mmol.) of triethylamine in acetonitrile (15 ml). The mixture was stirred for further one hour. The solvent was distilled off under reduced pressure. To the residue was added water, which was subjected to extraction with chloroform. The organic layer was washed with a saturated aqueous solution of sodium hydrogencarbonate and a saturated aqueous saline solution, which was dried over magnesium sulfate. Then, the solvent was distilled off under reduced pressure to leave a crude product, which was subjected to fractional purification by means of a column chromatography (methanol/ethyl acetate 30%) to afford the object compound as a reddish amorphous product. The yield was 1.00 g (48%).

$^1$H-NMR (CDCl$_3$, 200 MHz) δ: 1.03 (6H, d, J=6.2 Hz), 1.58–1.79 (2H, m), 1.83–1.94 (2H, m), 2.45–2.50 (2H, m), 2.62–2.93 (4H, m), 3.32–3.45 (2H, m), 3.77 (2H, s), 5.69 (1H, dd, J=6.2 & 1.8 Hz), 6.55–6.67 (3H, m), 6.98 (1H, s), 7.13–7.42 (5H, m), 8.03–8.14 (1H, m).

IR (KBr): 3283, 2960, 2810, 1618, 1543, 1479, 1279, 1151, 729 cm$^{-1}$.

2) Synthesis of N-cis-[3-(4-benzyl-3,5-dimethylpiperazin-1-yl)propan-1-yl]-5-thia-1,8b-diazaacenaphthylene-4-carboxamide trihydrochloride To a solution of 1.00 g (2.17 mmol.) of N-cis-[3-(4-benzyl-3.5-dimethylpiperazin-1-yl)propan-1-yl]-5-thia-1,8b-diazaacenaphthylene-4-carboxamide in ethanol (10 ml) was added 2.0 ml (36 nunol.) of 12N hydrochloric acid. The mixture was stirred for one hour. The solvent was distilled off under reduced pressure. To the residue were added 2-propanol and diethyl ether. The resulting crystals were collected by filtration and washed with 2-propanol and diethyl ether to afford the object compound as orange crystals. The yield was 0.8489 g (69%).

$^1$H-NMR (DMSO-$d_6$, 200, MHz) δ: 1.41–1.70 (6H, m), 1.78–1.98 (2H, m), 2.97–3.43 (6H, m), 3.55–3.82 (4H, m), 4.42–4.62 (2H, m), 6.61 (1H, d, J=7.4 Hz), 6.98 (1H, d, J=8.8 Hz), 7.19 (1H, s), 7.28 (1H, dd, J=9.2 & 7.2 Hz), 7.41–7.63 (5H, m), 7.66 (1H, s), 8.92–9.04 (1H, m).

IR (KBr): 3435, 3390, 1633, 1566, 1535, 1500, 1452, 1390, 1298, 1213, 785 cm$^{-1}$.

Elemental analysis for $C_{26}H_{34}N_5OSCl_3 \cdot 1.5H_2O$. Calcd.: C, 52.22; H, 6.24; N, 11.71 Found: C, 52.41; H, 6.40; N, 11.59.

Example 157

Synthesis of N-cis-[2-[4-(3-phenylpropan-1-yl)-3,5-dimethylpiperazin-1-yl]ethan-1-yl]-5-thia-1,8b-diazaacenaphthylene-4-carboxamide trihydrochloride 1) Synthesis of N-cis-[2-[4-(3-phenylpropan-1-yl)-3,5-dimethylpiperazin-1-yl]ethan-1-yl]-5-thia-1,8b-diazaacenaphthylene-4-carboxamide To s suspension of 1.0 g (4.58 mmol.) of 5-thia-1,8b-diazaacenaphthylene-4-carboxylic acid and 1.05 g (9.12 mmol.) of N-hydroxysuccinimide in acetonitrile (15 ml) was added 1.76 g (9.18 mmol.) of N-ethyl-N'-3-(N,N-dimethylamino)propylcarbodiimide hydrochloride. The mixture was stirred for 2 hours. To the reaction system was added a solution of 1.89 g (6.86 mmol.) of cis-1-(2-aminoethyl)-4-(3-phenylpropan-1-yl)-3,5-dimethylpiperazine and 2.0 ml (14.3 mmol.) of triethylamine in acetonitrile (15 ml). The mixture was stirred for 2 hours. The solvent was distilled off under reduced pressure. To the residue was added water, which was subjected to extraction with chloroform. The organic layer was washed with a saturated aqueous saline solution, which was dried over magnesium sulfate. The solvent was distilled off under reduced pressure to leave a crude product, which was purified by a column chromatography (methanol/ethyl acetate 30%) to afford the object compound as a reddish amorphous product. The yield was 1.33 g (61%).

$^1$H-NMR (CDCl$_3$, 200 MHz) δ: 1.03 (6H, d, J=5.8 Hz), 1.63–2.01 (4H, m), 2.44 (2H, t, J=5.6 Hz), 2.55 (2H, t, J=7.6 Hz), 2.61–2.88 (6H, m), 3.28–3.42 (2H, m), 5.74 (1H, dd, J=6.4 & 1.6 Hz), 6.40–6.49 (1H, m), 6.52–6.69 (3H, m), 7.03 (1H, s), 7.13–7.35 (5H, m).

IR (KBr): 3325, 2939, 2812, 1618, 1547, 1483, 1281, 1153, 773, 733, 700 cm$^{-1}$.

2) Synthesis of N-cis-[2-[4-(3-phenylpropan-1-yl)-3,5-dimethylpiperazin-1-yl]ethan-1-yl]-5-thia-1,8b-diazaacenaphthylene-4-carboxamide trihydrochloride To a solution of 1.32 g (2.78 mmol.) of N-cis-[2-[4-(3-phenylpropan-1-yl)-3,5-dimethylpiperazin-1-yl]ethan-1-yl]-5-thia-1,8b-diazaacenaphthylene-4-carboxamide in ethanol (10 ml) was added 2.0 ml (24 mmol.) of 12N hydrochloric acid. The mixture was stirred for one hour. The resulting crystals were collected by filtration, and washed with ethanol and diethyl ether to give the object compound as an orange crystalline product. The yield was 1.41 g (87%).

$^1$H-NMR (DMSO-$d_6$, 200 MHz) δ: 1.32 (6H, d, J=5.8 Hz), 1.79–2.04 (2H, m), 2.64–2.76 (2H, m), 3.07–3.39 (6H, m), 3.48–3.62 (2H, m), 3.72–4.06 (4H, m), 6.61 (1H, d, J=7.2 Hz), 6.96 (1H, d, J=9.2 Hz), 7.17–7.40 (7H, m), 7.64 (1H, s), 9.02–9.15 (1H, m).

IR (KBr): 2419, 2426, 2637, 1566, 1498, 1444, 1290, 1213 cm$^{-1}$.

Elemental analysis for $C_{27}H_{36}N_5OSCl_3$ Calcd.: C, 55.43; H, 6.20; N, 11.97 Found: C, 55.39; H, 6.23; N, 11.97.

Example 158

Synthesis of N-trans-[4-(4-benzyl-2,5-dimethylpiperazin-1-yl)butan-1-yl]-5-thia-1,8b-diazaacenaphthylene-4-carboxamide trihydrochloride 1) Synthesis of N-trans-[4-(4-benzyl-2,5-dimethylpiperazin-1-yl)butan-1-yl]-5-thia-1,8b-diazaacenaphthylene-4-carboxamide To a suspension of 1.0 g (4.58 mmol.) of 5-thia-1,8b-diazaacenaphthylene-4-carboxylic acid and 1.05 g (9.12 mmol.) of N-hydroxysuccinimide in acetonitrile (15 ml) was added, at room temperature, 1.76 g (9.18 mmol.) of N-ethyl-N'-3-(N,N-dimethylamino)propylcarbodimide hydrochloride. The mixture was stirred for 2 hours. To the reaction system was added a solution of 1.64 g (5.95 mmol.) of trans-1-(4-aminobutyl)-4-benzyl-2,5-dimethyl-piperazine and 2.0 ml (14.3 mmol.) of triethylamine in acetonitrile (15 ml). The mixture was stirred for further 2 hours. The solvent was distilled off under reduced pressure. To the residue was added water, and the mixture was subjected to extraction with chloroform. The organic layer was washed with a saturated aqueous saline solution, which was dried over magnesium sulfate, followed by distilling off the solvent to leave a crude product. The crude product was purified by means of a column chromatography (methanol/ethyl acetate 30%) to afford the object compound as a reddish amorphous product. The yield was 1.797 g (83%).

$^1$H-NMR (CDCl$_3$, 200 MHz) δ: 0.97 (3H, d, J=6.2 Hz), 1.17 (3H, d, J=5.8 Hz), 1.47–1.63 (4H, m), 1.83–2.52 (4H, m), 2.61 (1H, dd, J=11.0 & 2.8 Hz), 2.71–2.80 (1H, m), 2.84 (1H, dd, J=11.4 & 3.0 Hz), 3.05 (1H, d, J=13.2 Hz), 3.24–3.37 (2H, m), 4.09 (1H, d, J=13.2 Hz), 5.77 (1H, dd, J=6.4 & 1.8 Hz), 6.21–6.33 (1H, m), 6.57–6.70 (3H, m), 7.03 (1H, s), 7.17–7.36 (5H, m).

IR (KBr): 3325, 3253, 2935, 2800, 1618, 1547, 1279, 1151, 734 cm$^{-1}$.

2) Synthesis of N-trans-[4-(4-benzyl-2,5-dimethyl-piperazin-1-yl)butan-1-yl]-5-thia-1,8b-diazaacenaphthylene-4-carboxamide trihydrochloride To a solution of 1.65 g (3.47 mmol.) of N-trans-[4-(4-benzyl-2,5-dimethyl-piperazin-1-yl)butan-1-yl]-5-thia-1,8b-diazaacenaphthylene-4-carboxamide in ethanol (10 ml) was added 2.0 ml (24 mmol.) of 12N hydrochloric acid. The mixture was stirred for one hour. The solvent was distilled off under reduced pressure. To the residue was added 2-propanol. The resulting crystalline precipitate was collected by filtration and washed with 2-propanol and diethyl ether to give the object compound as an orange crystalline product. The yield was 1.844 g (91%).

$^1$H-NMR (DMSO-d$_6$, 200 MHz) δ: 1.30 (3H, d, J=5.6 Hz), 1.43–1.78 (7H, m), 2.93–3.90 (10H, m), 4.03–4.28 (1H, m), 4.55–4.73 (1H, m), 6.60 (1H, d, J=7.4 Hz), 6.96 (1H, d, J=8.8 Hz), 7.13–7.32 (2H, m), 7.39–7.50 (3H, m), 7.56–7.69 (3H, m), 8.77–8.92 (1H, m).

IR (KBr): 3453, 3223, 2611, 2463, 2353, 1633, 1497, 1443, 1298, 777, 746 cm$^{-1}$.

Elemental analysis for C$_{27}$H$_{36}$N$_5$OSCl$_3$ Calcd.: C, 55.43; H, 6.20; N, 11.97 Found: C, 55.37; H, 6.23; N, 11.96

Example 159

Synthesis of N-[2-(2,6-dioxo-4-(3-phenylpropan-1-yl)piperazin-1-yl)ethan-1-yl]-5-thia-1,8b-diazaacenaphthylene-4-carboxamide dihydrochloride 1) Synthesis of N-[2-(2,6-dioxo-4-(3-phenylpropan-1-yl)piperazin-1-yl)ethan-1-yl]-5-thia-1,8b-diazaacenaphthylene-4-carboxamide To a suspension of 0.8 g (3.67 mmol.) of ethyl 5-thia-1,8b-diazaacenaphthylene-4-carboxylate and 0.84 g (7.30 mmol.) of N-hydroxysuccinimide in acetonitrile (10 ml) was added, at room temperature, 1.41 g (7.36 mmol.) of N-ethyl-N'-3-(N,N-dimethylamino)propylcarbodimide. The mixture was stirred for 2 hours. To the reaction system was added a solution of 1.66 g (4.77 mmol.) of 1-(2-aminoethan-1-yl)-2,6-dioxo-4-(3-phenylpropan-1-yl)piperazine.dihydrochloride and 2.7 ml (19.4 mmol.) of triethylamine in chloroform (5 ml). The mixture was stirred for further one hour. The solvent was distilled off under reduced pressure. To the residue was added water, and the mixture was subjected to extraction with chloroform. The organic layer was washed with a saturated aqueous saline solution, which was dried over magnesium sulfate. The concentrate was purified by means of a column chromatography (methanol/ethyl acetate 20%) to afford the object compound as a reddish amorphous product. The yield was 1.56 g (89%).

$^1$H-NMR (CDCl$_3$, 200 MHz) δ: 1.72–1.92 (2H, m), 2.40–2.54 (2H, m), 2.60–2.73 (2H, m), 3.24–3.59 (6H, m), 3.97–4.06 (2H, m), 5.73 (1H, dd, J=6.2 & 1.4 Hz), 6.23–6.35 (1H, m), 6.54–6.66 (3H, m), 7.01 (1H, s), 7.11–7.35 (5H, m).

IR (KBr): 3350, 2941, 1736, 1682, 1620, 1545, 1346, 1279, 1234, 1182, 1151, 748, 700, 644 cm$^{-1}$.

2) Synthesis of N-[2-(2,6-dioxo-4-(3-phenylpropan-1-yl)piperazin-1-yl)ethan-1-yl]-5-thia-1,8b-diazaacenaphthylene-4-carboxamide dihydrochloride To a solution of 1.56 g (3.28 mmol.) of N-[2-(2,6-dioxo-4-(3-phenylpropan-1-yl)piperazin-1-yl)ethan-1-yl]-5-thia-1,8b-diazaacenaphthylene-4-carboxamide in ethanol (10 ml) was added, at room temperature, 2 ml (24 mmol.) of 12N hydrochloric acid. The mixture was stirred for several minutes, which was concentrated under reduced pressure to leave crystals. To the crystals was added ethanol, which was subjected to filtration to collect the crystals. The crystals was washed with ethanol and diethyl ether to give the object compound as an orange crystalline product. The yield was 1.20 g (66%).

$^1$H-NMR (DMSO-d$_6$, 200 MHz) δ: 1.87–2.08 (2H, m), 2.61–2.68 (2H, m), 2.96–3.13 (2H, m), 3.20–3.36 (2H, m), 3.72–3.85 (2H, m), 4.13 (4H, br s), 6.64 (1H, d, J=7.2 Hz), 6.97 (1H, d, J=9.2 Hz), 7.12 (1H, s), 7.14–7.37 (6H, m), 7.64 (1H, s), 8.81–8.92 (1H, m)

IR (KBr): 3260, 2952, 2590, 1745, 1697, 1633, 1562, 1529, 1500, 1438, 1345, 1293, 1212, 780, 630 cm$^{-1}$.

Elemental analysis for C$_{25}$H$_{27}$N$_5$O$_3$SCl$_2$·2.0H$_2$O. Calcd.: C, 51.37; H, 5.35; N, 11.98 Found: C, 51.69; H, 5.28; N, 12.05.

Example 160

Synthesis of N-[1-[3-(4-ethoxycarbonylphenoxy)propan-1-yl]piperidin-4-yl]-5-thia-1,8b-diazaacenaphthylene-4-carboxamide dihydrochloride 1) Synthesis of N-[1-[3-(4-ethoxycarbonylphenoxy)propan-1-yl]piperidin-4-yl]-5-thia-1,8b-diazaacenaphthylene-4-carboxamide To a solution of 0.80 g (2.14 mmol.) of N-(piperidin-4-yl)-5-thia-1,8b-diazaacenaphthylene-4-carboxamide.dihydrochloride, 1.5 ml (10.76 mmol.) of triethylamine and 0.38 g of sodium iodide in ethanol (20 ml) was added, at room temperature, 0.62 g (2.55 mmol.) of ethyl 4-(3-chloro-1-propoxy)benzoate. The mixture was heated under reflux for two days under nitrogen atmosphere. The reaction mixture was cooled to room temperature, to which was added water, followed by subjecting to extraction with ethyl acetate. The organic layer was washed with a saturated aqueous saline solution, dried over magnesium sulfate, and concentrated. The concentrate was purified by means of a column chromatography (methanol/ethyl acetate 20–40%) to give the object compound as a reddish solid product (758.4 mg, 75%). The product was recrystallized from ethanol to afford the object compound as reddish crystals.

$^1$H-NMR (CDCl$_3$, 200 MHz) δ: 1.38 (3H, t, J=7.2 Hz), 1.37–1.55 (2H, m), 1.87–2.03 (4H, m), 2.06–2.22 (2H, m), 2.49–2.56 (2H, m), 2.79–2.94 (2H, m), 3.74–3.94 (1H, m), 4.07 (2H, t, J=6.2 Hz), 4.35 (2H, q, J=7.2 Hz), 5.47–5.58 (1H, m), 5.80 (1H, dd, J=6.2 & 1.6 Hz), 6.59–6.71 (3H, m), 6.91 (2H, d, J=8.8 Hz), 7.07 (1H, s), 7.99 (2H, d, J=8.8 Hz).

IR (KBr): 3280, 2945, 1706, 1608, 1536, 1511, 1482, 1280, 1257, 1172, 1056, 954, 883, 844, 771 cm$^{-1}$.

2) Synthesis of N-[1-[3-(4-ethoxycarbonylphenoxy) propan-1-yl]piperidin-4-yl]-5-thia-1,8b-diazaacenaphthylene-4-carboxamide dihydrochloride To a solution of 329.7 mg (0.65 mmol.) of N-[1-[3-(4-ethoxycarbonylphenoxy)propan-1-yl]piperidin-4-yl]-5-thia-1,8b-diazaacenaphthylene-4-carboxamide in ethanol (5 ml) was added, at room temperature, 2 ml (24 mmol.) of 12N hydrochloric acid. The mixture was stirred for one hour. The resulting crystalline precipitate was collected by filtration, followed by washing with ethanol and diethyl ether to afford the object compound (369.8 mg, 98%) as orange crystals. m.p.162–166° C.

$^1$H-NMR (DMSO-d$_6$, 200 MHz) δ: 1.31 (6H, t, J=7.0 Hz), 1.83–2.10 (4H, m), 2.15–2.32 (2H, m), 2.89–3.24 (4H, m), 3.44–3.60 (2H, m), 3.74–3.96 (1H, m), 4.08–4.21 (2H, m), 4.28 (2H, q, J=7.0 Hz), 6.58 (1H, d, J=7.4 Hz), 6.95 (1H, d, J=8.8 Hz), 7.05 (2H, d, J=9.2 Hz), 7.20–7.29 (2H, m), 7.62 (1H, s), 7.92 (2H, d, J=9.2 Hz), 8.79–8.87 (1H, m).

IR (KBr): 3265, 2945, 2636, 1697, 1633, 1605, 1534, 1511, 1255, 1216, 1170, 1128, 1112, 852, 771 cm$^{-1}$.

Elemental analysis for C$_{27}$H$_{32}$N$_4$O$_4$SCl$_2$·2.0H$_2$O. Calcd.: C, 52.68; H, 5.89; N, 9.10 Found: C, 52.96; H, 5.68; N, 8.94.

Example 161

Synthesis of N-[1-[3-(3-ethoxycarbonylphenoxy) propan-1-yl]piperidin-4-yl]-5-thia-1,8b-diazaacenaphthylene-4-carboxamide dihydrochloride 1) Synthesis of N-[1-[3-(3-ethoxycarbonylphenoxy) propan-1-yl]piperidin-4-yl]-5-thia-1,8b-diazaacenaphthylene-4-carboxamide To a solution of 0.80 g (2.14 mmol.) of N-(piperidin-1-yl)-5-thia-1,8b-diazaacenaphthylene-4-carboxamide dihydrochloride, 1.5 ml (10.76 mmol.) of triethylamine and 0.38 g of sodium iodide in ethanol (20 ml) was added, at room temperature, 0.62 g (2.55 mmol.) of ethyl 4-(3-chloro-1-propoxy)benzoate. The mixture was heated under reflux for 2 days under nitrogen atmosphere. The reaction mixture was cooled to room temperature. To the reaction system was then added water, which was subjected to extraction with ethyl acetate. The organic layer was washed with a saturated aqueous saline solution, which was dried over magnesium sulfate, followed by concentration. The concentrate was purified by means of a column chromatography (methanol/ethyl acetate 30–40%) to afford the object compound (636.2 mg, 59%) as red crystals.

$^1$H-NMR (CDCl$_3$, 200 MHz) δ: 1.40 (3H, t, J=7.2 Hz), 1.41–1.58 (2H, m), 1.88–2.04 (4H, m), 2.06–2.21 (2H, m), 2.49–2.56 (2H, m), 2.80–2.94 (2H, m), 3.73–3.94 (1H, m), 4.01 (2H, t, J=6.2 Hz), 4.38 (2H, q, J=7.2 Hz), 5.57 (1H, d, J=8.2 Hz), 5.80 (1H, dd, J=6.2 & 1.6 Hz), 6.59–6.71 (3H, m), 7.06 (1H, s), 7.04–7.12 (1H, m), 7.30–7.38 (1H, m), 7.53–7.67 (2H, m).

IR (KBr): 3275, 2952, 1720, 1610, 1540, 1278, 1232, 1162, 873, 771 cm$^{-1}$.

2) Synthesis of N-[1-[3-(3-ethoxycarbonylphenoxy) propan-1-yl]piperidin-4-yl]-5-thia-1,8b-diazaacenaphthylene-4-carboxamide dihydrochloride To a solution of 473.3 mg (0.93 mmol.) of N-[1-[3-(3-ethoxycarbonylphenoxy)propan-1-yl]piperidin-4-yl]-5-thia-1,8b-diazaacenaphthylene-4-carboxamide in ethanol (5 ml) was added, at room temperature, 2 ml (24 mmol.) of 12N hydrochloric acid. The mixture was stirred for several minutes. The reaction mixture was concentrated under reduced pressure. To the concentrate was added ethanol. The resulting crystals were collected by filtration and washed with ethanol and diethyl ether to give the object compound (425.4 mg, 79%) as orange crystals, m.p.140–145° C.

$^1$H-NMR (DMSO-d$_6$, 200 MHz) δ: 1.32 (3H, t, J=7.0 Hz), 1.84–2.08 (4H, m), 2.14–2.31 (2H, m), 2.94–3.28 (4H, m), 3.47–3.61 (2H, m), 3.79–3.96 (1H, m), 4.08–4.20 (2H, m), 4.31 (2H, q, J=7..0 Hz), 6.59 (1H, d, J=7.4 Hz), 6.96 (1H, d, J=8.4 Hz), 7.18–7.30 (3H, m), 7.42–7.63 (4H, m), 8.85 (1H, d, J=7.2 Hz).

IR (KBr): 3370, 3053, 2607, 1699, 1635, 1565, 1540, 1444, 1290, 1233, 1203, 1124, 813, 751 cm$^{-1}$.

Elemental analysis for C$_{27}$H$_{32}$N$_4$O$_4$SCl$_2$·2.0H$_2$O. Calcd.: C, 52.68; H, 5.89; N, 9.10 Found: C, 52.80; H, 5.76; N, 9.17.

Example 162

Synthesis of N-[1-[3-(2-methoxycarbonylphenoxy) propan-1-yl]piperidin-4-yl]-5-thia-1,8b-diazaacenaphthylene-4-carboxamide dihydrochloride 1) Synthesis of N-[1-[3-(2-methoxycarbonylphenoxy) propan-1-yl]piperidin-4-yl]-5-thia-1,8b-diazaacenaphthylene-4-carboxamide To a solution of 0.80 g (2.14 mmol.) of N-(piperidin-4-yl)-5-thia-1,8b-diazaacenaphthylene-4-carboxamide dihydrochloride, 1.5 ml (10.76 mmol.) of triethylamine and 0.65 g (4.27 mmol.) of 1,8-diazabicyclo[5.4.0]unde-7-cene (DBU) in acetonitrile (20 ml) were added, at room temperature, 0.38 g of sodium iodide and 0.59 g (2.58 mmol.) of methyl 2-(3-chloro-1-propoxy)benzoate. The mixture was heated under reflux for 3 days under nitrogen atmosphere. The solvent was distilled off under reduced pressure. To the residue was added water, which was subjected to extraction with chloroform. The organic layer was washed with a saturated aqueous saline solution, which was dried over magnesium sulfate, followed by concentration. The concentrate was purified by means of a column chromatography (methanol/ethyl acetate 30–50%), followed by distilling off the solvent under reduced pressure to afford the object compound (0.81 g, 77%) as a reddish amorphous product.

$^1$H-NMR (CDCl$_3$, 200 MHz) δ: 1.37–1.61 (2H, m), 1.87–2.23 (4H, m), 2.57 (2H, t, J=7.4 Hz), 2.80–2.95 (2H, m), 3.89 (3H, s), 4.09 (2H, t, J=6.2 Hz), 5.51–5.62 (1H, m), 5.80 (1H, dd, J=6.2 & 1.8 Hz), 6.59–6.71 (3H, m), 6.94–7.02 (2H, m), 7.05 (1H, s), 7.40–7.49 (1H, m), 7.76–7.80 (1H, m).

IR (KBr): 3230, 2949, 1727, 1617, 1540, 1482, 1454, 1286, 1249, 1151, 1085, 772, 757 cm$^{-1}$.

2) Synthesis of N-[1-[3-(2-methoxycarbonylphenoxy)propan-1-yl]piperidin-4-yl]-5-thia-1,8b-diazaacenaphthylene-4-carboxamide dihydrochloride To a solution of 0.81 g (1.64 inmol.) of N-[1-[3-(2-methoxycarbonylphenoxy)propan-1-yl]piperidin-4-yl]-5-thia-1,8b-diazaacenaphthylene-4-carboxamide in ethanol (5 ml) was added, at room temperature, 1 ml (12 mmol.) of 12N hydrochloric acid. The mixture was stirred for several minutes. The reaction mixture was concentrated, to which was added acetonitrile. The resulting crystalline precipitate was collected by filtration, which was washed with ethanol and diethyl ether to give the object compound (809.1 mg, 87%) as orange crystals, m.p.164–168° C.

$^1$H-NMR (DMSO-$d_6$, 200 MHz) δ: 1.82–2.07 (4H, m), 2.15–2.32 (2H, m), 2.94–3.26 (4H, m), 3.43–3.58 (2H, m), 3.78–3.99 (1H, m), 3.83 (3H, s), 4.10–4.20 (2H, m), 6.60 (1H, d, J=7.4 Hz), 6.95–7.07 (2H, m), 7.14–7.32 (3H, m), 7.50–7.71 (3H, m), 8.87 (1H, d, J=6.8 Hz).

IR (KBr): 3159, 2643, 1687, 1629, 1314, 1247, 764 cm$^{-1}$.

Elemental analysis for $C_{26}H_{30}N_4O_4SCl_2 \cdot 0.5H_2O$. Calcd.: C, 54.36; H, 5.44; N, 9.75 Found: C, 54.30; H, 5.72; N, 9.80.

Example 163

2-[3-[4-(5-thia-1,8b-diazaacenaphthylene-4-carbonylamino)piperidin-1-yl]propan-1-yloxy]benzoic acid dihydrochloride N-[1-[3-(2-methoxycarbonylphenoxy)-propan-1-yl]-5-thia-1,8b-diazaacenaphthylene-4-carboxamide (400 mg) was mixed with 6N hydrochloric acid (20 ml). The mixture was stirred for 2.5 hours at 80° C. The solvent was distilled off under reduced pressure. The resulting crystals were collected by filtration and washed with isopropyl ether to give the object compound (379 mg, 97%), m.p.180–183° C.

$^1$H-NMR (DMSO-$d_6$, 200 MHz) δ: 10.70-10.40 (1H, br s), 8.89 (1H, d, J=7.4 Hz), 7.75-7.60 (2H, m), 7.60-7.40 (1H, m), 7.40-7.20 (2H, m), 7.20-6.90 (3H, m), 6.64 (1H, d, J=7.4 Hz), 4.20-2.80 (9H, m), 2.40-1.80 (6H, m).

IR (KBr) v: 3000, 1695, 1635, 1538, 1496, 1436, 1394, 1230, 1087, 1016, 753 cm$^{-1}$.

Elemental analysis for $C_{25}H_{28}N_4SCl_2 \cdot 3.5H_2O$. Calcd.: C, 48.86; H, 5.74; N, 9.12 Found: C, 48.62; H, 5.51; N, 9.13.

Example 164

3-[3-[4-(5-thia-1,8b-diazaacenaphthylene-4-carbonylamino)piperidin-1-yl]propan-1-yloxy]benzoic acid dihydrochloride N-[1-[3-(3-ethoxycarbonylphenoxy)-propan-1-yl]-5-thia-1,8b-diazaacenaphthylene-4-carboxamide (400 mg) was mixed with 6N hydrochloric acid. The mixture was stirred for 4 hours at 80° C. The resulting crystals were collected by filtration and washed with water to give the object compound (255 mg). The filtrate was concentrated under reduced pressure. The resulting crystals were collected by filtration and washed with isopropyl ether to give an additional object compound (122 mg) (total 377 mg, 87%), m.p.224–230° C.

$^1$H-NMR (DMSO-$d_6$, 200 MHz) δ: 8.90-8.75 (1H, m), 7.64-7.36 (4H, m), 7.30-7.15 (2H, m), 6.95 (1H, d, J=9.2 Hz), 6.58 (1H, d, J=7.8 Hz), 4.29-3.00 (9H, m), 2.35-2.10 (2H, m), 2.10–1.80 (4H, m).

IR (KBr) v: 3000, 1706, 1635, 1565, 1538, 1500, 1448, 1388, 1212, 1112, 952, 786, 763 cm$^{-1}$.

Elemental analysis for $C_{25}H_{28}N_4O_4SCl_2 \cdot 4.5H_2O$. Calcd.: C, 47.47; H, 5.90; N, 8.86 Found: C, 47.39; H, 5.62; N, 9.10.

Example 165

4-[3-[4-(5-thia-1,8b-diazaacenaphthylene-4-carbonylamino)piperidin-1-yl]propan-1-yloxy]benzoic acid dihydrochloride N-[1-[3-(4-ethoxycarbonylphenoxy)-propan-1-yl]-5-thia-1,8b-diazaacenaphthylene-4-carboxamide (400 mg) was mixed with 6N hydrochloric acid (20 ml). The mixture was stirred for 5 hours at 80° C. The resulting crystals were collected by filtration and washed with water to give the object compound (397 mg, 91%), m.p.277–280° C.

$^1$H-NMR (DMSO-$d_6$, 200 MHz) δ: 7.90 (2H, d, J=8.8 Hz), 7.58 (1H, s), 7.15–7.26 (2H, m), 7.03 (2H, d, J=8.8 Hz), 6.92 (1H, d, J=9.6 Hz), 6.53 (1H, d, J=8.0 Hz), 4.05–4.20 (1H, m), 3.15–4.00 (8H, m), 2.10–2.30 (2H, m), 1.80–2.00 (4H, m).

IR (KBr) v: 3051, 1683, 1633, 1606, 1569, 1502, 1440, 1316, 1259, 1212, 1168, 773 cm$^{-1}$.

Elemental analysis for $C_{25}H_{28}N_4O_4SCl_2 \cdot 4.0H_2O$. Calcd.: C, 48.16; H, 5.82; N, 8.99 Found: C, 48.18; H, 5.73; N, 9.08.

Example 166

N-[1-[3-(2-cyanophenyloxy)propan-1-yl]piperidin-4-yl)-5-thia-1,8b-diazaacenaphthylene-4-carboxamide dihydrochloride 1) N-[1-[3-(2-cyanophenyloxy)propan-1-yl]piperidin-4-yl]-5-thia-1,8b-diazaacenaphthylene-4-carboxamide 2-(3-Chloropropan-1-yl)oxybenzonitrile (503 mg) was added, at room temperature, to an acetonitrile solution (20 ml) of N-(piperidin-4-yl)-5-thia-1,8b-diazaacenaphthylene-4-carboxamide dihydrochloride (800 mg), 1,8-diazabicyclo[5.4.0]-7-undecene (662 mg), triethylamine (1.09 g) and sodium iodide (285 mg). The mixture was heated under reflux for 7.5 hours under nitrogen atmosphere. The reaction mixture was concentrated under reduced pressure. To the concentrate was added water, which was subjected to extraction with chloroform. The extract solution was washed with a saturated aqueous saline solution, which was dried over anhydrous magnesium sulfate, followed by concentration under reduced pressure. The concentrate was purified by means of a silica gel column chromatography (ethyl acetate/methanol=2/1) to afford the object compound (816 mg, 83%) as a reddish purple oily product.

$^1$H-NMR (CDCl$_3$, 200 MHz) δ: 7.55 (2H, d, J=8.0 Hz), 7.06–6.95 (3H, m), 6.78 (1H, s), 6.63 (1H, d, J=5.8 Hz), 6.10-5.80 (1H, m), 5.78 (1H, dd, J=1.8 & 5.8 Hz), 4.16 (2H, t, J=6.0 Hz), 4.00-3.80 (1H, m), 3.60-3.40 (2H, m), 3.10-2.90 (2H, m), 2.83-2.65 (2H, m), 2.20–1.90 (6H, m), 1.85-1.60 (2H, m).

2) N-[1-[3-(2-cyanophenyloxy)propan-1-yl]piperidin-4-yl]-5-thia-1,8b-diazaacenaphthylene-4-carboxamide dihydrochloride To an ethanol solution (8.0 ml) of N-[1-[3-(2-cyanophenyloxy)propan-1-yl]piperidin-4-yl]-5-thia-1,8b-diazaacenaphthylene-4-carboxamide (565 mg) was added conc. hydrochloric acid (3.0 ml). The mixture was stirred for 15 minutes at room temperature. The resulting crystals were collected by filtration and washed with ethanol to give the object compound (462 mg, 70%), m.p.234–240° C.

$^1$H-NMR (DMSO-d$_6$, 200 MHz) δ: 8.90-8.78 (1H, m), 7.80-7.58 (3H, m), 7.34-7.06 (4H, m), 6.96 (1H, d, J=8.8 Hz), 6.59 (1H, d, J=7.2 Hz), 4.40-4.20 (2H, m), 4.00-2.80 (7H, m), 2.40-2.20 (2H, m), 2.20-1.80 (4H, m).

IR (KBr) ν: 3290, 3031, 2638, 2225, 1644, 1633, 1569, 1540, 1498, 1450, 1291, 1263, 1218, 1112, 796 cm$^{-1}$.

Elemental analysis for C$_{25}$H$_{27}$N$_5$O$_2$SCl$_2$·2.0H$_2$O. Calcd.: C, 52.82; H, 5.50; N, 12.32 Found: C, 52.89; H, 5.24; N, 12.29

Example 167

N-[1-[3-(3-Cyanophenyloxy)propan-1-yl]piperidin-4-yl]-5-thia-1,8b-diazaacenaphthylene-4-carboxamide dihydrochloride 1) N-[1-[3-(3-Cyanophenyloxy)propan-1-yl]piperidin-4-yl]-5-thia-1,8b-diazaacenaphthylene-4-carboxamide 3-(3-Chloropropan-1-yl)oxybenzonitrile (503 mg) was added, at room temperature, to an acetonitrile solution (20 ml) of N-(piperidin-4-yl)-5-thia-1,8b-diazaacenaphthylene-4-carboxamide dihydrochloride (800 mg), 1,8b-diazabicyclo[5.4.0]-7-undecene (662 mg), triethylamine (1.09 g) and sodium iodide (285 mg). The mixture was heated under reflux for 6.5 hours under nitrogen atmosphere. The reaction mixture was concentrated under reduced pressure. To the concentrate was added water, which was subjected to extraction with chloroform. The extract solution was washed with a saturated aqueous saline solution, dried over anhydrous magnesium sulfate and concentrated under reduced pressure. The concentrate was purified by means of a silica gel chromatography (ethyl acetate/methanol=2/1) to afford the object compound (565 mg, 57%) as reddish purple crystals.

$^1$H-NMR (CDCl$_3$, 200 MHz) δ: 7.48-7.00 (4H, m), 6.80-6.58 (3H, m), 5.90-5.70 (2H, m), 4.04 (2H, t, J=6.1 Hz), 3.95-3.70 (1H, m), 3.00-2.81 (2H, m), 2.55 (2H, t, J=7.0 Hz), 2.30-1.80 (6H, m), 1.70-1.40 (2H, m).

2) N-[1-[3-(3-cyanophenyloxy)propan-1-yl]piperidin-4-yl]-5-thia-1,8b-diazaacenaphthylene-4-carboxamide dihydrochloride To an ethanol solution (8.0 ml) of N-[1-[3-(3-cyanophenyloxy)propan-1-yl]piperidin-4-yl]-5-thia-1,8b-diazaacenaphthylene-4-carboxamide (565 mg) was added conc. hydrochloric acid. The mixture was stirred for 15 minutes at room temperature. The resulting crystals were collected by filtration and washed with ethanol (4622 mg, 70%), m.p.169–172° C.

$^1$H-NMR (DMSO-d$_6$, 200 MHz) δ: 8.90-8.80 (1H, m), 7.62-7.39 (4H, m), 7.38-7.18 (3H, m), 6.95 (1H, d, J=8.6 Hz), 6.58 (1H, d, J=7.2 Hz), 4.20-4.10 (2H, m), 4.00-2.90 (7H, m), 2.20-2.10 (2H, m), 2.10-1.80 (4H, m).

IR (KBr) ν: 3224, 3055, 2549, 2227, 1635, 1565, 1502, 1432, 1317, 1301, 1264, 1214, 784 cm$^{-1}$.

Elemental analysis for C$_{25}$H$_{27}$N$_5$O$_2$SCl$_2$·2.0H$_2$O. Calcd.: C, 52.82; H, 5.50; N, 12.32 Found: C, 52.92; H, 5.34; N, 12.28.

Example 168

N-[1-[3-(4-Cyanophenyloxy)propan-1-yl]piperidin-4-yl]-5-thia-1,8b-diazaacenaphthylene-4-carboxamide dihydrochloride 1) 4-(3-Chloropropan-1-yl)oxybenzonitrile (503 mg) added, at room temperature, to an acetonitrile solution (20 ml) of N-(piperidin-4-yl)-5-thia-1,8b-diazaacenaphthylene-4-carboxamide dihydrochloride (800 mg), 1,8-diazabicyclo[5.4.0]-7-undecene (662 mg), triethylamine (1.09 g) and sodium iodide (285 mg). The mixture was heated under reflux for 19 hours under nitrogen atmosphere. The reaction mixture was concentrated under reduced pressure. To the concentrate was added water, and the mixture was subjected to extraction with chloroform. The extract solution was washed with a saturated aqueous saline solution, which was dried over anhydrous magnesium sulfate, followed by concentration under reduced pressure. The concentrate was purified by means of a silica gel chromatography (ethyl acetate/methanol=2/1) to afford the object compound (733 mg, 74%) as a reddish purple crystals.

$^1$H-NMR (CDCl$_3$, 200 MHz) δ: 7.58 (2H, d, J=8.8 Hz), 7.05 (1H, s), 6.94 (2H, d, J=8.8 Hz), 6.96-6.58 (3H, m), 5.88-5.74 (1H, m), 5.79 (1H, dd, J=1.8 & 6.2 Hz), 4.07 (2H, t, J=5.8 Hz), 4.00-3.75 (1H, m), 3.05-2.90 (2H, m), 2.61 (2H, t, J=7.0 Hz), 2.35-1.90 (6H, m), 1.80-1.50 (2H, m).

2) N-[1-[3-(4-Cyanophenyloxy)propan-1-yl]piperidin-4-yl]-5-thia-1,8b-diazaacenaphthylene-4-carboxamide dihydrochloride Conc. hydrochloric acid (3.0 ml) was added to an ethanol solution (8.0 ml) of N-[1-[3-(2-cyanophenyloxy)propan-1-yl]piperidin-4-yl]-5-thia-1,8b-diazaacenaphthylene-4-carboxamide (621 mg). The mixture was stirred for 15 minutes at room temperature. The resulting crystals were collected by filtration and washed with ethanol to give the object compound (572 mg, 79%), m.p.268–272° C.

$^1$H-NMR (DMSO-d$_6$, 200 MHz) δ: 8.86 (1H, d, J=7.8 Hz), 7.78 (2H, d, J=9.2 Hz), 7.68-7.58 (1H, m), 7.34-7.18 (2H, m), 7.11 (2H, d, J=9.2 Hz), 6.97 (1H, d, J=8.0 Hz), 6.60 (1H, d, J=7.6 Hz), 4.30-4.10 (2H, m), 4.00--2.94 (7H, m), 2.40-2.15 (2H, m), 2.15-1.80 (4H, m).

IR (KBr) ν: 3212, 3055, 2219, 1631, 1604, 1569, 1538, 1506, 1297, 1263, 1168, 1126, 834, 792 cm$^{-1}$.

Elemental analysis for C$_{25}$H$_{27}$N$_5$O$_2$SCl$_2$·0.8H$_2$O. Calcd.: C, 54.90; H, 5.27; N, 12.81 Found: C, 54.91; H, 5.06; N, 12.96.

Example 169

Synthesis of N-[1-(3-phenylpropan-1-yl)piperidin-4-yl]-5-thia-1,8b-diazaacenaphthylene-4-carboxamide Oxalyl chloride (4.00 ml) was added dropwise to a suspension of 5-thia-1,8b-diazaacenaphthylene-4-carboxylic acid (5.00 g), tetrahydrofuran (40 ml) and dimethylformamide (0.89 ml) for 10 minutes with cooling with ice. This was stirred for 2 hours at room temperature. The reaction solution was concentrated (concentrated material). Triethylamine (19.8 ml) was added dropwise to a suspension of 4-amino-1-(3-phenylpropyl)piperidine dihydrochloride (7.34 g) and dimethylformamide (20 ml). Insoluble materials were filtered out from the reaction mixture which was stirred for 30 minutes (amine solution). The amine solution was added dropwise to a suspension of the concentrated material and dimethylformamide (20 ml) for 1 hour at 50° C. (inner temperature), and then the reaction mixture was stirred for 1 hour at 50° C. (inner temperature). The reaction mixture which was added water (200 ml) and 1N-sodium hydroxide (20 ml) was extracted by ethyl acetate:tetrahydrofuran=4:1 (100 ml×3). The organic layer was washed with three times of 1N-sodium hydroxide (50 ml) and water (150 ml). Ethyl acetate:isopropyl ether=1:1 (20 ml) was added into the residual crystal obtained by concentrating the organic layer, and the mixture was stirred for 2 hours at room temperature, and then filtered. The residue was dried under reduced pressure to obtain N-[1-(3-phenylpropan-1-yl)piperidin-4-yl]-5-thia-1,8b-diazaacenaphthylene-4-carboxamide (7.45 g, 77.7%).

$^1$H-NMR (CDCl$_3$, 300 MHz, 2H) δ: 1.45–1.50 (m, 2H), 1.77–1.85 (m, 2H), 1.91–1.95 (d, J=12.68 Hz, 2H), 2.04–2.11 (t, J=9.62 Hz, 2H), 2.33–2.38(t, J=7.89 Hz, 2H), 2.60–2.65 (t, J=7.79 Hz, 2H), 2.81–2.85 (d, J=11.94 Hz, 2H), 3.79–3.81 (m, 1H), 5.68–5.70 (d, J=7.73 Hz, 1H), 5.76–5.78 (m, 1H), 6.58–6.68 (m, 3H), 7.03 (s, 1H), 7.16–7.20 (m, 3H), 7.25–7.30 (m, 2H).

Example 170

Synthesis of N-[1-(3-phenylpropan-1-yl)piperidin-4-yl]-5-thia-1,8b-diazaacenaphthylene-4-carboxamide Triethylamine (6.7 ml) was added dropwise to a suspension of 4-amino-1-(3-phenylpropyl)piperidine dihydrochloride (7.01 g) and dimethylformamide (40 ml). The mixture was stirred for 10 minutes. 5-Thia-1,8b-diazaacenaphthylene-4-carboxylic acid (5.00 g), 1-hydroxy-1H-benzotriazole monohydrate (0.710 g) and 1-ethyl-3-(3-dimethylaminopropyl)-carbodiimide (4.61 g) were added into the reaction mixture. This was stirred for 2 hours at 68–70° C. (inner temperature). Ethyl acetate:tetrahydrofuran=4:1 (380 ml), 1N-sodium hydroxide (50 ml) and water (80 ml) were added into the reaction solution. The aqueous layer was extracted by ethyl acetate:tetrahydrofuran=4:1 (120 ml×2). The organic layer was washed with water (130 ml×3), and then concentrated. The residue which was added ethyl acetate (15 ml) was stirred for 2 hours at room temperature. The reaction mixture was dried under reduced pressure to obtain N-[1-(3-phenylpropan-1-yl)piperidin-4-yl]-5-thia-1,8b-diazaacenaphthylene-4-carboxamide (8.87 g, 92.5%).

$^1$H-NMR (CDCl$_3$, 300 MHz) δ: 1.45–1.50 (m, 2H), 1.77–1.85 (m, 2H), 1.91–1.95 (d, J=12.68 Hz, 2H), 2.04–2.11 (t, J=9.62 Hz, 2H), 2.33–2.38 (t, J=7.89 Hz, 2H), 2.60–2.65 (t, J=7.79 Hz, 2H), 2.81–2.85 (d, J=11.94 Hz, 2H), 3.79–3.81 (m, 1H), 5.68–5.70 (d, J=7.73 Hz, 1H), 5.76–5.78 (m, 1H), 6.58–6.68 (m, 3H), 7.03 (s, 1H), 7.16–7.20 (m, 3H), 7.25–7.30 (m, 2H).

Example 171

Synthesis of N-[1-(3-phenylpropan-1-yl)piperidin-4-yl]-5-thia-1,8b-diazaacenaphthylene-4-carboxamide Triethylamine (1.34 ml) was added dropwise to a suspension of 4-amino-1-(3-phenylpropyl)piperidine dihydrochloride (1.40 g) and dimethylformamide (10 ml). Into the mixture which was stirred for 10 minutes, 5-thia-1,8b-diazaacenaphthylene-4-carboxylic acid (1.00 g) and diethyl cyanophosphonate (0.81 ml) were added. The mixture was stirred for 1 hour at room temperature, and 2 hours at 55° C. Ethyl acetate:tetrahydrofuran=4:1 (1.75 ml) and 1N-sodium hydroxide (30 ml) were added into the reaction mixture. The organic layer which was washed with sodium hydroxide (30 ml×3) and water (30 ml×2) was concentrated. The residual crystal which was added acetate (4 ml) was stirred for 1 hour at room temperature. This was dried under reduced pressure to obtain N-[1-(3-phenylpropan-1-yl)piperidin-4-yl]-5-thia-1,8b-diazaacenaphthylene-4-carboxamide (1.07 g, 63.6%).

$^1$H-NMR (CDCl$_3$, 300 MHz) δ: 1.45–1.50 (m, 2H), 1.77–1.85 (m, 2H), 1.91–1.95 (d, J=12.68 Hz, 2H), 2.04–2.11 (t, J=9.62 Hz, 2H), 2.33–2.38 (t, J=7.89 Hz, 2H), 2.60–2.65 (t, J=7.79 Hz, 2H), 2.81–2.85 (d, J=11.94 Hz, 2H), 3.79–3.81 (m, 1H), 6.58–6.68 (m, 3H), 7.03 (s, 1H), 7.16–7.20 (m, 3H), 7.25–7.30 (m, 2H).

Example 172

Synthesis of N-[3-(4-Phenylmethyl-2-oxopiperazin-1-yl)propan-1-yl]-5-thia-1,8b-diazaacenaphthylene-4-carboxamide dihydrochloride 1) Synthesis of N-[3-(4-tert-Butoxycarbonyl-2-oxopiperazin-1-yl)propan-1-yl]-5-thia-1,8b-diazaacenaphthylene-4-carboxamide 1-Ethyl-3-(3-dimethylaminopropyl)carbodiimide hydrochloride (4.22 g, 22.0 mmol) was added to a stirred suspension of 5-thia-1,8b-diazaacenaphtylene-4-carboxylic acid (2.40 g, 11.0 mmol) and N-hydroxysuccinimide (2.53 g, 22.0 mmol) in acetonotrile (30 ml) at room temperature and the mixture was stirred at room temperature for 1.5 hours. A solution of 1-(3-aminopropan-1-yl)-4-tert-butoxycarbonyl-2-oxopiperazine (3.67 g, 14.3 mmol) and triethylamine (4.45 g, 44.0 mmol) in acetonitrile (15 ml) was added to the mixture. After stirring at room temperature for 19 hours, the reaction mixture was concentrated in vacuo. The residue was dissolved in water and extracted with chloroform. The extract was washed with brine, dried over MgSO$_4$ and concentrated in vacuo. The residue was chromatographed on silica gel (50 g) with Ethyl acetate-Methanol (10:1) to give N-[3-(4-tert-butoxycarbonyl-2-oxopiperazin-1-yl)propan-1-yl]-5-thia-1,8b-diazaacenaphthylene-4-carboxamide as a purple amorphous powder(1.53 g, 30%).

$^1$H-NMR (200 MHz, CDCl$_3$) δ: 7.45-7.30 (1H, m), 7.03 (1H, s), 6.70-6.55 (3H, m), 5.75 (1H, dd, J=6.0 and 1.8 Hz), 4.13 (2H, s), 3.75-3.60 (2H, m), 3.60-3.40 (2H, m), 3.40-3.30 (2H, m), 3.30-3.15 (2H, m), 1.85-1.60 (2H, m), 1.48 (9H, s).

IR (KBr) : 3269, 2977, 2931, 1695, 1644, 1482, 1419, 1284, 1164 cm$^{-1}$.

2) Synthesis of N-[3-(2-Oxopiperazin-1-yl)propan-1-yl]-5-thia-1,8b-diazaacenaphthylene-4-carboxamide dihydrochloride Concentrated hydrochloric acid (4.0 ml) was added to N-[3-(4-tert-butoxycarbonyl-2-oxopiperazin-1-yl)propan-1-yl]-5-thia-1,8b-diazaacenaphthylene-4-carboxamide (1.53 g, 3.34 mmol) and the mixture was stirred at room temperature for 30 minutes. The reaction mixture was concentrated in vacuo to give N-[3-(2-oxopiperazin-1-yl)propan-1-yl]-5-thia-1,8b-diazaacenaphthylene-4-carboxamide dihydrochloride as an orange amorphous powder(1.53 g, quant.).

$^1$H-NMR (200 MHz, DMSO-d$_6$) δ: 10.00-9.60 (1H, m), 8.85-8.70 (1H, m), 7.68 (1H, s), 7.36-7.25 (1H, m), 7.14 (1H, s), 6.99 (1H, d, J=8.6 Hz), 6.65 (1H, d, J=7.4 Hz), 4.00-2.80 (6H, m), 2.40-2.10 (2H, m), 1.80-1.55 (4H, m).

3) Synthesis of N-[3-(4-Phenylmethyl-2-oxopiperazin-1-yl)propan-1-yl]-5-thia-1,8b-diazaacenaphthylene-4-carboxamide Benzylchloride (187 mg, 1.48 mmol) was added to a stirred solution of N-[3-(2-oxopiperazin-1-yl)propan-1-yl]-5-thia-1,8b-diazaacenaphthylene-4-carboxamide dihydrochloride (518 mg, 1.20 mmol), triethylamine (605 mg, 5.98 mmol), sodium iodide (216 mg, 1.44 mmol) and 1,8-diazabicyclo[5.4.0]undecene (366 mg, 2.41 mmol) in acetonitrile (20 ml) at room temperature. After refluxing under nitrogen for 2 days, the reaction mixture was concentrated in vacuo. The residue was dissolved in water and extracted with chloroform. The extract was washed with brine, dried over MgSO4 and concentrated in vacuo. The residue was chromatographed on silica gel (20 g) with Ethyl acetate-Methanol (8:1) to give N-[3-(4-phenylmethyl-2-oxopiperazine-1-yl)propane-1-yl]-5-thia-1,8b-diazaacenaphthylene-4-carboxamide as a purple amorphous powdeer (303 mg, 56%).

$^1$H-NMR (200 MHz, CDCl$_3$) δ: 7.62-7.45 (1H, m), 7.40-7.20 (5H, m), 7.00 (1H, s), 6.65 (1H, s), 6.60-6.50 (2H, m), 5.73 (1H, dd, J=5.6 and 2.4 Hz), 3.58 (2H, s), 3.52-3.38 (2H, m), 3.38-3.10 (4H, m), 3.20 (2H, s), 2.70 (2H, t, J=5.2 Hz), 1.80-1.60 (2H, m).

IR (KBr) 3242, 2937, 1627, 1505, 1482, 1282, 1156, 913, 734 cm$^{-1}$.

4) Synthesis of N-[3-(4-Phenylmethyl-2-oxopiperazin-1-yl)propan-1-yl]-5-thia-1,8b-diazaacenaphthylene-4-carboxamide dihydrochloride Concentrated hydrochloric acid(0.8 ml) was added to a stirred solution of N-[3-(4-phenylmethyl-2-oxopiperazin-1-yl)propan-1-yl]-5-thia-1,8b-diazaacenaphthylene-4-carboxamide (300 mg, 0.670 mmol) in ethanol (5.0 ml) at room temperature. After stirring at room temperature for 1 hour, the reaction mixture was concentrated in vacuo to give N-(3-(4-phenylmethyl-2-oxopiperazin-1-yl)propan-1-yl]-5-thia-1,8b-diazaacenaphthylene-4-carboxamide dihydrochloride as an orange amorphous powder (345 mg, 98%).

$^1$H-NMR (200 MHz, DMSO-d$_6$) δ: 8.80-8.60 (1H, m), 7.80-7.40 (6H, m), 7.40–7.15 (1H, m), 7.05 (1H, s), 6.95 (1H, d, J=8.4 Hz), 6.56 (1H, d, J=6.6 Hz), 4.38 (2H, s), 4.00-3.20 (8H, m), 3.20-3.00 (2H, m), 1.80-1.50 (2H, m).

IR (KBr): 3240, 3058, 2941, 1635, 1565, 1538, 1502, 1293, 1214, 759, 705 cm$^{-1}$.

Elemental analysis for C$_{24}$H$_{27}$Cl$_2$N$_5$O$_2$S·2.5H$_2$O. Calcd.: C, 50.97; H, 5.70; N, 12.38. Found: C, 50.90; H, 5.71; N, 12.08.

Example 173

Synthesis of N-[3-[4-(2-Phenylethan-1-yl)-2-oxopiperazin-1-yl]propan-1-yl]-5-thia-1,8b-diazaacenaphthylene-4-carboxamide dihydrochloride 1) Synthesis of N-[3-[4-(2-Phenylethan-1-yl)-2-oxopiperazin-1-yl]propan-1-yl]-5-thia-1,8b-diazaacenaphthylene-4-carboxamide (2-Bromoethyl)benzene (312 mg, 1.68 mmol) was added to a stirred solution of N-[3-(2-oxopiperazin-1-yl)propan-1-yl]-5-thia-1,8b-diazaacenaphthylene-4-carboxamide dihydrochloride (610 mg, 1.42 mmol), triethylamine (722 mg, 7.13 mmol), sodium iodide (255 mg, 1.70 mmol) and 1,8-diazabicyclo[5.4.0]undecene (438 mg, 2.88 mmol) in acetonitrile (20 ml) at room temperature. After refluxing under nitrogen for 2 days, the reaction mixture was concentrated in vacuo. The residue was dissolved in water and extracted with chloroform. The extract was washed with brine, dried over MgSO$_4$ and concentrated in vacuo. The residue was chromatographed on silica gel(20 g) with Ethyl acetate-Methanol (8:1) to give N-[3-[4-(2-phenylethan-1-yl)-2-oxopiperazin-1-yl]propan-1-yl]-5-thia-1,8b-diazaacenaphthylene-4-carboxamide as a purple amorphous powder (288 mg, 44%).

$^1$H-NMR (200 MHz, CDCl$_3$) δ: 7.65-7.45 (1H, m), 7.40-7.15 (5H, m), 7.01 (1H, s), 6.60-6.50 (2H, m), 5.74 (1H, dd, J=6.0 and 2.2 Hz), 3.60-3.40 (2H, m), 3.40-3.00 (6H, m), 3.00-2.60 (6H, m), 1.80-1.60 (2H, m).

IR (KBr) : 3286, 2935, 1714, 1635, 1506, 1482, 1282, 1156, 732 cm$^{-1}$.

2) Synthesis of N-[3-[4-(2-Phenylethan-1-yl)-2-oxopiperazin-1-yl]propan-1-yl]-5-thia-1,8b-diazaacenaphthylene-4-carboxamide dihydrochloride Concentrated hydrochloric acid (0.8 ml) was added to a stirred solution of N-[3-[4-(2-phenylethan-1-yl)-2-oxopiperazin-1-yl]propan-1-yl]-5-thia-1,8b-diazaacenaphthylene-4-carboxamide (369 mg, 0.799 mmol) in ethanol (5.0 ml) at room temperature. After stirring at room temperature for 1 hour, the reaction mixture was concentrated in vacuo to give N-[3-[4-(2-phenylethan-1-yl) 2-oxopiperazin-1-yl]propan-1-yl]-5-thia-1,8b-diazaacenaphthylene-4-carboxamide dihydrochloride as an orange amorphous powder (424 mg, 99%).

$^1$H-NMR (200 MHz, DMSO-d$_6$) δ: 8.80-8.65 (1H, m), 7.62 (1H, s), 7.60-7.20 (6H, m), 7.08 (1H, s), 7.00-6.90 (1H, m), 6.62-6.50 (1H, m), 4.20-3.20 (10H, m), 3.20-3.00 (4H, m), 1.85-1.55 (2H, m).

IR (KBr) : 3242, 2935, 1652, 1635, 1565, 1538, 1500, 1455, 1361, 1293, 1214, 784, 703 cm$^{-1}$.

Elemental analysis for C$_{25}$H$_{29}$Cl$_2$N$_5$O$_2$S·0.7C$_2$H$_5$OH·2.0H$_2$O. Calcd.: C, 52.60; H, 6.22; N, 11.62. Found: C, 52.74; H, 5.96; N, 11.68.

Example 174

Synthesis of N-[3-[4-(3-Phenylpropan-1-yl)-2-oxopiperazin-1-yl]propan-1-yl]-5-thia-1,8b-diazaacenaphthylene-4-carboxamide dihydrochloride 1) Synthesis of N-[3-[4-(3-Phenylpropan-1-yl)-2-oxopiperazin-1-yl]propan-1-yl]-5-thia-1,8b-diazaacenaphthylene-4-carboxamide 1-Bromo-3-phenylpropane (210 mg, 1.05 mmol) was added to a stirred solution of N-[3-(2-oxopiperazin-1-yl) propan-1-yl]-5-thia-1,8b-diazaacenaphthylene-4-carboxamide dihydrochloride (389 mg, 0.904 mmol), triethylamine (459 mg, 4.53 mmol), sodium iodide (163 mg, 1.09 mmol) and 1,8-diazabicyclo[5.4.0]undecene (275 mg, 1.81 mmol) in acetonitrile (10 ml) at room temperature. After refluxing under nitrogen for 2 days, the reaction mixture was concentrated in vacuo. The residue was dissolved in water and extracted with chloroform. The extract was washed with brine, dried over MgSO$_4$ and concentrated in vacuo. The residue was chromatographed on silica gel (15 g) with Ethyl acetate-Methanol (8:1) to give N-[3-[4-(3-phenylpropan-1-yl)-2-oxopiperazin-1-yl]propan-1-yl]-5-thia-1,8b-diazaacenaphthylene-4-carboxamide as a purple amorphous powder(285 mg, 66%).

$^1$H-NMR (200 MHz, CDCl$_3$) δ: 7.62-7.50 (1H, m), 7.40-7.15 (5H, m), 7.01 (1H, s), 6.66 (1H, s), 6.62-6.50 (2H, m), 5.74 (1H, dd, J=6.0 and 2.2 Hz), 3.54-3.40 (1H, m), 3.36-3.26 (2H, m), 3.26-3.12 (2H, m), 3.18 (2H, s), 2.67 (4H, t, J=7.4 Hz), 1.95-1.40 (4H, m).

IR (KBr) : 3294, 2935, 1714, 1635, 1506, 1282, 1156, 732 cm$^{-1}$.

2) Synthesis of N-[3-[4-(3-Phenylpropan-1-yl)-2-oxopiperazin-1-yl]propan-1-yl]-5-thia-1,8b-diazaacenaphthylene-4-carboxamide dihydrochloride Concentrated hydrochloric acid (0.8 ml) was added to a stirred solution of N-[3-[4-(3-phenylpropan-1-yl)-2-oxopiperazin-1-yl]propan-1-yl]-5-thia-1,8b-diazaacenaphthylene-4-carboxamide (261 mg, 0.549 mmol) in ethanol (5.0 ml) at room temperature. After stirring at room temperature for 1 hour, the reaction mixture was concentrated in vacuo to give N-[3-[4-(3-phenylpropan-1- yl)-2-oxopiperazin-1-yl]propan-1-yl]-5-thia-1,8b-diazaacenaphthylene-4-carboxamide dihydrochloride as an orange amorphous powder(295 mg, 98%).

$^1$H-NMR (200 MHz, DMSO-d$_6$) δ: 8.82-8.70 (1H, m), 7.67 (1H, s), 7.40-7.15 (6H, m), 7.10 (1H, s), 6.98 (1H, d, J=7.4 Hz), 6.63 (1H, d, J=7.4 Hz), 4.00-2.70 (8H, m), 2.64 (2H, t, J=7.2 Hz), 2.20–1.85 (4H, m), 1.80-1.50 (4H, m).

IR (KBr) : 3219, 2937, 1652, 1538, 1500, 1455, 1291, 1216, 786, 757 cm$^{-1}$.

Elemental analysis for C$_{26}$H$_{31}$Cl$_2$N$_5$O$_2$S·2.5H$_2$O. Calcd.: C, 52.61; H, 6.11; N, 11.80. Found: C, 52.88; H, 6.18; N, 11.58.

Example 175

Synthesis of N-[1-[3-(4-Aminophenyl)propan-1-yl]piperidin-4-yl]-5-thia-1,8b-diazaacenaphthylene-4-carboxamide trihydrochloride 1) Synthesis of N-[1-[3-(4-tert-Butoxycarbonylaminophenyl)propan-1-yl]piperidin-4-yl]-5-thia-1,8b-diazaacenaphthylene-4-carboxamide 3-(4-tert-Butoxycarbonylaminophenyl)propyl methanesulfonate (423 mg, 1.28 mmol) was added to a stirred solution of N-(piperidin-4-yl)-5-thia-1,8b-diazaacenaphthylene-4-carboxamide dihydrochloride (400 mg, 1.07 mmol), triethylamine (539 mg, 5.33 mmol), sodium iodide (192 mg, 1.28 mmol) and 1,8-diazabicyclo[5.4.0]undecene (326 mg, 2.14 mmol) in acetonitrile (20 ml) at room temperature. After refluxing under nitrogen for 1 day, the reaction mixture was concentrated in vacuo. The residue was dissolved in water and extracted with chloroform. The extract was washed with brine, dried over MgSO$_4$ and concentrated in vacuo. The residue was chromatographed on silica gel (20 g) with Ethyl acetate-Methanol (3:1) to give N-[1-[3-(4-tert-butoxycarbonylaminophenyl)propan-1-yl]piperidin-4-yl]-5-thia-1,8b-diazaacenaphthylene-4-carboxamide as purple amorphous powder (350 mg, 61%).

$^1$H-NMR (200 MHz, CDCl$_3$) δ: 7.40-7.00 (4H, m), 6.80-6.58 (3H, m), 6.45-6.38 (1H, m), 5.79 (1H, dd, J=5.8 and 1.4 Hz), 5.65-5.55 (1H, m), 3.90-3.70 (1H, m), 2.95-2.78 (2H, m), 2.70-2.50 (2H, m), 2.45-2.30 (2H, m), 2.20-1.58 (8H, m), 1.43 (9H, s).

2) Synthesis of N-[1-[3-(4-Aminophenyl)propan-1-yl]piperidin-4-yl]-5-thia-1,8b-diazaacenaphthylene-4-carboxamide trihydrochloride Concentrated hydrochloric acid (1.5 ml) was added to N-[1-[3-(4-tert-butoxycarbonylaminophenyl)propan-1-yl]piperidin-4-yl]-5-thia-1,8b-diazaacenaphthylene-4-carboxamide (350 mg, 0.656 mmol) and the mixture was stirred at room temperature for 2 hours. Ethanol was added to the mixture to give N-[1-[3-(4-aminophenyl)propan-1-yl]piperidin-4-yl]-5-thia-1,8b-diazaacenaphthylene-4-carboxamide trihydrochloride as orange crystals (251 mg, 71%), which were collected by filtration and washed with ethanol.

$^1$H-NMR (200 MHz, DMSO-d$_6$) δ: 8.80-8.70 (1H, m), 7.59 (1H, s), 7.40-7.15 (6H, m), 6.94 (1H, d, J=9.6 Hz), 6.54 (1H, d, J=7.8 Hz), 4.00-3.20 (3H, m), 3.20-2.80 (6H, m), 2.80-2.60 (2H, m), 2.20-1.80 (6H, m).

IR (KBr) : 3000, 2557, 1653, 1631, 1515, 1498, 1299, 1216, 1116, 823, 782 cm$^{-1}$.

Elemental analysis for C$_{24}$H$_{30}$Cl$_3$N$_5$OS·1.5H$_2$O. Calcd.: C, 50.57; H, 5.84; N, 12.29. Found: C, 50.60; H, 5.77; N, 12.33.

Example 176

Synthesis of N-[1-[3-(3-Aminophenyl)propan-1-yl]piperidin-4-yl]-5-thia-1,8b-diazaacenaphthylene-4-carboxamide trihydrochioride 1) Synthesis of N-[1-[3-(3-tert-Butoxycarbonylaminophenyl)propan-1-yl]piperidin-4-yl]-5-thia-1,8b-diazaacenaphthylene-4-carboxamide 3-(3-tert-Butoxycarbonylaminophenyl)propyl methanesulfonate (423 mg, 1.28 mmol) was added to a stirred solution of N-(piperidin-4-yl)-5-thia-1,8b-diazaacenaphthylene-4-carboxamide dihydrochloride (400 mg, 1.07 mmol), triethylamine (539 mg, 5.33 mmol), sodium iodide (192 mg, 1.28 mmol) and 1,8-diazabicyclo[5.4.0]undecene (326 mg, 2.14 mmol) in acetonitrile (20 ml) at room temperature. After refluxing under nitrogen for 16 hours, the reaction mixture was concentrated in vacuo. The residue was dissolved in water and extracted with chloroform. The extract was washed with brine, dried over MgSO$_4$ and concentrated in vacuo. The residue was chromatographed on silica gel (15 g) with Ethyl acetate-Methanol (3:1) to give N-[1-(3-(3-tert-butoxycarbonylaminophenyl)propan-1-yl]piperidin-4-yl]-5-thia-1,8b-diazaacenaphthylene-4-carboxamide as a purple amorphous powder(413 mg, 72%).

$^1$H-NMR (200 MHz, CDCl$_3$) δ: 7.23-7.00 (3H, m), 6.85 (1H, d, J=7.4 Hz), 6.70-6.50 (4H, m), 5.90-5.75 (1H, m), 5.78 (1H, dd, J=5.8 and 1.8 Hz), 4.00-3.75 (1H, m), 3.00-2.80 (2H, m), 2.62 (2H, t, J=7.2 Hz), 2.43 (2H, t, J=7.4 Hz), 2.30-1.55 (8H, m), 1.51 (9H, s).

2) Synthesis of N-[1-[3-(3-Aminophenyl)propan-1-yl]piperidin-4-yl]-5-thia-1,8b-diazaacenaphthylene-4-carboxamide trihydrochloride Concentrated hydrochloric aicd (1.5 ml) was added to N-[1-[3-(3-tert-butoxycarbonylaminophenyl)propan-1-yl]piperidin-4-yl]-5-thia-1,8b-diazaacenaphthylene-4-carboxamide (392 mg, 0.735 mmol) and the mixture was stirred at room temperature for 1 hour. Ethanol was added to the mixture to give N-[1-[3-(3-aminophenyl)propan-1-yl]piperidin-4-yl]-5-thia-1,8b-diazaacenaphthylene-4-carboxamide trihydrochloride as orange crystals (265 mg, 66%), which were collected by filtration and washed with ethanol.

$^1$H-NMR (200 MHz, DMSO-d$_6$) δ: 8.85-8.75(1H, m), 7.63 (1H, s), 7.50-7.36 (1H, m), 7.32-7.16 (5H, m), 6.96 (1H, d, J=9.2 Hz), 6.59 (1H, d, J=7.4 Hz), 4.20-3.20 (4H, m), 3.20-2.80 (5H, m), 2.68 (2H, t, J=6.8 Hz), 2.20-1.80 (6H,m).

IR (KBr) : 3050, 1633, 1567, 1540, 1498, 1307, 1220, 1112, 782 cm$^{-1}$.

Elemental analysis for C$_{24}$H$_{30}$Cl$_3$N$_5$OS·1.5H$_2$O. Cacld.: C, 50.57; H. 5.84; N, 12.29. Found: C, 50.27; H, 5.92; N, 12.05.

Example 177

Synthesis of N-[1-[3-(4-Cyanophenyl)propan-1-yl]piperidin-4-yl]-5-thia-1,8b-diazaacenaphthylene-4-carboxamide dihydrochloride 1) Synthesis of N-[1-[3-(4-Cyanophenyl)propan-1-yl]piperidin-4-yl]-5-thia-1,8b-diazaacenaphthylene-4-carboxamide 3-(4-Cyanophenyl)propyl methanesulfonate (307 mg, 1.28 mmol) was added to a stirred solution of N-(piperidin-4-yl)-5-thia-1,8b-diazaacenaphthylene-4-carboxamide dihydrochloride (400 mg, 1.07 mmol), triethylamine (539 mg, 5.33 mmol), sodium iodide (192 mg, 1.28 mmol) and 1,8-diazabicyclo[5.4.0]undecene (326 mg, 2.14 mmol) in acetonitrile (20 ml) at room temperature. After refluxing under nitrogen for 14 hours, the reaction mixture was concentrated in vacuo. The residue was dissolved in water and extracted with chloroform. The extract was washed with brine, dried over MgSO$_4$ and concentrated in vacuo. The residue was chromatographed on silica gel (20 g) with Ethyl acetate-Methanol (2:1) to give N-[1-[3-(4-cyanophenyl)propan-1-yl]piperidin-4-yl]-5-thia-1,8b-diazaacenaphthylene-4-carboxamide as a purple oil (298 mg, 63%).

$^1$H-NMR (200 MHz, CDCl$_3$) δ: 7.57 (2H, d, J=8.0 Hz), 7.28 (2H, d, J=8.0 Hz), 7.06 (1H, s), 6.75-6.55 (3H, m), 5.79 (1H, dd, J=6.0 and 1.6 Hz), 5.56 (1H, d, J=7.8 Hz), 3.92-3.70 (1H, m), 2.92-2.75 (2H, m), 2.69 (2H, t, J=7.8 Hz), 2.36 (2H, t, J=7.4 Hz), 2.20-2.02 (2H, m), 2.02-1.88 (2H, m), 1.88-1.76 (2H, m), 1.60-1.40 (2H, m).

IR (neat) : 3209, 2943, 2227, 1615, 1540, 1508, 1482, 1286, 1156, 734 cm$^{-1}$.

2) Synthesis of N-[1-[3-(4-Cyanophenyl)propan-1-yl]piperidin-4-yl]-5-thia-1,8b-diazaacenaphthylene-4-carboxamide dihydrochloride Concentrated hydrochloric acid (1.5 ml) was added to a stirred solution of N-[1-[3-(4-cyanophenyl)propan-1-yl]piperidin-4-yl]-5-thia-1,8b-diazaacenaphthylene-4-carboxamide (298 mg, 0.672 mmol) in ethanol (4.0 ml) at room temperature. After stirring at room temperature for 1 hour, the reaction mixture was concentrated in vacuo to give N-[1-[3-(4-cyanophenyl)propan-1-yl]piperidin-4-yl]-5-thia-1,8b-diazaacenaphthylene-4-carboxamide dihydrochloride as an orange amorphous powdeer (324 mg, 93%).

$^1$H-NMR (200 MHz, DMSO-d$_6$) δ: 8.85-8.75 (1H, m), 7.79 (2H, d, J=7.8 Hz), 7.62 (1H, s), 7.47 (2H, d, J=7.8 Hz), 7.32-7.10 (2H, m), 6.96 (1H, d, J=9.2 Hz), 6.59 (1H, d, J=7.6 Hz), 4.00-3.20 (3H, m), 3.15-2.90 (2H, m), 2.80-2.65 (2H, m), 2.20-1.90 (4H, m), 1.90-1.80 (2H, m).

IR (KBr) : 3037, 2939, 2223, 1633, 1500, 1307, 1220, 1114, 776 cm$^{-1}$.

Example 178

Synthesis of N-[3-[1-(3-Phenylpropan-1-yl)-2-oxopiperazin-4-yl]propane-1-yl]-5-thia-1,8b-diazaacenaphthylene-4-carboxamide dihydrochloride 1) Synthesis of N-[3-[1-(3-Phenylpropan-1-yl)-2-oxopiperazin-4-yl]propan-1-yl]-5-thia-1,8b-diazaacenaphthylene-4-carboxamide 1-Ethyl-3-(3-dimethylaminopropyl)carbodiimide hydrochloride (1.58 g, 8.24 mmol) was added to a stirred suspension of 5-thia-1,8b-diazaacenaphthylene-4-carboxylic acid (900 mg, 4.12 mmol) and N-hydroxysuccinimide (948 mg, 8.24 mmol) in acetonotrile (10 ml) at room temperature and the mixture was stirred at room temperature for 2 hours. A solution of 4-(3-aminopropan-1-yl)-1-(3-phenylpropan-1-yl)-2-oxopiperazine (1.38 g, 5.01 mmol), triethylamine (459 mg, 4.54 mmol) and 1,8-diazabicyclo[5.4.0]undecene (1.25 g, 8.24 mmol) in acetonitrile (20 ml) was added to the mixture. After stirring at room temperature for 1 day, the reaction mixture was concentrated in vacuo. The residue was dissolved in water and extracted with chloroform. The extract was washed with brine, dried over MgSO$_4$ and concentrated in vacuo. The residue was chromatographed on silica gel (60 g) with Ethyl acetate-Methanol (5:1) to give N-[3-[1-(3-phenylpropan-1-yl)-2-oxopiperazin-4-yl]propan-1-yl]-5-thia-1,8b-diazaacenaphthylene-4-carboxamide as a purple amorphous powder (978 mg, 50%).

$^1$H-NMR (200 MHz, CDCl$_3$) δ: 7.40-7.10 (5H, m), 7.02 (1H, s), 6.67 (1H, s), 6.66-6.50 (2H, m), 5.72 (1H, d, J=7.0 Hz), 3.60-3.20 (6H, m), 3.17 (2H, s), 2.75-2.60 (4H, m), 2.53 (2H, t, J=5.8 Hz), 2.00-1.78 (2H, m), 1.78-1.60 (2H, m).

IR (KBr) : 3248, 2941, 1639, 1544, 1504, 1482, 1282, 1155, 734 cm$^{-1}$.

2) Synthesis of N-[3-[1-(3-Phenylpropan-1-yl)-2-oxopiperazin-4-yl]propane-1-yl]-5-thia-1,8b-diazaacenaphthylene-4-carboxamide dihydrochloride Concentrated hydrochloric acid (4.5 ml) was added to a stirred solution of N-[3-[1-(3-phenylpropan-1-yl)-2-oxopiperazin-4-yl]propan-1-yl]-5-thia-1,8b-diazaacenaphthylene-4-carboxamide (954 mg, 2.01 mmol) in ethanol (12.0 ml) at room temperature. After stirring at room temperature for 1 hour, the reaction mixture was concentrated in vacuo to give N-[3-[1-(3-phenylpropan-1-yl)-2-oxopiperazin-4-yl]propan-1-yl]-5-thia-1,8b-diazaacenaphthylene-4-carboxamide dihydrochloride as an orange amorphous powder.

INDUSTRIAL APPLICABILITY

The compound (1) or itssalt has an excellent LDL receptor up-regulating, blood-lipids lowering, blood-sugar lowering and diabetic complication-ameliorating activity. Therefore, a pharmaceutical composition containing this compound can be safety useful prophylactic and therapeutic drug for atherosclerosis, hyperlipemia, diabetes, diabetic complications, and so on.

What is claimed is:

1. A compound of the formula:

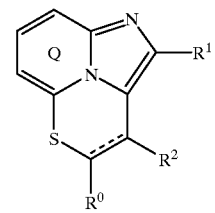

wherein ring Q is an optionally substituted pyridine ring;
one of $R^0$, $R^1$ and R is —$Y^0$—$Z^0$, and the other two groups are a hydrogen, a halogen, an optionally substituted hydroxy group, an optionally substituted hydrocarbon group or an acyl group;
$Y^0$ is a bond or an optionally substituted divalent hydrocarbon group;
$Z^0$ is a basic group which may be bonded via oxygen, nitrogen, —CO—, —CS—, —SO$_2$N(R$^3$)— (wherein R$^3$ is a hydrogen or an optionally substituted hydrocarbon group), or
—S(O)n— (wherein n is 0, 1 or 2); and
----- is a single bond or a double bond, or a salt thereof.

2. A compound of claim 1, wherein $R^0$ is —$Y^0$—$Z^0$, wherein $Y^0$ and $Z^0$ are of the same meanings as defined in claim 1.

3. A compound of claim 1, wherein $Z^0$ is a group with a molecular weight of not greater than 1000.

4. A compound of claim 1 which is a compound of the formula:

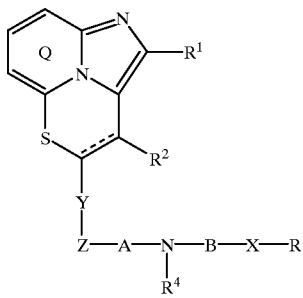

wherein ring Q is an optionally substituted pyridine ring;

A and B independently are an optionally substituted divalent hydrocarbon group which may be bonded via —CON($R^{4a}$)—, —CO— or —N($R^{4a}$)—;

X is a bond, oxygen, sulfur, —N($R^5$)CO—, —CO($R^5$)—, —CO— or —N($R^5$)—;

Y is a bond, —CH=CH— or —CH=CH

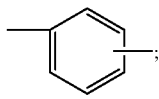

Z is —COO—, —COO—, —CON($R^3$)—, —$SO_2$N($R^3$)— or —S(O)m— (wherein m is 0, 1 or 2);

$R^1$ and $R^2$ independently are a hydrogen, a halogen, an optionally substituted hydroxy group, an optionally substituted hydrocarbon group or an acyl group;

$R^3$, $R^4$, $R^{4a}$ and $R^5$ independently are a hydrogen or an optionally substituted hydrocarbon group; or $R^3$ and A, $R^4$ and A, $R^4$ and B, $R^4$ and $R^5$, or $R^4$ and R may independently be bonded to each other to form a ring;

R is an optionally substituted hydrocarbon group or an optionally substituted heterocyclic group; and ----- is a single bond or a double bond, or a salt thereof.

5. A compound of claim 1 which is a compound of the formula:

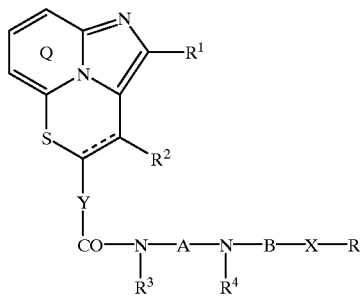

wherein ring Q is an optionally substituted pyridine ring;

A and B independently are an optionally substituted divalent hydrocarbon group which may be bonded via —CON($R^{4a}$)—, —CO— or —N($R^{4a}$)—;

X is a bond, oxygen, sulfur, —N($R^5$)CO—, —CO($R^5$)—, —CO— or —N($R^5$)—;

Y is a bond, —CH=CH— or —CH=CH

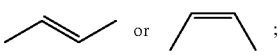

$R^1$ and $R^2$ independently are a hydrogen, a halogen, an optionally substituted hydroxy group, an optionally substituted hydrocarbon group or an acyl group;

$R^3$, $R^4$, $R^{4a}$ and $R^5$ independently are a hydrogen or an optionally substituted hydrocarbon group; or $R^3$ and A, $R^4$ and A, $R^4$ and B, $R^4$ and $R^5$, or $R^4$ and R independently may be bonded to each other to form a ring;

R is an optionally substituted hydrocarbon group or an optionally substituted heterocyclic group; and ----- is a single bond or a double bond, or a salt thereof.

6. A compound of claim 5, wherein A and B independently are an alkylene group; X is a bond; and $R^3$ and $R^4$ independently are a hydrogen or an optionally substituted alkyl, cycloalkyl, alkenyl, aralkyl or aryl group.

7. A compound of claim 5, wherein ring Q is an unsubstituted pyridine ring; X is a bond; Y is a bond, A and B independently are a $C_{1-15}$ alkylene group; $R^1$ and $R^2$ independently are a hydrogen;

$R^3$ and $R^4$ independently are a hydrogen or a $C_{1-15}$ alkyl, $C_{3-8}$ cycloalkyl, $C_{2-18}$ alkenyl, $C_{7-16}$ aralkyl or $C_{6-14}$ aryl group; and R is a $C_{6-14}$ aryl group.

8. A compound of claim 1 which is a compound of the formula:

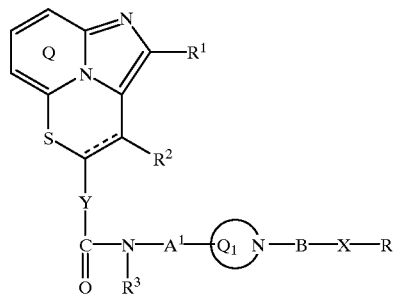

wherein ring Q is an optionally substituted pyridine ring;

ring $Q_1$ is an optionally substituted nitrogen-containing heterocyclic ring;

$A^1$ is a bond or an optionally substituted divalent hydrocarbon group which may be bonded via —CON($R^{4a}$)—, —CO— or —N($R^{4a}$)—;

B is an optionally substituted divalent hydrocarbon group;

X is a bond, oxygen, sulfur, —N($R^5$)CO—, —CO($R^5$)—, —CO— or —N($R^5$)—;

Y is a bond, —CH=CH— or —CH=CH

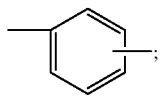

R$^1$ and R$^2$ independently are a hydrogen, a halogen, an optionally substituted hydroxy group, an optionally substituted hydrocarbon group or an acyl group;

R$^3$, R$^{4a}$ and R$^5$ independently are a hydrogen or an optionally substituted hydrocarbon group; or R$^3$ and A$^1$ may be bonded to each other to form a ring;

R is an optionally substituted hydrocarbon group or an optionally substituted heterocyclic group; and ----- is a single bond or a double bond, or a salt thereof.

9. A compound of claim 8, wherein ring Q is an unsubstituted pyridine ring; R$^1$ and R$^2$ are a hydrogen; R$^3$ is a hydrogen or a C$_{1-15}$ alkyl, C$_{3-8}$ cycloalkyl, C$_{2-18}$ alkenyl, C$_{7-16}$ aralkyl or C$_{6-14}$ aryl group; A$^1$ is (i) a bond, (ii) a C$_{1-15}$ alkylene group which may be substituted by 1 to 3 substituents selected from the group consisting of hydroxy, oxo and phenyl, (iii) a C$_{2-16}$ alkenylene group or (iv) a phenylene group; B is (i) a C$_{1-15}$ alkylene group which may be substituted by 1 to 3 substituents selected from the group consisting of hydroxy, oxo and phenyl, (ii) a C$_{2-16}$ alkenylene group or (iii) a phenylene group; ring Q$_1$ is a group of the formula:

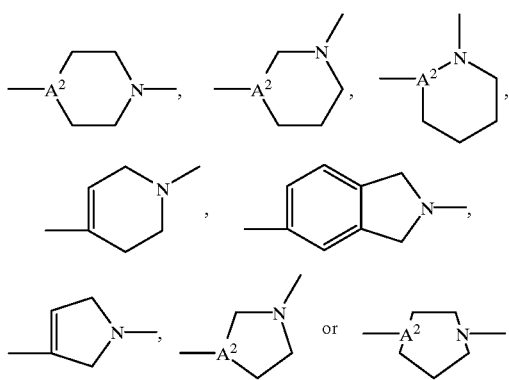

wherein A$^2$ is =C or CH; X is a bond, oxygen, sulfur or —CON(R$^5$)—; R$^5$ is a hydrogen or a C$_{1-15}$ alkyl group.

10. A compound of claim 1 which is a compound of the formula:

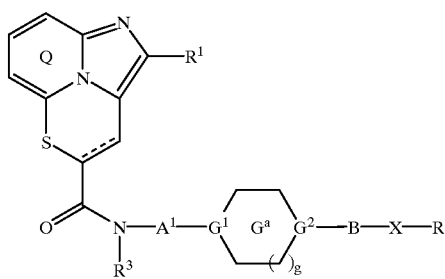

wherein ring Q is an optionally substituted pyridine ring;

A$^1$ is a bond or an optionally substituted divalent hydrocarbon group which may be bonded via —CON (R$^{4a}$)—, —CO— or —N(R$^{4a}$)—;

B is an optionally substituted divalent hydrocarbon group;

X is a bond, oxygen, sulfur, —N(R$^5$)CO—, —CON (R$^5$)—, —CO— or —N(R$^5$)—;

R$^1$ is a hydrogen, a halogen, an optionally substituted hydroxy group, an optionally substituted hydrocarbon group or an acyl group;

R$^3$, R$^{4a}$ and R$^5$ independently are a hydrogen or an optionally substituted hydrocarbon group;

R is an optionally substituted hydrocarbon group or an optionally substituted heterocyclic group;

one of G$^1$ and G$^2$ is N, and the other is CH or N;

ring G$^a$ is an optionally substituted ring;

g is 0, 1 or 2; and

----- is a single bond or a double bond, or a salt thereof.

11. A compound of claim 10, wherein ring Q is a pyridine ring which may be substituted by 1 to 3 substituents selected from the group consisting of nitro, hydroxy, cyano, carbamoyl, mono- or di-C$_{1-4}$ alkyl-carbamoyl, carboxy, C$_{1-4}$ alkoxy-carbonyl, sulfo, halogen, C$_{1-4}$ alkoxy, phenoxy, naphthoxy, benzyloxy, halophenoxy, C$_{1-4}$ alkylthio, mercapto, phenylthio, pyridylthio, C$_{1-4}$ alkylsulfinyl, phenylsulfinyl, C$_{1-4}$ alkylsulfonyl, phenylsulfonyl, amino, C$_{1-3}$ acylamino, mono- or di-C$_{1-4}$ alkylamino, C$_{1-4}$ alkyl and C$_{1-4}$ haloalkyl.

12. A compound of claim 10, wherein A$^1$ is a bond or a C$_{1-15}$ alkylene, C$_{2-16}$ alkenylene group which may be bonded via —CON(R$^{4a}$)—, —CO— or —N(R$^{4a}$)—, wherein R$^{4a}$ is of the same meaning as defined in claim 10.

13. A compound of claim 10, wherein B is a C$_{1-15}$ alkylene or C$_{2-16}$ alkenylene group.

14. A compound of claim 10, wherein X is a bond, oxygen, sulfur, —CONH— or —CO—.

15. A compound of claim 10, wherein R$^1$ is (1) a hydrogen, (2) a halogen, (3) a hydroxy group which may be substituted by a C$_{1-6}$ alkyl, phenyl, C$_{7-10}$ aralkyl, formyl, C$_{1-6}$ alkyl-carbonyl, phenyloxycarbonyl, C$_{7-10}$ aralkyloxycarbonyl, pyranyl, furyl or silyl group, (4) a C$_{1-15}$ alkyl, C$_{3-8}$ cycloalkyl, C$_{2-18}$ alkenyl, C$_{7-16}$ aralkyl or C$_{6-14}$ aryl group or (5) a C$_{1-6}$ alkoxy-carbonyl, mono-C$_{1-6}$ alkyl-carbamoyl, di-C$_{1-6}$ alkyl-carbamoyl or C$_{1-10}$ alkanoyl group.

16. A compound of claim 10, wherein R$^3$ is a hydrogen or a C$_{1-15}$ alkyl, C$_{3-8}$ cycloalkyl, C$_{2-18}$ alkenyl, C$_{7-16}$ aralkyl or C$_{6-14}$ aryl group.

17. A compound of claim 10, wherein R is (1) a C$_{1-15}$ alkyl, C$_{3-8}$ cycloalkyl or C$_{2-18}$ alkenyl group which may be substituted by 1 to 5 substituents selected from the group consisting of (i) nitro, (ii) hydroxy, (iii) cyano, (iv) carbamoyl, (v) mono- or di-C$_{1-4}$ alkyl-carbamoyl, (vi) carboxy, (vii) C$_{1-4}$ alkoxy-carbonyl, (viii) sulfo, (ix) halogen, (x) C$_{1-4}$ alkoxy, (xi) phenoxy, (xii) halophenoxy, (xiii) C$_{1-4}$ alkylthio, (xiv) mercapto, (xv) phenylthio, (xvi) pyridylthio, (xvii) C$_{1-4}$ alkylsulfinyl, (xviii) C$_{1-4}$ alkylsulfonyl, (xix) amino, (xx) C$_{1-3}$ alkanoylamino, (xxi) mono- or di-C$_{1-4}$ alkylamino, (xxii) 4- to 6-membered cyclic amino, (xxiii) C$_{1-3}$ alkanoyl, (xxiv) benzoyl and (xxv) 5- to 10-membered heterocyclic group;

(2) a $C_{7-16}$ aralkyl group which may be substituted by 1 to 4 substituents selected from the group consisting of (i) halogen, (ii) $C_{1-4}$ alkyl, (iii) $C_{2-6}$ alkenyl, (iv) $C_{1-3}$ alkanoyl, (v) $C_{1-4}$ alkoxy, (vi) nitro, (vii) cyano, (viii) hydroxy, (ix) $C_{1-4}$ alkoxy-carbonyl, (x) carbamoyl, (xi) mono- or di-$C_{1-4}$ alkyl-carbamoyl and (xii) mono- or di-$C_{2-4}$ alkenyl-carbamoyl;

(3) a $C_{6-14}$ aryl group which may be substituted by 1 to 4 substituents selected from the group consisting of (i) halogen, (ii) $C_{1-4}$ alkyl, (iii) $C_{1-4}$ haloalkyl, (iv) $C_{1-4}$ haloalkoxy, (v) $C_{1-4}$ alkoxy, (vi) $C_{1-4}$ alkylthio, (vii) hydroxy, (viii) carboxy, (ix) cyano, (x) nitro, (xi) amino, (xii) mono- or di-$C_{1-4}$ alkylamino, (xiii) formyl, (xiv) mercapto, (xv) $C_{1-4}$ alkyl-carbonyl, (xvi) $C_{1-4}$ alkoxy-carbonyl, (xvii) sulfo, (xviii) $C_{1-4}$ alkylsulfonyl, (xix) carbamoyl, (xx) mono- or di-$C_{1-4}$ alkyl-carbamoyl, (xxi) oxo and (xxii) thioxo; or (4) a 5- or 6-membered monocyclic heterocyclic group containing 1 to 4 hetero-atoms selected from oxygen, sulfur and nitrogen or a fused bicyclic heterocyclic group containing 1 to 6 hetero-atoms selected from oxygen, sulfur and nitrogen, each of which may be substituted by 1 to 4 substituents selected from the group consisting of (i) halogen, (ii) $C_{1-4}$ alkyl, (iii) $C_{1-4}$ haloalkyl, (iv) $C_{1-4}$ haloalkoxy, (v) $C_{1-4}$ alkoxy, (vi) $C_{1-4}$ alkylthio, (vii) hydroxy, (viii) carboxy, (ix) cyano, (x) nitro, (xi) amino, (xii) mono- or di-$C_{1-4}$ alkylamino, (xiii) formyl, (xiv) mercapto, (xv) $C_{1-4}$ alkyl-carbonyl, (xvi) $C_{1-4}$ alkoxy-carbonyl, (xvii) sulfo, (xviii) $C_{1-4}$ alkylsulfonyl, (xix) carbamoyl, (xx) mono- or di-$C_{1-4}$ alkyl-carbamoyl, (xxi) oxo and (xxii) thioxo.

18. A compound of claim 10, wherein ring $G^a$ is a ring which may be substituted by 1 or 2 substituents selected from the group consisting of oxo and $C_{1-6}$ alkyl.

19. A compound of claim 10, wherein ring Q is an unsubstituted pyridine ring; $R^1$ and $R^3$ are a hydrogen;

G is CH; $G^2$ is N; g is 1; and R is an optionally substituted hydrocarbon group or an optionally substituted heterocyclic group.

20. A compound of claim 19, wherein ring $G^a$ is an unsubstituted ring.

21. A compound of claim 19, wherein $A^1$ is a bond or a $C_{1-6}$ alkylene group.

22. A compound of claim 19, wherein $A^1$ is a bond.

23. A compound of claim 19, wherein B is a $C_{1-6}$ alkylene group.

24. A compound of claim 19, wherein X is a bond.

25. A compound of claim 10, wherein ring Q is an unsubstituted pyridine ring; $R^1$ and $R^3$ are a hydrogen; $A^1$ is a bond; $G^1$ is CH; $G^2$ is N; ring $G^1$ is a ring which may be substituted by 1 or 2 substituents selected from the group consisting of oxo and $C_{1-6}$ alkyl; g is 1; B is a $C_{1-6}$ alkylene group; X is a bond; and R is an optionally substituted phenyl group.

26. A compound of claim 25, wherein ring $G^a$ is an unsubstituted ring.

27. A compound of claim 25, wherein R is a phenyl group which may be substituted by 1 to 3 substituents selected from the group consisting of halogen, hydroxy, $C_{1-4}$ alkyl, $C_{1-4}$ haloalkyl, $C_{1-4}$ alkoxy and $C_{1-4}$ haloalkoxy.

28. A compound of claim 1 which is a compound of the formula:

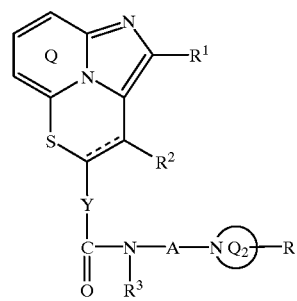

wherein ring Q is an optionally substituted pyridine ring;

ring $Q_2$ is an optionally substituted nitrogen-containing heterocyclic ring;

A is an optionally substituted divalent hydrocarbon group which may be bonded via —CON($R^a$)—, —CO— or —N($R^{4a}$)—;

Y is a bond, —CH=CH— or —CH=CH

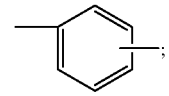

$R^1$ and $R^2$ independently are a hydrogen, a halogen, an optionally substituted hydroxy group, an optionally substituted hydrocarbon group or an acyl group;

$R^3$ and $R^{4a}$ independently are a hydrogen or an optionally substituted hydrocarbon group; or $R^3$ and A may be bonded to each other to form a ring;

R is an optionally substituted hydrocarbon group or an optionally substituted heterocyclic group; and ----- is a single bond or a double bond, or a salt thereof.

29. A compound of claim 28, wherein ring Q is an unsubstituted pyridine ring; $R^1$ and $R^2$ are a hydrogen;

$R^3$ is a hydrogen or a $C_{1-15}$ alkyl, $C_{3-8}$ cycloalkyl, $C_{2-18}$ alkenyl, $C_{7-16}$ aralkyl or $C_{6-14}$ aryl group; A is (i) a $C_{1-15}$ alkylene group which may be substituted by 1 to 3 substituents selected from the group consisting of hydroxy, oxo and phenyl, (ii) a $C_{2-16}$ alkenylene group or (iii) a phenylene group; ring $Q_2$ is a group of the formula:

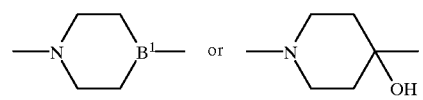

wherein $B^1$ is =C, CH or N.

30. A compound of claim 1 which is a compound of the formula:

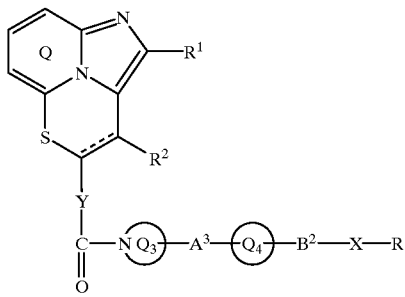

wherein ring Q is an optionally substituted pyridine ring;
rings $Q_3$ and $Q_4$ independently are an optionally substituted nitrogen-containing heterocyclic ring;
$A^3$ and $B^2$ independently are a bond or an optionally substituted divalent hydrocarbon group;
X is a bond, oxygen, sulfur, —N($R^5$)CO—, —CON($R^5$)—, —CO— or —N($R^5$)—;
Y is a bond, —CH=CH— or —CH=CH

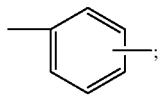

$R^1$ and $R^2$ independently are a hydrogen, a halogen, an optionally substituted hydroxy group, an optionally substituted hydrocarbon group or an acyl group;
$R^5$ is a hydrogen or an optionally substituted hydrocarbon group;
R is an optionally substituted hydrocarbon group or an optionally substituted heterocyclic group; and
----- is a single bond or a double bond, or a salt thereof.

31. A compound of claim 30, wherein ring Q is an unsubstituted pyridine ring; $R^1$ and $R^2$ are a hydrogen;
$A^3$ and $B^2$ independently are a bond or a $C_{1-15}$ alkylene, $C_{2-16}$ alkenylene or phenylene group; ring $Q_3$ is a group of the formula:

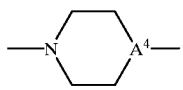

wherein $A^4$ is =C or CH; ring $Q_4$ is a group of the formula:

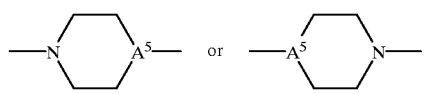

wherein $A^5$ is =C or CH.

32. A compound of claim 1 which is a compound of the formula:

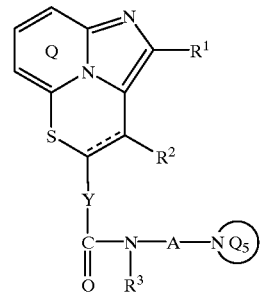

wherein ring Q is an optionally substituted pyridine ring;
ring $Q_5$ is an optionally substituted nitrogen-containing heterocyclic ring;
A is an optionally substituted divalent hydrocarbon group which may be bonded via —CON($R^{4a}$)—, —CO— or —N($R^{4a}$)—;
Y is a bond, —CH=CH— or —CH=CH

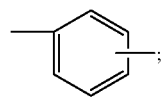

$R^1$ and $R^2$ independently are a hydrogen, a halogen, an optionally substituted hydroxy group, an optionally substituted hydrocarbon group or an acyl group;
$R^3$ and $R^{4a}$ independently are a hydrogen or an optionally substituted hydrocarbon group; and
----- is a single bond or a double bond, or a salt thereof.

33. A compound of claim 32, wherein ring Q is an unsubstituted pyridine ring; $R^1$ and $R^2$ are a hydrogen;
$R^3$ is a hydrogen or a $C_{1-15}$ alkyl, $C_{3-8}$ cycloalkyl, $C_{2-18}$ alkenyl, $C_{7-16}$ aralkyl or $C_{6-14}$ aryl group; A is a $C_{1-15}$ alkylene, $C_{2-16}$ alkenylene or phenylene group; ring $Q_5$ is a group of the formula:

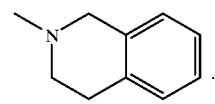

34. A compound of claim 1 which is (R)—N—[1-(1,4-benzodioxan-2-ylmethyl)piperidin-4-ylmethyl]-5-thia-1,8b-diazaacenaphthylene-4-carboxamide, or a pharmaceutically acceptable salt thereof.

35. A compound of claim 1 which is N-[1-(3-phenylpropyl)piperidin-4-ylmethyl]-3-(5-thia-1,8b-diazaacenaphthylene-4-yl)acrylamide, or a pharmaceutically acceptable salt thereof.

36. A compound of claim 1 which is N-[4-(4-phenylpiperidin-1-yl)butan-1-yl]-5-thia-1,8b-diazaacenaphthylene-4-carboxamide, or a pharmaceutically acceptable salt thereof.

37. A compound of claim 1 which is N-[1-(3-phenylpropan-1-yl)piperidin-4-yl]-5-thia-1,8b-diazaacenaphthylene-4-carboxamide, or a pharmaceutically acceptable salt thereof.

38. A process for producing a compound of claim 5, which comprises condensing a compound of the formula:

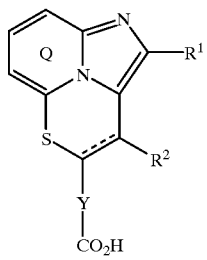

wherein all symbols are of the same meanings as defined in claim 5, or a salt thereof with a compound of the formula:

$R^3$—NH—A—N($R^4$)—B—X—R wherein all symbols are of the same meanings as defined in claim 5, or a salt thereof.

39. A compound of the formula:

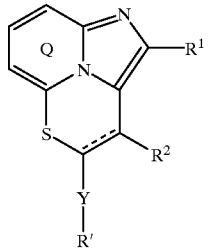

wherein R' is an optionally protected COOH, CH$_2$OH or CHO group; and the other symbols are of the same meanings as defined in claim 4, or a salt thereof.

40. A pharmaceutical composition which comprises a compound of claim 1.

41. A pharmaceutical composition of claim 40, which is an up-regulator of low density lipoprotein receptor.

42. A pharmaceutical composition of claim 40, which is a therapeutic agent for lowering lipids in blood.

43. A pharmaceutical composition of claim 40, which is a therapeutic agent for atherosclerosis.

44. A pharmaceutical composition of claim 40, which is an agent for lowering blood sugar.

45. A pharmaceutical composition of claim 40, which is a therapeutic agent for diabetic complications.

46. A method of using a compound of claim 1 for manufacturing a medicament for lowering lipids in blood comprising mixing the compound of claim 1 with a pharmaceutically acceptable carrier.

47. Method for lowering lipids in blood in a mammal which comprises administering to said mammal an effective amount of a compound of claim 1.

48. A compound of claim 1, wherein the basic group is (1)(i) an optionally substituted amino group and/or (ii) a hydrocarbon group which has a molecular weight not greater than 1000, and has 1 to 10 heterocyclic groups containing 1 to 4 hetero-atoms selected from nitrogen, oxygen or sulfur, which are terminal and/or interrupting groups of the hydrocarbon; or (2) a group of the formula:

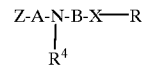

wherein A and B independently are an optionally substituted divalent hydrocarbon which may be bonded via —CON($R^{4a}$)—, —CO— or —N($R^{4a}$)—; Z is —CO—, —COO—, —CON($R^3$)—, —SO$_2$N($R^3$)— or —S(O)$_m$— (wherein m is 0, 1 or 2); X is a bond, oxygen, sulfur, —N($R^5$)CO—, —CO($R^5$)—, —CO— or —N($R^5$)—; $R^3$, $R^4$, $R^{4a}$ and $R^5$ independently are hydrogen or an optionally substituted hydrocarbon group; or $R^3$ and A, $R^4$ and A, $R^4$ and B, $R^4$ and $R^5$ or $R^4$ and R may independently be bonded to each other to form a ring; R is an optionally substituted hydrocarbon group or an optionally substituted heterocyclic group.

* * * * *